(12) United States Patent
Lee et al.

(10) Patent No.: US 9,944,600 B2
(45) Date of Patent: Apr. 17, 2018

(54) PIPERIDINE DERIVATIVES FOR GPR119 AGONIST

(71) Applicant: CHONG KUN DANG PHARMACEUTICAL CORP., Seoul (KR)

(72) Inventors: ChangSik Lee, Gyeonggi-do (KR);
TaegSu Jang, Gyeonggi-do (KR);
DaeKyu Choi, Gyeonggi-do (KR);
MooSung Ko, Gyeonggi-do (KR);
DoHoon Kim, Gyeonggi-do (KR);
SoYoung Kim, Gyeonggi-do (KR);
JaeKi Min, Gyeonggi-do (KR);
WooSik Kim, Gyeonggi-do (KR);
YoungTae Lim, Gyeonggi-do (KR)

(73) Assignee: CHONG KUN DANG PHARMACEUTICAL CORP., Seoul (KR)

(*) Notice: Subject to any disclaimer, the term of this patent is extended or adjusted under 35 U.S.C. 154(b) by 0 days.

(21) Appl. No.: 14/407,214

(22) PCT Filed: Jun. 11, 2013

(86) PCT No.: PCT/KR2013/005096
§ 371 (c)(1),
(2) Date: Dec. 11, 2014

(87) PCT Pub. No.: WO2013/187646
PCT Pub. Date: Dec. 19, 2013

(65) Prior Publication Data
US 2015/0166480 A1  Jun. 18, 2015

(30) Foreign Application Priority Data

Jun. 12, 2012 (KR) .................. 10-2012-0062784

(51) Int. Cl.
| | | |
|---|---|---|
| *C07D 211/22* | (2006.01) |
| *C07D 401/14* | (2006.01) |
| *C07D 401/12* | (2006.01) |
| *C07D 409/12* | (2006.01) |
| *C07D 487/04* | (2006.01) |
| *C07D 211/42* | (2006.01) |
| *C07D 211/60* | (2006.01) |
| *C07D 211/62* | (2006.01) |
| *A61K 31/454* | (2006.01) |
| *A61K 31/4545* | (2006.01) |
| *A61K 31/4985* | (2006.01) |
| *C07D 405/12* | (2006.01) |

(52) U.S. Cl.
CPC .......... *C07D 211/22* (2013.01); *A61K 31/454* (2013.01); *A61K 31/4545* (2013.01); *A61K 31/4985* (2013.01); *C07D 211/42* (2013.01); *C07D 211/60* (2013.01); *C07D 211/62* (2013.01); *C07D 401/12* (2013.01); *C07D 401/14* (2013.01); *C07D 405/12* (2013.01); *C07D 409/12* (2013.01); *C07D 487/04* (2013.01)

(58) Field of Classification Search
CPC ................................................... C07D 211/22
See application file for complete search history.

(56) References Cited

U.S. PATENT DOCUMENTS

| | | | | |
|---|---|---|---|---|
| 8,101,634 | B2 * | 1/2012 | Fang ................ | C07D 211/22 514/315 |
| 8,258,156 | B2 | 9/2012 | Alper et al. | |
| 8,334,288 | B2 | 12/2012 | Epple et al. | |
| 2012/0077812 | A1 | 3/2012 | Fang et al. | |
| 2015/0166480 | A1 | 6/2015 | Lee et al. | |

FOREIGN PATENT DOCUMENTS

| | | |
|---|---|---|
| CN | 101657471 A | 2/2010 |
| CN | 102137844 A | 7/2011 |
| CN | 104364246 A | 2/2015 |
| DE | 102004037515 A1 | 3/2005 |
| EA | 201100138 A1 | 8/2011 |
| EA | 015835 B1 | 12/2011 |
| JP | 2010501629 A | 1/2010 |
| JP | 2010501630 A | 1/2010 |
| JP | 2010512334 A | 4/2010 |
| JP | 2011527701 A | 11/2011 |
| JP | 2012533546 A | 12/2012 |
| JP | 2015522559 A | 8/2015 |

(Continued)

OTHER PUBLICATIONS

See Ritter "G Protein-Coupled Receptor 119 (GPR119) Agonists for the Treatment of Diabetes: Recent Progress and Prevailing Challenges" Journal of Medicinal Chemistry, Ahead of Print, 2015.*
Morrison, K. "Physical Science Level 3" Pearson Education: Capetown, 2008, pp. 16-18.*
Pourcet, et al; "Selective PPAR modulators, dual and pan PPAR agonists: multimodal drugs for the treatment of Type 2 diabetes and atherosclerosis," Expert Opinion Emerging Drugs, 2006, vol. 11, pp. 379-401.
R.R. Holman; "Long-term efficacy of sulfonylureas: a United Kingdom Prospective Diabetes Study perspective," Metabolism, 2006, vol. 55, pp. S2-S5.
Z.-L. Chu et al; "A Role for B-Cell-Expressed G Protein-Coupled Receptor 119 in Glycemic Control by Enhancing Glucose-Dependent Insulin Release," Endocrinology, 2007, vol. 148, pp. 2601-2609.

(Continued)

*Primary Examiner* — David K O'Dell
(74) *Attorney, Agent, or Firm* — Heslin Rothenberg Farley & Mesiti P.C.

(57) ABSTRACT

The present invention relates to novel piperidine derivatives, stereoisomers thereof or pharmaceutically acceptable salts thereof; methods for preparing the compound; and pharmaceutical compositions comprising the compound. The novel piperidine derivatives, according to the present invention, having an effect as GPR119 agonist can be used for treatment of metabolic disorders, including diabetes mellitus (especially type II) and related disorders.

8 Claims, No Drawings

(56) References Cited

FOREIGN PATENT DOCUMENTS

| | | | | |
|---|---|---|---|---|
| KR | 10-2009-0097184 | A | 9/2009 | |
| KR | 10-2012-0024964 | A | 3/2012 | |
| RU | 2443699 | C2 | 2/2012 | |
| WO | 199103243 | A1 | 3/1991 | |
| WO | WO 9103243 | A1 * | 3/1991 | ........... C07D 211/22 |
| WO | 0206196 | A1 | 1/2002 | |
| WO | 200206191 | A1 | 1/2002 | |
| WO | 0234739 | A1 | 5/2002 | |
| WO | 2008025798 | A1 | 3/2008 | |
| WO | 2008025799 | A1 | 3/2008 | |
| WO | 2008025800 | A1 | 3/2008 | |
| WO | 2008070692 | A2 | 6/2008 | |
| WO | 2008081204 | A1 | 7/2008 | |
| WO | 2009014910 | A2 | 1/2009 | |
| WO | 2009106561 | A1 | 9/2009 | |
| WO | 2009106565 | A1 | 9/2009 | |
| WO | 2010006191 | A1 | 1/2010 | |
| WO | 2010048149 | A2 | 4/2010 | |
| WO | 2011/008663 | | 1/2011 | |
| WO | 2011005929 | A1 | 1/2011 | |
| WO | 2011148922 | A | 1/2011 | |
| WO | 2011127051 | A1 | 10/2011 | |
| WO | 2011145718 | A | 11/2011 | |
| WO | 2012041158 | A1 | 4/2012 | |
| WO | 2012069917 | A1 | 5/2012 | |
| WO | WO 2012069917 | A1 * | 5/2012 | ........... C07D 401/12 |
| WO | 2012077655 | A | 6/2012 | |
| WO | 2012173174 | A | 12/2012 | |
| WO | 2013187646 | A1 | 12/2013 | |

OTHER PUBLICATIONS

H.A. Overton et al; "GPR119, a novel G protein-coupled receptor target for the treatment of type 2 diabetes and obesity," Brit. J. Pharmacol., 2008, vol. 153, pp. S76-81.

T. Soga et al; "Lysophosphatidylcholine enhances glucose-dependent insulin secretion via an orphan G-protein-coupled receptor," Biophys Res. Commun., 2005, vol. 326, pp. 744-751.

Z-L. Chu et al; "A Role for Intestinal Endocrine Cell Expressed G Protein-Couple Receptor 119 in Glycemic Control by Enhancing Glucagon-Like Peptide-1 and Glucose Dependent Insulinotropic Peptide Release," Endocrinology, vol. 149, Issue 5, pp. 2038-2047, 2008.

International Search Report for PCT/KR2013/005096 dated Oct. 24, 2013.

Faghih et al., "Synthesis and SAR of Aminoalkoxy-biaryl-4-carboxamides: Novel and Selective Histamine H3 Receptor Antagonists," Bioorganic & Medicinal Chemistry Letters 13, 2003, pp. 1325-1328.

Witte et al., "Detection of multiple H3 receptor affinity states utilizing [3H]A-349821, a novel selective, non-imidazole histamine H3 receptor inverse agonist radioligand," British Journal of Pharmacology, 2006, vol. 148, No. 5, pp. 657-670.

Wu, et al., "2,5-Disubstituted pyridines as potent GPR119 agonists," Bioorganic & Medicinal Chemistry Letters, 513, 20, 2577-2581 (2010).

Chinese Search Report for 2013800307723 dated Jul. 28, 2015.

Russian Search Report for Russian Patent Application No. 2014142328 based on PCT/KR2013/005096 dated Feb. 12, 2016.

* cited by examiner

PIPERIDINE DERIVATIVES FOR GPR119 AGONIST

CROSS REFERENCE TO RELATED APPLICATION

This application is the National Phase filing under 35 U.S.C. § 371 of PCT International Application No. PCT/KR2013/005096 filed Jun. 11, 2013, and published under PCT Article 21(2) in English as WO 2013/187646 A1 on Dec. 19, 2013, which claims priority to Korean Application No. 10-2012-0062784, filed Jun. 12, 2012. The contents of each of the prior applications are incorporated by reference herein in their entirety.

TECHNICAL FIELD

The present invention relates to novel compounds that are useful in the treatment of metabolic disorders, including diabetes mellitus (types I and II) and related disorders, pharmaceutical compositions comprising the compounds, and therapeutic uses for the compounds.

BACKGROUND ART

Diabetes mellitus is a severe disorder that affects more and more human in the world. The forecast of International Diabetes Federation alludes that the total worldwide number of human with diabetes mellitus will be 380,000,000 (three hundred eighty million) until 2025. The attack rate of diabetes mellitus is increasing along with a growing tendency of obesity in many countries. The severe effect of diabetes mellitus includes the increased risk of stroke, heart disease, kidney failure, blindness and amputation. Cardiovascular disorders are more than 70% leading cause of all death in human with Type II diabetes (T2DM) [B. Pourcet et al. Expert Opin. Emerging Drugs 2006, 11, 379-401].

Diabetes mellitus is characterized in the insulin secretion and/or the disturbance of insulin signal reaction in peripheral tissues. There are two types' diabetes mellitus, that is, insulin-dependent diabetes mellitus and non-insulin-dependent diabetes mellitus. Most of the patients with diabetes mellitus are suffering from non-insulin-dependent diabetes mellitus, which is known as Type II diabetes or NIDDM. Because of the severe consequence of diabetes mellitus, the control of diabetes mellitus is necessary desperately.

The treatment of NIDDM generally begins weight loss, healthy diet and exercise program. Although these factors are important especially to dissolve the increased risk of cardiovascular disorders related to diabetes mellitus, they are not effective generally for the control of diabetes mellitus itself. There are many drugs useful for the treatment of diabetes mellitus, including insulin, metformin, sulfonylureas, acarbose, thiazolidinedione, GLP-1 analogue and DPP IV inhibitor. However, some of such treatment agents have a problem including more than one disadvantage of hypoglycemic episodes, weight gain, gastrointestinal problems and loss in responsiveness to therapy over time.

Although many medicines for the treatment of diabetes mellitus through the various mechanisms are approved, lots of medicines still are under clinical appraisal, and there still is need to, develop novel compound for the treatment of diabetes mellitus. Recently, the research result showing the observation that beta-cell function of diabetes patient declines over time regardless of success or failure of treatment with diet, sulfonylureas, metformin or insulin has been published [R. R. Holman Metabolism 2006, 55, S2-S5].

GPR119 is a protein consisted of 335 amino acids expressed in beta-cell of pancreatic islet [Z.-L. Chu et al., Endocrinol. 2007, J 48, 2601-2609] and gastro-intestinal tract [Z.-L. Chu et. al. Endocrinol. 2008, 149, 2038-2047]. Said protein belongs to the receptor family coupled to G-protein, and some candidates including oleoylethanolamide (OEA), N-oleoyldopamine and olvanil are suggested as intrinsic ligand [H. A. Overton et al. Brit. J. Pharmacol. 2007, 1-6].

It is supported from many research using cell line and animal that GPR119 may perform a certain function in glucose-dependent secretion of insulin, and targeting to GPR119 receptor may be effective to the treatment of diabetes mellitus. Activation of GPR119 receptor by lisophosphatidilcholine forces up the glucose-dependent secretion in the pancreas beta-cell line of mice, and the insulin secretion can be blocked by GPR119-specific siRNA [T. Soga et al. Biochem. Biophys. Res. Commun. 2005, 326]

Therefore, GPR119 receptor activator is needed for the treatment of disorders, such as diabetes mellitus.

DISCLOSURE

Technical Problem

The object of this invention is to provide a novel piperidine derivative, stereoisomers thereof, pharmaceutically acceptable salts thereof, and a preparing method thereof.

The other object of this invention is to provide a novel piperidine derivative being able to control GPR119 activity with low adverse effect, stereoisomers thereof, pharmaceutically acceptable salts thereof, and a preparing method thereof.

Technical Solution

To achieve the above objects, the present invention provides a novel piperidine derivative of the following formula 1, stereoisomers thereof, and pharmaceutically acceptable salts thereof:

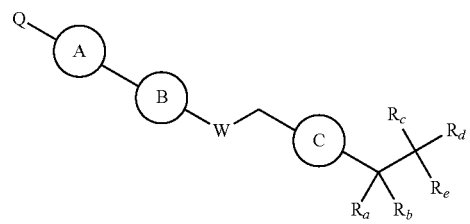

wherein
W is O or N—$R_h$;
$R_a$, $R_b$ and $R_h$ are each independently H or $C_{1-3}$ alkyl;
$R_c$ is —F or —$C_{1-3}$ hyperfluoride alkyl;
$R_d$ and $R_e$ are each independently selected from the group consisting of H, halogen, —$C_{1-5}$ alkyl and —$C_{3-7}$ cycloalkyl, wherein —$C_{1-5}$ alkyl and —$C_{3-7}$ cycloalkyl are each independently unsubstituted or substituted with halogen, —CN, —$OC_{1-5}$ alkyl or —$C_{1-5}$ alkyl;
or $R_d$ and $R_e$ are combined to form a —$C_{3-7}$ cycloalkyl, wherein the —$C_{3-7}$ cycloalkyl is unsubstituted or substituted with halogen, —$OC_{1-5}$ alkyl or —$C_{1-5}$ alkyl;

is selected from the group consisting of:

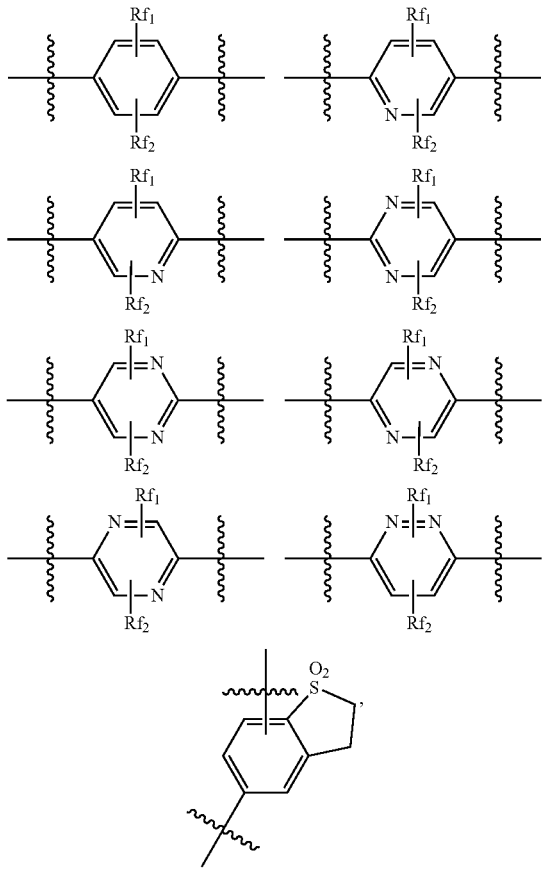

wherein $Rf_1$ and $Rf_2$ are each independently H, halogen, —$C_{1-5}$ alkyl, —$C_{1-5}$ alkyl (OH), —$OC_{1-5}$ alkyl or —CN;

Ⓑ is selected from the group consisting of:

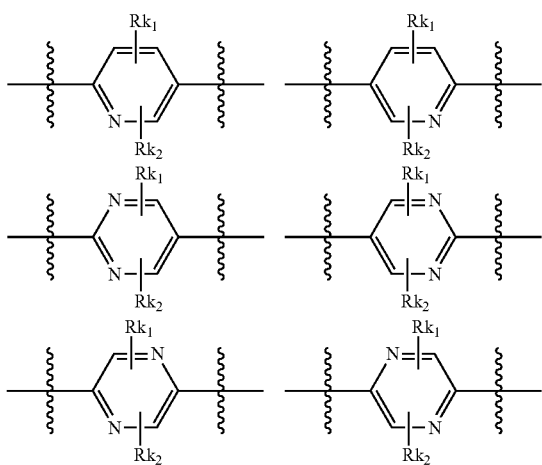

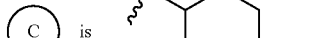

wherein $Rk_1$ and $Rk_2$ are each, independently H, halogen, —$C_{1-5}$ alkyl, —$C_{1-5}$ alkyl (OH), —$OC_{1-5}$ alkyl or —CN;

Ⓒ is  ;

Q is H, —$S(O)R_1$, —$S(O)_2R_1$, —$C(O)R_1$, —$C(O)OR_1$, —$C(O)NHR_1$, —$C(O)NR_2R_3$, —$S(O)_2NHR_1$, —$S(O)_2NR_2R_3$ or

wherein $R_1$ is H, —$CF_3$, —$C_{1-5}$ alkyl, 3 to 7-membered heterocyclic ring, $C_{3-7}$ cycloalkyl, or Ar, $R_2$ and $R_3$ are each independently $C_{1-5}$ alkyl, $C_{3-7}$ cycloalkyl, 3 to 7-membered heterocyclic ring or Ar (in $R_1$, $R_2$ and $R_3$, —$C_{1-5}$ alkyl, 3 to 7-membered heterocyclic ring, $C_{3-7}$ cycloalkyl and Ar may be each independently substituted with $Rx_1$ and $Rx_2$.), or $R_2$ and $R_3$ together with the N atoms to which they are bonded may form a 5- or 6-membered heterocyclic aromatic or non-aromatic ring compound further having 0 to 3 members selected independently from the group consisting of N, O, S and C(O), wherein the heterocyclic aromatic or non-aromatic ring compound may be substituted with $Rx_1$ and $Rx_2$, wherein Ar is C6 monocyclic aromatic compound; or 5- or 6-membered heteroaryl group comprising 1 to 3 members selected from the group consisting of N, O and S, wherein $Rx_1$ and $Rx_2$ are each independently H, —OH, halogen, —CN, —$CF_3$, 3- to 7-membered heterocyclic ring, —$C_{1-5}$ alkyl, —$C_{3-7}$ cycloalkyl, —$C_{1-5}$ alkyl(OH), —$C_{1-5}$ alkyl($OR_4$), —$C_{1-5}$ alkyl(halogen), —$C(O)NR_4R_5$, —$C(O)R_4$, —$C(O)OR_4$, —$S(O)_2R_4$, —$OR_4$,

 or

-continued

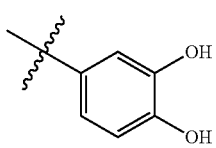

[wherein $R_4$ and $R_5$ are each independently H, —$C_{1-5}$ alkyl or —$C_{3-7}$ cycloalkyl.].

In addition, preferably,

W is O;

$R_a$ and $R_b$ are each independently H;

$R_c$ is —F or —$CF_3$;

$R_d$ and $R_e$ are each independently —$C_{1-5}$ alkyl, or $R_d$ and $R_e$ are combined to form a —$C_{3-7}$ cycloalkyl, wherein the —$C_{3-7}$ cycloalkyl is unsubstituted or substituted with halogen, —$OC_{1-5}$ alkyl or —$C_{1-5}$ alkyl;

Ⓐ is selected from the group consisting of:

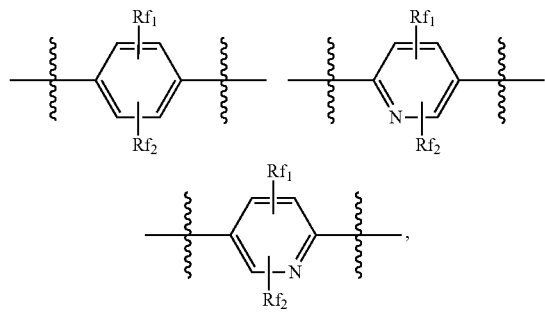

wherein $Rf_1$ and $Rf_2$ are each independently H, halogen, —$C_{1-5}$ alkyl, —$C_{1-5}$ alkyl(OH), —$OC_{1-5}$ alkyl or —CN;

Ⓑ is selected from the group consisting of:

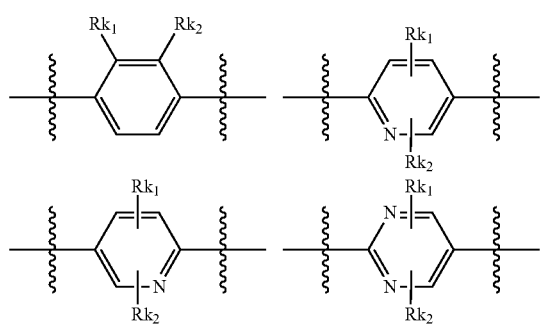

-continued

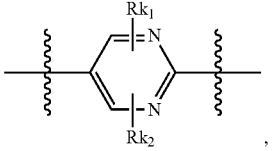

wherein $Rk_1$ and $Rk_2$ are each independently H, halogen, —$C_{1-5}$ alkyl, —$C_{1-5}$ alkyl(OH), —$OC_{1-5}$ alkyl or —CN;

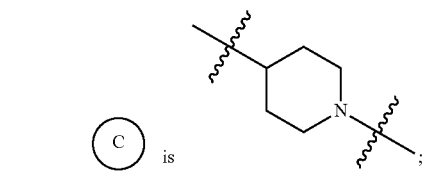

Ⓒ is ;

Q is —$S(O)_2R_1$, —$C(O)NR_2R_3$ or —$S(O)_2NR_2R_3$, wherein $R_1$, $R_2$ and $R_3$ are each independently $C_{1-5}$ alkyl substituted with $Rx_1$ and $Rx_2$, or $R_2$ and $R_3$ together with the N atoms to which they are bonded may form a 5- or 6-membered heterocyclic aromatic or non-aromatic ring compound further having 0 to 3 members selected independently from the group consisting of N, O, S and C(O), wherein the heterocyclic aromatic or non-aromatic ring compound may be substituted with $Rx_1$ and $Rx_2$, wherein $Rx_1$ and $Rx_2$ are each independently H, —OH, halogen, —CN, —$CF_3$, 3- to 7-membered heterocyclic ring, —$C_{1-5}$ alkyl, —$C_{3-7}$ cycloalkyl, —$C_{1-5}$ alkyl(OH), —$C_{1-5}$ alkyl($OR_4$), —$C_{1-5}$ alkyl(halogen), —$C(O)NR_4R_5$, —$C(O)R_4$, —$C(O)OR_4$, —$S(O)_2R_4$ or —$OR_4$ [wherein $R_4$ and $R_5$ are each independently H, —$C_{1-5}$ alkyl or —$C_{3-7}$ cycloalkyl.].

In addition, more preferably,

W is O;

$R_a$ and $R_b$ are each independently H;

$R_c$ is —F or —$CF_3$;

$R_d$ and $R_e$ are each independently —$C_{1-5}$ alkyl, or $R_d$ and $R_e$ are combined to form —$C_{3-7}$ cycloalkyl, wherein the —$C_{3-7}$ cycloalkyl is unsubstituted or substituted with halogen, —$OC_{1-5}$ alkyl or —$C_{1-5}$ alkyl;

Ⓐ is selected from the group consisting of:

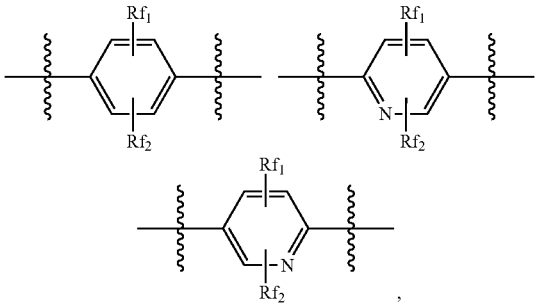

wherein $Rf_1$ and $Rf_2$ are each independently H, halogen, —$C_{1-5}$ alkyl, —$C_{1-5}$ alkyl(OH), —$OC_{1-5}$ alkyl or —CN;

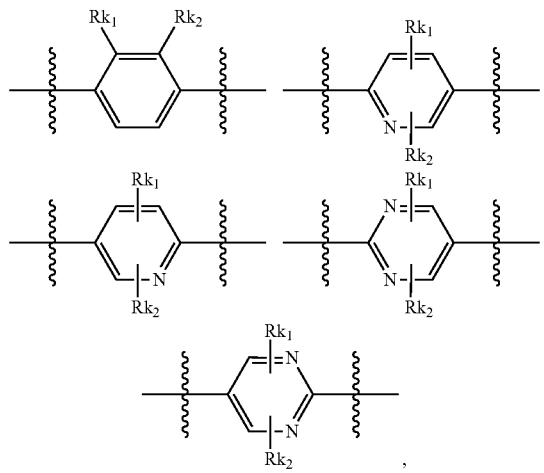

is selected from the group consisting of:

wherein $Rk_1$ and $Rk_2$ are each independently H, halogen, —$C_{1-5}$ alkyl, —$C_{1-5}$ alkyl(OH), —$OC_{1-5}$ alkyl or —CN;

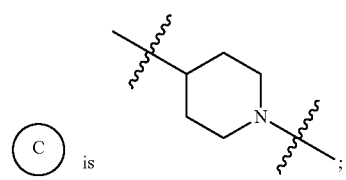

Q is —C(O)NR$_2$R$_3$, wherein R$_2$ and R$_3$ together with the N atoms to which they are bonded may form a 5- or 6-membered heterocyclic aromatic or non-aromatic ring compound further having 0 to 3 members selected independently from the group consisting of N, O, S and C(O), wherein the heterocyclic aromatic or non-aromatic ring compound may be substituted with Rx$_1$ and Rx$_2$, wherein Rx$_1$ and Rx$_2$ are each independently H, —OH, halogen, —CN, —CF$_3$, 3- to 7-membered heterocyclic ring, —$C_{1-5}$ alkyl, —$C_{3-7}$ cycloalkyl, —$C_{1-5}$ alkyl(OH), —$C_{1-5}$ alkyl(OR$_4$), —$C_{1-5}$ alkyl(halogen), —C(O)NR$_4$R$_5$, —C(O)R$_4$, —C(O)OR$_4$, —S(O)$_2$R$_4$ or —OR$_4$ [wherein R$_4$ and R$_5$ are each independently H, —$C_{1-5}$ alkyl or —$C_{3-7}$ cycloalkyl.].

Also, alternatively,

W is O;

R$_a$ and R$_b$ are each independently H;

R$_c$ is F or —CF$_3$;

R$_d$ and R$_e$ are each independently selected from the group consisting of —CH$_3$ and —CH$_2$CH$_3$.

is selected from the group consisting of

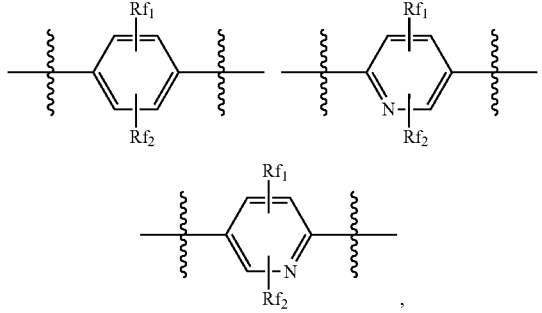

wherein $Rf_1$ and $Rf_2$ are each independently H, —F or —CN;

is selected from the group consisting of:

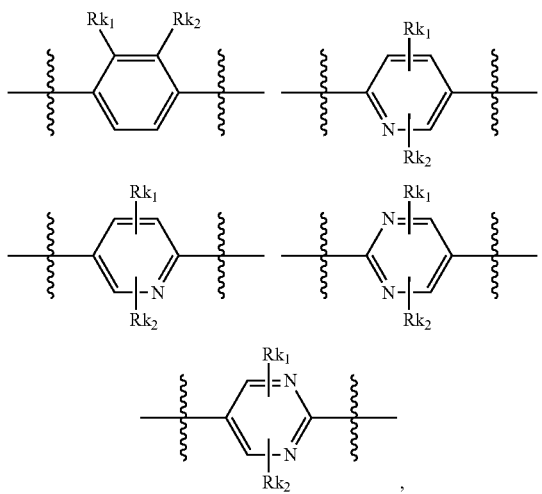

wherein $Rk_1$ and $Rk_2$ are each independently H, —F or —CN;

Q is selected from the group consisting of:

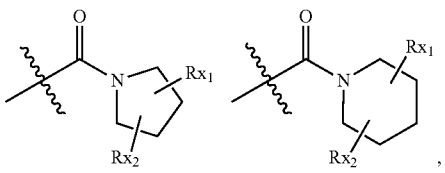

wherein $Rx_1$ and $Rx_2$ are each independently H, OH, —F, —CN, —CF$_3$, —CH$_2$OH or —C(O)NH$_2$.

The compound of formula 1 may be used generally as a form of pharmaceutically acceptable salt thereof. The pharmaceutically acceptable salts thereof include pharmaceutically acceptable base addition salts and acid addition salts, for example, metal salts, such as alkali and alkaline earth metal salts, ammonium salt, organic amine addition salt, amino acid addition salt and sulfonate salt. Acid addition salts include inorganic acid addition salts, such as hydrogen chloride salt, sulfonic acid salt and phosphoric acid salt; and organic acid addition salts, such as alkyl sulfonate, aryl sulfonate, acetate, malate, fumarate, tartrate, citrate and lactate. Examples of metal salts include alkali metal salt, such as lithium salt, sodium salt and potassium salt; alkaline earth metal salts, such as magnesium salt, calcium salt, aluminium salt and zinc salt. Examples of ammonium salt include ammonium salt and tetramethylammonium salt. Examples of organic amine addition salts include salts with morpholine and piperidine. Examples of amino acid addition salts include salts with glycine, phenylalanine, glutamic acid and lysine. Examples of sulfonate salt include mesylate, tosylate and benzenesulfonic acid salts.

The term of "stereoisomer" means the isomer molecules that have the same molecular formula and bonds, but differ by their three-dimensional orientation.

Specific examples of preferred compounds of formula 1 according to the present invention include:

Compound 431: 1-(2-fluoro-2-methylpropyl)-4-((4'-(methylsulfonyl)biphenyl-4-yloxy)methyl)piperidine Compound 470: 5-(4-((1-(2-fluoro-2-methylpropyl)piperidin-4-yl)methoxy)phenyl)-2,3-dihydrobenzo[b]thiophene 1,1-dioxide Compound 498: methyl 4'-((1-(2-fluoro-2-methylpropyl)piperidin-4-yl)methoxy)biphenyl-4-carboxylate Compound 499: 4-((4'-(methylsulfonyl)biphenyl-4-yloxy)methyl)-1-(2,2,2-trifluoroethyl)piperidine Compound 500: 4-((4'-(methylsulfonyl)biphenyl-4-yloxy)methyl)-1-(((1-(trifluoromethyl)cyclopropyl)methyl)piperidine Compound 515: 4'-((1-(2-fluoro-2-methylpropyl)piperidin-4-yl)methoxy)biphenyl-4-carboxamide Compound 516: 4'-((1-(2-fluoro-2-methylpropyl)piperidin-4-yl)methoxy)-N,N-dimethylbiphenyl-4-carboxamide Compound 517: (4'-((1-(2-fluoro-2-methylpropyl)piperidin-4-yl)methoxy)biphenyl-4-yl)(morpholino)methanone Compound 524: 4-((4'-(methylsulfonyl)biphenyl-4-yloxy)methyl)-1-(3,3,3-trifluoropropyl)piperidine Compound 526: N-cyclopropyl-4'-((1-(2-fluoro-2-methylpropyl)piperidin-4-yl)methoxy)biphenyl-4-carboxamide Compound 527: N-cyclobutyl-4'-((1-(2-fluoro-2-methylpropyl)piperidin-4-yl)methoxy)biphenyl-4-carboxamide Compound 528: N-cyclopentyl-4'-((1-(2-fluoro-2-methylpropyl)piperidin-4-yl)methoxy)biphenyl-4-carboxamide Compound 529: N-cyclohexyl-4'-((1-(2-fluoro-2-methylpropyl)piperidin-4-yl)methoxy)biphenyl-4-carboxamide Compound 530: (4'-((1-(2-fluoro-2-methylpropyl)piperidin-4-yl)methoxy)biphenyl-4-yl)(pyrrolidin-1-yl)methanone Compound 531: (4'-((1-(2-fluoro-2-methylpropyl)piperidin-4-yl)methoxy)biphenyl-4-yl)(piperidin-1-yl)methanone Compound 533: 4'-((1-(2-fluoro-2-methylpropyl)piperidin-4-yl)methoxy)-N-(4-hydroxybutyl)biphenyl-4-carboxamide Compound 534: 4'-((1-(2-fluoro-2-methylpropyl)piperidin-4-yl)methoxy)-N-methylbiphenyl-4-carboxamide Compound 540: 5-(4-((1-(2,2,2-trifluoroethyl)piperidin-4-yl)methoxy)phenyl)-2,3-dihydrobenzo[b]thiophene 1,1-dioxide Compound 542: 4-((4'-(methylsulfonyl)biphenyl-4-yloxy)methyl)-1-((1-(trifluoromethyl)cyclobutyl)methyl)piperidine Compound 546: 4-((4'-(methylsulfonyl)biphenyl-4-yloxy)methyl)-1-((1-(trifluoromethyl)cyclopentyl)methyl)piperidine Compound 547: 1-(2,2-difluoropropyl)-4-((4'-(methylsulfonyl)biphenyl-4-yloxy)methyl)piperidine Compound 548: 4'-((1-(2-fluoro-2-methylpropyl)piperidin-4-yl)methoxy)biphenyl-4-carboxylic acid Compound 549: 4'-((1-(2-fluoro-2-methylpropyl)piperidin-4-yl)methoxy)-N-(2-hydroxyethyl)biphenyl-4-carboxamide Compound 550: 4'-((1-(2-fluoro-2-methylpropyl)piperidin-4-yl)methoxy)-N-(3-hydroxypropyl)biphenyl-4-carboxamide Compound 551: 4'-((1-(2-fluoro-2-methylpropyl)piperidin-4-yl)methoxy)-N-(2-hydroxyethyl)-N-methylbiphenyl-4-carboxamide Compound 552: N,N-dimethyl-4'-((1-((1-(trifluoromethyl)cyclopropyl)methyl)piperidin-4-yl)methoxy)biphenyl-4-carboxamide Compound 553: (R)-(4'-((1-(2-fluoro-2-methylpropyl)piperidin-4-yl)methoxy)biphenyl-4-yl)(3-hydroxypyrrolidin-1-yl)methanone Compound 554: (S)-(4'-((1-(2-fluoro-2-methylpropyl)piperidin-4-yl)methoxy)biphenyl-4-yl)(3-hydroxypyrrolidin-1-yl)methanone Compound 555: (R)-(4'-((1-(2-fluoro-2-methylpropyl)piperidin-4-yl)methoxy)biphenyl-4-yl)(2-(hydroxymethyl)pyrrolidin-1-yl)methanone Compound 556: (S)-(4'-((1-(2-fluoro-2-methylpropyl)piperidin-4-yl)methoxy)biphenyl-4-yl)(2-(hydroxymethyl)pyrrolidin-1-yl)methanone Compound 557: (R)-(4'-((1-(2-fluoro-2-methylpropyl)piperidin-4-yl)methoxy)biphenyl-4-yl)(2-(methoxymethyl)pyrrolidin-1-yl)methanone Compound 558: (S)-(4'-((1-(2-fluoro-2-methylpropyl)piperidin-4-yl)methoxy)biphenyl-4-yl)(2-(methoxymethyl)pyrrolidin-1-yl)methanone Compound 559: N-butyl-4'-((1-(2-fluoro-2-methylpropyl)piperidin-4-yl)methoxy)-N-(2-hydroxyethyl)biphenyl-4-carboxamide Compound 560: 4'-((1-(2-fluoro-2-methylpropyl)piperidin-4-yl)methoxy)-N-(furan-2-ylmethyl)biphenyl-4-carboxamide Compound 561: 4'-((1-(2-fluoro-2-methylpropyl)piperidin-4-yl)methoxy)-N-propylbiphenyl-4-carboxamide Compound 562: 4'-((1-(2-fluoro-2-methylpropyl)piperidin-4-yl)methoxy)-N-propylbiphenyl-4-carboxamide Compound 563: N-benzyl-N-ethyl-4'-((1-(2-fluoro-2-methylpropyl)piperidin-4-yl)methoxy)biphenyl-4-carboxamide Compound 564: (S)-(4'-((1-(2-fluoro-2-methylpropyl)piperidin-4-yl)methoxy)biphenyl-4-yl)(2-(trifluoromethyl)pyrrolidin-1-yl)methanone Compound 565: (S)-1-(4'-((1-(2-fluoro-2-methylpropyl)piperidin-4-yl)methoxy)biphenylcarbonyl)pyrrolidine-2-carboxamide
Compound 566: (4'-((1-(2-fluoro-2-methylpropyl)piperidin-4-yl)methoxy)biphenyl-4-yl)(3-fluoropyrrolidin-1-yl)methanone
Compound 567: (4'-((1-(2-fluoro-2-methylpropyl)piperidin-4-yl)methoxy)biphenyl-4-yl)(4-(hydroxymethyl)piperidin-1-yl)methanone
Compound 568: (4'-((1-(2-fluoro-2-methylpropyl)piperidin-4-yl)methoxy)biphenyl-4-yl)(4-hydroxypiperidin-1-yl)methanone
Compound 569: (4'-((1-(2-fluoro-2-methylpropyl)piperidin-4-yl)methoxy)biphenyl-4-yl)(3-hydroxypiperidin-1-yl)methanone
Compound 570: (R)-(4'-((1-(2-fluoro-2-methylpropyl)piperidin-4-yl)methoxy)biphenyl-4-yl)(3-fluoropyrrolidin-1-yl)methanone
Compound 571: (S)-(4'-((1-(2-fluoro-2-methylpropyl)piperidin-4-yl)methoxy)biphenyl-4-yl)(3-fluoropyrrolidin-1-yl)methanone
Compound 574: 4-(6-((1-((1-(trifluoromethyl)cyclobutyl)methyl)piperidin-4-yl)methoxy)pyridin-3-yl)benzoic acid
Compound 575: 1-(4'-((1-((1-(trifluoromethyl)cyclobutyl)methyl)piperidin-4-yl)methoxy)biphenyl-4-yl)ethanone
Compound 576: N,N-dimethyl-4-(6-((1-((1-(trifluoromethyl)cyclobutyl)methyl)piperidin-4-yl)methoxy)pyridin-3-yl)benzamide
Compound 578: (S)-(3-hydroxypyrrolidin-1-yl)(4-(6-((1-((1-(trifluoromethyl)cyclobutyl)methyl)piperidin-4-yl)methoxy)pyridin-3-yl)phenyl)methanone
Compound 579: (R)-(2-(hydroxymethyl)pyrrolidin-1-yl)(4-(6-((1-((1-(trifluoromethyl)cyclobutyl)methyl)piperidin-4-yl)methoxy)pyridin-3-yl)phenyl)methanone
Compound 580: N,N-dimethyl-4-(6-((1-((1-(trifluoromethyl)cyclopropyl)methyl)piperidin-4-yl)methoxy)pyridin-3-yl)benzamide
Compound 581: (S)-1-(4-(6-((1-((1-(trifluoromethyl)cyclobutyl)methyl)piperidin-4-yl)methoxy)pyridin-3-yl)benzoyl)pyrrolidine-2-carboxamide
Compound 582: morpholino(4-(6-((1-((1-(trifluoromethyl)cyclopropyl)methyl)piperidin-4-yl)methoxy)pyridin-3-yl)phenyl)methanone
Compound 583: piperidin-1-yl(4-(6-((1-((1-(trifluoromethyl)cyclopropyl)methyl)piperidin-4-yl)methoxy)pyridin-3-yl)phenyl)methanone
Compound 584: pyrrolidin-1-yl(4-(6-((1-((1-(trifluoromethyl)cyclopropyl)methyl)piperidin-4-yl)methoxy)pyridin-3-yl)phenyl)methanone
Compound 585: (S)-(3-hydroxypyrrolidin-1-yl)(4-(6-((1-((1-(trifluoromethyl)cyclopropyl)methyl)piperidin-4-yl)methoxy)pyridin-3-yl)phenyl)methanone
Compound 586: (S)-1-(4-(6-((1-((1-(trifluoromethyl)cyclopropyl)methyl)piperidin-4-yl)methoxy)pyridin-3-yl)benzoyl)pyrrolidine-2-carboxamide
Compound 587: (4-(hydroxymethyl)piperidin-1-yl)(4-(6-((1-((1-(trifluoromethyl)cyclopropyl)methyl)piperidin-4-yl)methoxy)pyridin-3-yl)phenyl)methanone
Compound 588: (4-(hydroxymethyl)piperidin-1-yl)(4-(6-((1-((1-(trifluoromethyl)cyclobutyl)methyl)piperidin-4-yl)methoxy)pyridin-3-yl)phenyl)methanone
Compound 589: 5-(4-(methylsulfonyl)phenyl)-2-((1-((1-(trifluoromethyl)cyclopropyl)methyl)piperidin-4-yl)methoxy)pyridine
Compound 593: 1-(4-(5-((1-((1-(trifluoromethyl)cyclobutyl)methyl)piperidin-4-yl)methoxy)pyridin-2-yl)phenyl)ethanone
Compound 594: (4'-((1-(2-fluoro-2-methylpropyl)piperidin-4-yl)methoxy)biphenyl-4-yl)(3-(trifluoromethyl)-5,6-dihydro-[1,2,4]triazolo[4,3-a]pyrazin-7(8H)-yl)methanone
Compound 595: (3-(trifluoromethyl)-5,6-dihydro-[1,2,4]triazolo[4,3-a]pyrazin-7(8H)-yl)(4-(6-((1-((1-(trifluoromethyl)cyclobutyl)methyl)piperidin-4-yl)methoxy)pyridin-3-yl)phenyl)methanone
Compound 596: 2-((1-(2-fluoro-2-methylpropyl)piperidin-4-yl)methoxy)-5-(4-(methylsulfonyl)phenyl)pyridine
Compound 597: 5-((1-(2-fluoro-2-methylpropyl)piperidin-4-yl)methoxy)-2-(4-(methylsulfonyl)phenyl)pyridine
Compound 598: N-ethyl-4'-((1-(2-fluoro-2-methylpropyl)piperidin-4-yl)methoxy)-N-methylbiphenyl-4-carboxamide
Compound 599: 4'-((1-(2-fluoro-2-methylpropyl)piperidin-4-yl)methoxy)-N-isopropyl-N-methylbiphenyl-4-carboxamide
Compound 600: (4'-((1-(2-fluoro-2-methylpropyl)piperidin-4-yl)methoxy)biphenyl-4-yl)(3-hydroxyazetidin-1-yl)methanone
Compound 601: (3,3-difluoroazetidin-1-yl)(4'-((1-(2-fluoro-2-methylpropyl)piperidin-4-yl)methoxy)biphenyl-4-yl)methanone
Compound 602: N-tert-butyl-4'-((1-(2-fluoro-2-methylpropyl)piperidin-4-yl)methoxy)biphenyl-4-carboxamide
Compound 603: 4'-((1-(2-fluoro-2-methylpropyl)piperidin-4-yl)methoxy)-N-isopropylbiphenyl-4-carboxamide
Compound 604: N,N-diethyl-4'-((1-(2-fluoro-2-methylpropyl)piperidin-4-yl)methoxy)biphenyl-4-carboxamide
Compound 605: 4'-((1-(2-fluoro-2-methylpropyl)piperidin-4-yl)methoxy)-N-(1-hydroxy-2-methylpropan-2-yl)biphenyl-4-carboxamide
Compound 606: (S)-4'-((1-(2-fluoro-2-methylpropyl)piperidin-4-yl)methoxy)-N-(1-hydroxypropan-2-yl)biphenyl-4-carboxamide
Compound 607: (R)-4'-((1-(2-fluoro-2-methylpropyl)piperidin-4-yl)methoxy)-N-(1-hydroxybutan-2-yl)biphenyl-4-carboxamide
Compound 608: (R)-4'-((1-(2-fluoro-2-methylpropyl)piperidin-4-yl)methoxy)-N-(1-hydroxy-3-methylbutan-2-yl)biphenyl-4-carboxamide
Compound 609: (S)-4'-((1-(2-fluoro-2-methylpropyl)piperidin-4-yl)methoxy)-N-(1-hydroxy-3-methylbutan-2-yl)biphenyl-4-carboxamide
Compound 610: N-(1,3-dihydroxypropan-2-yl)-4'-((1-(2-fluoro-2-methylpropyl)piperidin-4-yl)methoxy)biphenyl-4-carboxamide
Compound 611: N-(2,3-dihydroxypropyl)-4'-((1-(2-fluoro-2-methylpropyl)piperidin-4-yl)methoxy)biphenyl-4-carboxamide
Compound 612: (R)-(4'-((1-(2-fluoro-2-methylpropyl)piperidin-4-yl)methoxy)biphenyl-4-yl)(3-hydroxypiperidin-1-yl)methanone
Compound 613: (S)-(4'-((1-(2-fluoro-2-methylpropyl)piperidin-4-yl)methoxy)biphenyl-4-yl)(3-hydroxypiperidin-1-yl)methanone
Compound 614: 4'-((1-(2-fluoro-2-methylpropyl)piperidin-4-yl)methoxy)-N,N-dimethylbiphenyl-4-sulfonamide
Compound 615: 1-(2-fluoro-2-methylpropyl)-4-((4'-(pyrrolidin-1-ylsulfonyl)biphenyl-4-yloxy)methyl)piperidine
Compound 616: 1-(2-fluoro-2-methylpropyl)-4-((4'-(piperidin-1-ylsulfonyl)biphenyl-4-yloxy)methyl)piperidine
Compound 617: 2-(4-((1-(2-fluoro-2-methylpropyl)piperidin-4-yl)methoxy)phenyl)-5-(methylsulfonyl)pyridine
Compound 618: 5-(4-((1-(2-fluoro-2-methylpropyl)piperidin-4-yl)methoxy)phenyl)-2-(methylsulfonyl)pyridine Compound 619: (R)-methyl 1-(4'-((1-(2-fluoro-2-methylpropyl)piperidin-4-yl)methoxy)biphenylcarbonyl)pyrrolidine-2-carboxylate Compound 620: (R)-1-(4'-((1-(2-fluoro-2-methylpropyl)piperidin-4-yl)methoxy)biphenylcarbonyl)pyrrolidine-2-carboxylic acid Compound 621: 2-(4'-((1-(2-fluoro-2-methylpropyl)piperidin-4-yl)methoxy)-N-methylbiphenyl-4-ylcarboxamido)acetic acid Compound 622: (4'-((1-(2-fluoro-2-methylpropyl)piperidin-4-yl)methoxy)biphenyl-4-yl)(thiazolidin-3-yl)methanone Compound 623: (4-(cyclopropanecarbonyl)piperazin-1-yl)(4'-((1-(2-fluoro-2-methylpropyl)piperidin-4-yl)methoxy)biphenyl-4-yl)methanone Compound 624: (4'-((1-(2-fluoro-2-methylpropyl)piperidin-4-yl)methoxy)biphenyl-4-yl)(4-(methylsulfonyl)piperazin-1-yl)methanone Compound 625: (S)-methyl 1-(4'-((1-(2-fluoro-2-methylpropyl)piperidin-4-yl)methoxy)biphenylcarbonyl)pyrrolidine-2-carboxylate Compound 626: tert-butyl 4-(4'-((1-(2-fluoro-2-methylpropyl)piperidin-4-yl)methoxy)biphenylcarbonyl)piperazine-1-carboxylate Compound 627: (4-benzylpiperazin-1-yl)(4'-((1-(2-fluoro-2-methylpropyl)piperidin-4-yl)methoxy)biphenyl-4-yl)methanone Compound 628: 1-(4-(4'-((1-(2-fluoro-2-methylpropyl)piperidin-4-yl)methoxy)biphenylcarbonyl)piperazin-1-yl)ethanone Compound 629: (3,3-difluoropyrrolidin-1-yl)(4'-((1-(2-fluoro-2-methylpropyl)piperidin-4-yl)methoxy)biphenyl-4-yl)methanone Compound 630: (4'-((1-(2-fluoro-2-methylpropyl)piperidin-4-yl)methoxy)biphenyl-4-yl)(piperazin-1-yl)methanone Compound 631: N,N-dimethyl-4'-((1-((1-(trifluoromethyl)cyclobutyl)methyl)piperidin-4-yl)methoxy)biphenyl-4-carboxamide Compound 632: (S)-(3-hydroxypyrrolidin-1-yl)(4'-((1-((1-(trifluoromethyl)cyclobutyl)methyl)piperidin-4-yl)methoxy)biphenyl-4-yl)methanone Compound 633: (R)-(2-(hydroxymethyl)pyrrolidin-1-yl)(4'-((1-((1-(trifluoromethyl)cyclobutyl)methyl)piperidin-4-yl)methoxy)biphenyl-4-yl)methanone Compound 634: (3-hydroxypiperidin-1-yl)(4'-((1-((1-(trifluoromethyl)cyclobutyl)methyl)piperidin-4-yl)methoxy)biphenyl-4-yl)methanone Compound 635: (S)-1-(4'-((1-((1-(trifluoromethyl)cyclobutyl)methyl)piperidin-4-yl)methoxy)biphenylcarbonyl)pyrrolidine-2-carboxamide Compound 636: N-(2-hydroxyethyl)-4'-((1-((1-(trifluoromethyl)cyclobutyl)methyl)piperidin-4-yl)methoxy)biphenyl-4-carboxamide Compound 637: N-(2-hydroxyethyl)-N-methyl-4'-((1-((1-(trifluoromethyl)cyclobutyl)methyl)piperidin-4-yl)methoxy)biphenyl-4-carboxamide Compound 638: 3-fluoro-4'-((1-(2-fluoro-2-methylpropyl)piperidin-4-yl)methoxy)-N,N-dimethylbiphenyl-4-carboxamide Compound 639: N,N-diethyl-3-fluoro-4'-((1-(2-fluoro-2-methylpropyl)piperidin-4-yl)methoxy)biphenyl-4-carboxamide Compound 640: (S)-(3-fluoro-4'-((1-(2-fluoro-2-methylpropyl)piperidin-4-yl)methoxy)biphenyl-4-yl)(3-hydroxypyrrolidin-1-yl)methanone Compound 641: (R)-(3-fluoro-4'-((1-(2-fluoro-2-methylpropyl)piperidin-4-yl)methoxy)biphenyl-4-yl)(2-(hydroxymethyl)pyrrolidin-1-yl)methanone Compound 642: (3-fluoro-4'-((1-(2-fluoro-2-methylpropyl)piperidin-4-yl)methoxy)biphenyl-4-yl)(3-hydroxypiperidin-1-yl)methanone Compound 643: 3-fluoro-4'-((1-(2-fluoro-2-methylpropyl)piperidin-4-yl)methoxy)-N-(1-hydroxy-2-methylpropan-2-yl)biphenyl-4-carboxamide Compound 644: (S)-1-(3-fluoro-4'-((1-(2-fluoro-2-methylpropyl)piperidin-4-yl)methoxy)biphenylcarbonyl)pyrrolidine-2-carboxamide Compound 645: methyl 2-(4'-((1-(2-fluoro-2-methylpropyl)piperidin-4-yl)methoxy)biphenyl-4-ylcarboxamido)acetate Compound 646: 4'-((1-(2-fluoro-2-methylpropyl)piperidin-4-yl)methoxy)-N-(oxetan-3-yl)biphenyl-4-carboxamide Compound 647: methyl 3-(4'-((1-(2-fluoro-2-methylpropyl)piperidin-4-yl)methoxy)biphenyl-4-ylcarboxamido)propanoate Compound 648: (R)-methyl 2-(4'-((1-(2-fluoro-2-methylpropyl)piperidin-4-yl)methoxy)biphenyl-4-ylcarboxamido)-3-hydroxypropanoate Compound 649: (S)-methyl 2-(4'-((1-(2-fluoro-2-methylpropyl)piperidin-4-yl)methoxy)biphenyl-4-ylcarboxamido)-3-hydroxypropanoate Compound 650: ethyl 4-(4'-((1-(2-fluoro-2-methylpropyl)piperidin-4-yl)methoxy)biphenyl-4-ylcarboxamido)piperidin-1-carboxylate Compound 651: 4'-((1-(2-fluoro-2-methylpropyl)piperidin-4-yl)methoxy)-N-pentylbiphenyl-4-carboxamide Compound 652: (R)-(4-(6-((1-(2-fluoro-2-methylpropyl)piperidin-4-yl)methoxy)pyridin-3-yl)phenyl)(2-(hydroxymethyl)pyrrolidin-1-yl)methanone Compound 653: (S)-1-(4-(6-((1-(2-fluoro-2-methylpropyl)piperidin-4-yl)methoxy)pyridin-3-yl)benzoyl)pyrrolidine-2-carboxamide Compound 654: (S)-(4-(6-((1-(2-fluoro-2-methylpropyl)piperidin-4-yl)methoxy)pyridin-3-yl)phenyl)(3-hydroxypiperidin-1-yl)methanone Compound 655: (R)-(4'-((1-(2-fluoropentyl)piperidin-4-yl)methoxy)biphenyl-4-yl)(2-(hydroxymethyl)pyrrolidin-1-yl)methanone Compound 656: (S)-1-(4'-((1-(2-fluoropentyl)piperidin-4-yl)methoxy)biphenylcarbonyl)pyrrolidine-2-carboxamide Compound 657: (R)-(2-fluoro-4-(6-((1-(2-fluoro-2-methylpropyl)piperidin-4-yl)methoxy)pyridin-3-yl)phenyl)(2-(hydroxymethyl)pyrrolidin-1-yl)methanone Compound 658: (S)-1-(2-fluoro-4-(6-((1-(2-fluoro-2-methylpropyl)piperidin-4-yl)methoxy)pyridin-3-yl)benzoyl)pyrrolidine-2-carboxamide Compound 659: (S)-(2-fluoro-4-(6-((1-(2-fluoro-2-methylpropyl)piperidin-4-yl)methoxy)pyridin-3-yl)phenyl)(3-hydroxypiperidin-1-yl)methanone Compound 666: (S)-1-(4'-((1-(2-fluoro-2-methylpropyl)piperidin-4-yl)methoxy)biphenyl-4-ylsulfonyl)pyrrolidin-3-ol Compound 667: (R)-(1-(4'-((1-(2-fluoro-2-methylpropyl)piperidin-4-yl)methoxy)biphenyl-4-ylsulfonyl)pyrrolidin-2-yl)methanol Compound 668: (S)-1-(4'-((1-(2-fluoro-2-methylpropyl)piperidin-4-yl)methoxy)biphenyl-4-ylsulfonyl)pyrrolidine-2-carboxamide Compound 669: (R)-1-(4'-((1-(2-fluoro-2-methylpropyl)piperidin-4-yl)methoxy)biphenyl-4-ylsulfonyl)piperidin-3-ol Compound 670: (S)-1-(4'-((1-(2-fluoro-2-methylpropyl)piperidin-4-yl)methoxy)biphenyl-4-ylsulfonyl)piperidin-3-ol Compound 671: (R)-1-(4-(6-((1-((1-(trifluoromethyl)cyclobutyl)methyl)piperidin-4-yl)methoxy)pyridin-3-yl)benzoyl)pyrrolidine-2-carboxamide Compound 672: (R)-(3-hydroxypiperidin-1-yl)(4-(6-((1-((1-(trifluoromethyl)cyclobutyl)methyl)piperidin-4-yl)methoxy)pyridin-3-yl)phenyl)methanone Compound 673: (S)-(3-hydroxypiperidin-1-yl)(4-(6-((1-((1-(trifluoromethyl)cyclobutyl)methyl)piperidin-4-yl)methoxy)pyridin-3-yl)phenyl)methanone Compound 674: 4'-((1-(2-fluoro-2-methylpropyl)piperidin-4-yl)methoxy)biphenyl-4-sulfonamide Compound 675: 4'-((1-(2-fluoro-2-methylpropyl)piperidin-4-yl)methoxy)-N-methylbiphenyl-4-sulfonamide Compound 676: 5-(4-(methylsulfonyl)phenyl)-2-((1-((1-(trifluoromethyl)cyclobutyl)methyl)piperidin-4-yl)methoxy)pyridine Compound 677: ethyl 1-(4'-((1-(2-fluoro-2-methylpropyl)piperidin-4-yl)methoxy)biphenylcarbonyl)piperidine-3-carboxylate Compound 678: ethyl 1-(4'-((1-(2-fluoro-2-methylpropyl)piperidin-4-yl)methoxy)biphenylcarbonyl)piperidine-4-carboxylate Compound 679: ethyl 1-(4'-((1-(2-fluoro-2-methylpropyl)piperidin-4-yl)methoxy)biphenylcarbonyl)piperidine-2-carboxylate Compound 680: (4-ethylpiperazin-1-yl)(4'-((1-(2-fluoro-2-methylpropyl)piperidin-4-yl)methoxy)biphenyl-4-yl)methanone Compound 681: (4'-((1-(2-fluoro-2-methylpropyl)piperidin-4-yl)methoxy)biphenyl-4-yl)(4-isopropylpiperazin-1-yl)methanone Compound 682: (R)-1-(4'-((1-(2-fluoro-2-methylpropyl)piperidin-4-yl)methoxy)biphenylcarbonyl)pyrrolidine-2-carboxamide Compound 683: (R)-1-(4'-((1-(2-fluoro-2-methylpropyl)piperidin-4-yl)methoxy)biphenylcarbonyl)-N,N-dimethylpyrrolidine-2-carboxamide Compound 684: (R)-1-(4'-((1-(2-fluoro-2-methylpropyl)piperidin-4-yl)methoxy)biphenylcarbonyl)-N-methylpyrrolidine-2-carboxamide Compound 685: (4'-((1-(2-fluoro-2-methylpropyl)piperidin-4-yl)methoxy)biphenyl-4-yl)(4-methylpiperazin-1-yl)methanone Compound 686: (3,5-dimethylpiperazin-1-yl)(4'-((1-(2-fluoro-2-methylpropyl)piperidin-4-yl)methoxy)biphenyl-4-yl)methanone Compound 687: (2,6-dimethylmorpholino)(4'-((1-(2-fluoro-2-methylpropyl)piperidin-4-yl)methoxy)biphenyl-4-yl)methanone Compound 688: 4'-((1-(2-fluoropropyl)piperidin-4-yl)methoxy)-N,N-dimethylbiphenyl-4-carboxamide Compound 689: (4'-((1-(2-fluoropropyl)piperidin-4-yl)methoxy)biphenyl-4-yl)(3-hydroxypiperidin-1-yl)methanone Compound 690: (4'-((1-(2-fluorobutyl)piperidin-4-yl)methoxy)biphenyl-4-yl)(3-hydroxypiperidin-1-yl)methanone Compound 691: (S)-1-(4-(5-((1-(2-fluoro-2-methylpropyl)piperidin-4-yl)methoxy)pyridin-2-yl)benzoyl)pyrrolidine-2-carboxamide Compound 692: (R)-(4-(5-((1-(2-fluoro-2-methylpropyl)piperidin-4-yl)methoxy)pyridin-2-yl)phenyl)(2-(hydroxymethyl)pyrrolidin-1-yl)methanone Compound 693: (S)-(4-(5-((1-(2-fluoro-2-methylpropyl)piperidin-4-yl)methoxy)pyridin-2-yl)phenyl)(3-hydroxypiperidin-1-yl)methanone Compound 694: (R)-(2-fluoro-4-(5-((1-(2-fluoro-2-methylpropyl)piperidin-4-yl)methoxy)pyridin-2-yl)phenyl)(2-(hydroxymethyl)pyrrolidin-1-yl)methanone Compound 695: (S)-(2-fluoro-4-(5-((1-(2-fluoro-2-methylpropyl)piperidin-4-yl)methoxy)pyridin-2-yl)phenyl)(3-hydroxypyrrolidin-1-yl)methanone Compound 696: (S)-1-(3-fluoro-4-(5-((1-(2-fluoro-2-methylpropyl)piperidin-4-yl)methoxy)pyridin-2-yl)benzoyl)pyrrolidine-2-carboxamide Compound 697: (R)-(3-fluoro-4-(5-((1-(2-fluoro-2-methylpropyl)piperidin-4-yl)methoxy)pyridin-2-yl)phenyl)(2-(hydroxymethyl)pyrrolidin-1-yl)methanone Compound 698: (R)-(3-fluoro-4-(5-((1-(2-fluoro-2-methylpropyl)piperidin-4-yl)methoxy)pyridin-2-yl)phenyl)(3-hydroxypiperidin-1-yl)methanone Compound 699: (S)-(3-fluoro-4-(5-((1-(2-fluoro-2-methylpropyl)piperidin-4-yl)methoxy)pyridin-2-yl)phenyl)(3-hydroxypyrrolidin-1-yl)methanone Compound 700: (R)-(3-fluoro-4'-((1-(2-fluoro-2-methylpropyl)piperidin-4-yl)methoxy)biphenyl-4-yl)(3-hydroxypiperidin-1-yl)methanone Compound 701: (S)-(3-fluoro-4'-((1-(2-fluoro-2-methylpropyl)piperidin-4-yl)methoxy)biphenyl-4-yl)(3-hydroxypiperidin-1-yl)methanone Compound 702: (R)-(3-fluoro-4'-((1-(2-fluoro-2-methylpropyl)piperidin-4-yl)methoxy)biphenyl-4-yl)(3-hydroxypyrrolidin-1-yl)methanone Compound 703: (S)-(3-fluoro-4'-((1-(2-fluoro-2-methylpropyl)piperidin-4-yl)methoxy)biphenyl-4-yl)(2-(hydroxymethyl)pyrrolidin-1-yl)methanone Compound 704: (2,2'-difluoro-4'-((1-(2-fluoro-2-methylpropyl)piperidin-4-yl)methoxy)biphenyl-4-yl)((R)-2-(hydroxymethyl)pyrrolidin-1-yl)methanone Compound 705: (2S)-1-(2,2'-difluoro-4'-((1-(2-fluoro-2-methylpropyl)piperidin-4-yl)methoxy)biphenylcarbonyl)pyrrolidine-2-carboxamide Compound 706: (S)-1-(2'-fluoro-4'-((1-(2-fluoro-2-methylpropyl)piperidin-4-yl)methoxy)biphenylcarbonyl)pyrrolidine-2-carboxamide Compound 707: (R)-(2'-fluoro-4'-((1-(2-fluoro-2-methylpropyl)piperidin-4-yl)methoxy)biphenyl-4-yl)(2-(hydroxymethyl)pyrrolidin-1-yl)methanone Compound 708: (R)-(2'-fluoro-4'-((1-(2-fluoro-2-methylpropyl)piperidin-4-yl)methoxy)biphenyl-4-yl)(3-hydroxypyrrolidin-1-yl)methanone Compound 709: (R)-(2'-fluoro-4'-((1-(2-fluoro-2-methylpropyl)piperidin-4-yl)methoxy)biphenyl-4-yl)(3-hydroxypiperidin-1-yl)methanone Compound 710: (S)-1-(2',3-difluoro-4'-((1-(2-fluoro-2-methylpropyl)piperidin-4-yl)methoxy)biphenylcarbonyl)pyrrolidine-2-carboxamide Compound 711: (R)-(2',3-difluoro-4'-((1-(2-fluoro-2-methylpropyl)piperidin-4-yl)methoxy)biphenyl-4-yl)(2-(hydroxymethyl)pyrrolidin-1-yl)methanone Compound 712: (R)-(2',3-difluoro-4'-((1-(2-fluoro-2-methylpropyl)piperidin-4-yl)methoxy)biphenyl-4-yl)(3-hydroxypyrrolidin-1-yl)methanone Compound 713: (R)-(2',3-difluoro-4'-((1-(2-fluoro-2-methylpropyl)piperidin-4-yl)methoxy)biphenyl-4-yl)(3-hydroxypiperidin-1-yl)methanone Compound 714: 1-(2-fluoro-2-methylpropyl)-4-((2-fluoro-4'-(methylsulfonyl)biphenyl-4-yloxy)methyl)piperidine Compound 715: (S)-(3-fluoro-4-(6-((1-((1-(trifluoromethyl)cyclobutyl)methyl)piperidin-4-yl)methoxy)pyridin-3-yl)phenyl)(3-hydroxypyrrolidin-1-yl)methanone Compound 716: (R)-(3-fluoro-4-(6-((1-((1-(trifluoromethyl)cyclobutyl)methyl)piperidin-4-yl)methoxy)pyridin-3-yl)phenyl)(2-(hydroxymethyl)pyrrolidin-1-yl)methanone Compound 717: (S)-1-(3-fluoro-4-(6-((1-((1-(trifluoromethyl)cyclobutyl)methyl)piperidin-4-yl)methoxy)pyridin-3-yl)benzoyl)pyrrolidine-2-carboxamide Compound 718: (R)-(3-fluoro-4-(6-((1-((1-(trifluoromethyl)cyclobutyl)methyl)piperidin-4-yl)methoxy)pyridin-3-yl)phenyl)(3-hydroxypiperidin-1-yl)methanone Compound 719: (S)-(3-fluoro-4-(6-((1-((1-(trifluoromethyl)cyclobutyl)methyl)piperidin-4-yl)methoxy)pyridin-3-yl)phenyl)(3-hydroxypiperidin-1-yl)methanone Compound 720: (S)-(2-fluoro-4-(6-((1-((1-(trifluoromethyl)cyclobutyl)methyl)piperidin-4-yl)methoxy)pyridin-3-yl)phenyl)(3-hydroxypyrrolidin-1-yl)methanone Compound 721: (R)-(2-fluoro-4-(6-((1-((1-(trifluoromethyl)cyclobutyl)methyl)piperidin-4-yl)methoxy)pyridin-3-yl)phenyl)(2-(hydroxymethyl)pyrrolidin-1-yl)methanone Compound 722: (S)-1-(2-fluoro-4-(6-((1-((1-(trifluoromethyl)cyclobutyl)methyl)piperidin-4-yl)methoxy)pyridin-3-yl)benzoyl)pyrrolidine-2-carboxamide Compound 723: (R)-(2-fluoro-4-(6-((1-((1-(trifluoromethyl)cyclobutyl)methyl)piperidin-4-yl)methoxy)pyridin-3-yl)phenyl)(3-hydroxypiperidin-1-yl)methanone Compound 724: (S)-(2-fluoro-4-(6-((1-((1-(trifluoromethyl)cyclobutyl)methyl)piperidin-4-yl)methoxy)pyridin-3-yl)phenyl)(3-hydroxypiperidin-1-yl)methanone Compound 725: (S)-(3'-fluoro-4'-((1-(2-fluoro-2-methylpropyl)piperidin-4-yl)methoxy)biphenyl-4-yl)(3-hydroxypiperidin-1-yl)methanone Compound 726: (R)-(3'-fluoro-4'-((1-(2-fluoro-2-methylpropyl)piperidin-4-yl)methoxy)biphenyl-4-yl)(3-hydroxypiperidin-1-yl)methanone Compound 727: (R)-(3'-fluoro-4'-((1-(2-fluoro-2-methylpropyl)piperidin-4-yl)methoxy)biphenyl-4-yl)(2-(hydroxymethyl)pyrrolidin-1-yl)methanone Compound 728: (S)-(3'-fluoro-4'-((1-(2-fluoro-2-methylpropyl)piperidin-4-yl)methoxy)biphenyl-4-yl)(2-(hydroxymethyl)pyrrolidin-1-yl)methanone Compound 729: (R)-(3'-fluoro-4'-((1-(2-fluoro-2-methylpropyl)piperidin-4-yl)methoxy)biphenyl-4-yl)(3-hydroxypyrrolidin-1-yl)methanone Compound 730: (S)-1-(3,3'-difluoro-4'-((1-(2-fluoro-2-methylpropyl)piperidin-4-yl)methoxy)biphenylcarbonyl)pyrrolidine-2-carboxamide Compound 731: (S)-(3,3'-difluoro-4'-((1-(2-fluoro-2-methylpropyl)piperidin-4-yl)methoxy)biphenyl-4-yl)(3-hydroxypiperidin-1-yl)methanone Compound 732: (S)-(3,3'-difluoro-4'-((1-(2-fluoro-2-methylpropyl)piperidin-4-yl)methoxy)biphenyl-4-yl)(3-hydroxypyrrolidin-1-yl)methanone Compound 733: (R)-(3,3'-difluoro-4'-((1-(2-fluoro-2-methylpropyl)piperidin-4-yl)methoxy)biphenyl-4-yl)(3-hydroxypyrrolidin-1-yl)methanone Compound 734: (R)-(3,3'-difluoro-4'-((1-(2-fluoro-2-methylpropyl)piperidin-4-yl)methoxy)biphenyl-4-yl)(3-hydroxypiperidin-1-yl)methanone Compound 735: (S)-(2,3'-difluoro-4'-((1-(2-fluoro-2-methylpropyl)piperidin-4-yl)methoxy)biphenyl-4-yl)(3-hydroxypiperidin-1-yl)methanone Compound 736: (R)-(2,3'-difluoro-4'-((1-(2-fluoro-2-methylpropyl)piperidin-4-yl)methoxy)biphenyl-4-yl)(3-hydroxypiperidin-1-yl)methanone Compound 737: (S)-(2,3'-difluoro-4'-((1-(2-fluoro-2-methylpropyl)piperidin-4-yl)methoxy)biphenyl-4-yl)(3-hydroxypyrrolidin-1-yl)methanone Compound 738: (S)-(2'-fluoro-4'-((1-(2-fluoro-2-methylpropyl)piperidin-4-yl)methoxy)biphenyl-4-yl)(3-hydroxypiperidin-1-yl)methanone Compound 739: (S)-(2'-fluoro-4'-((1-(2-fluoro-2-methylpropyl)piperidin-4-yl)methoxy)biphenyl-4-yl)(3-hydroxypyrrolidin-1-yl)methanone Compound 740: (S)-(2'-fluoro-4'-((1-(2-fluoro-2-methylpropyl)piperidin-4-yl)methoxy)biphenyl-4-yl)(2-(hydroxymethyl)pyrrolidin-1-yl)methanone Compound 741: (2,2'-difluoro-4'-((1-(2-fluoro-2-methylpropyl)piperidin-4-yl)methoxy)biphenyl-4-yl)((S)-3-hydroxypiperidin-1-yl)methanone Compound 742: (2,2'-difluoro-4'-((1-(2-fluoro-2-methylpropyl)piperidin-4-yl)methoxy)biphenyl-4-yl)((R)-3-hydroxypyrrolidin-1-yl)methanone Compound 743: (2,2'-difluoro-4'-((1-(2-fluoro-2-methylpropyl)piperidin-4-yl)methoxy)biphenyl-4-yl)((S)-3-hydroxypyrrolidin-1-yl)methanone Compound 744: (2,2'-difluoro-4'-((1-(2-fluoro-2-methylpropyl)piperidin-4-yl)methoxy)biphenyl-4-yl)((S)-2-(hydroxymethyl)pyrrolidin-1-yl)methanone Compound 745: (2,2'-difluoro-4'-((1-(2-fluoro-2-methylpropyl)piperidin-4-yl)methoxy)biphenyl-4-yl)((R)-3-hydroxypiperidin-1-yl)methanone Compound 746: (S)-(2',3-difluoro-4'-((1-(2-fluoro-2-methylpropyl)piperidin-4-yl)methoxy)biphenyl-4-yl)(3-hydroxypiperidin-1-yl)methanone Compound 747: (S)-(2',3-difluoro-4'-((1-(2-fluoro-2-methylpropyl)piperidin-4-yl)methoxy)biphenyl-4-yl)(3-hydroxypyrrolidin-1-yl)methanone Compound 748: (S)-(2',3-difluoro-4'-((1-(2-fluoro-2-methylpropyl)piperidin-4-yl)methoxy)biphenyl-4-yl)(2-(hydroxymethyl)pyrrolidin-1-yl)methanone Compound 749: (R)-(2-fluoro-4'-((1-(2-fluoro-2-methylpropyl)piperidin-4-yl)methoxy)biphenyl-4-yl)(3-hydroxypiperidin-1-yl)methanone Compound 750: (S)-1-(2-fluoro-4'-((1-(2-fluoro-2-methylpropyl)piperidin-4-yl)methoxy)biphenylcarbonyl)pyrrolidine-2-carboxamide Compound 751: (R)-(2,3'-difluoro-4'-((1-(2-fluoro-2-methylpropyl)piperidin-4-yl)methoxy)biphenyl-4-yl)(2-(hydroxymethyl)pyrrolidin-1-yl)methanone Compound 752: (S)-(2,3'-difluoro-4'-((1-(2-fluoro-2-methylpropyl)piperidin-4-yl)methoxy)biphenyl-4-yl)(2-(hydroxymethyl)pyrrolidin-1-yl)methanone Compound 753: (S)-1-(2,3'-difluoro-4'-((1-(2-fluoro-2-methylpropyl)piperidin-4-yl)methoxy)biphenylcarbonyl)pyrrolidine-2-carboxamide Compound 754: (R)-(2,3'-difluoro-4'-((1-(2-fluoro-2-methylpropyl)piperidin-4-yl)methoxy)biphenyl-4-yl)(3-hydroxypiperidin-1-yl)methanone Compound 755: 1-(4'-((1-(2-fluoro-2-methylpropyl)piperidin-4-yl)methoxy)biphenylcarbonyl)piperidine-3-carboxamide Compound 756: 1-(4'-((1-(2-fluoro-2-methylpropyl)piperidin-4-yl)methoxy)biphenylcarbonyl)piperidine-4-carboxamide Compound 757: 1-(4'-((1-(2-fluoro-2-methylpropyl)piperidin-4-yl)methoxy)biphenylcarbonyl)piperidine-2-carboxamide Compound 758: (R)-(6-(4-((1-(2-fluoro-2-methylpropyl)piperidin-4-yl)methoxy)phenyl)pyridin-3-yl)(3-hydroxypiperidin-1-yl)methanone Compound 759: (R)-(5-(4-((1-(2-fluoro-2-methylpropyl)piperidin-4-yl)methoxy)phenyl)pyridin-2-yl)(3-hydroxypiperidin-1-yl)methanone Compound 760: (S)-1-(4'-((1-((1-fluorocyclohexyl)methyl)piperidin-4-yl)methoxy)biphenylcarbonyl)pyrrolidine-2-carboxamide Compound 761: (R)-(4'-((1-((1-fluorocyclohexyl)methyl)piperidin-4-yl)methoxy)biphenyl-4-yl)(3-hydroxypiperidin-1-yl)methanone Compound 763: (R)-(4-(5-((1-(2-fluoro-2-methylpropyl)piperidin-4-yl)methoxy)pyridin-2-yl)phenyl)(3-hydroxypyrrolidin-1-yl)methanone Compound 764: (S)-(4-(5-((1-(2-fluoro-2-methylpropyl)piperidin-4-yl)methoxy)pyridin-2-yl)phenyl)(3-hydroxypyrrolidin-1-yl)methanone Compound 765: (S)-(4-(5-((1-(2-fluoro-2-methylpropyl)piperidin-4-yl)methoxy)pyridin-2-yl)phenyl)(2-(hydroxymethyl)pyrrolidin-1-yl)methanone Compound 766: (R)-(4-(5-((1-(2-fluoro-2-methylpropyl)piperidin-4-yl)methoxy)pyridin-2-yl)phenyl)(3-hydroxypiperidin-1-yl)methanone Compound 767: (S)-(2-fluoro-4-(5-((1-(2-fluoro-2-methylpropyl)piperidin-4-yl)methoxy)pyridin-2-yl)phenyl)(3-hydroxypiperidin-1-yl)methanone Compound 768: (R)-(2-fluoro-4-(5-((1-(2-fluoro-2-methylpropyl)piperidin-4-yl)methoxy)pyridin-2-yl)phenyl)(3-hydroxypyrrolidin-1-yl)methanone Compound 769: (S)-(2-fluoro-4-(5-((1-(2-fluoro-2-methylpropyl)piperidin-4-yl)methoxy)pyridin-2-yl)phenyl)(2-(hydroxymethyl)pyrrolidin-1-yl)methanone Compound 770: (S)-1-(2-fluoro-4-(5-((1-(2-fluoro-2-methylpropyl)piperidin-4-yl)methoxy)pyridin-2-yl)benzoyl)pyrrolidine-2-carboxamide Compound 771: (R)-(2-fluoro-4-(5-((1-(2-fluoro-2-methylpropyl)piperidin-4-yl)methoxy)pyridin-2-yl)phenyl)(3-hydroxypiperidin-1-yl)methanone Compound 772: (S)-(3-hydroxypyrrolidin-1-yl)(4-(6-((1-((1-(trifluoromethyl)cyclopentyl)methyl)piperidin-4-yl)methoxy)pyridin-3-yl)phenyl)methanone Compound 773: (R)-(2-(hydroxymethyl)pyrrolidin-1-yl)(4-(6-((1-((1-(trifluoromethyl)cyclopentyl)methyl)piperidin-4-yl)methoxy)pyridin-3-yl)phenyl)methanone Compound 774: (S)-1-(4-(6-((1-((1-(trifluoromethyl)cyclopentyl)methyl)piperidin-4-yl)methoxy)pyridine-3-yl)benzoyl)pyrrolidine-2-carboxamide Compound 775: (R)-(3-hydroxypiperidin-1-yl)(4-(6-((1-((1-(trifluoromethyl)cyclopentyl)methyl)piperidin-4-yl)methoxy)pyridin-3-yl)phenyl)methanone Compound 776: (S)-(3-hydroxypyrrolidin-1-yl)(4-(6-((1-((1-(trifluoromethyl)cyclohexyl)methyl)piperidin-4-yl)methoxy)pyridin-3-yl)phenyl)methanone Compound 777: (R)-(2-(hydroxymethyl)pyrrolidin-1-yl)(4-(6-((1-((1-(trifluoromethyl)cyclohexyl)methyl)piperidin-4-yl)methoxy)pyridin-3-yl)phenyl)methanone Compound 778: (S)-1-(4-(6-((1-((1-trifluoromethyl)cyclohexyl)methyl)piperidin-4-yl)methoxy)pyridin-3-yl)benzoyl)pyrrolidin-2-carboxamide Compound 779: (R)-(3-hydroxypiperidin-1-yl)(4-(6-((1-((1-(trifluoromethyl)cyclohexyl)methyl)piperidin-4-yl)methoxy)pyridin-3-yl)phenyl)methanone Compound 782: (S)-1-(5-(3-fluoro-4-((1-(2-fluoro-2-methylpropyl)piperidin-4-yl)methoxy)phenyl)picolinoyl)pyrrolidine-2-carboxamide Compound 783: (R)-(5-(3-fluoro-4-((1-(2-fluoro-2-methylpropyl)piperidin-4-yl)methoxy)phenyl)pyridin-2-yl)(3-hydroxypiperidin-1-yl)methanone Compound 784: (R)-(2-fluoro-4-(6-((1-(2-fluoro-2-methylpropyl)piperidin-4-yl)methoxy)pyridin-3-yl)phenyl)(3-hydroxypiperidin-1-yl)methanone Compound 785: (R)-(2-fluoro-4-(6-((1-(2-fluoro-2-methylpropyl)piperidin-4-yl)methoxy)pyridin-3-yl)phenyl)(3-hydroxypyrrolidin-1-yl)methanone Compound 786: (S)-(2-fluoro-4-(6-((1-(2-fluoro-2-methylpropyl)piperidin-4-yl)methoxy)pyridin-3-yl)phenyl)(3-hydroxypyrrolidin-1-yl)methanone Compound 787: (S)-(2-fluoro-4-(6-((1-(2-fluoro-2-methylpropyl)piperidin-4-yl)methoxy)pyridin-3-yl)phenyl)(2-(hydroxymethyl)pyrrolidin-1-yl)methanone Compound 789: 1-((1-fluoro cyclohexyl)methyl)-4-((4'-(methylsulfonyl)biphenyl-4-yloxy)methyl)piperidine Compound 790: 4-(4'-((1-(2-fluoro-2-methylpropyl)piperidin-4-yl)methoxy)biphenylcarbonyl)piperazin-2-one Compound 791: 1-(4'-((1-(2-fluoro-2-methylpropyl)piperidin-4-yl)methoxy)biphenylcarbonyl)piperidine-4-carbonitrile Compound 792: 1-(3-fluoro-4'-((1-(2-fluoro-2-methylpropyl)piperidin-4-yl)methoxy)biphenylcarbonyl)piperidine-4-carboxamide Compound 793: (3-fluoro-4'-((1-(2-fluoro-2-methylpropyl)piperidin-4-yl)methoxy)biphenyl-4-yl)(3-(trifluoromethyl)-5,6-dihydro-[1,2,4]triazolo[4,3-a]pyrazin-7(8H)-yl)methanone Compound 794: (R)-(3-hydroxypiperidin-1-yl)(4'-((1-((1-(trifluoromethyl)cyclobutyl)methyl)piperidin-4-yl)methoxy)biphenyl-4-yl)methanone Compound 795: (S)-(3-hydroxypiperidin-1-yl)(4'-((1-((1-(trifluoromethyl)cyclobutyl)methyl)piperidin-4-yl)methoxy)biphenyl-4-yl)methanone Compound 796: (R)-(3-hydroxypyrrolidin-1-yl)(4'-((1-((1-(trifluoromethyl)cyclobutyl)methyl)piperidin-4-yl)methoxy)biphenyl-4-yl)methanone Compound 797: (S)-(2-(hydroxymethyl)pyrrolidin-1-yl)(4'-((1-((1-(trifluoromethyl)cyclobutyl)methyl)piperidin-4-yl)methoxy)biphenyl-4-yl)methanone Compound 798: 1-(4'-((1-((1-(trifluoromethyl)cyclobutyl)methyl)piperidin-4-yl)methoxy)biphenylcarbonyl)piperidine-4-carboxamide Compound 799: 1-(3'-fluoro-4'-((1-(2-fluoro-2-methylpropyl)piperidin-4-yl)methoxy)biphenylcarbonyl)piperidine-4-carboxamide Compound 800: 1-(3,3'-difluoro-4'-((1-(2-fluoro-2-methylpropyl)piperidin-4-yl)methoxy)biphenylcarbonyl)piperidine-4-carboxamide Compound 801: 1-(2'-fluoro-4'-((1-(2-fluoro-2-methylpropyl)piperidin-4-yl)methoxy)biphenylcarbonyl)piperidine-4-carboxamide Compound 802: 1-(2',3-difluoro-4'-((1-(2-fluoro-2-methylpropyl)piperidin-4-yl)methoxy)biphenylcarbonyl)piperidine-4-carboxamide Compound 803: 1-(2,2'-difluoro-4'-((1-(2-fluoro-2-methylpropyl)piperidin-4-yl)methoxy)biphenylcarbonyl)piperidine-4-carboxamide Compound 804: 1-(4-(5-((1-(2-fluoro-2-methylpropyl)piperidin-4-yl)methoxy)pyridin-2-yl)benzoyl)piperidine-4-carboxamide Compound 805: 1-(2-fluoro-4-(5-((1-(2-fluoro-2-methylpropyl)piperidin-4-yl)methoxy)pyridin-2-yl)benzoyl)piperidine-4-carboxamide Compound 806: (R)-1-(3'-fluoro-4'-((1-(2-fluoro-2-methylpropyl)piperidin-4-yl)methoxy)biphenylcarbonyl)piperidine-2-carboxamide Compound 807: (S)-1-(3'-fluoro-4'-((1-(2-fluoro-2-methylpropyl)piperidin-4-yl)methoxy)biphenylcarbonyl)piperidine-2-carboxamide Compound 809: (R)-(4'-((1-(2-ethyl-2-fluorobutyl)piperidin-4-yl)methoxy)biphenyl-4-yl)(3-hydroxypiperidin-1-yl)methanone
Compound 810: (R)-(4'-((1-(2-ethyl-2-fluorobutyl)piperidin-4-yl)methoxy)-3-fluorobiphenyl-4-yl)(2-(hydroxymethyl)pyrrolidin-1-yl)methanone
Compound 811: (R)-(4'-((1-(2-ethyl-2-fluorobutyl)piperidin-4-yl)methoxy)-2-fluorobiphenyl-4-yl)(2-(hydroxymethyl)pyrrolidin-1-yl)methanone
Compound 812: (R)-(4'-((1-(2-ethyl-2-fluorobutyl)piperidin-4-yl)methoxy)-2-fluorobiphenyl-4-yl)(3-hydroxypiperidin-1-yl)methanone
Compound 813: 1-(3-fluoro-4-(5-((1-(2-fluoro-2-methylpropyl)piperidin-4-yl)methoxy)pyridin-2-yl)benzoyl)piperidine-4-carboxamide
Compound 814: 1-(4'-((1-(2-ethyl-2-fluorobutyl)piperidin-4-yl)methoxy)-3-fluorobiphenylcarbonyl)piperidine-4-carboxamide
Compound 815: (S)-(3-fluoro-4-(5-((1-(2-fluoro-2-methylpropyl)piperidin-4-yl)methoxy)pyridin-2-yl)phenyl)(2-(hydroxymethyl)pyrrolidin-1-yl)methanone
Compound 816: (R)-1-(3,3'-difluoro-4'-((1-(2-fluoro-2-methylpropyl)piperidin-4-yl)methoxy)biphenylcarbonyl)piperidine-2-carboxamide
Compound 817: (S)-1-(3,3'-difluoro-4'-((1-(2-fluoro-2-methylpropyl)piperidin-4-yl)methoxy)biphenylcarbonyl)piperidine-2-carboxamide
Compound 818: 1-(2,3'-difluoro-4'-((1-(2-fluoro-2-methylpropyl)piperidin-4-yl)methoxy)biphenylcarbonyl)piperidine-4-carboxamide
Compound 819: (R)-1-(2,3'-difluoro-4'-((1-(2-fluoro-2-methylpropyl)piperidin-4-yl)methoxy)biphenylcarbonyl)piperidine-2-carboxamide
Compound 820: (S)-1-(2,3'-difluoro-4'-((1-(2-fluoro-2-methylpropyl)piperidin-4-yl)methoxy)biphenylcarbonyl)piperidine-2-carboxamide
Compound 821: (R)-1-(4-(5-((1-(2-fluoro-2-methylpropyl)piperidin-4-yl)methoxy)pyridin-2-yl)benzoyl)piperidine-2-carboxamide
Compound 822: (R)-1-(2-fluoro-4-(5-((1-(2-fluoro-2-methylpropyl)piperidin-4-yl)methoxy)pyridin-2-yl)benzoyl)piperidine-2-carboxamide
Compound 823: (R)-1-(2',3-difluoro-4'-((1-(2-fluoro-2-methylpropyl)piperidin-4-yl)methoxy)biphenylcarbonyl)piperidine-2-carboxamide
Compound 824: (S)-1-(2-fluoro-4-(5-((1-(2-fluoro-2-methylpropyl)piperidin-4-yl)methoxy)pyridin-2-yl)benzoyl)piperidine-2-carboxamide
Compound 825: (2R)-1-(2,2'-difluoro-4'-((1-(2-fluoro-2-methylpropyl)piperidin-4-yl)methoxy)biphenylcarbonyl)piperidine-2-carboxamide
Compound 828: (S)-1-(4-(6-((1-(3,3,3-trifluoro-2,2-dimethylpropyl)piperidin-4-yl)methoxy)pyridin-3-yl)benzoyl)pyrrolidine-2-carboxamide
Compound 829: (R)-(3-hydroxypiperidin-1-yl)(4-(6-((1-(3,3,3-trifluoro-2,2-dimethylpropyl)piperidin-4-yl)methoxy)pyridin-3-yl)phenyl)methanone
Compound 830: N-(3,4-dihydroxyphenethyl)-4'-((1-(2-fluoro-2-methylpropyl)piperidin-4-yl)methoxy)biphenyl-4-carboxamide
Compound 831: (R)-1-(4'-((1-(2-fluoro-2-methylpropyl)piperidin-4-yl)methoxy)biphenylcarbonyl)piperidine-2-carboxamide
Compound 832: (S)-1-(4'-((1-(2-fluoro-2-methylpropyl)piperidin-4-yl)methoxy)biphenylcarbonyl)piperidine-2-carboxamide
Compound 833: (S)-1-(2'-fluoro-4'-((1-((1-(trifluoromethyl)cyclobutyl)methyl)piperidin-4-yl)methoxy)biphenylcarbonyl)pyrrolidine-2-carboxamide
Compound 834: (R)-(2'-fluoro-4'-((1-((1-(trifluoromethyl)cyclobutyl)methyl)piperidin-4-yl)methoxy)biphenyl-4-yl)(3-hydroxypiperidin-1-yl)methanone
Compound 835: (S)-(2'-fluoro-4'-((1-((1-(trifluoromethyl)cyclobutyl)methyl)piperidin-4-yl)methoxy)biphenyl-4-yl)(3-hydroxypyrrolidin-1-yl)methanone
Compound 836: (S)-(2'-fluoro-4'-((1-((1-(trifluoromethyl)cyclobutyl)methyl)piperidin-4-yl)methoxy)biphenyl-4-yl)(3-hydroxypiperidin-1-yl)methanone
Compound 837: (S)-1-(3'-fluoro-4'-((1-((1-(trifluoromethyl)cyclobutyl)methyl)piperidin-4-yl)methoxy)biphenylcarbonyl)pyrrolidine-2-carboxamide
Compound 838: (R)-(3'-fluoro-4'-((1-((1-(trifluoromethyl)cyclobutyl)methyl)piperidin-4-yl)methoxy)biphenyl-4-yl)(2-(hydroxymethyl)pyrrolidin-1-yl)methanone
Compound 839: (S)-(3'-fluoro-4'-((1-((1-(trifluoromethyl)cyclobutyl)methyl)piperidin-4-yl)methoxy)biphenyl-4-yl)(3-hydroxypyrrolidin-1-yl)methanone
Compound 840: (R)-(3'-fluoro-4'-((1-((1-(trifluoromethyl)cyclobutyl)methyl)piperidin-4-yl)methoxy)biphenyl-4-yl)(3-hydroxypiperidin-1-yl)methanone
Compound 842: (S)-(3-fluoro-4'-((1-((1-(trifluoromethyl)cyclobutyl)methyl)piperidin-4-yl)methoxy)biphenyl-4-yl)(3-hydroxypiperidin-1-yl)methanone
Compound 843: (S)-1-(3-fluoro-4'-((1-((1-(trifluoromethyl)cyclobutyl)methyl)piperidin-4-yl)methoxy)biphenylcarbonyl)pyrrolidine-2-carboxamide
Compound 844: (R)-(3-fluoro-4'-((1-((1-(trifluoromethyl)cyclobutyl)methyl)piperidin-4-yl)methoxy)biphenyl-4-yl)(2-(hydroxymethyl)pyrrolidin-1-yl)methanone
Compound 845: (S)-(3-fluoro-4'-((1-((1-(trifluoromethyl)cyclobutyl)methyl)piperidin-4-yl)methoxy)biphenyl-4-yl)(3-hydroxypyrrolidin-1-yl)methanone
Compound 846: (R)-(3-fluoro-4'-((1-((1-(trifluoromethyl)cyclobutyl)methyl)piperidin-4-yl)methoxy)biphenyl-4-yl)(3-hydroxypiperidin-1-yl)methanone
Compound 847: (S)-1-(2,3'-difluoro-4'-((1-((1-(trifluoromethyl)cyclobutyl)methyl)piperidin-4-yl)methoxy)biphenylcarbonyl)pyrrolidine-2-carboxamide
Compound 848: (R)-(2,3'-difluoro-4'-((1-((1-(trifluoromethyl)cyclobutyl)methyl)piperidin-4-yl)methoxy)biphenyl-4-yl)(3-hydroxypiperidin-1-yl)methanone
Compound 849: (R)-(2,3'-difluoro-4'-((1-((1-(trifluoromethyl)cyclobutyl)methyl)piperidin-4-yl)methoxy)biphenyl-4-yl)(2-(hydroxymethyl)pyrrolidin-1-yl)methanone
Compound 850: (S)-(2,3'-difluoro-4'-((1-((1-(trifluoromethyl)cyclobutyl)methyl)piperidin-4-yl)methoxy)biphenyl-4-yl)(3-hydroxypiperidin-1-yl)methanone
Compound 851: (S)-(2,3'-difluoro-4'-((1-((1-(trifluoromethyl)cyclobutyl)methyl)piperidin-4-yl)methoxy)biphenyl-4-yl)(3-hydroxypyrrolidin-1-yl)methanone
Compound 852: (R)-(4'-(((1-(2-fluoro-2-methylpropyl)piperidin-4-yl)methyl)(methyl)amino)biphenyl-4-yl)(3-hydroxypiperidin-1-yl)methanone
Compound 853: (R)-(4'-(ethyl((1-(2-fluoro-2-methylpropyl)piperidin-4-yl)methyl)amino)biphenyl-4-yl)(3-hydroxypiperidin-1-yl)methanone
Compound 854: (R)-1-(2-fluoro-4-(6-((1-(2-fluoro-2-methylpropyl)piperidin-4-yl)methoxy)pyridin-3-yl)benzoyl)piperidine-2-carboxamide
Compound 855: (S)-1-(2-fluoro-4-(6-((1-(2-fluoro-2-methylpropyl)piperidin-4-yl)methoxy)pyridin-3-yl)benzoyl)piperidine-2-carboxamide Compound 856: 1-(2-fluoro-4-(6-((1-(2-fluoro-2-methylpropyl)piperidin-4-yl)methoxy)pyridin-3-yl)benzoyl)piperidine-4-carboxamide Compound 857: (R)-1-(4'-((1-(2-fluoro-2-methylpropyl)piperidin-4-yl)methylamino)biphenylcarbonyl)piperidine-2-carboxamide Compound 858: (S)-(4'-((1-(2-fluoro-2-methylpropyl)piperidin-4-yl)methylamino)biphenyl-4-yl)(2-(hydroxymethyl)pyrrolidin-1-yl)methanone Compound 859: (R)-(4'-((1-(2-fluoro-2-methylpropyl)piperidin-4-yl)methylamino)biphenyl-4-yl)(2-(hydroxymethyl)pyrrolidin-1-yl)methanone Compound 860: (2S)-1-(2,6'-difluoro-4'-((1-(2-fluoro-2-methylpropyl)piperidin-4-yl)methoxy)biphenylcarbonyl)piperidine-2-carboxamide Compound 861: (S)-1-(3,6'-difluoro-4'-((1-(2-fluoro-2-methylpropyl)piperidin-4-yl)methoxy)biphenylcarbonyl)piperidine-2-carboxamide Compound 862: (R)-1-(3-fluoro-4-(6-((1-(2-fluoro-2-methylpropyl)piperidin-4-yl)methoxy)pyridin-3-yl)benzoyl)piperidine-2-carboxamide Compound 863: (S)-1-(3-fluoro-4-(6-((1-(2-fluoro-2-methylpropyl)piperidin-4-yl)methoxy)pyridin-3-yl)benzoyl)piperidine-2-carboxamide Compound 864: 1-(3-fluoro-4-(6-((1-(2-fluoro-2-methylpropyl)piperidin-4-yl)methoxy)pyridin-3-yl)benzoyl)piperidine-4-carboxamide Compound 866: (S)-1-(4'-((1-(2-ethyl-2-fluorobutyl)piperidin-4-yl)methoxy)-3-fluorobiphenylcarbonyl)pyrrolidine-2-carboxamide Compound 867: (R)-(4'-((1-(2-fluoro-2-methylpropyl)piperidin-4-yl)methylamino)biphenyl-4-yl)(3-hydroxypiperidin-1-yl)methanone Compound 868: (S)-1-(4'-((1-(2-fluoro-2-methylpropyl)piperidin-4-yl)methylamino)biphenylcarbonyl)pyrrolidine-2-carboxamide Compound 869: (S)-(4'-((1-(2-fluoro-2-methylpropyl)piperidin-4-yl)methylamino)biphenyl-4-yl)(3-hydroxypyrrolidin-1-yl)methanone Compound 870: (S)-1-(3-fluoro-4'-((1-(2-fluoro-2-methylpropyl)piperidin-4-yl)methylamino)biphenylcarbonyl)pyrrolidine-2-carboxamide Compound 871: (R)-1-(3-fluoro-4'-((1-(2-fluoro-2-methylpropyl)piperidin-4-yl)methylamino)biphenylcarbonyl)piperidine-3-carboxamide Compound 872: (R)-1-(3-fluoro-4'-((1-(2-fluoro-2-methylpropyl)piperidin-4-yl)methoxy)biphenylcarbonyl)piperidine-2-carboxamide Compound 873: (R)-1-(2'-fluoro-4'-((1-(2-fluoro-2-methylpropyl)piperidin-4-yl)methoxy)biphenylcarbonyl)piperidine-2-carboxamide Compound 874: (S)-1-(4'-((1-(2-fluoro-2-methylpropyl)piperidin-4-yl)methoxy)biphenylcarbonyl)piperidine-3-carboxamide Compound 875: (S)-1-(3-fluoro-4'-((1-(2-fluoro-2-methylpropyl)piperidin-4-yl)methoxy)biphenylcarbonyl)piperidine-2-carboxamide Compound 876: (S)-1-(2'-fluoro-4'-((1-(2-fluoro-2-methylpropyl)piperidin-4-yl)methoxy)biphenylcarbonyl)piperidine-2-carboxamide Compound 877: (R)-1-(2'-fluoro-4'-((1-((1-(trifluoromethyl)cyclobutyl)methyl)piperidin-4-yl)methoxy)biphenylcarbonyl)piperidine-2-carboxamide Compound 878: (S)-1-(2'-fluoro-4'-((1-((1-(trifluoromethyl)cyclobutyl)methyl)piperidin-4-yl)methoxy)biphenylcarbonyl)piperidine-2-carboxamide Compound 879: (R)-1-(4'-((1-(2-fluoro-2-methylpropyl)piperidin-4-yl)methoxy)biphenylcarbonyl)piperidine-3-carboxamide Compound 880: (R)-1-(3-fluoro-4'-((1-(2-fluoro-2-methylpropyl)piperidin-4-yl)methoxy)biphenylcarbonyl)piperidine-3-carboxamide Compound 881: (R)-1-(2'-fluoro-4'-((1-(2-fluoro-2-methylpropyl)piperidin-4-yl)methoxy)biphenylcarbonyl)piperidine-3-carboxamide Compound 882: (R)-1-(2'-fluoro-4'-((1-((1-(trifluoromethyl)cyclobutyl)methyl)piperidin-4-yl)methoxy)biphenylcarbonyl)piperidine-3-carboxamide Compound 883: (S)-(3'-fluoro-4'-((1-((1-(trifluoromethyl)cyclobutyl)methyl)piperidin-4-yl)methoxy)biphenyl-4-yl)(3-hydroxypiperidin-1-yl)methanone Compound 884: (S)-1-(3'-fluoro-4'-((1-((1-(trifluoromethyl)cyclobutyl)methyl)piperidin-4-yl)methoxy)biphenylcarbonyl)piperidine-3-carboxamide Compound 885: (R)-1-(3'-fluoro-4'-((1-((1-(trifluoromethyl)cyclobutyl)methyl)piperidin-4-yl)methoxy)biphenylcarbonyl)piperidine-3-carboxamide Compound 886: (R)-1-(3'-fluoro-4'-((1-((1-(trifluoromethyl)cyclobutyl)methyl)piperidin-4-yl)methoxy)biphenylcarbonyl)piperidine-2-carboxamide Compound 887: (S)-1-(3'-fluoro-4'-((1-((1-(trifluoromethyl)cyclobutyl)methyl)piperidin-4-yl)methoxy)biphenylcarbonyl)piperidine-2-carboxamide Compound 888: (S)-(4'-((1-(2-ethyl-2-fluorobutyl)piperidin-4-yl)methoxy)-3-fluorobiphenyl-4-yl)(3-hydroxypyrrolidin-1-yl)methanone Compound 889: (S)-(4'-((1-(2-ethyl-2-fluorobutyl)piperidin-4-yl)methoxy)-3-fluorobiphenyl-4-yl)(3-hydroxypiperidin-1-yl)methanone Compound 890: (R)-(4'-((1-(2-ethyl-2-fluorobutyl)piperidin-4-yl)methoxy)-3-fluorobiphenyl-4-yl)(3-hydroxypiperidin-1-yl)methanone Compound 891: (S)-1-(4'-((1-(2-ethyl-2-fluorobutyl)piperidin-4-yl)methoxy)biphenylcarbonyl)pyrrolidine-2-carboxamide Compound 892: (R)-(4'-((1-(2-ethyl-2-fluorobutyl)piperidin-4-yl)methoxy)biphenyl-4-yl)(2-(hydroxymethyl)pyrrolidin-1-yl)methanone Compound 893: (S)-(4'-((1-(2-ethyl-2-fluorobutyl)piperidin-4-yl)methoxy)biphenyl-4-yl)(3-hydroxypyrrolidin-1-yl)methanone Compound 894: (S)-(4'-((1-(2-ethyl-2-fluorobutyl)piperidin-4-yl)methoxy)biphenyl-4-yl)(3-hydroxypiperidin-1-yl)methanone Compound 895: (S)-1-(4'-((1-(2-ethyl-2-fluorobutyl)piperidin-4-yl)methoxy)-2-fluorobiphenylcarbonyl)pyrrolidine-2-carboxamide Compound 896: (S)-1-(4-(5-((1-(2-ethyl-2-fluorobutyl)piperidin-4-yl)methoxy)pyridin-2-yl)benzoyl)pyrrolidine-2-carboxamide Compound 897: (R)-(4-(5-((1-(2-ethyl-2-fluorobutyl)piperidin-4-yl)methoxy)pyridin-2-yl)phenyl)(3-hydroxypiperidin-1-yl)methanone Compound 898: (S)-1-(4-(5-((1-(2-ethyl-2-fluorobutyl)piperidin-4-yl)methoxy)pyridin-2-yl)-2-fluorobenzoyl)pyrrolidine-2-carboxamide Compound 899: (S)-(4-(5-((1-(2-ethyl-2-fluorobutyl)piperidin-4-yl)methoxy)pyridin-2-yl)-2-fluorophenyl)(3-hydroxypyrrolidin-1-yl)methanone Compound 900: (R)-(4-(5-((1-(2-ethyl-2-fluorobutyl)piperidin-4-yl)methoxy)pyridin-2-yl)-2-fluorophenyl)(3-hydroxypiperidin-1-yl)methanone Compound 901: (S)-1-(3,3'-difluoro-4'-((1-((1-(trifluoromethyl)cyclobutyl)methyl)piperidin-4-yl)methoxy)biphenylcarbonyl)pyrrlidine-2-carboxamide Compound 902: (R)-(3,3'-difluoro-4'-((1-((1-(trifluoromethyl)cyclobutyl)methyl)piperidin-4-yl)methoxy)biphenyl-4-yl)(3-hydroxypiperidin-1-yl)methanone Compound 903: (R)-(3,3'-difluoro-4'-((1-((1-(trifluoromethyl)cyclobutyl)methyl)piperidin-4-yl)methoxy)biphenyl-4-yl)(2-(hydroxymethyl)pyrrolidin-1-yl)methanone Compound 904: (S)-(3,3'-difluoro-4'-((1-((1-(trifluoromethyl)cyclobutyl)methyl)piperidin-4-yl)methoxy)biphenyl-4-yl)(3-hydroxypiperidin-1-yl)methanone Compound 905: (S)-(3,3'-difluoro-4'-((1-((1-(trifluoromethyl)cyclobutyl)methyl)piperidin-4-yl)methoxy)biphenyl-4-yl)(3-hydroxypyrrolidin-1-yl)methanone Compound 906: (S)-1-(5-(3-fluoro-4-((1-((1-(trifluoromethyl)cyclobutyl)methyl)piperidin-4-yl)methoxy)phenyl)picolinoyl)pyrrolidine-2-carboxamide Compound 907: (R)-(5-(3-fluoro-4-((1-((1-(trifluoromethyl)cyclobutyl)methyl)piperidin-4-yl)methoxy)phenyl)pyridin-2-yl)(3-hydroxypiperidin-1-yl)methanone Compound 908: (2,2'-difluoro-4'-((1-((1-(trifluoromethyl)cyclobutyl)methyl)piperidin-4-yl)methoxy)biphenyl-4-yl)((R)-2-(hydroxymethyl)pyrrolidin-1-yl)methanone Compound 909: (2S)-1-(2,2'-difluoro-4'-((1-((1-(trifluoromethyl)cyclobutyl)methyl)piperidin-4-yl)methoxy)biphenylcarbonyl)pyrrolidine-2-carboxamide Compound 910: (2,2'-difluoro-4'-((1-((1-(trifluoromethyl)cyclobutyl)methyl)piperidin-4-yl)methoxy)biphenyl-4-yl)((R)-3-hydroxypiperidin-1-yl)methanone Compound 911: (2,2'-difluoro-4'-((1-((1-(trifluoromethyl)cyclobutyl)methyl)piperidin-4-yl)methoxy)biphenyl-4-yl)((S)-3-hydroxypiperidin-1-yl)methanone Compound 912: (R)-(2',3-difluoro-4'-((1-((1-(trifluoromethyl)cyclobutyl)methyl)piperidin-4-yl)methoxy)biphenyl-4-yl)(2-(hydroxymethyl)pyrrolidin-1-yl)methanone Compound 913: (S)-1-(2',3-difluoro-4'-((1-((1-(trifluoromethyl)cyclobutyl)methyl)piperidin-4-yl)methoxy)biphenylcarbonyl)pyrrolidine-2-carboxamide Compound 914: (R)-(2',3-difluoro-4'-((1-((1-(trifluoromethyl)cyclobutyl)methyl)piperidin-4-yl)methoxy)biphenyl-4-yl)(3-hydroxypiperidin-1-yl)methanone Compound 915: (S)-(2',3-difluoro-4'-((1-((1-(trifluoromethyl)cyclobutyl)methyl)piperidin-4-yl)methoxy)biphenyl-4-yl)(3-hydroxypiperidin-1-yl)methanone Compound 916: (S)-(2',3-difluoro-4'-((1-((1-(trifluoromethyl)cyclobutyl)methyl)piperidin-4-yl)methoxy)biphenyl-4-yl)(3-hydroxypyrrolidin-1-yl)methanone Compound 917: (R)-(2-fluoro-4'-((1-((1-(trifluoromethyl)cyclobutyl)methyl)piperidin-4-yl)methoxy)biphenyl-4-yl)(2-(hydroxymethyl)pyrrolidin-1-yl)methanone Compound 918: (S)-1-(2-fluoro-4'-((1-((1-(trifluoromethyl)cyclobutyl)methyl)piperidin-4-yl)methoxy)biphenylcarbonyl)pyrrolidine-2-carboxamide Compound 919: (R)-(2-fluoro-4'-((1-((1-(trifluoromethyl)cyclobutyl)methyl)piperidin-4-yl)methoxy)biphenyl-4-yl)(3-hydroxypiperidin-1-yl)methanone Compound 920: (S)-(2-fluoro-4'-((1-((1-(trifluoromethyl)cyclobutyl)methyl)piperidin-4-yl)methoxy)biphenyl-4-yl)(3-hydroxypiperidin-1-yl)methanone Compound 921: (S)-(2-fluoro-4'-((1-((1-(trifluoromethyl)cyclobutyl)methyl)piperidin-4-yl)methoxy)biphenyl-4-yl)(3-hydroxypyrrolidin-1-yl)methanone Compound 922: (S)-1-(4'-((1-((1-fluorocyclobutyl)methyl)piperidin-4-yl)methoxy)biphenylcarbonyl)pyrrolidine-2-carboxamide Compound 923: (R)-(4'-((1-((1-fluorocyclobutyl)methyl)piperidin-4-yl)methoxy)biphenyl-4-yl)(2-(hydroxymethyl)pyrrolidin-1-yl)methanone Compound 924: (S)-(4'-((1-((1-fluorocyclobutyl)methyl)piperidin-4-yl)methoxy)biphenyl-4-yl)(3-hydroxypyrrolidin-1-yl)methanone Compound 925: (R)-(4'-((1-((1-fluorocyclobutyl)methyl)piperidin-4-yl)methoxy)biphenyl-4-yl)(3-hydroxypiperidin-1-yl)methanone Compound 926: (R)-(3-hydroxypiperidin-1-yl)(4'-((1-((1-(trifluoromethyl)cyclobutyl)methyl)piperidin-4-yl)methylamino)biphenyl-4-yl)methanone Compound 927: (R)-(3-hydroxypiperidin-1-yl)(4'-((1-(3,3,3-trifluoro-2,2-dimethylpropyl)piperidin-4-yl)methylamino)biphenyl-4-yl)methanone Compound 928: (R)-(3-hydroxypiperidin-1-yl)(4'-(methyl((1-((1-(trifluoromethyl)cyclobutyl)methyl)piperidin-4-yl)methyl)amino)biphenyl-4-yl)methanone Compound 929: (R)-(4'-(ethyl((1-((1-(trifluoromethyl)cyclobutyl)methyl)piperidin-4-yl)methyl)amino)biphenyl-4-yl)(3-hydroxypiperidin-1-yl)methanone Compound 930: (R)-(3-hydroxypiperidin-1-yl)(4'-(methyl((1-(3,3,3-trifluoro-2,2-dimethylpropyl)piperidin-4-yl)methyl)amino)biphenyl-4-yl)methanone Compound 931: (2S,4R)-methyl 4-hydroxy-1-(4-(6-((1-((1-(trifluoromethyl)cyclobutyl)methyl)piperidin-4-yl)methoxy)pyridin-3-yl)benzoyl)pyrrolidine-2-carboxylate Compound 932: (2S,4R)-methyl 1-(4'-((1-(2-fluoro-2-methylpropyl)piperidin-4-yl)methoxy)biphenylcarbonyl)-4-hydroxypyrrolidine-2-carboxylate Compound 933: (2S,4R)-4-hydroxy-1-(4-(6-((1-((1-(trifluoromethyl)cyclobutyl)methyl)piperidin-4-yl)methoxy)pyridin-3-yl)benzoyl)pyrrolidine-2-carboxamide Compound 934: (2S,4R)-1-(4'-((1-(2-fluoro-2-methylpropyl)piperidin-4-yl)methoxy)biphenylcarbonyl)-4-hydroxypyrrolidine-2-carboxamide Compound 935: (S)-1-(5-(2-fluoro-4-((1-(2-fluoro-2-methylpropyl)piperidin-4-yl)methoxy)phenyl)picolinoyl)pyrrolidine-2-carboxamide Compound 936: 1-(4-(3,3'-difluoro-4'-((1-((1-(trifluoromethyl)cyclobutyl)methyl)piperidin-4-yl)methoxy)biphenylcarbonyl)piperazin-1-yl)ethanone Compound 937: (S)-1-(4'-((1-(2-ethyl-2-fluorobutyl)piperidin-4-yl)methoxy)-2,3'-difluorobiphenylcarbonyl)pyrrolidine-2-carboxamide Compound 938: (S)-1-(3'-cyano-3-fluoro-4'-((1-(2-fluoro-2-methylpropyl)piperidin-4-yl)methoxy)biphenylcarbonyl)pyrrolidine-2-carboxamide Compound 939: (R)-3'-fluoro-4-((1-(2-fluoro-2-methylpropyl)piperidin-4-yl)methoxy)-4'-(3-hydroxypiperidine-1-carbonyl)biphenyl-3-carbonitrile Compound 940: (R)-(4'-((1-(2-ethyl-2-fluorobutyl)piperidin-4-yl)methoxy)-2,3'-difluorobiphenyl-4-yl)(3-hydroxypiperidin-1-yl)methanone Compound 941: (R)-(4'-((1-(2-ethyl-2-fluorobutyl)piperidin-4-yl)methoxy)-2,3'-difluorobiphenyl-4-yl)(2-(hydroxymethyl)pyrrolidin-1-yl)methanone Compound 942: (S)-(4'-((1-(2-ethyl-2-fluorobutyl)piperidin-4-yl)methoxy)-2,3'-difluorobiphenyl-4-yl)(3-hydroxypiperidin-1-yl)methanone Compound 943: (S)-(4'-((1-(2-ethyl-2-fluorobutyl)piperidin-4-yl)methoxy)-2,3'-difluorobiphenyl-4-yl)(3-hydroxypyrrolidin-1-yl)methanone Compound 944: (S)-1-(2-fluoro-4-(5-((1-(2-fluoro-2-methylpropyl)piperidin-4-yl)methoxy)pyrazin-2-yl)benzoyl)pyrrolidine-2-carboxamide Compound 945: (R)-(2-fluoro-4-(5-((1-(2-fluoro-2-methylpropyl)piperidin-4-yl)methoxy)pyrazin-2-yl)phenyl)(3-hydroxypiperidin-1-yl)methanone Compound 946: (S)-1-(3-fluoro-4'-((1-(2-fluoro-2-methylpropyl)piperidin-4-yl)methoxy)-3'-(hydroxymethyl)biphenylcarbonyl)pyrrolidine-2-carboxamide Compound 947: (S)-(3-fluoro-4'-((1-(2-fluoro-2-methylpropyl)piperidin-4-yl)methoxy)-5'-(hydroxymethyl)biphenyl-4-yl)(3-hydroxypyrrolidin-1-yl)methanone Compound 948: (R)-(4-(5-((1-(2-fluoro-2-methylpropyl)piperidin-4-yl)methoxy)pyrazin-2-yl)phenyl)(3-hydroxypiperidin-1-yl)methanone Compound 949: (S)-(4-(5-((1-(2-fluoro-2-methylpropyl)piperidin-4-yl)methoxy)pyrazin-2-yl)phenyl)(3-hydroxypyrrolidin-1-yl)methanone Compound 950: (S)-1-(4-(5-((1-(2-fluoro-2-methylpropyl)piperidin-4-yl)methoxy)pyrazin-2-yl)benzoyl)pyrrolidine-2-carboxamide Compound 951: (S)-(4-(5-((1-(2-fluoro-2-methylpropyl)piperidin-4-yl)methoxy)pyrazin-2-yl)phenyl)(3-hydroxypiperidin-1-yl)methanone Compound 953: (S)-1-(4-(6-((1-(2-ethyl-2-fluorobutyl)piperidin-4-yl)methoxy)pyridazin-3-yl)benzoyl)pyrrolidine-2-carboxamide Compound 954: (R)-(4-(6-((1-(2-ethyl-2-fluorobutyl)piperidin-4-yl)methoxy)pyridin-3-yl)phenyl)(3-hydroxypiperidin-1-yl)methanone Compound 955: (S)-(4-(6-((1-(2-ethyl-2-fluorobutyl)piperidin-4-yl)methoxy)pyridin-3-yl)phenyl)(3-hydroxypiperidin-1-yl)methanone Compound 956: (R)-(4-(6-((1-(2-ethyl-2-fluorobutyl)piperidin-4-yl)methoxy)pyridin-3-yl)-2-fluorophenyl)(3-hydroxypiperidin-1-yl)methanone Compound 957: (S)-(4-(6-((1-(2-ethyl-2-fluorobutyl)piperidin-4-yl)methoxy)pyridin-3-yl)-2-fluorophenyl)(3-hydroxypiperidin-1-yl)methanone Compound 963: (R)-4-((1-(2-fluoro-2-methylpropyl)piperidin-4-yl)methoxy)-4'-(3-hydroxypiperidine-1-carbonyl)biphenyl-3-carbonitrile Compound 964: (S)-4-((1-(2-fluoro-2-methylpropyl)piperidin-4-yl)methoxy)-4'-(3-hydroxypiperidine-1-carbonyl)biphenyl-3-carbonitrile Compound 965: (S)-1-(3'-cyano-4'-((1-(2-fluoro-2-methylpropyl)piperidin-4-yl)methoxy)biphenylcarbonyl)pyrrolidine-2-carboxamide Compound 966: (S)-4-((1-(2-fluoro-2-methylpropyl)piperidin-4-yl)methoxy)-4'-(3-hydroxypyrrolidine-1-carbonyl)biphenyl-3-carbonitrile Compound 967: (R)-2'-fluoro-4-((1-(2-fluoro-2-methylpropyl)piperidin-4-yl)methoxy)-4'-(3-hydroxypiperidine-1-carbonyl)biphenyl-3-carbonitrile Compound 968: (S)-2'-fluoro-4-((1-(2-fluoro-2-methylpropyl)piperidin-4-yl)methoxy)-4'-(3-hydroxypiperidine-1-carbonyl)biphenyl-3-carbonitrile Compound 969: (S)-1-(3'-cyano-2-fluoro-4'-((1-(2-fluoro-2-methylpropyl)piperidin-4-yl)methoxy)biphenylcarbonyl)pyrrolidine-2-carboxamide Compound 970: (S)-(3-hydroxypyrrolidin-1-yl)(4-(2-((1-((1-(trifluoromethyl)cyclobutyl)methyl)piperidin-4-yl)methoxy)pyrimidin-5-yl)phenyl)methanone Compound 971: (R)-(2-(hydroxymethyl)pyrrolidin-1-yl)(4-(2-((1-((1-(trifluoromethyl)cyclobutyl)methyl)piperidin-4-yl)methoxy)pyrimidin-5-yl)phenyl)methanone Compound 972: (R)-(3-hydroxypiperidin-1-yl)(4-(2-((1-((1-(trifluoromethyl)cyclobutyl)methyl)piperidin-4-yl)methoxy)pyrimidin-5-yl)phenyl)methanone Compound 973: (S)-1-(4-(2-((1-((1-(trifluoromethyl)cyclobutyl)methyl)piperidin-4-yl)methoxy)pyrimidin-5-yl)benzoyl)pyrrolidine-2-carboxamide Compound 974: (S)-(3-fluoro-4-(2-((1-((1-(trifluoromethyl)cyclobutyl)methyl)piperidin-4-yl)methoxy)pyrimidin-5-yl)phenyl)(3-hydroxypyrrolidin-1-yl)methanone Compound 975: (R)-(3-fluoro-4-(2-((1-((1-(trifluoromethyl)cyclobutyl)methyl)piperidin-4-yl)methoxy)pyrimidin-5-yl)phenyl)(2-(hydroxymethyl)pyrrolidin-1-yl)methanone Compound 976: (R)-(3-fluoro-4-(2-((1-((1-(trifluoromethyl)cyclobutyl)methyl)piperidin-4-yl)methoxy)pyrimidin-5-yl)phenyl)(3-hydroxypiperidin-1-yl)methanone Compound 977: (S)-1-(3-fluoro-4-(2-((1-((1-(trifluoromethyl)cyclobutyl)methyl)piperidin-4-yl)methoxy)pyrimidin-5-yl)benzoyl)pyrrolidine-2-carboxamide Compound 978: (S)-(2-fluoro-4-(2-((1-((1-(trifluoromethyl)cyclobutyl)methyl)piperidin-4-yl)methoxy)pyrimidin-5-yl)phenyl)(3-hydroxypyrrolidin-1-yl)methanone Compound 979: (R)-(2-fluoro-4-(2-((1-((1-(trifluoromethyl)cyclobutyl)methyl)piperidin-4-yl)methoxy)pyrimidin-5-yl)phenyl)(2-(hydroxymethyl)pyrrolidin-1-yl)methanone Compound 980: (R)-(2-fluoro-4-(2-((1-((1-(trifluoromethyl)cyclobutyl)methyl)piperidin-4-yl)methoxy)pyrimidin-5-yl)phenyl)(3-hydroxypiperidin-1-yl)methanone Compound 981: (S)-1-(2-fluoro-4-(2-((1-((1-(trifluoromethyl)cyclobutyl)methyl)piperidin-4-yl)methoxy)pyrimidin-5-yl)benzoyl)pyrrolidine-2-carboxamide Compound 982: (R)-(3-fluoro-4-(5-((1-(2-fluoro-2-methylpropyl)piperidin-4-yl)methoxy)pyrazin-2-yl)phenyl)(3-hydroxypiperidin-1-yl)methanone Compound 983: (S)-(3-fluoro-4-(5-((1-(2-fluoro-2-methylpropyl)piperidin-4-yl)methoxy)pyrazin-2-yl)phenyl)(3-hydroxypiperidin-1-yl)methanone Compound 984: (S)-(3-fluoro-4-(5-((1-(2-fluoro-2-methylpropyl)piperidin-4-yl)methoxy)pyrazin-2-yl)phenyl)(3-hydroxypyrrolidin-1-yl)methanone Compound 985: (R)-(3-fluoro-4-(5-((1-(2-fluoro-2-methylpropyl)piperidin-4-yl)methoxy)pyrazin-2-yl)phenyl)(2-(hydroxymethyl)pyrrolidin-1-yl)methanone Compound 986: (S)-(2-fluoro-4-(5-((1-(2-fluoro-2-methylpropyl)piperidin-4-yl)methoxy)pyrazin-2-yl)phenyl)(3-hydroxypiperidin-1-yl)methanone Compound 987: (S)-(2-fluoro-4-(5-((1-(2-fluoro-2-methylpropyl)piperidin-4-yl)methoxy)pyrazin-2-yl)phenyl)(3-hydroxypyrrolidin-1-yl)methanone Compound 988: (R)-(2-fluoro-4-(5-((1-(2-fluoro-2-methylpropyl)piperidin-4-yl)methoxy)pyrazin-2-yl)phenyl)(2-(hydroxymethyl)pyrrolidin-1-yl)methanone Compound 989: (S)-1-(4-(6-((1-(2-fluoro-2-methylpropyl)piperidin-4-yl)methoxy)pyridazin-3-yl)benzoyl)pyrrolidine-2-carboxamide Compound 990: (R)-(4-(6-((1-(2-fluoro-2-methylpropyl)piperidin-4-yl)methoxy)pyridazin-3-yl)phenyl)(3-hydroxypiperidin-1-yl)methanone Compound 991: (S)-1-(2-fluoro-4-(6-((1-(2-fluoro-2-methylpropyl)piperidin-4-yl)methoxy)pyridazin-3-yl)benzoyl)pyrrolidine-2-carboxamide Compound 992: (R)-(2-fluoro-4-(6-((1-(2-fluoro-2-methylpropyl)piperidin-4-yl)methoxy)pyridazin-3-yl)phenyl)(3-hydroxypiperidin-1-yl)methanone Compound 1000: (S)-1-(3'-cyano-4'-((1-(2-ethyl-2-fluorobutyl)piperidin-4-yl)methoxy)-3-fluorobiphenylcarbonyl)pyrrolidine-2-carboxamide Compound 1001: (R)-4-((1-(2-ethyl-2-fluorobutyl)piperidin-4-yl)methoxy)-3'-fluoro-4'-(3-hydroxypiperidine-1-carbonyl)biphenyl-3-carbonitrile Compound 1002: (R)-4-((1-(2-ethyl-2-fluorobutyl)piperidin-4-yl)methoxy)-3'-fluoro-4'-(2-(hydroxymethyl)pyrrolidine-1-carbonyl)biphenyl-3-carbonitrile Compound 1003: (S)-4-((1-(2-ethyl-2-fluorobutyl)piperidin-4-yl)methoxy)-3'-fluoro-4'-(3-hydroxypyrrolidine-1-carbonyl)biphenyl-3-carbonitrile Compound 1004: (S)-1-(3'-cyano-4'-((1-(2-ethyl-2-fluorobutyl)piperidin-4-yl)methoxy)biphenylcarbonyl)pyrrolidine-2-carboxamide Compound 1005: (R)-4-((1-(2-ethyl-2-fluorobutyl)piperidin-4-yl)methoxy)-4'-(2-(hydroxymethyl)pyrrolidine-1-carbonyl)biphenyl-3-carbonitrile Compound 1006: (S)-4-((1-(2-ethyl-2-fluorobutyl)piperidin-4-yl)methoxy)-4'-(3-hydroxypyrrolidine-1-carbonyl)biphenyl-3-carbonitrile Compound 1007: (R)-(2-(hydroxymethyl)pyrrolidin-1-yl)(4-(5-((1-((1-(trifluoromethyl)cyclobutyl)methyl)piperidin-4-yl)methoxy)pyrazin-2-yl)phenyl)methanone Compound 1008: (R)-(3-hydroxypiperidin-1-yl)(4-(5-((1-((1-(trifluoromethyl)cyclobutyl)methyl)piperidin-4-yl)methoxy)pyrazin-2-yl)phenyl)methanone Compound 1009: (S)-1-(4-(5-((1-((1-(trifluoromethyl)cyclobutyl)methyl)piperidin-4-yl)methoxy)pyrazin-2-yl)benzoyl)pyrrolidine-2-carboxamide Compound 1010: (R)-(3-fluoro-4-(5-((1-((1-(trifluoromethyl)cyclobutyl)methyl)piperidin-4-yl)methoxy)pyrazin-2-yl)phenyl)(3-hydroxypiperidin-1-yl)methanone Compound 1011: (S)-1-(3-fluoro-4-(5-((1-((1-(trifluoromethyl)cyclobutyl)methyl)piperidin-4-yl)methoxy)pyrazin-2-yl)benzoyl)pyrrolidine-2-carboxamide Compound 1012: (R)-(2-fluoro-4-(5-((1-((1-(trifluoromethyl)cyclobutyl)methyl)piperidin-4-yl)methoxy)pyrazin-2-yl)phenyl)(2-(hydroxymethyl)pyrrolidin-1-yl)methanone Compound 1013: (R)-(2-fluoro-4-(5-((1-((1-(trifluoromethyl)cyclobutyl)methyl)piperidin-4-yl)methoxy)pyrazin-2-yl)phenyl)(3-hydroxypiperidin-1-yl)methanone Compound 1014: (S)-1-(2-fluoro-4-(5-((1-((1-(trifluoromethyl)cyclobutyl)methyl)piperidin-4-yl)methoxy)pyrazin-2-yl)benzoyl)pyrrolidine-2-carboxamide Compound 1015: (R)-1-(3'-cyano-3-fluoro-4'-((1-(2-fluoro-2-methylpropyl)piperidin-4-yl)methoxy)biphenylcarbonyl)piperidine-2-carboxamide Compound 1016: (S)-3'-fluoro-4-((1-(2-fluoro-2-methylpropyl)piperidin-4-yl)methoxy)-4'-(3-hydroxypiperidine-1-carbonyl)biphenyl-3-carbonitrile Compound 1017: (S)-3'-fluoro-4-((1-(2-fluoro-2-methylpropyl)piperidin-4-yl)methoxy)-4'-(3-hydroxypyrrolidine-1-carbonyl)biphenyl-3-carbonitrile Compound 1018: (S)-1-(4-(5-((1-(2-ethyl-2-fluorobutyl)piperidin-4-yl)methoxy)pyrazin-2-yl)benzoyl)pyrrolidine-2-carboxamide Compound 1020: (S)-(3-hydroxypyrrolidin-1-yl)(4'-((1-((1-(trifluoromethyl)cyclobutyl)methyl)piperidin-4-yl)methylamino)biphenyl-4-yl)methanone Compound 1021: (S)-1-(4'-((1-((1-(trifluoromethyl)cyclobutyl)methyl)piperidin-4-yl)methylamino)biphenylcarbonyl)pyrrolidine-2-carboxamide Compound 1022: (S)-(3-hydroxypiperidin-1-yl)(4'-((1-((1-(trifluoromethyl)cyclobutyl)methyl)piperidin-4-yl)methylamino)biphenyl-4-yl)methanone Compound 1023: (R)-1-(4'-((1-((1-(trifluoromethyl)cyclobutyl)methyl)piperidin-4-yl)methylamino)biphenylcarbonyl)piperidine-2-carboxamide Compound 1024: (S)-(3-hydroxypyrrolidin-1-yl)(4'-((1-(3,3,3-trifluoro-2,2-dimethylpropyl)piperidin-4-yl)methylamino)biphenyl-4-yl)methanone Compound 1025: (S)-1-(4'-((1-(3,3,3-trifluoro-2,2-dimethylpropyl)piperidin-4-yl)methylamino)biphenylcarbonyl)pyrrolidine-2-carboxamide Compound 1026: (S)-(3-hydroxypiperidin-1-yl)(4'-((1-(3,3,3-trifluoro-2,2-dimethylpropyl)piperidin-4-yl)methylamino)biphenyl-4-yl)methanone Compound 1028: (S)-1-(2'-cyano-3-fluoro-4'-((1-(2-fluoro-2-methylpropyl)piperidin-4-yl)methoxy)biphenylcarbonyl)pyrrolidine-2-carboxamide Compound 1029: (R)-3'-fluoro-4-((1-(2-fluoro-2-methylpropyl)piperidin-4-yl)methoxy)-4'-(3-hydroxypiperidine-1-carbonyl)biphenyl-2-carbonitrile Compound 1030: (R)-1-(2'-cyano-3-fluoro-4'-((1-(2-fluoro-2-methylpropyl)piperidin-4-yl)methoxy)biphenylcarbonyl)piperidine-2-carboxamide Compound 1031: (S)-1-(2'-cyano-4'-((1-(2-fluoro-2-methylpropyl)piperidin-4-yl)methoxy)biphenylcarbonyl)pyrrolidine-2-carboxamide Compound 1032: (S)-1-(2-fluoro-4-(5-((1-(2-fluoro-2-methylpropyl)piperidin-4-yl)methoxy)pyrimidin-2-yl)benzoyl)pyrrolidine-2-carboxamide Compound 1033: (R)-(2-fluoro-4-(5-((1-(2-fluoro-2-methylpropyl)piperidin-4-yl)methoxy)pyrimidin-2-yl)phenyl)(3-hydroxypiperidin-1-yl)methanone Compound 1034: (S)-(2-fluoro-4-(5-((1-(2-fluoro-2-methylpropyl)piperidin-4-yl)methoxy)pyrimidin-2-yl)phenyl)(3-hydroxypiperidin-1-yl)methanone Compound 1035: (R)-(2-fluoro-4-(5-((1-(2-fluoro-2-methylpropyl)piperidin-4-yl)methoxy)pyrimidin-2-yl)phenyl)(3-hydroxypyrrolidin-1-yl)methanone Compound 1036: (S)-1-(5-(3-cyano-4-((1-(2-fluoro-2-methylpropyl)piperidin-4-yl)methoxy)phenyl)picolinoyl)pyrrolidine-2-carboxamide Compound 1037: (R)-1-(2-fluoro-4-(5-((1-(2-fluoro-2-methylpropyl)piperidin-4-yl)methoxy)pyrimidin-2-yl)benzoyl)piperidine-2-carboxamide Compound 1038: (S)-1-(5-(4-((1-(2-fluoro-2-methylpropyl)piperidin-4-yl)methoxy)phenyl)pyrazine-2-carbonyl)pyrrolidine-2-carboxamide Compound 1051: (S)-1-(4-(5-((1-(2-ethyl-2-fluorobutyl)piperidin-4-yl)methoxy)pyrimidin-2-yl)benzoyl)pyrrolidine-2-carboxamide Compound 1052: (R)-(4-(5-((1-(2-ethyl-2-fluorobutyl)piperidin-4-yl)methoxy)pyrimidin-2-yl)phenyl)(3-hydroxypiperidin-1-yl)methanone Compound 1053: (R)-1-(4-(5-((1-(2-ethyl-2-fluorobutyl)piperidin-4-yl)methoxy)pyrimidin-2-yl)benzoyl)piperidine-2-carboxamide Compound 1054: (S)-1-(4-(5-((1-(2-ethyl-2-fluorobutyl)piperidin-4-yl)methoxy)pyrimidin-2-yl)-2-fluorobenzoyl)pyrrolidine-2-carboxamide Compound 1055: (R)-1-(4-(5-((1-(2-ethyl-2-fluorobutyl)piperidin-4-yl)methoxy)pyrimidin-2-yl)-2-fluorobenzoyl)piperidine-2-carboxamide Compound 1056: (R)-(4-(5-((1-(2-ethyl-2-fluorobutyl)piperidin-4-yl)methoxy)pyrimidin-2-yl)-3-fluorophenyl)(3-hydroxypiperidin-1-yl)methanone Compound 1057: (R)-1-(4-(5-((1-(2-ethyl-2-fluorobutyl)piperidin-4-yl)methoxy)pyrimidin-2-yl)-3-fluorobenzoyl)piperidine-2-carboxamide Compound 1067: (2S,4R)-1-(2-fluoro-4-(5-((1-(2-fluoro-2-methylpropyl)piperidin-4-yl)methoxy)pyridin-2-yl)benzoyl)-4-hydroxypyrrolidine-2-carboxamide Compound 1072: (S)-1-(3-fluoro-4-(5-((1-(2-fluoro-2-methylpropyl)piperidin-4-yl)methoxy)pyrazin-2-yl)benzoyl)pyrrolidine-2-carboxamide Compound 1073: (R)-1-(3-fluoro-4-(5-((1-(2-fluoro-2-methylpropyl)piperidin-4-yl)methoxy)pyrazin-2-yl)benzoyl)piperidine-2-carboxamide Compound 1076: (R)-1-(4-(6-((1-(2-fluoro-2-methylpropyl)piperidin-4-yl)methoxy)pyridin-3-yl)benzoyl)piperidine-2-carboxamide Compound 1077: (R)-(4-(6-((1-(2-fluoro-2-methylpropyl)piperidin-4-yl)methoxy)pyridin-3-yl)phenyl) (3-hydroxypyrrolidin-1-yl)methanone Compound 1078: (S)-(4-(6-((1-(2-fluoro-2-methylpropyl)piperidin-4-yl)methoxy)pyridin-3-yl)phenyl) (3-hydroxypyrrolidin-1-yl)methanone Compound 1079: (S)-1-(4-(6-((1-(2-fluoro-2-methylpropyl)piperidin-4-yl)methoxy)pyridin-3-yl)benzoyl)piperidine-2-carboxamide Compound 1080: (R)-1-(4-(5-((1-(2-fluoro-2-methylpropyl)piperidin-4-yl)methoxy)pyrazin-2-yl)benzoyl)piperidine-2-carboxamide Compound 1081: (S)-1-(4-(5-((1-(2-fluoro-2-methylpropyl)piperidin-4-yl)methoxy)pyrazin-2-yl)benzoyl)piperidine-2-carboxamide Compound 1082: (S)-1-(5-(2-fluoro-4-((1-(2-fluoro-2-methylpropyl)piperidin-4-yl)methoxy)phenyl)pyrazine-2-carbonyl)pyrrolidine-2-carboxamide Compound 1097: (2S,4S)-4-fluoro-1-(3-fluoro-4'-((1-(2-fluoro-2-methylpropyl)piperidin-4-yl)methoxy)biphenylcarbonyl)pyrrolidine-2-carbonitrile Compound 1098: (2S,4R)-1-(3-fluoro-4'-((1-(2-fluoro-2-methylpropyl)piperidin-4-yl)methoxy)biphenylcarbonyl)-4-hydroxypyrrolidine-2-carbonitrile Compound 1099: (2S,4S)-4-fluoro-1-(3-fluoro-4'-((1-(2-fluoro-2-methylpropyl)piperidin-4-yl)methoxy)biphenylcarbonyl)pyrrolidine-2-carboxamide Compound 1100: (2S,4R)-1-(3-fluoro-4'-((1-(2-fluoro-2-methylpropyl)piperidin-4-yl)methoxy)biphenylcarbonyl)-4-hydroxypyrrolidine-2-carboxamide Compound 1115: 3'-fluoro-4-((1-(2-fluoro-2-methylpropyl)piperidin-4-yl)methoxy)-4'-(4-hydroxypiperidine-1-carbonyl)biphenyl-2-carbonitrile Compound 1119: (S)-1-(3'-cyano-4'-((1-(2-ethyl-2-fluorobutyl)piperidin-4-yl)methoxy)-2-fluorobiphenylcarbonyl)pyrrolidine-2-carboxamide Compound 1120: (R)-1-(3'-cyano-4'-((1-(2-ethyl-2-fluorobutyl)piperidin-4-yl)methoxy)-2-fluorobiphenylcarbonyl)piperidine-2-carboxamide Compound 1121: (S)-4-((1-(2-ethyl-2-fluorobutyl)piperidin-4-yl)methoxy)-2'-fluoro-4'-(3-hydroxypyrrolidine-1-carbonyl)biphenyl-3-carbonitrile Compound 1123: (R)-4-((1-(2-ethyl-2-fluorobutyl)piperidin-4-yl)methoxy)-2'-fluoro-4'-(3-hydroxypiperidine-1-carbonyl)biphenyl-3-carbonitrile Compound 1124: (S)-1-(2'-cyano-4'-((1-(2-ethyl-2-fluorobutyl)piperidin-4-yl)methoxy)biphenylcarbonyl)pyrrolidine-2-carboxamide Compound 1125: (R)-1-(2'-cyano-4'-((1-(2-ethyl-2-fluorobutyl)piperidin-4-yl)methoxy)biphenylcarbonyl)piperidine-2-carboxamide; and Compound 1126: (R)-4-((1-(2-ethyl-2-fluorobutyl)piperidin-4-yl)methoxy)-4'-(3-hydroxypiperidine-1-carbonyl)biphenyl-2-carbonitrile.

Specific examples of more preferred compounds of formula 1 according to the present invention include:

Compound 770: (S)-1-(2-fluoro-4-(5-((1-(2-fluoro-2-methylpropyl)piperidin-4-yl)methoxy)pyridin-2-yl)benzoyl)pyrrolidine-2-carboxamide;

Compound 896: (S)-1-(4-(5-((1-(2-ethyl-2-fluorobutyl)piperidin-4-yl)methoxy)pyridin-2-yl)benzoyl)pyrrolidine-2-carboxamide;

Compound 938: (S)-1-(3'-cyano-3-fluoro-4'-((1-(2-fluoro-2-methylpropyl)piperidin-4-yl)methoxy)biphenylcarbonyl)pyrrolidine-2-carboxamide;

Compound 1028: (S)-1-(2'-cyano-3-fluoro-4'-((1-(2-fluoro-2-methylpropyl)piperidin-4-yl)methoxy)biphenylcarbonyl)pyrrolidine-2-carboxamide; and Compound 1032: (S)-1-(2-fluoro-4-(5-((1-(2-fluoro-2-methylpropyl)piperidin-4-yl)methoxy)pyrimidin-2-yl)benzoyl)pyrrolidine-2-carboxamide.

The present invention also provides pharmaceutical composition comprising the piperidine derivative of the formula 1, stereoisomers thereof, or pharmaceutically acceptable salts thereof; and pharmaceutically acceptable carriers thereof.

Preferably, the composition is used for treatment of a disease associated with GPR119 agonist.

Preferably, said disease associated with GPR119 agonist is diabetes mellitus, and more preferably, Type II diabetes mellitus.

Advantageous Effects

The present invention can provide a novel piperidine derivative, stereoisomers thereof, and pharmaceutically acceptable salts thereof.

In addition, the present invention can provide a novel piperidine derivative being able to control GPR119 activity with low adverse effect, stereoisomers thereof, and pharmaceutically acceptable salts thereof.

Synthetic Schemes

The intermediate 5 can be synthesized according to the following reaction schemes 1 and 2.

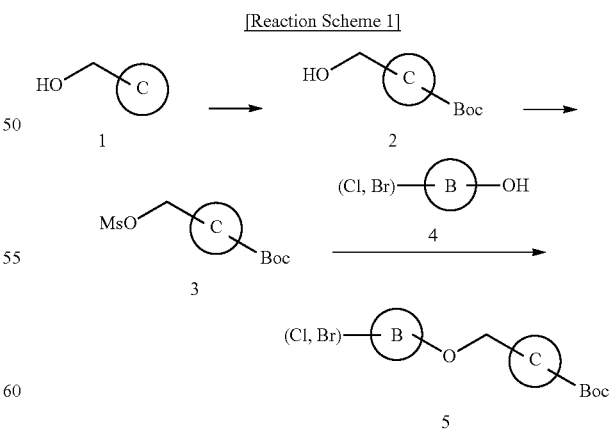

[Reaction Scheme 1]

As shown in the reaction scheme 1, Boc protecting group is introduced into the amine of compound 1. Hydroxyl group is activated with MsCl, and substituted with aryl alcohol of formula 4 to synthesize the desired compound of formula 5.

[Reaction Scheme 2]

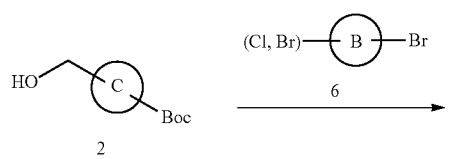

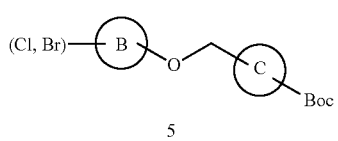

As shown in the reaction scheme 2, bromo or chloro compound 6 is substituted with compound 2 to prepare compound 5.

The intermediate 8 can be synthesized according to the following reaction scheme 3.

[Reaction Scheme 3]

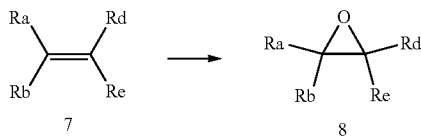

As shown in the reaction scheme 3, compound 8 is prepared through the oxidation reaction of compound 7.

The intermediate 13 can be synthesized according to the following reaction schemes 4, 5 and 6.

[Reaction Scheme 4]

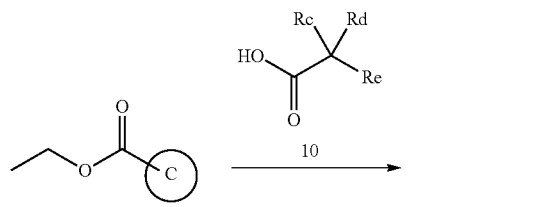

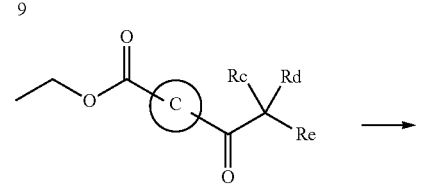

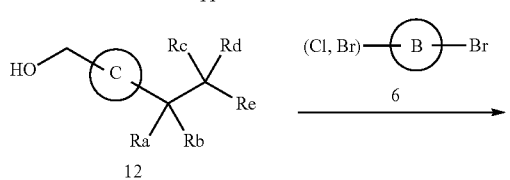

-continued

As shown in the reaction scheme 4, compound 11 is prepared by amide bond formation of compound 9 with compound 10, and then subjected to reduction thereby to obtain compound 12. Finally, the intermediate 13 is prepared through the substitution reaction of compound 12.

[Reaction Scheme 5]

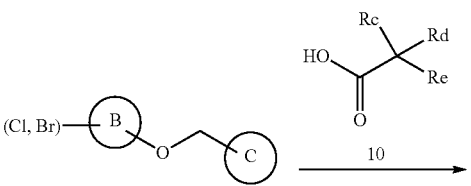

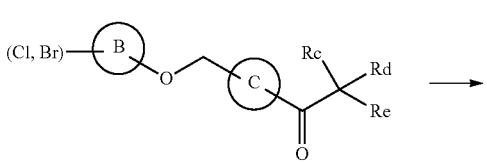

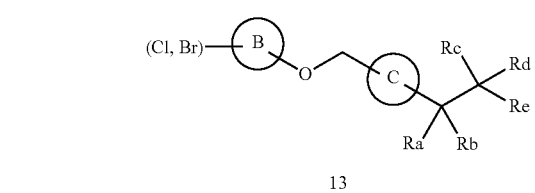

As shown in the reaction scheme 5, the protecting group of compound 5 is removed, and subjected to the formation of amide bond with compound 10 to prepare compound 15. Finally, compound 13 is prepared through reduction.

[Reaction Scheme 6]

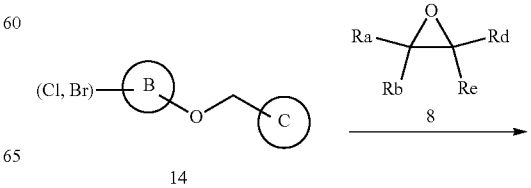

-continued

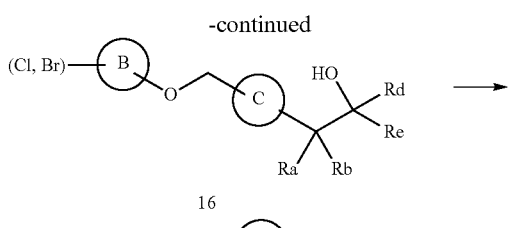

16

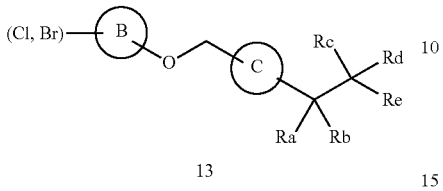

13

As shown in the reaction scheme 6, compound 16 is prepared using compound 14 and oxirane compound 8, and then hydroxyl group of compound 16 is substituted with fluoride to prepare compound 13.

The compounds 21 and 23 that Q is —S(O)₂R₁ in formula 1 can be synthesized according to the following reaction schemes 7, 8, 9, 10, 11 and 12.

[Reaction Scheme 7]

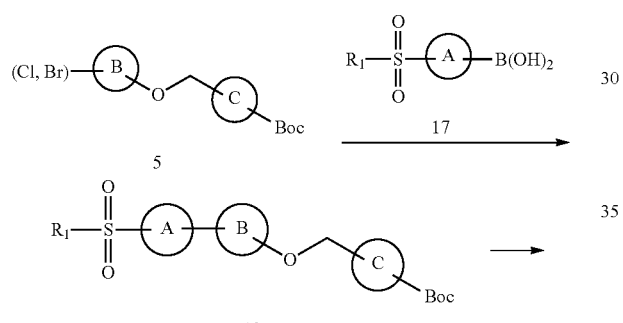

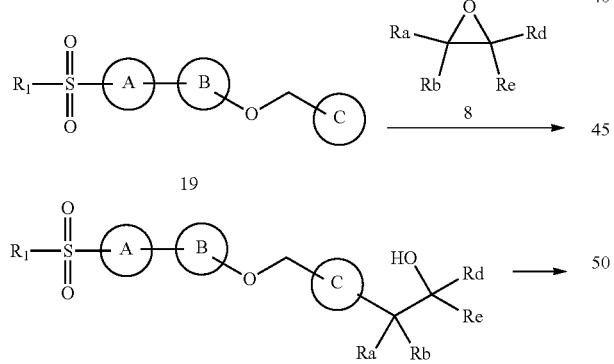

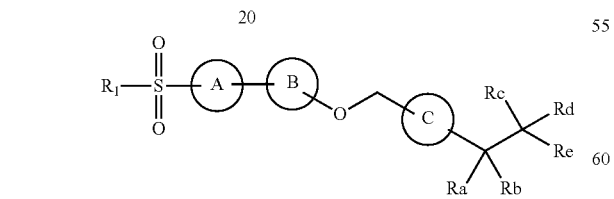

As shown in the reaction scheme 7, compound 18 is prepared through the Suzuki coupling reaction of compound 5 with boronic acid compound 17. The protection group of compound 18 is removed using acid, and reacted with oxirane compound 8 to obtain compound 20. Finally, hydroxyl group of compound 20 is substituted with fluoride to prepare compound 21.

[Reaction Scheme 8]

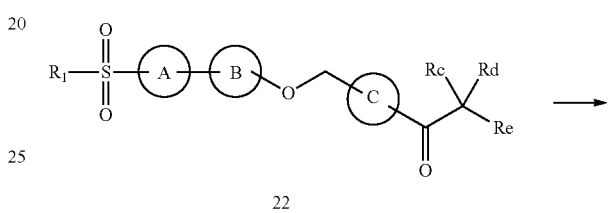

As shown in the reaction scheme 8, compound 22 is prepared by amide bond formation of compounds 19 and 10, and then subjected to reduction to prepare compound 21.

[Reaction Scheme 9]

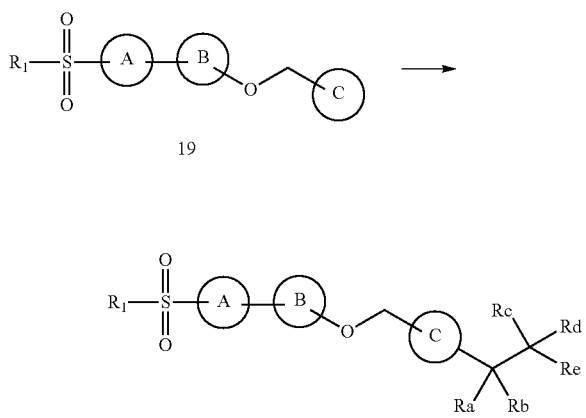

As shown in the reaction scheme 9, compound 19 is reacted with 2,2,2-trifluoroethyl trifluoromethanesulfonate to obtain compound 23.

[Reaction Scheme 10]

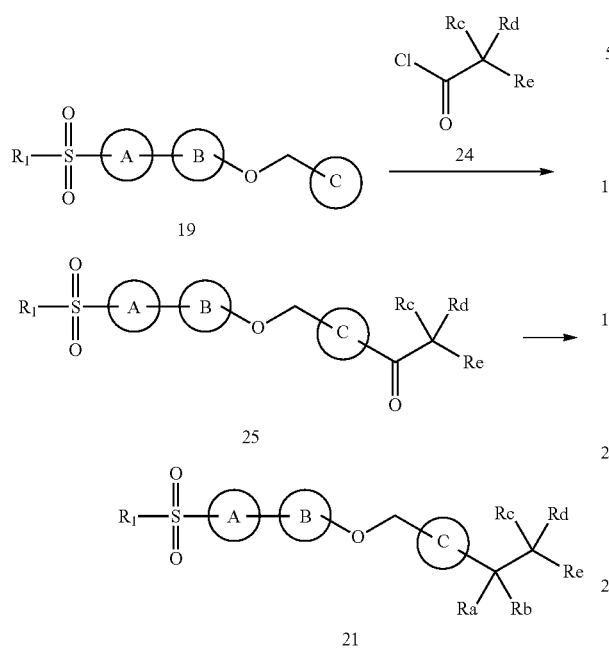

As shown in the reaction scheme 10, compound 25 is prepared by amide bond formation of compounds 19 and 24, and subjected to the reduction to prepare compound 21.

[Reaction Scheme 11]

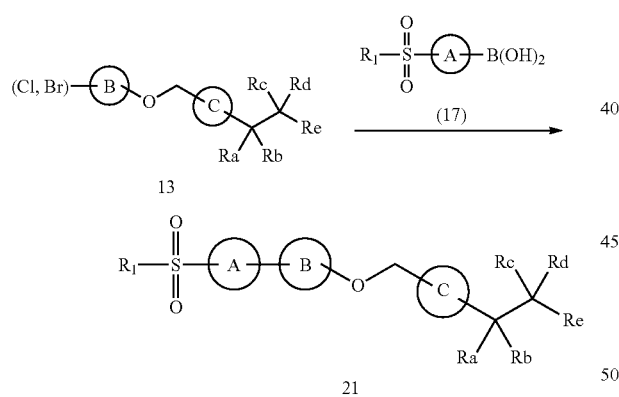

As shown in the reaction scheme 11, compound 13 is subjected to Suzuki coupling reaction with boronic acid compound 17 to prepare compound 21.

[Reaction Scheme 12]

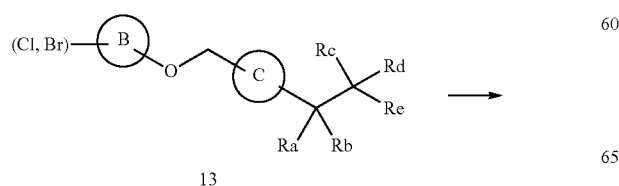

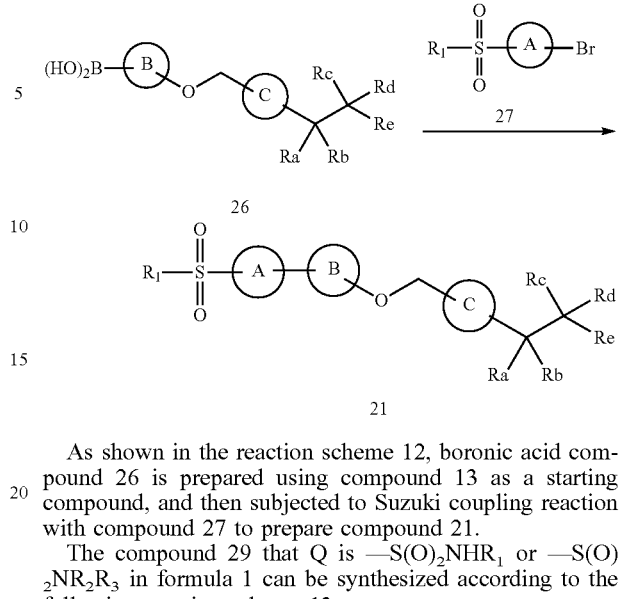

As shown in the reaction scheme 12, boronic acid compound 26 is prepared using compound 13 as a starting compound, and then subjected to Suzuki coupling reaction with compound 27 to prepare compound 21.

The compound 29 that Q is —S(O)$_2$NHR$_1$ or —S(O)$_2$NR$_2$R$_3$ in formula 1 can be synthesized according to the following reaction scheme 13.

[Reaction Scheme 13]

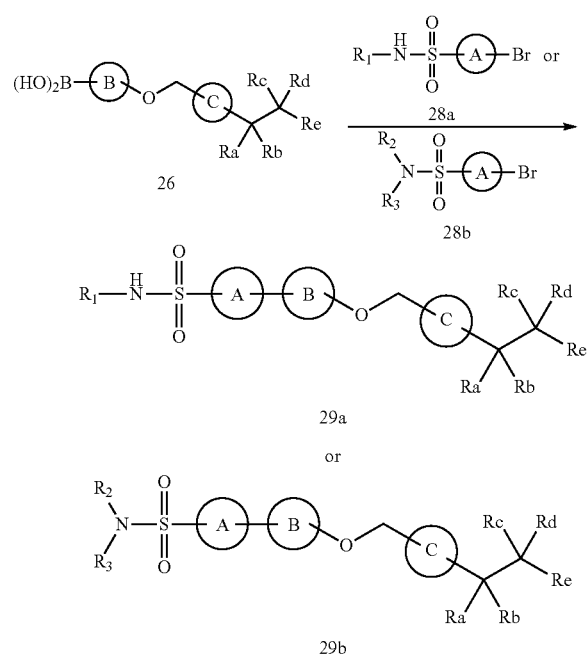

As shown in the reaction scheme 13, compound 26 is subjected to Suzuki coupling reaction with compound 28 to prepare compound 29.

The compound 38 that the ring A is in formula 1 can be synthesized according to the following reaction schemes 14 and 15.

oxirane compound 8 to prepare compound 37. Finally, hydroxyl group of compound 37 is substituted with fluoride to obtain compound 38.

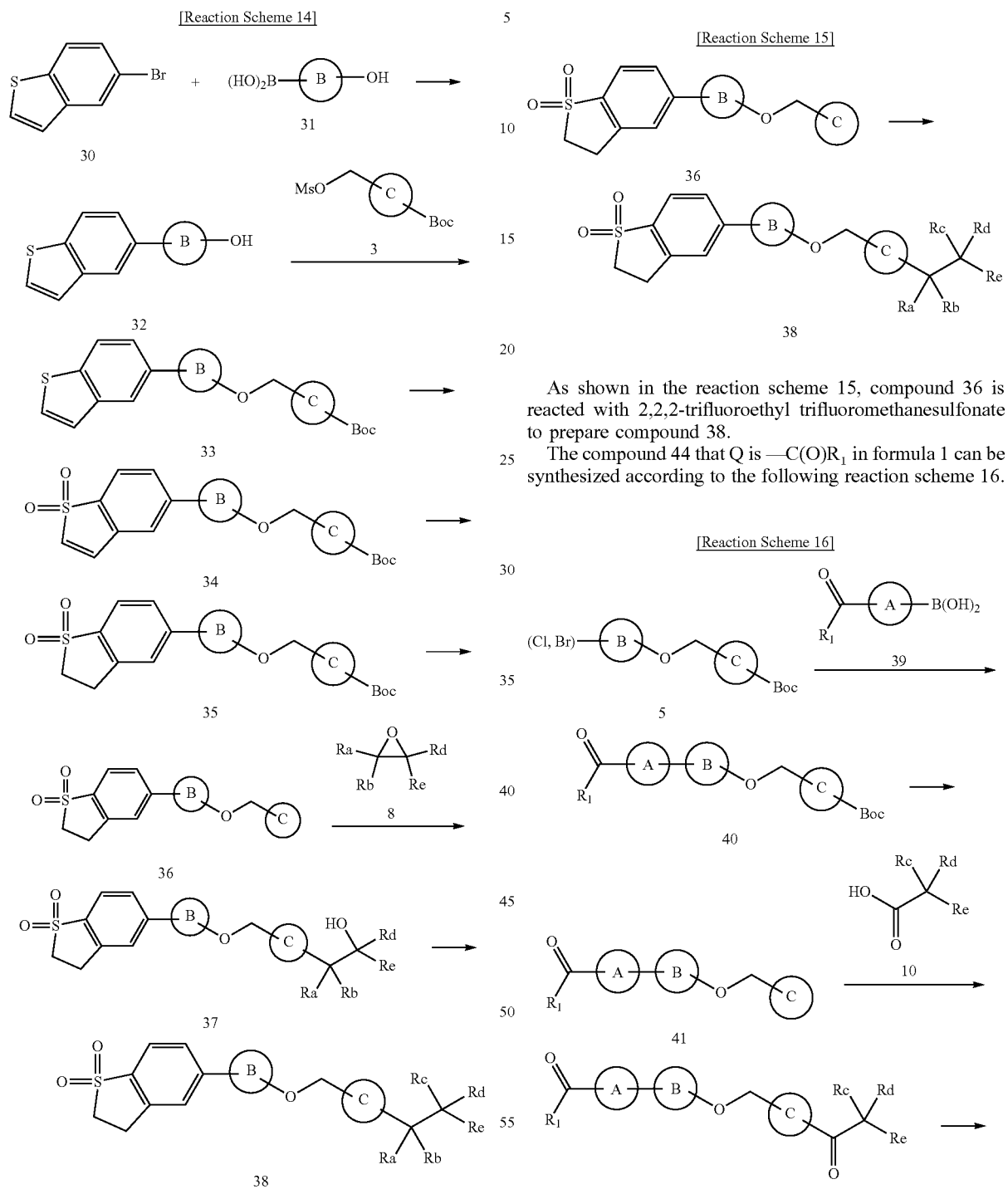

As shown in the reaction scheme 15, compound 36 is reacted with 2,2,2-trifluoroethyl trifluoromethanesulfonate to prepare compound 38.

The compound 44 that Q is —C(O)R₁ in formula 1 can be synthesized according to the following reaction scheme 16.

As shown in the reaction scheme 14, compound 30 is subjected to Suzuki coupling reaction with compound 31 to prepare compound 32. Compound 33 is prepared through the substitution reaction of compound 32 with compound 3, and subjected to the oxidation and hydrogenation reactions to prepare compound 35. The protecting group of compound 35 is removed with acid, following with reaction with

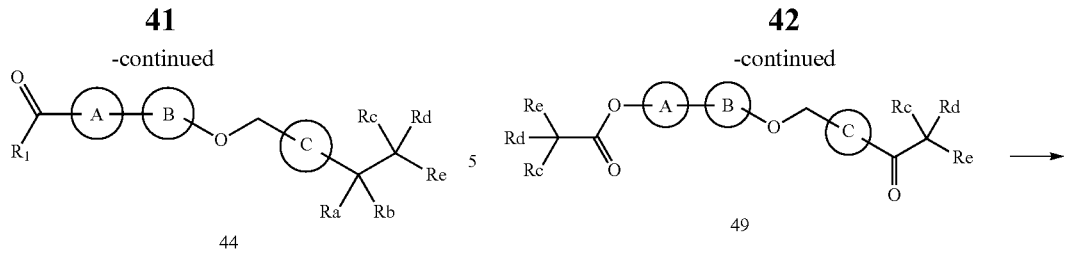

As shown in the reaction scheme 16, compound 5 is subjected to Suzuki coupling reaction with compound 39 to prepare compound 40. The protecting group of compound 40 is removed using acid, following with the formation of amide bond with compound 10 to prepare compound 42. The carbonyl group of amide in compound 42 is removed through reduction, and then, in order to re-introducing the undesired reduced keton group, following with oxidation to obtain compound 44.

The intermediate 46 can be synthesized according to the following reaction schemes 17, 18, 19 and 20.

[Reaction Scheme 17]

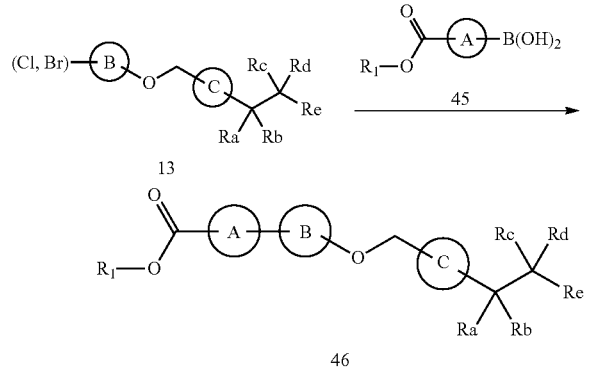

As shown in the reaction scheme 17, compound 13 is subjected to Suzuki coupling reaction with boronic acid compound 45 to prepare compound 46.

As shown in the reaction scheme 18, compound 5 is subjected to Suzuki coupling reaction with boronic acid compound 31 to prepare compound 47. The protecting group is removed using acid, following with the formation of amide bond with compound 10 to prepare compound 49. Through the reduction, the removal of carbonyl group from amide and the reduction of ester group proceeds at the same time, and then the formed hydroxyl group is activated with triflate group to prepare compound 51. Finally, compound 46 is synthesized using palladium catalyst and CO gas.

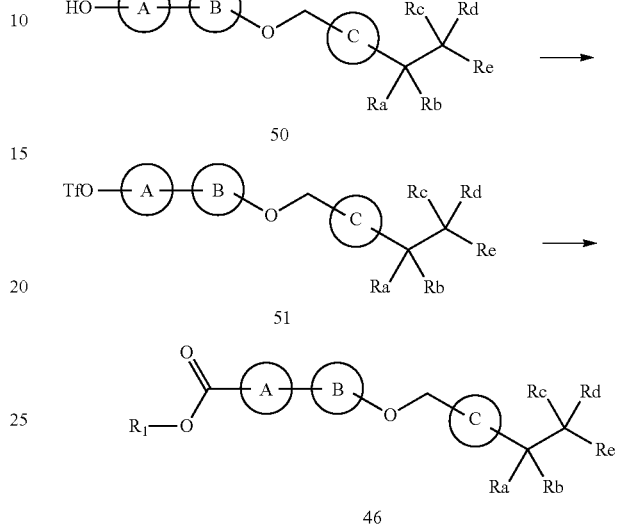

[Reaction Scheme 18]

[Reaction Scheme 19]

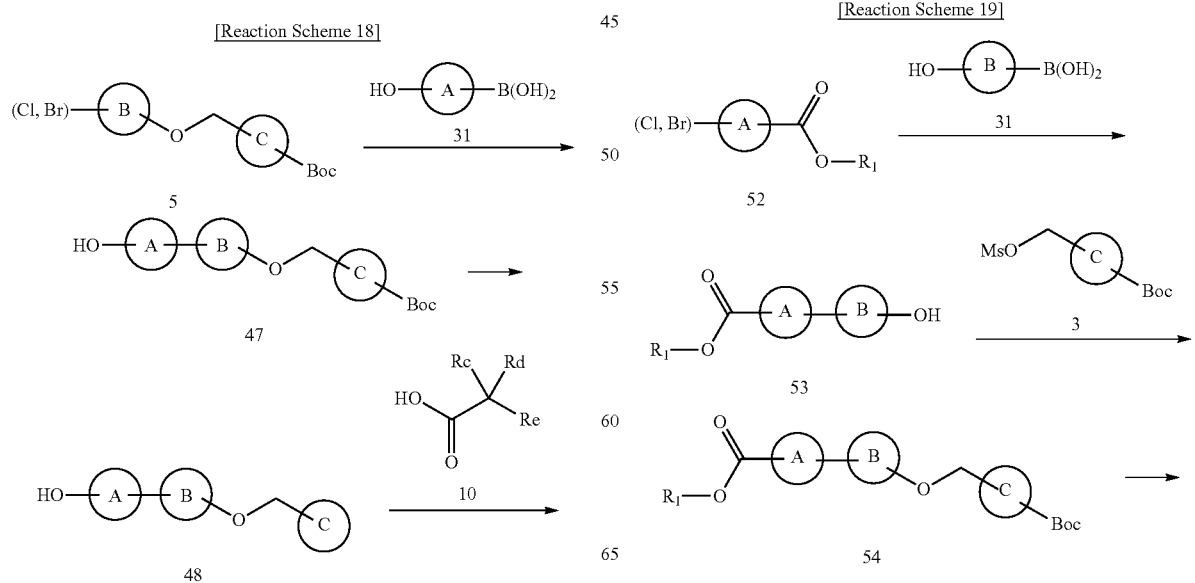

43

-continued

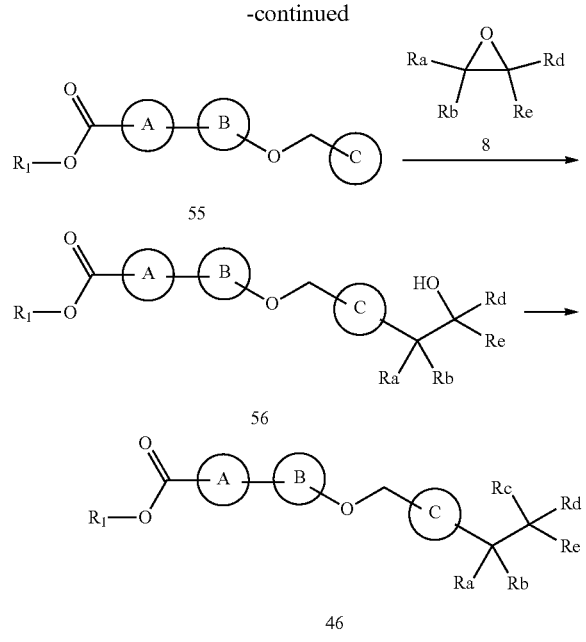

As shown in the reaction scheme 19, compound 52 is subjected to Suzuki coupling reaction with boronic acid compound 31 to prepare compound 53. Compound 53 is subjected to the substitution reaction with compound 3 to prepare compound 54. The protecting group of compound 54 is removed. The obtained compound 55 is reacted with oxirane compound 8 to prepare compound 56. Hydroxyl group of compound 56 is substituted with fluoride to obtained compound 46.

[Reaction Scheme 20]

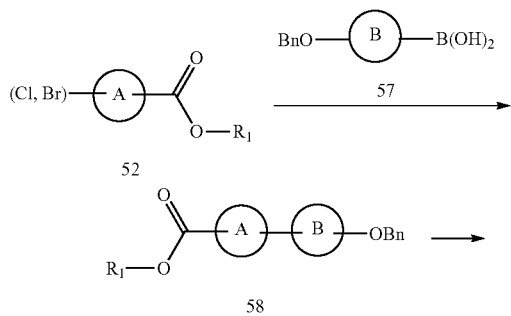

44

-continued

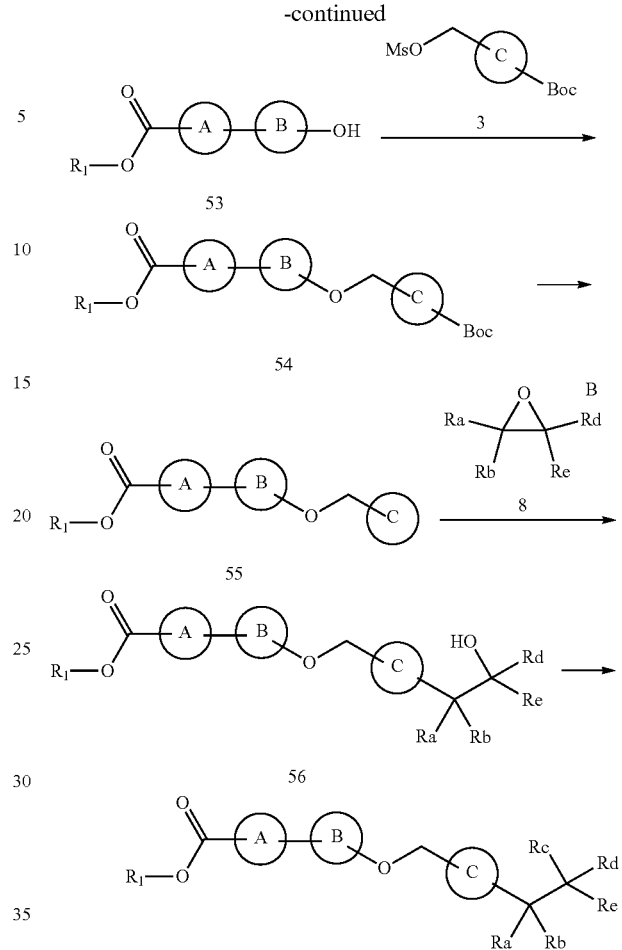

As shown in the reaction scheme 20, compound 52 is subjected to Suzuki coupling reaction with boronic acid compound 57 to prepare compound 58. Using palladium and hydrogen; compound 53 is synthesized, and then subjected to the substitution reaction with compound 3 to prepare compound 54. After removal of the protecting group from compound 54, compound 55 is reacted with oxirane compound 8 to prepare compound 56. Hydroxyl group of compound 56 is substituted with fluoride to obtain compound 46.

The compound 61 that Q is —C(O)NHR$_1$ or —C(O)NR$_2$R$_3$ in formula 1 can be synthesized according to the following reaction scheme 21.

[Reaction Scheme 21]

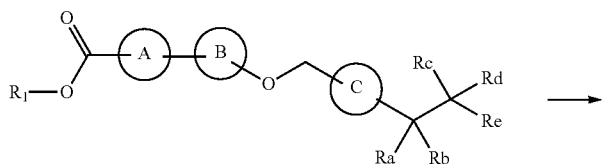

-continued

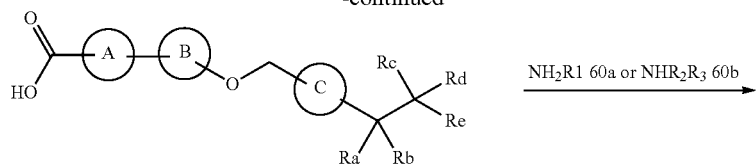

59

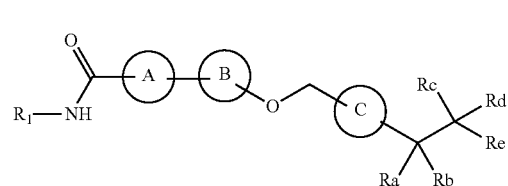

61a or

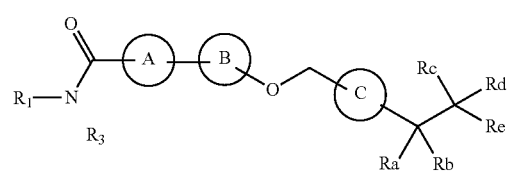

61b

As shown in the reaction scheme 21, compound 46 is hydrolyzed to prepare compound 59. Finally, compound 59 is subjected to the formation of amide bond with amine compound 60 to prepare compound 61a or compound 61b.

The intermediate 68 can be synthesized according to the following reaction scheme 22 and 23.

[Reaction Scheme 22]

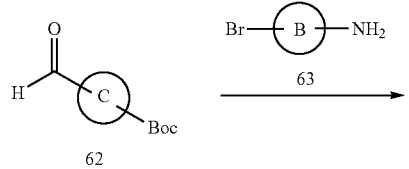

62

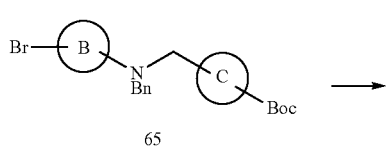

64

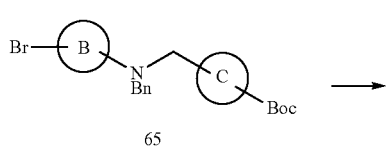

65

-continued

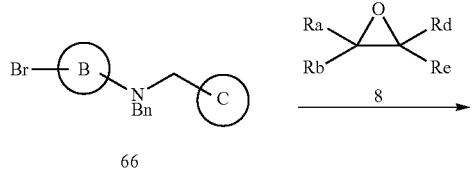

66

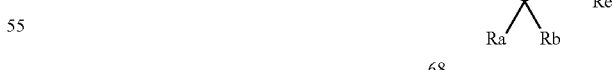

67

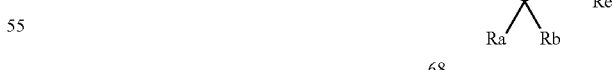

68

As shown in the reaction scheme 22, compound 62 is subjected to the reduction amination with compound 63 to prepare compound 64. Protecting group is introduced into the secondary amine of compound 64 to prepare compound 65. The protecting group of compound 65 is removed, following with the reaction with oxirane compound 8 to prepare compound 67. Finally, hydroxyl group of compound 67 is substituted with fluoride to prepare compound 68.

[Reaction Scheme 23]
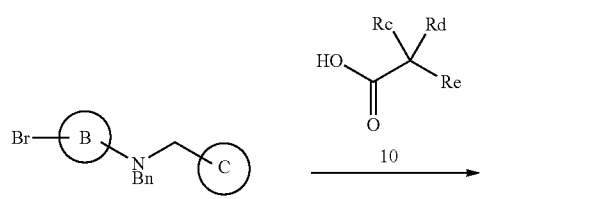
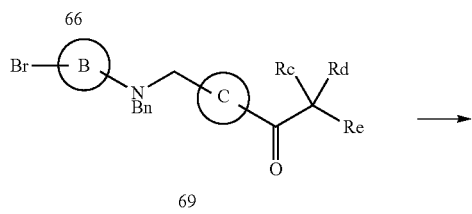
-continued
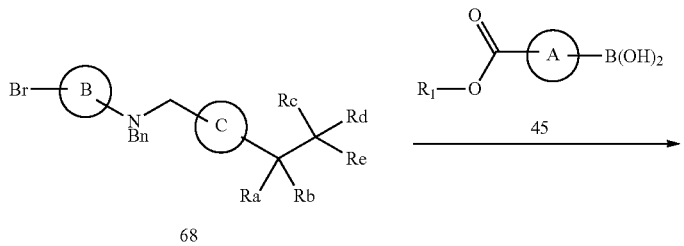
As shown in the reaction scheme 23, compound 66 is subjected to the formation of amide bond with compound 10 to prepare compound 69, following with a reduction to obtain compound 68.
The compounds 72 and 73 that Q is —C(O)NHR$_1$ or —C(O)NR$_2$R$_3$ in formula 1 can be synthesized according to the following reaction schemes 24 and 25.
[Reaction Scheme 24]
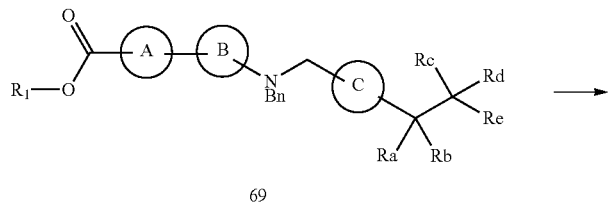
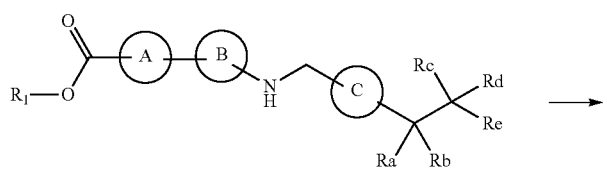
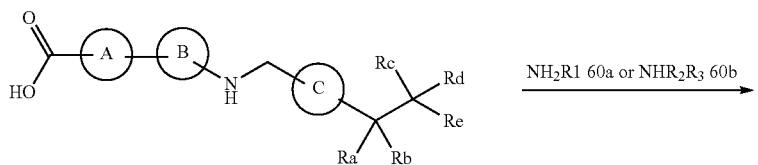

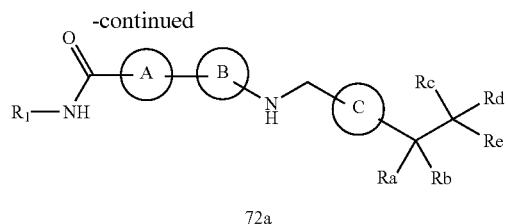

72a or

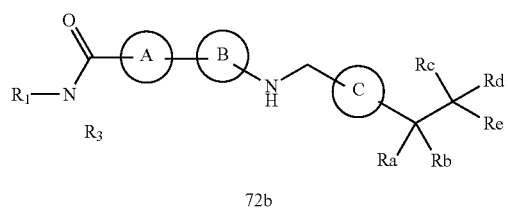

72b

As shown in the reaction scheme 24, compound 68 is subjected to Suzuki coupling reaction with boronic acid compound 45 to prepare compound 69. Secondary amine of compound 69 is removed to prepare compound 70. And then, compound 71 is prepared through the hydrolysis of compound 70, and subjected to the formation of amide bond with amine compound 60 to prepare compound 72.

[Reaction Scheme 25]

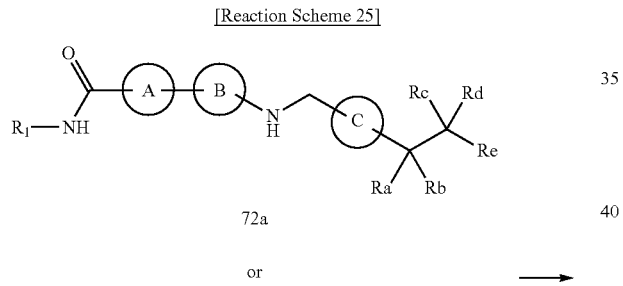

72a or

72b

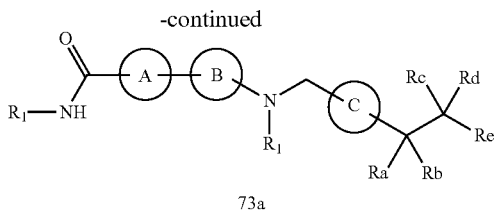

73a or

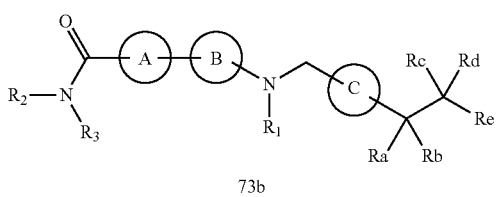

73b

As shown in the reaction scheme 25, compound 72 is subjected to the reduction amination with an aldehyde to prepare compound 73.

The compound 77 that Q or —C(O)NR$_2$R$_3$ in formula 1 can be synthesized according to the following reaction scheme 26

[Reaction Scheme 26]

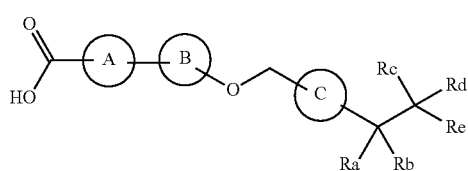 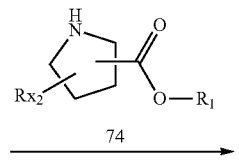

59

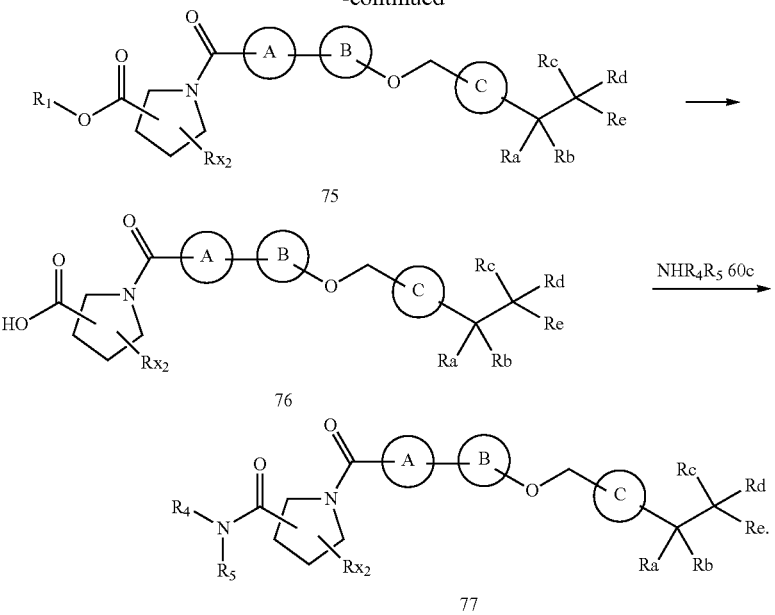

As shown in the reaction scheme 26, compound 59 is subjected to the formation of amide bond with amine compound 74 to prepare compound 75. Compound 75 is hydrolyzed to prepare compound 76. And compound 76 is subjected to the formation of amide bond with amine compound 60 to prepare compound 77.

ABBREVIATIONS

The following abbreviations and terms have the indicated meanings throughout:
Ac=acetyl
Boc=t-butoxycarbonyl
BOP=benzotriazol-1-yloxy-tris(dimethylamino)phosphonium hexafluorophosphate
Bu=butyl
DAST=diethylaminosulfur trifluoride
DCM=dichloromethane=methylene chloride=MC=CH$_2$Cl$_2$
DIPEA=N,N-diisopropylethylamine
DME=dimethoxyethane
DMF=N,N-dimethylformamide
DMSO=dimethyl sulfoxide
dppp=1,3-Bis(diphenylphosphino)propane
EDC=1-ethyl-3-(3-dimethylaminopropyl)carbodiimide=EDCI
Et=ethyl
EtOAc=ethyl acetate=EA
EtOH=ethanol
HOBt=1-hydroxybenzotriazole
HX=hexane
LAH=lithium aluminium hydride
m-CPBA=meta-chloroperoxybenzoic acid
Me=methyl
MeCN=methyl cyanide=acetonitrile=ACN
MeOH=methanol
MsCl=methanesulfonyl chloride
Pd(dbpf)Cl$_2$=[1,1'-Bis(di-tert-butylphosphino)ferrocene]dichloropalladium(II)
Pd(dppf)Cl$_2$=[1,1'-Bis(diphenylphosphino)ferrocene]dichloropalladium(II)
PyBOP=benzotriazol-1-yl-oxytripyrrolidinophosphonium hexafluorophosphate
t- or tert-=tertiary
TEA=triethylamine
TFA=trifluoroacetic acid
THF=tetrahydrofuran

BEST MODE FOR CARRYING OUT THE INVENTION

Preparation of Compounds and Preparing Method of Compounds

The compound of formula 1 can be prepared by the method known from various references. Hereinafter, the preparing method for compound of formula 1 will be described in further detail with reaction scheme.

Example 1. Compound 431

1-(2-fluoro-2-methylpropyl)-4-((4'-(methylsulfonyl)biphenyl-4-yloxy)methyl)piperidine

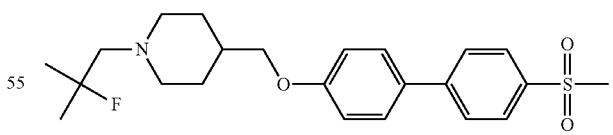

Step 1.

t-butyl 4-(hydroxymethyl)piperidin-1-carboxylate: 4-Piperidinemethanol (10.00 g, 86.83 mmol) was dissolved in CH$_2$Cl$_2$ 200 mL, and then cooled with ice bath. Di-t-butyl dicarbonate was added thereto, following with increasing temperature slowly to room temperature and stirring for 3 hours. The obtained reaction mixture was washed in order with water, saturated NH$_4$Cl aqueous solution and saturated aqueous brine solution. The washed reaction mixture was dried over MgSO₄ and filtered. After removing solid material, organic solvent was removed from the filtrate under reduced pressure to yield the title compound as white solid (18.35 g, 98%)
Step 2.

t-butyl 4-((methylsulfonyloxy)methyl)piperidin-1-carboxylate: t-Butyl 4-(hydroxymethyl)piperidin-1-carboxylate (18.35 g, 85.24 mmol) was dissolved in CH₂Cl₂ 200 mL. Et₃N (35.45 mL, 255.71 mmol) was added thereto, and then the mixture was cooled with ice bath. MsCl (9.83 mL, 127.86 mmol) was added dropwise slowly thereto, following with increasing temperature slowly to room temperature and stirring for 15 hours. The obtained reaction mixture was washed in order with 1 N HCl, saturated NaHCO₃ aqueous solution and saturated aqueous brine solution. The washed reaction mixture was dried over MgSO₄ and filtered. After removing solid material, organic solvent was removed from the filtrate under reduced pressure to yield the title compound as yellow solid (24.80 g, 99%).
Step 3.

t-butyl 4-((4-bromophenoxy)methyl)piperidin-1-carboxylate: t-Butyl 4-((methylsulfonyloxy)methyl)piperidin-1-carboxylate (13.63 g, 46.46 mmol) and 4-bromophenol (8.34 g, 46.46 mmol) were dissolved in DMF 100 mL, and then K₂CO₃ (19.26 g, 139.38 mmol) was added thereto, following with stirring at 80° C. for 15 hours. Sufficient amount of water was added thereto, following with filtering to obtain a solid. The obtained solid was recrystallized with MeOH to yield the title compound as white solid (11.31 g, 66%). The obtained filtrate was concentrated under reduced pressure. The obtained concentrate was purified by silica gel column chromatography (10% EtOAc/hexane) further to yield the title compound as white solid (2.38 g, 14%).
Step 4.

t-butyl 4-((4'-(methylsulfonyl)biphenyl-4-yloxy)methyl)piperidin-1-carboxylate: t-Butyl 4-((4-bromophenoxy)methyl)piperidin-1-carboxylate (3.00 g, 8.10 mmol) and 4-(methylsulfonyl)phenylboronic acid (1.78 g, 8.91 mmol) were dissolved in DME 15 mL, and then water 5 mL was added thereto. Pd(dbpf)Cl₂ (528 mg, 0.81 mmol) and Cs₂CO₃ (3.96 g, 12.15 mmol) were added thereto, and refluxed with heating at 80° C. for a day. The reaction mixture was diluted with water, and extracted with EtOAc three times. The obtained organic layer was dried over MgSO₄, and then concentrated under reduced pressure. The obtained concentrate was purified by silica gel column chromatography (50% EtOAc/hexane) to yield the title compound as yellow solid (2.50 g, 69%).
Step 5.

4-((4'-(methylsulfonyl)biphenyl-4-yloxy)methyl)piperidine 2,2,2-trifluoroacetate: t-Butyl 4-((4'-(methylsulfonyl)biphenyl-4-yloxy)methyl)piperidin-1-carboxylate (2.50 g, 5.61 mmol) was dissolved in CH₂Cl₂ 8 mL, and then TFA 644 μL was added thereto, following with stirring at room temperature for 3 hours. The obtained reaction mixture was filtered to yield the title compound as white solid (2.40 g, 96%). Alternatively, 4-((4'-(methylsulfonyl)biphenyl-4-yloxy)methyl)piperidine 2,2,2-trifluoroacetate (3.78 g, 8.48 mmol) was dissolved in dioxane 20 mL, and then 4 M HCl solution (14.85 mL, 59.39 mmol) was added thereto, following with stirring at room temperature for 1 hour. The reaction mixture was suspended in EtOAc, and then filtered to yield the title compound as white solid (3.15 g, 97%).
Step 6.

2-methyl-1-(4-((4'-(methylsulfonyl)biphenyl-4-yloxy)methyl)piperidin-1-yl)propan-2-ol: 4-((4'-(methylsulfonyl)biphenyl-4-yloxy)methyl)piperidine 2,2,2-trifluoroacetate (100 mg, 0.22 mmol) and K₂CO₃ (15 mg, 0.11 mmol) were suspended in EtOH 1 mL. Water 0.5 mL was added thereto, and then suspended with warming. 2,2-Dimethyl oxirane (0.19 mL, 2.18 mmol) was added thereto, and then the reaction was performed at 110° C. for 20 minutes with the radiation of micro-wave ray. A little of water was added thereto, and filtered to yield the title compound as white solid (90 mg, 99%).
Step 7.

Compound 431: 2-Methyl-1-(4-((4'-(methylsulfonyl)biphenyl-4-yloxy)methyl)piperidin-1-yl)propan-2-ol (50 mg, 0.12 mmol) was dissolved in CH₂Cl₂ 2 mL, and then Deoxo-Fluor (24 μL, 0.13 mmol) was added thereto. After stirring at room temperature for 3 hours, a saturated NaHCO₃ aqueous solution was added thereto, and the mixture was extracted with CH₂Cl₂. The obtained organic layer was dried over MgSO₄, and then filtered to remove the solid materials. The filtrate was concentrated under reduced pressure. The obtained concentrate was purified by silica gel column chromatography (10% MeOH/CH₂Cl₂) to yield the title compound as white solid (40 mg, 79%).

1H NMR (400 MHz, CDCl₃) δ 8.02-7.96 (m, 2H), 7.78-7.71 (m, 2H), 7.59-7.54 (m, 2H), 7.04-6.98 (m, 2H), 3.86 (d, 2H, J=6.0 Hz), 3.10 (s, 3H), 3.00 (d, 2H, J=11.5 Hz), 2.48 (s, 1H), 2.43 (s, 1H), 2.23-2.13 (m, 2H), 1.88-1.75 (m, 3H), 1.48-1.40 (m, 2H), 1.41 (s, 3H), 1.35 (s, 3H); MS (ESI) m/z 420 (M++H).

Example 2. Compound 596: 2-((1-(2-fluoro-2-methylpropyl)piperidin-4-yl)methoxy)-5-(4-(methylsulfonyl)phenyl)pyridine

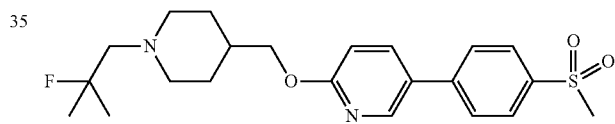

Step 1.

t-butyl 4-((5-bromopyridine-2-yloxy)methyl)piperidin-1-carboxylate: N-Boc-4-piperidinemethanol (500 mg, 2.32 mmol) was dissolved in DMF 10 mL. 2,5-bromopyridine (600 mg, 2.55 mmol) and 95% NaH (83 mg, 3.48 mmol) were added thereto slowly at 0° C., following with increasing the temperature and stirring at room temperature for 3 hours. After the completion of the reaction, the reaction mixture was extracted with EtOAc. The obtained organic layer was washed three times with saturated NH₄Cl aqueous solution and saturated aqueous brine solution. The obtained organic layer was dried over Na₂SO₄, and filtered. The filtrate was concentrated under reduced pressure. The obtained concentrate was purified by silica gel column chromatography (0-20% EtOAc/hexane) to yield the title compound as white solid (67 mg, 78%).
Step 2.

t-butyl 4-((5-(4-(methylsulfonyl)phenyl)pyridine-2-yloxy)methyl)piperidin-1-carboxylate: t-butyl 4-((5-bromopyridine-2-yloxy)methyl)piperidin-1-carboxylate (0.65 g, 1.80 mmol) was dissolved in dioxane 20 mL and H₂O 5 mL. 4-methylsulfonylphenylboronic acid (0.36 g, 1.80 mmol), Pd(dbpf)Cl₂ (59 mg, 0.09 mmol) and Cs₂CO₃ (1.17 g, 3.61 mmol) was added thereto, and refluxed with stirring for 2 hours. After the completion of the reaction, the reaction mixture was filtered through Celite. The obtained filtrate was concentrated under reduced pressure. The obtained concentrate was dissolved in $CH_2Cl_2$, washed with saturated aqueous brine solution three times. The obtained organic layer was dried over $Na_2SO_4$, and filtered. The filtrate was concentrated under reduced pressure. The obtained concentrate was purified by silica gel column chromatography (0-50% EtOAc/hexane) to yield the title compound as white solid (0.67 g, 83%).
Step 3.

5-(4-(methylsulfonyl)phenyl)-2-(piperidin-4-ylmethoxy) pyridine hydrochloride: t-butyl 4-((5-(4-(methylsulfonyl) phenyl)pyridine-2-yloxy)methyl)piperidin-1-carboxylate (0.2 g, 0.45 mmol) was dissolved in MeOH. 1.25 M HCl in MeOH (2.24 mmol, 1.8 mL) was added thereto. The solvent was removed completely and the residue was washed with ether to yield the title compound as white solid (0.15 g, 88%). The product was used without further purification.
Step 4.

2-methyl-1-(4-((5-(4-(methylsulfonyl)phenyl)pyridine-2-yloxy)methyl)piperidin-1-yl)propan-2-ol: 5-(4-(methylsulfonyl)phenyl)-2-(piperidin-4-ylmethoxy)pyridine hydrochloride (0.20 g, 0.58 mmol) was dissolved in EtOH 3 mL and $H_2O$ 3 mL. Isobutylene oxide (0.42 g, 5.77 mmol) and $K_2CO_3$ (0.40 g, 2.89 mmol) were added slowly thereto. With a microwave radiation, the mixture was heated at 110° C. for 20 minutes. After the completion of the reaction, the reaction mixture was concentrated under reduced pressure. The concentrate was dissolved in $CH_2Cl_2$, and washed with water three times. The obtained organic layer was dried over $Na_2SO_4$, and filtered. The filtrate was concentrated under reduced pressure. The obtained concentrate was purified by silica gel column chromatography (0-5% MeOH/$CH_2Cl_2$) to yield the title compound as white solid (0.15 g, 62%).
Step 5.

Compound 596: 2-methyl-1-(4-((5-(4-(methylsulfonyl) phenyl)pyridine-2-yloxy)methyl)piperidin-1-yl)propan-2-ol (0.15 g, 0.36 mmol) was dissolved in $CH_2Cl_2$ 2 mL, and then Deoxo-Fluor (0.34 mL, 1.80 mmol) was added slowly thereto, following with stirring at room temperature for 2 hours. After the completion of the reaction, the obtained $CH_2Cl_2$ layer was washed several times with water. The organic layer was concentrated under reduced pressure. The organic layer was distilled under reduced pressure. The obtained concentrate was purified by silica gel column chromatography (0-30% EtOAc/hexane) to yield the title compound as white solid (0.1 g, 66%).

1H NMR (400 MHz, $CDCl_3$) δ 8.41 (d, 1H, J=2.5 Hz), 8.02 (d, 2H, J=12.0 Hz), 7.82 (dd, 1H, J=8.6, 2.6 Hz), 7.72 (d, 2H, J=8.4 Hz), 6.86 (d, 1H, J=8.6 Hz), 4.22-4.20 (m, 2H), 3.10 (s, 3H), 3.0 (brs, 2H), 2.45 (d, 2H, J=24.0 Hz), 2.17 (brs, 2H), 1.81 (brs, 3H), 1.40-1.25 (m, 8H); MS (ESI) m/z 421 (M++H).

Example 3. Compound 597: 5-((1-(2-fluoro-2-methylpropyl)piperidin-4-yl)methoxy)-2-(4-(methylsulfonyl)phenyl)pyridine

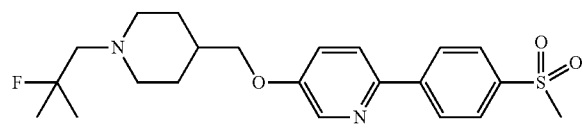

Step 1.

t-butyl 4-((6-chloropyridine-3-yloxy)methyl)piperidin-1-carboxylate: N-Boc-4-piperidinemethanol (0.50 g, 2.32 mmol) was dissolved in $CH_2Cl_2$ 5 mL, and then $Et_3N$ (0.48 mL, 3.48 mmol) and MsCl (0.32 g, 2.79 mmol) was added dropwise slowly thereto at 0° C. The mixture was stirred for 30 minutes, following with increasing the temperature and stirring at room temperature for 12 hours. After the completion of the reaction, the reaction mixture was washed with excess water three times. The obtained organic layer was dried over $Na_2SO_4$, and filtered. The filtrate was concentrated under reduced pressure to yield the title compound as white solid (0.68 g, 100%). The product was dissolved in DMF 10 mL. $K_2CO_3$ (1.13 g, 3.48 mmol) and 2-chloro-5-hydroxypyridine (0.3 g, 2.32 mmol) were added thereto slowly. After increasing the temperature, the mixture was stirred with heating at 100° C. for 3 hours. After the completion of the reaction, the reaction mixture was washed with saturated aqueous brine solution three times. The obtained organic layer was dried over $Na_2SO_4$, and filtered. The filtrate was concentrated under reduced pressure. The obtained concentrate was purified by silica gel column chromatography (0-30% EtOAc/hexane) to yield the title compound as white solid (0.45 g, 59%).
Step 2.

t-butyl 4-((6-(4-(methylsulfonyl)phenyl)pyridine-3-yloxy)methyl)piperidin-1-carboxylate: t-butyl 4-((6-chloropyridine-3-yloxy)methyl)piperidin-1-carboxylate (0.45 g, 1.37 mmol) was dissolved in dioxane 20 mL and $H_2O$ 5 mL. 4-Methylsulfonylphenylboronic acid (0.28 g, 1.38 mmol) and Pd(dbpf)$Cl_2$ (45 mg, 0.07 mmol), $Cs_2CO_3$ (0.89 g, 2.75 mmol) was added thereto, and refluxed with stirring for 2 hours. After the completion of the reaction, the reaction mixture was filtered through Celite. The obtained filtrate was washed with saturated aqueous brine solution three times. The obtained organic layer was dried over $Na_2SO_4$, and filtered. The filtrate was concentrated under reduced pressure. The obtained concentrate was purified by silica gel column chromatography (0-50% EtOAc/hexane) to yield the title compound as white solid (0.45 g, 73%).
Step 3.

2-(4-(methylsulfonyl)phenyl)-5-(piperidin-4-ylmethoxy) pyridine hydrochloride: t-butyl 4-((6-(4-(methylsulfonyl) phenyl)pyridine-3-yloxy)methyl)piperidin-1-carboxylate (0.45 g, 1.0 mmol) was dissolved in dioxane 10 mL. 4M HCl in MeOH (1.26 mL, 5.0 mmol) was added thereto. The solvent was removed completely and the residue was washed with ether to yield the title compound as white solid (0.36 g, 93%). The product was used without further purification.
Step 4.

2-methyl-1-(4-((6-(4-(methylsulfonyl)phenyl)pyridine-3-yloxy)methyl)piperidin-1-yl)propan-2-ol: 2-(4-(methylsulfonyl)phenyl)-5-(piperidin-4-ylmethoxy)pyridine hydrochloride (0.15 g, 0.39 mmol) was dissolved in EtOH 5 mL and $H_2O$ 5 mL. Isobutylene oxide (0.28 g, 3.92 mmol) and $K_2CO_3$ (0.27 g, 1.96 mmol) were added slowly thereto. With a microwave radiation, the mixture was heated at 110° C. for 20 minutes. After the completion of the reaction, the reaction mixture was concentrated under reduced pressure. The concentrate was dissolved in $CH_2Cl_2$, and washed with water three times. The obtained organic layer was dried over $Na_2SO_4$, and filtered. The filtrate was concentrated under reduced pressure. The obtained concentrate was purified by silica gel column chromatography (0-5% MeOH/$CH_2Cl_2$) to yield the title compound as white solid (0.15 g, 92%).
Step 5.

Compound 597: 2-methyl-1-(4-((6-(4-(methylsulfonyl) phenyl)pyridine-3-yloxy)methyl)piperidin-1-yl)propan-2-ol (0.15 g, 0.36 mmol) was dissolved in $CH_2Cl_2$ 10 mL.

Deoxo-Fluor (0.34 mL, 1.79 mmol) was added slowly thereto, following with stirring at room temperature for 2 hours. After the completion of the reaction, the obtained CH$_2$Cl$_2$ layer was washed several times with water. The organic layer was distilled under reduced pressure. The obtained concentrate was purified by silica gel column chromatography (0-30% EtOAc/hexane) to yield the title compound as white solid (0.1 g, 66%).

1H NMR (400 MHz, CDCl$_3$) δ 8.42 (d, 1H, J=12.0 Hz), 8.16 (d, 2H, J=1.6 Hz), 8.02 (d, 2H, J=8.5 Hz), 7.74 (d, 1H, J=8.7 Hz), 7.30 (s, 1H), 3.91 (d, 2H, J=5.5 Hz), 3.09 (s, 3H), 3.0 (brs, 2H), 2.48-2.42 (m, 2H), 2.25-2.15 (m, 2H), 1.93-1.78 (m, 3H), 1.47-1.35 (m, 8H); MS (ESI) m/z 421 (M++H).

Example 4. Compound 789

1-((1-fluorocyclohexyl)methyl)-4-((4'-(methylsulfonyl)biphenyl-4-yloxy)methyl)piperidine

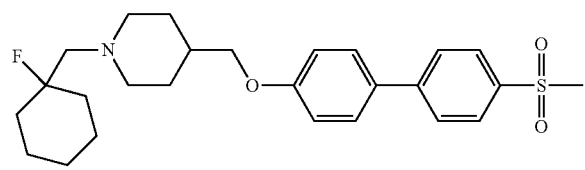 [SMILES: CS(=O)(=O)c1ccc(-c2ccc(OCC3CCN(CC4(F)CCCCC4)CC3)cc2)cc1]

Step 1.

1-((4-((4'-(methylsulfonyl)biphenyl-4-yloxy)methyl)piperidin-1-yl)methyl)cyclohexanol: 4-((4'-(methylsulfonyl)biphenyl-4-yloxy)methyl)piperidine hydrochloride (0.04 g, 0.11 mmol) and K$_2$CO$_3$ (0.01 g, 0.06 mmol) were suspended in EtOH (1 mL). Water (0.5 mL) was added thereto, and the mixture was suspended with a little heating. 1-oxaspiro[2,5]octane (0.13 g, 1.18 mmol) was added thereto. The reaction was performed in a microwave at 110° C. for 20 minutes. A little of water was added thereto, and filtered to yield the title compound as white solid (0.05 g, 87%).

Step 2.

Compound 789: 1-((4-((4'-(methylsulfonyl)biphenyl-4-yloxy)methyl)piperidin-1-yl)methyl)cyclohexanol (0.05 g, 0.10 mmol) was dissolved in CH$_2$Cl$_2$ (2 mL), and then the temperature was lowered with dry iceacetone. DAST (0.02 mL, 0.10 mmol) was added thereto little by little, and stirred for 4 hours, and then further stirred at room temperature for 1 hour. A saturated NaHCO$_3$ aqueous solution was added thereto, and extracted with CH$_2$Cl$_2$. The organic layer was dried over MgSO$_4$, filtered to remove the solid residue, and the filtrate was concentrated under reduced pressure. The concentrate was purified by column chromatography (4 g, ISU silica gel cartridge, 10% MeOH/CH$_2$Cl$_2$) to yield the title compound as brown solid (0.01 g, 27%).

1H NMR (400 MHz, CDCl$_3$) δ 7.97 (d, 2H, J=8.5 Hz), 7.72 (d, 2H, J=8.5 Hz), 7.55 (d, 2H, J=8.8 Hz), 6.99 (d, 2H, J=8.8 Hz), 3.85 (d, 2H, J=5.8 Hz), 3.08 (s, 3H), 2.98 (d, 2H, J=10.0 Hz), 2.48 (s, 1H), 2.42 (s, 1H), 2.16 (t, 2H, J=11.3 Hz), 1.92-1.74 (m, 5H), 1.68-1.55 (m, 4H), 1.55-1.35 (m, 6H); MS (ESI) m/z 460 (M++H).

Example 5. Compound 500: 4-((4'-(methylsulfonyl)biphenyl-4-yloxy)methyl)-1-((1-(trifluoromethyl)cyclopropyl)methyl)piperidine

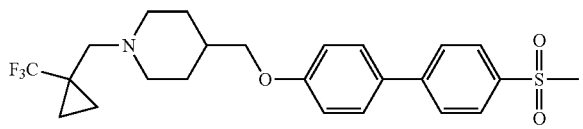

Step 1.

(4-((4'-(methylsulfonyl)biphenyl-4-yloxy)methyl)piperidin-1-yl)(1-(trifluoromethyl)cyclopropyl)methanone: 4-((4'-(methylsulfonyl)biphenyl-4-yloxy)methyl)piperidine hydrochloride [the product of synthesis step 5 of compound 431; 74 mg, 0.20 mmol], 1-(trifluoromethyl)cyclopropan-1-carboxylic acid (30 mg, 0.20 mmol), and EDC (74 mg, 0.39 mmol) and HOBt (52 mg, 0.39 mmol) were dissolved in DMF 3 mL, and then DIPEA (173 µL, 0.97 mmol) was added thereto. At 80° C., the reaction was performed for 16 hours. The reaction mixture was added with CH$_2$Cl$_2$, and washed with saturated NH$_4$Cl aqueous solution. The obtained organic layer was dried over MgSO$_4$, and filtered to remove a solid. The filtrate was concentrated under reduced pressure. The obtained concentrate was purified by silica gel column chromatography (10-70% EtOAc/hexane) to yield the title compound as white solid (30 mg, 32%).

Step 2.

Compound 500: (4-((4'-(methylsulfonyl)biphenyl-4-yloxy)methyl)piperidin-1-yl)(1-(trifluoromethyl)cyclopropyl)methanone (50 mg, 0.10 mmol) was dissolved in dry THF 2 mL, and then cooled with ice bath. LAH (1 M in THF, 0.21 mL, 0.21 mmol) was added dropwise slowly thereto, following with increasing the temperature to room temperature slowly and stirring for 4 hours. Water was poured into the reaction mixture. The formed solid was removed by filtration, and the filtrate was extracted with EtOAc three times. The organic layer was dried over MgSO$_4$, filtered to remove the solid residue, and the filtrate was concentrated under reduced pressure. The concentrate was purified by silica gel column chromatography (20-40% EtOAc/hexane) to yield the title compound as white solid (26 mg, 54%).

1H NMR (400 MHz, CDCl$_3$) δ 7.99-7.96 (m, 2H), 7.74-7.71 (m, 2H), 7.56-7.52 (m, 2H), 7.01-6.98 (m, 2H), 3.86 (d, 2H, J=6.0 Hz), 3.09 (s, 3H), 3.06-2.96 (m, 4H), 2.41 (t, 2H, J=10.9 Hz), 1.87-1.81 (m, 3H), 1.56 (s, 2H), 1.52-1.43 (m, 2H); MS (ESI) m/z 468 (M++H).

Example 6. Compound 542: 4-((4'-(methylsulfonyl)biphenyl-4-yloxy)methyl)-1-((1-(trifluoromethyl)cyclobutyl)methyl)piperidine

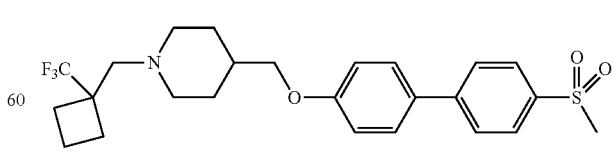

Step 1.

(4-((4'-(methylsulfonyl)biphenyl-4-yloxy)methyl)piperidin-1-yl)(1-(trifluoromethyl)cyclobutyl)methanone: 4-((4'-(methylsulfonyl)biphenyl-4-yloxy)methyl)piperidine 2,2,2- trifluoroacetate [the product of synthesis step 5 of compound 431; 140 mg, 0.37 mmol], 1-(trifluoromethyl)cyclobutanecarboxylic acid (92 mg, 0.55 mmol), EDC (141 mg, 0.73 mmol) and HOBt (99 mg, 0.73 mmol) were dissolved in DMF 2 mL, and then DIPEA (95 mg, 0.73 mmol) was added thereto. At 60° C., the reaction was performed for 10 hours. The reaction mixture was added with water, and extracted with EtOAc. The obtained organic layer was dried over MgSO$_4$, and filtered. The filtrate was concentrated under reduced pressure. The obtained concentrate was purified by silica gel column chromatography (50-60% EtOAc/hexane) to yield the title compound as white solid (105 mg, 57%).

Step 2.

Compound 542: (4-((4'-(methylsulfonyl)biphenyl-4-yloxy)methyl)piperidin-1-yl)(1-(trifluoromethyl)cyclobutyl)methanone (80 mg, 0.16 mmol) was dissolved in dry THF 6 mL, and then cooled with ice bath. LAH (1 M in THF, 0.18 mL, 0.18 mmol) was added dropwise slowly thereto, following with increasing the temperature to room temperature slowly and stirring for 1 hour. Water was poured into the reaction mixture. The formed solid was removed by filtration, and the filtrate was extracted with EtOAc three times. The organic layer was dried over MgSO$_4$, filtered to remove the solid residue, and the filtrate was concentrated under reduced pressure. The obtained concentrate was purified by silica gel column chromatography (50% EtOAc/hexane) to yield the title compound as white solid (9 mg, 11%).

1H NMR (400 MHz, CDCl$_3$) δ 7.97 (dd, 2H, J=6.7, 1.9 Hz), 7.73 (dd, 1H, J=6.7, 1.8 Hz), 7.55 (dd, 2H, J=6.8, 2.0 Hz), 7.00 (dd, 2H, J=6.3, 2.0 Hz), 3.85 (d, 2H, J=6.1 Hz), 3.08 (s, 3H), 2.09 (m, 2H), 2.53 (s, 2H), 2.23 (m, 4H), 1.92 (m, 7H), 1.45 (m, 2H); MS (ESI) mz 482 (M++H).

Example 7. Compound 546: 4-((4'-(methylsulfonyl)biphenyl-4-yloxy)methyl)-1-((1-(trifluoromethyl)cyclopentyl)methyl)piperidine

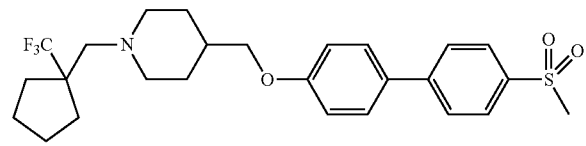 [SMILES: CS(=O)(=O)c1ccc(-c2ccc(OCC3CCN(CC4(C(F)(F)F)CCCC4)CC3)cc2)cc1]

Step 1.

(4-((4'-(methylsulfonyl)biphenyl-4-yloxy)methyl)piperidin-1-yl)(1-(trifluoromethyl)cyclopentyl)methanone: 4-((4'-(methylsulfonyl)biphenyl-4-yloxy)methyl)piperidine 2,2,2-trifluoroacetate [the product of synthesis step 5 of compound 431; 150 mg, 0.39 mmol], 1-(trifluoromethyl)cyclopentanecarboxylic acid (107 mg, 0.59 mmol), EDC (151 mg, 0.79 mmol) and HOBt (106 mg, 0.79 mmol) were dissolved in DMF 2 mL, and then DIPEA (101 mg, 0.79 mmol) was added thereto. At 60° C., the reaction was performed for 10 hours. The reaction mixture was added with water, and extracted with EtOAc. The obtained organic layer was dried over MgSO$_4$, and filtered. The filtrate was concentrated under reduced pressure. The concentrate was purified by silica gel column chromatography (50-60% EtOAc/hexane) to yield the title compound as white solid (90 mg, 45%).

Step 2.

Compound 546: (4-((4'-(methylsulfonyl)biphenyl-4-yloxy)methyl)piperidin-1-yl)(1-(trifluoromethyl)cyclopentyl)methanone (35 mg, 0.07 mmol) was dissolved in dry THF 4 mL, and then cooled with ice bath. LAH (1 M in THF, 0.18 mL, 0.18 mmol) was added dropwise slowly thereto, following with increasing the temperature to 60° C. slowly and stirring for a day. Water was poured into the reaction mixture. The formed solid was removed by filtration, and the filtrate was extracted with EtOAc three times. The organic layer was dried over MgSO$_4$, filtered to remove the solid residue, and the filtrate was concentrated under reduced pressure. The concentrate was purified by Prep. TLC (40% EtOAc/hexane) to yield the title compound as white solid (5 mg, 14%).

1H NMR (400 MHz, CDCl$_3$) δ 7.97 (dd, 2H, J=6.8, 1.9 Hz), 7.72 (dd, 2H, J=6.8, 1.9 Hz), 7.54 (dd, 2H, J=6.8, 2.0 Hz), 6.99 (dd, 2H, J=6.8, 2.0 Hz), 3.84 (d, 2H, J=6.0 Hz), 3.08 (s, 3H), 2.46 (s, 2H), 2.26 (m, 2H), 2.17 (s, 4H), 1.81 (m, 4H), 1.67 (m, 5H), 1.40 (m, 2H); MS (ESI) m/z 496 (M++H).

Example 8. Compound 547: 1-(2,2-difluoropropyl)-4-((4'-(methylsulfonyl)biphenyl-4-yloxy)methyl)piperidine

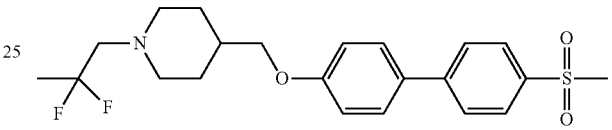

Step 1.

1-(4-((4'-(methylsulfonyl)biphenyl-4-yloxy)methyl)piperidin-1-yl)propan-2-one 4-((4'-(methylsulfonyl)biphenyl-4-yloxy)methyl)piperidine 2,2,2-trifluoroacetate (the product of synthesis step 5 of compound 431; 50 mg, 0.11 mmol) and 1-chloropropan-2-one (13 μL, 0.16 mmol) were dissolved in MeCN 2 mL. K$_2$CO$_3$ (53 mg, 0.38 mmol) was added thereto, following with stirring at room temperature for 15 hours. The reaction mixture was diluted with water, and extracted with CH$_2$Cl$_2$ three times. The organic layer was dried over MgSO$_4$, filtered to remove the solid residue, and the filtrate was concentrated under reduced pressure. The obtained concentrate was purified by silica gel column chromatography (0-5% MeOH/CH$_2$Cl$_2$) to yield the title compound as pale gray solid (30 mg, 68%).

Step 2.

Compound 547: 1-(4-((4'-(methylsulfonyl)biphenyl-4-yloxy)methyl)piperidin-1-yl)propan-2-one (32 mg, 0.08 mmol) was dissolved in CH$_2$Cl$_2$ 0.5 mL, and then Deoxo-Fluor (29 μL, 0.16 mmol) was added thereto. EtOH (1 μL, 0.02 mmol) was added thereto, following with increasing the temperature to room temperature and stirring for 15 hours. The reaction mixture was added with saturated NaHCO$_3$ aqueous solution, and extracted with CH$_2$Cl$_2$. The organic layer was dried over MgSO$_4$, filtered to remove the solid residue, and the filtrate was concentrated under reduced pressure. The obtained concentrate was purified by silica gel column chromatography (0-5% MeOH/CH$_2$Cl$_2$) to yield the title compound as yellow solid. The obtained product was purified again by silica gel column chromatography (0-50% EtOAc/Hexane) to yield the title compound as white solid (7 mg, 20%).

1H NMR (400 MHz, CDCl$_3$) δ 7.95-8.01 (m, 2H), 7.77-7.69 (m, 2H), 7.59-7.53 (m, 2H), 7.03-6.97 (m, 2H), 3.85 (d, 2H, J=5.8 Hz), 3.09 (s, 3H), 3.00 (d, 2H, J=11.8 Hz), 2.68 (t, 2H, J=13.8 Hz), 2.26 (td, 2H, J=11.7, 1.9 Hz), 1.88-1.77 (m, 3H), 1.65 (t, 3H, J=18.7 Hz), 1.46-1.42 (m, 2H); MS (ESI) m/z 424 (M++H).

Example 9. Compound 589: 5-(4-(methylsulfonyl)phenyl)-2-((1-((1-(trifluoromethyl)cyclopropyl)methyl)piperidin-4-yl)methoxy)pyridine

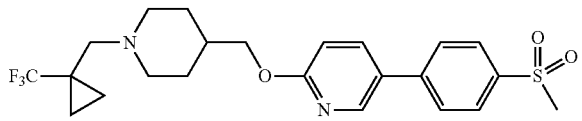 [SMILES: CS(=O)(=O)c1ccc(-c2ccc(OCC3CCN(CC4(C(F)(F)F)CC4)CC3)nc2)cc1]

Step 1.
Ethyl 1-(1-(trifluoromethyl)cyclopropanecarbonyl)piperidin-4-carboxylate: 1-(trifluoromethyl)cyclopropanecarboxylic acid (500 mg, 3.25 mmol), ethyl piperidin-4-carboxylate (561 mg, 3.57 mmol), EDC (1.24 g, 6.49 mmol) and HOBt (877 mg, 6.49 mmol) were dissolved in $CH_2Cl_2$ 10 mL, and then DIPEA (114 µL, 6.49 mmol) was added thereto. The reaction was performed at room temperature for 8 hours. The reaction mixture was added with saturated $NH_4Cl$ aqueous solution, and extracted with EtOAc. The obtained organic layer was dried over $MgSO_4$, and filtered. The filtrate was concentrated under reduced pressure. The obtained concentrate was purified by silica gel column chromatography (10-70% EtOAc/hexane) to yield the title compound as colorless oil (800 mg, 84%).

Step 2.
(1-((1-(trifluoromethyl)cyclopropyl)methyl)piperidin-4-yl)methanol: ethyl 1-(1-(trifluoromethyl)cyclopropanecarbonyl)piperidin-4-carboxylate (818 mg, 2.79 mmol) was dissolved in dry THF 20 mL. At 0° C., LAH (1 M in THF, 13.94 mL, 13.94 mmol) was added slowly thereto. At 50° C., the reaction was performed for 10 hours. The reaction was quenched by slow addition of MeOH at 0° C. The reaction mixture was added with water, and then extracted with EtOAc. The obtained extracted organic layer was dried over $MgSO_4$, and then filtered to yield the title compound as colorless oil (577 mg, 87%).

Step 3.
5-bromo-2-((1-((1-(trifluoromethyl)cyclopropyl)methyl)piperidin-4-yl)methoxy)pyridine: (1-((1-(trifluoromethyl)cyclopropyl)methyl)piperidin-4-yl)methanol (577 mg, 2.43 mmol) was dissolved in THF 10 mL. At 0° C., NaH (87 mg, 3.65 mmol) was added slowly thereto. The reaction was performed at room temperature for 20 minutes. At 0° C., 2,5-dibromopyridine (0.57 g, 2.43 mmol) in THF 5 mL was added slowly thereto. At 50° C., the reaction was performed for 10 hours. After the completion of the reaction, the reaction mixture was added with ice water, and extracted with EtOAc. The obtained extracted organic layer was dried over $MgSO_4$, and then filtered. The filtrate was concentrated under reduced pressure. The obtained concentrate was purified by silica gel column chromatography (10-70% EtOAc/hexane) to yield the title compound as white solid (500 mg, 52%).

Step 4.
Compound 589: 5-bromo-2-((1-((1-(trifluoromethyl)cyclopropyl)methyl)piperidin-4-yl)methoxy)pyridine (100 mg, 0.25 mmol), 4-(methylsulfonyl)phenylboronic acid (76 mg, 0.38 mmol), Pd(dbpf)$Cl_2$ (5 mg, 0.01 mmol), $Cs_2CO_3$ (247 mg, 0.76 mmol) were added into a microwave reactor, and then dioxane 6 mL and water 3 mL were added thereto. With a microwave radiation, the reaction was performed at 110° C. for 30 minutes. The reaction mixture was filtered through Celite. The filtrate was added with water, and extracted with EtOAc. The organic layer was dried over $MgSO_4$, and filtered. The filtrate was concentrated under reduced pressure. The concentrate was purified by silica gel column chromatography (10-50% EtOAc/hexane) to yield the title compound as white solid (38 mg, 32%).

1H NMR (400 MHz, $CDCl_3$) δ 8.40 (m, 1H), 8.02 (dd, 2H, J=5.2, 3.4 Hz), 7.83 (dd, 1H, J=8.6, 2.6 Hz), 7.72 (dt, 2H, J=8.6, 1.9 Hz), 6.86 (dd, 1H, J=8.6, 0.6 Hz), 4.21 (d, 2H, J=6.0 Hz), 3.10 (s, 3H), 2.98 (d, 2H, J=10.1 Hz), 2.54 (s, 2H), 1.99 (m, 2H), 1.81 (d, 2H, J=10.0 Hz), 1.41 (m, 2H), 0.98 (s, 2H), 0.65 (s, 2H); MS (ESI) m/z 469 (M++H).

Example 10. Compound 676: 5-(4-(methylsulfonyl)phenyl)-2-((1-((1-(trifluoromethyl)cyclobutyl)methyl)piperidin-4-yl)methoxy)pyridine

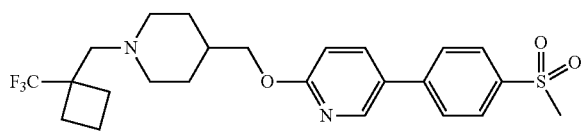 [SMILES: CS(=O)(=O)c1ccc(-c2ccc(OCC3CCN(CC4(C(F)(F)F)CCC4)CC3)nc2)cc1]

Step 1.
Ethyl 1-(1-(trifluoromethyl)cyclobutanecarbonyl)piperidin-4-carboxylate: 1-(trifluoromethyl)cyclobutanecarboxylic acid (500 mg, 2.97 mmol), ethyl piperidin-4-carboxylate (514 mg, 3.27 mmol), EDC (1.14 g, 5.94 mmol) and HOBt (803 mg, 5.95 mmol) was dissolved in $CH_2Cl_2$ 10 mL. DIPEA (1.05 mL, 5.95 mmol) was added thereto. The reaction was performed at room temperature for 8 hours. The reaction mixture was added with saturated $NH_4Cl$ aqueous solution, and extracted with EtOAc. The organic layer was dried over $MgSO_4$, and then filtered. The filtrate was concentrated under reduced pressure. The obtained concentrate was purified by silica gel column chromatography (10-70% EtOAc/hexane) to yield the title compound as colorless oil (750 mg, 82%).

Step 2.
(1-((1-(trifluoromethyl)cyclobutyl)methyl)piperidin-4-yl)methanol: ethyl 1-(1-(trifluoromethyl)cyclobutanecarbonyl)piperidin-4-carboxylate (759 mg, 2.47 mmol) was dissolved in dry THF 20 mL. At 0° C., LAH (1 M in THF, 12.34 mL, 12.34 mmol) was added slowly thereto. At 50° C., the reaction was performed for 10 hours. The reaction was quenched by slow addition of MeOH at 0° C. The reaction mixture was added with water, and then extracted with EtOAc. The obtained extracted organic layer was dried over $MgSO_4$, and then filtered to yield the title compound as colorless oil (581 mg, 94%).

Step 3.
5-bromo-2-((1-((1-(trifluoromethyl)cyclobutyl)methyl)piperidin-4-yl)methoxy)pyridine: (1-((1-(trifluoromethyl)cyclobutyl)methyl)piperidin-4-yl)methanol (581 mg, 2.31 mmol) were dissolved in THF 10 mL. At 0° C., NaH (83 mg, 3.47 mmol) was added slowly thereto. The reaction was performed at room temperature for 20 minutes. At 0° C., 2,5-dibromopyridine (547 mg, 2.31 mmol) in THF 5 mL was added slowly thereto. At 50° C., the reaction was performed for 10 hours. After the completion of the reaction, the reaction mixture was added with ice water, and extracted with EtOAc. The obtained organic layer was dried over $MgSO_4$, and filtered. The filtrate was concentrated under reduced pressure. The obtained concentrate was purified by silica gel column chromatography (10-70% EtOAc/hexane) to yield the title compound as white solid (500 mg, 53%).

Step 4.

Compound 676: 5-bromo-2-((1-((1-(trifluoromethyl)cyclobutyl)methyl)piperidin-4-yl)methoxy)pyridine (500 mg, 0.12 mmol), 4-(methylsulfonyl)phenylboronic acid (27 mg, 0.13 mmol), Pd(dbpf)Cl$_2$ (2 mg, 0.01 mmol), Cs$_2$CO$_3$ (119 mg, 0.37 mmol) were added into a microwave reactor, and then dioxane 2 mL and water 1 mL were added thereto. With a microwave radiation, the reaction was performed at 110° C. for 30 minutes. The reaction mixture was filtered through Celite. The filtrate was added with water, and extracted with EtOAc. The organic layer was dried over MgSO$_4$, and filtered. The filtrate was concentrated under reduced pressure. The concentrate was purified by silica gel column chromatography (10-50% EtOAc/hexane) to yield the title compound as white solid (20 mg, 34%).

1H NMR (400 MHz, CDCl$_3$) δ 8.41 (d, 1H, J=2.6 Hz), 8.02 (dd, 2H, J=8.5, 1.8 Hz), 7.83 (dd, 1H, J=8.7, 2.6 Hz), 7.72 (dd, 2H, J=6.6, 1.7 Hz), 6.87 (d, 1H, J=8.6 Hz), 4.22 (d, 2H, J=6.2 Hz), 3.10 (s, 3H), 2.90 (d, 2H, J=11.4 Hz), 2.53 (s, 2H), 2.24-2.18 (m, 4H), 2.10-1.79 (m, 7H), 1.47-1.43 (m, 2H); MS (ESI) m/z 483 (M++H).

Example 11. Compound 714: 1-(2-fluoro-2-methylpropyl)-4-((2-fluoro-4'-(methylsulfonyl)biphenyl-4-yloxy)methyl)piperidine

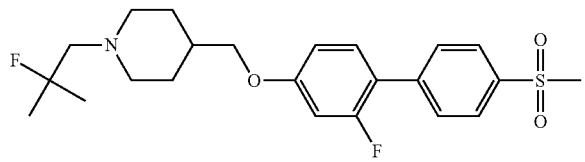 [SMILES: CC(C)(F)CN1CCC(COc2ccc(-c3ccc(S(C)(=O)=O)cc3)c(F)c2)CC1]

4-((4-bromo-3-fluorophenoxy)methyl)-1-(2-fluoro-2-methylpropyl)piperidine (the product of synthesis step 4 of compound 704; 850 mg, 2.35 mmol), 4-(methylsulfonyl)phenylboronic acid (563 mg, 2.82 mmol), Pd(dbpf)Cl$_2$ (77 mg, 0.12 mmol) and Cs$_2$CO$_3$ (1.53 g, 4.69 mmol) were added to water (2 mL)/1,4-dioxane (6 mL). With a microwave radiation, the mixture was heated at 110° C. for 15 minutes, and then cooled to room temperature. Water was poured thereto, and the reaction mixture was extracted with EtOAc, The organic layer was dried over anhydrous MgSO$_4$, and concentrated under reduced pressure. The obtained concentrate was purified by silica gel column chromatography (EtOAc/hexane=17) to yield the title compound as yellow solid (390 mg, 38%).

1H NMR (400 MHz, CDCl$_3$) δ 8.01-7.98 (m, 2H), 7.73-7.70 (m, 2H), 7.39-7.27 (m, 1H), 6.82-6.72 (m, 2H), 3.84 (d, 2H, J=6.0 Hz), 3.10 (s, 3H), 3.02 (brs, 2H), 2.49-2.44 (m, 2H), 2.19 (brs, 2H), 1.82-1.79 (m, 3H), 1.45-1.36 (m, 8H); MS (ESI) m/z 438 (M++H).

Example 12. Compound 617: 2-(4-((1-(2-fluoro-2-methylpropyl)piperidin-4-yl)methoxy)phenyl)-5-(methylsulfonyl)pyridine

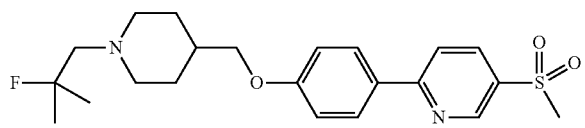 [SMILES: CC(C)(F)CN1CCC(COc2ccc(-c3ccc(S(C)(=O)=O)cn3)cc2)CC1]

Step 1.

4-((1-(2-fluoro-2-methylpropyl)piperidin-4-yl)methoxy)phenylboronic acid: 4-((4-bromophenoxy)methyl)-1-(2-fluoro-2-methylpropyl)piperidine (the product of synthesis step 3 of compound 498; 0.54 g, 1.57 mmol) was dissolved in dry THF 10 mL. At −78° C., n-BuLi (1.6 M in hexane, 1.17 mL, 1.88 mmol) was added slowly thereto. The reaction was performed at −78° C. for 30 minutes. At −78° C., triisopropyl borate (0.47 mL, 2.04 mmol) was added thereto. The reaction was performed at room temperature for 4 hours. At 0° C., 1 M HCl 5 mL was added thereto, and the reaction was performed for 1 hour. The reaction mixture was added with EtOAc, and stirred. The resulting precipitate was filtered to yield the title compound as white solid (0.40 g, 83%).

Step 2.

Compound 617: 4-((1-(2-fluoro-2-methylpropyl)piperidin-4-yl)methoxy)phenylboronic acid (50 mg, 0.16 mmol), 2-bromo-5-(methylsulfonyl)pyridine (42 mg, 0.18 mmol), Pd(dbpf)Cl$_2$ (3 mg, 0.01 mmol), Cs$_2$CO$_3$ (104 mg, 0.32 mmol) were added into a microwave reactor, and then dioxane 2 mL and water 1 mL were added thereto. With a microwave radiation, the reaction was performed at 110° C. for 30 minutes. The reaction mixture was filtered through Celite. The filtrate was added with water, and extracted with EtOAc. The obtained organic layer was dried over MgSO$_4$, and filtered. The filtrate was concentrated under reduced pressure. The obtained concentrate was purified by silica gel column chromatography (10-50% EtOAc/hexane) to yield the title compound as white solid (30 mg, 44%).

1H NMR (400 MHz, CDCl$_3$) δ 9.14 (m, 1H), 8.21 (dd, 1H, 3=8.5, 2.4 Hz), 8.05 (dt, 2H, J=9.0, 2.5 Hz), 7.85 (dd, 1H, J=8.5, 0.8 Hz), 7.02 (dt, 2H, J=8.9, 2.4 Hz), 3.88 (d, 2H, J=5.9 Hz), 3.14 (s, 3H), 3.07 (m, 2H), 2.60-2.40 (m, 2H), 2.22 (m, 2H), 1.85-1.82 (m, 3H), 1.47-1.37 (m, 8H); MS (ESI) m/z 421 (M++H).

According to the above-described synthesis process of compound 617 (Step 2), the compounds of Table 2 were synthesized using 4-((1-(2-fluoro-2-methylpropyl)piperidin-4-yl)methoxy)phenylboronic acid and the reactant of Table 1.

TABLE 1

| Compound No. | Reactant | Yield (%) |
|---|---|---|
| 618 | 5-bromo-2-(methylsulfonyl)pyridine | 47 |
| 614 | 4-bromo-N,N-dimethylbenzenesulfonamide | 43 |
| 615 | 1-(4-bromophenylsulfonyl)pyrrolidine | 35 |
| 616 | 1-(4-bromophenylsulfonyl)piperidine | 35 |
| 666 | (S)-1-(4-bromophenylsulfonyl)pyrrolidine-3-ol | 27 |
| 667 | (R)-(1-(4-bromophenylsulfonyl)pyrrolidine-2-yl)methanol | 30 |
| 668 | (S)-1-(4-bromophenylsulfonyl)pyrrolidine-2-carboxamide | 34 |
| 669 | (R)-1-(4-bromophenylsulfonyl)piperidin-3-ol | 33 |
| 670 | (S)-1-(4-bromophenylsulfonyl)piperidin-3-ol | 31 |
| 674 | 4-bromobenzenesulfonamide | 34 |
| 675 | 4-bromo-N-methylbenzenesulfonamide | 37 |

TABLE 2

| Compound No. | Compound Name, $^1$H-NMR, MS (ESI) |
|---|---|
| 618 | 5-(4-((1-(2-fluoro-2-methylpropyl)piperidin-4-yl)methoxy)phenyl)-2-(methylsulfonyl)pyridine<br>1 H NMR (400 MHz, CDCl$_3$) δ 8.90 (m, 1 H), 8.13 (dd, 1 H, J = 8.2, 0.8 Hz), 8.08 (dd, 1 H, J = 8.2, 2.2 Hz), 7.56 (dt, 2 H, J = 9.0, 2.5 Hz), 7.05 (dt, 2 H, J = 8.9, 2.4 Hz), 3.88 (d, 2 H, J = 5.9 Hz), 3.26 (s, 3 H), 3.07 (m, 2 H), 2.60 - 2.40 (m, 2 H), 2.22 (m, 2 H), 1.88 - 1.82 (m, 3 H), 1.47 - 1.37 (m, 8 H); MS (ESI) m/z 421 (M+ + H). |
| 614 | 4'-((1-(2-fluoro-2-methylpropyl)piperidin-4-yl)methoxy)-N,N-dimethylbiphenyl-4-sulfonamide<br>1 H NMR (400 MHz, CDCl$_3$) δ 7.82 (dd, 2 H, J = 8.6, 3.8 Hz), 7.71 (dd, 2 H, J = 8.6, 3.8 Hz), 7.56 (dd, 2 H, J = 9.7, 5.1 Hz), 7.01 (dd, 2 H, J = 9.7, 5.1 Hz), 3.86 (d, 2 H, J = 5.9 Hz), 3.00 (m, 2 H), 2.75 (s, 6 H), 2.49 - 2.42 (m, 2 H), 2.18 (m, 2 H), 1.82 (m, 3 H), 1.41 - 1.26 (m, 8 H); MS (ESI) m/z 449.1 (M+ + H). |
| 615 | 1-(2-fluoro-2-methylpropyl)-4-((4'-(pyrrolidine-1-ylsulfonyl)biphenyl-4-yloxy)methyl)piperidine<br>1 H NMR (400 MHz, CDCl$_3$) δ 7.86 (dd, 2 H, J = 8.6, 3.8 Hz), 7.69 (dd, 2 H, J = 8.6, 3.8 Hz), 7.56 (dd, 2 H, J = 9.7, 5.1 Hz), 7.00 (dd, 2 H, J = 9.7, 5.1 Hz), 3.86 (d, 2 H, J = 5.9 Hz), 3.28 (m, 4 H), 3.00 (m, 2 H), 2.50 - 2.44 (m, 2 H), 2.19 (m, 2 H), 1.83 - 1.75 (m, 7 H), 1.41 - 1.26 (m, 8 H); MS (ESI) m/z 475 (M+ + H). |
| 616 | 1-(2-fluoro-2-methylpropyl)-4-((4'-(piperidin-1-ylsulfonyl)biphenyl-4-yloxy)methyl)piperidine<br>1 H NMR (400 MHz, CDCl$_3$) δ 7.78 (dd, 2 H, J = 8.6, 3.8 Hz), 7.68 (dd, 2 H, J = 8.6, 3.8 Hz), 7.56 (dd, 2 H, J = 9.7, 5.1 Hz), 7.00 (dd, 2 H, J = 9.7, 5.1 Hz), 3.86 (d, 2 H, J = 5.9 Hz), 3.03 (m, 6 H), 2.49 - 2.44 (m, 2 H), 2.19 (m, 2 H), 1.83 - 1.81 (m, 3 H), 1.68 (m, 4 H), 1.47 - 1.36 (m, 10 H); MS (ESI) m/z 489 (M+ + H). |
| 666 | (S)-1-(4'-((1-(2-fluoro-2-methylpropyl)piperidin-4-yl)methoxy)biphenyl-4-ylsulfonyl)pyrrolidine-3-ol<br>1 H NMR (400 MHz, CDCl$_3$) δ 8.13 (dd, 2 H, J = 8.6, 1.9 Hz), 7.69 (dd, 2 H, J = 8.6, 1.9 Hz), 7.55 (dd, 2 H, J = 8.6, 1.9 Hz), 6.99 (dd, 2 H, J = 8.6, 1.9 Hz), 4.41 (m, 1 H), 3.86 (d, 2 H, J = 5.9 Hz), 3.44 (m, 3 H), 3.31 (m, 1 H), 3.20 - 3.02 (m, 2 H), 2.61 - 2.45 (m, 2 H), 2.38 - 2.20 (m, 2 H), 1.97 (m, 1 H), 1.88 - 1.83 (m, 4 H), 1.61 - 1.38 (m, 9 H); MS (ESI) m/z 491 (M+ + H). |
| 667 | (R)-(1-(4'-((1-(2-fluoro-2-methylpropyl)piperidin-4-yl)methoxy)biphenyl-4-ylsulfonyl)pyrrolidine-2-yl)methanol<br>1 H NMR (400 MHz, CDCl$_3$) δ 7.88 (dd, 2 H, J = 8.6, 1.9 Hz), 7.71 (dd, 2 H, J = 8.6, 1.9 Hz), 7.56 (dd, 2 H, J = 8.6, 1.9 Hz), 6.99 (dd, 2 H, J = 8.6, 1.9 Hz), 3.86 (d, 2 H, J = 5.9 Hz), 3.71 (m, 3 H), 3.52 (m, 1 H), 3.31 (m, 1 H), 3.08 - 2.90 (m, 2 H), 2.84 (in, 1 H), 2.60 - 2.40 (m, 2 H), 2.30 - 2.10 (m, 2 H), 1.84 - 1.70 (m, 6 H), 1.52 - 1.36 (m, 9 H); MS (ESI) m/z 505 (M+ + H). |
| 668 | (S)-1-(4'-((1-(2-fluoro-2-methylpropyl)piperidin-4-yl)methoxy)biphenyl-4-ylsulfonyl)pyrrolidine-2-carboxamide<br>1 H NMR (400 MHz, CDCl$_3$) δ 7.88 (dd, 2 H, J = 8.6, 1.9 Hz), 7.73 (dd, 2 H, J = 8.6, 1.9 Hz), 7.56 (dd, 2 H, J = 8.6, 1.9 Hz), 7.00 (dd, 2 H, J = 8.6, 1.9 Hz), 6.93 (m, 1 H), 5.59 (m, 1 H), 4.13 (m, 1 H), 3.87 (d, 2 H, J = 5.9 Hz), 3.62 (m, 1 H), 3.23 (m, 1 H), 3.02 (m, 2 H), 2.55 - 2.40 (m, 2 H), 2.30 - 2.12 (m, 2 H), 1.82 (m, 4 H), 1.65 (m, 3 H), 1.45 - 1.37 (m, 7 H); MS (ESI) m/z 518 (M+ + H). |
| 669 | (R)-1-(4'-((1-(2-fluoro-2-methylpropyl)piperidin-4-yl)methoxy)biphenyl-4-ylsulfonyl)piperidin-3-ol<br>1 H NMR (400 MHz, CDCl$_3$) δ 7.79 (dd, 2 H, J = 8.6, 1.9 Hz), 7.70 (dd, 2 H, J = 8.6, 1.9 Hz), 7.55 (dd, 2 H, J = 8.6, 1.9 Hz), 7.00 (dd, 2 H, J = 8.6, 1.9 Hz), 3.90 - 3.85 (m, 3 H), 3.37 (m, 1 H), 3.17 (m, 1 H), 3.02 (m, 2 H), 2.85 (m, 1 H), 2.77 (m, 1 H), 2.60 - 2.40 (m, 2 H), 2.30 - 2.18 (m, 2 H), 2.09 (m, 1 H), 1.85 - 1.60 (m, 6 H), 1.48 - 1.37 (m, 9 H); MS (ESI) m/z 505 (M+ + H). |
| 670 | (S)-1-(4'-((1-(2-fluoro-2-methylpropyl)piperidin-4-yl)methoxy)biphenyl-4-ylsulfonyl)piperidin-3-ol<br>1 H NMR (400 MHz, CDCl$_3$) δ 7.79 (dd, 2 H, J = 8.6, 1.9 Hz), 7.70 (dd, 2 H, J = 8.6, 1.9 Hz), 7.54 (dd, 2 H, J = 8.6, 1.9 Hz), 7.00 (dd, 2 H, J = 8.6, 1.9 Hz), 3.91 - 3.85 (m, 3 H), 3.36 (m, 1 H), 3.19 (m, 1 H), 3.01 (m, 2 H), 2.85 (m, 1 H), 2.77 (m, 1 H), 2.49 - 2.43 (m, 2 H), 2.18 (m, 2 H), 2.09 (m, 1 H), 1.86 - 1.60 (m, 6 H), 1.48 - 1.37 (m, 9 H); MS (ESI) m/z 505 (M+ + H). |

TABLE 2-continued

| Compound No. | Compound Name, ¹H-NMR, MS (ESI) |
|---|---|
| 674 | 4'-((1-(2-fluoro-2-methylpropyl)piperidin-4-yl)methoxy)biphenyl-4-sulfonamide<br>1 H NMR (400 MHz, CDCl₃) δ 7.96 (dd, 2 H, J = 8.6, 1.9 Hz), 7.70 (dd, 2 H, J = 8.6, 1.9 Hz), 7.54 (dd, 2 H, J = 8.6, 1.9 Hz), 7.00 (dd, 2 H, J = 8.6, 1.9 Hz), 4.83 (m, 2 H), 3.86 (d, 2 H, J = 6.0 Hz), 3.00 (d, 2 H, J = 9.7 Hz), 2.46 (d, 2 H, J = 23.2 Hz), 2.18 (m, 2 H), 1.82 (m, 3 H), 1.45 - 1.35 (m, 8 H); MS (ESI) m/z 421 (M+ + H). |
| 675 | 4'-((1-(2-fluoro-2-methylpropyl)piperidin-4-yl)methoxy)-N-methylbiphenyl-4-sulfonamide<br>1 H NMR (400 MHz, CDCl₃) δ 7.89 (dd, 2 H, J = 8.6, 1.9 Hz), 7.70 (dd, 2 H, J = 8.6, 1.9 Hz), 7.55 (dd, 2 H, J = 8.6, 1.9 Hz), 7.00 (dd, 2 H, J = 8.6, 1.9 Hz), 4.36 (m, 1 H), 3.86 (d, 2 H, J = 5.8 Hz), 3.00 (d, 2 H, J = 11.5 Hz), 2.72 (d, 3 H, J = 5.4 Hz), 2.46 (d, 2 H, J = 22.8 Hz), 2.18 (m, 2 H), 1.82 (d, 3 H, J = 10.8 Hz), 1.45 - 1.35 (m, 8 H); MS (ESI) m/z 435 (M+ + H). |

Example 13. Compound 499

4-((4'-(methylsulfonyl)biphenyl-4-yloxy)methyl)-1-(2,2,2-trifluoroethyl)piperidine

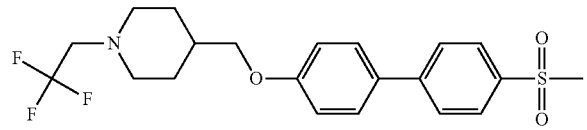 [SMILES: CS(=O)(=O)c1ccc(-c2ccc(OCC3CCN(CC(F)(F)F)CC3)cc2)cc1]

4-((4'-(methylsulfonyl)biphenyl-4-yloxy)methyl)piperidine hydrochloride (the product of synthesis step 5 of compound 431; 50 mg, 0.13 mmol) was dissolved in DMSO 2 mL. 2,2,2-trifluoroethyl trifluoromethanesulfonate (30 mg, 0.13 mmol) and K₂CO₃ (91 mg, 0.66 mmol) were added thereto, following with stirring at room temperature for 15 hours. The reaction mixture was added with EtOAc, and washed with water three times. The organic layer was dried over MgSO₄, filtered to remove the solid residue, and the filtrate was concentrated under reduced pressure. The obtained concentrate was purified by silica gel column chromatography (20-40% EtOAc/hexane) to yield the title compound as white solid (23 mg, 41%).

1H NMR (400 MHz, CDCl₃) δ 7.99-7.96 (m, 2H), 7.74-7.71 (m, 2H), 7.56-7.52 (m, 2H), 7.01-6.98 (m, 2H), 3.86 (d, 2H, J=6.0 Hz), 3.09 (s, 3H), 3.06-2.96 (m, 4H), 2.41 (t, 2H, J=10.9 Hz), 1.87-1.8.1 (m, 3H), 1.56 (s, 2H), 1.52-1.43 (m, 2H); MS (ESI) m/z 428 (M++H).

Example 14. Compound 524: 4-((4'-(methylsulfonyl)biphenyl-4-yloxy)methyl)-1-(3,3,3-trifluoropropyl)piperidine

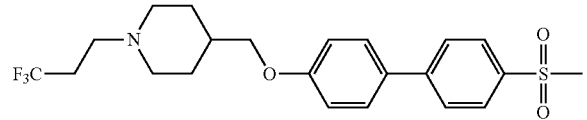 [SMILES: CS(=O)(=O)c1ccc(-c2ccc(OCC3CCN(CCC(F)(F)F)CC3)cc2)cc1]

Step 1.
3,3,3-trifluoro-1-(4-((4'-(methylsulfonyl)biphenyl-4-yloxy)methyl)piperidin-1-yl)propan-1-one: 4-((4'-(methylsulfonyl)biphenyl-4-yloxy)methyl)piperidine hydrochloride (the product of synthesis step 5 of compound 431; 40 mg, 0.11 mol) and CF₃CH₂COCl (16 μL, 0.16 mmol) were dissolved in CH₂Cl₂ 2 mL. Et₃N (44 μL, 0.31 mmol) was added thereto, following with stirring for 5 hours at room temperature. The reaction mixture was added with water, and extracted with CH₂Cl₂. The organic layer was dried over MgSO₄, filtered to remove solid, and then concentrated under reduced pressure The obtained concentrate was purified by silica gel column chromatography (20% EtOAc/hexane) to yield the title compound as white solid (54 mg, 113%).

Step 2.
Compound 524: 3,3,3-trifluoro-1-(4-((4'-(methylsulfonyl)biphenyl-4-yloxy)methyl)piperidin-1-yl)propan-1-one (46 mg, 0.10 mmol) was dissolved in dry THF 2 mL, and then cooled with ice bath. 1 M LAH in THF (0.20 mL, 0.20 mmol) was added dropwise slowly thereto, following with increasing the temperature to room temperature slowly and stirring for 4 hours. Water was poured into the reaction mixture. The formed solid was removed by filtration, and the filtrate was extracted with EtOAc three times. The organic layer was dried over MgSO₄, filtered to remove the solid residue, and the filtrate was concentrated under reduced pressure. The obtained concentrate was purified by silica gel column chromatography (20-40% EtOAc/hexane) to yield the title compound as white solid (9 mg, 19%).

1H NMR (400 MHz, CDCl₃) δ 8.00-7.93 (m, 2H), 7.77-7.69 (m, 2H), 7.59-7.52 (m, 2H), 7.03-6.95 (m, 2H), 3.86 (d, 2H, J=6.0 Hz), 3.08 (s, 3H), 2.95 (d, 2H, J=11.5 Hz), 2.66-2.57 (m, 2H), 2.41-2.26 (m, 2H), 2.11-2.01 (m, 2H), 1.93-1.81 (m, 3H), 1.50-1.36 (m, 2H); MS (ESI) m/z 468 (M++H).

Example 15. Compound 470: 5-(4-((1-(2-fluoro-2-methylpropyl)piperidin-4-yl)methoxy)phenyl)-2,3-dihydrobenzo[b]thiophene 1,1-dioxide

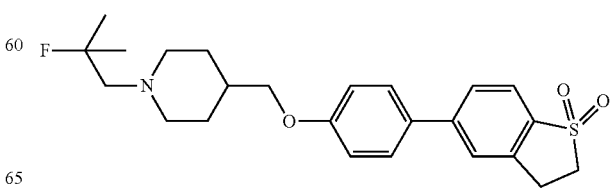

Step 1.
4-(benzo[b]thiophen-5-yl)phenol: 5-bromobenzo[b]thiophene (3.0 g, 14.08 mmol) and 4-hydroxyphenylboronic acid (2.91 g, 21.11 mmol) were dissolved in DME 40 mL. Water 10 mL was added thereto. Pd(dbpf)Cl₂ (459 mg, 0.70 mmol) and Cs₂CO₃ (13.68 g, 42.24 mmol) were added thereto, and refluxed with heating at 90° C. for a day. The reaction mixture was filtered through Celite. The obtained filtrate was extracted with EtOAc three times, dried over MgSO₄, and then concentrated under reduced pressure. The obtained concentrate was purified by silica gel column chromatography (15-20% EtOAc/hexane) to yield the title compound as white solid (2.30 g, 72%).

Step 2.
t-butyl 4-((4-(benzo[b]thiophen-5-yl)phenoxy)methyl)piperidin-1-carboxylate: 4-(benzo[b]thiophen-5-yl)phenol (1.30 g, 5.74 mmol) and t-butyl 4-((methylsulfonyloxy)methyl)piperidin-1-carboxylate (the product of synthesis step 2 of compound 431; 2.02 g, 6.89 mmol) were dissolved in ACN 10 mL Cs₂CO₃ (3.74 g, 11.49 mmol) was added thereto, and refluxed with heating for a day. The reaction mixture was diluted with water, and extracted with EtOAc. The organic layer was concentrated under reduced pressure. The obtained concentrate was purified by silica gel column chromatography (20-30% EtOAc/hexane) to yield the title compound as white solid (1.81 g, 74%).

Step 3.
t-butyl 4-((4-(1,1-dioxidobenzo[b]thiophen-5-yl)phenoxy)methyl)piperidin-1-carboxylate: t-butyl 4-((4-(benzo[b]thiophen-5-yl)phenoxy)methyl)piperidin-1-carboxylate (1.8 g, 4.28 mmol) was dissolved in CHCl₃ 30 mL. m-CPBA (1.85 g, 10.70 mmol) was added thereto, following with stirring for 1 hour. A saturated NaHCO₃ aqueous solution was added thereto, and then, and extracted with CH₂Cl₂. The obtained concentrate was purified by silica gel column chromatography (10-20% EtOAcCH₂Cl₂) to yield the title compound as white solid (1.50 g, 77%).

Step 4.
t-butyl 4-((4-(1,1-dioxido-2,3-dihydrobenzo[b]thiophen-5-yl)phenoxy)methyl)piperidin-1-carboxylate: t-butyl 4-((4-(1,1-dioxidobenzo[b]thiophen-5-yl)phenoxy)methyl)piperidin-1-carboxylate (700 mg, 1.54 mmol) was dissolved in THF 10 mL and EtOH 10 mL. 10% wt PdC (70 mg) was added thereto, following with hydrogen gas flowing and stirring at room temperature for two days. The reaction mixture was filtered through Celite to remove a solid. The obtained filtrate was concentrated. The obtained concentrate was purified by silica gel column chromatography (20-30% EtOAcCH₂Cl₂) to yield the title compound as white solid (680 mg, 96%).

Step 5.
5-(4-(piperidin-4-ylmethoxy)phenyl)-2,3-dihydrobenzo[b]thiophene 1,1-dioxide 2,2,2-trifluoroacetate: t-butyl 4-((4-(1,1-dioxido-2,3-dihydrobenzo[b]thiophen-5-yl)phenoxy)methyl)piperidin-1-carboxylate (800 mg, 1.75 mmol) was dissolved in CH₂Cl₂ 6 mL. TFA 161 μL was added thereto, following with stirring at room temperature for 2 hours. The reaction mixture was filtered, and a recrystallization was performed with ether to yield the title compound as white solid (740 mg, 93%).

Step 6.
5-(4-((1-(2-hydroxy-2-methylpropyl)piperidin-4-yl)methoxy)phenyl)-2,3-dihydrobenzo[b]thiophene 1,1-dioxide: 5-(4-(piperidin-4-ylmethoxy)phenyl)-2,3-dihydrobenzo[b]thiophene 1,1-dioxide 2,2,2-trifluoroacetate (50 mg, 0.13 mmol) and K₂CO₃ (35 mg, 0.25 mmol) were suspended in EtOH 0.5 mL. Water 0.5 mL was added thereto, and the mixture was suspended with a little heating. 2,2-dimethyl oxirane (35 mg, 1.27 mmol) was added thereto. With a microwave radiation, the reaction was performed at 110° C. for 20 minutes. The reaction mixture was diluted with water, and extracted with EtOAc. The obtained concentrate was purified by silica gel column chromatography (50-60% EtOAc/Hexane) to yield the title compound as white solid (31 mg, 57%).

Step 7.
Compound 470: 5-(4-((1-(2-hydroxy-2-methylpropyl)piperidin-4-yl)methoxy)phenyl)-2,3-dihydrobenzo[b]thiophene 1,1-dioxide (14 mg, 0.03 mmol) was dissolved in CH₂Cl₂ 1 mL. Deoxo-Fluor (8 mg, 0.04 mmol) was added thereto at 0° C., following with stirring at room temperature for 3 hours. A saturated NaHCO₃ aqueous solution was added thereto, and the mixture was extracted with CH₂Cl₂. The organic layer was dried over MgSO₄, filtered to remove solid, and then concentrated under reduced pressure. The obtained concentrate was purified by silica gel column chromatography (50-60% EtOAc/Hexane) to yield the title compound as white solid (11 mg, 78%).

1H NMR (400 MHz, CDCl₃) δ 7.76 (d, 1H, J=8.2 Hz), 7.63 (d, 1H, J=8.7 Hz), 7.49 (m, 3H), 6.98 (dd, 2H, J=9.2, 2.4 Hz), 3.84 (d, 2H, J=6.0 Hz), 3.53 (m, 2H), 3.42 (m, 2H), 2.98 (m, 2H), 2.47 (s, 1H), 2.41 (s, 1H), 2.17 (td, 2H, J=11.7, 1.6 Hz), 1.80 (m, 3H), 1.40 (m, 5H), 1.33 (s, 3H); MS (ESI) m/z 432 (M++H).

Example 16. Compound 540: 5-(4-((1-(2,2,2-trifluoroethyl)piperidin-4-yl)methoxy)phenyl)-2,3-dihydrobenzo[b]thiophene 1,1-dioxide

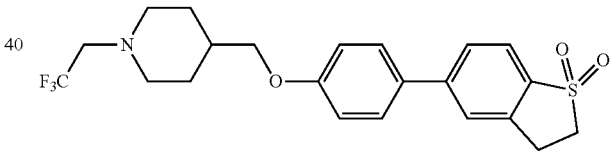

5-(4-(piperidin-4-ylmethoxy)phenyl)-2,3-dihydrobenzo[b]thiophene 1,1-dioxide 2,2,2-trifluoroacetate (the product of synthesis step 5 of compound 470; 50 mg, 0.11 mmol) was dissolved in DMSO 1 mL. 2,2,2-trifluoroethyl trifluoromethanesulfonate (26 mg, 0.11 mmol) and K₂CO₃ (76 mg, 0.55 mmol) were added thereto, and stirred at room temperature for 20 hours. The reaction mixture was added with water, and extracted with EtOAc. The organic layer was dried over MgSO₄, filtered to remove solid, and then concentrated under reduced pressure. The obtained concentrate was purified by silica gel column chromatography (40-60% EtOAc/Hexane) to yield the title compound as white solid (9 mg, 18%).

1H NMR (400 MHz, CDCl₃) δ 7.77 (d, 1H, J=8.2 Hz), 7.64 (m, 1H), 7.51 (m, 3H), 6.98 (dd, 2H, J=6.8, 2.0 Hz), 3.85 (d, 2H, J=5.9 Hz), 3.53 (m, 2H), 3.42 (m, 2H), 3.00 (m, 4H), 2.40 (m, 2H), 1.85 (m, 3H), 1.31 (m, 2H); MS (ESI) m/z 440 (M++H).

Example 17. Compound 574: 4-(6-((1-((1-(trifluoromethyl)cyclobutyl)methyl)piperidin-4-yl)methoxy)pyridine-3-yl)benzoic acid

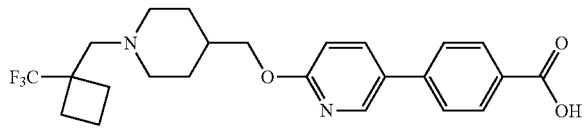 [SMILES: O=C(O)c1ccc(-c2ccc(OCC3CCN(CC4(C(F)(F)F)CCC4)CC3)nc2)cc1]

Step 1.

Methyl 4-(6-((1-((1-(trifluoromethyl)cyclobutyl)methyl)piperidin-4-yl)methoxy)pyridine-3-yl)benzoate: 5-bromo-2-((1-((1-(trifluoromethyl)cyclobutyl)methyl)piperidin-4-yl)methoxy)pyridine (the product of synthesis step 3 of compound 676; 0.34 g, 0.85 mmol), 4-(methoxycarbonyl)phenylboronic acid (306 mg, 1.70 mmol), Pd(dbpf)Cl$_2$ (55 mg, 0.09 mmol), Cs$_2$CO$_3$ (1.19 g, 3.68 mmol) were added into a microwave reactor, and then dioxane 5 mL and water 2 mL were added thereto. With a microwave radiation, the reaction was performed at 120° C. for 20 minutes. The reaction mixture was added with a saturated NaHCO$_3$ aqueous solution, and extracted with EtOAc. The obtained organic layer was dried over MgSO$_4$, and filtered. The filtrate was concentrated under reduced pressure. The obtained concentrate was purified by silica gel column chromatography (15-20% EtOAc/hexane) to yield the title compound as white solid (80 mg, 20%).

Step 2.

Compound 574: methyl 4-(6-((1-((1-(trifluoromethyl)cyclobutyl)methyl)piperidin-4-yl)methoxy)pyridine-3-yl)benzoate (135 mg, 0.29 mmol) was dissolved in the mixed solvents of THF 2 mL/MeOH 1 mL/water 0.5 mL. LiOH.H$_2$O (24 mg, 0.58 mmol) was added thereto, and refluxed with heating and stirring for 4 hours. The solvent was concentrated under reduced pressure. After the addition of 1M HCl 5 mL thereto, the resulting precipitate was filtered. The obtained solid was purified by silica gel column chromatography (30-80% EtOAc/hexane) to yield the title compound as white solid (80 mg, 62%).

1H NMR (400 MHz, DMSO) δ 8.53 (s, 1H), 8.07 (d, 1H, J=7.8 Hz), 7.99 (d, 2H, J=7.6 Hz), 7.78 (d, 2H, J=7.7 Hz), 6.92 (d, 1H, J=8.5 Hz), 4.15 (m, 2H), 2.94 (m, 2H), 2.51 (m, 2H), 2.12 (m, 7H), 1.90 (m, 2H), 1.71 (m, 2H), 1.28 (m, 2H); MS (ESI) m/z 449 (M++H).

Example 18. Compound 575: 1-(4'-((1-((1-(trifluoromethyl)cyclobutyl)methyl)piperidin-4-yl)methoxy)biphenyl-4-yl)ethanone

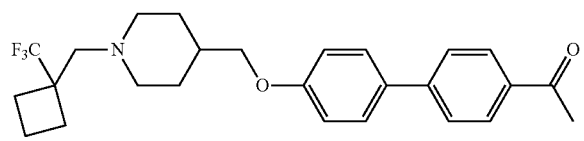 [SMILES: CC(=O)c1ccc(-c2ccc(OCC3CCN(CC4(C(F)(F)F)CCC4)CC3)cc2)cc1]

Step 1.

t-butyl 4-((4'-acetylbiphenyl-4-yloxy)methyl)piperidin-1-carboxylate: t-butyl 4-((4-bromophenoxy)methyl)piperidin-1-carboxylate (the product of synthesis step 3 of compound 431; 500 mg, 1.35 mmol) and 4-acetylphenylboronic acid (244 mg, 1.49 mmol) were dissolved in dioxane 4 mL. water 1.5 mL was added thereto. Pd(dbpf)Cl$_2$ (88 mg, 0.14 mmol) and Cs$_2$CO$_3$ (660 mg, 2.03 mmol) were added thereto. With a microwave radiation, the reaction was performed at 120° C. for 20 minutes. The reaction mixture was filtered through Celite, and the filtrate was dissolved in EtOAc. The solution was washed with saturated NaHCO$_3$ aqueous solution and water, dried over MgSO$_4$, and then concentrated under reduced pressure. The obtained concentrate was purified by silica gel column chromatography (30-40% EtOAc/hexane) to yield the title compound as yellow solid (400 mg, 72%).

Step 2.

1-(4'-(piperidin-4-ylmethoxy)biphenyl-4-yl)ethanone hydrochloride: t-butyl 4-((4'-acetylbiphenyl-4-yloxy)methyl)piperidin-1-carboxylate (400 mg, 0.98 mmol) was dissolved in CH$_2$Cl$_2$ 4 mL. 4 M HCl 488 µL was added thereto, following with stirring at room temperature for 2 hours. The obtained reaction mixture was filtered to yield the title compound as white solid (330 mg, 97%).

Step 3.

1-(4'-((1-(1-(trifluoromethyl)cyclobutanecarbonyl)piperidin-4-yl)methoxy)biphenyl-4-yl)ethanone: 1-(4'-(piperidin-4-ylmethoxy)biphenyl-4-yl)ethanone hydrochloride (380 mg, 1.10 mmol), 1-(trifluoromethyl)cyclobutanecarboxylic acid (185 mg, 1.10 mmol), EDC (421 mg, 2.20 mmol) and HOBt (270 mg, 2.20 mmol) were dissolved in DMF 6 mL. DIPEA (284 mg, 2.20 mmol) was added thereto, and the reaction was performed at 60° C. for 3 hours. The reaction mixture was added with water, and extracted with EtOAc. The obtained organic layer was dried over MgSO$_4$, and filtered. The filtrate was concentrated under reduced pressure. The obtained concentrate was purified by silica gel column chromatography (40-50% EtOAc/hexane) to yield the title compound as yellow solid (350 mg, 69%).

Step 4.

1-(4'-((1-((1-(trifluoromethyl)cyclobutyl)methyl)piperidin-4-yl)methoxy)biphenyl-4-yl)ethanol: 1-(4'-((1-(1-(trifluoromethyl)cyclobutanecarbonyl)piperidin-4-yl)methoxy)biphenyl-4-yl)ethanone (193 mg, 0.42 mmol) was dissolved in dry THF 10 mL, and then cooled with ice bath. LAH (1 M in THF, 0.13 mL, 0.13 mmol) was added dropwise slowly thereto, following with increasing the temperature to 50° C. and stirring for a day. Water was poured into the reaction mixture. The formed solid was removed by filtration, and the filtrate was extracted with EtOAc three times. The organic layer was dried over MgSO$_4$, and filtered to remove a solid. The filtrate was concentrated under reduced pressure to yield the title compound as white solid (90 mg, 48%).

Step 5.

Compound 575: 1-(4'-((1-((1-(trifluoromethyl)cyclobutyl)methyl)piperidin-4-yl)methoxy)biphenyl-4-yl)ethanol (27 mg, 0.06 mmol) was dissolved in CH$_2$Cl$_2$ 2 mL. Dess-Martin periodinane (38 mg, 0.09 mmol) was added thereto. The reaction was performed at room temperature for 3 hours. A saturated NaHCO$_3$ aqueous solution was added thereto, and the mixture was extracted with EtOAc. The obtained organic layer was washed with saturated aqueous brine solution, dried over MgSO$_4$, and filtered. The filtrate was concentrated under reduced pressure. The obtained concentrate was purified by silica gel column chromatography (EtOAc/hexane) to yield the title compound as white solid (16 mg, 59%).

1H NMR (400 MHz, CDCl$_3$) δ 8.02 (d, 2H, J=8.4 Hz), 7.66 (d, 2H, J=8.3 Hz), 7.58 (d, 2H, J=8.7 Hz), 7.00 (d, 2H, J=8.7 Hz), 3.86 (d, 2H, J=6.0 Hz), 2.91 (d, 2H, J=11.3 Hz), 2.64 (s, 3H), 2.54 (s, 2H), 2.22 (m, 4H), 2.01 (m, 4H), 1.82 (m, 3H), 1.43 (m, 2H); MS (ESI) mz 446 (M++H).

Example 19. Compound 593: 1-(4-(5-((1-((1-(trifluoromethyl)cyclobutyl)methyl)piperidin-4-yl)methoxy)pyridine-2-yl)phenyl)ethanone

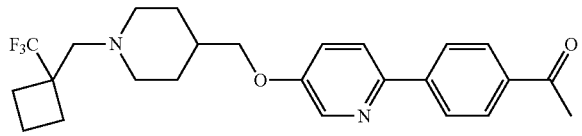 [SMILES: CC(=O)c1ccc(-c2ccc(OCC3CCN(CC4(C(F)(F)F)CCC4)CC3)cn2)cc1]

Step 1.
t-butyl 4-((6-(4-acetylphenyl)pyridine-3-yloxy)methyl)piperidin-1-carboxylate: t-butyl 4-((6-chloropyridine-3-yloxy)methyl)piperidin-1-carboxylate (the product of synthesis step 1 of compound 597; 500 mg, 1.53 mmol) and 4-acetylphenylboronic acid (276 mg, 1.68 mmol) were dissolved in dioxane 4 mL. water 1 mL was added thereto. Pd(dppf)Cl$_2$ (63 mg, 0.08 mmol) and Na$_2$CO$_3$ (660 mg, 2.03 mmol) were added thereto. With a microwave radiation, the reaction was performed at 120° C. for 20 minutes. The reaction mixture was filtered through Celite, and the obtained organic layer was washed with saturated NaHCO$_3$ aqueous solution and water, dried over MgSO$_4$, and then concentrated under reduced pressure. The obtained concentrate was purified by silica gel column chromatography (30-40% EtOAcCH$_2$Cl$_2$) to yield the title compound as white solid (300 mg, 47%).
Step 2.
1-(4-(5-(piperidin-4-ylmethoxy)pyridine-2-yl)phenyl)ethanone hydrochloride: t-butyl 4-((6-(4-acetylphenyl)pyridine-3-yloxy)methyl)piperidin-1-carboxylate (300 mg, 0.73 mmol) was dissolved in CH$_2$Cl$_2$ 3 mL. 4 M HCl 201 mL was added thereto, following with stirring at room temperature for 2 hours. The obtained reaction mixture was filtered to yield the title compound as white solid (250 mg, 98%).
Step 3.
1-(4-(5-((1-(1-(trifluoromethyl)cyclobutanecarbonyl)piperidin-4-yl)methoxy)pyridine-2-yl)phenyl)ethanone: 1-(4-(5-(piperidin-4-ylmethoxy)pyridine-2-yl)phenyl)ethanone hydrochloride (250 mg, 0.72 mmol), 1-(trifluoromethyl)cyclobutanecarboxylic acid (145 mg, 0.87 mmol), EDC (276 mg, 1.44 mmol) and HOBt (195 mg, 1.44 mmol) were dissolved in DMF 2 mL. DIPEA (186 mg, 1.44 mmol) was added thereto. At 50° C., the reaction was performed for a day. The reaction mixture was added with water, and extracted with EtOAc. The organic layer was dried over MgSO$_4$, and filtered. The filtrate was concentrated under reduced pressure. The obtained concentrate was purified by silica gel column chromatography (40-50% EtOAc/hexane) to yield the title compound as white solid (158 mg, 47%).
Step 4.
1-(4-(5-((1-((1-(trifluoromethyl)cyclobutyl)methyl)piperidin-4-yl)methoxy)pyridine-2-yl)phenyl)ethanol: 1-(4-(5-((1-(1-(trifluoromethyl)cyclobutanecarbonyl)piperidin-4-yl)methoxy)pyridine-2-yl)phenyl)ethanone (148 mg, 0.32 mmol) was dissolved in dry THF 7 mL, and then cooled with ice bath. LAH (1 M in THF, 0.96 mL, 0.96 mmol) was added dropwise slowly thereto, following with increasing the temperature to 50° C. and stirring for 6 hours. Water was poured into the reaction mixture. The formed solid was removed by filtration, and the reaction mixture was extracted with EtOAc three times. The organic layer was dried over MgSO$_4$, and filtered to remove a solid. The filtrate was concentrated under reduced pressure to yield the title compound as white solid (110 mg, 76%).
Step 5.
Compound 593: 1-(4-(5-((1-((1-(trifluoromethyl)cyclobutyl)methyl)piperidin-4-yl)methoxy)pyridine-2-yl)phenyl)ethanol (96 mg, 0.21 mmol) was dissolved in CH$_2$Cl$_2$ 2 mL. DMP (118 mg, 0.28 mmol) was added thereto. The reaction was performed at room temperature for 3 hours. A saturated NaHCO$_3$ aqueous solution was added thereto, and the mixture was extracted with EtOAc. The obtained organic layer was washed with saturated aqueous brine solution, dried over MgSO$_4$, and filtered. The filtrate was concentrated under reduced pressure. The obtained concentrate was purified by silica gel column chromatography (EtOAc/hexane) to yield the title compound as white solid (78 mg, 81%).

1H NMR (400 MHz, CDCl$_3$) δ 8.42 (d, 1H, J=2.9 Hz), 8.02 (s, 4H), 7.74 (d, 1H, J=8.7 Hz), 7.29 (dd, 1H, J=8.8, 3.0 Hz), 3.91 (d, 2H, J=6.0 Hz), 2.94 (d, 2H, J=11.4 Hz), 2.65 (s, 3H), 2.57 (s, 2H), 2.21 (m, 4H), 2.08 (m, 2H), 1.99 (m, 1H), 1.94 (m, 1H), 1.89 (m, 3H), 1.49 (m, 2H); MS (ESI) m/z 447 (M++H).

Example 20. Compound 498: methyl 4'-((1-(2-fluoro-2-methylpropyl)piperidin-4-yl)methoxy)biphenyl-4-carboxylate

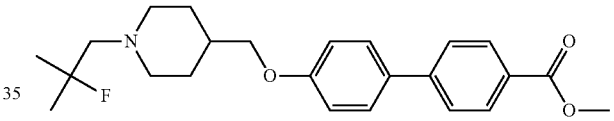

Step 1.
4-((4-bromophenoxy)methyl)piperidine hydrochloride: t-butyl 4-((4-bromophenoxyl)methyl)piperidin-1-carboxylate (the product of synthesis step 3 of compound 431; 5.00 g, 13.50 mmol) was dissolved in EtOAc 10 mL. 1 M HO 30 mL was added thereto, following with stirring at room temperature for 15 hours and refluxing with heating and stirring for 2 hours. The reaction mixture was cooled to room temperature, and filtered to yield the title compound as white solid (4.01 g, 97%).
Step 2.
1-(4-((4-bromophenoxy)methyl)piperidin-1-yl)-2-methylpropan-2-ol: 4-((4-bromophenoxy)methyl)piperidine hydrochloride (1.00 g, 3.26 mmol) and K$_2$CO$_3$ (0.23 g, 1.63 mmol) were suspended in EtOH 10 mL. Water 5 mL was added thereto to make a solution. 2,2-dimethyl oxirane (2.90 mL, 32.61 mmol) was added thereto. With a microwave radiation, the reaction was performed at 110° C. for 20 minutes. A little of water was added thereto, following with removing EtOH under reduced pressure, and extracting with CH$_2$Cl$_2$. The organic layer was dried over MgSO$_4$, and filtered to remove a solid. The filtrate was concentrated under reduced pressure to yield the title compound as white solid (1.10 g, 98%).
Step 3.
4-((4-bromophenoxy)methyl)-1-(2-fluoro-2-methylpropyl)piperidine: 1-(4-((4-bromophenoxy)methyl)piperidin-1-yl)-2-methylpropan-2-ol (1.10 g, 3.21 mmol) was dissolved in CH$_2$Cl$_2$ 10 mL. DAST (0.43 mL, 3.21 mmol) was added thereto, following with stirring with at room temperature for 1 hour. A saturated NaHCO₃ aqueous solution was added thereto, and the mixture was extracted with CH₂Cl₂. The organic layer was dried over MgSO₄, and filtered to remove a solid. The filtrate was concentrated under reduced pressure. The obtained concentrate was purified by silica gel column chromatography (0-5% MeOH/CH₂Cl₂) to yield the title compound as white solid (0.77 g, 70%).

Step 4.

Compound 498: 4-((4-bromophenoxy)methyl)-1-(2-fluoro-2-methylpropyl)piperidine (770 mg, 2.24 mmol) and 4-(methoxycarbonyl)phenylboronic acid (483 mg, 2.68 mmol) were dissolved in dioxane 3 mL. water 1 mL was added thereto. Pd(dbpf)Cl₂ (44 mg, 0.07 mmol) and Cs₂CO₃ (2.18 g, 6.71 mmol) were added thereto. With a microwave radiation, the reaction was performed at 140° C. for 15 minutes. The reaction mixture was diluted with water, and extracted with EtOAc three times. The organic layer was dried over MgSO₄, and then concentrated under reduced pressure. The concentrate was purified by silica gel column chromatography (20% EtOAc/hexane) to yield the title compound as white solid (682 mg, 76%).

1H NMR (400 MHz, CDCl₃) δ 8.11-8.04 (m, 2H), 7.66-7.60 (m, 2H), 7.59-7.53 (m, 2H), 7.02-6.94 (m, 2H), 3.93 (s, 3H), 3.84 (d, 2H, J=6.0 Hz), 2.99 (d, 2H, J=11.0 Hz), 2.47 (s, 1H), 2.42 (s, 1H), 2.22-2.12 (m, 2H), 1.82-1.79 (m, 3H), 1.49-1.37 (m, 1H), 1.39 (s, 3H), 1.34 (s, 3H); MS (ESI) m/z 400 (M++H).

Example 21. Compound 548: 4'-((1-(2-fluoro-2-methylpropyl)piperidin-4-yl)methoxy)biphenyl-4-carboxylic acid

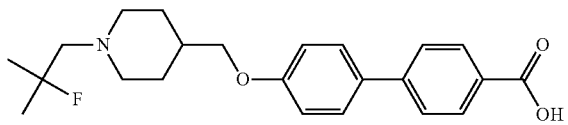 [SMILES: CC(C)(F)CN1CCC(COc2ccc(-c3ccc(C(=O)O)cc3)cc2)CC1]

Methyl 4'-((1-(2-fluoro-2-methylpropyl)piperidin-4-yl)methoxy)biphenyl-4-carboxylate (682 mg, 1.71 mmol) was dissolved in THF 6 mL. MeOH 2 mL and H₂O 2 mL were added thereto. LiOH (358 mg, 8.53 mmol) was added thereto, following with stirring at room temperature and refluxing with heating and stirring for 15 hours. After acidification with 1 N HCl, the resulting precipitate was filtered. The obtained solid was dissolved in MeOH, following with filtering to remove insoluble material and concentrating under reduced pressure to yield the title compound as pale gray solid (625 mg, 95.1%).

1H NMR (400 MHz, DMSO-d₆) δ 7.95 (d, 2H, J=8.3 Hz), 7.72 (d, 2H, J=8.3 Hz), 7.65 (d, 2H, J=8.7 Hz), 7.02 (d, 2H, J=8.7 Hz), 3.85 (d, 2H, J=5.8 Hz), 2.90 (d, 2H, J=11.2 Hz), 2.42 (s, 1H), 2.36 (s, 1H), 2.06 (t, 2H, J=11.4 Hz), 1.72-1.69 (m, 3H), 1.30 (m, 2H), 1.30 (s, 3H), 1.25 (s, 3H); MS (ESI) m/z 486 (M++H).

Example 22. Compound 515: 4'-((1-(2-fluoro-2-methylpropyl)piperidin-4-yl)methoxy)biphenyl-4-carboxamide

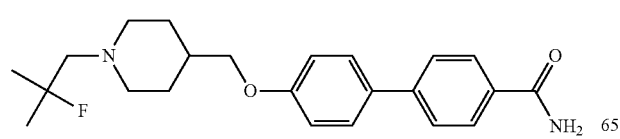

4'-((1-(2-fluoro-2-methylpropyl)piperidin-4-yl)methoxy)biphenyl-4-carboxylic acid (compound 548, 15 mg, 0.04 mmol) and NH₄Cl (4 mg, 0.08 mmol) were dissolved in DMF 1 mL. EDC (15 mg, 0.08 mmol) and HOBt (11 mg, 0.08 mmol) were added thereto. Lastly, DIPEA (34 μL, 0.20 mmol) was added thereto, following with stirring at room temperature for 15 hours. The solvent was concentrated under reduced pressure. The obtained concentrate was purified by silica gel column chromatography (10% MeOH/CH₂Cl₂) to yield the title compound as white solid (7 mg, 48%).

1H NMR (400 MHz, CDCl₃) δ 7.81-7.87 (m, 2H), 7.64-7.58 (m, 2H), 7.56-7.50 (m, 2H), 6.99-6.93 (m, 2H), 3.82 (d, 2H, J=6.0 Hz), 2.97 (d, 2H, J=11.8 Hz), 2.46 (s, 1H), 2.40 (s, 1H), 2.20-2.04 (m, 6H), 1.84-1.72 (m, 3H), 1.49-1.35 (m, 2H), 1.38 (s, 3H), 1.32 (s, 3 H); MS (ESI) m/z 385 (M++H).

Example 23. Compound 612: (R)-(4'-((1-(2-fluoro-2-methylpropyl)piperidin-4-yl)methoxy)biphenyl-4-yl)(3-hydroxypiperidin-1-yl)methanone

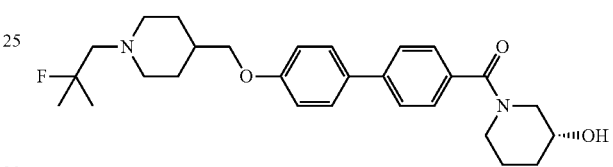

4'-((1-(2-fluoro-2-methylpropyl)piperidin-4-yl)methoxy)biphenyl-4-carboxylic acid (compound 548, 50 mg, 0.13 mmol) was suspended in CH₂Cl₂ 1 mL, and then added with EDC (50 mg, 0.26 mmol), HOBt (35 mg, 0.26 mmol) and DIPEA (113 μl, 0.65 mmol), thereby being dissolved completely. Lastly, (R)-hydroxypiperidine hydrochloride (36 mg, 0.26 mmol) was added thereto, following with stirring at room temperature for 6 hours. The reaction mixture was concentrated under reduced pressure, dissolved in a little of MeOH, and then added with water. The resulting precipitate was filtered to obtain a solid. The obtained solid was purified by silica gel column chromatography (0-10% MeOH/CH₂Cl₂) to yield the title compound as white solid (45 mg, 73%).

1H NMR (400 MHz, CDCl₃) δ 7.61-7.56 (m, 2H), 7.56-7.50 (m, 2H), 7.50-7.46 (m, 2H), 7.02-6.95 (m, 2H), 3.94 (brs, 1H), 3.85 (d, 2H, J=6.0 Hz), 3.47 (br, 4H), 3.00 (d, 2H, J=11.3 Hz), 2.48 (s, 1H), 2.43 (s, 1H), 2.18 (t, 2H, J=11.2 Hz), 1.97 (br, 2H), 1.83-1.80 (m, 3H), 1.67 (br, 2H), 1.52-1.38 (m, 2H), 1.41 (s, 3H), 1.35 (s, 3H); MS (ESI) m/z 469 (M++H).

According to the above-described synthesis process of compound 515, the compounds of Table 4 were synthesized using 4'-((1-(2-fluoro-2-methylpropyl)piperidin-4-yl)methoxy)biphenyl-4-carboxylic acid and the reactant of Table 3.

TABLE 3

| Compound No. | Reactant | Yield (%) |
| --- | --- | --- |
| 516 | dimethylamine hydrochloride | 73 |
| 517 | morpholine | 53 |
| 526 | cyclopropylamine | 69 |
| 527 | cyclobutylamine | 67 |
| 528 | cyclopentylamine | 73 |

TABLE 3-continued

| Compound No. | Reactant | Yield (%) |
|---|---|---|
| 529 | cyclohexylamine | 68 |
| 530 | pyrrolidine | 80 |
| 531 | piperidine | 66 |
| 533 | 4-aminobutan-1-ol | 64 |
| 534 | methylamine | 67 |
| 549 | 2-aminoethanol | 77 |
| 550 | 3-aminopropan-1-ol | 74 |
| 551 | 2-(methylamino)ethanol | 71 |
| 553 | (R)-3-pyrrolidinol | 72 |
| 554 | (S)-3-pyrrolidinol | 76 |
| 555 | (R)-prolinol | 77 |
| 556 | (S)-prolinol | 66 |
| 557 | (R)-2-(methoxymethyl)pyrrolidine | 80 |
| 558 | (S)-2-(methoxymethyl)pyrrolidine | 69 |
| 559 | 2-(butylamino)ethanol | 66 |
| 560 | furfurylamine | 78 |
| 561 | propylamine | 70 |
| 562 | benzylamine | 74 |
| 563 | N-ethylbenzylamine | 80 |
| 564 | (S)-2-trifluoromethylpyrrolidine | 71 |
| 565 | L-prolinamide | 67 |
| 566 | 3-fluoropyrrolidine hydrochloride | 76 |
| 567 | 4-piperidinemethanol | 69 |
| 568 | 4-hydroxypiperidine | 73 |
| 569 | 3-hydroxypiperidine hydrochloride | 55 |
| 570 | (R)-3-fluoropyrrolidine hydrochloride | 76 |
| 571 | (S)-3-fluoropyrrolidine hydrochloride | 72 |
| 594 | 3-(trifluoromethyl)-5,6,7,8-tetrahydro-[1,2,4]triazolo[4,3-a]pyrazine | 52 |
| 598 | N-methylethanamine | 76 |
| 599 | N-methylpropan-2-amine | 74 |
| 600 | azetidin-3-ol | 73 |
| 601 | 3,3-difluoroazetidine | 67 |
| 602 | t-butylamine | 79 |
| 603 | isopropylamine | 98 |
| 604 | diethylamine | 89 |
| 605 | 2-amino-2-methyl-1-propanol | 81 |
| 606 | (S)-2-amino-1-propanol | 83 |
| 607 | (R)-2-amino-1-butanol | 75 |
| 608 | D-valinol | 84 |
| 609 | L-valinol | 78 |
| 610 | serinol | 62 |
| 611 | 3-amino-1,2-propanediol | 65 |
| 613 | (S)-3-hydroxypipetidine hydrochloride | 79 |
| 619 | (R)-methyl pyrrolidine-2-carboxylate | 48 |
| 622 | (S)-methyl pyrrolidine-2-carboxylate | 42 |
| 623 | cyclopropyl(piperazin-1-yl)methanone | 83 |
| 624 | 1-(methylsulfonyl)piperazine | 87 |
| 625 | (S)-methyl pyrrolidine-2-carboxylate | 23 |
| 626 | t-butyl piperazin-1-carboxylate | 62 |
| 627 | 1-benzylpiperazine | 51 |
| 628 | 1-(piperazin-1-yl)ethanone | 17 |
| 629 | 3,3-difluoro pyrrolidine | 40 |
| 645 | glycine methyl ester hydrochloride | 82 |
| 646 | 3-oxetaneamine | 77 |
| 647 | β-alanine methyl ester | 78 |
| 648 | D-serine methyl ester hydrochloride | 71 |
| 649 | L-serine methyl ester hydrochloride | 57 |
| 650 | ethyl 4-amino-1-piperidinecarboxylate | 83 |
| 651 | amylamine | 81 |
| 677 | ethyl piperidin-2-carboxylate | 72 |
| 678 | ethyl piperidin-4-carboxylate | 83 |
| 679 | ethyl piperidin-3-carboxylate | 85 |
| 680 | 1-ethylpiperazine | 48 |
| 681 | 1-isopropylpiperazine | 42 |
| 685 | 1-methylpiperazine | 47 |
| 686 | 2,6-dimethylpiperazine | 17 |
| 687 | 2,6-dimethylmorpholine | 58 |
| 790 | piperazin-2-one | 82 |
| 791 | piperidin-4-carbonitrile | 77 |
| 830 | 4-(2-aminoethyl)benzene-1,2-diol | 25 |
| 831 | (R)-piperidin-2-carboxamide hydrochloride | 65 |
| 832 | (S)-piperidin-2-carboxamide hydrochloride | 71 |
| 874 | (S)-piperidin-3-carboxamide hydrochloride | 64 |
| 879 | (R)-piperidin-3-carboxamide hydrochloride | 79 |

TABLE 4

| Compound No. | Compound Name, $^1$H-NMR, MS (ESI) |
|---|---|
| 516 | 4'-((1-(2-fluoro-2-methylpropyl)piperidin-4-yl)methoxy)-N,N-dimethylbiphenyl-4-carboxamide<br>1 H NMR (400 MHz, CDCl$_3$) δ 7.61 - 7.56 (m, 2 H), 7.55 - 7.50 (m, 2 H), 7.50 - 7.45 (m, 2 H), 7.01 - 6.94 (m, 2 H), 3.84 (d, 2 H, J = 6.0 Hz), 3.13 (br, 3 H), 3.05 (br, 3 H), 2.99 (d, 2 H, J = 11.0 Hz), 2.47 (s, 1 H), 2.42 (s, 1 H), 2.22 - 2.12 (m, 2 H), 1.85 - 1.75 (m, 3 H), 1.50 - 1.38 (m, 2 H), 1.40 (s, 3 H), 1.34 (s, 3 H); MS (ESI) m/z 413 (M+ + H). |
| 517 | (4'-((1-(2-fluoro-2-methylpropyl)piperidin-4-yl)methoxy)biphenyl-4-yl)(morpholino)methanone<br>1 H NMR (400 MHz, CDCl$_3$) δ 7.57 - 7.62 (m, 2 H), 7.55 - 7.50 (m, 2 H), 7.49 - 7.44 (m, 2 H), 7.00 - 6.95 (m, 2 H), 3.84 (d, 2 H, J = 6.0 Hz), 3.81 - 3.45 (m, 8 H), 2.99 (d, 2 H, J = 11.8 Hz), 2.47 (s, 1 H), 2.42 (s, 1 H), 2.21 - 2.12 (m, 2 H), 1.85 - 1.76 (m, 3 H), 1.49 - 1.38 (m, 2 H), 1.40 (s, 3 H), 1.34 (s, 3 H); MS (ESI) m/z 455 (M+ + H). |
| 526 | N-cyclopropyl-4'-((1-(2-fluoro-2-methylpropyl)piperidin-4-yl)methoxy)biphenyl-4-carboxamide<br>1 H NMR (400 MHz, CDCl$_3$) δ 7.81 - 7.75 (m, 2 H), 7.62 - 7.57 (m, 2 H), 7.56 - 7.50 (m, 2 H), 7.00 - 6.94 (m, 2 H), 6.25 (s, 1 H), 3.84 (d, 2 H, J = 6.0 Hz), 2.99 (d, 2 H, J = 11.3 Hz), 2.95 - 2.89 (m, 1 H), 2.47 (s, 1 H), 2.41 (s, 1 H), 2.19 - 2.14 (m, 2 H), 1.85 - 1.75 (m, 3 H), 1.47 - 1.39 (m, 2 H), 1.39 (s, 3 H), 1.34 (s, 3 H), 0.93 - 0.85 (m, 2 H), 0.67 - 0.60 (m, 2 H); MS (ESI) m/z 425 (M+ + H). |
| 527 | N-cyclobutyl-4'-((1-(2-fluoro-2-methylpropyl)piperidin-4-yl)methoxy)biphenyl-4-carboxamide<br>1 H NMR (400 MHz, CDCl$_3$) δ 7.83 - 7.77 (m, 2 H), 7.63 - 7.58 (m, 2 H), 7.57 - 7.51 (m, 2 H), 7.01 - 6.95 (m, 2 H), 6.24 (d, 1 H, J = 8.0 Hz), 4.65 - 4.59 (m, 1 H), 3.84 (d, 2 H, J = 6.0 Hz), 2.99 (d, 2 H, J = 11.3 Hz), 2.51 - 2.40 (m, 4 H), 2.17 (t, 2 H, J = 10.8 Hz), 2.04 - 1.91 (m, 2 H), 1.85 - 1.75 (m, 5 H), 1.49 - 1.37 (m, 2 H), 1.39 (s, 3H), 1.34 (s, 3 H); MS (ESI) m/z 439 (M+ + H). |

TABLE 4-continued

| Compound No. | Compound Name, ¹H-NMR, MS (ESI) |
|---|---|
| 528 | N-cyclopentyl-4'-((1-(2-fluoro-2-methylpropyl)piperidin-4-yl)methoxy)biphenyl-4-carboxamide<br>1 H NMR (400 MHz, CDCl₃) δ 7.79 (d, 2 H, J = 8.5 Hz), 7.59 (d, 2 H, J = 8.3 Hz), 7.56 - 7.50 (m, 2 H), 7.00 - 6.94 (m, 2 H), 6.12 (d, 1 H, J = 7.3 Hz), 4.48 - 4.37 (m, 1 H), 3.84 (d, 2 H, J = 6.0 Hz), 2.99 (d, 2 H, J = 11.5 Hz), 2.47 (s, 1 H), 2.41 (s, 1 H), 2.21 - 2.05 (m, 4 H), 1.86 - 1.60 (m, 7 H), 1.56 - 1.37 (m, 4 H), 1.39 (s, 3 H), 1.34 (s, 3 H); MS (ESI) m/z 453 (M+ + H). |
| 529 | N-cyclohexyl-4'-((1-(2-fluoro-2-methylpropyl)piperidin-4-yl)methoxy)biphenyl-4-carboxamide<br>1 H NMR (400 MHz, CDCl₃) δ 7.80 (d, 2 H, J = 8.5 Hz), 7.60 (d, 2 H, J = 8.5 Hz), 7.56 - 7.51 (m, 2 H), 6.98 (d, 2 H, J = 8.8 Hz), 6.00 - 5.94 (m, 1 H), 4.07 - 3.94 (m, 1 H), 3.84 (d, 2 H, J = 6.0 Hz), 3.03 - 2.95 (m, 2 H), 2.47 (s, 1 H), 2.42 (s, 1 H), 2.19 - 2.14 (m, 2 H), 2.10 - 2.00 (m, 2 H), 1.82 - 1.75 (m, 5 H), 1.51 - 1.37 (m, 4 H), 1.39 (s, 3 H), 1.34 (s, 3 H), 1.31 - 1.20 (m, 4 H); MS (ESI) m/z 467 (M+ + H). |
| 530 | (4'-((1-(2-fluoro-2-methylpropyl)piperidin-4-yl)methoxy)biphenyl-4-yl)(pyrrolidine-1-yl)methanone<br>1 H NMR (400 MHz, CDCl₃) δ 7.57 (s, 4 H), 7.55 - 7.51 (m, 2 H), 7.00 - 6.95 (m, 2 H), 3.84 (d, 2 H, J = 6.0 Hz), 3.67 (t, 2 H, J = 7.0 Hz), 3.50 (t, 2 H, J = 6.5 Hz), 2.98 (d, 2 H, J = 11.3 Hz), 2.47 (s, 1 H), 2.41 (s, 1 H), 2.21 - 2.11 (m, 2 H), 2.02 - 1.93 (m, 2 H), 1.92 - 1.87 (m, 2 H), 1.84 - 1.74 (m, 3 H), 1.49 - 1.37 (m, 2 H), 1.39 (s, 3 H), 1.34 (s, 3 H); MS (ESI) m/z 439 (M+ + H). |
| 531 | (4'-((1-(2-fluoro-2-methylpropyl)piperidin-4-yl)methoxy)biphenyl-4-yl)(piperidin-1-yl)methanone<br>1 H NMR (400 MHz, CDCl₃) δ 7.59 - 7.55 (m, 2 H), 7.54 - 7.49 (m, 2 H), 7.47 - 7.41 (m, 2 H), 7.00 - 6.94 (m, 2 H), 3.84 (d, 2 H, J = 5.8 Hz), 3.72 (br, 2 H), 3.41 (br, 2 H), 2.98 (d, 2 H, J = 11.5 Hz), 2.47 (s, 1 H), 2.41 (s, 1 H), 2.17 (td, 2 H, J = 11.7, 2.0 Hz), 1.86 - 1.74 (m, 3 H), 1.74 - 1.50 (m, 6 H), 1.48 - 1.36 (m, 2 H), 1.39 (s, 3 H), 1.34 (s, 3 H); MS (ESI) m/z 453 (M+ + H). |
| 533 | 4'-((1-(2-fluoro-2-methylpropyl)piperidin-4-yl)methoxy)-N-(4-hydroxybutyl)biphenyl-4-carboxamide<br>1 H NMR (400 MHz, CDCl₃) δ 7.84 - 7.78 (m, 2 H), 7.64 - 7.58 (m, 2 H), 7.57 - 7.50 (m, 2 H), 7.01 - 6.94 (m, 2 H), 6.50 (t, 1 H, J = 5.6 Hz), 3.84 (d, 2 H, J = 5.8 Hz), 3.75 (t, 2 H, J = 6.0 Hz), 3.53 (q, 2 H, J = 6.5 Hz), 2.99 (d, 2 H, J = 11.3 Hz), 2.47 (s, 1 H), 2.42 (s, 1 H), 2.17 (t, 2 H, J = 10.8 Hz), 1.86 - 1.60 (m, 7 H), 1.49 - 1.37 (m, 2 H), 1.40 (s, 3 H), 1.34 (s, 3 H); MS (ESI) m/z 457 (M+ + H). |
| 534 | 4'-((1-(2-fluoro-2-methylpropyl)piperidin-4-yl)methoxy)-N-methylbiphenyl-4-carboxamide<br>1 H NMR (400 MHz, CDCl₃) δ 7.83 - 7.78 (m, 2 H), 7.64 - 7.58 (m, 2 H), 7.57 - 7.52 (m, 2 H), 7.01 - 6.94 (m, 2 H), 6.16 (d, 1 H, J = 4.3 Hz), 3.84 (d, 2 H, J = 6.0 Hz), 3.04 (d, 3 H, J = 4.8 Hz), 2.99 (d, 2 H, J = 11.5 Hz), 2.47 (s, 1 H), 2.42 (s, 1 H), 2.22 - 2.12 (m, 2 H), 1.85 - 1.75 (m, 3 H), 1.49 - 1.37 (m, 2 H), 1.39 (s, 3 H), 1.34 (s, 3 H); MS (ESI) m/z 399 (M+ + H). |
| 549 | 4'-((1-(2-fluoro-2-methylpropyl)piperidin-4-yl)methoxy)-N-(2-hydroxyethyl)biphenyl-4-carboxamide<br>1 H NMR (400 MHz, CDCl₃) δ 7.85 - 7.79 (m, 2 H), 7.62 - 7.56 (m, 2 H), 7.55 - 7.49 (m, 2 H), 7.00 - 6.93 (m, 2 H), 6.75 (t, 1 H, J = 5.4 Hz), 3.89 - 3.80 (m, 4 H), 3.69 - 3.61 (m, 2 H), 2.99 (d, 2 H, J = 11.5 Hz), 2.47 (s, 1 H), 2.42 (s, 1 H), 2.22 - 2.12 (m, 2 H), 1.86 - 1.74 (m, 3 H), 1.49 - 1.37 (m, 2 H), 1.41 (s, 3 H), 1.34 (s, 3 H); MS (ESI) m/z 429 (M+ + H). |
| 550 | 4'-((1-(2-fluoro-2-methylpropyl)piperidin-4-yl)methoxy)-N-(3-hydroxypropyl)biphenyl-4-carboxamide<br>1 H NMR (400 MHz, CDCl₃) δ 7.85 - 7.79 (m, 2 H), 7.63 - 7.57 (m, 2 H), 7.56 - 7.49 (m, 2 H), 7.00 - 6.93 (m, 2 H), 6.78 (br, 1 H), 3.83 (d, 2 H, J = 6.0 Hz), 3.73 (t, 2 H, J = 5.5 Hz), 3.65 (q, 2 H, J = 6.1 Hz), 2.99 (d, 2 H, J = 11.3 Hz), 2.47 (s, 1 H), 2.42 (s, 1 H), 2.22 - 2.12 (m, 2 H), 1.85 - 1.73 (m, 5 H), 1.49 - 1.37 (m, 2 H), 1.39 (s, 3 H), 1.34 (s, 3 H); MS (ESI) m/z 443 (M+ + H). |
| 551 | 4'-((1-(2-fluoro-2-methylpropyl)piperidin-4-yl)methoxy)-N-(2-hydroxyethyl)-N-methylbiphenyl-4-carboxamide<br>1 H NMR (400 MHz, CDCl₃) δ 7.63 - 7.45 (m, 6 H), 6.97 (d, 2 H, J = 8.8 Hz), 3.92 (br, 1 H), 3.84 (d, 2 H, J = 6.0 Hz), 3.75 (br, 2 H), 3.51 (br, 1 H), 3.11 (br, 3 H) 2.99 (d, 2 H, J = 11.5 Hz), 2.47 (s, 1 H), 2.42 (s, 1 H), 2.22 - 2.12 (m, 2 H), 1.86 - 1.73 (m, 3 H), 1.50 - 1.37 (m, 2 H), 1.39 (s, 3 H), 1.34 (s, 3 H); MS (ESI) m/z 443 (M+ + H). |
| 553 | (R)-(4'-((1-(2-fluoro-2-methylpropyl)piperidin-4-yl)methoxy)biphenyl-4-yl)(3-hydroxypyrrolidin-1-yl)methanone<br>1 H NMR (400 MHz, CDCl₃) δ 7.61 - 7.47 (m, 6 H), 6.96 (d, 2 H, J = 8.8 Hz), 3.83 (d, 2 H, J = 5.8), 3.80 - 3.47 (m, 4 H), 2.99 (d, 2 H, J = 11.5 Hz), 2.47 (s, 1 H), 2.42 (s, 1 H), 2.22 - 2.12 (m, 2 H), 2.10 - 1.91 (m, 3 H), 1.86 - 1.73 (m, 3 H), 1.50 - 1.37 (m, 2 H), 1.39 (s, 3 H), 1.34 (s, 3 H); MS (ESI) m/z 455 (M+ + H). |
| 554 | (S)-(4'-((1-(2-fluoro-2-methylpropyl)piperidin-4-yl)methoxy)biphenyl-4-yl)(3-hydroxypyrrolidin-1-yl)methanone<br>1 H NMR (400 MHz, CDCl₃) δ 7.60 - 7.46 (m, 6 H), 6.99 - 6.93 (m, 2 H), 3.83 (d, |

TABLE 4-continued

| Compound No. | Compound Name, ¹H-NMR, MS (ESI) |
|---|---|
| | 2 H, J = 5.8 Hz), 3.80 - 3.45 (m, 4 H), 2.98 (d, 2 H, J = 11.3 Hz), 2.47 (s, 1 H), 2.41 (s, 1 H), 2.22 - 2.11 (m, 2 H), 2.11 - 1.91 (d, 3 H, J = 3.5 Hz), 1.85 - 1.73 (m, 3 H), 1.49 - 1.37 (m, 2 H), 1.39 (s, 3 H), 1.33 (s, 3 H); MS (ESI) m/z 455 (M+ + H). |
| 555 | (R)-(4'-((1-(2-fluoro-2-methylpropyl)piperidin-4-yl)methoxy)biphenyl-4-yl)(2-(hydroxymethyl)pyrrolidin-1-yl)methanone<br>1 H NMR (400 MHz, CDCl₃) δ 7.62 - 7.55 (m, 4 H), 7.54 - 7.50 (m, 2 H), 7.00 - 6.94 (m, 2 H), 4.43 (d, 1 H, J = 6.0 Hz), 3.87 - 3.71 (m, 4 H), 3.66 - 3.49 (m, 2 H), 2.98 (d, 2 H, J = 11.5 Hz), 2.47 (s, 1 H), 2.41 (s, 1 H), 2.20 - 2.13 (m, 3 H), 1.95 - 1.58 (m, 6 H), 1.49 - 1.37 (m, 2 H), 1.39 (s, 3 H), 1.34 (s, 3 H); MS (ESI) m/z 469 (M+ + H). |
| 556 | (S)-(4'-((1-(2-fluoro-2-methylpropyl)piperidin-4-yl)methoxy)biphenyl-4-yl)(2-(hydroxymethyl)pyrrolidin-1-yl)methanone<br>1 H NMR (400 MHz, CDCl₃) δ 7.61 - 7.55 (m, 4 H), 7.54 - 7.50 (m, 2 H), 7.00 - 6.94 (m, 2 H), 4.48 - 4.38 (m, 1 H), 3.87 - 3.71 (m, 4 H), 3.66 - 3.48 (m, 2 H), 2.98 (d, 2 H, J = 11.5 Hz), 2.47 (s, 1 H), 2.41 (s, 1 H), 2.16 (m, 3 H), 1.94 - 1.58 (m, 6 H), 1.49 - 1.36 (m, 2 H), 1.39 (s, 3 H), 1.34 (s, 3 H); MS (ESI) m/z 469 (M+ + H). |
| 557 | (R)-(4'-((1-(2-fluoro-2-methylpropyl)piperidin-4-yl)methoxy)biphenyl-4-yl)(2-(methoxymethyl)pyrrolidin-1-yl)methanone<br>1 H NMR (400 MHz, CDCl₃) δ 7.57 (s, 4 H), 7.55 - 7.50 (m, 2 H), 7.00 - 6.94 (m, 2 H), 4.46 (br, 1 H), 3.84 (d, 2 H, J = 6.0 Hz), 3.74 - 3.47 (m, 4 H), 3.41 (s, 3 H), 2.98 (d, 2 H, J = 11.3 Hz), 2.47 (s, 1 H), 2.41 (s, 1 H), 2.22 - 2.12 (m, 2 H), 2.12 - 1.90 (m, 3 H), 1.86 - 1.69 (m, 4 H), 1.50 - 1.37 (m, 2 H), 1.39 (s, 3 H), 1.34 (s, 3 H); MS (ESI) m/z 483 (M+ + H). |
| 558 | (S)-(4'-((1-(2-fluoro-2-methylpropyl)piperidin-4-yl)methoxy)biphenyl-4-yl)(2-(methoxymethyl)pyrrolidin-1-yl)methanone<br>1 H NMR (400 MHz, CDCl₃) δ 7.57 (s, 3 H), 7.55 - 7.49 (m, 2 H), 7.01 - 6.93 (m, 2 H), 4.46 (br, 1 H), 3.84 (d, 2 H, J = 6.0 Hz), 3.74 - 3.47 (m, 4 H), 3.41 (s, 3 H), 2.98 (d, 2 H, J = 11.3 Hz), 2.47 (s, 1 H), 2.41 (s, 1 H), 2.22 - 2.12 (m, 2 H), 2.11 - 1.89 (m, 3 H), 1.85 - 1.72 (m, 4 H), 1.49 - 1.37 (m, 2 H), 1.39 (s, 3 H), 1.34 (s, 3 H); MS (ESI) m/z 483 (M+ + H). |
| 559 | N-butyl-4'-((1-(2-fluoro-2-methylpropyl)piperidin-4-yl)methoxy)-N-(2-hydroxyethyl)biphenyl-4-carboxamide<br>1 H NMR (400 MHz, CDCl₃) δ 7.58 (d, 2 H, J = 8.0 Hz), 7.53 (d, 2 H, J = 8.8 Hz), 7.47 - 7.42 (m, 2 H), 7.01 - 6.94 (m, 2 H), 3.90 (br, 2 H), 3.84 (d, 2 H, J = 6.0 Hz), 3.72 (br, 2 H), 3.33 (br, 2 H), 2.99 (d, 2 H, J = 11.5 Hz), 2.47 (s, 1 H), 2.42 (s, 1 H), 2.17 (t, 2 H, J = 10.9 Hz), 1.86 - 1.73 (m, 3 H), 1.58 (br, 2 H), 1.50 - 1.37 (m, 2 H), 1.39 (s, 3 H), 1.34 (s, 3 H), 1.28 - 1.14 (m, 2 H), 0.83 (br, 3 H); MS (ESI) m/z 485 (M+ + H). |
| 560 | 4'-((1-(2-fluoro-2-methylpropyl)piperidin-4-yl)methoxy)-N-(furan-2-ylmethyl)biphenyl-4-carboxamide<br>1 H NMR (400 MHz, CDCl₃) δ 7.86 - 7.80 (m, 2 H), 7.63 - 7.57 (m, 2 H), 7.56 - 7.50 (m, 2 H), 7.38 (dd, 1 H, J = 1.8, 0.8 Hz), 7.01 - 6.93 (m, 2 H), 6.49 (t, 1 H, J = 5.1 Hz), 6.37 - 6.29 (m, 2 H), 4.66 (d, 2 H, J = 5.5 Hz), 3.83 (d, 2 H, J = 6.0 Hz), 2.98 (d, 2 H, J = 11.5 Hz), 2.47 (s, 1 H), 2.41 (s, 1 H), 2.21 - 2.11 (m, 2 H), 1.86 - 1.70, (m, 3 H) 1.51 - 1.36, (m, 2 H), 1.39 (s, 3 H), 1.34 (s, 3 H); MS (ESI) m/z 465 (M+ + H). |
| 561 | 4'-((1-(2-fluoro-2-methylpropyl)piperidin-4-yl)methoxy)-N-propylbiphenyl-4-carboxamide<br>1 H NMR (400 MHz, CDCl₃) δ 7.88 - 7.78 (m, 2 H), 7.66 - 7.59 (m, 2 H), 7.59 - 7.49 (m, 2 H), 7.05 - 6.93 (m, 2 H), 6.17 (t, 1 H, J = 5.8 Hz), 3.85 (d, 2 H, J = 6.0 Hz), 3.52 - 3.41 (m, 2 H), 3.00 (d, 2 H, J = 11.3 Hz), 2.48 (s, 1 H), 2.43 (s, 1 H), 2.18 (t, 2 H, J = 10.8 Hz), 1.88 - 1.73 (m, 3 H), 1.72 - 1.63 (m, 2 H), 1.52 - 1.41 (m, 2H), 1.41 (s, 3H), 1.35 (s, 3H), 1.02 (t, 3 H, J = 7.4 Hz); MS (ESI) m/z 427 (M+ + H). |
| 562 | 4'-((1-(2-fluoro-2-methylpropyl)piperidin-4-yl)methoxy)-N-propylbiphenyl-4-carboxamide<br>1 H NMR (400 MHz, CDCl₃) δ 7.85 (d, 2 H, J = 8.5 Hz), 7.62 (d, 2 H, J = 8.5 Hz), 7.59 - 7.50 (m, 2 H), 7.44 - 7.29 (m, 5 H), 7.04 - 6.93 (m, 2 H), 6.44 (t, 1 H, J = 5.5 Hz), 4.69 (d, 2 H, J = 5.5 Hz), 3.85 (d, 2 H, J = 5.8 Hz), 3.00 (d, 2 H, J = 11.3 Hz), 2.48 (s, 1 H), 2.43 (s, 1 H), 2.18 (t, 2 H, J = 10.9 Hz), 1.83 - 1.82 (d, 3 H), 1.48 - 1.41 (m, 2 H), 1.41 (s 3H), 1.35 (s, 3H); MS (ESI) m/z 475 (M+ + H). |
| 563 | N-benzyl-N-ethyl-4'-((1-(2-fluoro-2-methylpropyl)piperidin-4-yl)methoxy)biphenyl-4-carboxamide<br>1 H NMR (400 MHz, CDCl₃) δ 7.66 - 7.45 (m, 6 H), 7.43 - 7.17 (m, 5 H), 6.98 (d, 2 H, J = 7.8 Hz), 4.81 (br, 1 H), 4.59 (br, 1 H), 3.84 (d, 2 H, J = 6.0 Hz), 3.55 - 3.53 (m, 1 H), 3.29 (br, 1 H), 3.00 (d, 2 H, J = 11.5 Hz), 2.48 (s, 1 H), 2.43 (s, 1 H), 2.18 (t, 2 H, J = 11.2 Hz), 1.83 - 1.80 (m, 3 H), 1.52 - 1.38 (m, 2 H), 1.41 (s, 3 H), 1.35 (s, 3 H), 1.29 - 1.12 (m, 3H); MS (ESI) m/z 503 (M+ + H). |
| 564 | (S)-(4'-((1-(2-fluoro-2-methylpropyl)piperidin-4-yl)methoxy)biphenyl-4-yl)(2-(trifluoromethyl)pyrrolidin-1-yl)methanone |

TABLE 4-continued

| Compound No. | Compound Name, ¹H-NMR, MS (ESI) |
|---|---|
| | 1 H NMR (400 MHz, CDCl₃) δ 7.69 - 7.58 (m, 4 H), 7.57 - 7.52 (m, 2 H), 7.02 - 6.96 (m, 2 H), 5.18 (br, 1 H), 3.85 (d, 2 H, J = 6.0 Hz), 3.73 - 3.55 (m, 2 H), 3.00 (d, 2 H, J = 11.5 Hz), 2.48 (s, 1 H), 2.43 (m, 1 H), 2.26 - 2.03 (m, 5 H), 1.96 - 1.74 (m, 4 H), 1.52 - 1.38 (m, 2 H), 1.41 (s, 3 H), 1.35 (s, 3 H); MS (ESI) m/z 507 (M+ + H). |
| 565 | (S)-1-(4'-((1-(2-fluoro-2-methylpropyl)piperidin-4-yl)methoxy)biphenylcarbonyl)pyrrolidine-2-carboxamide<br>1 H NMR (400 MHz, CDCl₃) δ 7.60 (s, 4 H) 7.53 (d, 2 H, 3 = 8.8 Hz) 7.07 (br, 1 H) 6.98 (d, 2 H, J = 8.5 Hz) 5.71 (br, 1 H) 4.82 (dd, 1 H, J = 7.4, 5.4 Hz) 3.84 (d, 2 H, J = 6.0 Hz) 3.70 - 3.53 (m, 2 H) 3.00 (d, 2 H, J = 11.5 Hz) 2.48 (s, 1 H) 2.46 - 2.39 (m, 1 H) 2.42 (s, 1 H) 2.23 - 1.96 (m, 4 H) 1.93 - 1.72 (m, 4 H) 1.52 - 1.38 (m, 2 H), 1.40 (s, 3 H), 1.35 (s, 3 H); MS (ESI) m/z 482 (M+ + H). |
| 566 | (4'-((1-(2-fluoro-2-methylpropyl)piperidin-4-yl)methoxy)biphenyl-4-yl)(3-fluoropyrrolidin-1-yl)methanone<br>1 H NMR (400 MHz, CDCl₃) δ 7.66 - 7.50 (m, 6 H) 7.03 - 6.95 (m, 2 H) 5.30 (t, 1 H, 51.3 Hz) 4.04 - 3.61 (m, 6 H) 3.00 (d, 2 H, J = 11.5 Hz) 2.48 (s, 1 H), 2.43 (s, 1 H) 2.43 - 2.18 (m, 1 H) 2.18 (t, 2 H, J = 10.8 Hz) 2.13 - 1.91 (m, 1 H) 1.88 - 1.74 (m, 3 H) 1.53 - 1.38 (m, 2 H), 1.41 (s, 3 H), 1.35 (s, 3 H); MS (ESI) m/z 457 (M+ + H). |
| 567 | (4'-((1-(2-fluoro-2-methylpropyl)piperidin-4-yl)methoxy)biphenyl-4-yl)(4-(hydroxymethyl)piperidin-1-yl)methanone<br>1 H NMR (400 MHz, CDCl₃) δ 7.61 - 7.56 (m, 2 H), 7.55 - 7.50 (m, 2 H), 7.47 - 7.42 (m, 2 H), 7.01 - 6.95 (m, 2 H), 4.76 (br, 1 H), 3.89 (br, 1 H), 3.84 (d, 2 H, J = 6.0 Hz), 3.53 (d, 2 H, J = 3.8 Hz), 3.03 (br, 1 H), 3.00 (d, 2 H, J = 11.5 Hz), 2.80 (br, 1 H), 2.48 (s, 1 H), 2.43 (s, 1 H), 2.23 - 2.12 (m, 2 H), 1.95 - 1.67 (m, 7 H), 1.52 - 1.38 (m, 2 H), 1.40 (s, 3 H), 1.35 (s, 3 H), 1.29 -1.19 (m, 2 H); MS (ESI) m/z 483 (M+ + H). |
| 568 | (4'-((1-(2-fluoro-2-methylpropyl)piperidin-4-yl)methoxy)biphenyl-4-yl)(4-hydroxypiperidin-1-yl)methanone<br>1 H NMR (400 MHz, CDCl₃) δ 7.61 - 7.56 (m, 2 H), 7.55 - 7.50 (m, 2 H), 7.45 (d, 2 H, J = 8.5 Hz), 7.01 - 6.95 (m, 2 H), 4.23 (br, 1 H), 4.01 - 3.95 (m, 1 H), 3.84 (d, 2 H, J = 6.0 Hz), 3.76 (br, 1 H), 3.48 - 3.15 (m, 2 H), 3.00 (d, 2 H, J = 11.3 Hz), 2.48 (s, 1 H), 2.43 (s, 1 H), 2.18 (t, 2 H, J = 11.0 Hz), 2.07 - 1.74 (m, 6 H), 1.71 - 1.38 (m, 4 H), 1.40 (s, 3 H), 1.35 (s, 3 H); MS (ESI) m/z 469 (M+ + H). |
| 569 | (4'-((1-(2-fluoro-2-methylpropyl)piperidin-4-yl)methoxy)biphenyl-4-yl)(3-hydroxypiperidin-1-yl)methanone<br>1 H NMR (400 MHz, CDCl₃) δ 7.61 - 7.56 (m, 2 H), 7.55 - 7.51 (m, 2 H), 7.48 (d, 2 H, J = 8.3 Hz,), 7.02 - 6.95 (m, 2 H), 3.94 (br, 1 H), 3.85 (d, 2 H, J = 6.0 Hz), 3.80 -3.16 (br, 3 H), 3.01 (d, 2 H, J = 10.8 Hz), 2.49 (s, 1 H), 2.44 (s, 1 H), 2.19 (t, 2 H, J = 11.0 Hz), 2.08 - 1.52 (m, 9 H), 1.51 - 1.39 (m, 2 H), 1.41 (s, 3 H), 1.36 (s, 3 H); MS (ESI) m/z 469 (M+ + H). |
| 570 | (R)-(4'-((1-(2-fluoro-2-methylpropyl)piperidin-4-yl)methoxy)biphenyl-4-yl)(3-fluoropyrrolidin-1-yl)methanone<br>1 H NMR (400 MHz, CDCl₃) δ 7.66 - 7.57 (m, 4 H), 7.54 (d, 2 H, J = 8.5 Hz), 7.02 - 6.96 (m, 2 H), 5.45 - 5.14 (m, 1 H), 4.02 - 3.87 (m, 2 H), 3.85 (d, 2 H, J = 6.0 Hz), 3.82 - 3.62 (m, 2 H), 3.00 (d, 2 H, J = 11.5 Hz), 2.48 (s, 1 H), 2.43 (s, 1 H), 2.39 - 2.22 (m, 1 H), 2.22 - 2.13 (m, 2 H), 2.13 - 1.91 (m, 1 H), 1.87 - 1.74 (m, 3 H), 1.52 - 1.38 (m, 2 H), 1.41 (s, 3 H), 1.35 (s, 3 H); MS (ESI) m/z 457 (M+ + H). |
| 571 | (S)-(4'-((1-(2-fluoro-2-methylpropyl)piperidin-4-yl)methoxy)biphenyl-4-yl)(3-fluoropyrrolidin-1-yl)methanone<br>1 H NMR (400 MHz, CDCl₃) δ 7.66 - 7.57 (m, 4 H), 7.54 (d, 2 H, J = 8.5 Hz), 7.02 - 6.95 (m, 2 H), 5.45 - 5.14 (m, 1 H), 4.04 - 3.87 (m, 2 H), 3.85 (d, 2 H, J = 6.0 Hz), 3.82 - 3.61 (m, 5 H), 3.00 (d, 5 H, J = 11.3 Hz), 2.48 (s, 3 H), 2.43 (s, 3 H), 2.40 - 2.23 (m, 1 H), 2.22 - 2.13 (m, 2 H), 2.12 - 1.92 (m, 1 H), 1.87 - 1.74 (m, 3 H), 1.52 - 1.38 (m, 2 H), 1.41 (s, 3 H), 1.35 (s, 8 H); MS (ESI) m/z 457 (M+ + H). |
| 594 | (4'-((1-(2-fluoro-2-methylpropyl)piperidin-4-yl)methoxy)biphenyl-4-yl)(3-(trifluoromethyl)-5,6-dihydro-[1,2,4]triazolo[4,3-a]pyrazin-7(8H)-yl)methanone<br>1 H NMR (400 MHz, CDCl₃) δ 7.65 (d, 2 H, J = 6.7 Hz), 7.54 (d, 4 H, J = 8.6 Hz), 7.00 (d, 2 H, J = 8.8 Hz), 5.10 (s, 2 H), 4.27 (m, 2 H), 4.13 (m, 2 H), 3.86 (d, 2 H, J = 6.0 Hz), 3.01 (m, 2 H), 2.48 (s, 1 H), 2.43 (s, 1 H), 2.18 (t, 2 H, J = 11.3 Hz), 1.82 (m, 2 H), 1.47 (m, 2 H), 1.40 (s, 3 H), 1.35 (s, 3 H); MS (ESI) m/z 560 (M+ + H) |
| 598 | N-ethyl-4'-((1-(2-fluoro-2-methylpropyl)piperidin-4-yl)methoxy)-N-methylbiphenyl-4-carboxamide<br>1 H NMR (400 MHz, CDCl₃) δ 7.58 (d, 2 H, J = 8.0 Hz), 7.53 (d, 2 H, J = 8.0 Hz), 7.46 (m, 2 H), 6.98 (d, 2 H, J = 8.5 Hz), 3.86 (d, 2 H, J = 5.6 Hz), 3.62 (brs, 1 H), 3.38 (brs, 1 H), 3.05 (m, 5 H), 2.47 - 2.38 (m, 4 H), 1.85 - 1.82 (m, 2 H), 1.53-1.37 (m, 10 H), 1.28 - 1.15 (m, 3 H); MS (ESI) m/z 427 (M+ + H). |
| 599 | 4'-((1-(2-fluoro-2-methylpropyl)piperidin-4-yl)methoxy)-N-isopropyl-N-methylbiphenyl-4-carboxamide<br>1 H NMR (400 MHz, CDCl₃) δ 7.58 (d, 2 H, J = 8.0 Hz), 7.53 (d, 2 H, J = 8.6 Hz), 7.43 - 7.42 (m, 2 H), 6.98 (d, 2 H, J = 8.6 Hz), 4.16 (brs, 1 H), 3.86 (d, 2 H, J = 5.8 |

| Compound No. | Compound Name, $^1$H-NMR, MS (ESI) |
|---|---|
| | Hz), 3.02 - 2.85 (m, 5 H), 2.32 (brs, 2 H), 2.20 (brs, 2 H), 1.82 - 1.68 (m, 3 H), 1.53 - 1.37 (m, 8 H), 1.19 (s, 6 H); MS (ESI) m/z 441 (M+ + H). |
| 600 | (4'-((1-(2-fluoro-2-methylpropyl)piperidin-4-yl)methoxy)biphenyl-4-yl)(3-hydroxyazetidin-1-yl)methanone<br>1 H NMR (400 MHz, CDCl$_3$) δ 7.65 (d, 2 H, J = 7.8 Hz), 7.54 (dd, 4 H, J = 20.0, 8.0 Hz), 6.97 (d, 2 H, J = 8.1 Hz), 4.71 (brs, 1 H), 4.49 (brs, 2 H), 4.22 (brs, 2 H), 3.84 (d, 2 H, J = 4.9 Hz), 3.53 (d, 1 H, J = 5.4 Hz), 3.03 (brs, 2 H), 2.49 (d, 2 H, J = 21.4 Hz), 2.21 (brs, 2 H), 1.84 - 1.82 (m, 3 H), 1.42 - 1.36 (m, 8 H); MS (ESI) m/z 441 (M+ + H) |
| 601 | (3,3-difluoroazetidin-1-yl)(4'-((1-(2-fluoro-2-methylpropyl)piperidin-4-yl)methoxy)biphenyl-4-yl)methanone<br>1 H NMR (400 MHz, CDCl$_3$) δ 7.70 (d, 2 H, J = 8.2 Hz), 7.63 (d, 2 H, J = 8.2 Hz), 7.55 (d, 2 H, J = 8.6 Hz), 6.99 (d, 2 H, J = 8.6 Hz), 4.58 (t, 4 H, J = 11.5 Hz), 3.86 (d, 2 H, J = 5.8 Hz), 3.03 (brs, 2 H), 2.52 - 2.45 (m, 2 H), 2.21 (brs, 2 H), 1.83 (d, 3 H, J = 10.0 Hz), 1.48 - 1.36 (m, 8 H); MS (ESI) m/z 461 (M+ + H). |
| 602 | N-t-butyl-4'-((1-(2-fluoro-2-methylpropyl)piperidin-4-yl)methoxy)biphenyl-4-carboxamide<br>1 H NMR (400 MHz, CDCl$_3$) δ 7.79 - 7.74 (m, 2 H), 7.62 - 7.57 (m, 2 H), 7.56 - 7.51 (m, 2 H), 7.01 - 6.95 (m, 2 H), 5.96 (s, 1 H), 3.84 (d, 2 H, J = 5.8 Hz), 2.98 (d, 2 H, J = 11.8 Hz), 2.47 (s, 1 H), 2.42 (s, 1 H), 2.19 - 2.14 (m, 2 H), 1.81 (d, 3 H, J = 11.5 Hz), 1.49 (s, 9 H), 1.38 - 1.46 (m, 2 H), 1.39 (s, 3 H), 1.34 (s, 3 H); MS (ESI) m/z 441 (M+ + H). |
| 603 | 4'-((1-(2-fluoro-2-methylpropyl)piperidin-4-yl)methoxy)-N-isopropylbiphenyl-4-carboxamide<br>1 H NMR (400 MHz, CDCl$_3$) δ 7.83 - 7.77 (m, 2 H), 7.63 - 7.58 (m, 2 H), 7.57 - 7.51 (m, 2 H), 7.01 - 6.95 (m, 2 H), 5.93 (d, 1 H, J = 8.0 Hz), 4.34 - 4.29 (m, 1 H), 3.84 (d, 2 H, J = 6.0 Hz), 2.99 (d, 2 H, J = 11.5 Hz), 2.47 (s, 1 H), 2.42 (s, 1 H), 2.21 - 2.12 (m, 2 H), 1.82 - 1.79 (m, 3 H), 1.49 - 1.37 (m, 2 H), 1.39 (s, 3 H), 1.34 (s, 3 H), 1.28 (d, 6 H, J = 6.5 Hz); MS (ESI) m/z 427 (M+ + H). |
| 604 | N,N-diethyl-4'-((1-(2-fluoro-2-methylpropyl)piperidin-4-yl)methoxy)biphenyl-4-carboxamide<br>1 H NMR (400 MHz, CDCl$_3$) δ 7.60 - 7.55 (m, 2 H), 7.55 - 7.50 (m, 2 H), 7.46 - 7.40 (m, 2 H), 7.01 - 6.94 (m, 2 H), 3.84 (d, 2 H, J = 5.8 Hz), 3.57 (br, 2 H), 3.32 (br, 2 H), 2.99 (d, 2 H, J = 11.5 Hz), 2.48 (s, 1 H), 2.42 (s, 1 H), 2.17 (t, 2 H, J = 10.9 Hz), 1.87 - 1.74 (m, 3 H), 1.52 - 1.37 (m, 2 H), 1.41 (s, 3 H), 1.34 (s, 3 H), 1.31 - 1.07 (m, 6 H); MS (ESI) m/z 441 (M+ + H). |
| 605 | 4'-((1-(2-fluoro-2-methylpropyl)piperidin-4-yl)methoxy)-N-(1-hydroxy-2-methylpropan-2-yl)biphenyl-4-carboxamide<br>1 H NMR (400 MHz, CDCl$_3$) δ 7.81 - 7.74 (m, 2 H), 7.63 - 7.58 (m, 2 H), 7.57 - 7.50 (m, 2 H), 7.01 - 6.94 (m, 2 H), 6.26 (s, 1 H), 3.84 (d, 2 H, J = 5.8 Hz), 3.71 (s, 2 H), 2.99 (d, 2 H, J = 11.5 Hz), 2.48 (s, 1 H), 2.42 (s, 1 H), 2.17 (t, 2 H, J = 10.8 Hz), 1.81 (dd, 3 H, J = 8.8, 2.8 Hz), 1.45 - 1.39 (m, 2 H), 1.44 (s, 6 H), 1.40 (s, 3 H), 1.34 (s, 3 H); MS (ESI) m/z 457 (M+ + H). |
| 606 | (S)-4'-((1-(2-fluoro-2-methylpropyl)piperidin-4-yl)methoxy)-N-(1-hydroxypropan-2-yl)biphenyl-4-carboxamide<br>1 H NMR (400 MHz, CDCl$_3$) δ 7.82 (d, 2 H, J = 8.5 Hz), 7.64 - 7.59 (m, 2 H), 7.57 - 7.51 (m, 2 H), 7.01 - 6.95 (m, 2 H), 6.34 (d, 1 H, J = 7.3 Hz), 4.37 - 4.27 (m, 1 H), 3.88 - 3.78 (m, 3 H), 3.68 (m, 1 H), 2.99 (d, 2 H, J = 11.0 Hz), 2.48 (s, 1 H), 2.42 (s, 1 H), 2.17 (t, 2 H, 3 = 11.8 Hz), 1.82 - 1.79 (m, 3 H), 1.51 - 1.38 (m, 2 H), 1.40 (s, 3 H), 1.35 (s, 3 H), 1.32 (d, 3 H, J = 6.8 Hz); MS (ESI) m/z 443 (M+ + H). |
| 607 | (R)-4'-((1-(2-fluoro-2-methylpropyl)piperidin-4-yl)methoxy)-N-(1-hydroxybutan-2-yl)biphenyl-4-carboxamide<br>1 H NMR (400 MHz, CDCl$_3$) δ 7.85 - 7.79 (m, 2 H), 7.62 - 7.57 (m, 2 H), 7.56 - 7.50 (m, 2 H), 7.00 - 6.94 (m, 2 H), 6.39 (d, 1 H, J = 7.8 Hz), 4.14 - 4.16 (m, 1 H), 3.87 - 3.79 (m, 3 H), 3.76 - 3.69 (m, 1 H), 2.99 (d, 2 H, J = 11.3 Hz), 2.48 (s, 1 H), 2.42 (s, 1 H), 2.17 (t, 2 H, J = 10.9 Hz), 1.86 - 1.58 (m, 5 H), 1.51 - 1.37 (m, 2 H), 1.41 (s, 3 H), 1.35 (s, 3 H), 1.04 (t, 3 H, J = 6.0 Hz); MS (ESI) m/z 457 (M+ + H). |
| 608 | (R)-4'-((1-(2-fluoro-2-methylpropyl)piperidin-4-yl)methoxy)-N-(1-hydroxy-3-methylbutan-2-yl)biphenyl-4-carboxamide<br>1 H NMR (400 MHz, CDCl$_3$) δ 7.86 - 7.80 (m, 2 H), 7.65 - 7.59 (m, 2 H), 7.57 - 7.51 (m, 2 H), 7.02 - 6.95 (m, 2 H), 6.36 (d, 1 H, J = 8.3 Hz), 4.01 - 3.94 (m, 1 H), 3.88 - 3.77 (m, 4 H), 2.99 (d, 2 H, J = 11.3 Hz), 2.48 (s, 1 H), 2.42 (s, 1 H), 2.17 (t, 2 H, J = 10.8 Hz), 2.10 - 1.99 (m, 1 H), 1.86 - 1.75 (m, 3 H), 1.50 - 1.37 (m, 2 H), 1.40 (s, 3 H), 1.35 (s, 3 H), 1.05 (t, 6 H, J = 6.4 Hz); MS (ESI) m/z 471 (M+ + H). |

TABLE 4-continued

| Compound No. | Compound Name, ¹H-NMR, MS (ESI) |
|---|---|
| 609 | (S)-4'-((1-(2-fluoro-2-methylpropyl)piperidin-4-yl)methoxy)-N-(1-hydroxy-3-methylbutan-2-yl)biphenyl-4-carboxamide<br>1 H NMR (400 MHz, CDCl₃) δ 7.86 - 7.81 (m, 2 H), 7.66 - 7.60 (m, 2 H), 7.57 - 7.51 (m, 2 H), 7.02 - 6.95 (m, 2 H), 6.35 (d, 1 H, J = 8.5 Hz), 4.03 - 3.93 (m, 1 H), 3.89 - 3.78 (m, 4 H), 2.99 (d, 2 H, J = 11.5 Hz), 2.48 (s, 1 H), 2.42 (s, 1 H), 2.22 - 2.12 (m, 2 H), 2.09 - 2.00 (m, 1 H), 1.83 - 1.80 (m, 3 H), 1.51 - 1.38 (m, 2 H), 1.40 (s, 3 H), 1.35 (s, 3 H), 1.05 (t, 6 H, J = 6.4 Hz); MS (ESI) m/z 471 (M+ + H). |
| 610 | N-(1,3-dihydroxypropan-2-yl)-4'-((1-(2-fluoro-2-methylpropyl)piperidin-4-yl)methoxy)biphenyl-4-carboxamide<br>1 H NMR (400 MHz, CDCl₃) δ 7.85 (d, 2 H, J = 8.5 Hz), 7.60 (d, 2 H, J = 8.5 Hz), 7.49 - 7.55 (m, 2 H), 7.21 (s, 1 H), 6.99 - 6.92 (m, 2 H), 4.12 - 4.03 (m, 1 H), 3.91 - 3.71 (m, 6 H), 2.97 (d, 2 H, J = 11.5 Hz), 2.46 (s, 1 H), 2.40 (s, 1 H), 2.15 (t, 2 H, J = 8.0 Hz), 1.80 - 1.77 (m, 3 H), 1.49 - 1.35 (m, 2 H), 1.38 (s, 3 H), 1.32 (s, 3 H); MS (ESI) m/z 459 (M+ + H). |
| 611 | N-(2,3-dihydroxypropyl)-4'-((1-(2-fluoro-2-methylpropyl)piperidin-4-yl)methoxy)biphenyl-4-carboxamide<br>1 H NMR (400 MHz, CDCl₃) δ 7.85 (d, 2 H, J = 8.3 Hz), 7.62 (d, 2 H, J = 8.5 Hz), 7.57 - 7.51 (m, 2 H), 7.27 (t, 1 H, J = 4.0 Hz), 7.01 - 6.95 (m, 2 H), 3.90 - 3.82 (m, 3 H), 3.68 - 3.53 (m, 4 H), 3.00 (d, 2 H, J = 11.5 Hz), 2.48 (s, 1 H), 2.43 (s, 1 H), 2.17 (t, 2 H, J = 11.3 Hz), 1.82 - 1.80 (m, 3 H), 1.37 - 1.51 (m, 2 H), 1.40 (s, 3 H), 1.35 (s, 3 H); MS (ESI) m/z 459 (M+ + H). |
| 613 | (S)-(4'-((1-(2-fluoro-2-methylpropyl)piperidin-4-yl)methoxy)biphenyl-4-yl)(3-hydroxypiperidin-1-yl)methanone<br>1 H NMR (400 MHz, CDCl₃) δ 7.61 - 7.56 (m, 2 H), 7.55 - 7.51 (m, 2 H), 7.50 - 7.46 (m, 2 H), 7.02 - 6.95 (m, 2 H), 4.07 - 3.89 (m, 1 H), 3.85 (d, 2 H, J = 6.0 Hz), 3.81 - 3.17 (m, 4 H), 3.00 (d, 2 H, 3 = 11.0 Hz), 2.48 (s, 1 H), 2.43 (s, 1 H), 2.18 (t, 2 H, J = 11.3 Hz), 1.96 (br, 2 H), 1.83 - 1.80 (m, 3 H), 1.67 (br, 2 H), 1.52 - 1.38 (m, 2 H), 1.41 (s, 3 H), 1.35 (s, 3 H); MS (ESI) m/z 469 (M+ + H). |
| 619 | (R)-methyl 1-(4'-((1-(2-fluoro-2-methylpropyl)piperidin-4-yl)methoxy)biphenylcarbonyl)pyrrolidine-2-carboxylate<br>1 H NMR (400 MHz, CDCl₃) δ 7.63 - 7.50 (m, 6 H), 6.95 (d, 2 H, J = 6.1 Hz), 4.64 (m, 1 H), 3.82 (d, 2 H, J = 5.8 Hz), 3.77 (s, 3 H), 3.68 - 3.46 (m. 4 H), 2.99 (d, 2 H, J = 10.2 Hz), 2.48 - 2.41 (m, 2 H), 2.32 (m, 1 H), 2.18 - 2.14 (m, 2 H), 2.02 - 2.00 (m, 2 H), 1.96 (brs, 1 H), 1.79 (d, 3 H, J = 10.5 Hz), 1.38 - 1.33 (m, 8 H); MS (ESI) m/z 497 (M+ + H). |
| 622 | (4'-((1-(2-fluoro-2-methylpropyl(piperidin-4-yl)methoxy)biphenyl-4-yl)thiazolidin-3-yl)methanone<br>1 H NMR (400 MHz, CDCl₃) δ 7.61 - 7.52 (m, 6 H), 6.98 (d, 2 H, J = 8.4 Hz), 4.65 (brs, 2H), 3.98 (brs, 2 H), 3.02 (brs, 4 H), 2.51 - 2.48 (m, 2 H), 2.20 (t, 2 H, J = 12.0 Hz), 1.82 (d, 3 H, J = 8.0 Hz), 1.48 - 1.45 (m, 2 H), 1.41 (s, 3 H), 1.35 (s, 3 H); MS (ESI) m/z 457 (M+ + H). |
| 623 | (4-(cyclopropanecarbonyl)piperazin-1-yl)(4'-((1-(2-fluoro-2-methylpropyl)piperidin-4-yl)methoxy)biphenyl-4-yl)methanone<br>1 H NMR (400 MHz, CDCl₃) δ 7.61 (d, 2 H, J = 6.1 Hz), 7.53 (d, 2 H, J = 6.5 Hz), 7.48 (d, 2 H, J = 6.1 Hz), 6.99 (d, 2 H, J = 6.5 Hz), 3.86 (d, 2 H, .1= 4.4 Hz), 3.76 - 3.69 (m, 8 H), 3.13 (brs, 2 H), 2.61 - 2.54 (m, 2 H), 2.29 (brs, 2 H), 1.87 - 1.84 (m, 3 H), 1.78 (brs, 1 H), 1.58 - 1.56 (brs, 2 H), 1.44 (s, 3 H), 1.39 (s, 3 H), 1.05 - 1.01 (m, 2 H), 0.82 - 0.81 (m, 2 H); MS (ESI) m/z 522 (M+ + H). |
| 624 | (4'-((1-(2-fluoro-2-methylpropyl)piperidin-4-yl)methoxy)biphenyl-4-yl)(4-(methylsulfonyl)piperazin-1-yl)methanone<br>1 H NMR (400 MHz, CDCl₃) δ 7.61 (d, 2 H, J = 6.2 Hz), 7.53 (d, 2 H, J = 6.6 Hz), 7.48 (d, 2 H, J = 6.2 Hz), 6.99 (d, 2 H, J = 6.5 Hz), 3.87 - 3.85 (m, 6 H), 3.28 (brs, 4 H), 3.13 (brs, 2 H), 2.82 (s, 3 H), 2.55 (brs, 2 H), 2.21 (brs, 2 H), 1.87 - 1.84 (m, 3 H), 1.42 - 1.37 (m, 8 H); MS (ESI) m/z 532 (M+ + H). |
| 625 | (S)-methyl 1-(4'-((1-(2-fluoro-2-methylpropyl)piperidin-4-yl)methoxy)biphenylcarbonyl)pyrrolidine-2-carboxylate<br>1 H NMR (400 MHz, CDCl₃) δ 7.66 - 7.52 (m, 6 H), 6.98 (d, 2 H, J = 12.0 Hz), 3.85 (d, 2 H, J = 5.9 Hz), 3.79 (s, 3 H), 3.83 - 3.62 (m, 3 H), 3.01 (d, 2 H, J = 11.9 Hz), 2.47 (d, 2 H, J = 24.0 Hz), 2.38 (m, 1 H), 2.51 - 2.44 (m, 2 H), 2.02 - 1.87 (m, 3 H), 1.82 (d, 3 H, J = 12.0 Hz), 1.47 - 1.36 (m, 8 H); MS (ESI) m/z 497 (M+ + H). |
| 626 | t-butyl 4-(4'-((1-(2-fluoro-2-methylpropyl)piperidin-4-yl)methoxy)biphenylcarbonyl)piperazin-1-carboxylate<br>1 H NMR (400 MHz, CDCl₃) δ 7.60 (d, 2 H, J = 8.3 Hz), 7.54 (d, 2 H, J = 1.8 Hz), 7.46 (d, 2 H, J = 8.3 Hz), 6.98 (d, 2 H, J = 9.9 Hz), 3.86 (d, 2 H, J = 5.1 Hz), 3.83 - 3.49 (m, 8 H), 3.01 (brs, 2 H), 2.47 - 2.41 (m, 2 H), 2.19 (brs, 2 H), 1.83 (brs, 3 H), 1.48 (s, 9 H), 1.42 - 1.37 (m, 8 H); MS (ESI) m/z 554 (M+ + H). |
| 627 | (4-benzylpiperazin-1-yl)(4'-((1-(2-fluoro-2-methylpropyl)piperidin-4-yl)methoxy)biphenyl-4-yl)methanone<br>1 H NMR (400 MHz, CDCl₃) δ 8.19 (d, 2 H, J = 9.3 Hz), 7.63 (d, 2 H, J = 5.1 Hz), 7.57 (d, 2 H, J = 4.5 Hz), 6.99 (d, 2 H, J = 6.9 Hz), 3.86 (m, 4 H), 3.56 (m, 4 H), 2.96 (brs, 2 H), 2.54 - 2.43 (m, 6 H), 2.18 (brs, 2 H), 1.82 (brs, 3 H), 1.59 - 1.26 (m, 8 H); MS (ESI) m/z 544 (M+ + H). |

TABLE 4-continued

| Compound No. | Compound Name, ¹H-NMR, MS (ESI) |
|---|---|
| 628 | 1-(4-(4'-((1-(2-fluoro-2-methylpropyl)piperidin-4-yl)methoxy)biphenylcarbonyl)piperazin-1-yl)ethanone<br>1 H NMR (400 MHz, CDCl$_3$) 7.59 (d, 2 H, J = 8.1 Hz), 7.51 (d, 2 H, J = 8.6 Hz), 7.45 (d, 2 H, J = 9.9 Hz), 6.96 (d, 2 H, J = 8.7 Hz), 3.83 (d, 2 H, J = 5.8 Hz), 3.63 (brs, 4 H), 3.52 (brs, 4 H), 2.98 (brs, 2 H), 2.47 (d, 2 H, J = 22.5 Hz), 2.19 -2.12 (m, 5 H), 1.80 (m, 3 H), 1.39 - 1.33 (m, 8 H); MS (ESI) m/z 496 (M+ + H). |
| 629 | (3,3-difluoropyrrolidine-1-yl)(4'-((1-(2-fluoro-2-methylpropyl)piperidin-4-yl)methoxy)biphenyl-4-yl)methanone<br>1 H NMR (400 MHz, CDCl$_3$) δ 7.62 - 7.52 (m, 6 H), 6.99 (d, 2 H, J = 6.5 Hz), 4.03 - 3.80 (m, 6 H), 3.10 - 3.01 (m, 2 H), 2.65 - 2.43 (m, 4 H), 2.19 - 2.05 (m, 2 H), 1.97 - 1.82 (m, 2 H), 1.59 - 1.41 (m, 2 H), 1.36 (s, 3 H), 1.27 (s, 3 H); MS (ESI) m/z 475 (M+ + H). |
| 645 | methyl 2-(4'-((1-(2-fluoro-2-methylpropyl)piperidin-4-yl)methoxy)biphenyl-4-ylcarboxamido)acetate<br>1 H NMR (400 MHz, CDCl$_3$) δ 7.91 - 7.85 (m, 2 H), 7.67 - 7.62 (m, 2 H), 7.59 - 7.53 (m, 2 H), 7.02 - 6.96 (m, 2 H), 6.68 (t, 1 H, J = 5.0 Hz), 4.29 (d, 2 H, J = 5.0 Hz), 3.86 (d, 2 H, J = 6.0 Hz), 3.83 (s, 3 H), 3.00 (d, 2 H, J = 11.0 Hz), 2.48 (s, 1 H), 2.43 (s, 1 H), 2.18 (t, 2 H, J = 11.2 Hz), 1.83 - 1.81 (m, 3 H), 1.38 - 1.51 (m, 2 H), 1.41 (s, 3 H), 1.35 (s, 3 H); MS (ESI) m/z 457 (M+ + H). |
| 646 | 4'-((1-(2-fluoro-2-methylpropyl)piperidin-4-yl)methoxy)-N-(oxetane-3-yl)biphenyl-4-carboxamide<br>1 H NMR (400 MHz, CDCl$_3$) δ 7.84 (d, 2 H, J = 8.5 Hz), 7.67 - 7.62 (m, 2 H), 7.59 - 7.53 (m, 2 H), 7.03 - 6.96 (m, 2 H), 6.65 (d, 1 H, J = 7.5 Hz), 5.35 - 5.24 (m, 1 H), 5.06 (t, 2 H, J = 7.2 Hz), 4.64 (t, 2 H, J = 6.5 Hz), 3.86 (d, 2 H, J = 5.8 Hz), 3.00 (d, 2 H, J = 11.5 Hz), 2.48 (s, 1 H), 2.43 (s, 1 H), 2.18 (t, 2 H, J = 10.8 Hz), 1.82 (d, 3 H, J = 11.5 Hz), 1.38 - 1.51 (m, 2 H), 1.41 (s, 3 H), 1.35 (s, 3 H); MS (ESI) m/z 441 (M+ + H). |
| 647 | methyl 3-(4'-((1-(2-fluoro-2-methylpropyl)piperidin-4-yl)methoxy)biphenyl-4-ylcarboxamido)propanoate<br>1 H NMR (400 MHz, CDCl$_3$) δ 7.86 - 7.79 (m, 2 H), 7.65 - 7.59 (m, 2 H), 7.58 - 7.52 (m, 2 H), 7.02 - 6.96 (m, 2 H), 6.87 (t, 1 H, J = 5.9 Hz), 3.85 (d, 2 H, J = 5.8 Hz), 3.80 - 3.75 (m, 2 H), 3.74 (s, 3 H), 3.00 (d, 2 H, J = 11.5 Hz), 2.69 (t, 2 H, J = 5.9 Hz), 2.48 (s, 1 H), 2.43 (s, 1 H), 2.18 (t, 2 H, J = 10.8 Hz), 1.83 - 1.80 (m, 3 H), 1.38 - 1.52 (m, 2 H), 1.41 (s, 3 H), 1.35 (s, 3 H); MS (ESI) m/z 471 (M+ + H). |
| 648 | (R)-methyl 2-(4'-((1-(2-fluoro-2-methylpropyl(piperidin-4-yl)methoxy)biphenyl-4-ylcarboxamido)-3-hydroxypropanoate<br>1 H NMR (400 MHz, CDCl$_3$) δ 7.86 - 7.93 (m, 2 H), 7.61 - 7.67 (m, 2 H), 7.52 - 7.59 (m, 2 H), 7.14 (d, J = 6.8 Hz, 1 H), 6.95 - 7.02 (m, 2 H), 4.88 - 4.95 (m, 1 H), 4.11 (dd, J = 3.5, 1.8 Hz, 2 H), 3.82 - 3.90 (m, 5 H), 3.00 (d, J = 11.3 Hz, 2 H), 2.57 - 2.69 (m, 1 H), 2.49 (s, 1 H), 2.43 (s, 1 H), 2.18 (t, J = 11.3 hz, 2 H), 2.57 - Hz, 3 H), 1.38 - 1.53 (m, 5 H), 1.35 (s, 3 H); MS (ESI) m/z 487 (M+ + H). |
| 649 | (S)-methyl 2-(4'-((1-(2-fluoro-2-methylpropyl)piperidin-4-yl)methoxy)biphenyl-4-ylcarboxamido)-3-hydroxypropanoate<br>1 H NMR (400 MHz, CDCl$_3$) δ 7.92 - 7.87 (m, 2 H), 7.67 - 7.61 (m, 2 H), 7.59 - 7.53 (m, 2 H), 7.15 (d, 1 H, J = 7.0 Hz), 6.99 (d, 2 H, J = 8.8 Hz), 4.94 - 4.89 (m, 1 H), 4.11 - 4.10 (m, 2 H), 3.89 - 3.83 (m, 5 H), 3.00 (d, 2 H, J = 11.0 Hz), 2.49 (s, 1 H), 2.43 (s, 1 H), 2.18 (t, 2 H, J = 11.0 Hz), 1.82 (d, 3 H, J = 11.8 Hz), 1.38 - 1.52 (m, 2 H), 1.41 (s, 3 H), 1.35 (s, 3 H); MS (ESI) m/z 487 (M+ + H). |
| 650 | ethyl 4-(4'-((1-(2-fluoro-2-methylpropyl)piperidin-4-yl)methoxy)biphenyl-4-ylcarboxamido)piperidin-1-carboxylate<br>1 H NMR (400 MHz, CDCl$_3$) δ 7.84 - 7.78 (m, 2 H), 7.65 - 7.60 (m, 2 H), 7.58 - 7.52 (m, 2 H), 7.02 - 6.96 (m, 2 H), 6.02 (d, 1 H, J = 7.5 Hz), 4.27 - 4.10 (m, 5 H), 3.85 (d, 2 H, J = 6.0 Hz), 3.01 - 2.98 (m, 4 H), 2.48 (s, 1 H), 2.43 (s, 1 H), 2.18 (t, 2 H, J = 11.4 Hz), 2.08 (d, 2 H, J = 10.3 Hz), 1.83 - 1.80 (m, 3 H), 1.52 - 1.38 (m, 4 H), 1.41 (s, 3 H), 1.35 (s, 3 H), 1.28 (t, 3 H, J = 7.2 Hz); MS (ESI) m/z 540 (M+ + H). |
| 651 | 4'-((1-(2-fluoro-2-methylpropyl)piperidin-4-yl)methoxy)-N-pentylbiphenyl-4-carboxamide<br>1 H NMR (400 MHz, CDCl$_3$) δ 7.84 - 7.79 (m, 2 H), 7.65 - 7.59 (m, 2 H), 7.58 - 7.52 (m, 2 H), 7.02 - 6.96 (m, 2 H), 6.15 (t, 1 H, J = 5.6 Hz), 3.85 (d, 2 H, J = 6.0 Hz), 3.52 - 3.44 (m, 2 H), 3.00 (d, 2 H, J = 11.3 Hz), 2.48 (s, 1 H), 2.43 (s, 1 H), 2.18 (t, 2 H, J = 11.0 Hz), 1.83 - 1.80 (m, 3 H), 1.70 - 1.60 (m, 3 H), 1.50 - 1.37 (m, 9 H), 1.35 (s, 3 H), 0.93 (t, 3 H, J = 7.1 Hz); MS (ESI) m/z 455 (M+ + H). |
| 677 | ethyl 1-(4'-((1-(2-fluoro-2-methylpropyl)piperidin-4-yl)methoxy)biphenylcarbonyl)piperidine-3-carboxylate<br>1 H NMR (400 MHz, CDCl$_3$) δ 7.59 (d, 2 H, J = 8.3 Hz), 7.53 (d, 2 H, J = 8.8 Hz), 7.46 (d, 2 H, J = 8.3 Hz), 6.98 (d, 2 H, J = 8.8 Hz), 4.22 - 4.07 (m, 2 H), 3.85 (d, 2 H, J = 6.0 Hz), 3.13 - 3.05 (m, 1 H), 3.00 (d, 2 H, J = 11.5 Hz), 2.48 (s, 1 H), 2.43 (s, 1 H), 2.24 - 2.10 (m, 3 H), 1.88 - 1.70 (m, 5 H), 1.50 - 1.38 (m, 2 H), 1.41 (s, 3 H), 1.35 (s, 3 H), 1.31 - 1.17 (m, 3 H); MS (ESI) m/z 525 (M+ + H). |

TABLE 4-continued

| Compound No. | Compound Name, ¹H-NMR, MS (ESI) |
|---|---|
| 678 | ethyl 1-(4'-((1-(2-fluoro-2-methylpropyl)piperidin-4-yl)methoxy)biphenylcarbonyl)piperidine-4-carboxylate<br>1 H NMR (400 MHz, CDCl₃) δ 7.61 - 7.56 (m, 2 H), 7.53 (d, 2 H, J = 9.0 Hz), 7.46 (d, 2 H, J = 8.5 Hz), 6.98 (d, 2 H, J = 8.8 Hz), 4.65 - 4.48 (m, 1 H), 4.18 (q, 2 H, J = 7.2 Hz), 3.85 (d, 2 H, J = 6.0 Hz), 3.04 - 3.19 (m, 2 H), 3.00 (d, 2 H, J = 11.0 Hz), 2.64 - 2.54 (m, 1 H), 2.48 (s, 1 H), 2.43 (s, 1 H), 2.18 (t, 2 H, J = 11.3 Hz), 2.10 - 1.89 (m, 2 H), 1.76 - 1.64 (m, 5 H), 1.38 - 1.52 (m, 2 H), 1.41 (s, 3 H), 1.35 (s, 3 H), 1.28 (t, 3 H, J = 7.0 Hz); MS (ESI) m/z 525 (M+ + H). |
| 679 | ethyl 1-(4'-((1-(2-fluoro-2-methylpropyl)piperidin-4-yl)methoxy)biphenylcarbonyl)piperidine-2-carboxylate<br>1 H NMR (400 MHz, CDCl₃) δ 7.64 - 7.39 (m, 6 H), 6.98 (d, 2 H, J = 8.8 Hz), 4.31 - 4.22 (m, 2 H), 3.85 (d, 2 H, J = 6.0 Hz), 3.76 (d, 1 H, J = 13.6 Hz), 3.34 - 3.27 (m, 1 H), 3.00 (d, 2 H, 3 = 11.3 Hz), 2.48 (s, 1 H), 2.43 (s, 1 H), 2.38 (d, 1 H, J = 13.3 Hz), 2.24 - 2.12 (m, 2 H), 1.88 - 1.72 (m, 5 H), 1.68 - 1.59 (m, 2 H), 1.53 - 1.38 (m, 2 H), 1.41 (s, 3 H), 1.37 - 1.26 (m, 2 H), 1.35 (s, 3 H); MS (ESI) m/z 525 (M+ + H). |
| 680 | (4-ethylpiperazin-1-yl)(4'-((1-(2-fluoro-2-methylpropyl)piperidin-4-yl)methoxy)biphenyl-4-yl)methanone<br>1 H NMR (400 MHz, CDCl₃) δ 7.59 (d, 2 H, J = 8.1 Hz), 7.53 (d, 2 H, J = 8.6 Hz), 7.46 (d, 2 H, J = 8.0 Hz), 6.98 (d, 2 H, J = 9.1 Hz), 3.85 - 3.84 (m, 4 H), 3.58 (brs, 2 H), 3.02 (d, 2 H, J = 10.0 Hz), 2.55 - 2.44 (m, 8 H), 2.20 (t, 2 H, J = 11.5 Hz), 1.82 (d, 3 H, J = 11.0 Hz), 1.47 - 1.40 (m, 2 H), 1.35 (s, 3 H), 1.26 (s, 3 H), 1.13 (t, 3 H, 3 = 8.0 Hz); MS (ESI) m/z 482 (M+ + H). |
| 681 | (4'-((1-(2-fluoro-2-methylpropyl)piperidin-4-yl)methoxy)biphenyl-4-yl)(4-isopropylpiperazin-1-yl)methanone<br>1 H NMR (400 MHz, CDCl₃) δ 7.58 (d, 2 H, J = 8.0 Hz), 7.52 (d, 2 H, J = 8.0 Hz), 7.47 (d, 2 H, J = 8.0 Hz), 6.98 (d, 2 H, J = 8.0 Hz), 3.85 - 3.84 (m, 4 H), 3.58 (brs, 2 H), 3.03 (d, 2 H, J = 11.1 Hz), 3.03 (d, 2 H, J = 11.1 Hz), 2.67 (m, 1 H), 2.56 - 2.45 (m, 6 H), 2.20 (t, 2 H, J = 12.0 Hz), 1.82 (d, 3 H, J = 7.2 Hz), 1.48 - 1.41 (m, 2 H), 1.36 (s, 3 H), 1.26 (s, 3 H), 1.11 (d, 6 H, J = 6.4 Hz); MS (ESI) m/z 496 (M+ + H). |
| 685 | (4'-((1-(2-fluoro-2-methylpropyl)piperidin-4-yl)methoxy)biphenyl-4-yl)(4-methylpiperazin-1-yl)methanone<br>1 H NMR (400 MHz, CDCl₃) δ 7.58 (d, 2 H, J = 6.0 Hz), 7.52 (d, 2 H, J = 8.0 Hz), 7.47 (d, 2 H, J = 8.0 Hz), 6.98 (d, 2 H, J = 8.5 Hz), 3.85 - 3.84 (m, 4 H), 3.55 (brs, 2 H), 3.02 (d, 2 H, J = 10.2 Hz), 2.50 - 2.45 (m, 6 H), 2.35 (s, 3 H), 2.20 (t, 2 H, J = 11.3 Hz), 1.82 (d, 3 H, J = 12.0 Hz), 1.47 - 1.44 (m, 2 H). 1.41 (s, 3 H), 1.35 (s, 3 H); MS (ESI) m/z 468 (M+ + H). |
| 686 | (3,5-dimethylpiperazin-1-yl)(4'-((1-(2-fluoro-2-methylpropyl(piperidin-4-yl)methoxy)biphenyl-4-yl)methanone<br>1 H NMR (400 MHz, CDCl₃) δ 7.60 (d, 2 H, J = 8.0 Hz), 7.54 (d, 2 H, J = 8.4 Hz), 7.46 (d, 2 H, J = 8.0 Hz), 6.99 (d, 2 H, J = 8.5 Hz), 4.64 (brs, 1 H), 3.85 (d, 2 H, J = 5.6 Hz), 3.01 - 3.00 (m, 2 H), 2.46 - 2.45 (m, 2 H), 2.19 (t, 2 H, J = 11.6 Hz), 1.82 (d, 3 H, J = 10.6 Hz), 1.48 - 1.35 (m, 8 H), 1.26 - 1.04 (m, 6 H); MS (ESI) m/z 482 (M+ + H) |
| 687 | (2,6-dimethylmorpholino)(4'-((1-(2-fluoro-2-methylpropyl)piperidin-4-yl)methoxy)biphenyl-4-yl)methanone<br>1 H NMR (400 MHz, CDCl₃) δ 7.60 (d, 2 H, J = 6.8 Hz), 7.53 (d, 2 H, J = 7.1 Hz), 7.45 (d, 2 H, J = 8.0 Hz), 6.98 (d, 2 H, J = 7.2 Hz), 3.85 (d, 2 H, J = 5.6 Hz), 3.64 (brs, 2 H), 3.02 (d, 2 H, J = 10.7 Hz), 2.48 - 2.47 (m, 2 H), 2.21 (t, 2 H, J = 7.5 Hz), 1.82 (d, 3 H, J = 10.5 Hz), 1.47 - 1.12 (m, 14 H); MS (ESI) m/z 483 (M+ + H) |
| 790 | 4-(4'-((1-(2-fluoro-2-methylpropyl)piperidin-4-yl)methoxy)biphenylcarbonyl)piperazin-2-one<br>1 H NMR (400 MHz, CDCl₃) δ 7.59 (d, 2 H, J = 8.0 Hz), 7.51 (d, 2 H, J = 8.8 Hz), 7.47 (d, 2 H, J = 8.0 Hz), 6.97 (d, 2 H, J = 8.8 Hz), 4.28 (s, 2 H), 3.84 (s, 2 H), 3.83 (d, 2 H, J = 6.0 Hz), 3.44 (s, 2 H), 2.98 (d, 2 H, J = 11.5 Hz), 2.47 (s, 1 H), 2.41 (s, 1 H), 2.16 (t, 2 H, J = 10.9 Hz), 1.85 - 1.72 (m, 3 H), 1.49 - 1.36 (m, 2 H), 1.39 (s, 3 H), 1.33 (s, 3 H); MS (ESI) m/z 468 (M+ + H). |
| 791 | 1-(4'-((1-(2-fluoro-2-methylpropyl)piperidin-4-yl)methoxy)biphenylcarbonyl)piperidin-4-carbonitrile<br>1 H NMR (400 MHz, CDCl₃) δ 7.59 (d, 2 H, J = 8.5 Hz), 7.51 (d, 2 H, J = 8.8 Hz), 7.44 (d, 2 H, J = 8.5 Hz), 6.97 (d, 2 H, J = 8.8 Hz), 3.84 (d, 2 H, J = 6.0 Hz), 3.74 (s, 4 H), 2.89 - 3.03 (m, 3 H), 2.47 (s, 1 H), 2.42 (s, 1 H), 2.17 (t, 2 H, J = 10.9 Hz), 1.92 (s, 4 H), 1.74 - 1.84 (m, 3 H), 1.37 - 1.50 (m, 2 H), 1.39 (s, 3 H), 1.34 (s, 3 H); MS (ESI) m/z 478 (M+ + H). |
| 830 | N-(3,4-dihydroxyphenethyl)-4'-((1-(2-fluoro-2-methylpropyl)piperidin-4-yl)methoxy)biphenyl-4-carboxamide<br>1 H NMR (400 MHz, CDCl₃) δ 7.68 (d, 2 H, J = 8.0 Hz), 7.54 (d, 2 H, J = 7.5 Hz), 7.48 (d, 2 H, J = 8.0 Hz), 6.92 (d, 2 H, J = 7.5 Hz), 6.75 (d, 1 H, J = 7.5 Hz), 6.71 (s, 1 H), 6.56 (d, 1 H, J = 7.5 Hz), 3.80 (d, 2 H, J = 5.8 Hz), 3.59 (d, 2 H, J = 5.8 |

TABLE 4-continued

| Compound No. | Compound Name, ¹H-NMR, MS (ESI) |
|---|---|
|  | Hz), 2.98 (d, 2 H, J = 10.0 Hz), 2.76 (t, 2 H, J = 6.9 Hz), 2.52 - 2.37 (m, 2 H), 2.22 - 2.09 (m, 2 H), 1.78 (d, 3 H, J = 10.8 Hz), 1.53 - 1.34 (m, 2 H), 1.36 (s, 3 H), 1.31 (s, 3 H); MS (ESI) m/z 521 (M+ + H). |
| 831 | (R)-1-(4'-((1-(2-fluoro-2-methylpropyl)piperidin-4-yl)methoxy)biphenylcarbonyl)piperidin-2-carboxamide<br>1 H NMR (400 MHz, CDCl₃) δ 7.65 - 7.41 (m, 6 H), 6.97 (d, 2 H, J = 8.5 Hz), 3.84 (d, 2 H, J = 5.8 Hz), 3.80 (s, 1 H), 3.11 (t, 1 H, J = 12.8 Hz), 3.00 (d, 2 H, J = 10.8 Hz), 2.48 (s, 1 H), 2.43 (s, 1 H), 2.34 (d, 1 H, J = 12.5 Hz), 2.18 (t, 2 H, J = 11.5 Hz), 1.91 - 1.73 (m, 6 H), 1.71 - 1.50 (m, 4 H), 1.49 - 1.37 (m, 2 H), 1.40 (s, 3 H), 1.34 (s, 3 H). |
| 832 | (S)-1-(4'-((1-(2-fluoro-2-methylpropyl)piperidin-4-yl)methoxy)biphenylcarbonyl)piperidin-2-carboxamide<br>1 H NMR (400 MHz, CDCl₃) δ 7.65 - 7.41 (m, 6 H), 6.97 (d, 2 H, J = 8.5 Hz), 3.84 (d, 2 H, J = 5.8 Hz), 3.80 (s, 1 H), 3.11 (t, 1 H, J = 13.3 Hz), 3.00 (d, 2 H, J = 10.3 Hz), 2.49 (s, 1 H), 2.43 (s, 1 H), 2.34 (d, 1 H, 3 = 12.3 Hz), 2.18 (t, 2 H, J = 11.2 Hz), 1.91 - 1.73 (m, 6 H), 1.72 - 1.51 (m, 3 H), 1.51 - 1.37 (m, 2 H), 1.40 (s, 3 H), 1.34 (s, 3 H); MS (ESI) m/z 496 (M+ + H). |
| 874 | (S)-1-(4'-((1-(2-fluoro-2-methylpropyl)piperidin-4-yl)methoxy)biphenylcarbonyl)piperidin-3-carboxamide<br>1 H NMR (400 MHz, CDCl₃) δ 7.59 (d, 2 H, J = 8.0 Hz), 7.53 (d, 2 H, J = 8.8 Hz), 7.45 (d, 2 H, J = 8.0 Hz), 6.98 (d, 2 H, J = 8.8 Hz), 4.15 - 4.01 (m, 1 H), 3.85 (d, 3 H, J = 6.0 Hz), 3.02 (d, 2 H, J = 10.8 Hz), 2.60 (s, 1 H), 2.51 (s, 1 H), 2.45 (s, 1 H), 2.20 (t, 2 H, J = 11.4 Hz), 2.06 - 1.87 (m, 3 H), 1.86 - 1.76 (m, 4 H), 1.62 (s, 1 H), 1.55 - 1.43 (m, 3 H), 1.41 (s, 3 H), 1.36 (s, 3 H); MS (ESI) m/z 496 (M+ + H). |
| 879 | (R)-1-(4'-((1-(2-fluoro-2-methylpropyl)piperidin-4-yl)methoxy)biphenylcarbonyl)piperidin-3-carboxamide<br>1 H NMR (400 MHz, CDCl₃) δ 7.59 (d, 2 H, J = 8.0 Hz), 7.53 (d, 2 H, J = 8.8 Hz), 7.45 (d, 2 H, J = 8.0 Hz), 6.98 (d, 2 H, J = 8.8 Hz), 4.01 - 4.10 (m, 1 H), 3.86 (d, 3 H, J = 6.0 Hz), 3.63 - 3.39 (m, 2 H), 2.65 - 2.40 (m, 3 H), 2.29 - 2.11 (m, 3 H), 1.98 - 1.79 (m, 5 H), 1.76 - 1.58 (m, 3 H), 1.56 - 1.46 (m, 2 H), 1.42 (s, 3 H), 1.37 (s, 3 H); MS (ESI) m/z 496 (M+ + H). |

Example 24. Compound 620: (R)-1-(4'-((1-(2-fluoro-2-methylpropyl)piperidin-4-yl)methoxy)biphenylcarbonyl)pyrrolidine-2-carboxylic acid

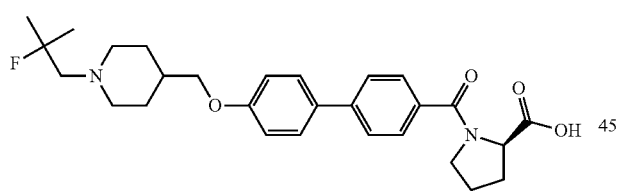

(R)-methyl 1-(4'-((1-(2-fluoro-2-methylpropyl)piperidin-4-yl)methoxy)biphenylcarbonyl)pyrrolidine-2-carboxylate (compound 619, 53 mg, 0.11 mmol) was dissolved in THF 1.5 mL, H₂O 0.5 mL and MeOH 0.5 mL. LiOH.H₂O (25 mg, 0.53 mmol) was added slowly thereto, following with stirring at room temperature for 2 hours. After the completion of the reaction, the reaction mixture was acidified to pH 5 by addition of 1 N HCl, following with adding excess amount of water. The resulting precipitate was filtered to yield the title compound as white solid (41 mg, 80%).

1H NMR (400 MHz, CDCl₃) δ 7.55 (d, 2H, J=10.2 Hz), 7.37-7.23 (m, 4H), 6.65 (d, 2H, J=7.6 Hz), 3.82 (d, 2H, J=5.8 Hz), 3.72-3.50 (m, 6H), 3.32-3.16 (m, 2H), 2.70 (brs, 2H), 2.32 (m, 1H), 2.18-2.14 (m, 2H), 2.02-2.00 (m, 2H), 1.96 (brs, 1H), 1.79 (d, 3H, J=10.5 Hz), 1.38-1.33 (m, 8H); MS (ESI) m/z 483 (M++H).

Example 25. Compound 621: 2-(4'-((1-(2-fluoro-2-methylpropyl)piperidin-4-yl)methoxy)-N-methylbiphenyl-4-ylcarboxamido)acetic acid

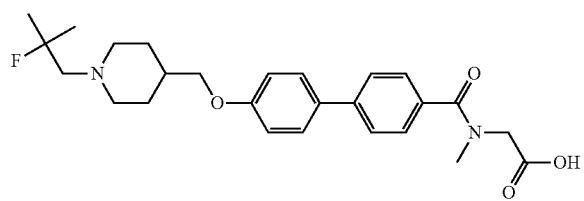 [SMILES: CN(CC(=O)O)C(=O)c1ccc(-c2ccc(OCC3CCN(CC(C)(C)F)CC3)cc2)cc1]

4'-((1-(2-fluoro-2-methylpropyl)piperidin-4-yl)methoxy)biphenyl-4-carboxylic acid (compound 548, 0.12 g, 0.31 mmol) and methyl 2-(methylamino)acetate (29 mg, 0.28 mmol) were dissolved in DMF 1 mL. EDC (0.12 g, 0.62 mmol) and HOBt (84 mg, 0.62 mmol) were added thereto. Lastly, DIPEA (0.27 mL, 1.56 mmol) was added thereto, following with stirring at room temperature for 15 hours. The reaction mixture was added with EtOAc, and washed three times with water. The organic layer was dried over MgSO₄, filtered to remove the solid residue, and the filtrate was concentrated under reduced pressure. The concentrate was purified by column chromatography (10% MeOH/CH₂Cl₂) to yield the title compound as white solid (0.12 g, 82%). The obtained product (90 mg, 0.19 mmol) was dissolved in THF 1.5 mL, H₂O 0.5 mL and MeOH 0.5 mL. LiOH.H₂O (40 mg, 0.96 mmol) was added slowly thereto, following with stirring at room temperature for 2 hours. After the completion of the reaction, the reaction mixture was acidified to pH 5 by addition of 1 N HCl. Excess amount of water was added thereto. The resulting precipitate was filtered to yield the title compound as white solid (16 mg, 18%).

1H NMR (400 MHz, CDCl$_3$) δ 7.51-7.42 (m, 6H), 6.92-6.89 (m, 2H), 4.03-3.85 (m, 2H), 3.80-3.79 (m, 2H), 2.83 (brs, 5H), 2.51-2.44 (m, 2H), 2.20-2.18 (m, 2H), 1.80-1.78 (m, 3H), 1.45-1.42 (m, 2H), 1.38 (s, 3H), 1.33 (s, 3H); MS (ESI) m/z 457 (M++H).

Example 26. Compound 630: (4'-((1-(2-fluoro-2-methylpropyl)piperidin-4-yl)methoxy)biphenyl-4-yl)(piperazin-1-yl)methanone

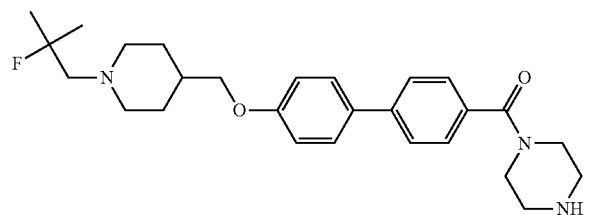 [SMILES: CC(C)(F)CN1CCC(COc2ccc(-c3ccc(C(=O)N4CCNCC4)cc3)cc2)CC1]

t-butyl 4-(4'-((1-(2-fluoro-2-methylpropyl)piperidin-4-yl)methoxy)biphenylcarbonyl)piperazin-1-carboxylate (compound 626, 20 mg, 0.04 mmol) was dissolved in MeOH. trifluoroacetic acid (8 μL, 0.11 mmol) was added slowly thereto, following with stirring at room temperature for 1 hour. After the completion of the reaction, the obtained reaction mixture was alkalinized with saturated NaHCO$_3$ aqueous solution, and extracted with CH$_2$Cl$_2$. The obtained organic layer was washed with saturated aqueous brine solution three times. The obtained organic layer was dried over MgSO$_4$ to yield the title compound as white solid (5 mg, 31%).

1H NMR (400 MHz, CDCl$_3$) δ 7.59 (d, 2H, 1=6.0 Hz), 7.53 (d, 2H, 1=6.5 Hz), 7.46 (d, 2H, J=6.2 Hz), 6.98 (d, 2H, J=6.5 Hz), 3.85 (d, 2H, J=4.2 Hz), 3.79 (brs, 4H), 3.01 (d, 2H, J=8.5 Hz), 2.93 (brs, 4H), 2.50-2.44 (m, 2H), 2.19 (t, 2H, J=8.3 Hz), 1.83-1.80 (m, 3H), 1.49-1.40 (m, 2H), 1.35 (s, 3H), 1.26 (s, 3H); MS (ESI) m/z 454 (M++H).

Example 27. Compound 682: (R)-1-(4'-((1-(2-fluoro-2-methylpropyl)piperidin-4-yl)methoxy)biphenylcarbonyl)pyrrolidine-2-carboxamide

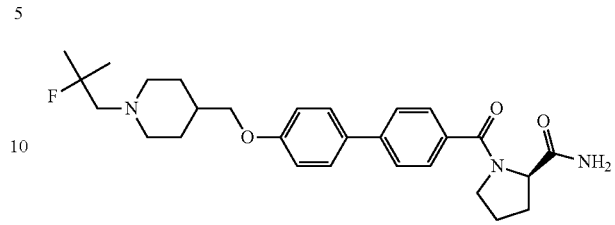

(R)-1-(4'-((1-(2-fluoro-2-methylpropyl)piperidin-4-yl)methoxy)biphenylcarbonyl)pyrrolidine-2-carboxylic acid (compound 620, 40 mg, 0.084 mmol) and NH$_4$Cl (6 mg, 0.12 mmol) were dissolved in DMF 1 mL. EDC (31 mg, 0.17 mmol) and HOBt (22 mg, 0.17 mmol) were added thereto. Lastly, DIPEA (72 μL, 0.42 mmol) was added thereto, following with stirring at room temperature for 15 hours. The reaction mixture was added with EtOAc, and washed three times with water. The organic layer was dried over MgSO$_4$, filtered to remove the solid residue, and the filtrate was concentrated under reduced pressure. The obtained concentrate was purified by silica gel column chromatography (10% MeOH/CH$_2$Cl$_2$) to yield the title compound as white solid (15 mg, 37%).

1H NMR (400 MHz, CDCl$_3$) δ 7.60 (s, 4H), 7.53 (d, 2H, J=8.0 Hz), 6.98 (d, 2H, J=8.0 Hz), 5.53 (s, 1H), 4.83 (t, 1H, J=6.0 Hz), 3.85 (d, 2H, J=8.0 Hz), 3.66-3.58 (m, 2H), 2.50-2.47 (m, 2H), 2.20-2.06 (m, 4H), 1.88-1.81 (m, 5H), 1.42-1.26 (m, 8H); MS (ESI) mz 482 (M++H).

According to the above-described synthesis process of compound 682, the compounds of Table 6 were synthesized using 4'-((1-(2-fluoro-2-methylpropyl)piperidin-4-yl)methoxy)biphenyl-4-carboxylic acid and the reactant of Table 5.

TABLE 5

| Compound No. | Reactant | Yield (%) |
| --- | --- | --- |
| 683 | dimethylamine hydrochloride | 21 |
| 684 | methylamine | 55 |

TABLE 6

| Compound No. | Compound Name, $^1$H-NMR, MS (ESI) |
| --- | --- |
| 683 | (R)-1-(4'-((1-(2-fluoro-2-methylpropyl)piperidin-4-yl)methoxy)biphenylcarbonyl)-N,N-dimethylpyrrolidine-2-carboxamide<br>1 H NMR (400 MHz, CDCl$_3$) δ 7.53 (d, 2 H, J = 8.0 Hz), 7.58 - 7.53 (m, 4 H), 6.97 (d, 2 H, J = 8.6 Hz), 5.10 (q, 1 H, J = 4.6 Hz), 3.86 - 3.63 (m, 4 H), 3.23 (s, 3 H), 3.02 (s, 3 H), 2.83 - 2.61 (m, 2 H), 2.28 - 1.84 (m, 9 H), 1.42 - 1.26 (m, 8 H);<br>MS (ESI) m/z 510 (M+ + H). |
| 684 | (R)-1-(4'-((1-(2-fluoro-2-methylpropyl)piperidin-4-yl)methoxy)biphenylcarbonyl)-N-methylpyrrolidine-2-carboxamide<br>1 H NMR (400 MHz, CDCl$_3$) δ 7.57 (s, 3 H), 7.53 (d, 2 H, J = 8.0 Hz), 7.10 (brs, 1 H), 6.98 (d, 2 H, J = 8.5 Hz), 4.80 - 4.79 (m, 1 H), 3.85 (d, 2 H, J = 5.8 Hz), 3.62 - 3.58 (m, 2 H), 3.01 (brs, 2 H), 2.96 - 2.88 (m, 2 H), 2.83 (d, 2 H, J = 4.8 Hz), 2.52 - 2.44 (m, 2 H), 2.20 (t, 2 H, J = 10.8 Hz), 2.07 - 2.05 (m, 2 H), 1.83 - 1.80 (m, 3 H), 1.46 - 1.43 (m, 2 H), 1.40 (s, 3 H), 1.35 (s, 3 H); MS (ESI) m/z 496 (M+ + H). |

Example 28. Compound 755: 1-(4-((1-(2-fluoro-2-methylpropyl)piperidin-4-yl)methoxy)biphenylcarbonyl)piperidin-3-carboxamide

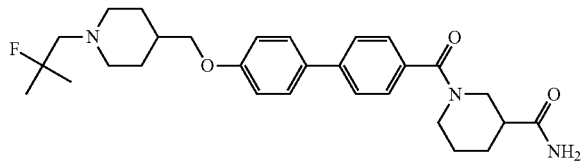 [SMILES: CC(C)(F)CN1CCC(COc2ccc(-c3ccc(C(=O)N4CCCC(C(N)=O)C4)cc3)cc2)CC1]

Step 1.

1-(4'-((1-(2-fluoro-2-methylpropyl)piperidin-4-yl)methoxy)biphenylcarbonyl)piperidin-3-carboxylic acid: ethyl 1-(4'-((1-(2-fluoro-2-methylpropyl)piperidin-4-yl)methoxy) biphenylcarbonyl)piperidine-3-carboxylate (compound 677, 0.07 g, 0.14 mmol) was dissolved in THF (1.5 mL). MeOH (0.5 mL) and $H_2O$ (0.5 mL) were poured thereto. LiOH (0.3 g, 0.70 mmol) was added thereto, and refluxed with heating and stirring for 4 hours. The reaction mixture was acidified with 1 N HCl, and extracted with EtOAc and $CH_2Cl_2$. The organic layer was dried over $MgSO_4$, and filtered to remove a solid. The filtrate was concentrated under reduced pressure to yield the title compound as yellow solid (0.070 g, 100%).

Step 2.

Compound 755: 1-(4'-((1-(2-fluoro-2-methylpropyl)piperidin-4-yl)methoxy) biphenylcarbonyl)piperidin-3-carboxylic acid (0.07 g, 0.14 mmol), EDC (0.05 g, 0.28 mmol), HOBt (0.05 g, 0.28 mmol) and DIPEA (0.12 mL, 0.70 mmol) were dissolved in DMF (21 mL) completely. Lastly, $NH_4Cl$ (0.02 g, 0.28 mmol) was added thereto, following with stirring at room temperature for 15 hours. Water (10 mL) was added with water, and extracted with EtOAc. The organic layer was washed with saturated $NH_4Cl$ aqueous solution, dried over $MgSO_4$, and filtered to remove a solid. The filtrate was concentrated under reduced pressure. The concentrate was purified by column chromatography (4 g, ISCO silica gel cartridge, 0-10% MeOH/$CH_2Cl_2$) to yield the title compound as yellow solid (0.03 g, 51%).

1H NMR (400 MHz, CDCl₃) δ 7.57 (d, 2H, J=8.3 Hz), 7.51 (d, 2H, J=8.8 Hz), 7.43 (d, 2H, J=8.5 Hz), 6.96 (d, 2H, J=8.8 Hz), 6.84-6.67 (m, 1H), 5.65 (s, 1H), 4.09 (s, 1H), 3.83 (d, 2H, J=5.8 Hz), 3.69-3.80 (m, 1H), 3.49-3.63 (m, 1H), 3.47-3.32 (m, 1H), 2.98 (d, 2H, J=11.3 Hz), 2.57 (s, 1H), 2.47 (s, 1H), 2.41 (s, 1H), 2.17 (t, 2H, J=11.0 Hz), 2.11-2.05 (m, 1H), 1.92 (s, 1H), 1.85-1.72 (m, 1H), 1.61 (s, 1H), 1.50-1.37 (m, 2H), 1.39 (s, 3H), 1.34 (s, 3H); MS (ESI) m/z 496 (M++H).

Example 29. Compound 756: 1-(4'-((1-(2-fluoro-2-methylpropyl)piperidin-4-yl)methoxy)biphenylcarbonyl)piperidin-4-carboxamide

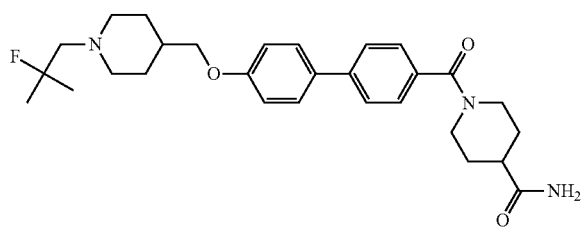 [SMILES: CC(C)(F)CN1CCC(COc2ccc(-c3ccc(C(=O)N4CCC(C(N)=O)CC4)cc3)cc2)CC1]

Step 1.

1-(4'-((1-(2-fluoro-2-methylpropyl)piperidin-4-yl)methoxy)biphenylcarbonyl)piperidin-4-carboxylic acid: ethyl 1-(4'-((1-(2-fluoro-2-methylpropyl)piperidin-4-yl)methoxy) biphenylcarbonyl)piperidine-4-carboxylate (compound 678, 0.09 g, 0.17 mmol) was dissolved in THF (1.5 mL). MeOH (0.5 mL) and $H_2O$ (0.5 mL) were poured thereto. LiOH (0.4 g, 0.87 mmol) was added thereto, and refluxed with heating and stirring for 4 hours. The reaction mixture was acidified with 1 N HCl, and extracted with EtOAc and $CH_2Cl_2$. The organic layer was dried over $MgSO_4$, and filtered to remove a solid. The filtrate was concentrated under reduced pressure to yield the title compound as yellow solid (0.087 g, 100%).

Step 2.

Compound 756: 1-(4'-((1-(2-fluoro-2-methylpropyl)piperidin-4-yl)methoxy) biphenylcarbonyl)piperidin-4-carboxylic acid (0.08 g, 0.17 mmol), EDC (0.06 g, 0.35 mmol), HOBt (0.05 g, 0.35 mmol) and DIPEA (0.11 mL, 0.87 mmol) were dissolved in DMF (21 mL) completely. Lastly, $NH_4Cl$ (0.02 g, 0.35 mmol) was added thereto, following with stirring at room temperature for 15 hours. Water (10 mL) was added with water, and extracted with EtOAc. The organic layer was washed with saturated $NH_4Cl$ aqueous solution, dried over $MgSO_4$, and filtered to remove a solid. The filtrate was concentrated under reduced pressure. The concentrate was purified by column chromatography (4 g, ISCO silica gel cartridge, 0-10% MeOH/$CH_2Cl_2$) to yield the title compound as yellow solid (0.06 g, 70%).

1H NMR (400 MHz, CDCl₃) δ 7.59-7.54 (m, 2H), 7.50 (d, 2H, J=8.8 Hz), 7.42 (d, 2H, J=8.5 Hz), 6.96 (d, 2H, J=8.8 Hz), 5.82 (d, 2H, J=15.6 Hz), 4.78-4.55 (m, 1H), 3.99-3.85 (m, 1H), 3.83 (d, 2H, J=5.8 Hz), 3.11-2.83 (m, 2H), 2.98 (d, 2H, J=11.3 Hz), 2.48-2.40 (m, 1H), 2.49-2.37 (m, 1H), 2.47 (s, 1H), 2.41 (s, 1H), 2.16 (t, 2H, J=11.0 Hz), 2.05-1.84 (m, 2H), 1.84-1.65 (m, 6H), 1.50-1.36 (m, 2H), 1.39 (s, 3H), 1.33 (s, 3H); MS (ESI) mz 496 (M++H).

Example 30. Compound 757: 1-(4'-((1-(2-fluoro-2-methylpropyl)piperidin-4-yl)methoxy)biphenylcarbonyl)piperidin-2-carboxamide

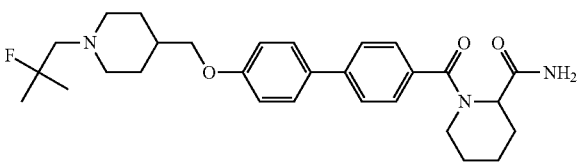 [SMILES: CC(C)(F)CN1CCC(COc2ccc(-c3ccc(C(=O)N4CCCCC4C(N)=O)cc3)cc2)CC1]

Step 1.

1-(4'-((1-(2-fluoro-2-methylpropyl)piperidin-4-yl)methoxy)biphenylcarbonyl)piperidin-2-carboxylic acid: ethyl 1-(4'-((1-(2-fluoro-2-methylpropyl)piperidin-4-yl)methoxy) biphenylcarbonyl)piperidine-2-carboxylate (compound 679, 0.09 g, 0.16 mmol) was dissolved in THF (1.5 mL). MeOH (0.5 mL) and $H_2O$ (0.5 mL) were poured thereto. LiOH (0.3 g, 0.83 mmol) was added thereto, and refluxed with heating and stirring for 4 hours. The reaction mixture was acidified with 1 N HCl, and extracted with EtOAc and $CH_2Cl_2$. The organic layer was dried over $MgSO_4$, and filtered to remove a solid. The filtrate was concentrated under reduced pressure to yield the title compound as yellow solid (0.082 g, 100%).

Step 2.

Compound 757: 1-(4'-((1-(2-fluoro-2-methylpropyl)piperidin-4-yl)methoxy) biphenylcarbonyl)piperidin-2-carboxylic acid (0.08 g, 0.17 mmol), EDC (0.06 g, 0.33 mmol), HOBt (0.05 g, 0.33 mmol) and DIPEA (0.11 mL, 0.83 mmol) were dissolved in DMF (21 mL) completely. Lastly, NH4Cl (0.02 g, 0.33 mmol) was added thereto, following with stirring at room temperature for 15 hours. Water (10 mL) was added with water, and extracted with EtOAc. The organic layer was washed with saturated NH4Cl aqueous solution, dried over MgSO4, and filtered to remove a solid. The filtrate was concentrated under reduced pressure. The concentrate was purified by column chromatography (4 g, ISCO silica gel cartridge, 0-10% MeOH/CH2Cl2) to yield the title compound as yellow solid (0.04 g, 46%).

1H NMR (400 MHz, CDCl3) δ 7.64-7.40 (m, 6H), 6.97 (d, 2H, J=8.5 Hz), 6.54 (s, 1H), 3.84 (d, 2H, J=5.8 Hz), 3.79 (s, 1H), 3.12 (t, 1H, J=13.8 Hz), 2.99 (d, 2H, J=11.0 Hz), 2.48 (s, 1H), 2.42 (s, 1H), 2.33 (d, 1H, J=12.3 Hz), 2.17 (t, 2H, J=11.2 Hz), 1.89-1.72 (m, 5H), 1.64 (s, 2H), 1.61-1.51 (m, 2H), 1.49-1.37 (m, 2H), 1.39 (s, 3H), 1.34 (s, 3H); MS (ESI) m/z 496 (M++H).

Example 31. Compound 932: (2S,4R)-methyl 1-(4'-((1-(2-fluoro-2-methylpropyl)piperidin-4-yl)methoxy)biphenylcarbonyl)-4-hydroxypyrrolidine-2-carboxylate

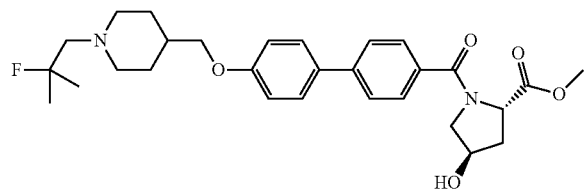 [SMILES: COC(=O)[C@@H]1C[C@@H](O)CN1C(=O)c1ccc(-c2ccc(OCC3CCN(CC(C)(C)F)CC3)cc2)cc1]

4'-((1-(2-fluoro-2-methylpropyl)piperidin-4-yl)methoxy) biphenyl-4-carboxylic acid (compound 548; 300 mg, 0.78 mmol), (2S,4R)-methyl 4-hydroxypyrrolidine-2-carboxylate hydrochloride (212 mg, 1.17 mmol), EDC (298 mg, 1.56 mmol), HOBt (210 mg, 1.56 mmol) and DIPEA (0.28 mL, 1.56 mmol) were dissolved in DMF (5 mL) at room temperature. After stirring at 80° C. for 12 hours, the reaction mixture was added with saturated NH4Cl aqueous solution, and extracted with dichloromethane. The obtained organic layer was washed with saturated aqueous brine solution, dried over anhydrous MgSO4, and filtered. The filtrate was concentrated under reduced pressure. The concentrate was purified by column chromatography (SiO2, 40 g cartridge; EtOAc/hexane=5% to 80%), and concentrated to yield the title compound as white solid (240 mg, 60%).

1H NMR (400 MHz, CDCl3) δ 7.63-7.50 (m, 6H), 6.97 (m, 2H), 4.87 (m, 1H), 4.53 (m, 1H), 3.89-3.79 (m, 5H), 3.62 (m, 1H), 3.11 (m, 2H), 2.59-2.13 (m, 7H), 1.86 (m, 4H), 1.58 (m, 2H), 1.41 (m, 6H); MS (ESI) m/z 513 (M++H).

Example 32. Compound 934: (2S,4R)-1-(4'-((1-(2-fluoro-2-methylpropyl)piperidin-4-yl)methoxy)biphenylcarbonyl)-4-hydroxypyrrolidine-2-carboxamide

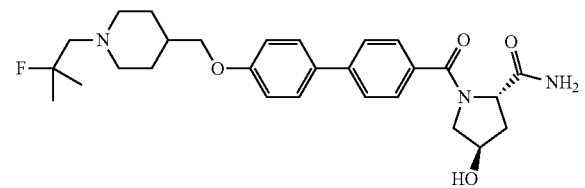 [SMILES: CC(C)(F)CN1CCC(COc2ccc(-c3ccc(C(=O)N4C[C@H](O)C[C@H]4C(N)=O)cc3)cc2)CC1]

Step 1.

(2S,4R)-1-(4'-((1-(2-fluoro-2-methylpropyl)piperidin-4-yl)methoxy)biphenylcarbonyl)-4-hydroxypyrrolidine-2-carboxylic acid: (2S,4R)-methyl 1-(4'-((1-(2-fluoro-2-methylpropyl)piperidin-4-yl)methoxy)biphenylcarbonyl)-4-hydroxypyrrolidine-2-carboxylate (400 mg, 0.78 mmol) and LiOH.H2O (65 mg, 1.56 mmol) were dissolved in THF (10 mL)/H2O (5 mL) at room temperature. The solution was stirred at 60° C. for 10 hours. The reaction mixture was concentrated under reduced pressure to remove the solvent. The obtained concentrate was added with 1 M–HCl aqueous solution, and concentrated under reduced pressure. The obtained material was used without further purifying process.

Step 2.

Compound 934: (2S,4R)-1-(4'-((1-(2-fluoro-2-methylpropyl)piperidin-4-yl)methoxy)biphenylcarbonyl)-4-hydroxypyrrolidine-2-carboxylic acid (400 mg, 0.80 mmol), ammonium chloride (64 mg, 1.20 mmol), EDC (231 mg, 1.20 mmol), HOBt (163 mg, 1.20 mmol) and DIPEA (21 mg, 1.61 mmol) were dissolved in DMF (10 mL) at room temperature. The solution was stirred at 60° C. for 10 hours, the reaction mixture was added with water (10 mL), and stirred. The resulting precipitate was filtered, and dried to yield the title compound as brown solid (100 mg, 25%).

1H NMR (400 MHz, CDCl3+MeOD) δ 7.58-7.46 (m, 6H), 7.22 (brs, 1H), 6.91 (m, 2H), 6.07 (br, 1H), 4.76 (m, 1H), 4.37 (m, 1H), 3.81-3.73 (m, 3H), 3.51 (m, 1H), 3.95 (m, 2H), 2.49-2.11 (m, 6H), 1.76 (m, 3H), 1.41-1.31 (m, 8H); MS (ESI) m/z 498 (M++H).

Example 33. Compound 749: (R)-(2-fluoro-4'-((1-(2-fluoro-2-methylpropyl)piperidin-4-yl)methoxy) biphenyl-4-yl)(3-hydroxypiperidin-1-yl)methanone

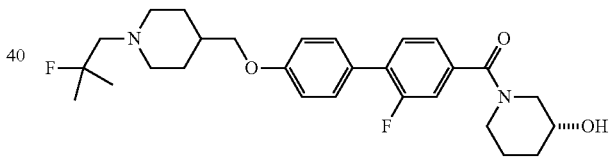

Step 1.

Methyl 2-fluoro-4'-((1-(2-fluoro-2-methylpropyl)piperidin-4-yl)methoxy)biphenyl-4-carboxylate: 4-((4-bromophenoxy)methyl)-1-(2-fluoro-2-methylpropyl)piperidine (the product of synthesis step 3 of compound 498; 180 mg, 0.52 mmol), 2-fluoro-4-(methoxycarbonyl)phenylboronic acid (124 mg, 0.63 mmol), Pd(dppf)Cl2 (43 mg, 0.05 mmol) and Cs2CO3 (341 mg, 1.05 mmol) were added to water (2 mL)/1,4-dioxane (6 mL). With a microwave radiation, the mixture was heated at 110° C. for 15 minutes, and then cooled to room temperature. The reaction mixture was added with water, and extracted with EtOAc. The organic layer was dried over anhydrous MgSO4, and concentrated under reduced pressure. The obtained concentrate was purified by silica gel column chromatography (30% EtOAc/hexane) to yield the title compound as white solid (114 mg, 52%).

Step 2.

2-fluoro-4'-((1-(2-fluoro-2-methylpropyl)piperidin-4-yl)methoxy)biphenyl-4-carboxylic acid: methyl 2-fluoro-4'-((1-(2-fluoro-2-methylpropyl)piperidin-4-yl)methoxy)biphenyl-4-carboxylate (114 mg, 0.27 mmol) was dissolved in THF (10 mL)/water (5 mL). At room temperature, LiOH.H$_2$O (57 mg, 1.36 mmol) was added thereto, following with stirring at the same temperature for 1 hour. The reaction mixture was acidified by the addition of 1N HCl. The resulting precipitate was filtered, and dried to yield the title compound as white solid (90 mg, 81%).

Step 3.

Compound 749: 2-fluoro-4'-((1-(2-fluoro-2-methylpropyl)piperidin-4-yl)methoxy) biphenyl-4-carboxylic acid (45 mg, 0.11 mmol), (R)-piperidin-3-ol hydrochloride (13 mg, 0.13 mmol), BOP (94 mg, 0.21 mmol) and Et$_3$N (30 µL, 0.21 mmol) were dissolved in DMF (1 mL). At 60° C., the reaction was performed for a day. After the completion of the reaction, the reaction mixture was added with a saturated NH$_4$Cl aqueous solution, and extracted with EtOAc. The organic layer was dried over anhydrous MgSO$_4$, and concentrated under reduced pressure. The concentrate was purified by silica gel column chromatography (10% MeOH/CH$_2$Cl$_2$) to yield the title compound as yellow solid (18 mg, 33%).

1H NMR (400 MHz, CDCl$_3$) δ 7.50-7.43 (m, 3H), 7.27-7.22 (m, 2H), 7.00-6.96 (m, 2H), 3.96 (brs, 1H), 3.85 (d, 2H, J=6.0 Hz), 3.68-3.39 (m, 3H), 3.04-3.02 (m, 2H), 2.52-2.46 (m, 2H), 2.35-2.21 (m, 2H), 2.20-1.95 (m, 2H), 1.84-1.82 (m, 4H), 1.69 (brs, 2H), 1.42 (m, 2H), 1.42 (s, 3H), 1.37 (s, 3H); MS (ESI) m/z 487 (M++H).

According to the above-described synthesis process of compound 749, the compounds of Table 8 were synthesized using 2-fluoro-4'-((1-(2-fluoro-2-methylpropyl)piperidin-4-yl)methoxy)biphenyl-4-carboxylic acid and the reactant of Table 7.

TABLE 7

| Compound No. | Reactant | Yield (%) |
|---|---|---|
| 750 | (S)-pyrrolidine-2-carboxamide | 28 |

TABLE 8

| Compound No. | Compound Name, 1H-NMR, MS (ESI) |
|---|---|
| 750 | (S)-1-(2-fluoro-4'-((1-(2-fluoro-2-methylpropyl)piperidin-4-yl)methoxy)biphenylcarbonyl)pyrrolidine-2-carboxamide MS (ESI) m/z 500 (M+ + H). |

Example 34. Compound 638: 3-fluoro-4'-((1-(2-fluoro-2-methylpropyl)piperidin-4-yl)methoxy)-N,N-dimethylbiphenyl-4-carboxamide

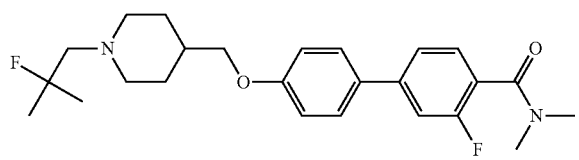 [SMILES: CN(C)C(=O)c1ccc(-c2ccc(OCC3CCN(CC(C)(C)F)CC3)cc2)cc1F]

Step 1.

Ethyl 3-fluoro-4'-((1-(2-fluoro-2-methylpropyl)piperidin-4-yl)methoxy)biphenyl-4-carboxylate: 4-((4-bromophenoxy)methyl)-1-(2-fluoro-2-methylpropyl)piperidine (the product of synthesis step 3 of compound 498; 450 mg, 1.31 mmol) and 4-(ethoxycarbonyl)-3-fluorophenylboronic acid (305 mg, 1.44 mmol) were dissolved in dioxane 6 mL. Water 2 mL was added thereto. Pd(dbpf)Cl$_2$ (43 mg, 0.07 mmol) and Cs$_2$CO$_3$ (851 mg, 2.61 mmol) were added thereto. With a microwave radiation, the reaction was performed at 120° C. for 20 minutes. The reaction mixture was filtered through Celite. The filtrate was added with a saturated NaHCO$_3$ aqueous solution, and extracted with EtOAc. The organic layer was dried over MgSO$_4$, and then concentrated under reduced pressure. The concentrate was purified by silica gel column chromatography (MeOH/CH$_2$Cl$_2$) to yield the title compound as white solid (350 mg, 62%).

Step 2.

3-fluoro-4'-((1-(2-fluoro-2-methylpropyl)piperidin-4-yl)methoxy)biphenyl-4-carboxylic acid: ethyl 3-fluoro-4'-((1-(2-fluoro-2-methylpropyl)piperidin-4-yl)methoxy)biphenyl-4-carboxylate (350 mg, 0.84 mmol) was dissolved in THF 2 mL. MeOH 1 mL and H$_2$O 0.5 mL were added thereto. LiOH (70 mg, 1.68 mmol) was added thereto, and refluxed with heating and stirring for 5 hours. After acidification with 1 N HCl, the resulting precipitate was filtered to yield the title compound as white solid (300 mg, 88%).

Step 3.

Compound 638: 3-fluoro-4'-((1-(2-fluoro-2-methylpropyl)piperidin-4-yl)methoxy) biphenyl-4-carboxylic acid (30 mg, 0.07 mmol), dimethylamine hydrochloride (9 mg, 0.11 mmol) and PyBOP (58 mg, 0.11 mmol) were dissolved in CH$_2$Cl$_2$ 1 mL. DIPEA (19 mg, 0.15 mmol) was added thereto. The reaction was performed at room temperature for 8 hours. The reaction mixture was added with water, and extracted with EtOAc. The obtained organic layer was dried over MgSO$_4$, and filtered. The filtrate was concentrated under reduced pressure. The obtained concentrate was purified by silica gel column chromatography (MeOH/CH$_2$Cl$_2$) to yield the title compound as white solid (15 mg, 47%).

1H NMR (400 MHz, CDCl$_3$) δ 7.50 (d, 2H, J=8.8 Hz), 7.39 (m, 2H), 7.27 (s, 1H), 6.97 (d, 2H, J=8.8 Hz), 3.84 (d, 2H, J=6.0 Hz), 3.15 (m, 3H), 2.99 (m, 5H), 2.52 (s, 1H), 2.47 (s, 1H), 2.22 (m, 2H), 1.82 (m, 3H), 1.44 (m, 5H), 1.27 (m, 3H); MS (ESI) m/z 431 (M++H).

Example 35. Compound 640: (S)-(3-fluoro-4'-((1-(2-fluoro-2-methylpropyl)piperidin-4-yl)methoxy)biphenyl-4-yl)(3-hydroxypyrrolidin-1-yl)methanone

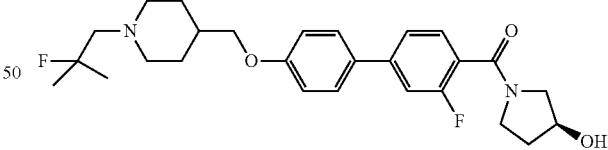

3-fluoro-4'-((1-(2-fluoro-2-methylpropyl)piperidin-4-yl)methoxy)biphenyl-4-carboxylic acid (30 mg, 0.07 mmol), (S)-3-pyrrolidinol (10 mg, 0.11 mmol) and PyBOP (58 mg, 0.11 mmol) were dissolved in CH$_2$Cl$_2$ 1 mL, following with stirring for 10 minutes. DIPEA (19 mg, 0.15 mmol) was added thereto, following with stirring at room temperature for 8 hours. The reaction mixture was added with water, and extracted with EtOAc. The obtained organic layer was washed with saturated aqueous brine solution, dried over MgSO$_4$, filtered to remove a solid, and then concentrated under reduced pressure. The obtained concentrate was purified by silica gel column chromatography (MeOH/CH$_2$Cl$_2$) to yield the title compound as white solid (18 mg, 51%).

1H NMR (400 MHz, CDCl$_3$) δ 7.46 (m, 3H), 7.35 (m, 1H), 7.24 (m, 1H), 6.96 (d, 2H, J=8.6 Hz), 4.57 (m, 0.5H), 4.44 (m, 0.5H), 3.83 (d, 2H, J=6.0 Hz), 3.78 (m, 1H), 3.75 (m, 2H), 3.53 (m, 2H), 3.13 (m, 2H), 3.01 (m, 2H), 2.50 (s, 1H), 2.44 (s, 1H), 2.20 (m, 2H), 1.98 (m, 1H), 1.40 (m, 5H), 1.25 (s, 3H); MS (ESI) m/z 473 (M++H).

According to the above-described synthesis process of compound 638 (Step 3), the compounds of Table 10 were synthesized using 3-fluoro-4'-((1-(2-fluoro-2-methylpropyl)piperidin-4-yl)methoxy)biphenyl-4-carboxylic acid and the reactant of Table 9.

TABLE 9

| Compound No. | Reactant | Yield (%) |
|---|---|---|
| 639 | dimethylamine hydrochloride | 44 |
| 641 | (R)-prolinol | 55 |
| 642 | 3-hydroxypiperidine | 38 |

TABLE 9-continued

| Compound No. | Reactant | Yield (%) |
|---|---|---|
| 643 | 2-amino-2-methyl-1-propanol | 53 |
| 644 | L-prolinamide | 45 |
| 700 | (R)-piperidin-3-ol hydrochloride | 46 |
| 701 | (S)-piperidin-3-ol hydrochloride | 30 |
| 702 | (R)-pyrrolidine-3-ol | 45 |
| 703 | (S)-pyrrolidine-2-ylmethanol | 41 |
| 792 | piperidin-4-carboxamide hydrochloride | 39 |
| 793 | 3-(trifluoromethyl)-5,6,7,8-tetrahydro-[1,2,4]triazolo[4,3-a]pyrazine | 29 |
| 872 | (R)-piperidin-2-carboxamide hydrochloride | 63 |
| 875 | (S)-piperidin-2-carboxamide hydrochloride | 65 |
| 880 | (R)-piperidin-3-carboxamide hydrochloride | 63 |
| 1097 | (2S,4S)-4-fluoropyrrolidine-2-carbonitrile hydrochloride | 49 |
| 1098 | (2S,4R)-4-hydroxypyrrolidine-2-carbonitrile hydrochloride | 49 |

TABLE 10

| Compound No. | Compound Name, $^1$H-NMR, MS (ESI) |
|---|---|
| 639 | N,N-diethyl-3-fluoro-4'-((1-(2-fluoro-2-methylpropyl)piperidin-4-yl)methoxy)biphenyl-4-carboxamide<br>1H NMR (400 MHz, CDCl$_3$) δ 7.50 (d, 2 H, J = 8.8 Hz), 7.37 (m, 2 H), 7.27 (m, 1 H), 6.97 (d, 2 H, J = 8.8 Hz), 3.84 (d, 2 H, J = 6.0 Hz), 3.61 (m, 2 H), 3.27 (m, 2 H), 3.01 (m, 2 H), 2.51 (s, 1 H), 2.45 (s, 1 H), 2.20 (m, 2 H), 1.45 (m, 5 H), 1.35 (s, 3 H), 1.28 (t, 4 H, J = 7.1 Hz), 1.12 (t, 3 H, J = 7.1 Hz); MS (ESI) m/z 459 (M+ + H). |
| 641 | (R)-(3-fluoro-4'-((1-(2-fluoro-2-methylpropyl)piperidin-4-yl)methoxy)biphenyl-4-yl)(2-(hydroxymethyl)pyrrolidine-1-yl)methanone<br>1H NMR (400 MHz, CDCl$_3$) δ 7.49 (m, 3 H), 7.39 (m, 1 H), 7.29 (d, 1 H, J = 9.8 Hz), 6.98 (d, 2 H, J = 8.8 Hz), 4.40 (m, 1 H), 3.75 (m, 4 H), 3.47 (m, 2 H), 3.01 (d, 2 H, J = 11.5 Hz), 2.49 (s, 1 H), 2.43 (s, 1 H), 2.18 (m, 3 H), 1.76 (m, 6 H), 1.46 (m, 5 H), 1.40 (s, 3 H); MS (ESI) m/z 487 (M+ + H). |
| 642 | (3-fluoro-4'-((1-(2-fluoro-2-methylpropyl)piperidin-4-yl)methoxy)biphenyl-4-yl)(3-hydroxypiperidin-1-yl)methanone<br>1H NMR (400 MHz, CDCl$_3$) δ 7.50 (dd, 2 H, J = 8.8, 2.3 Hz), 7.39 (m, 2 H), 7.27 (m, 1 H), 6.98 (d, 2 H, J = 6.8 Hz), 4.41 (m, 1 H), 3.93 (m, 1 H), 3.84 (d, 2 H, J = 6.0 Hz), 3.38 (m, 2 H), 3.14 (m, 2 H), 3.01 (d, 2 H, J = 11.5 Hz), 2.49 (s, 1 H), 2.44 (s, 1 H), 2.19 (m, 2 H), 1.82 (m, 5 H), 1.61 (m, 1 H), 1.43 (m, 5 H), 1.35 (s, 3 H); MS (ESI) m/z 487 (M+ + H). |
| 643 | 3-fluoro-4'-((1-(2-fluoro-2-methylpropyl)piperidin-4-yl)methoxy)-N-(1-hydroxy-2-methylpropan-2-yl)biphenyl-4-carboxamide<br>1H NMR (400 MHz, CDCl$_3$) δ 8.09 (t, 1 H, J = 8.4 Hz), 7.54 (dd, 2 H, J = 6.9, 1.9 Hz), 7.46 (dd, 1 H, J = 8.2, 1.7 Hz), 7.30 (dd, 1 H, J = 13.9, 1.6 Hz), 6.99 (dd, 2 H, J = 6.9, 1.9 Hz), 6.88 (d, 1 H, J = 15.2 Hz), 4.73 (s, 1 H), 3.85 (d, 2 H, J = 6.0 Hz), 3.72 (s, 2 H), 3.00 (d, 2 H, J = 11.5 Hz), 2.48 (s, 1 H), 2.42 (s, 1 H), 2.18 (td, 2 H, J = 11.7, 1.7 Hz), 1.80 (m, 3 H), 1.43 (s, 6 H), 1.40 (s, 3 H), 1.35 (s, 3 H); MS (ESI) m/z 475 (M + H). |
| 644 | (S)-1-(3-fluoro-4'-((1-(2-fluoro-2-methylpropyl)piperidin-4-yl)methoxy)biphenylcarbonyl)pyrrolidine-2-carboxamide<br>1H NMR (400 MHz, CDCl$_3$) δ 7.50 (m, 2 H), 7.47 (m, 1 H), 7.40 (m, 1 H), 7.29 (m, 1 H), 6.99 (d, 2 H, J = 8.7 Hz), 5.46 (s, 1 H), 4.83 (m, 1 H), 3.85 (d, 2 H, J = 5.9 Hz), 3.53 (m, 1 H), 3.43 (m, 1 H), 2.99 (m, 2 H), 2.48 (m, 3 H), 2.10 (m, 5 H), 1.95 (m, 4 H), 1.26 (m, 5 H), 1.20 (s, 3 H); MS (ESI) m/z 450 (M+ + H). |
| 700 | (R)-(3-fluoro-4'-((1-(2-fluoro-2-methylpropyl)piperidin-4-yl)methoxy)biphenyl-4-yl)(3-hydroxypiperidin-1-yl)methanone MS (ESI) m/z 487 (M+ + H). |
| 701 | (S)-(3-fluoro-4'-((1-(2-fluoro-2-methylpropyl)piperidin-4-yl)methoxy)biphenyl-4-yl)(3-hydroxypiperidin-1-yl)methanone<br>MS (ESI) m/z 487 (M+ + H). |
| 702 | (R)-(3-fluoro-4'-((1-(2-fluoro-2-methylpropyl)piperidin-4-yl)methoxy)biphenyl-4-yl)(3-hydroxypyrrolidine-1-yl)methanone<br>MS (ESI) m/z 473 (M+ + H). |
| 703 | (S)-(3-fluoro-4'-((1-(2-fluoro-2-methylpropyl)piperidin-4-yl)methoxy)biphenyl-4-yl)(2-(hydroxymethyl)pyrrolidine-1-yl)methanone<br>1H NMR (400 MHz, CDCl$_3$) δ 7.52-7.40 (m, 3 H), 7.39-7.30 (m, 1 H), 7.30-7.27 (m, 1 H), 6.98-6.95 (m, 2 H), 4.41-4.12 (m, 1 H), 3.88-3.82 (m, 2 H), 3.80-3.75 (m, 1 H), 3.49-3.45 (m, 2 H), 3.30-3.21 (m, 2 H), 2.78-2.73 (m, 2 H), 2.50-2.38 (m, 1 H), 2.23-2.19 (m, 1 H), 1.92-1.81 (m, 3 H), 1.79-1.70 (m, 4 H), 1.51 (s, 3 H), 1.43 (s, 3 H), 1.28-1.22 (m, 3 H); MS (ESI) m/z 487 (M+ + H). |

TABLE 10-continued

| Compound No. | Compound Name, $^1$H-NMR, MS (ESI) |
|---|---|
| 792 | 1-(3-fluoro-4'-((1-(2-fluoro-2-methylpropyl)piperidin-4-yl)methoxy)biphenylcarbonyl)piperidin-4-carboxamide<br>1H NMR (400 MHz, CDCl$_3$) δ 7.50 (m, 2 H), 7.36 (m, 2 H), 7.24 (m, 1 H), 6.91 (m, 2 H), 5.50 (m, 2 H), 4.74 (m, 1 H), 3.84 (d, 2 H, J = 6.0 Hz), 3.71 (m, 2 H), 3.01 (m, 4 H), 2.41 (m, 3 H), 2.22 (m, 2 H), 2.02 (m, 1 H), 1.80 (m, 6 H), 1.55 (m, 2 H), 1.40 (s, 3 H), 1.35 (s, 3 H); MS (ESI) m/z 514 (M + H). |
| 793 | (3-fluoro-4'-((1-(2-fluoro-2-methylpropyl)piperidin-4-yl)methoxy)biphenyl-4-yl)(3-(trifluoromethyl)-5,6-dihydro-[1,2,4]triazolo[4,3-a]pyrazine-7(8H)-yl)methanone<br>1H NMR (400 MHz, CDCl$_3$) δ 7.69 (m, 4 H), 7.33 (d, 1 H, J = 11.3 Hz), 7.00 (d, 2 H, J = 8.5 Hz), 5.22 (s, 1 H), 4.94 (s, 1 H), 4.28 (m, 2 H), 3.87 (m, 2 H), 3.04 (m, 2 H), 2.87 (d, 1 H, J = 10.2 Hz), 2.50 (s, 1 H), 2.44 (s, 1 H), 2.19 (m, 2 H), 1.82 (m, 4 H), 1.40 (m, 5 H), 1.19 (s, 3 H). |
| 872 | (R)-1-(3-fluoro-4'-((1-(2-fluoro-2-methylpropyl)piperidin-4-yl)methoxy)biphenylcarbonyl)piperidin-2-carboxamide<br>1H NMR (400 MHz, CDCl$_3$) δ 7.38-7.55 (m, 4 H), 7.32-7.28 (m, 1 H), 6.99 (d, 2 H, J = 8.8 Hz), 3.85 (d, 2 H, J = 6.0 Hz), 3.62 (d, 1 H, J = 12.0 Hz), 3.22 (t, 1 H, J = 12.5 Hz), 3.02 (d, 2 H, J = 9.8 Hz), 2.55-2.35 (m, 3 H), 2.20 (t, 2 H, J = 11.2 Hz), 1.88-1.70 (m, 6 H), 1.64 (d, 3 H, J = 12.5 Hz), 1.53-1.39 (m, 2 H), 1.41 (s, 3 H), 1.36 (s, 3 H); MS (ESI) m/z 514 (M+ + H). |
| 875 | (S)-1-(3-fluoro-4'-((1-(2-fluoro-2-methylpropyl)piperidin-4-yl)methoxy)biphenylcarbonyl)piperidin-2-carboxamide<br>1H NMR (400 MHz, CDCl$_3$) δ 7.55-7.37 (m, 4 H), 7.32-7.28 (m, 1 H), 6.99 (d, 1 H, J = 9.0 Hz), 3.85 (d, 2 H, J = 6.0 Hz), 3.62 (d, 1 H, J = 12.3 Hz), 3.22 (t, 1 H, J = 13.2 Hz), 3.02 (d, 2 H, J = 11.0 Hz), 2.50 (s, 1 H), 2.45 (s, 1 H), 2.42-2.35 (m, 1 H), 2.20 (t, 2 H, J = 11.3 Hz), 1.88-1.71 (m, 6 H), 1.70-1.54 (m, 3 H), 1.53-1.43 (m, 3 H), 1.41 (s, 3 H), 1.36 (s, 3 H); MS (ESI) m/z 514 (M+ + H). |
| 880 | (R)-1-(3-fluoro-4'-((1-(2-fluoro-2-methylpropyl)piperidin-4-yl)methoxy)biphenylcarbonyl)piperidin-3-carboxamide<br>1H NMR (400 MHz, CDCl$_3$) δ 7.51 (d, 2 H, J = 8.5 Hz), 7.40 (d, 2 H, J = 3.5 Hz), 7.31-7.24 (m, 1 H), 6.98 (d, 2 H, J = 8.8 Hz), 3.86 (d, 2 H, J = 5.8 Hz), 3.82-3.74 (m, 1 H), 3.49-3.43 (m, 1 H), 3.37-3.31 (m, 1 H), 3.03 (s, 2 H), 2.62-2.56 (m, 1 H), 2.54-2.43 (m, 2 H), 2.28-2.04 (m, 3 H), 1.97-1.77 (m, 5 H), 1.74-1.60 (m, 4 H), 1.42 (s, 3 H), 1.37 (s, 3 H); MS (ESI) m/z 514 (M+ + H). |
| 1097 | (2S,4S)-4-fluoro-1-(3-fluoro-4'-((1-(2-fluoro-2-methylpropyl)piperidin-4-yl)methoxy)biphenylcarbonyl)pyrrolidine-2-carbonitrile<br>1H NMR (400 MHz, CDCl$_3$) δ 7.59-7.45 (m, 4 H), 7.33-7.28 (m, 1 H), 7.00 (m, 2 H), 5.45-5.32 (m, 1 H), 5.13 (m, 1 H), 3.88-3.77 (m, 4 H), 3.16-3.01 (m, 3 H), 2.82-2.42 (m, 6 H), 1.98-1.80 (m, 4 H), 1.47-1.29 (m, 6 H); MS (ESI) m/z 500.2 (M+ + H). |
| 1098 | (2S,4R)-1-(3-fluoro-4'-((1-(2-fluoro-2-methylpropyl)piperidin-4-yl)methoxy)biphenylcarbonyl)-4-hydroxypyrrolidine-2-carbonitrile<br>1H NMR (400 MHz, CDCl$_3$) δ 7.57-7.49 (m, 3 H), 7.41-7.38 (m, 1 H), 7.30-7.27 (m, 1 H), 6.98 (m, 2 H), 5.04 (t, 1 H, J = 8.2 Hz), 4.58 (m, 1 H), 3.86 (m, 2 H), 3.80-3.76 (m, 1 H), 3.49-3.46 (m, 1 H), 3.15 (s, 2 H), 2.58-2.47 (m, 4 H), 2.38 (s, 2 H), 1.87-1.85 (m, 3 H), 1.49-1.27 (m, 9 H); MS (ESI) m/z 498.2 (M+ + H). |

Example 36. Compound 1099: (2S,4S)-4-fluoro-1-(3-fluoro-4'-((1-(2-fluoro-2-methylpropyl)piperidin-4-yl)methoxy)biphenylcarbonyl)pyrrolidine-2-carboxamide

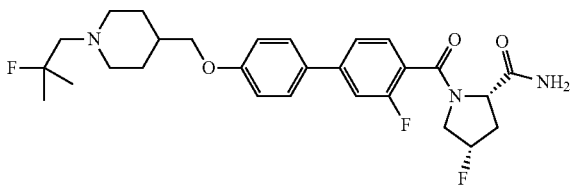 [SMILES: CC(C)(F)CN1CCC(COc2ccc(-c3ccc(C(=O)N4C[C@@H](F)C[C@H]4C(N)=O)c(F)c3)cc2)CC1]

Step 1.

(2S,4S)-methyl 4-fluoro-1-(3-fluoro-4'-((1-(2-fluoro-2-methylpropyl)piperidin-4-yl)methoxy)biphenylcarbonyl)pyrrolidine-2-carboxylate: 3-fluoro-4'-((1-(2-fluoro-2-methylpropyl)piperidin-4-yl)methoxy)biphenyl-4-carboxylic acid (150 mg, 0.37 mmol), (2S,4S)-methyl 4-fluoropyrrolidine-2-carboxylate (55 mg, 0.37 mmol), EDC (107 mg, 0.56 mmol), HOBt (75 mg, 0.56 mmol) and DIPEA (0.13 mL, 0.74 mmol) were dissolved in DMF (4 mL) at room temperature. The solution was stirred at 80° C. for 12 hours, the reaction mixture was concentrated under reduced pressure. The concentrate was purified by column chromatography (SiO$_2$, 4 g cartridge; ethyl acetate:hexane=10% to 50%), and concentrated to yield the title compound as colorless oil (0.12 g, 61%).

Step 2.

(2S,4S)-4-fluoro-1-(3-fluoro-4'-((1-(2-fluoro-2-methylpropyl)piperidin-4-yl)methoxy) biphenylcarbonyl)pyrrolidine-2-carboxylic acid: (2S,4S)-methyl 4-fluoro-1-(3-fluoro-4'-((1-(2-fluoro-2-methylpropyl)piperidin-4-yl)methoxy)biphenylcarbonyl)pyrrolidine-2-carboxylate (120 mg, 0.23 mmol) and LiOH.H$_2$O (19 mg, 0.45 mmol) were dissolved in THF (10 mL)/H$_2$O (5 mL) at room temperature. The solution was stirred at 60° C. for 4 hours. The reaction mixture was concentrated under reduced pressure. The obtained material was used without further purifying process.

Step 3.

Compound 1099: (2S,4S)-4-fluoro-1-(3-fluoro-4'-((1-(2-fluoro-2-methylpropyl)piperidin-4-yl)methoxy)biphenylcarbonyl)pyrrolidine-2-carboxylic acid (200 mg, 0.39 mmol), ammonium chloride (31 mg, 0.58 mmol), EDC (111 mg, 0.58 mmol), HOBt (78 mg, 0.58 mmol) and DIPEA (0.14 mL, 0.77 mmol) were dissolved in DMF (6 mL) at room temperature. The solution was stirred at 80° C. for 12 hours, the reaction mixture was concentrated under reduced pressure. The concentrate was purified by column chromatography (SiO$_2$, 4 g cartridge; ethyl acetatehexane=10% to 90%), and concentrated to yield the title compound as light-red solid (30 mg, 15%).

1H NMR (400 MHz, CDCl$_3$) δ 7.53-7.28 (m, 5H), 7.00-6.96 (m, 2H), 6.68 (s, 0.78H), 6.35 (s, 0.16H), 5.70 (m, 1H), 5.33-5.20 (m, 1H), 5.00 (m, 1H), 3.92-3.83 (m, 3H), 3.74-3.62 (m, 1H), 3.18-2.89 (m, 3H), 2.58-2.18 (m, 5H), 1.85 (m, 3H), 1.43-1.27 (m, 8H); MS (ESI) m/z 518.2 (M++H).

Example 37. Compound 1100: (2S,4R)-1-(3-fluoro-4'-((1-(2-fluoro-2-methylpropyl)piperidin-4-yl)methoxy)biphenylcarbonyl)-4-hydroxypyrrolidine-2-carboxamide

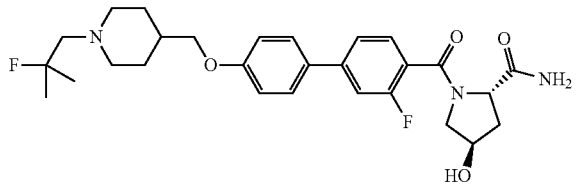

Step 1.
(2S,4R)-methyl 1-(3-fluoro-4'-((1-(2-fluoro-2-methylpropyl)piperidin-4-yl)methoxy)biphenylcarbonyl)-4-hydroxypyrrolidine-2-carboxylate: 3-fluoro-4'-((1-(2-fluoro-2-methylpropyl)piperidin-4-yl)methoxy)biphenyl-4-carboxylic acid (100 mg, 0.25 mmol), (2S,4R)-methyl 4-hydroxypyrrolidine-2-carboxylate hydrochloride (45 mg, 0.25 mmol), EDC (71 mg, 0.37 mmol), HOBt (50 mg, 0.37 mmol) and DIPEA (0.09 mL, 0.50 mmol) were dissolved in DMF (4 mL) at room temperature. The solution was stirred at 80° C. for 12 hours, the reaction mixture was concentrated under reduced pressure. The concentrate was purified by column chromatography (SiO$_2$, 4 g cartridge; ethyl acetate-hexane=10% to 80%), and concentrated to yield the title compound as colorless oil (70 mg, 53%).

Step 2.
(2S,4R)-1-(3-fluoro-4'-((1-(2-fluoro-2-methylpropyl)piperidin-4-yl)methoxy)biphenylcarbonyl)-4-hydroxypyrrolidine-2-carboxylic acid: (2S,4R)-methyl 1-(3-fluoro-4'-((1-(2-fluoro-2-methylpropyl)piperidin-4-yl)methoxy)biphenylcarbonyl)-4-hydroxypyrrolidine-2-carboxylate (70 mg, 0.13 mmol) and LiOH.H$_2$O (11 mg, 0.26 mmol) were dissolved in THF (6 mL)/H$_2$O (3 mL) at room temperature. The solution was stirred at 60° C. for 4 hours. The reaction mixture was concentrated under reduced pressure. The obtained material was used without further purifying process.

Step 3.
Compound 1100: (2S,4R)-1-(3-fluoro-4'-((1-(2-fluoro-2-methylpropyl)piperidin-4-yl)methoxy)biphenylcarbonyl)-4-hydroxypyrrolidine-2-carboxylic acid (100 mg, 0.19 mmol), ammonium chloride (16 mg, 0.29 mmol), EDC (56 mg, 0.29 mmol), HOBt (39 mg, 0.29 mmol) and DIPEA (0.07 mL, 0.39 mmol) were dissolved in DMF (5 mL) at room temperature. The solution was stirred at 80° C. for 12 hours, the reaction mixture was concentrated under reduced pressure. The concentrate was purified by column chromatography (SiO$_2$, 4 g cartridge; methanol/dichloromethane=0% to 10%), and concentrated to yield the title compound as light-red solid (15 mg, 15%).

1H NMR (400 MHz, CDCl$_3$+MeOD) δ 7.57-7.44 (m, 3H), 7.38-7.31 (m, 1H), 7.28-7.27 (m, 1H), 6.93 (m, 2H), 4.79 (t, 1H, J=8.2 Hz), 4.41 (m, 1H), 3.86 (m, 2H), 3.72-3.68 (m, 2H), 3.41-3.37 (m, 2H), 2.34-2.25 (m, 3H), 2.01-1.90 (m, 4H), 1.47-1.38 (m, 6H), 1.37-1.21 (m, 4H); MS (ESI) m/z 516.2 (M++H).

Example 38. Compound 758: (R)-(6-(4-((1-(2-fluoro-2-methylpropyl)piperidin-4-yl)methoxy)phenyl)pyridine-3-yl)(3-hydroxypiperidin-1-yl)methanone

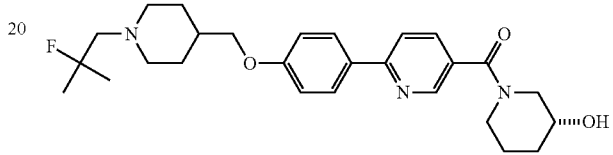

Step 1.
Methyl 6-(4-((1-(2-fluoro-2-methylpropyl)piperidin-4-yl)methoxy)phenyl)nicotinate: Methyl 6-bromonicotinate (0.07 g, 46%) was dissolved in 1,4-dioxane 2 mL and H$_2$O 1 mL. 4-((1-(2-fluoro-2-methylpropyl)piperidin-4-yl)methoxy)phenylboronic acid (the product of synthesis step 1 of compound 617; 0.1 g, 0.32 mmol), Pd(dbpf)Cl$_2$ (0.01 g, 0.02 mmol) and Cs$_2$CO$_3$ (0.21 g, 0.65 mmol) were added thereto. The mixture was stirred in a microwave at 110° C. for 30 minutes. After the completion of the reaction, the reaction mixture was filtered through Celite. The filtrate was added with water, and extracted with CH$_2$Cl$_2$. The obtained organic layer was washed with saturated aqueous brine solution, dried over MgSO$_4$, and concentrated under reduced pressure. The concentrate was purified by column chromatography (12 g ISCO silica gel cartridge, 0-20% EtOAc/Hexane) to yield the title compound as yellow solid (0.06 g, 46%).

Step 2.
6-(4-((1-(2-fluoro-2-methylpropyl)piperidin-4-yl)methoxy)phenyl)nicotinic acid: Methyl 6-(4-((1-(2-fluoro-2-methylpropyl)piperidin-4-yl)methoxy)phenyl)nicotinate (0.06 g, 0.15 mmol) were dissolved in THF 10 mL, H$_2$O 3 mL and MeOH 3 mL. LiOH.H$_2$O (0.03 g, 0.75 mmol) was added thereto, following with increasing the temperature slowly. The mixture was refluxed with stirring for 3 hours. After the completion of the reaction, HCl was added thereto to acidify to pH 5. The resulting precipitate was filtered to yield the title compound as light-yellow solid (0.03 g, 55%).

Step 3.
Compound 758: 6-(4-((1-(2-fluoro-2-methylpropyl)piperidin-4-yl)methoxy)phenyl)nicotinic acid (0.03 g, 0.08 mmol) and (R)-piperidin-3-ol (0.02 g, 0.15 mmol) were dissolved in DMF 2 mL. DIPEA (0.05 g; 0.38 mmol), EDCI (0.03 g, 0.15 mmol) and HOBt (0.02 g, 0.15 mmol) were added thereto slowly, following with stirring at room temperature for 3 hours. The reaction mixture was added with water, and extracted with EtOAc. The obtained organic layer was washed with saturated NH$_4$Cl aqueous solution, dried over MgSO$_4$, and concentrated under reduced pressure. The concentrate was purified by column chromatography (12 g ISCO silica gel cartridge, 0-20% MeOH/CH$_2$Cl$_2$) to yield the title compound as brown solid (0.02 g, 61%).

1H NMR (400 MHz, CDCl$_3$) δ 8.70 (s, 1H), 7.96 (d, 2H, J=8.4 Hz), 7.82 (d, 1H, J=6.8 Hz), 7.71 (d, 1H, J=8.4 Hz), 7.00 (d, 2H, J=8.8 Hz), 3.99-3.57 (m, 7H), 3.00 (d, 2H, J=10.4 Hz), 2.48-2.43 (m, 2H), 2.19 (t, 2H, J=11.2 Hz), 2.05-1.67 (m, 7H), 1.55-1.35 (m, 8H).

Example 39. Compound 759: (R)-(5-(4-((1-(2-fluoro-2-methylpropyl)piperidin-4-yl)methoxy)phenyl)pyridine-2-yl)(3-hydroxypiperidin-1-yl)methanone

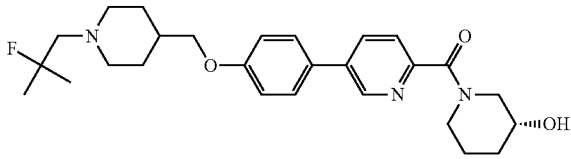 [SMILES: CC(C)(F)CN1CCC(COc2ccc(-c3ccc(C(=O)N4CCC[C@@H](O)C4)nc3)cc2)CC1]

Step 1.

Methyl 5-(4-((1-(2-fluoro-2-methylpropyl)piperidin-4-yl)methoxy)phenyl)picolinate: Methyl 5-bromopicolinate (0.10 g, 0.46 mmol) was dissolved in 1,4-dioxane 2 mL and H$_2$O 1 mL. 4-((1-(2-fluoro-2-methylpropyl)piperidin-4-yl)methoxy)phenylboronic acid (Synthesis step 1 of compound 617, 0.13 g, 0.42 mmol), Pd(dbpf)Cl$_2$ (0.01 g, 0.02 mmol) and Cs$_2$CO$_3$ (0.27 g, 0.84 mmol) were added thereto. The mixture was stirred in a microwave at 110° C. for 30 minutes. After the completion of the reaction, the reaction mixture was filtered through Celite. The filtrate was added with water, and extracted with CH$_2$Cl$_2$. The obtained organic layer was washed with saturated aqueous brine solution, dried over MgSO$_4$, and concentrated under reduced pressure. The concentrate was purified by column chromatography (12 g ISCO silica gel cartridge, 0-20% EtOAcHex) to yield the title compound as light-yellow solid (0.03 g, 18%).

Step 2.

5-(4-((1-(2-fluoro-2-methylpropyl)piperidin-4-yl)methoxy)phenyl) picolinic acid: methyl 5-(4-((1-(2-fluoro-2-methylpropyl)piperidin-4-yl)methoxy)phenyl) picolinate (0.03 g, 0.08 mmol) was dissolved in THF 10 mL, H$_2$O 3 mL, MeOH 3 mL. LiOH.H$_2$O (0.02 g, 0.38 mmol) was added thereto, following with increasing the temperature slowly and then refluxing with stirring for 3 hours. After the completion of the reaction, the reaction mixture was acidified to pH 5 by the addition of HCl. The resulting precipitate was filtered to yield the title compound as white solid (0.03 g, 97%).

Step 3.

Compound 759: 5-(4-((1-(2-fluoro-2-methylpropyl)piperidin-4-yl)methoxy)phenyl) picolinic acid (0.03 g, 0.07 mmol) and (R)-piperidin-3-ol (0.01 g, 0.08 mmol) were dissolved in DMF. DIPEA (0.05 g, 0.36 mmol), EDCI (0.03 g, 0.15 mmol) and HOBt (0.02 g, 0.15 mmol) were added thereto slowly, following with stirring at room temperature for 3 hours. The reaction mixture was added with water, and extracted with EtOAc. The obtained organic layer was washed with saturated NH$_4$Cl aqueous solution, dried over MgSO$_4$, and concentrated under reduced pressure. The concentrate was purified by column chromatography (12 g ISCO silica gel cartridge, 0-20% MeOH/CH$_2$Cl$_2$) to yield the title compound as light-yellow solid (0.01 g, 38%).

1H NMR (400 MHz, CDCl$_3$) δ 8.72 (s, 1H), 8.00 (d, 1H, J=6.1 Hz), 7.84 (d, 1H, J=8.4 Hz), 7.53 (d, 2H, J=7.7 Hz), 7.02 (d, 2H, J=7.6 Hz), 5.84 (s, 1H), 4.61 (d, 1H, J=12.8 Hz), 4.10-4.03 (m, 2H), 3.86 (d, 2H, J=5.4 Hz), 3.27 (d, 1H, J=14.0 Hz), 3.01-2.91 (m, 3H), 2.48-2.43 (m, 2H), 2.21-1.98 (m, 4H), 1.82-1.48 (m, 5H), 1.46-1.26 (m, 8H); MS (ESI) mz 470 (M++H).

Example 40. Compound 1038: (S)-1-(5-(4-((1-(2-fluoro-2-methylpropyl)piperidin-4-yl)methoxy)phenyl)pyrazine-2-carbonyl)pyrrolidine-2-carboxamide

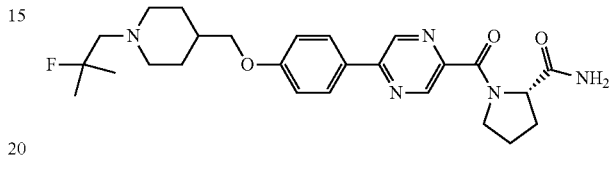

Step 1.

Methyl 5-(4-hydroxymethyl)pyrazine-2-carboxylate: methyl 5-bromopyrazine-2-carboxylate (500 mg, 2.30 mmol), 4-hydroxyphenylboronic acid (381 mg, 2.77 mmol), methyl 5-bromopyrazine-2-carboxylate, Pd(dppf)Cl$_2$ (188 mg, 0.23 mmol) and Cs$_2$CO$_3$ (1.50 g, 4.61 mmol) were added to water (2 mL)/DME (6 mL). With a microwave radiation, the mixture was heated at 110° C. for 15 minutes, and then cooled to room temperature. The reaction mixture was added with water, and extracted with EtOAc. The obtained organic layer was washed with saturated aqueous brine solution, dried over anhydrous MgSO$_4$, and concentrated under reduced pressure. The obtained concentrate was purified by silica gel column chromatography (30% EtOAc/hexane) to yield the title compound as brown solid (210 mg, 40%).

Step 2.

Methyl 5-(4-((1-(t-butoxycarbonyl)piperidin-4-yl)methoxy)phenyl)pyrazine-2-carboxylate: methyl 5-(4-hydroxymethyl)pyrazine-2-carboxylate (150 mg, 0.65 mmol) was dissolved in DMF (10 mL). At room temperature, K$_2$CO$_3$ (318 mg, 0.98 mmol) was added thereto. After 5 minutes, t-butyl 4-(hydroxymethyl)piperidin-1-carboxylate (229 mg, 0.78 mmol) was added thereto, following with stirring at 80° C. for 5 hours. The reaction mixture was added with water, and extracted with EtOAc. The obtained organic layer was washed with saturated aqueous brine solution, dried over anhydrous MgSO$_4$, and concentrated under reduced pressure. The obtained material was used without further purifying process. (170 mg, 61%).

Step 3.

Methyl 5-(4-(piperidin-4-ylmethoxy)phenyl)pyrazine-2-carboxylate hydrochloride: Methyl 5-(4-((1-(t-butoxycarbonyl)piperidin-4-yl)methoxy)phenyl)pyrazine-2-carboxylate (170 mg, 0.39 mmol) was dissolved in CH$_2$Cl$_2$ (10 mL). At room temperature, 4 M HCl in 1,4-dioxane (1.99 mL, 7.95 mmol) was added thereto, following with stirring at the same temperature for 1 hour. The resulting precipitate was filtered, and dried to yield the title compound as white solid (142 mg, 98%).

Step 4.

Methyl 5-(4-((1-(2-hydroxy-2-methylpropyl)piperidin-4-yl)methoxy)phenyl)pyrazine-2-carboxylate: Methyl 5-(4-(piperidin-4-ylmethoxy)phenyl)pyrazine-2-carboxylate hydrochloride (142 mg, 0.39 mmol), 2,2-dimethyloxirane (352 μL, 0.28 mmol) and K$_2$CO$_3$ (27 mg, 0.19 mmol) were dissolved in ethanol (10 mL), With a microwave radiation, the mixture was heated at 110° C. for 15 minutes, and then cooled to room temperature. The reaction mixture was added with water, and extracted with EtOAc. The organic layer was washed with saturated aqueous brine solution, dried over anhydrous $MgSO_4$, and concentrated under reduced pressure. The obtained material was used without further purifying process (117 mg, 100%).

Step 5.

Methyl 5-(4-((1-(2-fluoro-2-methylpropyl)piperidin-4-yl)methoxy)phenyl)pyrazine-2-carboxylate: methyl 5-(4-((1-(2-hydroxy-2-methylpropyl)piperidin-4-yl)methoxy)phenyl)pyrazine-2-carboxylate (117 mg, 0.29 mmol) was dissolved in $CH_2Cl_2$ (15 mL). At room temperature, DAST (39 μL, 0.29 mmol) was added thereto, following with stirring at the same temperature for 1 hour. The reaction mixture was added with water, and extracted with EtOAc. The obtained organic layer was washed with saturated aqueous brine solution, dried over anhydrous $MgSO_4$, and concentrated under reduced pressure. The obtained material was used without further purifying process (100 mg, 85%).

Step 6.

5-(4-((1-(2-fluoro-2-methylpropyl)piperidin-4-yl)methoxy)phenyl)pyrazine-2-carboxylic acid: methyl 5-(4-((1-(2-fluoro-2-methylpropyl)piperidin-4-yl)methoxy)phenyl)pyrazine-2-carboxylate (100 mg, 0.24 mmol) was dissolved in THF (10 mL)/water (5 mL). At room temperature, $LiOH.H_2O$ (52 mg, 1.24 mmol) was added thereto, following with stirring at the same temperature for 1 hour. The reaction mixture was concentrated under reduced pressure. The obtained solid was filtered, and dried to yield the title compound as white solid (75 mg, 78%).

Step 7.

Compound 1038: 5-(4-((1-(2-fluoro-2-methylpropyl)piperidin-4-yl)methoxy)phenyl)pyrazine-2-carboxylic acid (35 mg, 0.09 mmol), (S)-pyrrolidine-2-carboxamide (21 mg, 0.18 mmol), EDC (35 mg, 0.18 mmol), HOBt (24 mg, 0.18 mmol) and DIPEA (32 μL, 0.18 mmol) were dissolved in $CH_2Cl_2$ (1 mL), following with stirring at room temperature for a day. The reaction mixture was added with water, and extracted with EtOAc. The obtained organic layer was washed with saturated aqueous brine solution, dried over anhydrous $MgSO_4$, and concentrated under reduced pressure. The concentrate was purified by silica gel column chromatography (10% $MeOH/CH_2Cl_2$) to yield the title compound as white solid (19 mg, 44%).

1H NMR (400 MHz, $CDCl_3$) δ 9.25-9.15 (m, 1H), 8.93-8.87 (m, 1H), 8.05-7.99 (m, 2H), 7.05-6.99 (m, 2H), 5.48 (brs, 1H), 5.04-4.85 (m, 1H), 4.12-4.06 (m, 1H), 3.95-3.84 (m, 3H), 3.04 (brs, 2H), 2.50-2.41 (m, 3H), 2.39-2.20 (m, 3H), 2.18-1.97 (m, 3H), 1.83 (brs, 3H), 1.61-1.22 (m, 8H); MS (ESI) m/z 484 (M++H).

Example 41. Compound 725: (S)-(3'-fluoro-4'-((1-(2-fluoro-2-methylpropyl)piperidin-4-yl)methoxy)biphenyl-4-yl)(3-hydroxypiperidin-1-yl)methanone

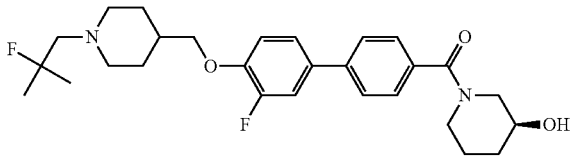 [SMILES: CC(C)(F)CN1CCC(COc2ccc(-c3ccc(C(=O)N4CCC[C@H](O)C4)cc3)cc2F)CC1]

Step 1.

t-butyl 4-((4-bromo-2-fluorophenoxy)methyl)piperidin-1-carboxylate: t-butyl 4-((methylsulfonyloxy)methyl)piperidin-1-carboxylate (the product of synthesis step 2 of compound 431; 4.50 g, 15.34 mmol) was dissolved in DMF. $K_2CO_3$ (4.24 g, 30.67 mmol) and 2-fluoro-4-bromo phenol (1.85 mL, 16.87 mmol) were added thereto slowly, following with increasing the temperature and stirring at 60° C. for 3 hours. After the completion of the reaction, the reaction mixture was extracted with EtOAc. The obtained organic layer was washed with saturated aqueous brine solution three times, dried over $MgSO_4$, and filtered. The filtrate was concentrated under reduced pressure. The concentrate was purified by column chromatography (4 g ISCO silica gel cartridge, 0-20% EtOAc/Hex) to yield the title compound as white solid (5.10 g, 86%).

Step 2.

4-((4-bromo-2-fluorophenoxy)methyl)piperidine hydrochloride: t-butyl 4-((4-bromo-2-fluorophenoxy)methyl)piperidin-1-carboxylate (5.60 g, 14.42 mmol) was dissolved in MeOH. And 1.25 M HCl in MeOH (57.69 mL, 72.12 mmol) was added thereto. After the solvent was distilled out completely, the residue was washed with ether to yield the title compound as white solid (4.1 g, 99%).

Step 3.

1-(4-((4-bromo-2-fluorophenoxy)methyl)piperidin-1-yl)-2-methylpropan-2-ol: 4-((4-bromo-2-fluorophenoxy)methyl)piperidine hydrochloride (2.30 g, 7.98 mmol) was dissolved in EtOH 50 mL and $H_2O$ 50 mL. And 1,2-epoxy-2-methylpropane (5.76 g, 79.82 mmol) and $K_2CO_3$ (5.52 g, 39.91 mmol) were added slowly thereto. The mixture was stirred in a microwave at 120° C. for 20 minutes. After the completion of the reaction, the reaction mixture was concentrated under reduced pressure. Excess amount of $H_2O$ was added thereto, and then a little of MeOH was added thereto. The resulting precipitate was filtered to yield the title compound as white solid (2.4 g, 86%).

Step 4.

4-((4-bromo-2-fluorophenoxy)methyl)-1-(2-fluoro-2-methylpropyl)piperidine: 1-(4-((4-bromo-2-fluorophenoxy)methyl)piperidin-1-yl)-2-methylpropan-2-ol (4.88 g, 13.55 mmol) was dissolved in $CH_2Cl_2$. At 0° C., DAST (1.97 mL, 14.90 mmol) was added slowly thereto, following with stirring with at 0° C. for 2 hours. The reaction mixture was neutralized with saturated $NaHCO_3$ aqueous solution to pH 7, and then washed with saturated aqueous brine solution three times. The organic layer was dried over $Na_2SO_4$, and filtered. The filtrate was concentrated under reduced pressure. The concentrate was purified by column chromatography (40 g ISCO silica gel cartridge, 0-40% EtOAc/Hex) to yield the title compound as light-yellow solid (3.3 g, 67%).

Step 5.

Methyl 3'-fluoro-4'-((1-(2-fluoro-2-methylpropyl)piperidin-4-yl)methoxy)biphenyl-4-carboxylate: 4-((4-bromo-2-fluorophenoxy)methyl)-1-(2-fluoro-2-methylpropyl)piperidine (0.62 g, 1.71 mmol) was dissolved in 1,4-dioxane 12 mL and $H_2O$ 3 mL. And then, 4-(methoxycarbonyl)phenylboronic acid (0.31 g, 1.71 mmol), $Pd(dbpf)Cl_2$ (0.056 g, 0.086 mmol) and $Cs_2CO_3$ (1.12 g, 3.42 mmol) were added thereto, following with increasing the temperature slowly and stirring at 120° C. for 3 hours. After the completion of the reaction, the reaction mixture was filtered through Celite. The filtrate was added with saturated $NaHCO_3$ aqueous solution, and extracted with $CH_2Cl_2$. The obtained organic layer was washed with saturated aqueous brine solution three times. The obtained organic layer was dried over $Na_2SO_4$, and filtered. The filtrate was concentrated under reduced pressure. MeOH was added thereto. The resulting precipitate was filtered to yield the title compound as white solid (0.23 g, 32%).

Step 6.

3'-fluoro-4'-((1-(2-fluoro-2-methylpropyl)piperidin-4-yl)methoxy)biphenyl-4-carboxylic acid: methyl 3'-fluoro-4'-((1-(2-fluoro-2-methylpropyl)piperidin-4-yl)methoxy)biphenyl-4-carboxylate (0.32 g, 0.77 mmol) was dissolved in THF 10 mL, $H_2O$ 3 mL and MeOH 3 mL. $LiOH \cdot H_2O$ (0.26 g, 6.13 mmol) was added thereto, following with stirring at room temperature for 12 hours. After the completion of the reaction, The reaction mixture was acidified to pH 5 by the addition of HCl. The reaction mixture was extracted with $CH_2Cl_2$. The organic layer was washed with saturated aqueous brine solution three times, dried over $Na_2SO_4$, and filtered. The filtrate was concentrated under reduced pressure to yield the title compound as white solid (0.12 g, 39%).

Step 7.

Compound 725: 3'-fluoro-4'-((1-(2-fluoro-2-methylpropyl)piperidin-4-yl)methoxy) biphenyl-4-carboxylic acid (0.04 g, 0.10 mmol) and (S)-piperidin-3-ol (0.02 g, 0.20 mmol) were dissolved in DMF 2 mL. DIPEA (0.06 g, 0.50 mmol), EDCI (0.04 g, 0.20 mmol) and HOBt (0.03 g, 0.20 mmol) were added thereto slowly, following with stirring at room temperature for 3 hours. After the completion of the reaction, excess amount of water was added to the reaction mixture. The resulting precipitate was filtered, and then dissolved in $CH_2Cl_2$. The solution was concentrated under reduced pressure. The obtained concentrate was purified by column chromatography (40 g ISCO silica gel cartridge, 0-20% MeOH/$CH_2Cl_2$) to yield the title compound as light-yellow solid (0.032 g, 68%).

1H NMR (400 MHz, $CDCl_3$) δ 7.50 (m, 4H), 7.32-7.24 (m, 2H), 7.00 (t, 1H, J=8.5 Hz), 3.89 (d, 2H, J=6.0 Hz), 3.44-2.98 (m, 6H), 2.47 (s, 1H), 2.41 (s, 1H), 2.17-1.65 (m, 9H), 1.38-1.23 (m, 8H); MS (ESI) m/z 487 (M++H).

According to the above-described synthesis process of compound 725, the compounds of Table 12 were synthesized using 3'-fluoro-4'-((1-(2-fluoro-2-methylpropyl)piperidin-4-yl)methoxy)biphenyl-4-carboxylic acid and the reactant of Table 11.

TABLE 11

| Compound No. | Reactant | Yield (%) |
|---|---|---|
| 726 | (R)-piperidin-3-ol | 85 |
| 727 | (R)-pyrrolidine-2-ylmethanol | 3 |
| 728 | (S)-pyrrolidine-2-ylmethanol | 27 |
| 729 | (R)-pyrrolidine-3-ol | 28 |
| 799 | piperidin-4-carboxamide | 47 |
| 806 | (R)-piperidin-2-carboxamide | 47 |
| 807 | (S)-piperidin-2-carboxamide | 16 |

TABLE 12

| Compound No. | Compound Name, $^1$H-NMR, MS (ESI) |
|---|---|
| 726 | (R)-(3'-fluoro-4'-((1-(2-fluoro-2-methylpropyl)piperidin-4-yl)methoxy)biphenyl-4-yl)(3-hydroxypiperidin-1-yl)methanone<br>1H NMR (400 MHz, $CDCl_3$) δ 7.53-7.44 (m, 4 H), 7.32-7.24 (m, 2 H), 7.00 (t, 1 H, J = 8.5 Hz), 3.89-3.44 (m, 6 H), 2.98 (d, 2 H, J = 9.6 Hz), 2.47 (s, 1 H), 2.41 (s, 1 H), 2.17 (t, 2 H, J = 11.1 Hz), 1.91-1.38 (m, 9 H), 1.32 (s, 3 H), 1.23 (s, 3 H); MS (ESI) m/z 487 (M+ + H) |
| 727 | (R)-(3'-fluoro-4'-((1-(2-fluoro-2-methylpropyl)piperidin-4-yl)methoxy)biphenyl-4-yl)(2-(hydroxymethyl)pyrrolidin-1-yl)methanone<br>1H NMR (400 MHz, $CDCl_3$) δ 7.66-7.19 (m, 5 H), 7.01 (t, 1 H, J = 8.5 Hz), 4.98 (brs, 1 H), 3.90 (d, 2 H, J = 5.9 Hz), 3.80-3.74 (m, 2 H), 3.58-3.50 (m, 3 H), 3.01-2.48 (m, 4 H), 2.19-1.60 (m, 9 H), 1.40-1.34 (m, 8 H); MS (ESI) m/z 487 (M+ + H). |
| 728 | (S)-(3'-fluoro-4'-((1-(2-fluoro-2-methylpropyl)piperidin-4-yl)methoxy)biphenyl-4-yl)(2-(hydroxymethyl)pyrrolidin-1-yl)methanone<br>1H NMR (400 MHz, CDCl3) δ 7.55 (brs, 4 H), 7.33-7.24 (m, 2 H), 7.01 (t, 1 H, J = 8.5 Hz), 4.98 (brs, 1 H), 3.90 (d, 2 H, J = 5.9 Hz), 3.80-3.74 (m, 2 H), 3.58-3.50 (m, 3 H), 3.01-2.48 (m, 4 H), 2.19-1.60 (m, 9 H), 1.40-1.34 (m, 8 H); MS (ESI) m/z 487 (M+ + H). |
| 729 | (R)-(3'-fluoro-4'-((1-(2-fluoro-2-methylpropyl)piperidin-4-yl)methoxy)biphenyl-4-yl)(3-hydroxypyrrolidin-1-yl)methanone<br>1H NMR (400 MHz, $CDCl_3$) δ 7.60-7.50 (m, 4 H), 7.33-7.24 (m, 2 H), 7.00 (t, 1 H, J = 8.5 Hz), 4.60 (s, 0.5 H), 4.47 (s, 0.5 H), 3.90 (d, 2 H, J = 6.0 Hz), 3.83-3.76 (m, 2 H), 3.68-3.45 (m, 2 H), 3.00 (brs, 2 H), 2.47-1.85 (m, 7 H), 1.44-0.83 (m, 8 H); MS (ESI) m/z 473 (M+ + H). |
| 799 | 1-(3'-fluoro-4'-((1-(2-fluoro-2-methylpropyl)piperidin-4-yl)methoxy)biphenylcarbonyl)piperidin-4-carboxamide<br>1H NMR (400 MHz, $CDCl_3$) δ 7.56 (d, 2 H, J = 8.0 Hz), 7.46 (d, 2 H, J = 8.0 Hz), 7.34-7.27 (m, 2 H), 7.03 (t, 1 H, J = 8.4 Hz), 5.58 (d, 2 H, J = 12.9 Hz), 3.91-3.90 (m, 4 H), 3.01-2.98 (m, 4 H), 2.48-2.42 (m, 3 H), 2.19 (t, 2 H, J = 11.4 Hz), 1.85-1.82 (m, 7 H), 1.47-1.26 (m, 8 H); MS (ESI) m/z 514 (M+ + H). |
| 806 | (R)-1-(3'-fluoro-4'-((1-(2-fluoro-2-methylpropyl)piperidin-4-yl)methoxy)biphenylcarbonyl)piperidin-2-carboxamide<br>1H NMR (400 MHz, $CDCl_3$) δ 7.55 (dd, 4 H, J = 28.0, 7.2 Hz), 7.35-7.27 (m, 2 H), 7.03 (t, 1 H, J = 8.5 Hz), 6.53 (brs, 1 H), 5.70 (brs, 1 H), 5.29 (brs, 1 H), 3.91 (d, 2 H, J = 6.2 Hz), 3.79 (d, 1 H, J = 13.2 Hz), 3.14 (t, 1 H, J = 12.6 Hz), 2.99 (d, 2 H, J = 11.2 Hz), 2.47 (s, 1 H), 2.42 (s, 1 H), 2.34 (d, 1 H, J = 12.4 Hz), 2.18 (t, 2 H, J = 11.1 Hz), 1.88-1.53 (m, 8 H), 1.49-1.25 (m, 8 H); MS (ESI) m/z 514 (M+ + H). |

TABLE 12-continued

| Compound No. | Compound Name, $^1$H-NMR, MS (ESI) |
|---|---|
| 807 | (S)-1-(3'-fluoro-4'-((1-(2-fluoro-2-methylpropyl)piperidin-4-yl)methoxy)biphenylcarbonyl)piperidin-2-carboxamide<br>1H NMR (400 MHz, CDCl$_3$) δ 7.60-7.50 (m, 4 H), 7.35-7.27 (m, 1 H), 7.03 (t, 1 H, J = 8.4 Hz), 6.49 (brs, 1 H), 5.48 (brs, 1 H), 5.29 (brs, 1 H), 3.91 (d, 2 H, J = 5.2 Hz), 3.80 (d, 1 H, J = 13.2 Hz), 3.13 (t, 1 H, J = 12.2 Hz), 3.00 (d, 2 H, J = 11.2 Hz), 2.48 (s, 1 H), 2.42 (s, 1 H), 2.35 (d, 1 H, J = 12.8 Hz), 2.19 (t, 2 H, J = 11.0 Hz), 1.89-1.44 (m, 8 H), 1.41-1.26 (m, 8 H); MS (ESI) m/z 514 (M+ + H). |

Example 42. Compound 730: (S)-1-(3,3'-difluoro-4'-((1-(2-fluoro-2-methylpropyl)piperidin-4-yl)methoxy)biphenylcarbonyl)pyrrolidine-2-carboxamide

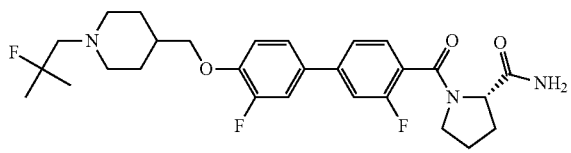 [SMILES: CC(C)(F)CN1CCC(COc2ccc(-c3ccc(C(=O)N4CCC[C@H]4C(N)=O)c(F)c3)cc2F)CC1]

Step 1.

Methyl 3,3'-difluoro-4'-((1-(2-fluoro-2-methylpropyl)piperidin-4-yl)methoxy)biphenyl-4-carboxylate: 4-((4-bromo-2-fluorophenoxy)methyl)-1-(2-fluoro-2-methylpropyl)piperidine (the product of synthesis step 4 of compound 725; 0.6 g, 1.66 mmol) was dissolved in 1,4-dioxane 12 mL and H$_2$O 3 mL. 4-(ethoxycarbonyl)-3-fluorophenylboronic acid, Pd(dbpf)Cl$_2$ (0.05 g, 0.08 mmol) and Cs$_2$CO$_3$ (1.07 g, 3.13 mmol) were added thereto, following with increasing the temperature slowly and stirring at 120° C. for 3 hours. After the completion of the reaction, the reaction mixture was filtered through Celite. The filtrate was added with saturated NaHCO$_3$ aqueous-solution, and extracted with CH$_2$Cl$_2$. The obtained organic layer was washed with saturated aqueous brine solution three times. The obtained organic layer was dried over Na$_2$SO$_4$, and filtered. The filtrate was concentrated under reduced pressure. MeOH was added thereto. The resulting precipitate was filtered to yield the title compound as brown solid (0.5 g, 69%).

Step 2.

3,3'-difluoro-4'-((1-(2-fluoro-2-methylpropyl)piperidin-4-yl)methoxy)biphenyl-4-carboxylic acid: methyl 3,3'-difluoro-4'-((1-(2-fluoro-2-methylpropyl)piperidin-4-yl)methoxy)biphenyl-4-carboxylate (0.5 g, 1.15 mmol) was dissolved in THF 10 mL, H$_2$O 3 mL and MeOH 3 mL. LiOH.H$_2$O (0.24 g, 5.74 mmol) was added thereto, following with stirring at room temperature for 12 hours. After the completion of the reaction, The reaction mixture was acidified to pH 5 by the addition of HCl. The reaction mixture was extracted with CH$_2$Cl$_2$. The obtained organic layer was washed with saturated aqueous brine solution three times, dried over Na$_2$SO$_4$, and filtered. The filtrate was concentrated under reduced pressure to yield the title compound as white solid (0.37 g, 77%).

Step 3.

Compound 730: 3,3'-difluoro-4'-((1-(2-fluoro-2-methylpropyl)piperidin-4-yl)methoxy)biphenyl-4-carboxylic acid (0.04 g, 0.10 mmol) and (S)-pyrrolidine-2-carboxamide (0.02 g, 0.19 mmol) were dissolved in DMF 1 mL. DIPEA (0.08 mL, 0.47 mmol), EDCI (0.04 g, 0.19 mmol) and HOBt (0.03 g, 0.19 mmol) were added thereto slowly, following with stirring at 60° C. for 3 hours. After the completion of the reaction, excess amount of water was added to the reaction mixture. The resulting precipitate was filtered to yield the title compound as brown solid (0.04 g, 75%).

1H NMR (400 MHz, CDCl$_3$) δ 7.24-7.21 (m, 5H), 7.00 (t, 1H, J=8.4 Hz), 6.89 (brs, 1H), 5.41 (brs, 1H), 4.81-4.80 (m, 1H), 3.91 (brs, 2H), 3.53-3.41 (m, 2H), 3.13-2.43 (m, 4H), 2.21-1.86 (m, 3H), 1.71-1.23 (m, 10H); MS (ESI) m/z 518 (M++H).

According to the above-described synthesis process of compound 730, the compounds of Table 14 were synthesized using 3,3'-difluoro-4'-((1-(2-fluoro-2-methylpropyl)piperidin-4-yl)methoxy)biphenyl-4-carboxylic acid and the reactant of Table 13.

TABLE 13

| Compound No. | Reactant | Yield (%) |
|---|---|---|
| 731 | (S)-piperidin-3-ol | 48 |
| 732 | (S)-pyrrolidine-3-ol | 22 |
| 733 | (R)-pyrrolidine-3-ol | 28 |
| 734 | (R)-piperidin-3-ol | 65 |
| 800 | piperidin-4-carboxamide | 53 |
| 816 | (R)-piperidin-2-carboxamide | 51 |
| 817 | (S)-piperidin-2-carboxamide | 42 |

TABLE 14

| Compound No. | Compound Name, $^1$H-NMR, MS (ESI) |
|---|---|
| 731 | (S)-(3,3'-difluoro-4'-((1-(2-fluoro-2-methylpropyl)piperidin-4-yl)methoxy)biphenyl-4-yl)(3-hydroxypiperidin-1-yl)methanone<br>1H NMR (400 MHz, CDCl$_3$) δ 7.43-7.02 (m, 5 H), 6.99 (t, 1 H, J = 10.2 Hz), 3.89 (d, 2 H, J = 6.4 Hz), 3.56-3.08 (m, 4 H), 3.06 (brs, 2 H), 2.48 (s, 1 H), 2.42 (s, 1 H), 2.28-1.54 (m, 9 H), 1.38-0.86 (m, 8 H); MS (ESI) m/z 505 (M+ + H). |
| 732 | (S)-(3,3'-difluoro-4'-((1-(2-fluoro-2-methylpropyl)piperidin-4-yl)methoxy)biphenyl-4-yl)(3-hydroxypyrrolidin-1-yl)methanone<br>1H NMR (400 MHz, CDCl$_3$) δ 7.51-7.46 (m, 1 H), 7.37-7.10 (m, 4 H), 7.04-7.00 (m, 1 H) 4.62 (s, 1 H), 4.50 (s, 1 H), 3.92 (d, 2 H, J = 4.6 Hz), 3.85-3.33 (m, 4 H), 3.02 (brs, 2 H), 2.49 (d, 2 H, J = 16.1 Hz), 2.30-1.84 (m, 7 H), 1.66-1.26 (m, 8 H); MS (ESI) m/z 491 (M+ + H). |

TABLE 14-continued

| Compound No. | Compound Name, ¹H-NMR, MS (ESI) |
|---|---|
| 733 | (R)-(3,3'-difluoro-4'-((1-(2-fluoro-2-methylpropyl)piperidin-4-yl)methoxy)biphenyl-4-yl)(3-hydroxypyrrolidine-1-yl)methanone<br>1H NMR (400 MHz, CDCl₃) δ 7.59-7.46 (m, 1 H), 7.41-7.25 (m, 4 H), 7.03 (t, 1 H, J = 6.3 Hz), 4.62 (s, 0.5 H), 4.49 (s, 0.5 H), 3.92 (d, 2 H, J = 4.5 Hz), 3.85-3.03 (m, 4 H), 3.03 (brs, 2 H), 2.51 (s, 1 H), 2.47 (s, 1 H), 2.31-1.84 (m, 7 H), 1.69-1.36 (m, 8 H); MS (ESI) m/z 491 (M+ + H). |
| 734 | (R)-(3,3'-difluoro-4'-((1-(2-fluoro-2-methylpropyl)piperidin-4-yl)methoxy)biphenyl-4-yl)(3-hydroxypiperidin-1-yl)methanone<br>1H NMR (400 MHz, CDCl₃) δ 7.41 (t, 1 H, J = 5.3 Hz), 7.34-7.20 (m, 4 H), 7.00 (t, 1 H, J = 6.3 Hz), 3.88 (d, 2 H, J = 4.6 Hz), 3.56-3.08 (m, 4 H), 2.98 (d, 2 H, J = 8.1 Hz), 2.47 (s, 1 H), 2.41 (s, 1 H), 2.17 (t, 2 H, J = 8.5 Hz), 1.98-1.59 (m, 7 H), 1.43-1.23 (m, 8 H); MS (ESI) m/z 505 (M+ + H). |
| 800 | 1-(3,3'-difluoro-4'-((1-(2-fluoro-2-methylpropyl)piperidin-4-yl)methoxy)biphenylcarbonyl)piperidin-4-carboxamide<br>H NMR (400 MHz, CDCl₃) δ 7.59-7.27 (m, 5 H), 7.07 (t, 1 H, J = 8.3 Hz), 5.70 (brs, 2 H), 4.78 (d, 1 H, J = 12.9 Hz), 3.95 (d, 2 H, J = 5.9 Hz), 3.75 (d, 1 H, J = 12.8 Hz), 3.16-2.95 (m, 4 H), 2.51-2.46 (m, 3 H), 2.22 (t, 2 H, J = 11.2 Hz), 2.06-1.59 (m, 7 H), 1.48-0.92 (m, 8 H); MS (ESI) m/z 532 (M+ + H). |
| 816 | (R)-1-(3,3'-difluoro-4'-((1-(2-fluoro-2-methylpropyl)piperidin-4-yl)methoxy)biphenylcarbonyl)piperidin-2-carboxamide<br>1H NMR (400 MHz, CDCl₃) δ 7.49 (t, 1 H, J = 7.4 Hz), 7.42-7.25 (m, 4 H), 7.03 (t, 1 H, J = 8.4 Hz), 6.32 (brs, 1 H), 5.68 (brs, 1 H), 5.44 (brs, 1 H), 3.91 (d, 2 H, J = 6.4 Hz), 3.60 (d, 1 H, J = 12.7 Hz), 3.22 (t, 1 H, J = 12.0 Hz), 2.99 (d, 2 H, J = 8.0 Hz), 2.48-2.42 (m, 3 H), 2.15-1.39 (m, 8 H), 1.34-1.26 (m, 8 H); MS (ESI) m/z 532 (M+ + H). |
| 817 | (S)-1-(3,3'-difluoro-4'-((1-(2-fluoro-2-methylpropyl)piperidin-4-yl)methoxy)biphenylcarbonyl)piperidin-2-carboxamide<br>H NMR (400 MHz, CDCl₃) δ 7.48 (t, 1 H, J = 6.0 Hz), 7.42-7.27 (m, 5 H), 7.03 (t, 1 H, J = 7.0 Hz), 6.31 (brs, 1 H), 5.52 (brs, 1 H), 5.45 (brs, 1 H), 3.92 (d, 2 H, J = 5.8 Hz), 3.61 (d, 1 H, J = 13.9 Hz), 3.21 (brs, 1 H), 3.00 (d, 2 H, J = 11.1 Hz), 2.48-2.42 (m, 3 H), 2.19 (t, 2 H, J = 11.6 Hz), 2.05-1.45 (m, 8 H), 1.40-1.25 (m, 8 H); MS (ESI) m/z 532 (M+ + H). |

Example 43. Compound 735: (S)-(2,3'-difluoro-4'-((1-(2-fluoro-2-methylpropyl)piperidin-4-yl)methoxy)biphenyl-4-yl)(3-hydroxypiperidin-1-yl)methanone

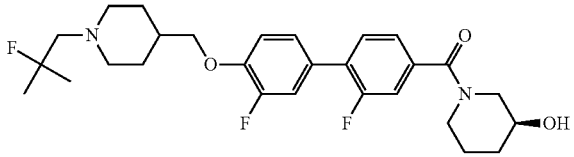 [SMILES: CC(C)(F)CN1CCC(COc2ccc(-c3ccc(C(=O)N4CCC[C@H](O)C4)cc3F)cc2F)CC1]

Step 1.

Methyl 2,3'-difluoro-4'-((1-(2-fluoro-2-methylpropyl)piperidin-4-yl)methoxy)biphenyl-4-carboxylate: 4-((4-bromo-2-fluorophenoxy)methyl)-1-(2-fluoro-2-methylpropyl)piperidine (the product of synthesis step 4 of compound 725; 0.60 g, 1.66 mmol) was dissolved in 1,4-dioxane 12 mL and H₂O 3 mL. 2-Fluoro-4-(methoxycarbonyl)phenylboronic acid (0.33 g, 1.66 mmol), Pd(dbpf)Cl₂ (0.05 g, 0.08 mmol) and Cs₂CO₃ (1.07 g, 3.31 mmol) was added thereto. The mixture was stirred in a microwave at 120° C. for 30 minutes. After the completion of the reaction, the reaction mixture was filtered through Celite. The filtrate was added with saturated NaHCO₃ aqueous solution, and extracted with CH₂Cl₂. The obtained organic layer was washed with saturated aqueous brine solution three times. The obtained organic layer was dried over Na₂SO₄, and filtered. The filtrate was concentrated under reduced pressure. MeOH was added thereto. The resulting precipitate was filtered to yield the title compound as light-yellow solid (0.35 g, 49%).

Step 2.

2,3'-difluoro-4'-((1-(2-fluoro-2-methylpropyl)piperidin-4-yl)methoxy)biphenyl-4-carboxylic acid: methyl 2,3'-difluoro-4'-((1-(2-fluoro-2-methylpropyl)piperidin-4-yl)methoxy)biphenyl-4-carboxylate (0.35 g, 0.80 mmol) was dissolved in THF 10 mL, H₂O 3 mL and MeOH 3 mL. LiOH.H₂O (0.17 g, 4.02 mmol) was added thereto, following with increasing the temperature slowly and then refluxing with stirring for 3 hours. After the completion of the reaction, The reaction mixture was acidified to pH 5 by the addition of HCl. The reaction mixture was extracted with CH₂Cl₂. The obtained organic layer was washed with saturated aqueous brine solution three times. The organic layer was dried over Na₂SO₄, and filtered. The filtrate was concentrated under reduced pressure to yield the title compound as white solid (0.33 g, 97%).

Step 3.

Compound 735: 2,3'-difluoro-4'-((1-(2-fluoro-2-methylpropyl)piperidin-4-yl)methoxy)biphenyl-4-carboxylic acid (0.04 g, 0.10 mmol) and (S)-piperidin-3-ol (0.02 g, 0.19 mmol) were dissolved in DMF 2 mL. DIPEA (0.08 mL, 0.48 mmol), EDCI (0.04 g, 0.19 mmol) and HOBt (0.03 g, 0.19 mmol) were added thereto slowly, following with stirring at 60° C. for 3 hours. After the completion of the reaction, excess amount of water was added to the reaction mixture. The resulting precipitate was filtered, and dissolved in CH₂Cl₂. The solution was concentrated under reduced pressure. The obtained concentrate was purified by column chromatography (40 g ISCO silica gel cartridge, 0-20% MeOH/CH₂Cl₂) to yield the title compound as light-yellow solid (0.02 g, 42%).

1H NMR (400 MHz, CDCl₃) δ 7.40 (t, 1H, J=5.8 Hz), 7.29-7.21 (m, 4H), 6.99 (t, 1H, J=6.4 Hz), 3.88 (d, 2H, J=4.6 Hz), 3.78-3.27 (m, 4H), 2.97 (d, 2H, J=8.2 Hz), 2.45 (s, 1H), 2.40 (s, 1H), 2.16 (t, 2H, J=8.5 Hz), 1.91-1.65 (m, 7H), 1.45-1.23 (m, 8H); MS (ESI) mz 505 (M++H).

According to the above-described synthesis process of compound 735, the compounds of Table 16 were synthesized using 2,3'-difluoro-4'-((1-(2-fluoro-2-methylpropyl) piperidin-4-yl)methoxy)biphenyl-4-carboxylic acid and the reactant of Table 15.

TABLE 15

| Compound No. | Reactant | Yield (%) |
| --- | --- | --- |
| 736 | (R)-pyrrolidine-3-ol | 43 |
| 737 | (S)-pyrrolidine-3-ol | 21 |
| 751 | (R)-pyrrolidine-2-ylmethanol | 10 |
| 752 | (S)-pyrrolidine-2-ylmethanol | 6 |
| 753 | (S)-pyrrolidine-2-carboxamide | 71 |
| 754 | (R)-piperidin-3-ol | 31 |
| 818 | piperidin-4-carboxamide | 41 |
| 819 | (R)-piperidin-2-carboxamide | 43 |
| 820 | (S)-piperidin-2-carboxamide | 40 |

TABLE 16

| Compound No. | Compound Name, $^1$H-NMR, MS (ESI) |
| --- | --- |
| 736 | (R)-(2,3'-difluoro-4'-((1-(2-fluoro-2-methylpropyl)piperidin-4-yl)methoxy)biphenyl-4-yl)(3-hydroxypyrrolidin-1-yl)methanone<br>1H NMR (400 MHz, CDCl$_3$) δ 7.42-7.22 (m, 5 H), 6.99 (t, 1 H, J = 8.5 Hz), 4.57 (brs, 0.5 H), 4.46 (brs, 0.5 H), 3.88 (d, 2 H, J = 6.1 Hz), 3.80-3.45 (m, 4 H), 2.98 (d, 2 H, J = 11.2 Hz), 2.46 (s, 1 H), 2.41 (s, 1 H), 2.17 (t, 2 H, J = 11.3 Hz), 2.07-1.98 (m, 2 H), 1.82-1.80 (m, 3 H), 1.43-1.23 (m, 8 H); MS (ESI) m/z 491(M+ + H). |
| 737 | (S)-(2,3'-difluoro-4'-((1-(2-fluoro-2-methylpropyl)piperidin-4-yl)methoxy)biphenyl-4-yl)(3-hydroxypyrrolidin-1-yl)methanone<br>1H NMR (400 MHz, CDCl$_3$) δ 7.42-7.22 (m, 5 H), 6.99 (t, 1 H, J = 8.7 Hz), 4.52 (d, 1 H, J = 46.7 Hz), 3.88 (d, 2 H, J = 8.0 Hz), 3.82-3.45 (m, 4 H), 2.98 (d, 2 H, J = 12.0 Hz), 2.44 (d, 2 H, J = 22.3 Hz), 2.17 (t, 2 H, J = 11.2 Hz), 2.11-1.80 (m, 5 H), 1.42-1.23 (m. 8 H); MS (ESI) m/z 491(M+ + H). |
| 751 | (R)-(2,3'-difluoro-4'-((1-(2-fluoro-2-methylpropyl)piperidin-4-yl)methoxy)biphenyl-4-yl)(2-(hydroxymethyl)pyrrolidin-1-yl)methanone<br>1H NMR (400 MHz, CDCl$_3$) δ 8.02-7.22 (m, 5 H), 7.03 (t, 1 H, J = 8.6 Hz), 4.73 (d, 1 H, J = 8.0 Hz), 4.44-4.40 (m, 1 H), 3.93 (d, 2 H, J = 6.0 Hz), 3.86-3.42 (m, 4 H), 3.01 (brs, 2 H), 2.50 (s, 1 H), 2.45 (s, 1 H), 2.22-1.42 (m, 9 H), 1.36-1.15 (m, 8 H); MS (ESI) m/z 505 (M+ + H). |
| 752 | (S)-(2,3'-difluoro-4'-((1-(2-fluoro-2-methylpropyl)piperidin-4-yl)methoxy)biphenyl-4-yl)(2-(hydroxymethyl)pyrrolidin-1-yl)methanone<br>1H NMR (400 MHz, CDCl$_3$) δ 7.48-7.27 (m, 5 H), 7.03 (t, 1 H, J = 8.6 Hz), 4.73 (brs, 1 H), 4.43-4.41 (m, 1 H), 3.92 (d, 2 H, J = 5.9 Hz), 3.85-3.50 (m, 4 H), 3.02-2.71 (m, 2 H), 2.52-2.46 (d, 2 H, J = 22.3 Hz), 2.22-1.41 (m, 11 H), 1.36-1.13 (m, 6 H); MS (ESI) m/z 505 (M+ + H). |
| 753 | (S)-1-(2,3'-difluoro-4'-((1-(2-fluoro-2-methylpropyl)piperidin-4-yl)methoxy)biphenylcarbonyl)pyrrolidine-2-carboxamide<br>1H NMR (400 MHz, CDCl$_3$) δ 7.47-7.25 (m, 5 H), 7.02 (t, 1 H, J = 8.0 Hz), 6.96 (brs, 1 H), 5.81 (brs, 1 H), 4.76-4.75 (m, 1 H), 3.91 (d, 2 H, J = 5.6 Hz), 3.66-3.57 (m, 2 H), 3.00 (d, 2 H, J = 12.0 Hz), 2.48-2.37 (m, 2 H), 2.21-1.81 (m, 9 H), 1.44-1.25 (m, 8 H); MS (ESI) m/z 518 (M+ + H). |
| 754 | (R)-(2,3'-difluoro-4'-((1-(2-fluoro-2-methylpropyl)piperidin-4-yl)methoxy)biphenyl-4-yl)(3-hydroxypiperidin-1-yl)methanone<br>1H NMR (400 MHz, CDCl$_3$) δ 7.42 (t, 1 H, J = 8.8 Hz), 7.31-7.23 (m, 4 H), 7.02 (t, 1 H, J = 8.6 Hz), 3.91-3.35 (m, 7 H), 3.00 (d, 2 H, J = 11.2 Hz), 2.48-2.42 (m, 2 H), 2.18 (t, 2 H, J = 11.4 Hz), 1.93-1.41 (m, 7 H), 1.39-1.25 (m, 8 H); MS (ESI) m/z 505 (M+ + H). |
| 818 | 1-(2,3'-difluoro-4'-((1-(2-fluoro-2-methylpropyl)piperidin-4-yl)methoxy)biphenylcarbonyl)piperidin-4-carboxamide<br>1H NMR (400 MHz, CDCl$_3$) δ3.00 (d, 2 H, J = 11.1 Hz), 7.32-7.19 (m, 4 H), 7.03 (t, 1 H, J = 8.4 Hz), 5.59 (brs, 2 H), 4.73 (brs, 1 H), 3.92-3.90 (m, 3 H), 3.00-2.97 (m, 4 H), 2.49-2.42 (m, 3 H), 2.18 (t, 2 H, J = 11.0 Hz), 1.88-1.81 (m, 7 H), 1.47-1.26 (m, 8 H); MS (ESI) m/z 532 (M+ + H). |
| 819 | (R)-1-(2,3'-difluoro-4'-((1-(2-fluoro-2-methylpropyl)piperidin-4-yl)methoxy)biphenylcarbonyl)piperidin-2-carboxamide<br>1H NMR (400 MHz, CDCl$_3$) δ 7.46-7.44 (m, 1 H), 7.33-7.25 (m, 4 H), 7.03 (t, 1 H, J = 8.6 Hz), 6.45 (brs, 1 H), 5.56 (brs, 1 H), 5.27 (brs, 1 H), 3.92 (d, 2 H, J = 6.2 Hz), 3.78-3.73 (m, 1 H), 3.16-3.18 (m, 1 H), 3.01 (d, 2 H, J = 11.2 Hz), 2.49 (s, 1 H), 2.43 (s, 1 H), 2.34 (d, 1 H, J = 12.0 Hz), 2.19 (t, 2 H, J = 11.2 Hz), 2.05-1.40 (m, 8 H), 1.34-1.24 (m, 8 H); MS (ESI) m/z 532 (M+ + H). |
| 820 | (S)-1-(2,3'-difluoro-4'-((1-(2-fluoro-2-methylpropyl)piperidin-4-yl)methoxy)biphenylcarbonyl)piperidin-2-carboxamide<br>1H NMR (400 MHz, CDCl$_3$) δ7.47 (t, 1 H, J = 7.6 Hz), 7.33-7.25 (m, 4 H), 7.03 (t, 1 H, J = 8.6 Hz), 6.41 (brs, 1 H), 5.56 (brs, 1 H), 5.26 (brs, 1 H), 3.92 (d, 2 H, J = 6.0 Hz), 3.78 (d, 1 H, J = 13.6 Hz), 3.17 (m, 1 H), 3.00 (d, 2 H, J = 11.2 Hz), 2.48 (s, 1 H), 2.42 (s, 1 H), 2.34 (d, 1 H, J = 12.4 Hz), 2.19 (t, 2 H, J = 11.1 Hz), 2.05-1.43 (m, 8 H), 1.40-1.24 (m, 8 H); MS (ESI) m/z 532 (M+ + H). |

Example 44. Compound 782: (S)-1-(5-(3-fluoro-4-((1-(2-fluoro-2-methylpropyl)piperidin-4-yl)methoxy)phenyl)picolinoyl)pyrrolidine-2-carboxamide

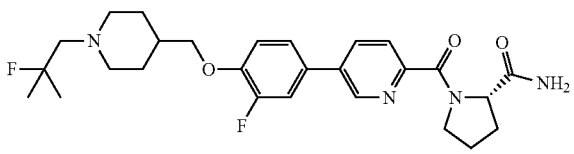 [SMILES: CC(C)(F)CN1CCC(COc2ccc(-c3ccc(C(=O)N4CCC[C@H]4C(N)=O)nc3)cc2F)CC1]

Step 1.

Methyl 5-(3-fluoro-4-((1-(2-fluoro-2-methylpropyl)piperidin-4-yl)methoxy)phenyl) picolinate: 4-((4-bromo-2-fluorophenoxy)methyl)-1-(2-fluoro-2-methylpropyl)piperidine (the product of synthesis step 4 of compound 725; 1.0 g, 2.76 mmol) was dissolved in 1,4-dioxane 8 mL and $H_2O$ 2 mL. 6-(Methoxycarbonyl)pyridine-3-ylboronic acid (0.50 g, 2.76 mmol), Pd(dbpf)Cl$_2$ (0.22 g, 0.28 mmol) and Cs$_2$CO$_3$ (1.80 g, 5.52 mmol) were added thereto. The mixture was stirred in a microwave at 110° C. for 30 minutes. After the completion of the reaction, the reaction mixture was filtered through Celite. The filtrate was added with saturated NaHCO$_3$ aqueous solution, and extracted with CH$_2$Cl$_2$. The organic layer was washed three times with saturated aqueous brine solution, dried over Na$_2$SO$_4$, and filtered. The filtrate was concentrated under reduced pressure. MeOH was added thereto. The resulting precipitate was filtered to yield the title compound as dark brown solid (0.1 g, 9%).

Step 2.

5-(3-fluoro-4-((1-(2-fluoro-2-methylpropyl)piperidin-4-yl)methoxy)phenyl)picolinic acid: methyl 5-(3-fluoro-4-((1-(2-fluoro-2-methylpropyl)piperidin-4-yl)methoxy)phenyl) picolinate (0.12 g, 0.29 mmol) was dissolved in THF 10 mL, H$_2$O 3 mL and MeOH 3 mL. LiOH.H$_2$O (0.06 g, 1.43 mmol) was added thereto, following with increasing the temperature slowly and then refluxing with stirring for 3 hours. After the completion of the reaction, The reaction mixture was acidified to pH 5 by the addition of HCl, and extracted with EtOAc. The obtained organic layer was washed with saturated NaHCO$_3$ aqueous solution three times, dried over Na$_2$SO$_4$, and filtered. The filtrate was concentrated under reduced pressure to yield the title compound as dark brown solid (0.08 g, 69%).

Step 3.

Compound 782: 5-(3-fluoro-4-((1-(2-fluoro-2-methylpropyl)piperidin-4-yl)methoxy)phenyl)picolinic acid (0.03 g, 0.07 mmol) and (S)-pyrrolidine-2-carboxamide (0.02 g, 0.15 mmol) was dissolved in DMF 1 mL. DIPEA (0.05 g, 0.37 mmol, EDCI (0.03 g, 0.15 mmol) and HOBt (0.02 g, 0.15 mmol) were added thereto slowly, following with stirring at 60° C. for 3 hours. After the completion of the reaction, excess amount of water was added to the reaction mixture. The resulting precipitate was filtered, and dissolved in CH$_2$Cl$_2$ again. The concentrate was purified by column chromatography (40 g ISCO silica gel cartridge, 0-20% MeOH/CH$_2$Cl$_2$) to yield the title compound as light-yellow solid (0.01 g, 38%).

1H NMR (400 MHz, CDCl$_3$) δ 8.77 (brs, 1H), 8.14-7.93 (m, 2H), 7.37-7.29 (m, 2H), 7.07-7.05 (m, 1H), 5.50 (brs, 1H), 5.16-4.82 (m, 1H), 3.93-3.89 (m, 5H), 3.02 (d, 2H, J=12.5 Hz), 2.50-1.78 (m, 11H), 1.47-1.26 (m, 8H); MS (ESI) m/z 501 (M++H).

According to the above-described synthesis process of compound 782, the compounds of Table 18 were synthesized using 5-(3-fluoro-4-((1-(2-fluoro-2-methylpropyl)piperidin-4-yl)methoxy)phenyl)picolinic acid and the reactant of Table 17.

TABLE 17

| Compound No. | Reactant | Yield (%) |
|---|---|---|
| 783 | (R)-piperidin-3-ol | 44 |

TABLE 18

| Compound No. | Compound Name, $^1$H-NMR, MS (ESI) |
|---|---|
| 783 | (R)-(5-(3-fluoro-4-((1-(2-fluoro-2-methylpropyl)piperidin-4-yl)methoxy)phenyl)pyridine-2-yl)(3-hydroxypiperidin-1-yl)methanone 1H NMR (400 MHz, CDCl3) δ 8.70 (s, 1 H), 7.99 (d, 1 H, J = 2.4 Hz), 7.85 (d, 1 H, J = 8.4 Hz), 7.36-7.27 (m, 2 H), 7.07 (t, 1 H, J = 8.3 Hz), 5.69 (s, 1 H), 4.61 (d, 1 H, J = 12.8 Hz), 4.08-4.04 (m, 2 H), 3.92 (d, 2 H, J = 8.0 Hz), 3.29-2.92 (m, 4 H), 2.49-2.43 (m, 2 H), 2.26-1.56 (m, 9 H), 1.46-1.35 (m, 8 H); MS (ESI) m/z 488 (M+ + H). |

Example 45. Compound 706: (S)-1-(2'-fluoro-4'-((1-(2-fluoro-2-methylpropyl)piperidin-4-yl)methoxy)biphenylcarbonyl)pyrrolidine-2-carboxamide Step 1.

Methyl 2'-fluoro-4'-((1-(2-fluoro-2-methylpropyl)piperidin-4-yl)methoxy)biphenyl-4-carboxylate: 4-((4-bromo-3-fluorophenoxy)methyl)-1-(2-fluoro-2-methylpropyl)piperidine (the product of synthesis step 4 of compound 704; 500 mg, 1.38 mmol), 4-(methoxycarbonyl)phenylboronic acid (298 mg, 1.57 mmol), Pd(dppf)Cl$_2$ (56 mg, 0.07 mmol) and Cs$_2$CO$_3$ (341 mg, 1.05 mmol) were added to water (2 mL)/1,4-dioxane (6 mL). With a microwave radiation, the mixture was heated at 110° C. for 15 minutes, and then cooled to room temperature. The reaction mixture was added with water, and extracted with EtOAc. The organic layer was dried over anhydrous MgSO$_4$, and concentrated under reduced pressure. The obtained concentrate was purified by silica gel column chromatography (EtOAc/hexane=17) to yield the title compound as white solid (210 mg, 36%).

Step 2.

2'-fluoro-4'-((1-(2-fluoro-2-methylpropyl)piperidin-4-yl)methoxy)biphenyl-4-carboxylic acid: methyl 2'-fluoro-4'-((1-(2-fluoro-2-methylpropyl)piperidin-4-yl)methoxy)biphenyl-4-carboxylate (210 mg, 0.50 mmol) was dissolved in THF (10 mL) and water (5 mL). LiOH.H₂O (106 mg, 2.52 mmol) was added thereto little by little at room temperature, following with stirring for 1 hour. After the completion of the reaction, the reaction mixture was acidified by the addition of 1N HCl. The resulting precipitate was filtered to yield the title compound as white solid (200 mg, 98%).

Step 3.

Compound 706: 2'-fluoro-4'-((1-(2-fluoro-2-methylpropyl)piperidin-4-yl)methoxy)biphenyl-4-carboxylic acid (50 mg, 0.12 mmol), (S)-pyrrolidine-2-carboxamide (17 mg, 0.15 mmol), Bop (110 mg, 0.248 mmol) and Et₃N (34 μL, 0.25 mmol) were dissolved in DMF. The reaction was performed at 60° C. for a day. After the completion of the reaction, the reaction mixture was added with a saturated NH₄Cl aqueous solution, and extracted with EtOAc. The organic layer was dried over anhydrous MgSO₄, and concentrated under reduced pressure. The obtained concentrate was purified by silica gel column chromatography (CH₂Cl₂/MeOH=101) to yield the title compound as yellow solid (23 mg, 37%).

1H NMR (400 MHz, CDCl₃) δ 7.61-7.53 (m, 4H), 7.37-7.27 (m, 1H), 7.04 (brs, 1H), 6.79-6.70 (m, 2H), 5.53 (brs, 1H), 4.85-4.82 (m, 1H), 3.83 (d, 2H, J=5.8 Hz), 3.67-3.56 (m, 2H), 3.01 (brs, 1H), 2.50-2.39 (m, 2H), 2.20-2.12 (m, 2H), 2.10-2.06 (m, 2H), 1.89-1.80 (m, 4H), 1.42-1.37 (m, 8H), 1.29-1.21 (m, 2H); MS (ESI) m/z 500 (M++H).

According to the above-described synthesis process of compound 706, the compounds of Table 20 were synthesized using 2'-fluoro-4'-((1-(2-fluoro-2-methylpropyl)piperidin-4-yl)methoxy)biphenyl-4-carboxylic acid and the reactant of Table 19.

TABLE 19

| Compound No. | Reactant | Yield (%) |
|---|---|---|
| 707 | (R)-pyrrolidine-2-ylmethanol | 21 |
| 708 | (R)-pyrrolidine-3-ol | 22 |
| 709 | (R)-piperidin-3-ol hydrochloride | 34 |
| 738 | (S)-piperidin-3-ol hydrochloride | 29 |
| 739 | (S)-pyrrolidine-3-ol | 35 |
| 740 | (S)-pyrrolidine-2-ylmethanol | 29 |
| 801 | piperidin-4-carboxamide | 62 |
| 873 | (R)-piperidin-2-carboxamide hydrochloride | 77 |
| 876 | (S)-piperidin-2-carboxamide hydrochloride | 64 |
| 881 | (R)-piperidin-3-carboxamide hydrochloride | 80 |

TABLE 20

| Compound No. | Compound Name, ¹H-NMR, MS (ESI) |
|---|---|
| 707 | (R)-(2'-fluoro-4'-((1-(2-fluoro-2-methylpropyl)piperidin-4-yl)methoxy)biphenyl-4-yl)(2-(hydroxymethyl)pyrrolidin-1-yl)methanone<br>1H NMR (400 MHz, CDCl₃) δ 7.57-7.53 (m, 4 H), 7.37-7.33 (m, 1 H), 6.79-6.69 (m, 2 H), 5.00 (brs, 1 H), 4.47-4.42 (m, 1 H), 3.84-3.61 (m, 3 H), 3.57-3.51 (m, 2 H), 3.04-3.02 (m, 2 H), 2.51-2.46 (m, 2 H), 2.28-2.18 (m, 3 H), 1.91-1.60 (m, 6 H), 1.42-1.27 (m, 8 H); MS (ESI) m/z 487 (M+ + H). |
| 708 | (R)-(2'-fluoro-4'-((1-(2-fluoro-2-methylpropyl)piperidin-4-yl)methoxy)biphenyl-4-yl)(3-hydroxypyrrolidin-1-yl)methanone<br>1H NMR (400 MHz, CDCl₃) δ 7.62-7.54 (m, 4 H), 7.37-7.27 (m, 1 H), 6.79-6.69 (m, 2 H), 4.62-4.49 (m, 1 H), 3.90-3.77 (m, 4 H), 3.71-3.68 (m, 1 H), 3.66-3.49 (m, 1 H), 3.03 (brs, 1 H), 2.57 (brs, 2 H), 2.26 (brs, 2 H), 2.16-2.06 (m, 2 H), 1.99-1.73 (m, 3 H), 1.55-1.44 (m, 6 H), 1.33 (s, 2 H), 0.91-0.86 (m, 1 H); MS (ESI) m/z 487 (M+ + H). |
| 709 | (R)-(2'-fluoro-4'-((1-(2-fluoro-2-methylpropyl)piperidin-4-yl)methoxy)biphenyl-4-yl)(3-hydroxypiperidin-1-yl)methanone<br>MS (ESI) m/z 487 (M+ + H). |
| 738 | (S)-(2'-fluoro-4'-((1-(2-fluoro-2-methylpropyl)piperidin-4-yl)methoxy)biphenyl-4-yl)(3-hydroxypiperidin-1-yl)methanone<br>1H NMR (400 MHz, CDCl₃) δ 7.56-7.52 (m, 4 H), 7.49-7.32 (m, 1 H), 6.79-6.70 (m, 2 H), 3.99 (brs, 1 H), 3.83 (d, 2 H, J = 5.9 Hz), 3.51 (brs, 2 H), 3.03 (brs, 2 H), 2.51-2.46 (m, 2 H), 2.20 (brs, 2 H), 2.05-2.03 (m, 2 H), 1.97-1.67 (m, 4 H), 1.55 (brs, 2 H), 1.42-1.32 (m, 8 H), 1.26-1.20 (m, 1 H); MS (ESI) m/z 487 (M+ + H). |
| 739 | (S)-(2'-fluoro-4'-((1-(2-fluoro-2-methylpropyl)piperidin-4-yl)methoxy)biphenyl-4-yl)(3-hydroxypyrrolidin-1-yl)methanone<br>1H NMR (400 MHz, CDCl₃) δ 7.62-7.54 (m, 4 H), 7.34 (t, 1 H, J = 8.7 Hz), 6.78-6.69 (m, 2 H), 4.60-4.48 (m, 1 H), 3.87-3.81 (m, 4 H), 3.79-3.71 (m, 1 H), 3.69-3.49 (m, 1 H), 3.03 (brs, 2 H), 2.52-2.46 (m, 2 H), 2.21-2.18 (m, 2 H), 2.15-2.13 (m, 1 H), 2.12-2.00 (m, 2 H), 1.99-1.71 (m, 3 H), 1.57-1.54 (m, 1 H), 1.47 (s, 3 H), 1.42 (s, 3 H); MS (ESI) m/z 473 (M+ + H). |
| 740 | (S)-(2'-fluoro-4'-((1-(2-fluoro-2-methylpropyl)piperidin-4-yl)methoxy)biphenyl-4-yl)(2-(hydroxymethyl)pyrrolidin-1-yl)methanone<br>1H NMR (400 MHz, CDCl₃) δ 7.60-7.55 (m, 4 H), 7.35 (t, 1 H, J = 8.8 Hz), 6.77-6.69 (m, 2 H), 4.97-4.95 (m, 1 H), 4.46-4.44 (m, 1 H), 3.87-3.75 (m, 4 H), 3.65-3.46 (m, 3 H), 2.24-2.22 (m, 1 H), 2.20-2.00 (m, 1 H), 1.97-1.92 (m, 2 H), 1.90-1.81 (m, 2 H), 1.70-1.32 (m, 10 H), 1.29-1.26 (m, 3 H); MS (ESI) m/z 487 (M+ + H). |
| 801 | 1-(2'-fluoro-4'-((1-(2-fluoro-2-methylpropyl)piperidin-4-yl)methoxy)biphenylcarbonyl)piperidin-4-carboxamide<br>1H NMR (400 MHz, CDCl₃) δ 7.59 (d, 2 H, J = 7.6 Hz), 7.49 (d, 2 H, J = 7.7 Hz), 7.38 (t, 1 H, J = 8.6 Hz), 6.81 (d, 1 H, J = 8.4 Hz), 6.75 (d, 1 H, J = 12.7 Hz), 5.73 (d, 2 H, J = 19.0 Hz), 4.73 (brs, 1 H), 3.95 (brs, 1 H), 3.86 (d, 2 H, J = 5.6 Hz), 3.04-3.01 (m, 4 H), 2.51-2.46 (m, 3 H), 2.22 (t, 2 H, J = 11.4 Hz), 1.84-1.48 (m, 7 H), 1.44-0.89 (m, 8 H); MS (ESI) m/z 514 (M+ + H). |
| 873 | (R)-1-(2'-fluoro-4'-((1-(2-fluoro-2-methylpropyl)piperidin-4-yl)methoxy)biphenylcarbonyl)piperidin-2-carboxamide |

TABLE 20-continued

| Compound No. | Compound Name, $^1$H-NMR, MS (ESI) |
|---|---|
| | 1H NMR (400 MHz, CDCl$_3$) δ 7.64-7.43 (m, 4 H), 7.35 (t, 1 H, J = 8.8 Hz), 6.82-6.67 (m, 2 H), 3.83 (d, 3 H, J = 6.0 Hz), 3.13 (t, 1 H, J = 13.3 Hz), 3.01 (d, 2 H, J = 11.3 Hz), 2.50 (s, 1 H), 2.44 (s, 1 H), 2.34 (d, 1 H, J = 12.5 Hz), 2.19 (t, 2 H, J = 11.2 Hz), 1.93-1.74 (m, 6 H), 1.72-1.52 (m, 3 H), 1.52-1.38 (m, 2 H), 1.41 (s, 3 H), 1.35 (s, 3 H); MS (ESI) m/z 514 (M+ + H). |
| 876 | (S)-1-(2'-fluoro-4'-((1-(2-fluoro-2-methylpropyl)piperidin-4-yl)methoxy)biphenylcarbonyl)piperidin-2-carboxamide<br>1H NMR (400 MHz, CDCl$_3$) δ 7.63-7.43 (m, 4 H), 7.35 (t, 1 H, J = 8.9 Hz), 6.82-6.67 (m, 2 H), 3.83 (d, 3 H, J = 5.8 Hz), 3.13 (t, 1 H, J = 12.8 Hz), 3.01 (d, 2 H, J = 11.3 Hz), 2.50 (s, 1 H), 2.44 (s, 1 H), 2.34 (d, 1 H, J = 12.3 Hz), 2.19 (t, 2 H, J = 11.5 Hz), 1.95-1.73 (m, 6 H), 1.73-1.52 (m, 3 H), 1.52-1.42 (m, 2 H), 1.41 (s, 3 H), 1.35 (s, 3 H); MS (ESI) m/z 514 (M+ + H). |
| 881 | (R)-1-(2'-fluoro-4'-((1-(2-fluoro-2-methylpropyl)piperidin-4-yl)methoxy)biphenylcarbonyl)piperidin-3-carboxamide<br>1H NMR (400 MHz, CDCl$_3$) δ 7.56 (d, 2 H, J = 7.0 Hz), 7.45 (d, 2 H, J = 8.3 Hz), 7.34 (t, 1 H, J = 8.8 Hz), 6.81-6.67 (m, 2 H), 3.84 (d, 3 H, J = 5.8 Hz), 3.57 (s, 1 H), 3.47 (s, 1 H), 3.03 (s, 2 H), 2.66-2.40 (m, 3 H), 2.21 (s, 2 H), 1.99-1.47 (m, 10 H), 1.42 (s, 3 H), 1.37 (s, 3 H); MS (ESI) m/z 514 (M+ + H). |

Example 46. Compound 704: (2,2'-difluoro-4'-((1-(2-fluoro-2-methylpropyl)piperidin-4-yl)methoxy)biphenyl-4-yl)((R)-2-(hydroxymethyl)pyrrolidine-1-yl)methanone

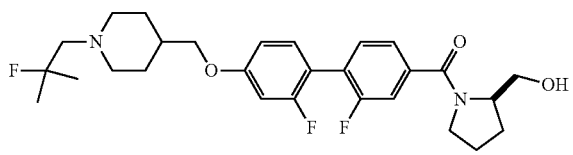 [SMILES: CC(C)(F)CN1CCC(COc2ccc(-c3ccc(C(=O)N4CCC[C@@H]4CO)cc3F)c(F)c2)CC1]

Step 1.

t-butyl 4-((4-bromo-3-fluorophenoxy)methyl)piperidin-1-carboxylate: t-butyl 4-((methylsulfonyloxy)methyl)piperidin-1-carboxylate (the product of synthesis step 2 of compound 431; 6.0 g, 20.45 mmol) was dissolved in DMF (60 mL). 4-Bromo-3-fluorophenol (3.91 g, 20.45 mmol) and K$_2$CO$_3$ (8.48 g, 61.35 mmol) were added thereto slowly, following with stirring at 80° C. for 5 hours. After the completion of the reaction, the reaction mixture was added with a saturated NH$_4$Cl aqueous solution, and extracted with EtOAc. The organic layer was dried over anhydrous MgSO$_4$, and concentrated under reduced pressure. The obtained concentrate was purified by silica gel column chromatography (EtOAc/hexane 110) to yield the title compound as white solid (6.27 g, 79%).

Step 2.

4-((4-bromo-3-fluorophenoxy)methyl)piperidine hydrochloride: t-butyl 4-((4-bromo-3-fluorophenoxy)methyl)piperidin-1-carboxylate (6.27 g, 16.15 mmol) was dissolved in CH$_2$Cl$_2$ (70 mL). 4 M HCl in 1,4-dioxane (80.74 mL, 322.97 mmol) was added thereto, following with stirring for 1 hour. The resulting precipitate was filtered to yield the title compound as white solid (5.03 g, 96%).

Step 3.

1-(4-((4-bromo-3-fluorophenoxy)methyl)piperidin-1-yl)-2-methylpropan-2-ol: 4-((4-bromo-3-fluorophenoxy)methyl)piperidine hydrochloride (5.32 g, 16.39 mmol) was dissolved in EtOH (5 mL) and H$_2$O (5 mL). 2,2-Dimethyloxirane (14.59 mL, 163.88 mmol) and K$_2$CO$_3$ (1.13 g, 8.19 mmol) were added thereto slowly. With a microwave radiation, the mixture was heated at 110° C. for 20 minutes, and then cooled to room temperature. The reaction mixture was added with a saturated NH$_4$Cl aqueous solution, and extracted with EtOAc. The organic layer was dried over anhydrous MgSO$_4$, and concentrated under reduced pressure. The obtained concentrate was purified by silica gel column chromatography (EtOAc/hexane=14) to yield the title compound as white solid (5.2 g, 88%).

Step 4.

4-((4-bromo-3-fluorophenoxy)methyl)-1-(2-fluoro-2-methylpropyl)piperidine: 1-(4-((4-bromo-3-fluorophenoxy)methyl)piperidin-1-yl)-2-methylpropan-2-ol (5.2 g, 14.43 mmol) was dissolved in CH$_2$Cl$_2$ (15 mL). At 0° C., DAST (1.91 mL, 14.43 mmol) was added slowly thereto. After stirring for 1 hour at room temperature, the reaction mixture was added with a saturated NH$_4$Cl aqueous solution, and extracted with EtOAc. The organic layer was dried over anhydrous MgSO$_4$, and concentrated under reduced pressure. The obtained concentrate was purified by silica gel column chromatography (EtOAc/hexane=17) to yield the title compound as yellow solid (2.50 g, 48%).

Step 5.

Methyl 2,2'-difluoro-4'-((1-(2-fluoro-2-methylpropyl)piperidin-4-yl)methoxy)biphenyl-4-carboxylate: 4-((4-bromo-3-fluorophenoxy)methyl)-1-(2-fluoro-2-methylpropyl)piperidine (200 mg, 0.55 mmol), 2-fluoro-4-(methoxycarbonyl)phenylboronic acid (131 mg, 0.06 mmol), Pd(dppf)Cl$_2$ (22 mg, 0.03 mmol) and Cs$_2$CO$_3$ (360 mg, 1.10 mmol) were added to water (2 mL)/1,4-dioxane (6 mL). With a microwave radiation, the mixture was heated at 110° C. for 15 minutes, and then cooled to room temperature. The reaction mixture was added with water, and extracted with EtOAc. The organic layer was dried over anhydrous MgSO$_4$, and concentrated under reduced pressure. The obtained concentrate was purified by silica gel column chromatography (EtOAc/hexane=17) to yield the title compound as white solid (81 mg, 34%).

Step 6.

2,2'-difluoro-4'-((1-(2-fluoro-2-methylpropyl)piperidin-4-yl)methoxy)biphenyl-4-carboxylic acid: methyl 2,2'-difluoro-4'-((1-(2-fluoro-2-methylpropyl)piperidin-4-yl)methoxy)biphenyl-4-carboxylate (81 mg, 0.19 mmol) was dissolved in THF (10 mL) and water (5 mL). LiOH.H$_2$O (39 mg, 0.93 mmol) was added thereto little by little at room temperature, following with stirring for 1 hour. After the completion of the reaction, the reaction mixture was acidified by the addition of 1N HCl. The resulting precipitate was filtered to yield the title compound as white solid (60 mg, 77%).

Step 7.

Compound 704: 2,2'-difluoro-4'-((1-(2-fluoro-2-methylpropyl)piperidin-4-yl)methoxy)biphenyl-4-carboxylic acid (30 mg, 0.07 mmol), (R)-pyrrolidine-2-ylmethanol (9 mg, 0.09 mmol), Bop (63 mg, 0.14 mmol) and Et₃N (20 μL, 0.14 mmol) were dissolved in DMF, and at 60° C. The reaction was performed at a day. After the completion of the reaction, the reaction mixture was added with a saturated NH₄Cl aqueous solution, and extracted with EtOAc. The organic layer was dried over anhydrous MgSO₄, and concentrated under reduced pressure. The obtained concentrate was purified by silica gel column chromatography (CH₂Cl₂/MeOH=101) to yield the title compound as yellow solid (17 mg, 47%).

1H NMR (400 MHz, CDCl₃) δ 7.44-7.27 (m, 4H), 6.77-6.70 (m, 2H), 4.43-3.83 (m, 1H), 4.12-3.83 (m, 3H), 3.78-3.47 (m, 4H), 3.05-2.81 (m, 2H), 2.67-2.49 (m, 2H), 2.22-2.21 (m, 1H), 2.20 (s, 1H), 2.06-1.85 (m, 5H), 1.57 (s, 3H), 1.51 (s, 3H), 1.36-1.31 (m, 3H); MS (ESI) m/z 505 (M++H).

According to the above-described synthesis process of compound 704, the compounds of Table 22 were synthesized using 2,2'-difluoro-4'-((1-(2-fluoro-2-methylpropyl)piperidin-4-yl)methoxy)biphenyl-4-carboxylic acid and the reactant of Table 21.

TABLE 21

| Compound No. | Reactant | Yield (%) |
|---|---|---|
| 705 | (S)-pyrrolidine-2-carboxamide | 35 |
| 741 | (S)-piperidin-3-ol hydrochloride | 25 |
| 742 | (R)-pyrrolidine-3-ol | 30 |
| 743 | (S)-pyrrolidine-3-ol | 36 |
| 744 | (S)-pyrrolidine-2-ylmethanol | 33 |
| 745 | (R)-piperidin-3-ol hydrochloride | 31 |
| 803 | piperidin-4-carboxamide | 61 |
| 825 | (R)-piperidin-2-carboxamide | 48 |
| 860 | (S)-piperidin-2-carboxamide | 41 |

TABLE 22

| Compound No. | Compound Name, ¹H-NMR, MS (ESI) |
|---|---|
| 705 | (2S)-1-(2,2'-difluoro-4'-((1-(2-fluoro-2-methylpropyl)piperidin-4-yl)methoxy)biphenylcarbonyl)pyrrolidine-2-carboxamide<br>1H NMR (400 MHz, CDCl₃) δ 7.45-7.27 (m, 4 H), 6.90 (brs, 1 H), 6.79-6.70 (m, 2 H), 5.46 (brs, 1 H), 3.87-3.85 (m, 2 H), 3.68-3.57 (m, 2 H), 2.18-2.03 (m, 3 H), 1.91-1.87 (m, 4 H), 1.59-1.38 (m, 6 H), 1.34 (s, 6 H), 0.89-0.76 (m, 3 H); MS (ESI) m/z 518 (M+ + H). |
| 741 | (2,2'-difluoro-4'-((1-(2-fluoro-2-methylpropyl)piperidin-4-yl)methoxy)biphenyl-4-yl)((S)-3-hydroxypiperidin-1-yl)methanone<br>1H NMR (400 MHz, CDCl₃) δ 7.40 (t, 1 H, J = 7.4 Hz), 7.30-7.22 (m, 3 H), 6.79-6.70 (m, 2 H), 3.97-3.95 (m, 1 H), 3.84-3.82 (m, 3 H), 3.57 (brs, 1 H), 3.46 (brs, 1 H), 3.04-3.01 (m, 2 H), 2.51-2.45 (m, 2 H), 2.20 (t, 2 H, J = 11.5 Hz), 1.94 (brs, 2 H), 1.89-1.79 (m, 3 H), 1.68 (brs, 2 H), 1.47-1.44 (m, 3 H), 1.41 (s, 3 H), 1.36 (s, 3 H); MS (ESI) m/z 505 (M+ + H). |
| 742 | (2,2'-difluoro-4'-((1-(2-fluoro-2-methylpropyl)piperidin-4-yl)methoxy)biphenyl-4-yl)((R)-3-hydroxypyrrolidin-1-yl)methanone<br>1H NMR (400 MHz, CDCl₃) δ 7.40-7.27 (m, 4 H), 6.79-6.71 (m, 2 H), 4.63-4.51 (m, 1 H), 3.84-3.80 (m, 3 H), 3.77-3.66 (m, 1 H), 3.65-3.49 (m, 1 H), 3.03 (brs, 2 H), 2.52-2.46 (m, 2 H), 2.21-2.13 (m, 2 H), 2.09-2.02 (m, 3 H), 1.97-1.70 (m, 3 H), 1.69-1.26 (m, 8 H); MS (ESI) m/z 491 (M+ + H). |
| 743 | (2,2'-difluoro-4'-((1-(2-fluoro-2-methylpropyl)piperidin-4-yl)methoxy)biphenyl-4-yl)((S)-3-hydroxypyrrolidin-1-yl)methanone<br>1H NMR (400 MHz, CDCl₃) δ 7.40-7.27 (m, 4 H), 6.79-6.71 (m, 2 H), 4.63-4.51 (m, 1 H), 3.84-3.80 (m, 3 H), 3.77-3.66 (m, 1 H), 3.65-3.49 (m, 1 H), 3.03 (brs, 2 H), 2.52-2.46 (m, 2 H), 2.21-2.13 (m, 2 H), 2.09-2.02 (m, 3 H), 1.97-1.70 (m, 3 H), 1.69-1.26 (m, 8 H); MS (ESI) m/z 491 (M+ + H). |
| 744 | (2,2'-difluoro-4'-((1-(2-fluoro-2-methylpropyl)piperidin-4-yl)methoxy)biphenyl-4-yl)((S)-2-(hydroxymethyl)pyrrolidin-1-yl)methanone<br>1H NMR (400 MHz, CDCl₃) δ 7.44-7.27 (m, 4 H), 6.77-6.69 (m, 2 H), 4.43-4.41 (m, 1 H), 3.85 (d, 2 H , J = 5.3 Hz), 3.78-3.74 (m, 1 H), 3.62-3.52 (m, 2 H), 3.24 (brs, 2 H), 2.72-2.67 (m, 2 H), 2.36-2.33 (brs, 2 H), 2.23-2.18 (m, 1 H), 1.94-1.81 (m, 5 H), 1.79-1.65 (m, 3 H), 1.63 (s, 3 H), 1.48 (s, 3 H), 1.26-1.21 (m, 1 H); MS (ESI) m/z 505 (M+ + H). |
| 745 | (2,2'-difluoro-4'-((1-(2-fluoro-2-methylpropyl)piperidin-4-yl)methoxy)biphenyl-4-yl)((R)-3-hydroxypiperidin-1-yl)methanone<br>1H NMR (400 MHz, CDCl₃) δ 7.39 (t, 1 H, J = 7.7 Hz), 7.31-7.22 (m, 3 H), 6.77-6.69 (m, 2 H), 4.14-4.12 (m, 1 H), 3.96-3.81 (m, 3 H), 3.79-3.46 (m, 5 H), 2.91 (brs, 2 H), 2.58 (brs, 2 H), 1.94-1.79 (m, 6 H), 1.69 (brs, 2 H), 1.56 (s, 3 H), 1.50 (s, 3 H), 1.31-1.23 (m, 1 H); MS (ESI) m/z 505 (M+ + H). |
| 803 | 1-(2,2'-difluoro-4'-((1-(2-fluoro-2-methylpropyl)piperidin-4-yl)methoxy)biphenylcarbonyl)piperidin-4-carboxamide<br>1H NMR (400 MHz, CDCl₃) δ 7.46 (t, 1 H, J = 7.4 Hz), 7.34-7.23 (m, 3 H), 6.83-6.75 (m, 2 H), 5.51 (d, 2 H, J = 32.0 Hz), 4.73 (brs, 1 H), 3.96 (brs, 1 H), 3.87 (d, 2 H, J = 5.6 Hz), 3.05-3.02 (m, 4 H), 2.52-2.46 (m, 3 H), 2.22 (t, 2 H, J = 11.2 Hz), 2.09-1.66 (m, 7 H), 1.60-0.90 (m, 8 H); MS (ESI) m/z 532 (M+ + H). |
| 825 | (2R)-1-(2,2'-difluoro-4'-((1-(2-fluoro-2-methylpropyl)piperidin-4-yl)methoxy)biphenylcarbonyl)piperidin-2-carboxamide<br>1H NMR (400 MHz, CDCl₃) δ 7.46-7.25 (m, 4 H), 6.80-6.71 (m, 2 H), 6.40 (brs, 1 H), 5.42 (brs, 1 H), 5.28 (brs, 1 H), 3.86-3.79 (m, 3 H), 3.16-3.13 (m, 1 H), 3.00 (d, 2 H, J = 11.2 Hz), 2.48 (s, 1 H), 2.43 (s, 1 H), 2.35 (d, 1 H, J = 13.6 Hz), 2.18 (t, 2 H, J = 11.2 Hz), 1.86-1.55 (m, 8 H), 1.50-1.26 (m, 8 H); MS (ESI) m/z 532 (M+ + H). |
| 860 | (2S)-1-(2,6'-difluoro-4'-((1-(2-fluoro-2-methylpropyl)piperidin-4-yl)methoxy)biphenylcarbonyl)piperidin-2-carboxamide |

TABLE 22-continued

| Compound No. Compound Name, ¹H-NMR, MS (ESI) |
|---|
| 1H NMR (400 MHz, CDCl₃) δ 7.45-7.24 (m, 4 H), 6.78-6.71 (m, 2 H), 6.46 (brs, 1 H), 5.69 (brs, 1 H), 5.28 (brs, 1 H), 3.83-3.77 (m, 3 H), 3.19-3.17 (m, 1 H), 3.00 (d, 2 H, J = 9.6 Hz), 2.48 (s, 1 H), 2.43 (s, 1 H), 2.33 (d, 1 H, J = 12.4 Hz), 2.18 (t, 2 H, J = 11.0 Hz), 1.81-1.52 (m, 8 H), 1.48-1.25 (m, 8 H) |

Example 47. Compound 710: (S)-1-(2',3-difluoro-4'-((1-(2-fluoro-2-methylpropyl)piperidin-4-yl)methoxy)biphenylcarbonyl)pyrrolidine-2-carboxamide

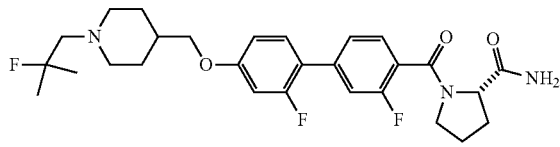 [SMILES: CC(C)(F)CN1CCC(COc2ccc(-c3ccc(C(=O)N4CCC[C@H]4C(N)=O)c(F)c3)c(F)c2)CC1]

Step 1.

Ethyl 2',3-difluoro-4'-((1-(2-fluoro-2-methylpropyl)piperidin-4-yl)methoxy)biphenyl-4-carboxylate: 4-((4-bromo-3-fluorophenoxy)methyl)-1-(2-fluoro-2-methylpropyl)piperidine (the product of synthesis step 4 of compound 704; 500 mg, 1.38 mmol), 4-(ethoxycarbonyl)-3-fluorophenylboronic acid (351 mg, 1.66 mmol), Pd(dppf)Cl₂ (56 mg, 0.07 mmol) and Cs₂CO₃ (899 mg, 2.76 mmol) were added to water (2 mL)/1,4-dioxane (6 mL). With a microwave radiation, the mixture was heated at 110° C. for 15 minutes, and then cooled to room temperature. The reaction mixture was added with water, and extracted with EtOAc. The organic layer was dried over anhydrous MgSO₄, and concentrated under reduced pressure. The obtained concentrate was purified by silica gel column chromatography (EtOAc/hexane=17) to yield the title compound as white solid (287 mg, 46%).

Step 2.

2',3-difluoro-4'-((1-(2-fluoro-2-methylpropyl)piperidin-4-yl)methoxy)biphenyl-4-carboxylic acid: ethyl 2',3-difluoro-4'-((1-(2-fluoro-2-methylpropyl)piperidin-4-yl)methoxy)biphenyl-4-carboxylate (287 mg, 0.64 mmol) was dissolved in THF (10 mL) and water (5 mL). LiOH.H₂O (134 mg, 3.19 mmol) was added thereto little by little at room temperature, following with stirring for 1 hour. After the completion of the reaction, the reaction mixture was acidified by the addition of 1N HCl. The resulting precipitate was filtered to yield the title compound as white solid (220 mg, 82%).

Step 3.

Compound 710: 2',3-difluoro-4'-((1-(2-fluoro-2-methylpropyl)piperidin-4-yl)methoxy)biphenyl-4-carboxylic acid (50 mg, 0.12 mmol), (S)-pyrrolidine-2-carboxamide (16 mg, 0.14 mmol), Bop (105 mg, 0.24 mmol) and Et₃N (33 µL, 0.24 mmol) were dissolved in DMF. The reaction was performed at 60° C. for a day. After the completion of the reaction, the reaction mixture was added with a saturated NH₄Cl aqueous solution, and extracted with EtOAc. The organic layer was dried over anhydrous MgSO₄, and concentrated under reduced pressure. The obtained concentrate was purified by silica gel column chromatography (CH₂Cl₂/MeOH=10/1) to yield the title compound as yellow solid (19 mg, 31%).

1H NMR (400 MHz, CDCl₃) δ 7.49-7.45 (m, 1H), 7.39-7.32 (m, 3H), 6.95 (brs, 1H), 6.80-6.70 (m, 2H), 5.56 (brs, 1H), 4.84-4.81 (m, 1H), 3.83 (d, 2H, J=6.0 Hz), 3.58-3.51 (m, 1H), 3.47-3.52 (m, 1H), 3.00 (brs, 2H), 2.51-2.43 (m, 3H), 2.20 (brs, 2H), 2.18-2.04 (m, 2H), 1.94-1.91 (m, 1H), 1.89-1.82 (m, 3H), 1.80-1.42 (m, 8H); MS (ESI) m/z 518 (M+H).

According to the above-described synthesis process of compound 710, the compounds of Table 24 were synthesized using 2',3-difluoro-4'-((1-(2-fluoro-2-methylpropyl)piperidin-4-yl)methoxy)biphenyl-4-carboxylic acid and the reactant of Table 23.

TABLE 23

| Compound No. | Reactant | Yield (%) |
|---|---|---|
| 711 | (R)-pyrrolidine-2-ylmethanol | 31 |
| 712 | (R)-pyrrolidine-3-ol | 46 |
| 713 | (R)-piperidin-3-ol hydrochloride | 30 |
| 746 | (S)-piperidin-3-ol hydrochloride | 38 |
| 747 | (S)-pyrrolidine-3-ol | 30 |
| 748 | (S)-pyrrolidine-2-ylmethanol | 35 |
| 802 | piperidin-4-carboxamide | 59 |
| 823 | (R)-piperidin-2-carboxamide | 52 |
| 861 | (S)-piperidin-2-carboxamide | 49 |

TABLE 24

| Compound No. | Compound Name, ¹H-NMR, MS (ESI) |
|---|---|
| 711 | (R)-(2',3-difluoro-4'-((1-(2-fluoro-2-methylpropyl)piperidin-4-yl)methoxy)biphenyl-4-yl)(2-(hydroxymethyl)pyrrolidine-1-yl)methanone<br>1H NMR (400 MHz, CDCl₃) δ 7.50-7.46 (m, 1 H), 7.38-7.27 (m, 3 H), 6.80-6.70 (m, 2 H), 4.80-4.78 (m, 1 H), 4.43-4.38 (m, 1 H), 3.85-3.75 (m, 4 H), 3.50-3.46 (m, 2 H), 3.16 (brs, 1 H), 2.50 (brs, 1 H), 2.24-2.03 (m, 3 H), 1.94-1.80 (m, 5 H), 1.53-1.43 (m, 6 H), 1.38 (s, 3 H), 0.90-0.88 (m, 1 H); MS (ESI) m/z 505 (M+ + H). |
| 712 | (R)-(2',3-difluoro-4'-((1-(2-fluoro-2-methylpropyl)piperidin-4-yl)methoxy)biphenyl-4-yl)(3-hydroxypyrrolidine-1-yl)methanone<br>1H NMR (400 MHz, CDCl₃) δ 7.51-7.46 (m, 1 H), 7.36-7.27 (m, 3 H), 6.79-6.69 (m, 2 H), 4.62-4.50 (m, 1 H), 3.84-3.80 (m, 3 H), 3.79-3.61 (m, 1 H), 3.59-3.35 (m, 1 H), 3.01 (brs, 2 H), 2.54 (brs, 2 H), 2.32-2.21 (m, 2 H), 2.19-2.02 (m, 3 H), 1.90-1.71 (m, 3 H), 1.69-1.31 (m, 7 H), 1.29-1.26 (m, 1 H); MS (ESI) m/z 491 (M+ + H). |

TABLE 24-continued

| Compound No. | Compound Name, ¹H-NMR, MS (ESI) |
|---|---|
| 713 | (R)-(2',3-difluoro-4'-((1-(2-fluoro-2-methylpropyl)piperidin-4-yl)methoxy)biphenyl-4-yl)(3-hydroxypiperidin-1-yl)methanone<br>1H NMR (400 MHz, CDCl₃) δ 7.46-7.42 (m, 1 H), 7.37-7.26 (m, 3 H), 6.79-6.70 (m, 2 H), 4.12-3.95 (m, 1 H), 3.83 (d, 2 H, J = 5.8 Hz), 3.68-3.59 (m, 1 H), 3.39-3.26 (m, 1 H), 3.16-3.00 (m, 2 H), 2.50 (brs, 2 H), 2.21-2.03 (m, 2 H), 1.99-1.91 (m, 2 H), 1.93-1.75 (m, 4 H), 1.72-1.69 (m, 2 H), 1.68-1.43 (m, 8 H), 1.37-1.27 (m, 2 H); MS (ESI) m/z 505 (M+ + H). |
| 746 | (S)-(2',3-difluoro-4'-((1-(2-fluoro-2-methylpropyl)piperidin-4-yl)methoxy)biphenyl-4-yl)(3-hydroxypiperidin-1-yl)methanone<br>1H NMR (400 MHz, CDCl₃) δ 7.44 (t, 1 H, J = 7.6 Hz), 7.35-7.24 (m, 3 H), 6.76-6.67 (m, 2 H), 4.12 (brs, 1 H), 3.95-3.89 (m, 3 H), 3.75-3.58 (m, 1 H), 3.46 (brs, 1 H), 3.36 (brs, 1 H), 3.16-3.00 (m, 3 H), 2.68 (brs, 2 H), 2.10-1.89 (m, 7 H), 1.83-1.53 (m, 9 H); MS (ESI) m/z 505 (M+ + H). |
| 747 | (S)-(2',3-difluoro-4'-((1-(2-fluoro-2-methylpropyl)piperidin-4-yl)methoxy)biphenyl-4-yl)(3-hydroxypyrrolidin-1-yl)methanone<br>1H NMR (400 MHz, CDCl₃) δ 7.52-7.48 (m, 1 H), 7.46-7.27 (m, 3 H), 6.79-6.70 (m, 2 H), 3.86-3.81 (m, 3 H), 3.79-3.60 (m, 2 H), 3.50-3.46 (m, 1 H), 3.38-3.35 (m, 1 H), 3.04 (brs, 2 H), 2.44 (brs, 2 H), 2.21-2.18 (m, 2 H), 2.14 (brs, 2 H), 1.89-1.81 (m, 4 H), 1.60 (brs, 1 H), 1.43-1.38 (m, 7 H); MS (ESI) m/z 491 (M+ + H). |
| 748 | (S)-(2',3-difluoro-4'-((1-(2-fluoro-2-methylpropyl)piperidin-4-yl)methoxy)biphenyl-4-yl)(2-(hydroxymethyl)pyrrolidin-1-yl)methanone<br>1H NMR (400 MHz, CDCl₃) δ 7.48 (t, 1 H, J = 7.5 Hz), 7.38-7.17 (m, 3 H), 6.80-6.70 (m, 2 H), 4.83-4.81 (m, 1 H), 4.42-4.40 (m, 1 H), 3.86-3.78 (m, 4 H), 3.50-3.46 (m, 2 H), 3.01 (brs, 1 H), 2.48 (brs, 1 H), 2.23-2.18 (m, 2 H), 1.92-1.88 (m, 1 H), 1.87-1.71 (m, 4 H), 1.70-1.64 (m, 2 H), 1.42-1.24 (m, 8 H), 1.22 (brs, 1 H); MS (ESI) m/z 505 (M+ + H). |
| 802 | 1-(2',3-difluoro-4'-((1-(2-fluoro-2-methylpropyl)piperidin-4-yl)methoxy)biphenylcarbonyl)piperidin-4-carboxamide<br>1H NMR (400 MHz, CDCl₃) δ 7.47-7.30 (m, 4 H), 6.82 (d, 1 H, J = 8.4 Hz), 6.76 (d, 1 H, J = 12.6 Hz), 5.62 (d, 2 H, J = 24.5 Hz), 4.79 (d, 1 H, J = 12.9 Hz), 3.87 (d, 2 H, J = 5.5 Hz), 3.78 (d, 1 H, J = 13.0 Hz), 3.17-2.95 (m, 4 H), 2.52-2.46 (m, 3 H), 2.22 (t, 2 H, J = 11.5 Hz), 2.07-1.82 (m, 7 H), 1.48-0.92 (m, 6 H); MS (ESI) m/z 532 (M+ + H). |
| 823 | (R)-1-(2',3-difluoro-4'-((1-(2-fluoro-2-methylpropyl)piperidin-4-yl)methoxy)biphenylcarbonyl)piperidin-2-carboxamide<br>1H NMR (400 MHz, CDCl₃) δ 7.60-7.27 (m, 4 H), 6.80-6.68 (m, 2 H), 6.33 (brs, 1 H), 5.64 (brs, 1 H), 5.44 (brs, 1 H), 3.90 (brs, 2 H), 3.63-3.59 (m, 1 H), 3.25-3.19 (m, 1 H), 2.96 (d, 2 H, J = 26.4 Hz), 2.89-2.86 (m, 3 H), 2.73-2.70 (m, 2 H), 2.44-1.57 (m, 8 H), 1.27-1.14 (m, 8 H); MS (ESI) m/z 532 (M+ + H) |
| 861 | (S)-1-(3,6'-difluoro-4'-((1-(2-fluoro-2-methylpropyl)piperidin-4-yl)methoxy)biphenylcarbonyl)piperidin-2-carboxamide<br>1H NMR (400 MHz, CDCl₃) δ 7.45-7.24 (m, 4 H), 6.77-6.67 (m, 2 H), 6.28 (brs, 1 H), 5.71 (brs, 1 H), 5.42 (brs, 1 H), 3.80 (d, 2 H, J = 6.2 Hz), 3.61-3.58 (m, 1 H), 3.23-3.19 (m, 1 H), 2.97 (d, 2 H, J = 11.5 Hz), 2.45-2.40 (m, 3 H), 2.15 (t, 2 H, J = 11.0 Hz), 1.78-1.60 (m, 8 H), 1.42-1.32 (m, 8 H) |

Example 48. Compound 1082: (S)-1-(5-(2-fluoro-4-((1-(2-fluoro-2-methylpropyl)piperidin-4-yl)methoxy)phenyl)pyrazine-2-carbonyl)pyrrolidine-2-carboxamide

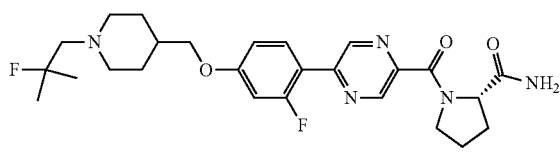 [SMILES: CC(C)(F)CN1CCC(COc2ccc(-c3cnc(C(=O)N4CCC[C@H]4C(N)=O)cn3)c(F)c2)CC1]

Step 1.

Methyl 5-(4-(benzoxy)-2-fluorophenyl)pyrazine-2-carboxylate: DME (8 mL)/H₂O (2 mL) was added to 4-(benzoxy)-2-fluorophenylboronic acid (1.00 g, 4.06 mmol), methyl 5-bromopyrazine-2-carboxylate (0.77 g, 4.47 mmol), Pd(dppf)Cl₂ (0.16 g, 0.20 mmol) and Cs₂CO₃ (2.64 g, 8.12 mmol). With a microwave radiation, the mixture was heated at 110° C. for 25 minutes, and then cooled to room temperature. The reaction mixture was filtered through a Celite pad to remove a solid. The filtrate was added with saturated NH₄Cl aqueous solution, and extracted with ethyl acetate. The organic layer was washed with saturated aqueous brine solution, dried over anhydrous MgSO₄, and filtered. The filtrate was concentrated under reduced pressure. The concentrate was purified by column chromatography (SiO₂, 12 g cartridge; ethyl acetatehexane=0% to 30%), and concentrated to yield the title compound as white solid (0.75 g, 54%).

Step 2.

Methyl 5-(2-fluoro-4-hydroxyphenyl)pyrazine-2-carboxylate: methyl 5-(4-(benzoxy)-2-fluorophenyl)pyrazine-2-carboxylate (0.750 g, 2.21 mmol) was dissolved in MeOH (10 mL)/THF (10 mL) at room temperature. 10% wt PdC (150 mg) was added slowly thereto, and then following with stirring at the same temperature for 1 hour under hydrogen gas balloon. The reaction mixture was filtered through a Celite pad to remove a solid. The obtained filtrate was concentrated under reduced pressure. To the obtained concentrate, methanol (5 mL) and hexane (20 mL) were added thereto, following with stirring. The resulting precipitate was filtered, and dried to yield the title compound as green solid (0.19 g, 34%).

Step 3.

Methyl 5-(4-((1-(t-butoxycarbonyl)piperidin-4-yl)methoxy)-2-fluorophenyl)pyrazine-2-carboxylate: methyl 5-(2-fluoro-4-hydroxyphenyl)pyrazine-2-carboxylate (0.19 g, 0.76 mmol), t-butyl 4-((methylsulfonyloxy)methyl)piperidin-1-carboxylate (0.22 g, 0.76 mmol) and $K_2CO_3$ (0.15 g, 1.14 mmol) were dissolved in 70° C. for DMF (10 mL), following with stirring at the same temperature for 18 hours. The reaction mixture was added with saturated $NH_4Cl$ aqueous solution, and extracted with ethyl acetate. The organic layer was washed with water, dried over anhydrous $MgSO_4$, and filtered. The filtrate was concentrated under reduced pressure. The obtained material was used without further purifying process (0.28 g, 82%, white solid).

Step 4.

Methyl 5-(2-fluoro-4-(piperidin-4-ylmethoxy)phenyl)pyrazine-2-carboxylate hydrochloride: methyl 5-(4-((1-(t-butoxycarbonyl)piperidin-4-yl)methoxy)-2-fluorophenyl)pyrazine-2-carboxylate (0.28 g, 0.62 mmol) was dissolved in DCM (10 mL). At room temperature, HCl (4.00M solution in dioxane, 0.62 mL, 2.51 mmol) was added thereto, following with stirring at the same temperature for 18 hours. The resulting precipitate was filtered, and dried to yield the title compound as white solid (0.14 g, 59%).

Step 5.

Methyl 5-(2-fluoro-4-((1-(2-hydroxy-2-methylpropyl)piperidin-4-yl)methoxy)phenyl)pyrazine-2-carboxylate:

EtOH (10 mL) was added to methyl 5-(2-fluoro-4-(piperidin-4-ylmethoxy)phenyl)pyrazine-2-carboxylate hydrochloride (0.14 g, 0.29 mmol), 2,2-dimethyl oxirane (0.26 mL, 2.96 mmol) and $K_2CO_3$ (0.20 g, 1.48 mmol). With a microwave radiation, the mixture was heated at 110° C. for 20 minutes, and then cooled to room temperature. The reaction mixture was added with saturated $NH_4Cl$ aqueous solution, and extracted with ethyl acetate. The organic layer was washed with water, dried over anhydrous $MgSO_4$, and filtered. The filtrate was concentrated under reduced pressure. The obtained material was used without further purifying process (0.12 g, 96%, red solid).

Step 6.

Methyl 5-(2-fluoro-4-((1-(2-fluoro-2-methylpropyl)piperidin-4-yl)methoxy)phenyl)pyrazine-2-carboxylate:

methyl 5-(2-fluoro-4-((1-(2-hydroxy-2-methylpropyl)piperidin-4-yl)methoxy)phenyl)pyrazine-2-carboxylate (0.12 g, 0.28 mmol) and DAST (0.05 mL, 0.34 mmol) were dissolved in DCM (10 mL) at room temperature. The solution was stirred at the same temperature for 4 hours. The reaction mixture was added with saturated $NaHCO_3$ aqueous solution, and extracted with ethyl acetate. The organic layer was washed with water, dried over anhydrous $MgSO_4$, and filtered. The filtrate was concentrated under reduced pressure. The obtained material was used without further purifying process (0.09 g, 73%, yellow solid).

Step 7.

5-(2-fluoro-4-((1-(2-fluoro-2-methylpropyl)piperidin-4-yl)methoxy)phenyl)pyrazine-2-carboxylic acid: methyl 5-(2-fluoro-4-((1-(2-fluoro-2-methylpropyl)piperidin-4-yl)methoxy)phenyl)pyrazine-2-carboxylate (0.09 g, 0.21 mmol) and $LiOH \cdot H_2O$ (0.04 g, 1.04 mmol) were dissolved in THF/MeOH (8 mL)/$H_2O$ (1 mL) at room temperature. The solution was stirred at the same temperature for 18 hours, the reaction mixture was concentrated under reduced pressure. The concentrate was added with water (10 mL), and stirred. The resulting precipitate was filtered, and dried to yield the title compound as white solid (0.06 g, 76%).

Step 8.

Compound 1082: 5-(2-fluoro-4-((1-(2-fluoro-2-methylpropyl)piperidin-4-yl)methoxy)phenyl)pyrazine-2-carboxylic acid (0.06 g, 0.14 mmol), (S)-pyrrolidine-2-carboxamide (0.01 g, 0.17 mmol), HOBt (0.04 g, 0.29 mmol), EDC (0.05 g, 0.29 mmol) and $iPr_2NEt$ (0.05 mL, 0.29 mmol) were dissolved in DCM (2 mL) at room temperature. The solution was stirred at the same temperature for 18 hours. The reaction mixture was added with saturated $NH_4Cl$ aqueous solution, and extracted with ethyl acetate. The organic layer was washed with saturated aqueous brine solution, dried over anhydrous $MgSO_4$, and filtered. The filtrate was concentrated under reduced pressure. The concentrate was purified by column chromatography ($SiO_2$, 4 g cartridge; methanol/dichloromethane=0% to 30%), and concentrated to yield the title compound as white solid (0.02 g, 35%).

1H NMR (400 MHz, $CDCl_3$) δ 9.18-9.19 (m, 1H), 8.95-9.02 (m, 1H), 8.06 (td, 1H, J=8.9, 2.5 Hz), 6.85 (td, 1H, J=8.4, 2.2 Hz), 6.68-6.74 (m, 1H), 6.19 (s, 1H), 5.44 (s, 1H), 5.04-4.83 (m, 1H), 4.83-4.86 (m, 1H), 4.06-4.11 (m, 1H), 3.88-3.96 (m, 1H), 3.83-3.86 (m, 2H), 2.97-3.00 (m, 2H), 2.41-2.47 (m, 3H), 2.13-2.21 (m, 3H), 1.97-2.06 (m, 2H), 1.77-1.80 (m, 3H), 1.41-1.47 (m, 2H), 1.39 (s, 3H), 1.33 (s, 3H); MS (ESI) m/z 502.3 (M++H).

Example 49. Compound 935: (S)-1-(5-(2-fluoro-4-((1-(2-fluoro-2-methylpropyl)piperidin-4-yl)methoxy)phenyl)picolinoyl)pyrrolidine-2-carboxamide

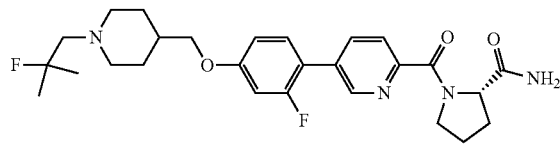 [SMILES: CC(C)(F)CN1CCC(COc2ccc(-c3ccc(C(=O)N4CCC[C@H]4C(N)=O)nc3)c(F)c2)CC1]

Step 1.

Methyl 5-(2-fluoro-4-((1-(2-fluoro-2-methylpropyl)piperidin-4-yl)methoxy)phenyl)picolinate: 4-((4-bromo-3-fluorophenoxy)methyl)-1-(2-fluoro-2-methylpropyl)piperidine (the product of synthesis step 4 of compound 704; 1.00 g, 2.76 mmol), 6-(methoxycarbonyl)pyridine-3-ylboronic acid (600 mg, 3.31 mmol), $Pd(dppf)Cl_2$ (113 mg, 0.14 mmol) and $Cs_2CO_3$ (1.80 g, 5.52 mmol) were added to water (2 mL)/1,4-dioxane (6 mL). With a microwave radiation, the mixture was heated at 110° C. for 15 minutes, and then cooled to room temperature. The reaction mixture was added with water, and extracted with EtOAc. The organic layer was dried over anhydrous $MgSO_4$, and concentrated under reduced pressure. The obtained concentrate was purified by silica gel column chromatography (EtOAc/hexane=17) to yield the title compound as white solid (200 g, 17%).

Step 2.

5-(2-fluoro-4-((1-(2-fluoro-2-methylpropyl)piperidin-4-yl)methoxy)phenyl)picolinic acid: methyl 5-(2-fluoro-4-((1-(2-fluoro-2-methylpropyl)piperidin-4-yl)methoxy)phenyl)picolinate (200 mg, 0.48 mmol) was dissolved in THF (10 mL) and water (5 mL). $LiOH \cdot H_2O$ (100 g, 2.39 mmol) was added thereto little by little at room temperature, following with stirring for 1 hour. After the completion of the reaction, the reaction mixture was acidified by the addition of 1N HCl. The resulting precipitate was filtered to yield the title compound as white solid (145 mg, 75%).

Step 3.

Compound 935: 5-(2-fluoro-4-((1-(2-fluoro-2-methylpropyl)piperidin-4-yl)methoxy)phenyl)picolinic acid (30 mg, 0.07 mmol), EDC (28 mg, 0.15 mmol) and HOBt (20 mg, 0.15 mmol) was added thereto, DIPEA (26 µL, 0.15 mmol) was dissolved in CH$_2$Cl$_2$ (1 mL). At room temperature, (S)-pyrrolidine-2-carboxamide (17 mg, 0.15 mmol) was added thereto, following with stirring with at the same temperature for a day. The reaction mixture was added with water, and extracted with EtOAc. The organic layer was washed with saturated NH$_4$Cl aqueous solution, dried over anhydrous MgSO$_4$, and concentrated under reduced pressure. The obtained concentrate was purified by silica gel column chromatography (CH$_2$Cl$_2$/MeOH=95%~5%) to yield the title compound as white solid (19 mg, 51%).

1H NMR (400 MHz, CDCl$_3$) δ 8.75-8.70 (m, 1H), 8.10-7.91 (m, 2H), 7.40-7.34 (m, 1H), 6.95 (brs, 0.5H), 6.84-6.73 (m, 2H), 5.44 (brs, 0.5H), 5.07 (d, 0.5H, J=7.1 Hz), 4.88-4.85 (m, 0.5H), 3.84 (d, 2H, J=5.9 Hz), 3.01 (d, 2H, J=10.4 Hz), 2.49-2.41 (m, 2H), 2.21-1.95 (m, 5H), 1.82-1.61 (m, 7H), 1.49-1.46 (m, 2H), 1.41 (s, 3H), 1.35 (s, 3H); MS (ESI) mz 501 (M++H).

Example 50. Compound 963: (R)-4-((1-(2-fluoro-2-methylpropyl)piperidin-4-yl)methoxy)-4'-(3-hydroxypiperidin-1-carbonyl)biphenyl-3-carbonitrile

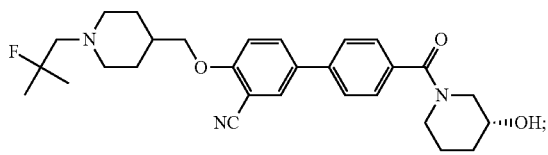 [SMILES: CC(C)(F)CN1CCC(COc2ccc(-c3ccc(C(=O)N4CCC[C@@H](O)C4)cc3)cc2C#N)CC1]

Step 1.

Methyl 3'-cyano-4'-((1-(2-fluoro-2-methylpropyl)piperidin-4-yl)methoxy)biphenyl-4-carboxylate: DME (4 mL)/H$_2$O) (1 mL) was added to 5-bromo-2-((1-(2-fluoro-2-methylpropyl)piperidin-4-yl)methoxy)benzonitrile (the product of synthesis step 4 of compound 938; 0.25 g, 0.67 mmol), 4-(methoxycarbonyl)phenylboronic acid (0.14 g, 0.81 mmol), Pd(dppf)Cl$_2$ (0.02 g, 0.03 mmol) and Cs$_2$CO$_3$ (0.44 g, 1.35 mmol). With a microwave radiation, the mixture was heated at 110° C. for 20 minutes, and then cooled to room temperature. The reaction mixture was filtered through a Celite pad to remove a solid. The obtained filtrate was diluted with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; EtOAc/hexane=0% to 30%), and concentrated to yield the title compound as white solid (0.22 g, 78%).

Step 2.

3'-cyano-4'-((1-(2-fluoro-2-methylpropyl)piperidin-4-yl)methoxy)biphenyl-4-carboxylic acid: Methyl 3'-cyano-4'-((1-(2-fluoro-2-methylpropyl)piperidin-4-yl)methoxy)biphenyl-4-carboxylate (0.22 g, 0.53 mmol) and LiOH.H$_2$O (0.11 g, 2.65 mmol) were dissolved in THF/MeOH (8 mL)/H$_2$O (2 mL) at room temperature. The solution was stirred at the same temperature for 2 hours, the reaction mixture was concentrated under reduced pressure. The resulting precipitate was filtered, and dried to yield the title compound as white solid (0.18 g, 86%).

Step 3.

Compound 963: 3'-cyano-4'-((1-(2-fluoro-2-methylpropyl)piperidin-4-yl)methoxy)biphenyl-4-carboxylic acid (0.04 g, 0.09 mmol), (R)-piperidin-3-ol (0.01 g, 0.11 mmol), HOBt (0.02 g, 0.19 mmol), EDC (0.03 g, 0.19 mmol) and DIPEA (0.02 g, 0.19 mmol) were dissolved in CH$_2$Cl$_2$ (1 mL) at room temperature. The solution was stirred at the same temperature for 18 hours, the reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 4 g cartridge; dichloromethane/methanol=0% to 10%), and concentrated to yield the title compound as red solid (0.02 g, 49%).

1H NMR (400 MHz, CDCl$_3$) δ 7.72-7.74 (m, 2H), 7.53 (dd, 4H, J=14.7, 8.5 Hz), 7.04 (d, 1H, J=8.8 Hz), 3.95-4.01 (m, 3H), 3.43-3.94 (m, 4H), 2.99-3.02 (m, 2H), 2.49 (s, 1H), 2.44 (s, 1H), 2.17-2.23 (m, 2H), 1.86-1.95 (m, 6H), 1.63-1.72 (m, 2H), 1.42-1.56 (m, 2H), 1.40 (s, 3H), 1.35 (s, 3H); MS (ESI) m/z 494.3 (M++H).

According to the above-described synthesis process of compound 963, the compounds of Table 26 were synthesized using 3'-cyano-4'-((1-(2-fluoro-2-methylpropyl)piperidin-4-yl)methoxy)biphenyl-4-carboxylic acid and the reactant of Table 25.

TABLE 25

| Compound No. | Reactant | Yield (%) |
| --- | --- | --- |
| 964 | (S)-piperidin-3-ol hydrochloride | 83 |
| 965 | L-prolinamide | 26 |
| 966 | (R)-pyrrolidine-3-ol | 49 |

TABLE 26

| Compound No. | Compound Name, $^1$H-NMR, MS (ESI) |
| --- | --- |
| 964 | (S)-4-((1-(2-fluoro-2-methylpropyl)piperidin-4-yl)methoxy)-4'-(3-hydroxypiperidin-1-carbonyl)biphenyl-3-carbonitrile<br>1H NMR (400 MHz, CDCl$_3$) δ 7.71-7.73 (m, 2 H), 7.52 (dd, 4 H, J = 14.4, 8.5 Hz), 7.04 (d, 1 H, J = 8.8 Hz), 3.93-3.95 (m, 3 H), 3.02-3.92 (m, 5 H), 2.99-3.02 (m, 2 H), 2.43-2.49 (m, 3 H), 2.16-2.22 (m, 2 H), 1.85-1.93 (m, 5 H), 1.42-1.45 (m, 3 H), 1.39 (s, 3 H), 1.34 (s, 3 H); MS (ESI) m/z 494.3 (M+ + H). |
| 965 | (S)-1-(3'-cyano-4'-((1-(2-fluoro-2-methylpropyl)piperidin-4-yl)methoxy)biphenylcarbonyl)pyrrolidine-2-carboxamide<br>1H NMR (400 MHz, CDCl$_3$) δ 7.73-7.79 (m, 2 H), 7.63 (d, 2 H, J = 8.2 Hz), 7.57 (d, 2 H, J = 8.2 Hz), 7.05 (d, 1 H, J = 8.8 Hz), 6.97 (s, 1 H), 5.56 (s, 1 H), 4.82 (dd,<br>1 H, J = 7.4, 5.0 Hz), 3.95 (d, 2 H, J = 6.4 Hz), 3.53-3.67 (m, 2 H), 2.99-3.02 (m, 2 H), 2.43-2.49 (m, 3 H), 2.10-2.22 (m, 2 H), 1.98-2.10 (m, 2 H), 1.78-1.92 (m, 5 H), 1.35-1.49 (m, 7 H); MS (ESI) m/z 507.3 (M+ + H). |
| 966 | (S)-4-((1-(2-fluoro-2-methylpropyl)piperidin-4-yl)methoxy)-4'-(3-hydroxypyrrolidine-1-carbonyl)biphenyl-3-carbonitrile |

TABLE 26-continued

Compound No. Compound Name, $^1$H-NMR, MS (ESI)

1H NMR (400 MHz, CDCl$_3$) δ 8.13 (d, 1 H, J = 7.9 Hz), 7.71-7.78 (m, 2 H), 7.53-7.64 (m, 3 H), 7.01 (t, 1 H, J = 8.8 Hz), 4.49-4.61 (m, 1 H), 3.96 (d, 2 H, J = 6.0 Hz), 3.51-3.83 (m, 2 H), 3.20-3.27 (m, 2 H), 2.68 (dd, 2 H, J = 22.7, 15.3 Hz), 2.32-2.40 (m, 2 H), 1.92-2.08 (m, 5 H), 1.47-1.66 (m, 2 H), 1.40-1.46 (m, 9 H); MS (ESI) m/z 480.3 (M+ + H).

Example 51. Compound 967: (R)-2'-fluoro-4-((1-(2-fluoro-2-methylpropyl)piperidin-4-yl)methoxy)-4'-(3-hydroxypiperidin-1-carbonyl)biphenyl-3-carbonitrile

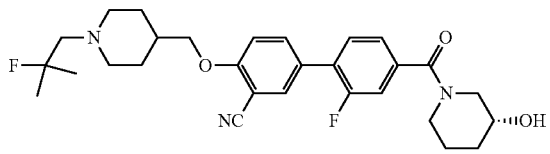 [SMILES: CC(C)(F)CN1CCC(COc2ccc(-c3ccc(C(=O)N4CCC[C@@H](O)C4)cc3F)cc2C#N)CC1]

Step 1.

Methyl 3'-cyano-2-fluoro-4'-((1-(2-fluoro-2-methylpropyl)piperidin-4-yl)methoxy)biphenyl-4-carboxylate: DME (4 mL)/H$_2$O (1 mL) was added to 5-bromo-2-((1-(2-fluoro-2-methylpropyl)piperidin-4-yl)methoxy)benzonitrile (the product of synthesis step 4 of compound 938; 0.25 g, 0.67 mmol), 2-fluoro-4-(methoxycarbonyl)phenylboronic acid (0.14 g, 0.81 mmol), Pd(dppf)Cl$_2$ (0.02 g, 0.03 mmol) and Cs$_2$CO$_3$ (0.44 g, 1.35 mmol). With a microwave radiation, the mixture was heated at 110° C. for 20 minutes, and then cooled to room temperature. The reaction mixture was filtered through a Celite pad to remove a solid. The obtained filtrate was diluted with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; EtOAc/hexane=0% to 30%), and concentrated to yield the title compound as white solid (0.14 g, 49%).

Step 2.

3'-cyano-2-fluoro-4'-((1-(2-fluoro-2-methylpropyl)piperidin-4-yl)methoxy)biphenyl-4-carboxylic acid: Methyl 3'-cyano-2-fluoro-4'-((1-(2-fluoro-2-methylpropyl)piperidin-4-yl)methoxy)biphenyl-4-carboxylate (0.14 g, 0.32 mmol) and LiOH.H$_2$O (0.06 g, 1.63 mmol) were dissolved in THF/MeOH (8 mL)/H$_2$O (2 mL) at room temperature. The solution was stirred at the same temperature for 2 hours, the reaction mixture was concentrated under reduced pressure. The resulting precipitate was filtered, and dried to yield the title compound as white solid (0.13 g, 95%).

Step 3.

Compound 967: 3'-cyano-2-fluoro-4'-((1-(2-fluoro-2-methylpropyl)piperidin-4-yl)methoxy)biphenyl-4-carboxylic acid (0.04 g, 0.093 mmol), (R)-piperidin-3-ol (0.01 g, 0.11 mmol), HOBt (0.02 g, 0.18 mmol), EDC (0.03 g, 0.18 mmol) and DIPEA (0.03 mL, 0.18 mmol) were dissolved in CH$_2$Cl$_2$ (1 mL) at room temperature. The solution was stirred at the same temperature for 18 hours, the reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 4 g cartridge; dichloromethane/methanol=0% to 10%), and concentrated to yield the title compound as yellow oil (0.02 g, 46%).

1H NMR (400 MHz, CDCl$_3$) δ 7.69-7.70 (m, 2H), 7.42 (t, 1H, J=7.8 Hz), 7.24-7.30 (m, 2H), 7.04 (d, 1H, J=8.8 Hz), 3.95 (d, 2H, J=6.4 Hz), 3.38-3.78 (m, 4H), 2.99-3.02 (m, 2H), 2.49 (s, 1H), 2.43 (s, 1H), 2.17-2.27 (m, 3H), 1.85-1.95 (m, 5H), 1.63-1.71 (m, 1H), 1.42-1.56 (m, 3H), 1.40 (s, 3H), 1.35 (s, 3H); MS (ESI) m/z 512.3 (M++H).

According to the above-described synthesis process of compound 967, the compounds of Table 28 were synthesized using 3'-cyano-2-fluoro-4'-((1-(2-fluoro-2-methylpropyl)piperidin-4-yl)methoxy)biphenyl-4-carboxylic acid and the reactant of Table 27.

TABLE 27

| Compound No. | Reactant | Yield (%) |
| --- | --- | --- |
| 968 | (S)-piperidin-3-ol hydrochloride | 52 |
| 969 | L-prolinamide | 42 |

TABLE 28

| Compound No. | Compound Name, $^1$H-NMR, MS (ESI) |
| --- | --- |
| 968 | (S)-2'-fluoro-4-((1-(2-fluoro-2-methylpropyl)piperidin-4-yl)methoxy)-4'-(3-hydroxypiperidin-1-carbonyl)biphenyl-3-carbonitrile<br>1H NMR (400 MHz, CDCl$_3$) δ 7.69-7.71 (m, 2 H), 7.42 (t, 1 H, J = 7.8 Hz), 7.24-7.30 (m, 2 H), 7.04 (d, 1 H, J = 8.8 Hz), 3.95 (d, 2 H, J = 6.4 Hz), 3.36-3.79 (m, 4 H), 2.99-3.02 (m, 2 H), 2.49 (s, 1 H), 2.43 (s, 1 H), 2.17-2.22 (m, 3 H), 1.91-2.11 (m, 6 H), 1.43-1.71 (m, 3 H), 1.40 (s, 3 H), 1.34 (s, 3 H); MS (ESI) m/z 512.3 (M+ + H). |
| 969 | (S)-1-(3'-cyano-2-fluoro-4'-((1-(2-fluoro-2-methylpropyl)piperidin-4-yl)methoxy)biphenylcarbonyl)pyrrolidine-2-carboxamide<br>1H NMR (400 MHz, CDCl$_3$) δ 7.70-7.75 (m, 2 H), 7.36-7.46 (m, 3 H), 7.05 (d, 1 H, J = 8.8 Hz), 6.87 (s, 1 H), 5.66 (s, 1 H), 4.77-4.80 (m, 1 H), 3.95 (d, 2 H, J = 6.4 Hz), 3.56-3.68 (m, 2 H), 2.99-3.02 (m, 2 H), 2.41-2.49 (m, 2 H), 2.07-2.33 (m, 5 H), 1.85-1.92 (m, 4 H), 1.42-1.48 (m, 2 H), 1.40 (s, 3 H), 1.34 (s, 3 H); MS (ESI) m/z 525.3 (M+ + H). |

Example 52. Compound 938: (S)-1-(3'-cyano-3-fluoro-4'-((1-(2-fluoro-2-methylpropyl)piperidin-4-yl)methoxy)biphenylcarbonyl)pyrrolidine-2-carboxamide

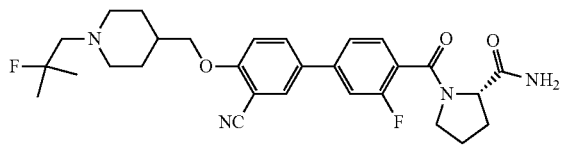 [SMILES: CC(C)(F)CN1CCC(COc2ccc(-c3ccc(C(=O)N4CCC[C@H]4C(N)=O)c(F)c3)cc2C#N)CC1]

Step 1.

t-butyl 4-((4-bromo-2-cyanophenoxy)methyl)piperidin-1-carboxylate: t-butyl 4-((methylsulfonyloxy)methyl)piperidine-1-carboxylate (the product of synthesis step 2 of compound 431; 800 mg, 2.73 mmol) was dissolved in ACN (80 mL). At room temperature, 5-bromo-2-hydroxybenzonitrile (540 mg, 2.73 mmol) was added thereto, and stirred for 5 minutes. $Cs_2CO_3$ (1.33 g, 4.09 mmol) was added thereto, following with stirring at 80° C. for 5 hours. The reaction mixture was added with water, and extracted with EtOAc. The obtained organic layer was washed with saturated aqueous brine solution, dried over anhydrous $MgSO_4$, and filtered. The filtrate was concentrated under reduced pressure. The concentrate was purified by column chromatography ($SiO_2$, 12 g cartridge; EtOAc/hexane=30%~70%), and concentrated to yield the title compound as white solid (655 mg, 60%).

Step 2.

5-bromo-2-(piperidin-4-ylmethoxy)benzonitrile hydroxychloride: t-butyl 4-((4-bromo-2-cyanophenoxy)methyl)piperidin-1-carboxylate (655 mg, 1.66 mmol) was dissolved in $CH_2Cl_2$ (10 mL). 4 M HCl solution in 1,4-dioxane (414 μL, 1.66 mmol) was added thereto at room temperature. The mixture was stirred at the same temperature for 1 hour. The resulting precipitate was filtered, and dried to yield the title compound as white solid (540 mg, 98%).

Step 3.

5-bromo-2-((1-(2-hydroxy-2-methylpropyl)piperidin-4-yl)methoxy)benzonitrile: To 5-bromo-2-(piperidin-4-ylmethoxy)benzonitrile hydroxychloride (540 mg, 1.63 mmol), 2,2-dimethyl oxirane (1.45 mL, 16.3 mmol) and $K_2CO_3$ (112 mg, 0.81 mmol), EtOH (5 mL)/$H_2O$ (5 mL) was added. With a microwave radiation, the mixture was heated at 110° C. for 20 minutes, and then cooled to room temperature. The reaction mixture was added with water, and extracted with EtOAc. The obtained organic layer was washed with saturated aqueous brine solution, dried over anhydrous $MgSO_4$, and filtered. The filtrate was concentrated under reduced pressure. The obtained material, which is the title compound as white solid (440 mg, 73%), was used without further purification.

Step 4.

5-bromo-2-((1-(2-fluoro-2-methylpropyl)piperidin-4-yl)methoxy)benzonitrile: 5-bromo-2-((1-(2-hydroxy-2-methylpropyl)piperidin-4-yl)methoxy)benzonitrile (440 mg, 1.20 mmol) was dissolved in $CH_2Cl_2$ (10 mL). At 0° C., DAST (158 μL, 1.20 mmol) was added thereto, following with stirring at room temperature for 1 hour. The reaction mixture was added with water, and extracted with EtOAc. The obtained organic layer was washed with saturated aqueous brine solution, dried over anhydrous $MgSO_4$, and filtered. The filtrate was concentrated under reduced pressure. The concentrate was purified by column chromatography ($SiO_2$, 12 g cartridge; EtOAc/hexane=30%~70%), and concentrated to yield the title compound as white solid (254 mg, 57%).

Step 5.

Ethyl 3'-cyano-3-fluoro-4'-((1-(2-fluoro-2-methylpropyl)piperidin-4-yl)methoxy) biphenyl-4-carboxylate: 5-bromo-2-((1-(2-fluoro-2-methylpropyl)piperidin-4-yl)methoxy) benzonitrile (the product of synthesis step 4 of compound 963; 254 mg, 0.69 mmol), 4-(ethoxycarbonyl)-3-fluorophenylboronic acid (160 mg, 0.76 mmol), Pd(dppf)Cl₂ (56 mg, 0.07 mmol) and $Cs_2CO_3$ (448 mg, 1.38 mmol) were added to water (2 mL)/DME (6 mL). With a microwave radiation, the mixture was heated at 110° C. for 15 minutes, and then cooled to room temperature. The reaction mixture was, added with water, and extracted with EtOAc. The obtained organic layer was washed with saturated aqueous brine solution, dried over anhydrous $MgSO_4$, and concentrated under reduced pressure. The obtained concentrate was purified by silica gel column chromatography (EtOAc/hexane=30%~70%) to yield the title compound as white solid (205 mg, 65%).

Step 6.

3'-cyano-3-fluoro-4'-((1-(2-fluoro-2-methylpropyl)piperidin-4-yl)methoxy)biphenyl-4-carboxylic acid: Ethyl 3'-cyano-3-fluoro-4'-((1-(2-fluoro-2-methylpropyl)piperidin-4-yl)methoxy)biphenyl-4-carboxylate (205 mg, 0.45 mmol) was dissolved in THF (10 mL) and water (5 mL). LiOH.$H_2O$ (94 mg, 2.25 mmol) was added thereto little by little at room temperature, following with stirring for 1 hour. After the completion of the reaction, the reaction mixture was concentrated under reduced pressure. The resulting precipitate was filtered, and dried to yield the title compound as white solid (120 mg, 62%).

Step 7.

Compound 938: 3'-cyano-3-fluoro-4'-((1-(2-fluoro-2-methylpropyl)piperidin-4-yl)methoxy)biphenyl-4-carboxylic acid (30 mg, 0.07 mmol), EDC (27 mg, 0.14 mmol) and HOBt (19 mg, 0.14 mmol) was added thereto, DIPEA (25 μL, 0.14 mmol) was dissolved in $CH_2Cl_2$ (1 mL). At room temperature, (S)-pyrrolidine-2-carboxamide (16 mg, 0.14 mmol) was added thereto, following with stirring with at the same temperature for a day. The reaction mixture was added with water, and extracted with EtOAc. The organic layer was washed with saturated $NH_4Cl$ aqueous solution, dried over anhydrous $MgSO_4$, and concentrated under reduced pressure. The obtained concentrate was purified by silica gel column chromatography ($CH_2Cl_2$/MeOH=95%~5%) to yield the title compound as white solid (21 mg, 57%).

1H NMR (400 MHz, CDCl₃) δ 7.77-7.71 (m, 2H), 7.52 (t, 1H, J=7.5 Hz), 7.44-7.39 (m, 1H), 7.37-7.23 (m, 1H), 7.06 (d, 1H, J=8.9 Hz), 6.89 (brs, 1H), 5.50 (brs, 1H), 4.83-4.80 (m, 1H), 3.96 (d, 2H, J=6.4 Hz), 3.56-3.39 (m, 2H), 3.03 (brs, 2H), 2.52-2.41 (m, 2H), 2.22-2.14 (m, 2H), 2.12-2.01 (m, 2H), 1.94-1.87 (m, 4H), 1.67 (brs, 2H), 1.57-1.45 (brs, 1H), 1.42 (s, 3H), 1.36 (s, 3H); MS (ESI) m/z 525 (M++H).

According to the above-described synthesis process of compound 938, the compounds of Table 30 were synthesized using 3'-cyano-3-fluoro-4'-((1-(2-fluoro-2-methylpropyl)piperidin-4-yl)methoxy)biphenyl-4-carboxylic acid and the reactant of Table 29.

TABLE 29

| Compound No. | Reactant | Yield (%) |
| --- | --- | --- |
| 939 | (R)-piperidin-3-ol hydrochloride | 53 |
| 1015 | (S)-piperidin-2-carboxamide hydrochloride | 33 |

TABLE 29-continued

| Compound No. | Reactant | Yield (%) |
|---|---|---|
| 1016 | (S)-piperidin-2-ol hydrochloride | 50 |
| 1017 | (S)-pyrrolidine-3-ol | 46 |

TABLE 30

Compound No. Compound Name, $^1$H-NMR, MS (ESI)

939  (R)-3'-fluoro-4-((1-(2-fluoro-2-methylpropyl)piperidin-4-yl)methoxy)-4'-(3-hydroxypiperidin-1-carbonyl)biphenyl-3-carbonitrile
1H NMR (400 MHz, CDCl$_3$) δ 7.76-7.70 (m, 2 H), 7.48 (t, 1 H, J = 7.3 Hz), 7.36-7.34 (m, 1 H), 7.27-7.22 (m, 1 H), 7.05 (d, 1 H, J = 8.8 Hz), 4.14-4.07 (m, 1 H), 3.96 (d, 2 H, J = 6.4 Hz), 3.58-3.52 (m, 1 H), 3.38-3.23 (m, 1 H), 3.16-3.13 (m, 2 H), 2.51-2.46 (m, 2 H), 2.22-2.17 (m, 2 H), 2.05-1.87 (m, 6 H), 1.76-1.71 (m, 3 H), 1.70-1.48 (m, 2 H), 1.41 (s, 3 H), 1.36 (s, 3 H); MS (ESI) m/z 512 (M+ + H).

1015  (R)-1-(3'-cyano-3-fluoro-4'-((1-(2-fluoro-2-methylpropyl)piperidin-4-yl)methoxy)biphenylcarbonyl)piperidin-2-carboxamide
1H NMR (400 MHz, CDCl$_3$) δ 7.69-7.78 (m, 2 H), 7.50-7.54 (m, 1 H), 7.40 (dd, 1 H, J = 8.0, 1.5 Hz), 7.22-7.32 (m, 1 H), 7.06 (d, 1 H, J = 8.9 Hz), 6.28 (s, 1 H), 5.31 (s, 1 H), 3.96 (d, 2 H, J = 6.4 Hz), 3.58 (d, 1 H, J = 13.0 Hz), 3.18-3.25 (m, 1 H), 2.99-3.02 (m, 2 H), 2.49 (s, 1 H), 2.43 (s, 1 H), 2.17-2.23 (m, 2 H), 1.86-1.92 (m, 3 H), 1.73-1.76 (m, 2 H), 1.53-1.66 (m, 5 H), 1.42-1.48 (m, 2 H), 1.40 (s, 3 H), 1.35 (s, 3 H); MS (ESI) m/z 539.3 (M+ + H).

1016  (S)-3'-fluoro-4-((1-(2-fluoro-2-methylpropyl)piperidin-4-yl)methoxy)-4'-(3-hydroxypiperidin-1-carbonyl)biphenyl-3-carbonitrile
1H NMR (400 MHz, CDCl$_3$) δ 7.75-7.76 (m, 1 H), 7.70-7.73 (m, 1 H), 7.48 (t, 1 H, J = 7.4 Hz), 7.32-7.37 (m, 1 H), 7.22-7.27 (m, 1 H), 7.05 (d, 1 H, J = 8.8 Hz), 4.06-4.10 (m, 1 H), 4.00 (d, 2 H, J = 6.3 Hz), 3.11-3.58 (m, 3 H), 2.99-3.02 (m, 2 H), 2.49 (s, 1 H), 2.43 (s, 1 H), 2.17-2.23 (m, 2 H), 1.81-2.05 (m, 5 H), 1.48-1.68 (m, 4 H), 1.42-1.46 (m, 2 H), 1.40 (s, 3 H), 1.35 (s, 3 H); MS (ESI) m/z 512.3 (M+ + H).

1017  (S)-3'-fluoro-4-((1-(2-fluoro-2-methylpropyl)piperidin-4-yl)methoxy)-4'-(3-hydroxypyrrolidine-1-carbonyl)biphenyl-3-carbonitrile
1H NMR (400 MHz, CDCl$_3$) δ 7.76-7.77 (m, 1 H), 7.72 (dd, 1 H, J = 8.8, 1.6 Hz), 7.53 (dd, 1 H, J = 13.3, 7.4 Hz), 7.22-7.32 (m, 1 H), 7.05 (d, 2 H, J = 8.8 Hz), 4.51-4.64 (m, 1 H), 3.95 (d, 2 H, J = 6.3 Hz), 3.33-3.85 (m, 4 H), 2.99-3.02 (m, 2 H), 2.49 (s, 1 H), 2.43 (s, 1 H), 2.15-2.22 (m, 3 H), 2.02-2.08 (m, 1 H), 1.85-1.91 (m, 2 H), 1.70-1.63 (m, 2 H), 1.42-1.49 (m, 2 H), 1.40 (s, 3 H), 1.35 (s, 3 H); MS (ESI) m/z 498.3 (M+ + H).

Example 53. Compound 1036: (S)-1-(5-(3-cyano-4-((1-(2-fluoro-2-methylpropyl)piperidin-4-yl)methoxy)phenyl)picolinoyl)pyrrolidine-2-carboxamide

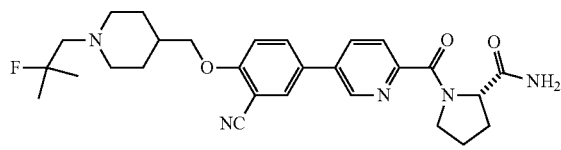 [SMILES: CC(C)(F)CN1CCC(COc2ccc(-c3ccc(C(=O)N4CCC[C@H]4C(N)=O)nc3)cc2C#N)CC1]

Step 1.

Methyl 5-(3-cyano-4-((1-(2-fluoro-2-methylpropyl)piperidin-4-yl)methoxy)phenyl) picolinate: 5-bromo-2-((1-(2-fluoro-2-methylpropyl)piperidin-4-yl)methoxy)benzonitrile (the product of synthesis step 4 of compound 938; 673 mg, 1.82 mmol), 6-(methoxycarbonyl)pyridine-3-ylboronic acid (330 mg, 1.82 mmol), Pd(dppf)Cl$_2$ (59 mg, 0.09 mmol) and Cs$_2$CO$_3$ (1.19 g, 3.65 mmol) were added to water (2 mL)/1,4-dioxane (6 mL). With a microwave radiation, the mixture was heated at 110° C. for 15 minutes, and then cooled to room temperature. The reaction mixture was added with water, and extracted with EtOAc. The obtained organic layer was washed with saturated aqueous brine solution, dried over anhydrous MgSO$_4$, and concentrated under reduced pressure. The obtained concentrate was purified by silica gel column chromatography (EtOAc/hexane=30%~70%) to yield the title compound as brown solid (150 mg, 19%).

Step 2.

5-(3-cyano-4-((1-(2-fluoro-2-methylpropyl)piperidin-4-yl)methoxy)phenyl)picolinic acid: Methyl 5-(3-cyano-4-((1-(2-fluoro-2-methylpropyl)piperidin-4-yl)methoxy)phenyl) picolinate (150 mg, 0.35 mmol) was dissolved in THF (10 mL) and water (5 mL). LiOH.H$_2$O (74 mg, 1.76 mmol) was added thereto little by little at room temperature, following with stirring for 1 hour. After the completion of the reaction, the reaction mixture was concentrated under reduced pressure. The resulting precipitate was filtered, and dried to yield the title compound as white solid (41 mg, 28%).

Step 3.

Compound 1036: 5-(3-cyano-4-((1-(2-fluoro-2-methylpropyl)piperidin-4-yl)methoxy)phenyl)picolinic acid (30 mg, 0.07 mmol), (S)-pyrrolidine-2-carboxamide (22 mg, 0.19 mmol), EDC (37 mg, 0.19 mmol), HOBt (26 mg, 0.19 mmol) and DIPEA (34 µL, 0.19 mmol) were dissolved in CH$_2$Cl$_2$ (1 mL), following with stirring at the same temperature for a day. The reaction mixture was added with water, and extracted with EtOAc. The obtained organic layer was washed with saturated aqueous brine solution, dried over anhydrous MgSO$_4$, and concentrated under reduced pressure. The obtained concentrate was purified by silica gel column chromatography (CH$_2$Cl$_2$/MeOH=95%~5%) to yield the title compound as white solid (21 mg, 42%).

1H NMR (400 MHz, CDCl$_3$) δ 8.77-8.72 (m, 1H), 8.14-8.12 (m, 0.4H), 7.99-7.93 (m, 1.6H), 7.82-7.75 (m, 2H), 7.11-7.08 (m, 1H), 6.39 (brs, 0.5H), 6.39 (brs, 0.5H), 5.43 (brs, 1H), 4.87-4.86 (m, 0.5H), 4.85-4.84 (m, 0.5H), 4.06-3.87 (m, 4H), 3.05 (brs, 2H), 2.46-2.36 (m, 2H), 2.21-2.15 (m, 2H), 2.13-1.97 (m, 5H), 1.64 (brs, 2H), 1.58-1.39 (m, 6H), 1.36-1.25 (m, 2H); MS (ESI) m/z 508 (M++H).

Example 54. Compound 1031: (S)-1-(2'-cyano-4'-((1-(2-fluoro-2-methylpropyl)piperidin-4-yl)methoxy)biphenylcarbonyl)pyrrolidine-2-carboxamide

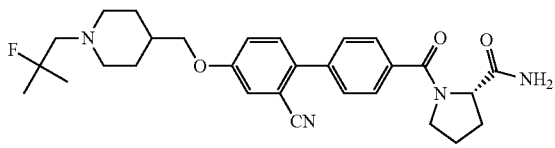 [SMILES: CC(C)(F)CN1CCC(COc2ccc(-c3ccc(C(=O)N4CCC[C@H]4C(N)=O)cc3)c(C#N)c2)CC1]

Step 1.

Methyl 2'-cyano-4'-((1-(2-fluoro-2-methylpropyl)piperidin-4-yl)methoxy)biphenyl-4-carboxylate: DME (4 mL)/H$_2$O (1 mL) was added to 2-bromo-5-((1-(2-fluoro-2-methylpropyl)piperidin-4-yl)methoxy)benzonitrile (the product of synthesis step 4 of compound 1028; 0.30 g, 0.81 mmol), 4-(methoxycarbonyl)phenylboronic acid (0.17 g, 0.97 mmol), Pd(dppf)Cl$_2$ (0.03 g, 0.04 mmol) and Cs$_2$CO$_3$ (0.52 g, 1.62 mmol). With a microwave radiation, the mixture was heated at 110° C. for 20 minutes, and then cooled to room temperature. The reaction mixture was filtered through a Celite pad to remove a solid. The obtained filtrate was diluted with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 4 g cartridge; EtOAc/hexane=0% to 40%), and concentrated to yield the title compound as white solid (0.05 g, 14%).

Step 2.

2'-cyano-4'-((1-(2-fluoro-2-methylpropyl)piperidin-4-yl)methoxy)biphenyl-4-carboxylic acid: Methyl 2'-cyano-4'-((1-(2-fluoro-2-methylpropyl)piperidin-4-yl)methoxy)biphenyl-4-carboxylate (0.05 g, 0.11 mmol) and LiOH.H$_2$O (0.02 g, 0.58 mmol) were dissolved in THF/MeOH (8 mL)/H$_2$O (2 mL) at room temperature. The solution was stirred at the same temperature for 12 hours. The reaction mixture was concentrated under reduced pressure. The concentrate was added with water (10 mL), and stirred. The resulting precipitate was filtered, and dried to yield the title compound as white solid (0.01 g, 20%).

Step 3.

Compound 1031: 2'-cyano-4'-((1-(2-fluoro-2-methylpropyl)piperidin-4-yl)methoxy)biphenyl-4-carboxylic acid (0.03 g, 0.08 mmol), L-prolinamide (0.01 g, 0.10 mmol), HOBt (0.02 g, 0.17 mmol), EDC (0.03 g, 0.17 mmol) and DIPEA (0.02 mL, 0.17 mmol) were dissolved in CH$_2$Cl$_2$ (1 mL) at room temperature. The solution was stirred at the same temperature for 18 hours, added with saturated NH$_4$Cl aqueous solution, and extracted with EtOAc. The organic layer was washed with water, dried over anhydrous MgSO$_4$, and filtered. The filtrate was concentrated under reduced pressure. The concentrate was purified by column chromatography (SiO$_2$, 4 g cartridge; methanol/dichloromethane=0% to 15%), and concentrated to yield the title compound as white solid (0.02 g, 64%).

1H NMR (400 MHz, CDCl$_3$) δ 7.65 (d, 2H, J=8.2 Hz), 7.59 (d, 2H, J=8.3 Hz), 7.42 (d, 1H, J=8.7 Hz), 7.25 (d, 1H, J=2.6 Hz), 7.19 (dd, 1H, J=8.7, 2.6 Hz), 7.01 (s, 1H), 5.59 (s, 1H), 4.83 (dd, 1H, J=7.4, 5.2 Hz), 3.86 (d, 2H, J=6.0 Hz), 3.57-3.68 (m, 2H), 2.99-3.02 (m, 2H), 2.43-2.50 (m, 3H), 2.05-2.21 (m, 4H), 1.78-1.92 (m, 4H), 1.43-1.49 (m, 2H), 1.40 (s, 3H), 1.35 (s, 3H); MS (ESI) m/z 507.3 (M++H).

Example 55. Compound 1028: (S)-1-(2'-cyano-3-fluoro-4'-((1-(2-fluoro-2-methylpropyl)piperidin-4-yl)methoxy)biphenylcarbonyl)pyrrolidine-2-carboxamide

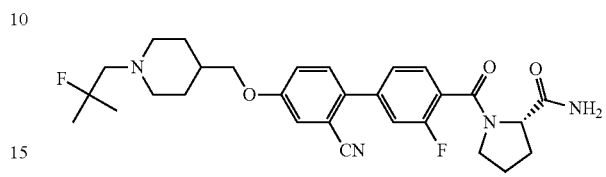

Step 1.

t-butyl 4-(hydroxymethyl)piperidin-1-carboxylate: Piperidin-4-ylmethanol (10.0 g, 86.8 mmol), (Boc)$_2$O (21.9 mL, 95.5 mmol) and TEA (14.4 mL, 104.1 mmol) were dissolved in DCM (50 mL) at room temperature. The solution was stirred at the same temperature for 1 hour. The reaction mixture was added with water, and extracted with ethyl acetate. The organic layer was washed with saturated NH$_4$Cl aqueous solution, dried over anhydrous MgSO$_4$, and filtered. The filtrate was concentrated under reduced pressure. The concentrate was recrystallized with ethyl acetate (10 mL) and hexane (150 mL) at 25° C. to yield the title compound as white solid (18.0 g, 96%).

Step 2.

t-butyl 4-((methylsulfonyloxy)methyl)piperidin-1-carboxylate: t-butyl 4-(hydroxymethyl)piperidin-1-carboxylate (18.0 g, 83.6 mmol), MsCl (7.16 mL, 91.9 mmol) and TEA (13.9 mL, 100.3 mmol) were dissolved in DCM (50 mL) at 0° C., following with stirring at room temperature for 2 hours. The reaction mixture was added with water, and extracted with ethyl acetate. The organic layer was washed with saturated aqueous brine solution, dried over anhydrous MgSO$_4$, and filtered. The filtrate was concentrated under reduced pressure. The concentrate was recrystallized with ethyl acetate (10 mL) and hexane (150 mL) at 25° C. to yield the title compound as white solid (16.0 g, 65%).

Step 3.

t-butyl 4-((4-bromo-3-cyanophenoxy)methyl)piperidin-1-carboxylate: t-butyl 4-((methylsulfonyloxy)methyl)piperidin-1-carboxylate (2.00 g, 6.81 mmol), 2-bromo-5-hydroxybenzonitrile (1.35 g, 6.87 mmol) and K$_2$CO$_3$ (1.88 g, 13.63 mmol) were dissolved in DMF (50 mL) at 80° C., following with stirring at the same temperature for 5 hours. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; EtOAc/hexane=0% to 30%), and concentrated to yield the title compound as white solid (1.90 g, 70%).

Step 4.

2-bromo-5-(piperidin-4-ylmethoxy)benzonitrile hydrochloride: t-butyl 4-((4-bromo-3-cyanophenoxy)methyl)piperidin-1-carboxylate (1.90 g, 4.80 mmol) and 4 M HCl solution in 1,4-dioxane (6.00 mL, 24.03 mmol) were dissolved in CH$_2$Cl$_2$ mL) at room temperature. The solution was stirred at the same temperature for 2 hours. The resulting precipitate was filtered, and dried to yield the title compound as white solid (1.52 g, 95%).

Step 5.

2-bromo-5-((1-(2-hydroxy-2-methylpropyl)piperidin-4-yl)methoxy)benzonitrile: EtOH (8 mL)/H$_2$O (2 mL) was added to 2-bromo-5-(piperidin-4-ylmethoxy)benzonitrile hydrochloride (1.72 g, 5.18 mmol), 2,2-dimethyl oxirane (4.61 mL, 51.86 mmol) and K$_2$CO$_3$ (3.58 g, 25.93 mmol). With a microwave radiation, the mixture was heated at 110° C. for 20 minutes, and then cooled to room temperature. The reaction mixture was added with water, and extracted with EtOAc. The obtained organic layer was washed with saturated aqueous brine solution, dried over anhydrous MgSO$_4$, and filtered. The filtrate was concentrated under reduced pressure. The obtained material was used without further purifying process (1.70 g, 89%, white solid).

Step 6.

2-bromo-5-((1-(2-fluoro-2-methylpropyl)piperidin-4-yl)methoxy)benzonitrile: 2-bromo-5-((1-(2-hydroxy-2-methylpropyl)piperidin-4-yl)methoxy)benzonitrile (1.70 g, 4.62 mmol) was dissolved in CH$_2$Cl$_2$ (20 mL). At 0° C., DAST (0.72 mL, 5.55 mmol) was added thereto, following with stirring at the same temperature for 2 hours. The reaction mixture was added with saturated NaHCO$_3$ aqueous solution, and extracted with EtOAc. The organic layer was washed with saturated NaHCO$_3$ aqueous solution. The organic layer was dried over anhydrous MgSO$_4$, and filtered. The filtrate was concentrated under reduced pressure. The concentrate was purified by column chromatography (SiO$_2$, 12 g cartridge; EtOAc/hexane=0% to 30%), and concentrated to yield the title compound as white solid (1.10 g, 64%).

Step 7.

Ethyl 2'-cyano-3-fluoro-4'-((1-(2-fluoro-2-methylpropyl)piperidin-4-yl)methoxy)biphenyl-4-carboxylate: DME (4 mL)/H$_2$O (1 mL) was added to 2-bromo-5-((1-(2-fluoro-2-methylpropyl)piperidin-4-yl)methoxy)benzonitrile (0.30 g, 0.81 mmol), 4-(ethoxycarbonyl)-3-fluorophenylboronic acid (0.17 g, 0.97 mmol), Pd(dppf)Cl$_2$ (0.03 g, 0.04 mmol) and Cs$_2$CO$_3$ (0.52 g, 1.62 mmol). With a microwave radiation, the mixture was heated at 110° C. for 20 minutes, and then cooled to room temperature. The reaction mixture was filtered through a Celite pad to remove a solid. The obtained filtrate was diluted with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 4 g cartridge; EtOAc/hexane=0% to 40%), and concentrated to yield the title compound as white solid (0.16 g, 43%).

Step 8.

2'-cyano-3-fluoro-4'-((1-(2-fluoro-2-methylpropyl)piperidin-4-yl)methoxy)biphenyl-4-carboxylic acid: Ethyl 2'-cyano-3-fluoro-4'-((1-(2-fluoro-2-methylpropyl)piperidin-4-yl)methoxy)biphenyl-4-carboxylate (0.16 g, 0.35 mmol) and LiOH.H$_2$O (0.07 g, 1.75 mmol) were dissolved in THF/MeOH (8 mL)/H$_2$O (2 mL) at room temperature. The solution was stirred at the same temperature for 12 hours, the reaction mixture was concentrated under reduced pressure. The concentrate was added with water (15 mL), and stirred. The resulting precipitate was filtered, and dried to yield the title compound as white solid (0.15 g, 93%).

Step 9.

Compound 1028: 2'-cyano-3-fluoro-4'-((1-(2-fluoro-2-methylpropyl)piperidin-4-yl)methoxy)biphenyl-4-carboxylic acid (0.04 g, 0.10 mmol), L-prolinamide (0.01 g, 0.12 mmol), HOBt (0.02 g, 0.21 mmol), EDC (0.04 g, 0.21 mmol) and DIPEA (0.03 mL, 0.21 mmol) were dissolved in CH$_2$Cl$_2$ (1 mL) at room temperature. The solution was stirred at the same temperature for 18 hours, added with saturated NR$_4$Cl aqueous solution, and extracted with EtOAc. The organic layer was washed with water, dried over anhydrous MgSO$_4$, and filtered. The filtrate was concentrated under reduced pressure. The concentrate was purified by column chromatography (SiO$_2$, 4 g cartridge; methanol/dichloromethane=0% to 15%), and concentrated to yield the title compound as white solid (0.05 g, 92%).

1H NMR (400 MHz, CDCl$_3$) δ 7.52-7.56 (m, 1H), 7.41 (dd, 2H, J=8.0, 1.7 Hz), 7.30-7.33 (m, 2H), 7.19-7.22 (m, 1H), 6.91 (s, 1H), 5.45 (s, 1H), 4.83 (dd, 1H, J=7.6, 3.9 Hz), 3.87 (d, 2H, J=6.0 Hz), 3.44-3.56 (m, 2H), 2.99-3.02 (m, 2H), 2.48-2.52 (m, 2H), 2.43 (s, 1H), 2.06-2.21 (m, 4H), 1.91-1.94 (m, 2H), 1.79-1.81 (m, 2H), 1.635 (s, 2H), 1.41 (s, 3H), 1.35 (s, 3H); MS (ESI) m/z 525.3 (M++H).

According to the above-described synthesis process of compound 1028, the compounds of Table 32 were synthesized using 2'-cyano-3-fluoro-4'-((1-(2-fluoro-2-methylpropyl)piperidin-4-yl)methoxy)biphenyl-4-carboxylic acid and the reactant of Table 31.

TABLE 31

| Compound No. | Reactant | Yield (%) |
| --- | --- | --- |
| 1029 | (R)-piperidin-3-ol | 89 |
| 1030 | (R)-piperidin-2-carboxamide hydrochloride | 60 |
| 1115 | piperidin-4-ol | 16 |

TABLE 32

| Compound No. | Compound Name, $^1$H-NMR, MS (ESI) |
| --- | --- |
| 1029 | (R)-3'-fluoro-4-((1-(2-fluoro-2-methylpropyl)piperidin-4-yl)methoxy)-4'-(3-hydroxypiperidin-1-carbonyl)biphenyl-2-carbonitrile<br>1H NMR (400 MHz, CDCl$_3$) δ 7.49 (t, 1 H, J = 7.4 Hz), 7.37-7.41 (m, 2 H), 7.22-7.29 (m, 2 H), 7.19 (dd, 1 H, J = 8.7, 2.7 Hz), 3.90-3.93 (m, 1 H), 3.86 (d, 2 H, J = 6.0 Hz), 3.37-3.61 (m, 3 H), 2.99-3.02 (m, 2 H), 2.49 (s, 1 H), 2.43 (s, 1 H), 2.18 (t, 3 H, J = 10.9 Hz), 1.91-2.05 (m, 2 H), 1.79-1.86 (m, 4 H), 1.60-1.69 (m, 2 H), 1.42-1.49 (m, 2H), 1.40 (s, 3 H), 1.35 (s, 3 H); MS (ESI) m/z 512.3 (M+ + H). |
| 1030 | (R)-1-(2'-cyano-3-fluoro-4'-((1-(2-fluoro-2-methylpropyl)piperidin-4-yl)methoxy)biphenylcarbonyl)piperidin-2-carboxamide<br>1H NMR (400 MHz, CDCl$_3$) δ 7.65 (t, 1 H, J = 5.7 Hz), 7.38 (t, 2 H, J = 5.7 Hz), 7.30 (d, 2 H, J = 10.4 Hz), 7.20 (dd, 1 H, J = 8.7, 2.5 Hz), 6.30 (s, 1 H), 5.65 (s, 1 H), 5.45 (s, 1 H), 3.86 (d, 2 H, J = 6.0 Hz), 3.59-3.63 (m, 1 H), 3.21-3.24 (m, 1H), 2.99-3.02 (m, 2 H), 2.43-2.48 (m, 2 H), 2.18 (t, 2 H, J = 11.0 Hz), 1.56-1.81 (m, 8 H), 1.42-1.48 (m, 2 H), 1.40 (s, 3 H), 1.35 (s, 3 H); MS (ESI) m/z 539.3 (M+ + H). |

| Compound No. | Compound Name, $^1$H-NMR, MS (ESI) |
|---|---|
| 1115 | 3'-fluoro-4-((1-(2-fluoro-2-methylpropyl)piperidin-4-yl)methoxy)-4'-(4-hydroxypiperidin-1-carbonyl)biphenyl-2-carbonitrile<br>1H NMR (400 MHz, CDCl$_3$) δ 7.46 (t, 1 H, J = 7.4 Hz), 7.34-7.38 (m, 2 H), 7.22-7.25 (m, 2 H), 7.17 (dd, 1 H, J = 8.8, 2.8 Hz), 4.20 (m, 1 H), 3.99 (s, 1 H), 3.83 (d, 2 H, J = 5.6 Hz), 3.59 (m, 1 H), 3.20-3.46 (s, 2 H), 2.96-2.99 (m, 2 H), 2.40-2.45 (m, 2 H), 2.12-2.18 (m, 2 H), 1.98-2.02 (m, 2 H), 1.75-1.87 (m, 3 H), 1.59-1.68 (m, 1 H), 1.21-1.55 (m, 2 H), 1.42-1.45 (m, 2 H), 1.37 (s, 3 H), 1.32 (s, 3 H); MS (ESI) m/z 512.2 (M+ + H). |

Example 56. Compound 691: (S)-1-(4-(5-((1-(2-fluoro-2-methylpropyl)piperidin-4-yl)methoxy)pyridine-2-yl)benzoyl)pyrrolidine-2-carboxamide

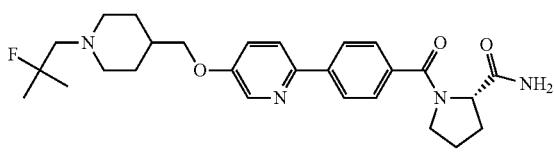 [SMILES: CC(C)(F)CN1CCC(COc2ccc(-c3ccc(C(=O)N4CCC[C@H]4C(N)=O)cc3)nc2)CC1]

Step 1.

t-butyl 4-((6-chloropyridine-3-yloxy)methyl)piperidin-1-carboxylate: t-Butyl 4-((methylsulfonyloxy)methyl)piperidin-1-carboxylate (the product of synthesis step 2 of compound 431; 2.0 g, 6.82 mmol) was dissolved in ACN 10 mL. 6-chloropyridine-3-ol (1.06 g, 8.18 mmol), Cs$_2$CO$_3$ (3.33 g, 10.23 mmol) was added thereto, and refluxed with heating for a day. The reaction mixture was added with water, and extracted with EtOAc. The obtained organic layer was washed with saturated aqueous brine solution, dried over MgSO$_4$, filtered to remove the solid residue, and the filtrate was concentrated under reduced pressure. The concentrate was purified by column chromatography (ISCO silica gel cartridge, EtOAc/Hexane) to yield the title compound as white solid (1.6 g, 72%).

Step 2.

2-chloro-5-(piperidin-4-ylmethoxy)pyridine hydrochloride: t-butyl 4-((6-chloropyridine-3-yloxy)methyl)piperidin-1-carboxylate (1.6 g, 4.90 mmol) was dissolved in CH$_2$Cl$_2$ 8 mL. 4 M HCl 1.47 mL was added thereto, following with stirring at room temperature for 2 hours. The reaction mixture was filtered, washed with hexane, and evaporated under reduced pressure to yield the title compound as white solid (1.25 g, 97%).

Step 3.

1-(4-((6-chloropyridine-3-yloxy)methyl)piperidin-1-yl)-2-methylpropan-2-ol: 2-chloro-5-(piperidin-4-ylmethoxy)pyridine hydrochloride (1.25 g, 4.75 mmol) was dissolved in EtOH 6 mL. 2,2-dimethyloxirane (3.42 g, 47.5 mmol), K$_2$CO$_3$ (1.31 g, 9.5 mmol) and water 3 mL were added thereto. With a microwave radiation, the mixture was stirred at 110° C. for 20 minutes. After the completion of the reaction, EtOH was evaporated from the reaction mixture under reduced pressure, and then a little of water was added to thereto. The resulting precipitate was filtered, and dried under reduced pressure to yield the title compound as white solid (980 g, 69%).

Step 4.

2-chloro-5-((1-(2-fluoro-2-methylpropyl)piperidin-4-yl)methoxy)pyridine: 1-(4-((6-chloropyridine-3-yloxy)methyl)piperidin-1-yl)-2-methylpropan-2-ol (980 mg, 3.28 mmol) was dissolved in CH$_2$Cl$_2$ 6 mL. And then, DAST (793 mg, 4.92 mmol) was added thereto, following with stirring at room temperature for 3 hours. After the completion of the reaction, the reaction mixture was added with a saturated NaHCO$_3$ aqueous solution, and extracted with CH$_2$Cl$_2$. The organic layer washed with saturated aqueous brine solution, dried over MgSO$_4$, and filtered to remove the solid residue. The filtrate was concentrated under reduced pressure to yield the title compound as yellow solid (460 mg, 46%).

Step 5.

Methyl 4-(5-((1-(2-fluoro-2-methylpropyl)piperidin-4-yl)methoxy)pyridine-2-yl)benzoate: 2-chloro-5-((1-(2-fluoro-2-methylpropyl)piperidin-4-yl)methoxy)pyridine (230 mg, 0.77 mmol), 4-(methoxycarbonyl)phenylboronic acid (165 mg, 0.92 mmol), Pd(dppf)Cl$_2$ (62 mg, 0.08 mmol), Na$_2$CO$_3$ (162 mg, 1.53 mmol) were dissolved in DME 6 mL and water 2 mL, and then refluxed with heating for a day. The reaction mixture was filtered through Celite. The filtrate was added with saturated NaHCO$_3$ aqueous solution, and extracted with EtOAc. The organic layer was dried over MgSO$_4$, filtered to remove the solid residue, and the filtrate was concentrated under reduced pressure. The concentrate was purified by column chromatography (ISCO silica gel cartridge, MeOH/CH$_2$Cl$_2$) to yield the title compound as yellow solid (220 mg, 71%).

Step 6.

4-(5-((1-(2-fluoro-2-methylpropyl)piperidin-4-yl)methoxy)pyridine-2-yl)benzoic acid: methyl 4-(5-((1-(2-fluoro-2-methylpropyl)piperidin-4-yl)methoxy)pyridine-2-yl)benzoate (220 mg, 0.55 mmol) was dissolved in THF:MeOH:Water=210.5 mL. LiOH.H$_2$O (46 mg, 1.10 mmol) was added thereto. And then, the mixture was refluxed with heating for 3 hours. After the completion of the reaction, the solvent was dried under reduced pressure to yield the title compound as yellow solid (210 mg, 98%).

Step 7.

Compound 691: 4-(5-((1-(2-fluoro-2-methylpropyl)piperidin-4-yl)methoxy)pyridine-2-yl)benzoic acid (40 mg, 0.10 mmol), (S)-pyrrolidine-2-carboxamide (24 mg, 0.20 mmol) and BOP (91 mg, 0.21 mmol) were dissolved in DMF 1 mL. After stirring for 10 minutes at room temperature, TEA (31 mg, 0.31 mmol) was added thereto, following with stirring at 50° C. for 8 hours. The reaction mixture was added with water, and extracted with EtOAc. The organic layer was washed with saturated aqueous brine solution, dried over MgSO$_4$, and filtered to remove the solid residue. The filtrate was concentrated under reduced pressure. The concentrate was purified by column chromatography (ISCO silica gel cartridge, MeOH/CH$_2$Cl$_2$) to yield the title compound as yellow solid (19 mg, 38%).

1H NMR (400 MHz, CDCl$_3$) δ 8.39 (d, 1H, J=2.9 Hz), 7.97 (d, 2H, J=8.2 Hz), 7.68 (d, 1H, J=8.7 Hz), 7.52 (d, 2H, J=8.2 Hz), 3.90 (d, 2H, J=6.0 Hz), 3.14 (m, 3H), 3.02 (m, 5H), 2.46 (m, 2H), 2.04 (m, 2H), 1.73 (m, 2H), 1.46 (m, 2H), 1.36 (m, 8H); MS (ESI) m/z 469 (M+H).

According to the above-described synthesis process of compound 691, the compounds of Table 34 were synthesized using 4-(5-((1-(2-fluoro-2-methylpropyl)piperidin-4-yl)methoxy)pyridine-2-yl)benzoic acid and the reactant of Table 33.

TABLE 33

| Compound No. | Reactant | Yield (%) |
| --- | --- | --- |
| 692 | (R)-pyrrolidine-2-ylmethanol | 51 |
| 693 | (S)-piperidin-3-ol | 42 |

TABLE 33-continued

| Compound No. | Reactant | Yield (%) |
| --- | --- | --- |
| 763 | (R)-pyrrolidine-3-ol | 40 |
| 764 | (S)-pyrrolidine-3-ol | 42 |
| 765 | (S)-pyrrolidine-2-ylmethanol | 32 |
| 766 | (R)-piperidin-3-ol hydrochloride | 30 |
| 804 | piperidin-4-carboxamide | 66 |
| 821 | (R)-piperidin-2-carboxamide | 49 |

TABLE 34

| Compound No. | Compound Name, $^1$H-NMR, MS (ESI) |
| --- | --- |
| 692 | (R)-(4-(5-((1-(2-fluoro-2-methylpropyl)piperidin-4-yl)methoxy)pyridine-2-yl)phenyl)(2-(hydroxymethyl)pyrrolidine-1-yl)methanone<br>1H NMR (400 MHz, CDCl$_3$) δ 8.46 (s, 2 H), 8.20 (d, 1 H, J = 8.0 Hz), 8.10 (d, 1 H, J = 10.8 Hz), 7.48 (t, 1 H, J = 7.4 Hz), 4.12-4.09 (m, 1 H), 3.96 (d, 2 H, J = 5.9 Hz), 3.58-3.54 (m, 1 H), 3.37-3.33 (m, 1 H), 3.25-3.20 (m, 1 H), 3.13-3.03 (m, 2 H), 2.56-2.45 (m, 2 H), 2.27-2.16 (m, 2 H), 2.05-1.81 (m, 6 H), 1.69-1.62 (m, 3 H), 1.47 (s, 3 H), 1.42 (s, 3 H), 1.37-1.28 (m, 2 H); MS (ESI) m/z 489 (M+ + H). |
| 693 | (S)-(4-(5-((1-(2-fluoro-2-methylpropyl)piperidin-4-yl)methoxy)pyridine-2-yl)phenyl)(3-hydroxypiperidin-1-yl)methanone<br>1H NMR (400 MHz, CDCl$_3$) δ 8.37 (d, 1 H, J = 2.7 Hz), 7.95 (d, 2 H, J = 8.4 Hz), 7.66 (d, 1 H, J = 8.7 Hz), 7.49 (d, 2 H, J = 8.3 Hz), 7.24 (m, 1 H), 3.88 (m, 4 H), 3.60 (m, 4 H), 3.01 (m, 2 H), 2.48 (s, 1 H), 2.43 (s, 1 H), 2.09 (m, 2 H), 1.82 (m, 6 H), 1.44 (m, 3 H), 1.39 (s, 3 H), 1:34 (s, 3 H); MS (ESI) m/z 470 (M + H). |
| 763 | (R)-(4-(5-((1-(2-fluoro-2-methylpropyl)piperidin-4-yl)methoxy)pyridine-2-yl)phenyl)(3-hydroxypyrrolidine-1-yl)methanone<br>1H NMR (400 MHz, CDCl$_3$) δ 8.38 (d, 1 H, J = 2.7 Hz), 7.97-7.94 (m, 2 H), 7.68-7.59 (m, 3 H), 7.28-7.25 (m, 1 H), 4.59-4.46 (m, 1 H), 3.90 (d, 2 H, J = 6.0 Hz), 3.85-3.81 (m, 2 H), 3.78-3.62 (m, 1 H), 3.56-3.46 (m, 1 H), 3.07-3.04 (m, 2 H), 2.53-2.48 (m, 2 H), 2.37-2.34 (m, 1 H), 2.26-2.20 (m, 2 H), 2.12-1.98 (m, 2 H), 1.84-1.82 (m, 3 H), 1.51-1.48 (m, 2 H), 1.42 (s, 3 H), 1.40 (s, 3 H); MS (ESI) m/z 456 (M+ + H). |
| 764 | (S)-(4-(5-((1-(2-fluoro-2-methylpropyl)piperidin-4-yl)methoxy)pyridine-2-yl)phenyl)(3-hydroxypyrrolidine-1-yl)methanone<br>1H NMR (400 MHz, CDCl$_3$) δ 8.38 (d, 1 H, J = 2.7 Hz), 7.97-7.94 (m, 2 H), 7.68-7.59 (m, 3 H), 7.28-7.25 (m, 1 H), 4.59-4.46 (m, 1 H), 3.90 (d, 2 H, J = 6.0 Hz), 3.85-3.81 (m, 2 H), 3.78-3.62 (m, 1 H), 3.56-3.46 (m, 1 H), 3.07-3.04 (m, 2 H), 2.53-2.48 (m, 2 H), 2.37-2.34 (m, 1 H), 2.26-2.20 (m, 2 H), 2.12-1.98 (m, 2 H), 1.84-1.82 (m, 3 H), 1.51-1.48 (m, 2 H), 1.42 (s, 3 H), 1.40 (s, 3 H); MS (ESI) m/z 456 (M+ + H). |
| 765 | (S)-(4-(5-((1-(2-fluoro-2-methylpropyl)piperidin-4-yl)methoxy)pyridine-2-yl)phenyl)(2-(hydroxymethyl)pyrrolidine-1-yl)methanone<br>1H NMR (400 MHz, CDCl$_3$) δ 8.39 (d, 1 H, J = 2.9 Hz), 7.99 (d, 2 H, J = 8.2 Hz), 7.69 (d, 1 H, J = 8.7 Hz), 7.60 (d, 1 H, J = 8.2 Hz), 7.29-7.26 (m, 2 H), 4.95-4.93 (m, 1 H), 4.46-4.41 (m, 1 H), 3.90 (d, 2 H, J = 5.9 Hz), 3.85-3.74 (m, 2 H), 3.60-3.49 (m, 2 H), 3.03 (brs, 2 H), 2.51-2.46 (brs, 2 H), 2.27-2.18 (m, 2 H), 2.05-1.81 (m, 5 H), 1.78-1.63 (m, 2 H), 1.60-1.48 (m, 2 H), 1.42 (s, 3 H), 1.36 (s, 3 H); MS (ESI) m/z 470 (M+ + H). |
| 766 | (R)-(4-(5-((1-(2-fluoro-2-methylpropyl)piperidin-4-yl)methoxy)pyridine-2-yl)phenyl)(3-hydroxypiperidin-1-yl)methanone<br>1H NMR (400 MHz, CDCl$_3$) δ 8.38 (d, 2 H, J = 2.6 Hz), 7.97 (d, 2 H, J = 8.2 Hz), 7.68 (d, 1 H, J = 8.7 Hz), 7.51 (d, 2 H, J = 8.2 Hz), 7.28-7.25 (m, 1 H), 4.02-4.00 (m, 1 H), 3.91 (d, 2 H, J = 5.8 Hz), 3.80-3.46 (m, 3 H), 3.25-3.06 (m, 2 H), 2.67-2.49 (m, 2 H), 2.37-2.12 (m, 2 H), 2.05-1.94 (m, 2 H), 1.85-1.83 (m, 4 H), 1.71-1.66 (m, 3 H), 1.52-1.50 (m, 2 H), 1.43 (s, 3 H), 1.38 (s, 3 H); MS (ESI) m/z 471 (M+ + H). |
| 804 | 1-(4-(5-((1-(2-fluoro-2-methylpropyl)piperidin-4-yl)methoxy)pyridine-2-yl)benzoyl)piperidin-4-carboxamide<br>1H NMR (400 MHz, CDCl$_3$) δ 8.42-8.41 (m, 1 H), 8.00 (d, 2 H, J = 8.4 Hz), 7.71 (d, 1 H, J = 8.4 Hz), 7.51 (d, 2 H, J = 6.4 Hz), 7.29-7.28 (m, 1 H), 5.71 (d, 2 H, J = 30.8 Hz), 4.73 (brs, 1 H), 3.93-3.92 (m, 3 H), 3.05-3.02 (m, 4 H), 2.51-2.46 (m, 3 H), 2.22 (t, 2 H, J = 11.4 Hz), 1.98-1.83 (m, 7 H), 1.58-1.22 (m, 8 H); MS (ESI) m/z 497 (M+ + H) |
| 821 | (R)-1-(4-(5-((1-(2-fluoro-2-methylpropyl)piperidin-4-yl)methoxy)pyridine-2-yl)benzoyl)piperidin-2-carboxamide<br>1H NMR (400 MHz, CDCl$_3$) δ 8.39-8.38 (m, 1 H), 7.99 (d, 2 H, J = 8.0 Hz), 7.69 (d, 2 H, J = 8.7 Hz), 7.54 (d, 2 H, J = 7.6 Hz), 7.28-7.25 (m, 1 H), 6.52 (brs, 1 H), 5.53 (brs, 1 H), 5.29 (brs, 1 H), 3.90 (d, 2 H, J = 6.0 Hz), 3.78 (d, 1 H, J = 12.7 Hz), 3.12-3.10 (m, 1 H), 3.01 (d, 2 H, J = 11.2 Hz), 2.48 (s, 1 H), 2.43 (s, 1 H), 2.34 (d, 1 H, J = 13.2 Hz), 2.19 (t, 2 H, J = 11.0 Hz), 2.05-1.43 (m, 8 H), 1.40-1.24 (m, 8 H); MS (ESI) m/z 497 (M+ + H). |

Example 57. Compound 696: (S)-1-(3-fluoro-4-(5-((1-(2-fluoro-2-methylpropyl)piperidin-4-yl)methoxy)pyridine-2-yl)benzoyl)pyrrolidine-2-carboxamide

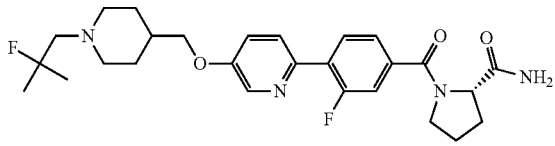 [SMILES: CC(C)(F)CN1CCC(COc2ccc(-c3ccc(C(=O)N4CCC[C@H]4C(N)=O)cc3F)nc2)CC1]

Step 1.

Methyl 3-fluoro-4-(5-((1-(2-fluoro-2-methylpropyl)piperidin-4-yl)methoxy)pyridine-2-yl)benzoate: 2-chloro-5-((1-(2-fluoro-2-methylpropyl)piperidin-4-yl)methoxy)pyridine (the product of synthesis step 5 of compound 691; 366 mg, 1.06 mmol), 2-fluoro-4-(methoxycarbonyl)phenylboronic acid (231 mg, 1.17 mmol), Pd(dppf)Cl$_2$ (87 mg, 0.11 mmol), Na$_2$CO$_3$ (225 mg, 2.12 mmol) were dissolved in DME 6 mL and water 2 mL, and then refluxed with heating for a day. The reaction mixture was filtered through Celite. The filtrate was added with saturated NaHCO$_3$ aqueous solution, and extracted with EtOAc. The organic layer was dried over MgSO$_4$, filtered to remove the solid residue, and the filtrate was concentrated under reduced pressure. The concentrate was purified by column chromatography (ISCO silica gel cartridge, MeOH/CH$_2$Cl$_2$) to yield the title compound as yellow solid (210 mg, 47%).

Step 2.

3-fluoro-4-(5-((1-(2-fluoro-2-methylpropyl)piperidin-4-yl)methoxy)pyridine-2-yl)benzoic acid: Methyl 3-fluoro-4-(5-((1-(2-fluoro-2-methylpropyl)piperidin-4-yl)methoxy)pyridine-2-yl)benzoate (220 mg, 0.53 mmol) was dissolved in THF/MeOH/H$_2$O=210.5 mL. LiOH.H$_2$O (44 mg, 1.05 mmol) was added thereto, and refluxed with heating for 3 hours. After the completion of the reaction, the solvent was dried under reduced pressure, following with adjusting pH to below 6 using 1N HCl. The resulting precipitate was filtered to yield the title compound as white solid (195 mg, 91%).

Step 3.

Compound 696: 3-fluoro-4-(5-((1-(2-fluoro-2-methylpropyl)piperidin-4-yl)methoxy)pyridine-2-yl)benzoic acid (40 mg, 0.10 mmol), (R)-pyrrolidine-2-ylmethanol (23 mg, 0.20 mmol) and BOP (88 mg, 0.20 mmol) were dissolved in DMF 1 mL, following with stirring for 10 minutes at room temperature. TEA (30 mg, 0.30 mmol) was added thereto, following with stirring at 50° C. for 8 hours. The reaction mixture was added with water, and extracted with EtOAc. The organic layer was washed with saturated aqueous brine solution, dried over MgSO$_4$, filtered to remove the solid residue, and the filtrate was concentrated under reduced pressure. The concentrate was purified by column chromatography (ISCO silica gel cartridge, MeOH/CH$_2$Cl$_2$) to yield the title compound as yellow solid (20 mg, 40%).

1H NMR (400 MHz, CDCl$_3$) δ 8.42 (d, 1H, J=2.8 Hz), 8.05 (t, 1H, J=7.9 Hz), 7.78 (d, 1H, J=8.8 Hz), 7.38 (m, 2H), 7.27 (m, 2H), 6.92 (s, 1H), 5.51 (s, 1H), 4.79 (m, 1H), 3.91 (d, 2H, J=5.9 Hz), 3.55 (m, 2H), 3.01 (m, 2H), 2.46 (m, 3H), 2.13 (m, 2H), 2.06 (m, 2H), 1.92 (m, 4H), 1.35 (m, 5H), 1.26 (s, 3H); MS (ESI) m/z 501 (M+H).

According to the above-described synthesis process of compound 696, the compounds of Table 36 were synthesized using 2-fluoro-4-(5-((1-(2-fluoro-2-methylpropyl)piperidin-4-yl)methoxy)pyridine-2-yl)benzoic acid and the reactant of Table 35.

TABLE 35

| Compound No. | Reactant | Yield (%) |
| --- | --- | --- |
| 697 | (R)-pyrrolidine-2-ylmethanol | 47 |
| 698 | (R)-piperidin-3-ol | 39 |
| 699 | (S)-pyrrolidine-3-ol | 17 |
| 813 | piperidin-4-carboxamide hydrochloride | 39 |
| 815 | (R)-pyrrolidine-3-ol | 52 |

TABLE 36

| Compound No. | Compound Name, $^1$H-NMR, MS (ESI) |
| --- | --- |
| 697 | (R)-(3-fluoro-4-(5-((1-(2-fluoro-2-methylpropyl)piperidin-4-yl)methoxy)pyridine-2-yl)phenyl)(2-(hydroxymethyl)pyrrolidine-1-yl)methanone<br>1H NMR (400 MHz, CDCl$_3$) δ 8.42 (d, 1 H, J = 2.9 Hz), 8.04 (t, 1 H, J = 7.9 Hz), 7.77 (d, 1 H, J = 8.4 Hz), 7.39 (d, 1 H, J = 8.0 Hz), 7.33 (d, 1 H, J = 11.4 Hz), 7.26 (m, 1 H), 4.73 (s, 1 H), 4.41 (m, 1 H), 3.90 (d, 2 H, J = 6.0 Hz), 3.76 (m, 2 H), 3.57 (m, 2 H), 3.01 (m, 2 H), 2.49 (s, 1 H), 2.43 (s, 1 H), 2.19 (m, 3 H), 1.80 (m, 6 H), 1.47 (m, 5 H), 1.30 (s, 3 H); MS (ESI) m/z 488 (M + H). |
| 698 | (R)-(3-fluoro-4-(5-((1-(2-fluoro-2-methylpropyl)piperidin-4-yl)methoxy)pyridine-2-yl)phenyl)(3-hydroxypiperidin-1-yl)methanone<br>1H NMR (400 MHz, CDCl$_3$) δ 8.41 (d, 1 H, J = 2.8 Hz), 8.00 (t, 1 H, J = 7.9 Hz), 7.74 (m, 1 H), 7.25 (m, 3 H), 3.86 (m, 4 H), 3.33 (m, 3 H), 3.01 (m, 2 H), 2.50 (s, 3 H), 2.44 (s, 3 H), 2.20 (m, 2 H), 1.80 (m, 6 H), 1.66 (m, 2 H), 1.43 (m, 5 H), 1.31 (s, 3 H); MS (ESI) m/z 488 (M + H). |
| 699 | (S)-(3-fluoro-4-(5-((1-(2-fluoro-2-methylpropyl)piperidin-4-yl)methoxy)pyridine-2-yl)phenyl)(3-hydroxypyrrolidine-1-yl)methanone<br>1H NMR (400 MHz, CDCl$_3$) δ 8.41 (m, 1 H), 8.01 (m, 1 H), 7.77 (d, 1 H, J = 8.6 Hz), 7.40 (m, 2 H), 7.25 (m, 1 H), 4.62 (m, 0.5 H), 4.50 (m, 0.5 H), 3.90 (m, 2 H), 3.79 (m, 2 H), 3.55 (m, 1 H), 2.90 (m, 2 H), 2.43 (m, 2 H), 2.01 (m, 2 H), 1.88 (m, 2 H), 1.59 (m, 4 H), 1.26 (m, 9 H); MS (ESI) m/z 474 (M + H). |
| 813 | 1-(3-fluoro-4-(5-((1-(2-fluoro-2-methylpropyl)piperidin-4-yl)methoxy)pyridine-2-yl)benzoyl)piperidin-4-carboxamide<br>1H NMR (400 MHz, CDCl$_3$) δ 8.40 (m, 1 H), 8.00 (t, 1 H, J = 7.9 Hz), 7.75 (m, 1 H), 7.16 (m, 3 H), 5.63 (m, 2 H), 4.87 (s, 1 H), 3.89 (m, 3 H), 3.03 (m, 4 H), 2.42 (m, 3 H), 2.22 (m, 2 H), 1.51 (m, 7 H), 1.35 (m, 5 H), 1.25 (s, 3 H) |

TABLE 36-continued

Compound No. Compound Name, $^1$H-NMR, MS (ESI)

815    (S)-(3-fluoro-4-(5-((1-(2-fluoro-2-methylpropyl)piperidin-4-yl)methoxy)pyridine-
2-yl)phenyl)(2-(hydroxymethyl)pyrrolidine-1-yl)methanone
1H NMR (400 MHz, CDCl$_3$) δ 8.40 (m, 1 H), 8.02 (t, 1 H, J = 2.8 Hz), 7.75 (m, 1
H), 7.31 (m, 2 H), 7.25 (m, 1 H), 4.76 (s, 1 H), 4.41 (m, 1 H), 3.89 (d, 2 H, J = 7.4
Hz), 3.75 (m, 2 H), 3.52 (m, 2 H), 3.00 (m, 2 H), 2.49 (s, 1 H), 2.43 (s, 1 H), 1.92
(m, 2 H), 1.77 (m, 6 H), 1.45 (m, 5 H), 1.31 (m, 2 H)

Example 58. Compound 770: (S)-1-(2-fluoro-4-(5-((1-(2-fluoro-2-methylpropyl)piperidin-4-yl)methoxy)pyridine-2-yl)benzoyl)pyrrolidine-2-carboxamide

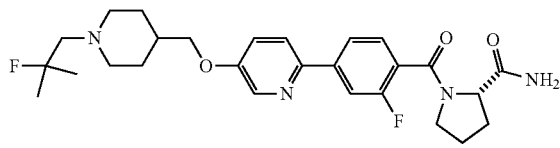 [SMILES: CC(C)(F)CN1CCC(COc2ccc(-c3ccc(C(=O)N4CCC[C@H]4C(N)=O)c(F)c3)nc2)CC1]

Step 1.

t-butyl 4-(hydroxymethyl)piperidin-1-carboxylate: Piperidin-4-ylmethanol (33.0 g, 286.53 mmol) was dissolved in DCM (400 mL). TEA (47.9 mL, 343.84 mmol) was added thereto, (Boc)$_2$O (68.79 g, 315.18 mmol) was added thereto, following with stirring at room temperature for 1 hour. After the completion of the reaction, the reaction mixture was added with a saturated NH$_4$Cl aqueous solution, and extracted with DCM. The organic layer was dried over anhydrous MgSO$_4$, and concentrated under reduced pressure. The concentrate was recrystallized with HX:EA=(4:1) to yield the title compound as yellow solid (59.0 g, 96%).

Step 2.

t-butyl 4-((methylsulfonyloxy)methyl)piperidin-1-carboxylate: t-butyl 4-(hydroxymethyl)piperidin-1-carboxylate (59.0 g, 274.05 mmol) was dissolved in DCM (400 mL). TEA (45.84 mL, 328.86 mmol) was added thereto. At 0° C., MsCl (23.4 mL, 301.45 mmol) was added thereto, following with stirring at room temperature for 2 hours. After the completion of the reaction, reaction mixture was added with water, and extracted with DCM. The organic layer was dried over anhydrous MgSO$_4$, and filtered. The filtrate was concentrated under reduced pressure. The concentrate was recrystallized with HX:EA=(4:1) to yield the title compound as white solid (70.0 g, 87%).

Step 3.

t-butyl 4-((6-chloropyridine-3-yloxy)methyl)piperidin-1-carboxylate: t-butyl 4-((methylsulfonyloxy)methyl)piperidin-1-carboxylate (3.00 g, 10.23 mmol) was dissolved in ACN (50 mL). Cs$_2$CO$_3$ (4.99 g, 15.34 mmol) was added thereto. And then, 6-chloropyridine-3-ol (1.32 g, 10.23 mmol) was added thereto, following with stirring for 5 hours at the reflux temperature. After the completion of the reaction, the reaction mixture was added with water, and then extracted with EtOAc. The organic layer was washed with saturated aqueous brine solution, dried over Na$_2$SO$_4$, and filtered. The filtrate was concentrated under reduced pressure. The concentrate was purified by column chromatography (SiO$_2$; hexaneEtOAc=5/1) to yield the title compound as white solid (2.8 g, 83%).

Step 4.

2-chloro-5-(piperidin-4-ylmethoxy)pyridine hydrochloride: t-butyl 4-((6-chloropyridine-3-yloxy)methyl)piperidin-1-carboxylate (2.80 g, 8.57 mmol) was dissolved in DCM (70 mL) was added thereto, following with stirring for 5 minutes. And then, 4 M HCl solution in 1,4-dioxane (42.84 mL, 171.35 mmol) was added dropwise slowly thereto, following with stirring for 1 hour at room temperature. After the completion of the reaction, the reaction mixture was filtered to yield the title compound as white solid (1.50 g, 77%).

Step 5.

1-(4-((6-chloropyridine-3-yloxy)methyl)piperidin-1-yl)-2-methylpropan-2-ol: 2-chloro-5-(piperidin-4-ylmethoxy) pyridine hydrochloride (1.50 g, 5.70 mmol), 2,2-dimethyl oxirane (5.07 mL, 57.0 mmol) and K$_2$CO$_3$ (0.39 g, 2.85 mmol) were dissolved in EtOH (5 mL)/H$_2$O (5 mL). With a microwave radiation, the mixture was heated at 110° C. for 20 minutes. After the completion of the reaction, the reaction mixture was added with a saturated NH$_4$Cl aqueous solution, and extracted with EtOAc. The organic layer was dried over anhydrous MgSO$_4$, and filtered. The filtrate was concentrated under reduced pressure. The concentrate was purified by column chromatography (SiO$_2$; hexaneEtOAc=41) to yield the title compound as white solid (1.3 g, 76%).

Step 6.

2-chloro-5-((1-(2-fluoro-2-methylpropyl)piperidin-4-yl)methoxy)pyridine: 1-(4-((6-chloropyridine-3-yloxy)methyl)piperidin-1-yl)-2-methylpropan-2-ol (1.30 g, 4.35 mmol) was dissolved in CH$_2$Cl$_2$ (15 mL). At 0° C., DAST (0.57 mL, 4.35 mmol) was added thereto little by little. The reaction mixture was stirred for 1 hour at room temperature. After the completion of the reaction, the reaction mixture was added with a saturated NaHCO$_3$ aqueous solution, and extracted with EtOAc. The organic layer was dried over anhydrous MgSO$_4$, and filtered. The filtrate was concentrated under reduced pressure. The concentrate was purified by column chromatography (SiO$_2$; hexaneEtOAc=71) to yield the title compound as white solid (1.20 g, 92%).

Step 7.

Ethyl 2-fluoro-4-(5-((1-(2-fluoro-2-methylpropyl)piperidin-4-yl)methoxy)pyridine-2-yl)benzoate: 2-chloro-5-((1-(2-fluoro-2-methylpropyl)piperidin-4-yl)methoxy)pyridine (0.60 g, 1.99 mmol), 4-(ethoxycarbonyl)-3-fluorophenylboronic acid (0.51 g, 2.39 mmol), Pd(dppf)Cl$_2$ (0.08 g, 0.10 mmol) and Cs$_2$CO$_3$ (1.29 g, 3.98 mmol) were added to 1,4-dioxane (6 mL)/H$_2$O (2 mL). With a microwave radiation, the reaction was performed at 110° C. for 15 minutes. After the completion of the reaction, the reaction mixture was added with water, and extracted with EtOAc. The organic layer was dried over anhydrous MgSO$_4$, and concentrated under reduced pressure. The concentrate was purified by column chromatography (SiO$_2$; hexaneEtOAc=71) to yield the title compound as white solid (0.66 g, 76%).

Step 8.

2-fluoro-4-(5-((1-(2-fluoro-2-methylpropyl)piperidin-4-yl)methoxy)pyridine-2-yl)benzoic acid: Ethyl 2-fluoro-4-(5-((1-(2-fluoro-2-methylpropyl)piperidin-4-yl)methoxy)pyridine-2-yl)benzoate (0.66 g, 0.35 mmol) was dissolved in THF (10 mL)/MeOH (10 mL)/H$_2$O (5 mL). LiOH.H$_2$O (0.32 g, 7.64 mmol) was added thereto little by little at room temperature, following with stirring for 1 hour. After the completion of the reaction, the reaction mixture was acidified by the addition of 1N HCl. The resulting precipitate was filtered to yield the title compound as white solid (0.60 g, 97%).

Step 9.

Compound 770: 2-fluoro-4-(5-((1-(2-fluoro-2-methylpropyl)piperidin-4-yl)methoxy)pyridine-2-yl)benzoic acid (0.08 g, 0.19 mmol), L-prolinamide (0.03 g, 0.24 mmol), BOP (0.17 g, 0.39 mmol) and TEA (0.06 mL, 0.39 mmol) were dissolved in DMF (1 mL). At 60° C., the reaction was performed for a day. After the completion of the reaction, the reaction mixture was added with a saturated NH$_4$Cl aqueous solution, and extracted with EtOAc. The organic layer was dried over anhydrous MgSO$_4$, and filtered. The filtrate was concentrated under reduced pressure. The concentrate was purified by column chromatography (SiO$_2$; MC/MeOH=10/1) to yield the title compound as yellow solid (0.03 g, 35%).

1H NMR (400 MHz, CDCl$_3$) δ 8.39 (m, 1H), 7.78-7.75 (m, 2H), 7.68-7.66 (m, 1H), 7.50 (t, 1H, J=7.5 Hz), 7.29-7.26 (m, 1H), 6.93 (brs, 1H), 5.50 (brs, 1H), 4.84-4.81 (m, 1H), 3.90 (d, 2H, J=5.8 Hz), 3.55-3.40 (m, 2H), 3.03 (brs, 2H), 2.51-2.45 (m, 3H), 2.21-2.19 (m, 2H), 2.16-2.01 (m, 2H), 1.93-1.90 (m, 1H), 1.89-1.81 (m, 3H), 1.57-1.48 (m, 2H), 1.41 (s, 3H), 1.36 (s, 3H); MS (ESI) m/z 501 (M++H).

Example 59. Compound 694: (R)-(2-fluoro-4-(5-((1-(2-fluoro-2-methylpropyl)piperidin-4-yl)methoxy)pyridine-2-yl)phenyl)(2-(hydroxymethyl)pyrrolidine-1-yl)methanone

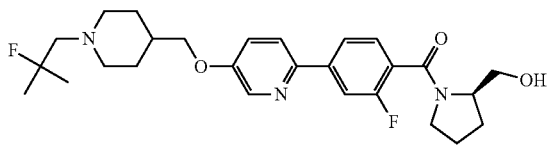 [SMILES: CC(C)(F)CN1CCC(COc2ccc(-c3ccc(C(=O)N4CCC[C@@H]4CO)c(F)c3)nc2)CC1]

Step 1.

Ethyl 2-fluoro-4-(5-((1-(2-fluoro-2-methylpropyl)piperidin-4-yl)methoxy)pyridine-2-yl)benzoate: 2-chloro-5-((1-(2-fluoro-2-methylpropyl)piperidin-4-yl)methoxy)pyridine (the product of synthesis step 5 of compound 691; 230 mg, 0.77 mmol), 4-(ethoxycarbonyl)-3-fluorophenylboronic acid (195 mg, 0.92 mmol), Pd(dppf)Cl$_2$ (62 mg, 0.08 mmol) and Na$_2$CO$_3$ (162 mg, 1.35 mmol) were dissolved in DME 6 mL and water 2 mL, and then refluxed with heating for a day. The reaction mixture was filtered through Celite. The filtrate was added with saturated NaHCO$_3$ aqueous solution, and extracted with EtOAc. The organic layer was dried over MgSO$_4$, filtered to remove the solid residue, and the filtrate was concentrated under reduced pressure. The concentrate was purified by column chromatography (ISCO silica gel cartridge, MeOH/CH$_2$Cl$_2$) to yield the title compound as yellow solid (210 mg, 68%).

Step 2.

2-fluoro-4-(5-((1-(2-fluoro-2-methylpropyl)piperidin-4-yl)methoxy)pyridine-2-yl)benzoic acid: Ethyl 2-fluoro-4-(5-((1-(2-fluoro-2-methylpropyl)piperidin-4-yl)methoxy)pyridine-2-yl)benzoate (210 mg, 0.49 mmol) was dissolved in THF/MeOH/H$_2$O=2/1/0.5 mL. LiOH.H$_2$O (41 mg, 0.97 mmol) was added thereto, and refluxed with heating and stirring for 3 hours. After the completion of the reaction, the solvent was dried under reduced pressure to yield the title compound as yellow solid (195 mg, 99%).

Step 3.

Compound 694: 2-fluoro-4-(5-((1-(2-fluoro-2-methylpropyl)piperidin-4-yl)methoxy)pyridine-2-yl)benzoic acid (40 mg, 0.10 mmol), (R)-pyrrolidine-2-ylmethanol (20 mg, 0.20 mmol), and BOP (88 mg, 0.20 mmol) were dissolved in DMF 1 mL. After stirring for 10 minutes at room temperature, TEA (30 mg, 0.30 mmol) was added thereto, following with stirring at 50° C. for 8 hours. The reaction mixture was added with water, and extracted with EtOAc. The organic layer was washed with saturated aqueous brine solution, dried over MgSO$_4$, filtered to remove the solid residue, and the filtrate was concentrated under reduced pressure. The concentrate was purified by column chromatography (ISCO silica gel cartridge, MeOH/CH$_2$Cl$_2$) to yield the title compound as yellow solid (22 mg, 45%).

1H NMR (400 MHz, CDCl$_3$) δ 8.38 (d, 1H, J=2.7 Hz), 7.75 (m, 2H), 7.65 (m, 1H), 7.49 (m, 1H), 7.26 (m, 1H), 4.78 (s, 1H), 4.40 (m, 2H), 3.90 (d, 2H, J=6.0 Hz), 3.77 (m, 2H), 3.43 (m, 2H), 3.15 (m, 2H), 3.00 (m, 2H), 2.49 (s, 1H), 2.43 (s, 1H), 2.19 (m, 2H), 1.81 (m, 3H), 1.68 (m, 1H), 1.47 (m, 5H), 1.34 (s, 3H)

According to the above-described synthesis process of compound 694, the compounds of Table 38 were synthesized using 2-fluoro-4-(5-((1-(2-fluoro-2-methylpropyl)piperidin-4-yl)methoxy)pyridine-2-yl)benzoic acid and the reactant of Table 37.

TABLE 37

| Compound No. | Reactant | Yield (%) |
| --- | --- | --- |
| 695 | (S)-pyrrolidine-3-ol | 49 |
| 767 | (S)-piperidin-3-ol hydrochloride | 42 |
| 768 | (R)-pyrrolidine-3-ol | 41 |
| 769 | (S)-pyrrolidine-2-ylmethanol | 38 |
| 771 | (R)-piperidin-3-ol hydrochloride | 34 |
| 805 | piperidin-4-carboxamide | 72 |
| 822 | (R)-piperidin-2-carboxamide | 47 |
| 824 | (S)-piperidin-2-carboxamide | 61 |

TABLE 38

| Compound No. | Compound Name, $^1$H-NMR, MS (ESI) |
| --- | --- |
| 695 | (S)-(2-fluoro-4-(5-((1-(2-fluoro-2-methylpropyl)piperidin-4-yl)methoxy)pyridine-2-yl)phenyl)(3-hydroxypyrrolidine-1-yl)methanone<br>1H NMR (400 MHz, CDCl$_3$) δ 8.36 (m, 1 H), 7.72 (m, 2 H), 7.69 (m, 1 H), 7.48 (m, 1 H), 7.25 (m, 1 H), 4.57 (m, 0.5 H), 4.45 (m, 0.5 H), 3.89 (d, 2 H, J = 6.0 Hz), 3.73 (m, 3 H), 3.13 (m, 1 H), 3.02 (m, 2 H), 3.00 (m, 2 H), 2.49 (s, 1 H), 2.43 (s, 1 H), 2.05 (m, 2 H), 1.99 (m, 2 H), 1.41 (m, 5 H), 1.35 (s, 3 H); MS (ESI) m/z 474 (M + H). |
| 767 | (S)-(2-fluoro-4-(5-((1-(2-fluoro-2-methylpropyl)piperidin-4-yl)methoxy)pyridine-2-yl)phenyl)(3-hydroxypiperidin-1-yl)methanone<br>1H NMR (400 MHz, CDCl$_3$) δ 8.38 (d, 1 H, J = 3.0 Hz), 7.76-7.71 (m, 2 H), 7.67-7.65 (m, 1 H), 7.48-7.44 (m, 1 H), 7.29-7.26 (m, 1 H), 4.12-3.90 (m, 3 |

TABLE 38-continued

| Compound No. | Compound Name, $^1$H-NMR, MS (ESI) |
|---|---|
| | H), 3.59-3.55 (m, 1 H), 3.49-3.46 (m, 1 H), 3.38-3.26 (m, 1 H), 3.25-3.02 (m, 1 H), 2.97-2.46 (m, 2 H), 2.21-2.28 (m, 2 H), 2.06-2.01 (m, 1 H), 1.98-1.91 (m, 1 H), 1.89-1.82 (m, 4 H), 1.68-1.62 (m, 4 H), 1.60-1.48 (m, 2 H), 1.42 (s, 3 H), 1.37 (s, 3 H); MS (ESI) m/z 488(M+ + H). |
| 768 | (R)-(2-fluoro-4-(5-((1-(2-fluoro-2-methylpropyl)piperidin-4-yl)methoxy)pyridine-2-yl)phenyl)(3-hydroxypyrrolidine-1-yl)methanone<br>1H NMR (400 MHz, CDCl$_3$) δ 8.38 (d, 1 H, J = 2.8 Hz), 7.76-7.72 (m, 2 H), 7.67-7.65 (m, 1 H), 7.54-7.49 (m, 1 H), 7.29-7.26 (m, 1 H), 4.62-4.49 (m, 1 H), 3.91 (d, 2 H, J = 5.8 Hz), 3.86-3.80 (m, 2 H), 3.79-3.61 (m, 2 H), 3.04 (brs, 2 H), 2.52-2.48 (m, 2 H), 2.29-2.18 (m, 2 H), 2.17-2.01 (m, 2 H), 1.99-1.83 (m, 4 H), 1.67-1.53 (m, 2 H), 1.43 (s, 3 H), 1.37 (s, 3 H); MS (ESI) m/z 474 (M+ + H). |
| 769 | (S)-(2-fluoro-4-(5-((1-(2-fluoro-2-methylpropyl)piperidin-4-yl)methoxy)pyridine-2-yl)phenyl)(2-(hydroxymethyl)pyrrolidine-1-yl)methanone<br>1H NMR (400 MHz, CDCl$_3$) δ 8.38 (d, 1 H, J = 2.9 Hz), 7.77-7.73 (m, 2 H), 7.67 (d, 1 H, J = 8.7 Hz), 7.52-7.48 (m, 1 H), 7.28-7.26 (m, 1 H), 4.77-4.74 (m, 1 H), 4.41-4.39 (m, 1 H), 3.90 (d, 2 H, J = 6.0 Hz), 3.83-3.77 (m, 2 H), 3.46-3.43 (m, 2 H), 3.02 (brs, 2 H), 2.51-2.45 (m, 2 H), 2.24-2.17 (m, 3 H), 1.91-1.87 (m, 1 H), 1.86-1.81 (m, 4 H), 1.79-1.71 (m, 1 H), 1.70-1.66 (m, 1 H), 1.41 (s, 3 H), 1.36 (s, 3 H); MS (ESI) m/z 488 (M+ + H). |
| 771 | (R)-(2-fluoro-4-(5-((1-(2-fluoro-2-methylpropyl)piperidin-4-yl)methoxy)pyridine-2-yl)phenyl)(3-hydroxypiperidin-1-yl)methanone<br>1H NMR (400 MHz, CDCl$_3$) δ 8.38 (d, 1 H, J = 3.0 Hz), 7.76-7.71 (m, 2 H), 7.67-7.65 (m, 1 H), 7.48-7.44 (m, 1 H), 7.29-7.26 (m, 1 H), 4.12-3.90 (m, 3 H), 3.59-3.55 (m, 1 H), 3.49-3.46 (m, 1 H), 3.38-3.26 (m, 1 H), 3.25-3.02 (m, 1 H), 2.97-2.46 (m, 2 H), 2.21-2.28 (m, 2 H), 2.06-2.01 (m, 1 H), 1.98-1.91 (m, 1 H), 1.89-1.82 (m, 4 H), 1.68-1.62 (m, 4 H), 1.60-1.48 (m, 2 H), 1.42 (s, 3 H), 1.37 (s, 3 H); MS (ESI) m/z 488 (M+ + H). |
| 805 | 1-(2-fluoro-4-(5-((1-(2-fluoro-2-methylpropyl)piperidin-4-yl)methoxy)pyridine-2-yl)benzoyl)piperidin-4-carboxamide<br>1H NMR (400 MHz, CDCl$_3$) δ 8.41-8.40 (m, 1 H), 7.78-7.68 (m, 3 H), 7.47 (t, 1 H, J = 7.2 Hz), 7.31-7.29 (m, 1 H), 5.75 (d, 2 H, J = 21.6 Hz), 4.77 (d, 2 H, J = 13.2 Hz), 3.93 (d, 2 H, J = 6.0 Hz), 3.73 (d, 1 H, J = 14.0 Hz), 3.13-2.93 (m, 4 H), 2.52-2.46 (m, 3 H), 2.22 (t, 2 H, J = 11.6 Hz), 2.05-1.78 (m, 7 H), 1.59-0.90 (m, 8 H); MS (ESI) m/z 515 (M+ + H) |
| 822 | (R)-1-(2-fluoro-4-(5-((1-(2-fluoro-2-methylpropyl)piperidin-4-yl)methoxy)pyridine-2-yl)benzoyl)piperidin-2-carboxamide<br>1H NMR (400 MHz, CDCl$_3$) δ 8.39-8.38 (m, 1 H), 7.79-7.75 (m, 2 H), 7.68 (d, 1 H, J = 8.8 Hz), 7.50 (t, 1 H, J = 7.7 Hz), 7.29-7.26 (m, 2 H), 6.33 (brs, 1 H), 5.58 (brs, 1 H), 5.47 (brs, 1 H), 3.90 (d, 2 H, J = 6.0 Hz), 3.59 (d, 1 H, J = 14.4 Hz), 3.29-3.16 (m, 1 H), 3.01 (d, 2 H, J = 11.4 Hz), 2.48-2.43 (m, 3 H), 2.18 (t, 2 H, J = 12.0 Hz), 1.85-1.60 (m, 8 H), 1.49-1.24 (m, 8 H); MS (ESI) m/z 515 (M+ + H). |
| 824 | (S)-1-(2-fluoro-4-(5-((1-(2-fluoro-2-methylpropyl)piperidin-4-yl)methoxy)pyridine-2-yl)benzoyl)piperidin-2-carboxamide<br>1H NMR (400 MHz, CDCl$_3$) δ 8.39-8.35 (m, 1 H), 7.78-7.69 (m, 3 H), 7.60 (t, 1 H, J = 12.0 Hz), 7.36-7.25 (m, 1 H), 6.34 (brs, 1 H), 5.75 (brs, 1 H), 5.44 (brs, 1 H), 3.89 (d, 2 H, J = 4.0 Hz), 3.58 (d, 1 H, J = 12.8 Hz), 3.23-3.20 (m, 1 H), 3.00 (d, 2 H, J = 11.2 Hz), 2.48-2.37 (m, 3 H), 2.17 (t, 2 H, J = 11.0 Hz), 1.86-1.62 (m, 8 H), 1.59-1.29 (m, 8 H); MS (ESI) m/z 515 (M+ + H) |

Example 60. Compound 1067: (2S,4R)-1-(2-fluoro-4-(5-((1-(2-fluoro-2-methylpropyl)piperidin-4-yl)methoxy)pyridine-2-yl)benzoyl)-4-hydroxypyrrolidine-2-carboxamide

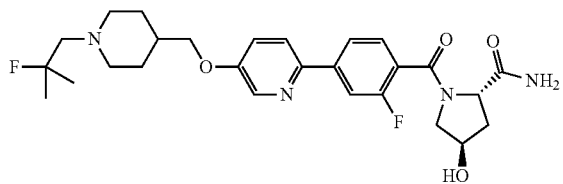 [SMILES: CC(C)(F)CN1CCC(COc2ccc(-c3ccc(C(=O)N4C[C@H](O)C[C@H]4C(N)=O)c(F)c3)nc2)CC1]

Step 1.

(2S,4R)-methyl 1-(2-fluoro-4-(5-((1-(2-fluoro-2-methylpropyl)piperidin-4-yl)methoxy)pyridine-2-yl)benzoyl)-4-hydroxypyrrolidine-2-carboxylate: 2-fluoro-4-(5-((1-(2-fluoro-2-methylpropyl)piperidin-4-yl)methoxy)pyridine-2-yl)benzoic acid (the product of synthesis step 2 of compound 694; 200 mg, 0.49 mmol), (2S,4R)-methyl 4-hydroxypyrrolidine-2-carboxylate hydrochloride (135 mg, 0.74 mmol), EDC (190 mg, 0.99 mmol), HOBt (134 mg, 0.99 mmol) and DIPEA (0.18 mL, 0.99 mmol) were dissolved in DMF (10 mL) at room temperature. The solution was stirred at 80° C. for 14 hours. The reaction mixture was added with water (20 mL), and stirred. The resulting precipitate was filtered, and dried to yield the title compound as red solid (230 mg, 88%).

Step 2.

(2S,4R)-1-(2-fluoro-4-(5-((1-(2-fluoro-2-methylpropyl)piperidin-4-yl)methoxy)pyridine-2-yl)benzoyl)-4-hydroxypyrrolidine-2-carboxylic acid: (2S,4R)-methyl 1-(2-fluoro-4-(5-((1-(2-fluoro-2-methylpropyl)piperidin-4-yl)methoxy)pyridine-2-yl)benzoyl)-4-hydroxypyrrolidine-2-carboxylate (230 mg, 0.43 mmol) and LiOH.H$_2$O (36 mg, 0.86 mmol) were dissolved in THF (20 mL)/H$_2$O (5 mL) at room temperature. The solution was stirred at 60° C. for 14 hours. The reaction mixture was concentrated under reduced pressure. The obtained material was used without further purifying process.

Step 3.

Compound 1067: (2S,4R)-1-(2-fluoro-4-(5-((1-(2-fluoro-2-methylpropyl)piperidin-4-yl)methoxy)pyridine-2-yl)benzoyl)-4-hydroxypyrrolidine-2-carboxylic acid (290 mg, 0.56 mmol), ammonium chloride (45 mg, 0.84 mmol), EDC (161 mg, 0.84 mmol), HOBt (114 mg, 0.84 mmol) and DIPEA (0.20 mL, 1.12 mmol) were dissolved in DMF (10 mL) at room temperature. The solution was stirred at 80° C. for 16 hours. The reaction mixture was added with saturated NH$_4$Cl aqueous solution, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 4 g cartridge; methanol/dichloromethane=0% to 15%), and concentrated to yield the title compound as yellow solid (10 mg, 3%).

1H NMR (400 MHz, CDCl$_3$+MeOD) δ 8.33 (m, 1H), 7.72-7.64 (m, 3H), 7.54 (m, 1H), 7.26 (m, 1H), 7.01 (br, 1H), 5.99 (br, 1H), 4.84 (m, 1H), 4.42 (m, 1H), 3.89 (m, 2H), 3.68 (m, 1H), 3.38 (m, 1H), 2.99 (m, 2H), 2.51-2.01 (m, 7H), 1.80 (m, 2H), 1.63-1.25 (m, 9H); MS (ESI) m/z 517 (M++H).

Example 61. Synthesis of compound 652: (R)-(4-(6-((1-(2-fluoro-2-methylpropyl)piperidin-4-yl)methoxy)pyridin-3-yl)phenyl)(2-(hydroxymethyl)pyrrolidine-1-yl)methanone

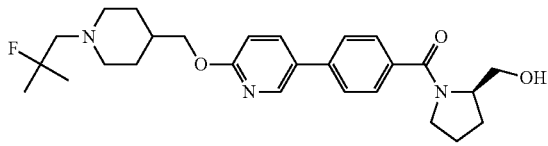 [SMILES: CC(C)(F)CN1CCC(COc2ccc(-c3ccc(C(=O)N4CCC[C@@H]4CO)cc3)cn2)CC1]

Step 1.

5-bromo-2-(piperidin-4-ylmethoxy)pyridine hydrochloride: t-butyl 4-((5-bromopyridine-2-yloxy)methyl)piperidin-1-carboxylate (the product of synthesis step 1 of compound 596; 710 mg, 1.91 mmol) was dissolved in CH$_2$Cl$_2$ 5 mL. 4 M HCl 526 μl was added thereto. And then, the reaction mixture was stirred for 1 hour at room temperature. The obtained reaction mixture was filtered to yield the title compound as white solid (580 mg, 98%).

Step 2.

1-(4-((5-bromopyridine-2-yloxy)methyl)piperidin-1-yl)-2-methylpropan-2-ol: 5-bromo-2-(piperidin-4-ylmethoxy)pyridine hydrochloride (500 mg, 1.63 mmol) and K$_2$CO$_3$ (450 mg, 3.25 mmol) were suspended in EtOH 2 mL. Water 2 mL was added thereto, and the mixture was suspended with a little heating. 2,2-dimethyl oxirane (1.17 g, 16.25 mmol) was added thereto. With a microwave radiation, the reaction was performed at 110° C. for 20 minutes. The reaction mixture was added with water, and the resulting precipitate was filtered to yield the title compound as white solid (490 mg, 88%).

Step 3.

5-bromo-2-((1-(2-fluoro-2-methylpropyl)piperidin-4-yl)methoxy)pyridine: 1-(4-((5-bromopyridine-2-yloxy)methyl)piperidin-1-yl)-2-methylpropan-2-ol (490 mg, 1.43 mmol) was dissolved in CH$_2$Cl$_2$ 4 mL. Deoxo-Fluor (347 mg, 1.57 mmol) was added thereto. After stirring for 3 hours at room temperature, A saturated NaHCO$_3$ aqueous solution was added thereto, and the mixture was extracted with CH$_2$Cl$_2$. The organic layer was dried over MgSO$_4$, and filtered to remove a solid. The filtrate was concentrated under reduced pressure to yield the title compound as yellow liquid (470 mg, 95%).

Step 4.

Methyl 4-(6-((1-(2-fluoro-2-methylpropyl)piperidin-4-yl)methoxy)pyridine-3-yl)benzoate: 5-bromo-2-((1-(2-fluoro-2-methylpropyl)piperidin-4-yl)methoxy)pyridine (270 mg, 0.78 mmol) and 4-(methoxycarbonyl)phenylboronic acid (169 mg, 0.94 mmol) were dissolved in dioxane 2 mL. Water 0.5 mL was added thereto. Pd(dbpf)Cl$_2$ (26 mg, 0.04 mmol) and Cs$_2$CO$_3$ (510 mg, 1.56 mmol) were added thereto. With a microwave radiation, the reaction was performed at 120° C. for 20 minutes. The reaction mixture was filtered through Celite. A saturated NaHCO$_3$ aqueous solution was added thereto, and the mixture was extracted with CH$_2$Cl$_2$. The obtained organic layer was dried over MgSO$_4$, and then concentrated under reduced pressure. The obtained concentrate was purified by silica gel column chromatography (MeOH/CH$_2$Cl$_2$) to yield the title compound as white solid (210 mg, 67%).

Step 5.

4-(6-((1-(2-fluoro-2-methylpropyl)piperidin-4-yl)methoxy)pyridine-3-yl)benzoic acid: methyl 4-(6-((1-(2-fluoro-2-methylpropyl)piperidin-4-yl)methoxy)pyridine-3-yl)benzoate (210 mg, 0.52 mmol) was dissolved in THF 2 mL. MeOH 1 mL and H$_2$O 0.5 mL were poured therein. LiOH (44 mg, 1.05 mmol) was added thereto, and refluxed with heating and stirring for a day. After acidification with 1 N HCl, the resulting precipitate was filtered to yield the title compound as white solid (110 mg, 54%).

Step 6.

Compound 652: 4-(6-((1-(2-fluoro-2-methylpropyl)piperidin-4-yl)methoxy)pyridine-3-yl)benzoic acid (35 mg, 0.09 mmol), (R)-pyrrolidine-2-ylmethanol (14 mg, 0.14 mmol) and PyBOP (71 mg, 0.14 mmol) were dissolved in DMF 1 mL. DIPEA (23 mg, 0.18 mmol) was added thereto. The reaction was performed at room temperature for 10 hours. The reaction mixture was added with water, and extracted with EtOAc. The obtained organic layer was dried over MgSO$_4$, and filtered. The filtrate was concentrated under reduced pressure. The obtained concentrate was purified by silica gel column chromatography (MeOH/CH$_2$Cl$_2$) to yield the title compound as white solid (23 mg, 54%).

1H NMR (400 MHz, CDCl$_3$) δ 8.36 (d, 1H, J=2.0 Hz), 7.78 (dd, 1H, J=8.6, 2.3 Hz), 7.56 (m, 4H), 6.80 (d, 1H, J=8.6 Hz), 4.94 (s, 1H), 4.41 (m, 2H), 4.17 (d, 2H, J=6.1 Hz), 3.74 (m, 2 H), 3.55 (m, 2H), 2.97 (d, 2H, J=11.2 Hz), 2.46 (s, 1H), 2.40 (s, 1H), 2.15 (m, 3H), 1.76 (m, 5H), 1.40 (m, 5H), 1.23 (s, 3H); MS (ESI) m/z 470 (M++H).

According to the above-described synthesis process of compound 652, the compounds of Table 40 were synthesized using 4-(6-((1-(2-fluoro-2-methylpropyl)piperidin-4-yl)methoxy)pyridine-3-yl)benzoic acid and the reactant of Table 39.

TABLE 39

| Compound No. | Reactant | Yield (%) |
| --- | --- | --- |
| 653 | L-prolinamide | 57 |
| 654 | (S)-3-hydroxypiperidine | 35 |
| 1076 | (R)-piperidin-2-carboxamide hydrochloride | 54 |
| 1077 | (R)-pyrrolidine-3-ol | 65 |
| 1078 | (S)-pyrrolidine-3-ol | 61 |
| 1079 | (S)-piperidin-2-carboxamide hydrochloride | 33 |

TABLE 40

Compound No. Compound Name, <sup>1</sup>H-NMR, MS (ESI)

| | |
|---|---|
| 653 | (S)-1-(4-(6-((1-(2-fluoro-2-methylpropyl)piperidin-4-yl)methoxy)pyridine-3-yl)benzoyl)pyrrolidine-2-carboxamide<br>1H NMR (400 MHz, CDCl$_3$) δ 8.39 (d, 1 H, J = 2.1 Hz), 7.81 (dd, 1 H, J = 8.6, 2.4 Hz), 7.60 (m, 4 H), 6.99 (s, 1 H), 6.83 (d, 1 H, J = 8.6 Hz), 5.46 (s, 1 H), 4.83 (m, 1 H), 4.19 (d, 2 H, J = 6.2 Hz), 3.60 (m, 2 H), 3.02 (m, 2 H), 2.48 (m, 3 H), 2.17 (m, 2 H), 2.09 (m, 2 H), 1.86 (m, 4 H), 1.41 (m, 5 H), 1.35 (s, 3 H); MS (ESI) m/z 483 (M+ + H). |
| 654 | (S)-(4-(6-((1-(2-fluoro-2-methylpropyl)piperidin-4-yl)methoxy)pyridine-3-yl)phenyl)(3-hydroxypiperidin-1-yl)methanone<br>1H NMR (400 MHz, CDCl$_3$) δ 8.37 (d, 1 H, J = 2.3 Hz), 7.79 (dd, 1 H, J = 8.6, 2.6 Hz), 7.53 (m, 4 H), 6.82 (d, 1 H, J = 8.6 Hz), 4.19 (d, 2 H, J = 8.6 Hz), 4.19 (d, 2 H, J = 6.2 Hz), 3.99 (m, 2 H), 3.76 (m, 1 H), 3.37 (m, 2 H), 3.02 (m, 2 H), 2.51 (s, 2 H), 2.46 (s, 1 H), 1.98 (m, 5 H), 1.66 (m, 2 H), 1.45 (m, 5 H), 1.35 (s, 3 H); MS (ESI) m/z 470 (M+ + H). |
| 1076 | (R)-1-(4-(6-((1-(2-fluoro-2-methylpropyl)piperidin-4-yl)methoxy)pyridine-3-yl)benzoyl)piperidin-2-carboxamide<br>1H NMR (400 MHz, CDCl$_3$) δ 8.38 (s, 1 H), 7.81-7.78 (m, 1 H), 7.59-7.52 (m, 4 H), 6.83 (d, 1 H, J = 8.4 Hz), 6.46 (brs, 1 H), 5.39 (brs, 1 H), 5.28 (brs, 1 H), 4.19 (d, 2 H, J = 6.0 Hz), 3.79 (brs, 1 H), 3.12 (t, 1 H, J = 12.4 Hz), 2.98 (d, 2 H, J = 12.6 Hz), 2.47 (s, 1 H), 2.41 (s, 1 H), 2.34 (d, 1 H, J = 13.6 Hz), 2.16 (t, 2 H, J = 10.8 Hz), 1.86-1.78 (m, 5 H), 1.67-1.55 (m, 4 H), 1.48-1.42 (m, 2 H), 1.39 (s, 3 H), 1.34 (s, 3 H); MS (ESI) m/z 497 (M+ + H). |
| 1077 | (R)-(4-(6-((1-(2-fluoro-2-methylpropyl)piperidin-4-yl)methoxy)pyridine-3 -yl)phenyl)(3-hydroxypyrrolidine-1-yl)methanone<br>1H NMR (400 MHz, CDCl$_3$) δ 8.37 (s, 1 H), 7.81-7.78 (m, 1 H), 7.64-7.61 (m, 2 H), 7.59-7.54 (m, 2 H), 6.82 (d, 1 H, J = 8.4 Hz), 4.62 (brs, 0.5 H), 4.49 (brs, 0.5 H), 4.19 (d, 2 H, J = 6.4 Hz), 3.86-3.76 (m, 2 H), 3.70-3.65 (m, 1 H), 3.60-3.48 (m, 1 H), 2.98 (d, 2 H, J = 11.6 Hz), 2.47 (s, 1 H), 2.41 (s, 1 H), 2.19-2.13 (m, 2 H), 2.04-2.00 (m, 2 H), 1.81-1.78 (m, 4 H), 1.45-1.42 (m, 2 H), 1.39 (s, 3 H), 1.34 (s, 3 H); MS (ESI) m/z 456 (M+ + H). |
| 1078 | (S)-(4-(6-((1-(2-fluoro-2-methylpropyl)piperidin-4-yl)methoxy)pyridine-3-yl)phenyl)(3-hydroxypyrrolidine-1-yl)methanone<br>1H NMR (400 MHz, CDCl$_3$) δ 8.37 (s, 1 H), 7.81-7.78 (m, 1 H), 7.64-7.61 (m, 2 H), 7.59-7.54 (m, 2 H), 6.82 (d, 1 H, J = 8.4 Hz), 4.62 (brs, 0.5 H), 4.49 (brs, 0.5 H), 4.19 (d, 2 H, J = 6.4 Hz), 3.86-3.76 (m, 2 H), 3.70-3.65 (m, 1 H), 3.60-3.48 (m, 1 H), 2.98 (d, 2 H, J = 11.6 Hz), 2.47 (s, 1 H), 2.41 (s, 1 H), 2.19-2.13 (m, 2 H), 2.04-2.00 (m, 2 H), 1.81-1.78 (m, 4 H), 1.45-1.42 (m, 2 H), 1.39 (s, 3 H), 1.34 (s, 3 H); MS (ESI) m/z 456 (M+ + H). |
| 1079 | (S)-1-(4-(6-((1-(2-fluoro-2-methylpropyl)piperidin-4-yl)methoxy)pyridine-3-yl)benzoyl)piperidin-2-carboxamide<br>1H NMR (400 MHz, CDCl$_3$) δ 8.38 (s, 1 H), 7.81-7.78 (m, 1 H), 7.59-7.52 (m, 4 H), 6.83 (d, 1 H, J = 8.4 Hz), 6.46 (brs, 1 H), 5.39 (brs, 1 H), 5.28 (brs, 1 H), 4.19 (d, 2 H, J = 6.0 Hz), 3.79 (brs, 1 H), 3.12 (t, 1 H, J = 12.4 Hz), 2.98 (d, 2 H, J = 12.6 Hz), 2.47 (s, 1 H), 2.41 (s, 1 H), 2.34 (d, 1 H, J = 13.6 Hz), 2.16 (t, 2 H, J = 10.8 Hz), 1.86-1.78 (m, 5 H), 1.67-1.55 (m, 4 H), 1.48-1.42 (m, 2 H), 1.39 (s, 3 H), 1.34 (s, 3 H); MS (ESI) m/z 497 (M+ + H). |

Example 62. Compound 862: (R)-1-(3-fluoro-4-(6-((1-(2-fluoro-2-methylpropyl)piperidin-4-yl)methoxy)pyridine-3-yl)benzoyl)piperidin-2-carboxamide

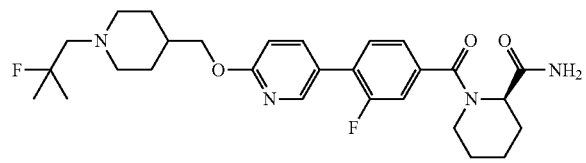 [SMILES: CC(C)(F)CN1CCC(COc2ccc(-c3ccc(C(=O)N4CCCC[C@@H]4C(N)=O)cc3F)cn2)CC1]

Step 1.

Methyl 3-fluoro-4-(6-((1-(2-fluoro-2-methylpropyl)piperidin-4-yl)methoxy)pyridine-3-yl)benzoate: 5-bromo-2-((1-(2-fluoro-2-methylpropyl)piperidin-4-yl)methoxy)pyridine (the product of synthesis step 4 of compound 784; 0.5 g, 1.45 mmol) was dissolved in 1,4-dioxane 12 mL and H$_2$O 3 mL. 2-Fluoro-4-(methoxycarbonyl)phenylboronic acid (0.29 g, 1.45 mmol), Pd(dbpf)Cl$_2$ (0.05 g, 0.07 mmol) and Cs$_2$CO$_3$ (0.94 g, 2.90 mmol) were added thereto. With a microwave radiation, the mixture was heated at 120° C. for 45 minutes. After the completion of the reaction, the reaction mixture was filtered through Celite. The filtrate was added with saturated NaHCO$_3$ aqueous solution, and extracted with CH$_2$Cl$_2$. The obtained organic layer was washed with saturated aqueous brine solution three times. The obtained organic layer was dried over Na$_2$SO$_4$, and filtered. The filtrate was concentrated under reduced pressure. MeOH was added and the resulting precipitate was filtered to yield the title compound as light-yellow solid (0.48 g, 79%).

Step 2.

3-fluoro-4-(6-((1-(2-fluoro-2-methylpropyl)piperidin-4-yl)methoxy)pyridine-3-yl)benzoic acid: Methyl 3-fluoro-4-(6-((1-(2-fluoro-2-methylpropyl)piperidin-4-yl)methoxy)pyridine-3-yl)benzoate (0.47 g, 1.12 mmol) was dissolved in THF 3 mL, H$_2$O 1 mL and MeOH 1 mL. LiOH.H$_2$O (0.24 g, 5.62 mmol) was added thereto, following with increasing the temperature slowly and stirring at 50° C. for a day. After the completion of the reaction, the solvent was distilled under reduced pressure. Excess amount of water was added thereto, and the resulting precipitate was filtered to yield the title compound as white solid (0.45 g, 99%).

Step 3.

Compound 862: 3-fluoro-4-(6-((1-(2-fluoro-2-methylpropyl)piperidin-4-yl)methoxy)pyridine-3-yl)benzoic acid (0.05 g, 0.12 mmol) and (R)-piperidin-2-carboxamide (0.032 g, 0.25 mmol) were dissolved in DMF 2 mL. DIPEA (0.10 mL, 0.62 mmol), EDCI (0.05 g, 0.25 mmol) and HOBt (0.03 g, 0.25 mmol) were added thereto slowly, following with stirring at 60° C. for 3 hours. After the completion of the reaction, excess amount of water was added to the reaction mixture. The resulting precipitate was filtered, and dissolved in $CH_2Cl_2$ again. The concentrate was purified by column chromatography (40 g ISCO silica gel cartridge, 0-20% MeOH/$CH_2Cl_2$) to yield the title compound as light-yellow solid (0.016 g, 25%).

1H NMR (400 MHz, $CDCl_3$) δ 8.33 (s, 1H), 7.79-7.77 (m, 1H), 7.49-7.45 (m, 1H), 7.32-7.27 (m, 2H), 6.84 (d, 1H, J=8.6 Hz), 6.40 (brs, 1H), 5.26 (brs, 1H), 4.20 (d, 2H, J=6.4 Hz), 3.78 (d, 1H, J=12.8 Hz), 3.19-3.17 (m, 1H), 2.99 (d, 2H, J=9.6 Hz), 2.48 (s, 1H), 2.42 (s, 1H), 2.34 (d, 1H, J=13.2 Hz), 2.17 (t, 2H, J=11.2 Hz), 2.05-1.54 (m, 8H), 1.48-1.24 (m, 8H)

According to the above-described synthesis process of compound 862, the compounds of Table 42 were synthesized using 3-fluoro-4-(6-((1-(2-fluoro-2-methylpropyl)piperidin-4-yl)methoxy)pyridine-3-yl)benzoic acid and the reactant of Table 41.

TABLE 41

| Compound No. | Reactant | Yield (%) |
| --- | --- | --- |
| 863 | (S)-piperidin-2-carboxamide | 53 |
| 864 | piperidin-4-carboxamide | 37 |

TABLE 42

| Compound No. | Compound Name, $^1$H-NMR, MS (ESI) |
| --- | --- |
| 863 | (S)-1-(3-fluoro-4-(6-((1-(2-fluoro-2-methylpropyl)piperidin-4-yl)methoxy)pyridine-3-yl)benzoyl)piperidin-2-carboxamide<br>1H NMR (400 MHz, $CDCl_3$) δ 8.32 (brs, 1 H), 7.83-7.76 (m, 1 H), 7.52-7.43 (m, 1 H), 7.28-7.27 (m, 1 H), 6.83-6.81 (m, 2 H), 6.48 (brs, 1 H), 6.78 (brs, 1 H), 5.32 (brs, 1 H), 4.19 (d, 2 H, J = 6.0 Hz), 2.98 (d, 2 H, J = 11.4 Hz), 2.47 (s, 1 H), 2.41 (s, 1 H), 2.37-2.26 (m, 1 H), 2.17 (t, 2 H, J = 11.0 Hz), 1.80-1.78 (m, 8 H), 1.45-1.25 (m, 8 H) |
| 864 | 1-(3-fluoro-4-(6-((1-(2-fluoro-2-methylpropyl)piperidin-4-yl)methoxy)pyridine-3-yl)benzoyl)piperidin-4-carboxamide<br>1H NMR (400 MHz, $CDCl_3$) δ 8.31 (s, 1 H), 7.77 (d, 1 H, J = 7.2 Hz), 7.44 (t, 1 H, J = 7.8 Hz), 7.27-7.20 (m, 2 H), 6.82 (d, 1 H, J = 8.8 Hz), 5.74 (d, 2 H, J = 22.4 Hz), 4.63 (brs, 1 H), 4.18 (d, 2 H, J = 6.0 Hz), 3.87 (brs, 1 H), 3.17-2.96 (m, 4 H), 2.47-2.41 (m, 3 H), 2.17 (t, 2 H, J = 11.0 Hz), 2.02-1.77 (m, 7 H), 1.47-1.25 (m, 8 H) |

Example 63. Compound 784: (R)-(2-fluoro-4-(6-((1-(2-fluoro-2-methylpropyl)piperidin-4-yl)methoxy)pyridine-3-yl)phenyl)(3-hydroxypiperidin-1-yl)methanone

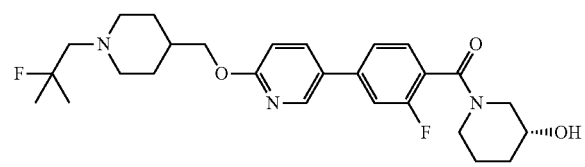 [SMILES: CC(C)(F)CN1CCC(COc2ccc(-c3ccc(C(=O)N4CCC[C@@H](O)C4)c(F)c3)cn2)CC1]

Step 1.

t-butyl 4-((5-bromopyridine-2-yloxy)methyl)piperidin-1-carboxylate: t-Butyl 4-(hydroxymethyl)piperidin-1-carboxylate (the product of synthesis step 1 of compound 431; 7.0 g, 32.51 mmol) was dissolved in DMF. 2,5-bromopyridine (8.47 g, 35.77 mmol) and NaH (1.23 g, 48.77 mmol) were added thereto slowly, following with stirring at room temperature for 3 hours. After the completion of the reaction, the reaction mixture was washed with saturated aqueous brine solution three times. The obtained organic layer was dried over $Na_2SO_4$, and filtered. The filtrate was concentrated under reduced pressure. The concentrate was purified by column chromatography (4 g ISCO silica gel cartridge, 0-20% EtOAc/hexane) to yield the title compound as white solid (11.8 g, 98%).

Step 2.

5-bromo-2-(piperidin-4-ylmethoxy)pyridine hydrochloride: t-butyl 4-((5-bromopyridine-2-yloxy)methyl)piperidin-1-carboxylate (22.0 g, 59.26 mmol) was dissolved in 1,4-dioxane 300 mL. 4 M HCl in 1,4-dioxane (74.0 mL, 296.28 mmol) was added thereto. After the solvent was distilled out completely, the residue was washed with ether to yield the title compound as white solid (17.0 g, 93%).

Step 3.

1-(4-((5-bromopyridine-2-yloxy)methyl)piperidin-1-yl)-2-methylpropan-2-ol: 5-bromo-2-(piperidin-4-ylmethoxy)pyridine hydrochloride (4.5 g, 14.63 mmol) was dissolved in EtOH 50 mL and $H_2O$ 50 mL. 1,2-epoxy-2-methylpropane (10.55 g, 146.29 mmol) and $K_2CO_3$ (10.11 g, 73.15 mmol) were added slowly thereto. The mixture was stirred in a microwave at 110° C. for 20 minutes. After the completion of the reaction, the reaction mixture was concentrated under reduced pressure, following with washing with $H_2O$ three times. The obtained organic layer was dried over $Na_2SO_4$, and filtered. The filtrate was concentrated under reduced pressure to yield the title compound as white solid (5.00 g, 99%).

Step 4.

5-bromo-2-((1-(2-fluoro-2-methylpropyl)piperidin-4-yl)methoxy)pyridine: 1-(4-((5-bromopyridine-2-yloxy)methyl)piperidin-1-yl)-2-methylpropan-2-ol (10.20 g, 29.71 mmol) was dissolved in $CH_2Cl_2$ 200 mL. DAST (4.32 mL, 32.69 mmol) was added dropwise slowly thereto at 0° C., following with stirring at 0° C. for 2 hours. After the completion of the reaction, the reaction mixture was washed with a saturated $NaHCO_3$ aqueous solution several times. The $CH_2Cl_2$ layer was distilled under reduced pressure. The concentrate was purified by column chromatography (4 g ISCO silica gel cartridge, 0-10% EtOAc/hexane) to yield the title compound as white solid (5.80 g, 57%).

Step 5.
Ethyl 2-fluoro-4-(6-((1-(2-fluoro-2-methylpropyl)piperidin-4-yl)methoxy)pyridine-3-yl)benzoate: 5-bromo-2-((1-(2-fluoro-2-methylpropyl)piperidin-4-yl)methoxy)pyridine (0.5 g, 1.45 mmol) was dissolved in 1,4-dioxane 12 mL and H$_2$O 3 mL. 4-(Ethoxycarbonyl)-3-fluorophenylboronic acid (0.31 g, 1.45 mmol), Pd(dbpf)Cl$_2$ (0.05 g, 0.07 mmol) and Cs$_2$CO$_3$ (0.94 g, 2.90 mmol) were added thereto. The mixture was stirred in a microwave at 110° C. for 45 minutes. After the completion of the reaction, the reaction mixture was filtered through Celite. The filtrate was added with saturated NaHCO$_3$ aqueous solution, and extracted with CH$_2$Cl$_2$. The obtained organic layer was washed with saturated aqueous brine solution three times. The obtained organic layer was dried over Na$_2$SO$_4$, and filtered. The filtrate was concentrated under reduced pressure. MeOH was added thereto. The resulting precipitate was filtered to yield the title compound as transparent oil (0.17 g, 27%).
Step 6.
2-fluoro-4-(6-((1-(2-fluoro-2-methylpropyl)piperidin-4-yl)methoxy)pyridine-3-yl)benzoic acid: Ethyl 2-fluoro-4-(6-((1-(2-fluoro-2-methylpropyl)piperidin-4-yl)methoxy)pyridine-3-yl)benzoate (0.17 g, 0.39 mmol) was dissolved in THF (3 mL)/H$_2$O (1 mL)/MeOH 1 mL). LiOH.H$_2$O (0.08 g, 1.97 mmol) was added thereto, following with increasing the temperature slowly, and then refluxing with stirring at 80° C. for 30 minutes. After the completion of the reaction, the solvent was distilled under reduced pressure. Excess amount of water was added thereto, and the resulting precipitate was filtered to yield the title compound as yellow solid (0.12 g, 76%).
Step 7.
Compound 784: 2-fluoro-4-(6-((1-(2-fluoro-2-methylpropyl)piperidin-4-yl)methoxy)pyridine-3-yl)benzoic acid (0.04 g, 0.10 mmol) and (R)-piperidin-3-ol (0.02 g, 0.19 mmol) were dissolved in DMF 2 mL. DIPEA (0.06 g, 0.47 mmol), EDCI (0.04 g, 0.19 mmol) and HOBt (0.03 g, 0.19 mmol) were added thereto slowly, following with stirring at 60° C. for 3 hours. After the completion of the reaction, excess amount of water was added to the reaction mixture. The resulting precipitate was filtered, and dissolved in CH$_2$Cl$_2$ again. The concentrate was purified by column chromatography (40 g ISCO silica gel cartridge, 0-20% MeOH/CH$_2$Cl$_2$) to yield the title compound as brown solid (0.02 g, 47%).

1H NMR (400 MHz, CDCl$_3$) δ 8.36 (s, 1H), 7.78 (d, 1H, J=2.0 Hz), 7.49-7.24 (m, 4H), 6.83 (d, 1H, J=8.6 Hz), 4.20 (d, 2H, J=6.0 Hz), 4.10-3.11 (m, 5H), 3.01 (brs, 2H), 2.49-2.44 (m, 2H), 2.18-1.61 (m, 9H), 1.41-1.26 (m, 8H); MS (ESI) m/z 488 (M++H).

According to the above-described synthesis process of compound 784, the compounds of Table 44 were synthesized using 2-fluoro-4-(6-((1-(2-fluoro-2-methylpropyl)piperidin-4-yl)methoxy)pyridine-3-yl)benzoic acid and the reactant of Table 43.

TABLE 43

| Compound No. | Reactant | Yield (%) |
|---|---|---|
| 785 | (R)-pyrrolidine-3-ol | 40 |
| 786 | (S)-pyrrolidine-3-ol | 13 |
| 787 | (S)-pyrrolidine-2-ylmethanol | 29 |
| 854 | (R)-piperidin-2-carboxamide | 49 |
| 855 | (S)-piperidin-2-carboxamide | 44 |
| 856 | piperidin-4-carboxamide | 27 |
| 657 | (R)-pyrrolidine-2-ylmethanol | 58 |
| 658 | L-prolinamide | 48 |
| 659 | (S)-3-hydroxypiperidine hydrochloride | 60 |

TABLE 44

| Compound No. | Compound Name, $^1$H-NMR, MS (ESI) |
|---|---|
| 785 | (R)-(2-fluoro-4-(6-((1-(2-fluoro-2-methylpropyl)piperidin-4-yl)methoxy)pyridine-3-yl)phenyl)(3-hydroxypyrrolidine-1-yl)methanone<br>1H NMR (400 MHz, CDCl$_3$) δ 8.34 (t, 1 H, J = 2.6 Hz), 7.76-7.73 (m, 1 H), 7.50-7.45 (m, 1 H), 7.35-7.21 (m, 2 H), 6.81 (d, 1 H, J = 8.6 Hz), 4.57 (brs, 0.5 H), 4.45 (brs, 0.5 H), 4.18 (d, 2 H, J = 6.0 Hz), 3.82-3.32 (m, 5 H), 2.98 (d, 2 H, J = 11.3 Hz), 2.47 (s, 1 H), 2.41 (s, 1 H), 2.19-1.97 (m, 4 H), 1.80-1.77 (m, 3 H), 1.48-1.25 (m, 8 H); MS (ESI) m/z 474 (M+ + H). |
| 786 | (S)-(2-fluoro-4-(6-((1-(2-fluoro-2-methylpropyl)piperidin-4-yl)methoxy)pyridine-3-yl)phenyl)(3-hydroxypyrrolidine-1-yl)methanone<br>1H NMR (400 MHz, CDCl$_3$) δ 8.35 (s, 1 H), 7.77 (d, 1 H, J = 8.6 Hz), 7.53-7.48 (m, 1 H), 7.37-7.25 (m, 1 H), 7.23-7.14 (m, 1 H), 6.83 (d, 1 H, J = 8.4 Hz), 4.62 (brs, 0.5 H), 4.49 (brs, 0.5 H), 4.20 (d, 2 H, J = 6.1 Hz), 3.85-3.57 (m, 4 H), 3.48-3.34 (m, 1 H), 3.04 (d, 2 H, J = 9.2 Hz), 2.52 (s, 1 H), 2.47 (s, 1 H), 2.35-1.80 (m, 7 H), 1.50-1.18 (m, 6 H); MS (ESI) m/z 474 (M+ + H). |
| 787 | (S)-(2-fluoro-4-(6-((1-(2-fluoro-2-methylpropyl)piperidin-4-yl)methoxy)pyridine-3-yl)phenyl)(2-(hydroxymethyl)pyrrolidine-1-yl)methanone<br>1H NMR (400 MHz, CDCl$_3$) δ 8.35 (s, 1 H), 7.76 (dt, 1 H, J = , 2.1 Hz), 7.49 (t, 1 H, J = 6.8 Hz), 7.36 (d, 1 H, J = 4.4 Hz), 7.26 (d, 1 H, J = 12.0 Hz), 6.82 (dd, 1 H, J = 8.8, 1.2 Hz), 4.39-4.37 (m, 1 H), 4.19-4.17 (m, 2 H), 3.82-3.73 (m, 2 H), 3.45 (t, 2 H, J = 6.4 Hz), 2.98 (d, 2 H, J = 10.8 Hz), 2.47 (s, 1 H), 2.41 (s, 1 H), 2.22-2.13 (m, 3 H), 1.91-1.67 (m, 6 H), 1.48-1.33 (m, 8 H); MS (ESI) m/z 488 (M+ + H). |
| 854 | (R)-1-(2-fluoro-4-(6-((1-(2-fluoro-2-methylpropyl)piperidin-4-yl)methoxy)pyridine-3-yl)benzoyl)piperidin-2-carboxamide<br>1H NMR (400 MHz, CDCl$_3$) δ 8.37-8.36 (m, 1 H), 7.79-7.76 (m, 1 H), 7.51 (t, 1 H, J = 7.6 Hz), 7.43-7.39 (m, 1 H), 6.84 (d, 1 H, J = 8.8 Hz), 6.31 (brs, 1 H), 5.65 (brs, 1 H), 5.44 (brs, 1 H), 4.20 (d, 2 H, J = 6.1 Hz), 3.60 (d, 1 H, J = 12.8 Hz), 3.23-3.21 (m, 1 H), 2.99 (d, 2 H, J = 11.2 Hz), 2.47-2.42 (m, 3 H), 2.17 (t, 2 H, J = 11.2 Hz), 1.80-1.63 (m, 8 H), 1.48-1.25 (m, 8 H); MS (ESI) m/z 515 (M+ + H). |
| 855 | (S)-1-(2-fluoro-4-(6-((1-(2-fluoro-2-methylpropyl)piperidin-4-yl)methoxy)pyridine-3-yl)benzoyl)piperidin-2-carboxamide |

TABLE 44-continued

| Compound No. | Compound Name, $^1$H-NMR, MS (ESI) |
|---|---|
| | 1H NMR (400 MHz, CDCl$_3$) δ 8.37-8.36 (m, 1 H), 7.78-7.75 (m, 1 H), 7.51 (t, 1 H, J = 7.4 Hz), 7.41-7.39 (m, 1 H), 7.28-7.25 (m, 1 H), 6.83 (d, 1 H, J = 8.0 Hz), 6.33 (brs, 1 H), 5.74 (brs, 1 H), 5.48 (brs, 1 H), 4.19 (d, 2 H, J = 7.6 Hz), 3.60 (d, 1 H, J = 12.8 Hz), 3.32-3.21 (m, 1 H), 2.99 (d, 2 H, J = 11.2 Hz), 2.47-2.41 (m, 3 H), 2.17 (t, 2 H, J = 11.2 Hz), 1.80-1.62 (m, 8 H), 1.48-1.25 (m, 6 H); MS (ESI) m/z 515 (M+ + H). |
| 856 | 1-(2-fluoro-4-(6-((1-(2-fluoro-2-methylpropyl)piperidin-4-yl)methoxy)pyridine-3-yl)benzoyl)piperidin-4-carboxamide<br>1H NMR (400 MHz, CDCl$_3$) δ 8.36 (d, 1 H, J = 4.0 Hz), 7.77 (dd, 1 H, J = 8.5, 2.4 Hz), 7.45 (t, 1 H, J = 7.4 Hz), 7.37-7.23 (m, 2 H), 6.83 (d, 1 H, J = 8.4 Hz), 5.61 (d, 2 H, J = 12.8 Hz), 4.74 (d, 1 H, J = 13.2 Hz), 4.19 (d, 2 H, J = 6.2 Hz), 3.72 (d, 1 H, J = 13.9 Hz), 3.13-2.92 (m, 4 H), 2.48-2.42 (m, 3 H), 2.18 (t, 2 H, J = 11.2 Hz), 2.04-1.78 (m, 7 H), 1.48-0.88 (m, 8 H); MS (ESI) m/z 515 (M+ + H). |
| 657 | (R)-(2-fluoro-4-(6-((1-(2-fluoro-2-methylpropyl)piperidin-4-yl)methoxy)pyridine-3-yl)phenyl)(2-(hydroxymethyl)pyrrolidine-1-yl)methanone<br>1H NMR (400 MHz, CDCl$_3$) δ 8.35 (d, 1 H, J = 2.4 Hz), 7.76 (dd, 1 H, J = 7.4, 1.3 Hz), 7.50 (t, 1H, J = 7.5 Hz), 7.36 (dd, 1 H, J = 8.0, 1.5 Hz), 7.26 (dd, 1 H, J = 11.1, 1.6 Hz), 6.82 (d, 1 H, J = 8.6 Hz), 4.38 (m, 1 H), 4.18 (d, 2 H, J = 6.1 Hz), 3.76 (m, 2 H), 3.45 (m, 2 H), 2.97 (m, 2 H), 2.46 (s, 1 H), 2.41 (s, 1 H), 2.13 (m, 3 H), 1.87 (m, 1 H), 1.79 (m, 5 H), 1.44 (m, 5 H), 1.41 (s, 3 H); MS (ESI) m/z 488 (M + H). |
| 658 | (S)-1-(2-fluoro-4-(6-((1-(2-fluoro-2-methylpropyl)piperidin-4-yl)methoxy)pyridine-3-yl)benzoyl)pyrrolidine-2-carboxamide<br>1H NMR (400 MHz, CDCl$_3$) δ 8.36 (d, 1 H, J = 2.4 Hz), 7.77 (dd, 1 H, J = 8.6, 1.3 Hz), 7.50 (t, 1H, J = 7.5 Hz), 7.38 (dd, 1 H, J = 7.9, 1.5 Hz), 7.28 (dd, 1 H, J = 10.8, 1.4 Hz), 6.92 (s, 1 H), 6.83 (d, 1 H, J = 8.6 Hz), 5.62 (s, 1 H), 4.80 (m, 1 H), 4.19 (d, 2 H, J = 6.2 Hz), 3.54 (m, 1 H), 3.43 (s, 1 H), 2.99 (m, 2 H), 2.45 (m, 2 H), 2.09 (m, 4 H), 1.93 (m, 1 H), 1.84 (m, 4 H), 1.46 (m, 5 H), 1.39 (s, 3 H); MS (ESI) m/z 501 (M + H). |
| 659 | (S)-(2-fluoro-4-(6-((1-(2-fluoro-2-methylpropyl)piperidin-4-yl)methoxy)pyridine-3-yl)phenyl)(3-hydroxypiperidin-1-yl)methanone<br>1H NMR (400 MHz, CDCl$_3$) δ 8.33 (t, 1 H, J = 2.7 Hz), 7.74 (m, 1 H), 7.43 (t, 1H, J = 7.4 Hz), 7.32 (m, 1 H), 7.21 (m, 1 H), 6.80 (d, 1 H, J = 8.6 Hz), 4.17 (d, 2 H, J = 6.2 Hz), 3.62 (m, 1 H), 3.37 (m, 2 H), 3.13 (m, 2 H), 2.98 (m, 2 H), 2.78 (s, 1 H), 2.45 (s, 1 H), 2.40 (s, 1 H), 2.15 (t, 2 H, J = 11.1 Hz), 1.86 (m, 2 H), 1.76 (m, 4 H), 1.58 (m, 1 H), 1.40 (m, 5 H), 1.32 (s, 3 H); MS (ESI) m/z 488 (M + H). |

Example 64. Compound 946: (S)-1-(3-fluoro-4'-((1-(2-fluoro-2-methylpropyl)piperidin-4-yl)methoxy)-3'-(hydroxymethyl)biphenylcarbonyl)pyrrolidine-2-carboxamide

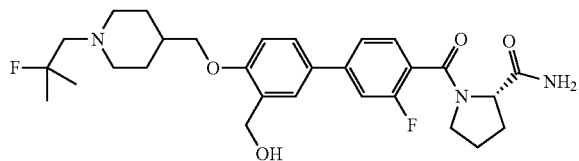 [SMILES: CC(C)(F)CN1CCC(COc2ccc(-c3ccc(C(=O)N4CCC[C@H]4C(N)=O)c(F)c3)cc2CO)CC1]

Step 1.

t-butyl 4-((4-bromo-2-formylphenoxy)methyl)piperidin-1-carboxylate: t-butyl 4-((methylsulfonyloxy)methyl)piperidin-1-carboxylate (the product of synthesis step 2 of compound 431; 1.00 g, 3.41 mmol) was dissolved in DMF (80 mL). K$_2$CO$_3$ (1.67 g, 5.11 mmol) was added thereto, and stirred for 5 minutes. 5-bromo-2-hydroxybenzaldehyde (685 mg, 3.41 mmol) was added thereto, following with stirring at 80° C. for a day. The reaction mixture was added with water, and extracted with EtOAc. The organic layer was washed with saturated NH$_4$Cl aqueous solution. The organic layer was dried over anhydrous MgSO$_4$, and concentrated under reduced pressure. The obtained concentrate was purified by silica gel column chromatography (EtOAc/hexane=30%~70%) to yield the title compound as white solid (840 mg, 61%).

Step 2.

5-bromo-2-(piperidin-4-ylmethoxy)benzaldehyde hydrochloride: t-butyl 4-((4-bromo-2-formylphenoxy)methyl)piperidin-1-carboxylate (840 mg, 2.11 mmol) was dissolved in CH$_2$Cl$_2$ (20 mL). 4 M HCl in 1,4-dioxane (1.06 mL, 4.22 mmol) was added thereto, following with stirring for 1 hour. The resulting precipitate was filtered to yield the title compound as white solid (500 mg, 70%).

Step 3.

5-bromo-2-((1-2-hydroxy-2-methylpropyl)piperidin-4-yl)methoxy)benzaldehyde: 5-bromo-2-(piperidin-4-ylmethoxy)benzaldehyde hydrochloride (500 mg, 1.68 mmol) was dissolved in EtOH (5 mL) and H$_2$O (5 mL). 2,2-Dimethyloxirane (1.49 mL, 16.77 mmol) and K$_2$CO$_3$ (116 mg, 0.84 mmol) were added thereto slowly. With a microwave radiation, the mixture was heated at 110° C. for 15 minutes, and then cooled to room temperature. The reaction mixture was added with water, and extracted with EtOAc. The obtained organic layer was washed with saturated aqueous brine solution, and then. The organic layer was dried over anhydrous MgSO$_4$, and concentrated under reduced pressure. The obtained material, which is the title compound as white solid (620 mg, 99%), was used without further purification.

Step 4.

5-bromo-2-((1-(2-fluoro-2-methylpropyl)piperidin-4-yl)methoxy)benzaldehyde: 5-bromo-2-((1-2-hydroxy-2-methylpropyl)piperidin-4-yl)methoxy)benzaldehyde (620 mg, 1.67 mmol) was dissolved in CH$_2$Cl$_2$ (10 mL). At 0° C., DAST (221 μL, 1.67 mmol) was added slowly thereto. After stirring for 1 hour at room temperature, The reaction mixture was added with water, and extracted with EtOAc. The obtained organic layer was washed with saturated aqueous brine solution, and then. The organic layer was dried over anhydrous MgSO$_4$, and concentrated under reduced pressure. The obtained concentrate was purified by silica gel column chromatography (EtOAc/hexane=40%~60%) to yield the title compound as white solid (310 mg, 49%).

Step 5.

(5-bromo-2-((1-(2-fluoro-2-methylpropyl)piperidin-4-yl)methoxy)phenyl)methanol: 5-bromo-2-((1-(2-fluoro-2-methylpropyl)piperidin-4-yl)methoxy)benzaldehyde (310 mg, 0.83 mmol) was dissolved in THF (10 mL). At room temperature, NaBH$_4$ (95 mg, 2.50 mmol) was added thereto, following with stirring at the same temperature for 1 hour. The reaction mixture was added with water, and extracted with EtOAc. The obtained organic layer was washed with saturated aqueous brine solution, and then. The organic layer was dried over anhydrous MgSO$_4$, and concentrated under reduced pressure. The obtained concentrate was purified by silica gel column chromatography (EtOAc/hexane=50%) to yield the title compound as white solid (200 mg, 64%).

Step 6.

Ethyl 3-fluoro-4'-((1-(2-fluoro-2-methylpropyl)piperidin-4-yl)methoxy)-3'-(hydroxymethyl)biphenyl-4-carboxylate: (5-bromo-2-((1-(2-fluoro-2-methylpropyl)piperidin-4-yl)methoxy)phenyl)methanol (200 mg, 0.534 mmol), 4-(ethoxycarbonyl)-3-fluorophenylboronic acid (125 mg, 0.59 mmol), Pd(dppf)Cl$_2$ (44 mg, 0.05 mmol) and Cs$_2$CO$_3$ (348 mg, 1.07 mmol) were added to water (2 mL)/DME (6 mL). With a microwave radiation, the mixture was heated at 110° C. for 15 minutes, and then cooled to room temperature. The reaction mixture was added with water, and extracted with EtOAc. The obtained organic layer was washed with saturated aqueous brine solution, and then. The organic layer was dried over anhydrous MgSO$_4$, and concentrated under reduced pressure. The obtained concentrate was purified by silica gel column chromatography (EtOAc/hexane=40%~60%) to yield the title compound as white solid (146 mg, 59%).

Step 7.

3-fluoro-4'-((1-(2-fluoro-2-methylpropyl)piperidin-4-yl)methoxy)-3'-(hydroxymethyl)biphenyl-4-carboxylic acid: Ethyl 3-fluoro-4'-((1-(2-fluoro-2-methylpropyl)piperidin-4-yl)methoxy)-3'-(hydroxymethyl)biphenyl-4-carboxylate (146 mg, 0.32 mmol) was dissolved in THF (10 mL) and water (5 mL). LiOH.H$_2$O (66 mg, 1.58 mmol) was added thereto little by little at room temperature, following with stirring for 1 hour. The reaction mixture was concentrated under reduced pressure. The resulting precipitate was filtered to yield the title compound as white solid (120 mg, 87%).

Step 8.

Compound 946: 3-fluoro-4'-((1-(2-fluoro-2-methylpropyl)piperidin-4-yl)methoxy)-3'-(hydroxymethyl)biphenyl-4-carboxylic acid (30 mg, 0.07 mmol), (S)-pyrrolidine-2-carboxamide (16 mg, 0.14 mmol), EDC (27 mg, 0.14 mmol), HOBt (19 mg, 0.14 mmol) and DIPEA (25 µL, 0.14 mmol) were dissolved in CH$_2$Cl$_2$ (1 mL), following with stirring with at the same temperature for a day. The reaction mixture was added with water, and extracted with EtOAc. The organic layer was washed with saturated NH$_4$Cl aqueous solution. The organic layer was dried over anhydrous MgSO$_4$, and concentrated under reduced pressure. The obtained concentrate was purified by silica gel column chromatography (CH$_2$Cl$_2$/MeOH=95%~5%) to yield the title compound as white solid (21 mg, 42%).

1H NMR (400 MHz, CDCl$_3$) δ 7.56-7.55 (m, 1H), 7.49-7.41 (m, 3H), 7.33-7.27 (m, 1H), 6.96-6.94 (m, 1H), 5.50 (brs, 1H), 5.31-4.81 (m, 3H), 3.93 (d, 2H, J=5.4 Hz), 3.57-3.40 (m, 2H), 3.03 (brs, 1H), 2.51-2.43 (m, 3H), 2.23-2.21 (m, 2H), 2.16-2.03 (m, 3H), 1.94-1.80 (m, 4H), 1.69 (brs, 2H), 1.43 (s, 3H), 1.38 (s, 3H), 1.32-1.28 (m, 2H); MS (ESI) mz 530 (M++H).

According to the above-described synthesis process of compound 946, the compounds of Table 46 were synthesized using 3-fluoro-4'-((1-(2-fluoro-2-methylpropyl)piperidin-4-yl)methoxy)-3'-(hydroxymethyl)biphenyl-4-carboxylic acid and the reactant of Table 45.

TABLE 45

| Compound No. | Reactant | Yield (%) |
|---|---|---|
| 947 | (S)-pyrrolidine-3-ol | 78 |

TABLE 46

| Compound No. | Compound Name, $^1$H-NMR, MS (ESI) |
|---|---|
| 947 | (S)-(3-fluoro-4'-((1-(2-fluoro-2-methylpropyl)piperidin-4-yl)methoxy)-5'-(hydroxymethyl)biphenyl-4-yl)(3-hydroxypyrrolidine-1-yl)methanone<br>1H NMR (400 MHz, CDCl$_3$) δ 7.55 (s, 1 H), 7.54-7.44 (m, 2 H), 7.38 (d, 1 H, J = 8.0 Hz), 7.30-7.26 (m, 1 H), 6.93 (d, 1 H, J = 8.6 Hz), 4.77 (d, 2 H, J = 6.0 Hz), 4.61 (brs, 0.5 H), 4.48 (brs, 0.5 H), 3.93 (d, 2 H, J = 5.4 Hz), 3.85-3.78 (m, 2 H), 3.73-3.57 (m, 2 H), 3.46 (brs, 0.5 Hz), 3.33 (brs, 0.5 H), 3.08 (brs, 2 H), 2.50 (brs, 2 H), 2.18-2.00 (m, 4 H), 1.99-1.81 (m, 4 H), 1.45 (s, 3 H), 1.40 (s, 3 H), 1.29-1.23 (m, 2 H); MS (ESI) m/z 503 (M+ + H). |

Example 65. Compound 948: (R)-(4-(5-((1-(2-fluoro-2-methylpropyl)piperidin-4-yl)methoxy)pyrazine-2-yl)phenyl)(3-hydroxypiperidin-1-yl)methanone

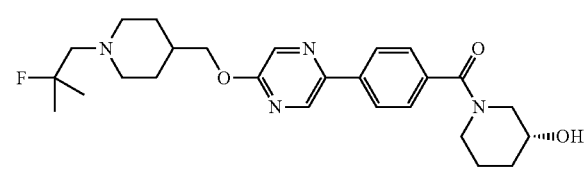 [SMILES: CC(C)(F)CN1CCC(COc2cnc(-c3ccc(C(=O)N4CCC[C@@H](O)C4)cc3)cn2)CC1]

Step 1.

Methyl 4-(5-((1-(2-fluoro-2-methylpropyl)piperidin-4-yl)methoxy)pyrazine-2-yl)benzoate: To 2-((1-(2-fluoro-2-methylpropyl)piperidin-4-yl)methoxy)-5-iodopyrazine (the product of synthesis step 4 of compound 944; 0.35 g, 0.89 mmol), 4-(methoxycarbonyl)phenylboronic acid (0.19 g, 1.06 mmol), Pd(dbpf)Cl$_2$ (0.03 g, 0.04 mmol) and Cs$_2$CO$_3$ (0.58 g, 1.78 mmol), DME (9 mL)/H$_2$O (3 mL) was added. With a microwave radiation, the mixture was heated at 110° C. for 20 minutes, and then cooled to room temperature. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, EtOAc/hexane=0% to 15%), and concentrated to yield the title compound as white solid (0.21 g, 59%).

Step 2.

4-(5-((1-(2-fluoro-2-methylpropyl)piperidin-4-yl)methoxy)pyrazine-2-yl)benzoic acid: Methyl 4-(5-((1-(2-fluoro-2-methylpropyl)piperidin-4-yl)methoxy)pyrazine-2-yl)benzoate (0.21 g, 0.52 mmol) and LiOH.H$_2$O (0.11 g, 2.62 mmol) were dissolved in THF (2 mL)/H$_2$O/MeOH (3 mL) at room temperature. The solution was stirred at the same temperature for 12 hours, the reaction mixture was concentrated under reduced pressure. The concentrate was added with water (10 mL) to be suspended, and filtered. The obtained solid was dried to yield the title compound as white solid (0.16 g, 78%).

Step 3.

Compound 948: 4-(5-((1-(2-fluoro-2-methylpropyl)piperidin-4-yl)methoxy)pyrazine-2-yl)benzoic acid (0.04 g, 0.10 mmol), EDCI (0.04 g, 0.20 mmol), HOBt (0.02 g, 0.20 mmol) and DIPEA (0.09 mL, 0.51 mmol) were dissolved in DMF (2 ml). At room temperature, (R)-piperidin-3-ol (0.02 g, 0.20 mmol) was added thereto, following with stirring at 60° C. for 12 hours. The concentrate was added with water (10 mL) to be suspended, and filtered. The obtained solid was dried, and purified by column chromatography (SiO$_2$, 4 g cartridge; methanol/dichloromethane=0% to 10%), and concentrated to yield the title compound as yellow solid (0.02 g, 49%).

1H NMR (400 MHz, CDCl$_3$) δ 8.48 (s, 1H), 8.26 (s, 1H), 7.93 (d, 2H, J=8.4 Hz), 7.51 (d, 2H, J=8.0 Hz), 4.20 (d, 2H, J=6.1 Hz), 3.98-3.25 (m, 5H), 2.97 (d, 2H, J=11.2 Hz), 2.45 (s, 1H), 2.39 (s, 1H), 2.18-1.67 (m, 9H), 1.44-1.32 (m, 8H); MS (ESI) m/z 471 (M++H).

According to the above-described synthesis process of compound 948, the compounds of Table 48 were synthesized using 4-(5-((1-(2-fluoro-2-methylpropyl)piperidin-4-yl)methoxy)pyrazine-2-yl)benzoic acid and the reactant of Table 47.

TABLE 47

| Compound No. | Reactant | Yield (%) |
|---|---|---|
| 949 | (S)-pyrrolidine-3-ol | 45 |
| 950 | (S)-pyrrolidine-2-carboxamide | 40 |
| 951 | (S)-piperidin-3-ol | 52 |
| 1080 | (R)-piperidin-2-carboxamide hydrochloride | 62 |
| 1081 | (S)-piperidin-2-carboxamide hydrochloride | 70 |

TABLE 48

| Compound No. | Compound Name, $^1$H-NMR, MS (ESI) |
|---|---|
| 949 | (S)-(4-(5-((1-(2-fluoro-2-methylpropyl)piperidin-4-yl)methoxy)pyrazine-2-yl)phenyl)(3-hydroxypyrrolidine-1-yl)methanone<br>1H NMR (400 MHz, CDCl$_3$) δ 8.49 (s, 1 H), 8.26 (s, 1 H), 7.94-7.92 (m, 2 H), 7.64-7.59 (m, 2 H), 4.53 (d, 1 H, J = 52.8 Hz), 4.20 (d, 2 H, J = 6.0 Hz), 3.82-3.43 (m, 5 H), 2.97 (d, 2 H, J = 11.2 Hz), 2.45 (s, 1 H), 2.39 (s, 1 H), 2.15 (t, 2 H, J = 11.6 Hz), 2.10-1.53 (m, 5 H), 1.44-1.23 (m, 8 H); MS (ESI) m/z 457 (M+ + H). |
| 950 | (S)-1-(4-(5-((1-(2-fluoro-2-methylpropyl)piperidin-4-yl)methoxy)pyrazine-2-yl)benzoyl)pyrrolidine-2-carboxamide<br>1H NMR (400 MHz, CDCl$_3$) δ 8.50 (s, 1 H), 8.27 (s, 1 H), 7.96 (d, 2 H, J = 8.2 Hz), 7.62 (d, 2 H, J = 8.4 Hz), 6.96 (brs, 1 H), 5.47 (brs, 1 H), 4.81-4.80 (m, 1 H), 4.20 (d, 2 H, J = 3.2 Hz), 3.61-3.53 (m, 2 H), 2.97 (d, 2 H, J = 11.6 Hz), 2.45-2.39 (m, 3 H), 2.17-1.66 (m, 6 H), 1.44-1.32 (m, 8 H); MS (ESI) m/z 484 (M+ + H). |
| 951 | (S)-(4-(5-((1-(2-fluoro-2-methylpropyl)piperidin-4-yl)methoxy)pyrazine-2-yl)phenyl)(3-hydroxypiperidin-1-yl)methanone<br>1H NMR (400 MHz, CDCl$_3$) δ 8.48 (s, 1 H), 8.26 (s, 1 H), 7.93 (d, 2 H, J = 8.0 Hz), 7.51 (d, 2 H, J = 8.0 Hz), 4.20 (d, 2 H, J = 6.0 Hz), 3.98-3.22 (m, 5 H), 2.97 (d, 2 H, J = 11.6 Hz), 2.45 (s, 1 H), 2.39 (s, 1 H), 2.17 (t, 2 H, J = 6.0 Hz), 1.78-1.67 (m, 7 H), 1.44-1.32 (m, 8 H); MS (ESI) m/z 471 (M+ + H). |
| 1080 | (R)-1-(4-(5-((1-(2-fluoro-2-methylpropyl)piperidin-4-yl)methoxy)pyrazine-2-yl)benzoyl)piperidin-2-carboxamide<br>1H NMR (400 MHz, CDCl$_3$) δ 8.51 (s, 1 H), 8.28 (s, 1 H), 7.89-8.00 (m, 2 H), 7.51-7.56 (m, 2 H), 6.49 (s, 1 H), 5.56 (s, 1 H), 5.27-5.29 (m, 1 H), 4.21 (d, 2 H, J = 6.2 Hz), 3.74-3.77 (m, 1H), 3.08-3.14 (m, 1 H), 2.97-2.99 (m, 2 H), 2.41-2.46 (m, 2 H), 2.31-2.34 (m, 1 H), 2.13-2.19 (m, 2 H), 1.59-1.83 (m, 5 H), 1.53-1.56 (m, 3 H), 1.42-1.48 (m, 2 H), 1.38 (s, 3 H), 1.33 (s, 3 H); MS (ESI) m/z 498.3 (M+ + H). |
| 1081 | (S)-1-(4-(5-((1-(2-fluoro-2-methylpropyl)piperidin-4-yl)methoxy)pyrazine-2-yl)benzoyl)piperidin-2-carboxamide<br>1H NMR (400 MHz, CDCl$_3$) δ 8.51 (s, 1 H), 8.28 (s, 1 H), 7.89-8.01 (m, 2 H), 7.54-7.56 (m, 2 H), 6.48 (s, 1 H), 5.50 (s, 1 H), 5.27-5.28 (m, 1 H), 4.21 (d, 2 H, J = 6.2 Hz), 3.74-3.78 (m, 1 H), 3.07-3.14 (m, 1 H), 2.97-2.99 (m, 2 H), 2.41-2.46 (m, 2 H), 2.31-2.35 (m, 1 H), 2.13-2.18 (m, 2 H), 1.76-1.87 (m, 5 H), 1.53-1.69 (m, 3 H), 1.43-1.48 (m, 2 H), 1.38 (s, 3 H), 1.33 (s, 3 H); MS (ESI) m/z 498.3 (M+ + H). |

Example 66. Compound 982: (R)-(3-fluoro-4-(5-((1-(2-fluoro-2-methylpropyl)piperidin-4-yl)methoxy)pyrazine-2-yl)phenyl)(3-hydroxypiperidin-1-yl)methanone

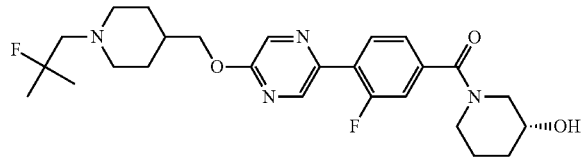 [SMILES: CC(C)(F)CN1CCC(COc2cnc(-c3ccc(C(=O)N4CCC[C@@H](O)C4)cc3F)cn2)CC1]

Step 1.

Methyl 3-fluoro-4-(5-((1-(2-fluoro-2-methylpropyl)piperidin-4-yl)methoxy)pyrazine-2-yl)benzoate: To 2-((1-(2-fluoro-2-methylpropyl)piperidin-4-yl)methoxy)-5-iodopyrazine (the product of synthesis step 4 of compound 944; 0.50 g, 1.27 mmol), 2-fluoro-4-(methoxycarbonyl)phenylboronic acid (0.29 g, 1.39 mmol), Pd(dppf)Cl$_2$ (0.05 g, 0.06 mmol) and Cs$_2$CO$_3$ (0.82 g, 2.54 mmol), DME (9 mL)/H$_2$O (3 mL) was added. With a microwave radiation, the mixture was heated at 110° C. for 20 minutes, and then cooled to room temperature. The reaction mixture was filtered through a Celite pad to remove a solid. The obtained filtrate was diluted with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 4 g cartridge; EtOAc/hexane=0% to 30%), and concentrated to yield the title compound as white solid (0.24 g, 45%).

Step 2.

3-fluoro-4-(5-((1-(2-fluoro-2-methylpropyl)piperidin-4-yl)methoxy)pyrazine-2-yl)benzoic acid: Methyl 3-fluoro-4-(5-((1-(2-fluoro-2-methylpropyl)piperidin-4-yl)methoxy)pyrazine-2-yl)benzoate (0.24 g, 0.57 mmol) and LiOH.H$_2$O (0.12 g, 2.86 mmol) were dissolved in THF/MeOH (16 mL)/H$_2$O (4 mL) at room temperature. The solution was stirred at the same temperature for 2 hours, the reaction mixture was concentrated under reduced pressure. The resulting precipitate was filtered, and dried to yield the title compound as white solid (0.20 g, 86%).

Step 3.

Compound 982: 3-fluoro-4-(5-((1-(2-fluoro-2-methylpropyl)piperidin-4-yl)methoxy)pyrazine-2-yl)benzoic acid (0.04 g, 0.09 mmol), (R)-piperidin-3-ol (0.01 g, 0.11 mmol), HOBt (0.02 g, 0.19 mmol), EDC (0.03 g, 0.19 mmol) and DIPEA (0.03 mL, 0.19 mmol) were dissolved in CH$_2$Cl$_2$ (1 mL) at room temperature. The solution was stirred at the same temperature for 18 hours, the reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 4 g cartridge; dichloromethane/methanol=0% to 30%), and concentrated to yield the title compound as white solid (0.02 g, 41%).

1H NMR (400. MHz, CDCl$_3$) δ 8.61 (s, 1H), 8.32 (s, 1H), 8.00 (t, 1H, J=7.8 Hz), 7.26-7.32 (m, 2H), 4.23 (d, 2H, J=6.2 Hz), 3.27-3.95 (m, 5H), 2.98-3.01 (m, 2H), 2.42-2.48 (m, 2H), 2.14-2.22 (m, 3H), 1.77-2.05 (m, 4H), 1.43-1.67 (m, 5H), 1.40 (s, 3H), 1.34 (s, 3H); MS (ESI) m/z 489.2 (M++H).

According to the above-described synthesis process of compound 982, the compounds of Table 50 were synthesized using 3-fluoro-4-(5-((1-(2-fluoro-2-methylpropyl)piperidin-4-yl)methoxy)pyrazine-2-yl)benzoic acid and the reactant of Table 49.

TABLE 49

| Compound No. | Reactant | Yield (%) |
|---|---|---|
| 983 | (S)-piperidin-3-ol hydrochloride | 37 |
| 984 | (S)-pyrrolidine-3-ol | 47 |
| 935 | (R)-pyrrolidine-2-ylmethanol | 35 |
| 1072 | (S)-pyrrolidine-2-carboxamide | 57 |
| 1073 | (R)-piperidin-2-carboxamide hydrochloride | 27 |

TABLE 50

| Compound No. | Compound Name, $^1$H-NMR, MS (ESI) |
|---|---|
| 983 | (S)-(3-fluoro-4-(5-((1-(2-fluoro-2-methylpropyl)piperidin-4-yl)methoxy)pyrazine-2-yl)phenyl)(3-hydroxypiperidin-1-yl)methanone<br>1H NMR (400 MHz, CDCl$_3$) δ 8.62 (s, 1 H), 8.33 (s, 1 H), 8.01 (t, 1 H, J = 7.8 Hz), 7.22-7.34 (m, 2 H), 4.24 (d, 2 H, J = 6.3 Hz), 3.35-3.96 (m, 5 H), 2.97-3.01 (m, 2 H), 2.48 (s, 1 H), 2.43 (s, 1 H), 2.15-2.20 (m, 2 H), 1.68-2.05 (m, 6 H), 1.49-1.56 (m, 2 H), 1.43-1.47 (m, 2 H), 1.40 (s, 3 H), 1.35 (s, 3 H); MS (ESI) m/z 489.2 (M+ + H). |
| 984 | (S)-(3-fluoro-4-(5-((1-(2-fluoro-2-methylpropyl)piperidin-4-yl)methoxy)pyrazine-2-yl)phenyl)(3-hydroxypyrrolidine-1-yl)methanone<br>1H NMR (400 MHz, CDCl$_3$) δ 8.63 (s, 1 H), 8.33 (s, 1 H), 8.03 (t, 1 H, J = 7.7 Hz), 7.36-7.53 (m, 2 H), 4.51-4.63 (m, 1 H), 4.24 (d, 2 H, J = 6.2 Hz), 3.75-3.87 (m, 2 H), 3.46-3.71 (m, 2 H), 2.99-3.01 (m, 2 H), 2.43-2.55 (m, 2 H), 1.93-2.21 (m, 4 H), 1.60-1.82 (m, 4 H), 1.44-1.47 (m, 2 H), 1.41 (s, 3 H), 1.36 (s, 3 H); MS (ESI) m/z 475.2 (M+ + H). |
| 985 | (R)-(3-fluoro-4-(5-((1-(2-fluoro-2-methylpropyl)piperidin-4-yl)methoxy)pyrazine-2-yl)phenyl)(2-(hydroxymethyl)pyrrolidine-1-yl)methanone<br>1H NMR (400 MHz, CDCl$_3$) δ 8.63 (s, 1 H), 8.33 (s, 1 H), 8.04 (t, 1 H, J = 7.9 Hz), 7.42 (d, 1 H, J = 8.1 Hz), 7.36 (d, 1 H, J = 11.4 Hz), 5.31 (s, 1 H), 4.40-4.45 (m, 1 H), 4.24 (d, 2 H, J = 6.3 Hz), 3.74-3.85 (m, 2 H), 3.49-3.60 (m, 2 H), 2.98-3.01 (m, 2 H), 2.48 (s, 1 H), 2.42 (s, 1 H), 2.14-2.23 (m, 3 H), 1.64-1.93 (m, 6 H), 1.43-1.50 (m, 2 H), 1.40 (s, 3 H), 1.35 (s, 3 H); MS (ESI) m/z 489.2 (M+ + H). |
| 1072 | (S)-1-(3-fluoro-4-(5-((1-(2-fluoro-2-methylpropyl)piperidin-4-yl)methoxy)pyrazine-2-yl)benzoyl)pyrrolidine-2-carboxamide<br>1H NMR (400 MHz, CDCl$_3$) δ 8.60 (s, 1 H), 8.30 (s, 1 H), 8.02 (t, 1 H, J = 7.8 |

TABLE 50-continued

Compound No. Compound Name, $^1$H-NMR, MS (ESI)

Hz), 7.34-7.43 (m, 2 H), 6.87 (s, 1 H), 5.51 (s, 1 H), 4.77 (dd, 1 H, J = 7.4, 5.0 Hz), 4.21 (d, 2 H, J = 6.4 Hz), 3.51-3.64 (m, 2 H), 2.97-3.00 (m, 2 H), 2.41-2.47 (m, 2 H), 2.02-2.19 (m, 5 H), 1.75-1.90 (m, 4 H), 1.42-1.48 (m, 2 H), 1.37 (s, 3 H), 1.32 (s, 3 H); MS (ESI) m/z 502.2 (M+ + H).

1073 (R)-1-(3-fluoro-4-(5-((1 -(2-fluoro-2-methylpropyl)piperidin-4-yl)methoxy)pyrazine-2-yl)benzoyl)piperidin-2-carboxamide
1H NMR (400 MHz, CDCl$_3$) δ 8.60 (s, 1 H), 8.30 (s, 1 H), 8.03 (t, 1 H, J = 8.0 Hz), 7.26-7.33 (m, 2 H), 6.36 (s, 1 H), 5.41 (s, 1 H), 5.24-5.28 (m, 1 H), 4.21 (d, 2 H, J = 6.0 Hz), 3.71-3.74 (m, 1 H), 3.09-3.16 (m, 1 H), 2.99-3.01 (m, 2 H), 2.43-2.48 (m, 2 H), 2.29-2.32 (m, 1 H), 2.14-2.20 (m, 2 H), 1.43-1.83 (m, 10 H), 1.38 (s, 3 H), 1.33 (s, 3 H); MS (ESI) m/z 516.2 (M+ + H).

Example 67. Compound 944: (S)-1-(2-fluoro-4-(5-((1-(2-fluoro-2-methylpropyl)piperidin-4-yl)methoxy)pyrazine-2-yl)benzoyl)pyrrolidine-2-carboxamide

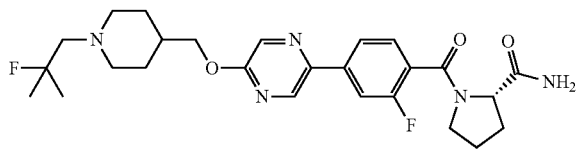 [SMILES: CC(C)(F)CN1CCC(COc2cnc(-c3ccc(C(=O)N4CCC[C@H]4C(N)=O)c(F)c3)cn2)CC1]

Step 1.

t-butyl 4-((5-iodopyrazine-2-yloxy)methyl)piperidin-1-carboxylate: t-butyl 4-(hydroxymethyl)piperidin-1-carboxylate (the product of synthesis step 1 of compound 431; 2.70 g, 12.54 mmol), 2-bromo-5-iodopyrazine (3.57 g, 12.54 mmol) and NaH (0.36 g, 15.05 mmol) were dissolved in 70° C. for THF (30 mL), following with stirring at the same temperature for 6 hours. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; EtOAc/hexane=0% to 20%), and concentrated to yield the title compound as white solid (4.04 g, 76%).

Step 2.

2-iodo-5-(piperidin-4-ylmethoxy)pyrazine hydrochloride: t-butyl 4-((5-iodopyrazine-2-yloxy)methyl)piperidin-1-carboxylate (4.00 g, 9.54 mmol) was dissolved in CH$_2$Cl$_2$ (30 mL). At room temperature, 4 M HCl solution in 1,4-dioxane (11.92 mL, 47.70 mmol) was added thereto, following with stirring at the same temperature for 2 hours. The reaction mixture was concentrated under reduced pressure. The resulting precipitate was filtered, and dried to yield the title compound as white solid (3.20 g, 94%).

Step 3.

1-(4-((5-iodopyrazine-2-yloxy)methyl)piperidin-1-yl)-2-methylpropan-2-ol: To 2-iodo-5-(piperidin-4-ylmethoxy)pyrazine hydrochloride (1.20 g, 3.37 mmol), 2,2-dimethyl oxirane (3.00 mL, 33.74 mmol) and K$_2$CO$_3$ (2.33 g, 16.87 mmol), EtOH (8 mL)/H$_2$O (2 mL) was added. With a microwave radiation, the mixture was heated at 110° C. for 20 minutes, and then cooled to room temperature. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The resulting precipitate was filtered, and dried to yield the title compound as white solid (1.30 g, 98%).

Step 4.

2-((1-(2-fluoro-2-methylpropyl)piperidin-4-yl)methoxy)-5-iodopyrazine: 1-(4-((5-iodopyrazine-2-yloxy)methyl)piperidin-1-yl)-2-methylpropan-2-ol (1.30 g, 3.32 mmol) and DAST (0.53 mL, 3.98 mmol) were dissolved in CH$_2$Cl$_2$ (20 mL) at 0° C., following with stirring at room temperature for 2 hours. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; EtOAc/hexane=0% to 20%), and concentrated to yield the title compound as white solid (0.81 g, 62%).

Step 5.

Ethyl 2-fluoro-4-(5-((1-(2-fluoro-2-methylpropyl)piperidin-4-yl)methoxy)pyrazine-2-yl)benzoate: To 2-((1-(2-fluoro-2-methylpropyl)piperidin-4-yl)methoxy)-5-iodopyrazine (250 mg, 0.64 mmol), 4-(ethoxycarbonyl)-3-fluorophenylboronic acid (162 mg, 0.76 mmol), Pd(dppf)Cl$_2$ (26 mg, 0.03 mmol) and Cs$_2$CO$_3$ (414 mg, 1.27 mmol), DME (9 mL)/H$_2$O (3 mL) was added. With a microwave radiation, the mixture was heated at 110° C. for 20 minutes, and then cooled to room temperature. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The obtained concentrate was purified by silica gel column chromatography (EtOAc/hexane=0%~15%) to yield the title compound as white solid (162 mg, 58%).

Step 6.

2-fluoro-4-(5-((1-(2-fluoro-2-methylpropyl)piperidin-4-yl)methoxy)pyrazine-2-yl)benzoic acid: Ethyl 2-fluoro-4-(5-((1-(2-fluoro-2-methylpropyl)piperidin-4-yl)methoxy)pyrazine-2-yl)benzoate (158 mg, 0.36 mmol) was dissolved in THF (10 mL) and H$_2$O (5 mL). At room temperature, LiOH.H$_2$O (77 mg, 1.82 mmol) was added thereto, following with stirring for 1 hour. The reaction mixture was concentrated under reduced pressure. The resulting precipitate was filtered, and dried to yield the title compound as white solid (120 mg, 81%).

Step 7.

Compound 944: 2-fluoro-4-(5-((1-(2-fluoro-2-methylpropyl)piperidin-4-yl)methoxy)pyrazine-2-yl)benzoic acid (30 mg, 0.07 mmol), EDC (28 mg, 0.15 mmol) and HOBt (20 mg, 0.15 mmol) was added thereto, DIPEA (26 μL, 0.15 mmol) were dissolved in CH$_2$Cl$_2$ (1 mL). At room temperature, (S)-pyrrolidine-2-carboxamide (17 mg, 0.15 mmol) was added thereto, following with stirring for a day. The reaction mixture was added with water, and extracted with EtOAc. The organic layer was washed with saturated NH$_4$Cl aqueous solution, dried over dried over anhydrous MgSO₄, and concentrated under reduced pressure. The obtained concentrate was purified by silica gel column chromatography (CH₂Cl₂/MeOH=95%~5%) to yield the title compound as white solid (20 mg, 53%).

1H NMR (400 MHz, CDCl₃) δ 8.50 (s, 1H), 8.29 (s, 1H), 7.78-7.51 (m, 2H), 7.53 (t, 1H, J=7.5 Hz), 6.91 (s, 1H), 5.54 (s, 1H), 4.84-4.81 (m, 1H), 4.33 (d, 2H, J=5.6 Hz), 3.85-3.81 (m, 2H), 3.56-3.38 (m, 2H), 3.26-3.21 (m, 2H), 2.92-2.85 (m, 2H), 2.51-2.46 (m, 1H), 2.27-2.26 (m, 2H), 2.18-2.06 (m, 6H), 1.66 (s, 3H), 1.60 (s, 3H); MS (ESI) m/z 502 (M++H).

According to the above-described synthesis process of compound 944, the compounds of Table 52 were synthesized using 2-fluoro-4-(5-((1-(2-fluoro-2-methylpropyl)piperidin-4-yl)methoxy)pyrazine-2-yl)benzoic acid and the reactant of Table 51.

TABLE 51

| Compound No. | Reactant | Yield (%) |
|---|---|---|
| 945 | (R)-piperidin-3-ol hydrochloride | 49 |
| 986 | (S)-piperidin-2-ol hydrochloride | 54 |
| 987 | (S)-pyrrolidine-3-ol | 53 |
| 988 | (R)-pyrrolidine-2-ylmethanol | 54 |

TABLE 52

| Compound No. | Compound Name, ¹H-NMR, MS (ESI) |
|---|---|
| 945 | (R)-(2-fluoro-4-(5-((1-(2-fluoro-2-methylpropyl)piperidin-4-yl)methoxy)pyrazine-2-yl)phenyl)(3-hydroxypiperidin-1-yl)methanone<br>1H NMR (400 MHz, CDCl₃) δ 8.50 (s, 1 H), 8.28 (s, 1 H), 7.75-7.69 (m, 2 H), 7.49 (t, 1 H, J = 7.2 Hz), 4.24 (d, 2 H, J = 6.2 Hz), 4.11-4.08 (m, 1 H), 3.94 (brs, 1 H), 3.58-3.55 (m, 1 H), 3.46-3.19 (m, 1 H), 3.14-2.96 (m, 2 H), 2.64-2.50 (m, 2 H), 2.18 (brs, 2 H), 2.01-1.81 (m, 6 H), 1.72-1.50 (m, 5 H), 1.43 (s, 3 H), 1.38 (s, 3 H); MS (ESI) m/z 489 (M+ + H). |
| 986 | (S)-(2-fluoro-4-(5-((1-(2-fluoro-2-methylpropyl)piperidin-4-yl)methoxy)pyrazine-2-yl)phenyl)(3-hydroxypiperidin-1-yl)methanone<br>1H NMR (400 MHz, CDCl₃) δ 8.51 (s, 1 H), 8.29 (s, 1 H), 7.70-7.76 (m, 2 H), 7.48-7.53 (m, 1 H), 4.23 (d, 2 H, J = 6.2 Hz), 3.74-4.12 (m, 2 H), 3.25-3.58 (m, 3 H), 3.10-3.15 (m, 2 H), 2.98-3.01 (m, 2 H), 2.48 (s, 1 H), 2.43 (s, 1 H), 2.18 (t, 2 H, J = 10.9 Hz), 1.62-2.03 (m, 6 H), 1.43-1.56 (m, 2 H), 1.40 (s, 3 H), 1.35 (s, 3 H); MS (ESI) m/z 489.2 (M+ + H). |
| 987 | (S)-(2-fluoro-4-(5-((1-(2-fluoro-2-methylpropyl)piperidin-4-yl)methoxy)pyrazine-2-yl)phenyl)(3-hydroxypyrrolidine-1-yl)methanol<br>1H NMR (400 MHz, CDCl₃) δ 8.51 (s, 1 H), 8.29 (s, 1 H), 7.70-7.76 (m, 2 H), 7.52-7.57 (m, 1 H), 4.51-4.63 (m, 1 H), 4.23 (d, 2 H, J = 6.2 Hz), 3.42-3.86 (m, 3 H), 3.33-3.36 (m, 1 H), 2.98-3.01 (m, 2 H), 2.48 (s, 1 H), 2.43 (s, 1 H), 2.11-2.20 (m, 3 H), 2.01-2.07 (m, 3 H), 1.78-1.85 (m, 2 H), 1.43-1.63 (m, 2 H), 1.40 (s, 3 H), 1.35 (s, 3 H); MS (ESI) m/z 475.2 (M+ + H). |
| 988 | (R)-(2-fluoro-4-(5-((1-(2-fluoro-2-methylpropyl)piperidin-4-yl)methoxy)pyrazine-2-yl)phenyl)(2-(hydroxymethyl)pyrrolidine-1-yl)methanone<br>1H NMR (400 MHz, CDCl₃) δ 8.51 (s, 1 H), 8.28 (s, 1 H), 7.71-7.74 (m, 2 H), 7.53 (t, 1 H, J = 7.5 Hz), 4.39-4.41 (m, 1 H), 4.22 (d, 2 H, J = 6.2 Hz), 3.75-3.85 (m, 2 H), 3.43-3.46 (m, 2 H), 3.00-2.98 (m, 2 H), 2.48 (s, 1 H), 2.43 (s, 1 H), 2.14-2.24 (m, 3 H), 1.67-1.92 (m, 7 H), 1.40 (s, 3 H), 1.34 (s, 3 H), 1.21 - 1.31 (m, 2 H); MS (ESI) m/z 489.2 (M+ + H). |

Example 68. Compound 989: (S)-1-(4-(6-((1-(2-fluoro-2-methylpropyl)piperidin-4-yl)methoxy)pyridazine-3-yl)benzoyl)pyrrolidine-2-carboxamide

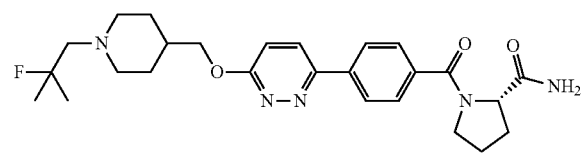 [SMILES: CC(C)(F)CN1CCC(COc2ccc(-c3ccc(C(=O)N4CCC[C@H]4C(N)=O)c(F)c3)nn2)CC1]

Step 1.

t-butyl 4-((6-chloropyridazine-3-yloxy)methyl)piperidin-1-carboxylate: t-butyl 4-(hydroxymethyl)piperidin-1-carboxylate (the product of synthesis step 1 of compound 431; 3.00 g, 13.94 mmol) and NaH (0.50 g, 20.90 mmol) were dissolved in DMF (100 mL). At 0° C., 3,6-dichloropyridazine (2.49 g, 16.72 mmol) was added thereto, following with stirring at room temperature for 12 hours. The reaction mixture was added with water, and extracted with EtOAc. The organic layer was washed with saturated NH₄Cl aqueous solution, dried over anhydrous MgSO₄, and filtered. The filtrate was concentrated under reduced pressure. The concentrate was purified by column chromatography (SiO₂, 40 g cartridge; EtOAc/hexane=0% to 50%), and concentrated to yield the title compound as white solid (2.60 g, 56%).

Step 2.

3-chloro-6-(piperidin-4-ylmethoxy)pyridazine hydrochloride: t-butyl 4-((6-chloropyridazine-3-yloxy)methyl)piperidin-1-carboxylate (2.60 g, 7.93 mmol) and 4.0 M solution in 1,4-dioxane (9.91 mL, 39.66 mmol) were dissolved in MeOH (30 mL) at room temperature. The solution was stirred at the same temperature for 3 hours, the reaction mixture was concentrated under reduced pressure. The resulting precipitate was filtered, and dried to yield the title compound as white solid (1.80 g, 85%).

Step 3.

1-(4-((6-chloropyridazine-3-yloxy)methyl)piperidin-1-yl)-2-methylpropan-2-ol: To 3-chloro-6-(piperidin-4-ylmethoxy)pyridazine hydrochloride (0.60 g, 2.27 mmol), 2,2-dimethyloxirane (1.64 g, 22.71 mmol) and K₂CO₃ (0.63 g, 4.54 mmol), EtOH (4 mL)/H₂O (4 mL) was added. With a microwave radiation, the mixture was heated at 110° C. for 20 minutes, and then cooled to room temperature, following with concentrating under reduced pressure. The concentrate was added with water (10 mL) to be suspended, and filtered. The obtained solid was dried to yield the title compound as white solid (0.44 g, 64%).

Step 4.

3-chloro-6-((1-(2-fluoro-2-methylpropyl)piperidin-4-yl)methoxy)pyridazine: 1-(4-((6-chloropyridazine-3-yloxy)methyl)piperidin-1-yl)-2-methylpropan-2-ol (0.55 g, 1.84 mmol) was dissolved in CH$_2$Cl$_2$ (8 mL). At 0° C., DAST (0.26 mL, 2.02 mmol) was added thereto, following with stirring at room temperature for 5 hours. The reaction mixture was added with water, and extracted with CH$_2$Cl$_2$. The obtained organic layer was washed with saturated aqueous brine solution, dried over anhydrous MgSO$_4$, and filtered. The filtrate was concentrated under reduced pressure. The obtained material was used without further purifying process (0.40 g, 72%, yellow oil).

Step 5.

Methyl 4-(6-((1-(2-fluoro-2-methylpropyl)piperidin-4-yl)methoxy)pyridazine-3-yl)benzoate: To 3-chloro-6-((1-(2-fluoro-2-methylpropyl)piperidin-4-yl)methoxy)pyridazine (0.20 g, 0.66 mmol), 4-(methoxycarbonyl)phenylboronic acid (0.13 g, 0.73 mmol), Pd(dppf)Cl$_2$ (0.05 g, 0.07 mmol) and Na$_2$CO$_3$ (0.14 g, 1.33 mmol), DME (12 mL)/water (3 mL) was added. With a microwave radiation, the mixture was heated at 120° C. for 20 minutes, and then cooled to room temperature. The reaction mixture was filtered through a Celite pad to remove a solid. The obtained filtrate was diluted with water, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=20% to 30%), and concentrated to yield the title compound as white solid (0.17 g, 63%).

Step 6.

4-(6-((1-(2-fluoro-2-methylpropyl)piperidin-4-yl)methoxy)pyridazine-3-yl)benzoic acid: Methyl 4-(6-((1-(2-fluoro-2-methylpropyl)piperidin-4-yl)methoxy)pyridazine-3-yl)benzoate (0.17 g, 0.42 mmol) and LiOH.H$_2$O (0.04 g, 0.85 mmol) were added in THF/MeOH (63 mL)/water (2 mL). The mixture was refluxed with heating for 8 hours, and then cooled to room temperature, following with concentrating under reduced pressure. The concentrate was added with water (2 mL), and stirred. The resulting precipitate was filtered, and dried to yield the title compound as yellow solid (0.12 g, 73%).

Step 7.

Compound 989: 4-(6-((1-(2-fluoro-2-methylpropyl)piperidin-4-yl)methoxy)pyridazine-3-yl)benzoic acid (0.03 g, 0.08 mmol), EDC (0.03 g, 0.16 mmol), HOBt (0.02 g, 0.16 mmol) and DIPEA (0.04 mL, 0.23 mmol) were dissolved in DMF (1 mL). At room temperature, (S)-pyrrolidine-2-carboxamide (0.01 g, 0.12 mmol) was added thereto, following with stirring at 50° C. for 8 hours. The reaction mixture was added with water, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 4 g cartridge; methanol/dichloromethane=0% to 5%), and concentrated to yield the title compound as colorless oil (2 mg, 5%).

1H NMR (400 MHz, CDCl$_3$) δ 8.07 (d, 2H, J=8.3 Hz), 7.82 (d, 1H, J=9.2 Hz), 7.67 (d, 2H, J=8.3 Hz), 7.09 (d, 2H, J=8.3 Hz), 6.97 (s, 1H), 5.52 (s, 1H), 4.82 (m, 1H), 4.48 (d, 2H, J=6.3 Hz), 3.60 (m, 3H), 3.07 (m, 1H), 2.44 (m, 4H), 1.62 (m, 4H), 1.45 (m, 9H).

According to the above-described synthesis process of compound 989, the compounds of Table 54 were synthesized using 4-(6-((1-(2-fluoro-2-methylpropyl)piperidin-4-yl)methoxy)pyridazine-3-yl)benzoic acid and the reactant of Table 53.

TABLE 53

| Compound No. | Reactant | Yield (%) |
|---|---|---|
| 990 | (R)-piperidin-3-ol | 54 |

TABLE 54

| Compound No. | Compound Name, $^1$H-NMR, MS (ESI) |
|---|---|
| 990 | (R)-(4-(6-((1-(2-fluoro-2-methylpropyl)piperidin-4-yl)methoxy)pyridazine-3-yl)phenyl)(3-hydroxypiperidin-1-yl)methanone<br>1H NMR (400 MHz, CDCl$_3$) δ 8.04 (d, 2 H, J = 8.2 Hz), 7.80 (d, 1 H, J = 9.2 Hz), 7.55 (d, 2 H, J = 8.2 Hz), 7.06 (d, 1 H, J = 9.2 Hz), 4.44 (d, 2 H, J = 6.5 Hz), 4.08-3.09 (m, 5 H), 2.98 (m, 2 H), 2.47-2.41 (m, 2 H), 2.14 (m, 2 H), 1.87 (m, 7 H), 1.42 (m, 9 H). |

Example 69. Compound 991: (S)-1-(2-fluoro-4-(6-((1-(2-fluoro-2-methylpropyl)piperidin-4-yl)methoxy)pyridazine-3-yl)benzoyl)pyrrolidine-2-carboxamide

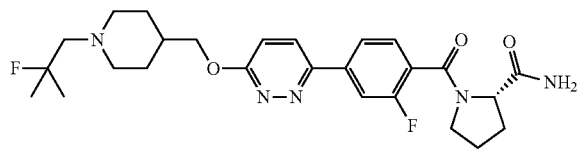

Step 1.

Ethyl 2-fluoro-4-(6-((1-(2-fluoro-2-methylpropyl)piperidin-4-yl)methoxy)pyridazine-3-yl)benzoate: 3-chloro-6-((1-(2-fluoro-2-methylpropyl)piperidin-4-yl)methoxy)pyridazine (the product of synthesis step 4 of compound 989; 0.20 g, 0.66 mmol), 4-(ethoxycarbonyl)-3-fluorophenylboronic acid (0.16 g, 0.73 mmol), Pd(dppf)Cl$_2$ (0.05 g, 0.06 mmol) and Na$_2$CO$_3$ (0.14 g, 1.33 mmol) were dissolved in DME (12 mL)/water (3 mL) at 120° C., following with stirring at the same temperature for 20 minutes. The reaction mixture was added with water, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=20% to 30%), and concentrated to yield the title compound as white solid (0.17 g, 59%).

Step 2.

2-fluoro-4-(6-((1-(2-fluoro-2-methylpropyl)piperidin-4-yl)methoxy)pyridazine-3-yl)benzoic acid: Ethyl 2-fluoro-4-

(6-((1-(2-fluoro-2-methylpropyl)piperidin-4-yl)methoxy) pyridazine-3-yl)benzoate (0.17 g, 0.39 mmol) and LiOH.H₂O (0.03 g, 0.78 mmol) were added to THF/MeOH (63 mL)/water (2 mL). The mixture was refluxed with heating for 8 hours, and then cooled to room temperature, following with concentrating under reduced pressure. The concentrate was added with water (2 mL), and stirred. The resulting precipitate was filtered, and dried to yield the title compound as yellow solid (0.13 g, 81%).

Step 3.

Compound 991: 2-fluoro-4-(6-((1-(2-fluoro-2-methylpropyl)piperidin-4-yl)methoxy)pyridazine-3-yl)benzoic acid (0.03 g, 0.07 mmol), EDC (0.03 g, 0.15 mmol), HOBt (0.02 g, 0.15 mmol) and DIPEA (0.03 g, 0.22 mmol) were dissolved in DMF (1 mL). At room temperature, (S)-pyrrolidine-2-carboxamide (0.01 g, 0.11 mmol) was added thereto, following with stirring at 50° C. for 8 hours. The reaction mixture was added with water, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, 4 g cartridge; methanol/dichloromethane=0% to 5%), and concentrated to yield the title compound as colorless oil (2 mg, 5%).

According to the above-described synthesis process of compound 991, the compounds of Table 56 were synthesized using 2-fluoro-4-(6-((1-(2-fluoro-2-methylpropyl)piperidin-4-yl)methoxy)pyridazine-3-yl)benzoic acid and the reactant of Table 55.

TABLE 55

| Compound No. | Reactant | Yield (%) |
| --- | --- | --- |
| 992 | (S)-piperidin-3-ol | 57 |

TABLE 56

| Compound No. | Compound Name, ¹H-NMR, MS (ESI) |
| --- | --- |
| 992 | (R)-(2-fluoro-4-(6-((1-(2-fluoro-2-methylpropyl)piperidin-4-yl)methoxy)pyridazine-3-yl)phenyl)(3-hydroxypiperidin-1-yl)methanone<br>1H NMR (400 MHz, CDCl₃) δ 7.78 (m, 3 H), 7.51 (t, 1 H, J = 7.3 Hz), 7.07 (d, 1 H, J = 9.2 Hz), 4.44 (d, 2 H, J = 6.5 Hz), 4.08-3.62 (m, 2 H), 3.58-3.02 (m, 3 H), 2.99 (m, 2 H), 2.47-2.42 (m, 2 H), 2.14 (m, 2 H), 2.02-1.60 (m, 10 H), 1.41 (m, 9 H) |

Example 70. Compound 1032: (S)-1-(2-fluoro-4-(5-((1-(2-fluoro-2-methylpropyl)piperidin-4-yl)methoxy)pyrimidin-2-yl)benzoyl)pyrrolidine-2-carboxamide

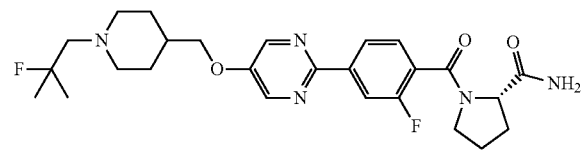 [SMILES: CC(C)(F)CN1CCC(COc2cnc(-c3ccc(C(=O)N4CCC[C@H]4C(N)=O)c(F)c3)nc2)CC1]

Step 1.

t-butyl 4-((2-chloropyrimidin-5-yloxy)methyl)piperidin-1-carboxylate: t-butyl 4-((methylsulfonyloxy)methyl)piperidin-1-carboxylate (the product of synthesis step 2 of compound 431; 2.00 g, 6.82 mmol) was dissolved in DMF (80 mL). K₂CO₃ (3.33 g, 10.23 mmol) was added thereto, and stirred for 5 minutes. 2-chloropyrimidin-5-ol (890 mg, 6.82 mmol) was added thereto, following with stirring at 80° C. for 5 hours. The reaction mixture was added with water, and extracted with EtOAc. The organic layer was washed with saturated NH₄Cl aqueous solution, dried over anhydrous MgSO₄, and concentrated under reduced pressure. The obtained concentrate was purified by silica gel column chromatography (EtOAc/hexane=30%~70%) to yield the title compound as white solid (2.10 g, 94%).

Step 2.

2-chloro-5-(piperidin-4-ylmethoxy)pyrimidine hydrochloride: t-butyl 4-((2-chloropyrimidin-5-yloxy)methyl)piperidin-1-carboxylate (2.10 g, 6.41 mmol) was dissolved in CH₂Cl₂ (50 mL). 4 M HCl in 1,4-dioxane (32.03 mL, 128.12 mmol) was added thereto, following with stirring for 1 hour. The resulting precipitate was filtered to yield the title compound as white solid (1.50 g, 88%).

Step 3.

1-(4-((2-chloropyrimidin-5-yloxy)methyl)piperidin-1-yl)-2-methylpropan-2-ol: 2-chloro-5-(piperidin-4-ylmethoxy)pyrimidine hydrochloride (1.50 g, 5.68 mmol), 2,2-dimethyloxirane (5.06 mL, 56.79 mmol) and K₂CO₃ (392 mg, 2.84 mmol) were dissolved in EtOH (5 mL) and H₂O (5 mL). With a microwave radiation, the mixture was heated at 110° C. for 15 minutes, and then cooled to room temperature. The reaction mixture was added with water, and extracted with EtOAc. The obtained organic layer was washed with saturated aqueous brine solution, and then. The organic layer was dried over anhydrous MgSO₄, and concentrated under reduced pressure. The obtained material, which is the title compound as white solid (1.70 g, 99%), was used without further purification.

Step 4.

2-chloro-5-((1-(2-fluoro-2-methylpropyl)piperidin-4-yl)methoxy)pyrimidine: 1-(4-((2-chloropyrimidin-5-yloxy)methyl)piperidin-1-yl)-2-methylpropan-2-ol (1.70 g, 5.67 mmol) was dissolved in CH₂Cl₂ (15 mL). At 0° C., DAST (749 μL, 5.67 mmol) was added slowly thereto. After stirring for 1 hour at room temperature, The reaction mixture was added with water, and extracted with EtOAc. The obtained organic layer was washed with saturated aqueous brine solution, and then. The organic layer was dried over anhydrous MgSO₄, and concentrated under reduced pressure. The obtained material, which is the title compound as white solid (1.20 g, 70%), was used without further purification.

Step 5.

Ethyl 2-fluoro-4-(5-((1-(2-fluoro-2-methylpropyl)piperidin-4-yl)methoxy)pyrimidin-2-yl)benzoate: 2-chloro-5-((1-(2-fluoro-2-methylpropyl)piperidin-4-yl)methoxy)pyrimidine (600 mg, 1.99 mmol), 4-(ethoxycarbonyl)-3-fluorophenylboronic acid (421 mg, 1.99 mmol), Pd(dppf)Cl₂ (81 mg, 0.10 mmol) and Cs₂CO₃ (1.30 g, 3.98 mmol) were added to water (2 mL)/DME (6 mL). With a microwave radiation, the mixture was heated at 110° C. for 15 minutes, and then cooled to room temperature. The reaction mixture was added with water, and extracted with EtOAc. The obtained organic layer was washed with saturated aqueous brine solution, and then. The organic layer was dried over anhydrous MgSO₄, and concentrated under reduced pressure. The obtained concentrate was purified by silica gel column chromatography (EtOAc/hexane=30%~70%) to yield the title compound as white solid (480 mg, 55%).
Step 6.

2-fluoro-4-(5-((1-(2-fluoro-2-methylpropyl)piperidin-4-yl)methoxy)pyrimidin-2-yl)benzoic acid: Ethyl 2-fluoro-4-(5-((1-(2-fluoro-2-methylpropyl)piperidin-4-yl)methoxy)pyrimidin-2-yl)benzoate (480 mg, 1.11 mmol) was dissolved in THF (10 mL) and water (5 mL). LiOH.H₂O (232 mg, 5.54 mmol) was added thereto little by little at room temperature, following with stirring for 1 hour. The reaction mixture was concentrated under reduced pressure. The resulting precipitate was filtered to yield the title compound as white solid (360 mg, 80%).
Step 7.

Compound 1032: 2-fluoro-4-(5-((1-(2-fluoro-2-methylpropyl)piperidin-4-yl)methoxy)pyrimidin-2-yl)benzoic acid 2H, J=5.9 Hz), 3.55-3.49 (m, 1H), 3.43-3.37 (m, 1H), 3.03 (brs, 2H), 2.51-2.45 (m, 2H), 2.19 (brs, 2H), 2.16-2.01 (m, 3H), 1.96-1.81 (m, 4H), 1.70-1.36 (m, 8H); MS (ESI) mz 502 (M++H).

According to the above-described synthesis process of compound 1032, the compounds of Table 58 were synthesized using 2-fluoro-4-(5-((1-(2-fluoro-2-methylpropyl)piperidin-4-yl)methoxy)pyrimidin-2-yl)benzoic acid and the reactant of Table 57.

TABLE 57

| Compound No. | Reactant | Yield (%) |
| --- | --- | --- |
| 1033 | (R)-piperidin-3-ol hydrochloride | 37 |
| 1034 | (S)-piperidin-3-ol hydrochloride | 39 |
| 1035 | (R)-pyrrolidine-3-ol | 36 |
| 1037 | (R)-piperidin-2-carboxamide hydrochloride | 28 |

TABLE 58

| Compound No. | Compound Name, ¹H-NMR, MS (ESI) |
| --- | --- |
| 1033 | (R)-(2-fluoro-4-(5-((1-(2-fluoro-2-methylpropyl)piperidin-4-yl)methoxy)pyrimidin-2-yl)phenyl)(3-hydroxypiperidin-1-yl)methanone 1H NMR (400 MHz, CDCl₃) δ 8.46 (s, 2 H), 8.20 (d, 1 H, J = 8.0 Hz), 8.10 (d, 1 H, J = 10.8 Hz), 7.48 (t, 1 H, J = 7.4 Hz), 4.12-4.09 (m, 1 H), 3.96 (d, 2 H, J = 5.9 Hz), 3.58-3.54 (m, 1 H), 3.37-3.33 (m, 1 H), 3.25-3.20 (m, 1 H), 3.13-3.03 (m, 2 H), 2.56-2.45 (m, 2 H), 2.27-2.16 (m, 2 H), 2.05-1.81 (m, 6 H), 1.69-1.62 (m, 3 H), 1.47 (s, 3 H), 1.42 (s, 3 H), 1.37-1.28 (m, 2 H); MS (ESI) m/z 489 (M+ + H). |
| 1034 | (S)-(2-fluoro-4-(5-((1-(2-fluoro-2-methylpropyl)piperidin-4-yl)methoxy)pyrimidin-2-yl)phenyl)(3-hydroxypiperidin-1-yl)methanone 1H NMR (400 MHz, CDCl₃) δ 8.46 (s, 2 H), 8.20 (d, 1 H, J = 8.0 Hz), 8.10 (d, 1 H, J = 10.8 Hz), 7.48 (t, 1 H, J = 7.4 Hz), 4.12-4.09 (m, 1 H), 3.96 (d, 2 H, J = 5.9 Hz), 3.58-3.54 (m, 1 H), 3.37-3.33 (m, 1 H), 3.25-3.20 (m, 1 H), 3.13-3.03 (m, 2 H), 2.56-2.45 (m, 2 H), 2.27-2.16 (m, 2 H), 2.05-1.81 (m, 6 H), 1.69-1.62 (m, 3 H), 1.47 (s, 3 H), 1.42 (s, 3 H), 1.37-1.28 (m, 2 H); MS (ESI) m/z 489 (M+ + H). |
| 1035 | (R)-(2-fluoro-4-(5-((1-(2-fluoro-2-methylpropyl)piperidin-4-yl)methoxy)pyrimidin-2-yl)phenyl)(3-hydroxypyrrolidine-1-yl)methanone 1H NMR (400 MHz, CDCl₃) δ 8.46 (s, 2 H), 8.21-8.18 (m, 1 H), 8.13-8.08 (m, 1 H), 7.55-7.49 (m, 1 H), 4.61 (brs, 0.5 H), 4.48 (brs, 0.5 H), 3.96 (d, 2 H, J = 5.8 Hz), 3.85-3.71 (m, 2 H), 3.65-3.55 (m, 1 H), 3.46-3.42 (m, 0.5 H), 3.34-3.31 (m, 0.5 H), 3.04 (brs, 2 H), 2.49 (brs, 2 H), 2.20-2.00 (m, 6 H), 1.99-1.85 (m, 3 H), 1.42 (s, 3 H), 1.37 (s, 3 H); MS (ESI) m/z 475 (M+ + H). |
| 1037 | (R)-1-(2-fluoro-4-(5-((1-(2-fluoro-2-methylpropyl)piperidin-4-yl)methoxy)pyrimidin-2-yl)benzoyl)piperidin-2-carboxamide 1H NMR (400 MHz, CDCl₃) δ 8.52-8.42 (m, 2 H), 8.25 (d, 1 H, J = 8.0 Hz), 8.13 (d, 1 H, J = 11.1 Hz), 7.52 (t, 1 H, J = 7.5 Hz), 6.32 (brs, 1 H), 5.65 (brs, 1 H), 5.46 (brs, 1 H), 3.96 (d, 2 H, J = 6.0 Hz), 3.58 (d, 1 H, J = 13.0 Hz), 3.22-3.21 (m, 1 H), 3.01-2.96 (m, 2 H), 2.49-2.44 (m, 3 H), 2.19-2.17 (m, 2 H), 1.83-1.74 (m, 5 H), 1.63-1.60 (m, 3 H), 1.46 (brs, 2 H), 1.41 (s, 3 H), 1.35 (s, 3 H); MS (ESI) m/z 516 (M+ + H). |

(40 mg, 0.10 mmol), (S)-pyrrolidine-2-carboxamide (23 mg, 0.20 mmol), EDC (38 mg, 0.20 mmol) and HOBt (27 mg, 0.20 mmol) was added thereto. DIPEA (35 μL, 0.20 mmol) was dissolved in CH₂Cl₂ (1 mL), following with stirring with at the same temperature for a day. The reaction mixture was added with water, and extracted with EtOAc. The obtained organic layer was washed with saturated aqueous brine solution, and then. The organic layer was dried over anhydrous MgSO₄, and concentrated under reduced pressure. The obtained concentrate was purified by silica gel column chromatography (CH₂Cl₂/MeOH=95%~5%) to yield the title compound as white solid (21 mg, 42%).

1H NMR (400 MHz, CDCl₃) δ 8.46 (s, 2H), 8.23 (d, 1H, J=6.6 Hz), 8.16 (d, 1H, J=10.2 Hz), 7.51 (t, 1H, J=7.4 Hz), 6.94 (brs, 1H), 5.56 (brs, 1H), 4.84-4.81 (m, 1H), 3.96 (d, Example 71. Compound 631: N,N-dimethyl-4'-((1-((1-(trifluoromethyl)cyclobutyl)methyl)piperidin-4-yl)methoxy)biphenyl-4-carboxamide

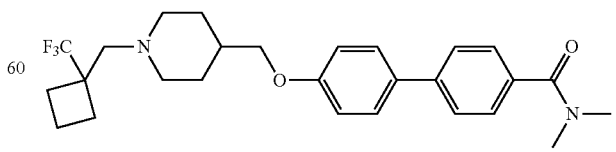

Step 1.
t-butyl 4-((4'-hydroxybiphenyl-4-yloxy)methyl)piperidin-1-carboxylate: t-butyl 4-((4-bromophenoxy)methyl)piperidin-1-carboxylate (the product of synthesis step 3 of compound 431; 3.45 g, 9.32 mmol) and 4-hydroxyphenylboronic acid (1.41 g, 10.25 mmol) were dissolved in dioxane 12 mL. Water 3 mL was added thereto. Pd(dbpf)Cl₂ (607 mg, 0.93 mmol) and Cs₂CO₃ (6.07 g, 18.64 mmol) were added thereto, and refluxed with heating for a day. The reaction mixture was filtered through Celite, and the obtained organic layer was washed with saturated NaHCO₃ aqueous solution and water, dried over MgSO₄, and then concentrated under reduced pressure. The obtained concentrate was purified by silica gel column chromatography (EtOAcCH₂Cl₂), and then recrystallized with CH₂Cl₂ and hexane to yield the title compound as white solid (2.50 g, 70%).

Step 2.

4'-(piperidin-4-ylmethoxy)biphenyl-4-ol hydrochloride: t-butyl 4-((4'-hydroxybiphenyl-4-yloxy)methyl)piperidin-1-carboxylate (2.50 g, 6.51 mmol) was dissolved in CH₂Cl₂ 6 mL. 4 M HCl 1.79 mL was added thereto, following with stirring for 1 hour at room temperature. The obtained reaction mixture was filtered to yield the title compound as white solid (2.00 g, 96%).

Step 3.

4'-((1-(1-(trifluoromethyl)cyclobutanecarbonyl)piperidin-4-yl)methoxy)biphenyl-4-yl 1-(trifluoromethyl)cyclobutanecarboxylate: 4'-(piperidin-4-ylmethoxy)biphenyl-4-ol hydrochloride (1.50 g, 4.69 mmol), 1-(trifluoromethyl)cyclobutanecarboxylic acid (946 mg, 5.63 mmol) and PyBOP (3.66 g, 7.04 mmol) were dissolved in DMF 4 mL. DIPEA (3.63 g, 28.14 mmol) was added thereto. At 50° C., the reaction was performed for 8 hours. The reaction mixture was added with water, and extracted with EtOAc. The obtained organic layer was dried over MgSO₄, and filtered. The filtrate was concentrated under reduced pressure. The obtained concentrate was purified by silica gel column chromatography (EtOAcCH₂Cl₂) to yield the title compound as yellow solid (1.16 g, 42%).

Step 4.

4'-((1-((1-(trifluoromethyl)cyclobutyl)methyl)piperidin-4-yl)methoxy)biphenyl-4-ol: 4'-((1-(1-(trifluoromethyl)cyclobutanecarbonyl)piperidin-4-yl)methoxy)biphenyl-4-yl 1-(trifluoromethyl)cyclobutanecarboxylate (1.16 g, 2.67 mmol) was dissolved in dry THF 15 mL, and then cooled with ice bath. LAH (1 M in THF, 8.03 mL, 8.03 mmol) was added dropwise slowly thereto, following with increasing the temperature to 50° C. and stirring for a day. Water was poured into the reaction mixture. The formed solid was removed by filtration, and the filtrate was extracted with EtOAc three times. The organic layer was dried over MgSO₄, filtered to remove the solid residue, and the filtrate was concentrated under reduced pressure. The obtained concentrate was purified by silica gel column chromatography (EtOAc/Hexane) to yield the title compound as white solid (640 mg, 57%).

Step 5

4'-((1-((1-(trifluoromethyl)cyclobutyl)methyl)piperidin-4-yl)methoxy)biphenyl-4-yl trifluoromethanesulfonate: 4'-((1-((1-(trifluoromethyl)cyclobutyl)methyl)piperidin-4-yl)methoxy)biphenyl-4-ol (640 mg, 1.53 mmol) was dissolved in CH₂Cl₂ 6 mL. At 0° C., pyridine (181 mg, 2.29 mmol) and trifluoromethanesulfonic anhydride (560 mg, 1.98 mmol) were added thereto, The reaction was performed at room temperature for 3 hours. The reaction mixture was added with water, and extracted with CH₂Cl₂. The obtained organic layer was dried over MgSO₄, and filtered. The filtrate was concentrated under reduced pressure. The obtained concentrate was purified by silica gel column chromatography (EtOAc/Hexane) to yield the title compound as white solid (590 mg, 70%).

Step 6.

Methyl 4'-((1-((1-(trifluoromethyl)cyclobutyl)methyl)piperidin-4-yl)methoxy)biphenyl-4-carboxylate: 4'-((1-((1-(trifluoromethyl)cyclobutyl)methyl)piperidin-4-yl)methoxy)biphenyl-4-yl trifluoromethanesulfonate (200 mg, 0.36 mmol), Pd(OAc)₂ (4 mg, 0.02 mmol) and dppp (9 mg, 0.02) were dissolved in DMSO 3 mL. MeOH 3 mL was added thereto, following with sufficient CO gas flowing. Lastly, TEA (184 mg, 1.81 mmol) was added thereto, following with stirring at 120° C. for 4 hours. The reaction mixture was filtered through Celite. The filtrate was added with water, and extracted with EtOAc. The obtained organic layer was concentrated under reduced pressure, and purified by silica gel column chromatography (EtOAcCH₂Cl₂) to yield the title compound as pink solid (105 mg, 62%).

Step 7.

4'-((1-((1-(trifluoromethyl)cyclobutyl)methyl)piperidin-4-yl)methoxy)biphenyl-4-carboxylic acid: Methyl 4'-((1-((1-(trifluoromethyl)cyclobutyl)methyl)piperidin-4-yl)methoxy)biphenyl-4-carboxylate (105 mg, 0.23 mmol) was dissolved in THF 2 mL. MeOH 1 mL and H₂O 0.5 mL were poured therein. LiOH (19 mg, 0.46 mmol) was added thereto, and refluxed with heating and stirring for 5 hours. After acidification with 1 N HCl, the resulting precipitate was filtered to yield the title compound as white solid (98 mg, 96%).

Step 8.

Compound 631: 4'-((1-((1-(trifluoromethyl)cyclobutyl)methyl)piperidin-4-yl)methoxy)biphenyl-4-carboxylic acid (30 mg, 0.07 mmol), dimethylamine hydrochloride (11 mg, 0.13 mmol) and PyBOP (52 mg, 0.10 mmol) were dissolved in DMF 0.5 mL. DIPEA (43 mg, 0.34 mmol) was added thereto. The reaction was performed at room temperature for 8 hours. The reaction mixture was added with water, and extracted with EtOAc. The obtained organic layer was dried over MgSO₄, and filtered. The filtrate was concentrated under reduced pressure. The obtained concentrate was purified by silica gel column chromatography (MeOH/CH₂Cl₂) to yield the title compound as white solid (16 mg, 50%).

1H NMR (400 MHz, CDCl₃) δ 7.52 (m, 6H), 6.98 (d, 2H, J=6.8 Hz), 3.85 (d, 2H, J=6.0 Hz), 3.14 (s, 3H), 3.05 (s, 3H), 2.85 (m, 2H), 2.53 (s, 2H), 2.19 (m, 4H), 2.01 (m, 3H), 1.96 (m, 1H), 1.83 (m, 3H), 1.46 (m, 2H); MS (ESI) m/z 475 (M++H).

Example 72. Compound 633: (R)-(2-(hydroxymethyl)pyrrolidine-1-yl)(4'-((1-((1-(trifluoromethyl)cyclobutyl)methyl)piperidin-4-yl)methoxy)biphenyl-4-yl)methanone

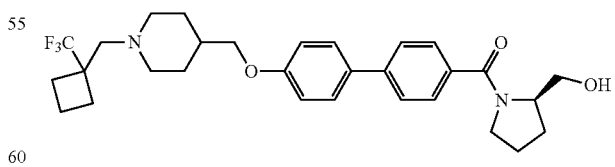

4'-((1-((1-(trifluoromethyl)cyclobutyl)methyl)piperidin-4-yl)methoxy)biphenyl-4-carboxylic acid (30 mg, 0.07 mmol), (R)-prolinol (14 mg, 0.13 mmol) and PyBOP (52 mg, 0.10 mmol) were dissolved in DMF 0.5 mL following with stirring for 10 minutes at room temperature. DIPEA (43 mg, 0.34 mmol) was added thereto, following with stirring at room temperature for 8 hours. Water was poured into the reaction mixture. The formed solid was filtered, and dried to yield the title compound as white solid (17 mg, 47%).

1H NMR (400 MHz, CDCl$_3$) δ 7.56 (m, 6H), 6.99 (d, 2H, J=8.7 Hz), 5.01 (d, 1H, J=8.7 Hz), 4.46 (m, 1H), 3.77 (m, 4H), 3.53 (m, 2H), 2.90 (m, 2H), 2.54 (s, 2H), 2.22 (m, 5H), 2.11 (m, 3H), 1.92 (m, 6H), 1.64 (m, 2H), 1.48 (m, 2H); MS (ESI) m/z 531 (M++H).

According to the above-described synthesis process of compound 631 (Step 8), the compounds of Table 60 were synthesized using 4'-((1-((1-(trifluoromethyl)cyclobutyl)methyl)piperidin-4-yl)methoxy)biphenyl-4-carboxylic acid and the reactant of Table 59.

TABLE 59

| Compound No. | Reactant | Yield (%) |
| --- | --- | --- |
| 632 | (S)-3-pyrrolidinol | 46 |
| 634 | 3-hydroxypiperidine | 45 |
| 635 | L-prolinamide | 43 |
| 636 | 2-aminoethanol | 57 |
| 637 | 2-(methylamino)ethanol | 58 |
| 794 | (R)-piperidin-3-ol hydrochloride | 40 |
| 795 | (S)-piperidin-3-ol | 40 |
| 796 | (R)-pyrrolidine-3-ol | 44 |
| 797 | (S)-pyrrolidine-2-ylmethanol | 43 |
| 798 | piperidin-4-carboxamide | 50 |

TABLE 60

| Compound No. | Compound Name, $^1$H-NMR, MS (ESI) |
| --- | --- |
| 632 | (S)-(3-hydroxypyrrolidine-1-yl)(4'-((1-((1-(trifluoromethyl)cyclobutyl)methyl)piperidin-4-yl)methoxy)biphenyl-4-yl)methanone<br>1H NMR (400 MHz, CDCl$_3$) δ 7.56 (m, 6 H), 6.97 (d, 2 H, J = 8.8 Hz), 4.59 (m, 1 H), 3.79 (m, 4 H), 3.63 (m, 1 H), 3.55 (m, 1 H), 3.14 (m, 1 H), 2.90 (m, 2 H), 2.68 (s, 1 H), 2.54 (s, 2 H), 2.23 (m, 4 H), 2.04 (m, 4 H), 1.87 (m, 4 H), 1.31 (m, 2 H); MS (ESI) m/z 517 (M+ + H). |
| 634 | (3-hydroxypiperidin-1-yl)(4'-((1-((1-(trifluoromethyl)cyclobutyl)methyl)piperidin-4-yl)methoxy)biphenyl-4-yl)methanone<br>1H NMR (400 MHz, CDCl$_3$) δ 7.51 (m, 6 H), 6.98 (d, 2 H, J = 6.9 Hz), 3.85 (m, 5 H), 3.46 (m, 3 H), 2.89 (m, 2 H), 2.54 (s, 2 H), 2.22 (m, 4 H), 1.96 (m, 10 H), 1.46 (m, 3 H); MS (ESI) m/z 531 (M+ + H). |
| 635 | (S)-1-(4'-((1-((1-(trifluoromethyl)cyclobutyl)methyl)piperidin-4-yl)methoxy)biphenylcarbonyl)pyrrolidine-2-carboxamide<br>1H NMR (400 MHz, CDCl$_3$) δ 7.54 (m, 5 H), 6.98 (d, 2 H, J = 8.7 Hz), 5.64 (s, 1 H), 4.82 (m, 1 H), 3.85 (d, 2 H, J = 8.7 Hz), 2.89 (m, 2 H), 2.49 (s, 2 H), 2.43 (m, 1 H), 2.15 (m, 4 H), 2.11 (m, 5 H), 1.93 (m, 4 H), 1.41 (m, 2 H); MS (ESI) m/z 544 (M+ + H). |
| 636 | N-(2-hydroxyethyl)-4'-((1-((1-(trifluoromethyl)cyclobutyl)methyl)piperidin-4-yl)methoxy)biphenyl-4-carboxamide<br>1H NMR (400 MHz, CDCl$_3$) δ 7.84 (d, 2 H, J = 8.4 Hz), 7.62 (d, 2 H, J = 8.4 Hz), 7.55 (d, 2 H, J = 8.8 Hz), 6.98 (d, 2 H, J = 8.7 Hz), 6.67 (t, 1 H, J = 5.3 Hz), 3.86 (m, 4 H), 3.66 (m, 2 H), 2.90 (m, 2 H), 2.73 (s, 1 H), 2.66 (s, 2 H), 2.24 (m, 4 H), 2.06 (m, 3 H), 1.88 (m, 4 H), 1.45 (m, 2 H); MS (ESI) m/z 491 (M+ + H). |
| 637 | N-(2-hydroxyethyl)-N-methyl-4'-((1-((1-(trifluoromethyl)cyclobutyl)methyl)piperidin-4-yl)methoxy)biphenyl-4-carboxamide<br>1H NMR (400 MHz, CDCl$_3$) δ 7.56 (m, 6 H), 6.98 (d, 2 H, J = 8.7 Hz), 3.57 (m, 7 H), 3.12 (s, 3 H), 2.90 (m, 2 H), 2.54 (s, 4 H), 2.19 (m, 4 H), 2.04 (m, 3 H), 1.93 (m, 1 H), 1.83 (m, 3 H), 1.40 (m, 2 H); MS (ESI) m/z 505 (M+ + H). |
| 794 | (R)-(3-hydroxypiperidin-1-yl)(4'-((1-((1-(trifluoromethyl)cyclobutyl)methyl)piperidin-4-yl)methoxy)biphenyl-4-yl)methanone<br>1H NMR (400 MHz, CDCl$_3$) δ 7.51 (m, 6 H), 6.98 (d, 2 H, J = 8.7 Hz), 3.85 (m, 4 H), 3.45 (m, 3 H), 2.90 (m, 2 H), 2.54 (m, 2 H), 2.21 (m, 4 H), 1.96 (m, 11 H), 1.46 (m, 3 H); MS (ESI) m/z 531 (M+ + H). |
| 795 | (S)-(3-hydroxypiperidin-1-yl)(4'-((1-((1-(trifluoromethyl)cyclobutyl)methyl)piperidin-4-yl)methoxy)biphenyl-4-yl)methanone<br>1H NMR (400 MHz, CDCl$_3$) δ 7.58 (d, 2 H, J = 8.1 Hz), 7.52 (d, 2 H, J = 8.6 Hz), 7.47 (d, 2 H, J = 8.0 Hz), 6.98 (d, 2 H, J = 8.6 Hz), 3.86 (m, 4 H), 3.44 (m, 3 H), 2.90 (m, 2 H), 2.55 (s, 2 H), 2.23 (m, 4 H), 1.98 (m, 11 H), 1.44 (m, 3 H); MS (ESI) m/z 531 (M+ + H). |
| 796 | (R)-(3-hydroxypyrrolidine-1-yl)(4'-((1-((1-(trifluoromethyl)cyclobutyl)methyl)piperidin-4-yl)methoxy)biphenyl-4-yl)methanone<br>MS (ESI) m/z 517 (M+ + H). |
| 797 | (S)-(2-(hydroxymethyl)pyrrolidine-1-yl)(4'-((1-((1-(trifluoromethyl)cyclobutyl)methyl)piperidin-4-yl)methoxy)biphenyl-4-yl)methanone<br>1H NMR (400 MHz, CDCl$_3$) δ 7.55 (m, 6 H), 6.97 (d, 2 H, J = 8.6 Hz), 4.57 (s, 0.5 H), 4.44 (s, 0.5 H), 3.79 (m, 4 H), 3.63 (m, 1 H), 3.54 (m, 1 H), 2.83 (m, 3 H), 2.54 (s, 2 H), 2.23 (m, 4 H), 1.92 (m, 10 H), 1.80 (m, 2 H); MS (ESI) m/z 531 (M+ + H). |
| 798 | 1-(4'-((1-((1-(trifluoromethyl)cyclobutyl)methyl)piperidin-4-yl)methoxy)biphenylcarbonyl)piperidin-4-carboxamide<br>1H NMR (400 MHz, CDCl$_3$) δ 7.58 (d, 2 H, J = 8.2 Hz), 7.52 (d, 2 H, J = 8.7 Hz), 7.44 (d, 2 H, J = 8.1 Hz), 6.97 (d, 2 H, J = 8.7 Hz), 5.70 (m, 2 H), 4.69 (s, 1 H), 3.90 (m, 3 H), 2.71 (m, 4 H), 2.55 (s, 2 H), 2.42 (m, 1 H), 2.23 (m, 4 H), 1.96 (m, 11 H), 1.46 (m, 2 H); MS (ESI) m/z 558 (M+ + H). |

Example 73. Compound 917: (R)-(2-fluoro-4'-((1-((1-(trifluoromethyl)cyclobutyl)methyl)piperidin-4-yl)methoxy)biphenyl-4-yl)(2-(hydroxymethyl)pyrrolidine-1-yl)methanone

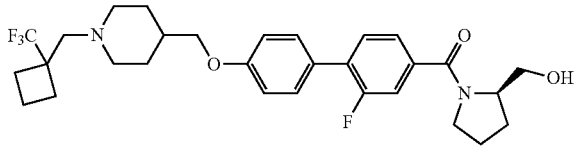 [SMILES: O=C(c1ccc(-c2ccc(OCC3CCN(CC4(C(F)(F)F)CCC4)CC3)cc2)c(F)c1)N1CCC[C@@H]1CO]

Step 1.

Methyl 2-fluoro-4'-((1-((1-(trifluoromethyl)cyclobutyl)methyl)piperidin-4-yl)methoxy)biphenyl-4-carboxylate: To 4-((4-bromophenoxy)methyl)-1-((1-(trifluoromethyl)cyclobutyl)methyl)piperidine (the product of synthesis step 2 of compound 842; 0.78 g, 1.92 mmol), 2-fluoro-4-(methoxycarbonyl)phenylboronic acid (0.45 g, 2.30 mmol), Pd(dppf)Cl$_2$ (0.07 g, 0.09 mmol) and Cs$_2$CO$_3$ (1.25 g, 3.84 mmol), DME (9 mL)/H$_2$O (3 mL) was added. With a microwave radiation, the mixture was heated at 110° C. for 20 minutes, and then cooled to room temperature. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, EtOAc/hexane=0% to 100%), and concentrated to yield the title compound as white solid (0.54 g, 59%).

Step 2.

2-fluoro-4'-((1-((1-(trifluoromethyl)cyclobutyl)methyl)piperidin-4-yl)methoxy) biphenyl-4-carboxylic acid: Methyl 2-fluoro-4'-((1-((1-(trifluoromethyl)cyclobutyl)methyl)piperidin-4-yl)methoxy)biphenyl-4-carboxylate (0.54 g, 1.13 mmol) and LiOH.H$_2$O (0.23 g, 5.68 mmol) were dissolved in THF/MeOH (16 mL)/H$_2$O (4 mL) at room temperature. The solution was stirred at the same temperature for 1 hour. The resulting precipitate was filtered, and dried to yield the title compound as white solid (0.50 g, 94%).

Step 3.

Compound 917: 2-fluoro-4'-((1-((1-(trifluoromethyl)cyclobutyl)methyl)piperidin-4-yl)methoxy)biphenyl-4-carboxylic acid (0.07 g, 0.15 mmol), (R)-pyrrolidine-2-ylmethanol (0.01 g, 0.18 mmol), HOBt (0.04 g, 0.30 mmol), EDC (0.05 g, 0.30 mmol) and DIPEA (0.05 mL, 0.30 mmol) were dissolved in CH$_2$Cl$_2$ (1 mL) at room temperature. The solution was stirred at the same temperature for 18 hours, the reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, dichloromethane/methanol=0% to 15%), and concentrated to yield the title compound as white solid (0.05 g, 69%).

1H NMR (400 MHz, CDCl$_3$) δ 7.45-7.51 (m, 3H), 7.31-7.37 (m, 2H), 6.99 (d, 2H, J=8.6 Hz), 4.75 (s, 1H), 4.40-4.45 (m, 1H), 3.74-3.87 (m, 4H), 3.51-3.65 (m, 2H), 2.89-2.92 (m, 2H), 2.54 (s, 2H), 2.20-2.28 (m, 5H), 1.87-2.11 (m, 6H), 1.72-183 (m, 4H), 1.43-1.49 (m, 2H); MS (ESI) m/z 549.2 (M++H).

According to the above-described synthesis process of compound 917, the compounds of Table 62 were synthesized using 2-fluoro-4'-((1-((1-(trifluoromethyl)cyclobutyl)methyl)piperidin-4-yl)methoxy)biphenyl-4-carboxylic acid and the reactant of Table 61.

TABLE 61

| Compound No. | Reactant | Yield (%) |
| --- | --- | --- |
| 918 | L-prolinamide | 58 |
| 919 | (R)-piperidin-3-ol hydrochloride | 67 |
| 920 | (S)-piperidin-3-ol hydrochloride | 76 |
| 921 | (S)-pyrrolidine-3-ol | 54 |

TABLE 62

| Compound No. | Compound Name, $^1$H-NMR, MS (ESI) |
| --- | --- |
| 918 | (S)-1-(2-fluoro-4'-((1-((1-(trifluoromethyl)cyclobutyl)methyl)piperidin-4-yl)methoxy)biphenylcarbonyl)pyrrolidine-2-carboxamide<br>1H NMR (400 MHz, CDCl$_3$) δ 7.46-7.51 (m, 3 H), 7.33-7.39 (m, 2 H), 6.98-7.00 (m, 2 H), 6.92 (s, 1 H), 5.48 (s, 1 H), 4.81 (dd, 1 H, J = 7.4, 5.2 Hz), 3.86 (d, 2 H, J = 6.0 Hz), 3.56-3.69 (m, 2 H), 2.89-2.92 (m, 2 H), 2.54 (s, 2 H), 2.46-2.52 (m, 1 H), 2.20-2.28 (m, 4 H), 1.91-2.16 (m, 5 H), 1.80-1.90 (m, 5 H), 1.40-1.49 (m, 2 H); MS (ESI) m/z 562.3 (M+ + H). |
| 919 | (R)-(2-fluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, CDCl$_3$) δ 7.43-7.50 (m, 3 H), 7.22-7.27 (m, 2 H), 6.97-7.01 (m, 2 H), 3.85-3.95 (m, 3 H), 3.37-3.62 (m, 3 H), 2.89-2.92 (m, 2 H), 2.54 (s, 2 H), 2.20-2.28 (m, 4 H), 2.00-2.11 (m, 2 H), 1.90-1.99 (m, 4 H), 1.80-1.89 (m, 3 H), 1.57-1.78 (m, 4 H), 1.39-1.50 (m, 2 H); MS (ESI) m/z 549.3 (M+ + H). |
| 920 | (S)-(2-fluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, CDCl$_3$) δ 7.44-7.50 (m, 3 H), 7.22-7.27 (m, 2 H), 6.97-7.00 (m, 2 H), 3.79-3.95 (m, 3 H), 3.34-3.67 (m, 3 H), 2.89-2.92 (m, 2 H), 2.54 (s, 2 H), 2.20-2.28 (m, 4 H), 2.00-2.15 (m, 2 H), 1.82-1.99 (m, 4 H), 1.77-1.81 (m, 4 H), 1.50-1.64 (m, 3 H), 1.40-1.49 (m, 2 H); MS (ESI) m/z 549.3 (M+ + H). |
| 921 | (S)-(2-fluoro-4'-((1-((1-(trifluoromethyl)cyclobutyl)methyl)piperidin-4-yl)methoxy)biphenyl-4-yl)(3-hydroxypyrrolidin-1-yl)methanone<br>1H NMR (400 MHz, CDCl$_3$) δ 7.44-7.53 (m, 3 H), 7.31-7.41 (m, 2 H), 6.97-7.01 (m, 2 H), 4.51-4.63 (m, 1 H), 3.77-3.87 (m, 4 H), 3.50-3.71 (m, 2 H), 2.89-2.92 (m, 2 H), 2.54 (s, 2 H), 2.22-2.28 (m, 4 H), 2.11-2.21 (m, 6 H), 1.66-1.89 (m, 4 H), 1.40-1.49 (m, 2 H); MS (ESI) m/z 535.2 (M+ + H). |

Example 74. Compound 842: (S)-(3-fluoro-4'-((1-((1-(trifluoromethyl)cyclobutyl)methyl)piperidin-4-yl)methoxy)biphenyl-4-yl)(3-hydroxypiperidin-1-yl)methanone

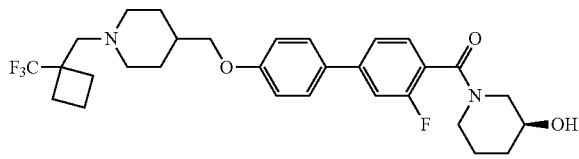 [SMILES: O=C(c1ccc(-c2ccc(OCC3CCN(CC4(C(F)(F)F)CCC4)CC3)cc2)cc1F)N1CCC[C@H](O)C1]

Step 1.

(4-((4-bromophenoxy)methyl)piperidin-1-yl)(1-(trifluoromethyl)cyclobutyl)methanone: 4-((4-bromophenoxy)methyl)piperidine hydrochloride (the product of synthesis step 1 of compound 498; 2.00 g, 6.52 mmol) was dissolved in $CH_2Cl_2$ (40 mL). EDC (2.50 g, 13.05 mmol), HOBt (1.76 g, 13.05 mmol), DIPEA (2.31 mL, 13.05 mmol), 1-(trifluoromethyl)cyclobutanecarboxylic acid (1.09 g, 6.52 mmol) was added thereto, following with stirring at room temperature for 12 hours. After the completion of the reaction, the reaction mixture was added with a saturated $NaHCO_3$ aqueous solution, and extracted with $CH_2Cl_2$. The organic layer was dried over anhydrous $MgSO_4$, and concentrated under reduced pressure. The obtained concentrate was purified by silica gel column chromatography (EtOAc/hexane=14) to yield the title compound as white solid (2.10 g, 76%).

Step 2.

4-((4-bromophenoxy)methyl)-1-((1-(trifluoromethyl)cyclobutyl)methyl)piperidine: (4-((4-bromophenoxy)methyl)piperidin-1-yl)(1-(trifluoromethyl)cyclobutyl)methanone (812 mg, 1.93 mmol) was dissolved in THF (10 mL). 2.0 M Borane dimethyl sulfide complex solution in THF (4.83 mL, 9.66 mmol) was added thereto, following with stirring at room temperature for 2 hours. After the completion of the reaction, the reaction mixture was added with a saturated $NaHCO_3$ aqueous solution, and extracted with EtOAc. The organic layer was dried over anhydrous $MgSO_4$, and concentrated under reduced pressure. The obtained concentrate was purified by silica gel column chromatography (EtOAc/hexane=18) to yield the title compound as yellow solid (480 mg, 61%).

Step 3.

Methyl 3-fluoro-4'-((1-((1-(trifluoromethyl)cyclobutyl)methyl)piperidin-4-yl)methoxy)biphenyl-4-carboxylate: To 4-((4-bromophenoxy)methyl)-1-((1-(trifluoromethyl)cyclobutyl)methyl)piperidine (480 mg, 1.18 mmol), 4-(ethoxycarbonyl)-3-fluorophenylboronic acid (300 mg, 1.42 mmol), Pd(dppf)$Cl_2$ (97 mg, 1.42 mmol) and $Cs_2CO_3$ (770 mg, 2.36 mmol), DME (6 mL)/$H_2O$ (2 mL) was added, and refluxed with heating for a day. After the completion of the reaction, the reaction mixture was added with water, and extracted with EtOAc. The organic layer was dried over anhydrous $MgSO_4$, and filtered. The filtrate was concentrated under reduced pressure. The concentrate was purified by silica gel column chromatography (EtOAc/hexane=17) to yield the title compound as white solid (250 mg, 42%).

Step 4.

3-fluoro-4'-((1-((1-(trifluoromethyl)cyclobutyl)methyl)piperidin-4-yl)methoxy)biphenyl-4-carboxylic acid: Methyl 3-fluoro-4'-((1-((1-(trifluoromethyl)cyclobutyl)methyl)piperidin-4-yl)methoxy)biphenyl-4-carboxylate (250 mg, 0.51 mmol) was dissolved in THF (10 mL) and $H_2O$ (5 mL). At room temperature, LiOH.$H_2O$ (106 mg, 2.53 mmol) was added thereto, following with stirring for 1 hour. After the completion of the reaction, the reaction mixture was acidified with 1 N HCl. The resulting precipitate was filtered, and dried to yield the title compound as white solid (201 mg, 85%).

Step 5.

Compound 842: 3-fluoro-4'-((1-((1-(trifluoromethyl)cyclobutyl)methyl)piperidin-4-yl)methoxy)biphenyl-4-carboxylic acid (40 mg, 0.09 mmol), EDC (33 mg, 0.17 mmol) and HOBt (23 mg, 0.17 mmol) was added thereto, DIPEA (30 μL, 0.17 mmol) were dissolved in (S)-piperidin-3-ol hydrochloride (24 mg, 0.17 mmol) was dissolved in $CH_2Cl_2$ (1 mL), following with stirring for a day. The reaction mixture was added with water, and extracted with EtOAc. The organic layer was washed with saturated $NH_4Cl$ aqueous solution, dried over anhydrous $MgSO_4$, and concentrated under reduced pressure. The obtained concentrate was purified by silica gel column chromatography ($CH_2Cl_2$/MeOH=95%~5%) to yield the title compound as yellow solid (24 mg, 50%).

1H NMR (400 MHz, $CDCl_3$) δ 7.51 (d, 2H, J=8.6 Hz), 7.45-7.38 (m, 2H), 7.27-7.26 (m, 1H), 6.98 (d, 2H, J=8.6 Hz), 4.11-3.94 (m, 1H), 3.85 (d, 2H, J=6.0 Hz), 3.62-3.50 (m, 1H), 3.40-3.27 (m, 1H), 2.90 (d, 2H, J=10.9 Hz), 2.54 (s, 2H), 2.28-2.20 (m, 4H), 2.11-2.01 (m, 10H), 1.99-1.63 (m, 3H), 1.49-1.34 (m, 3H); MS (ESI) m/z 549 (M++H).

According to the above-described synthesis process of compound 842, the compounds of Table 64 were synthesized using 3-fluoro-4'-((1-((1-(trifluoromethyl)cyclobutyl)methyl)piperidin-4-yl)methoxy)biphenyl-4-carboxylic acid and the reactant of Table 63.

TABLE 63

| Compound No. | Reactant | Yield (%) |
| --- | --- | --- |
| 843 | (S)-pyrrolidine-3-carboxamide | 41 |
| 844 | (R)-pyrrolidine-2-ylmethanol | 42 |
| 845 | (S)-pyrrolidine-3-ol | 32 |
| 846 | (R)-piperidin-3-ol hydrochloride | 50 |

TABLE 64

| Compound No. | Compound Name, 1H-NMR, MS (ESI) |
| --- | --- |
| 843 | (S)-1-(3-fluoro-4'-((1-((1-(trifluoromethyl)cyclobutyl)methyl)piperidin-4-yl)methoxy)biphenylcarbonyl)pyrrolidine-2-carboxamide<br>1H NMR (400 MHz, $CDCl_3$) δ 7.53-7.45 (m, 2 H), 7.43-7.40 (m, 2 H), 7.32-7.29 (m, 1 H), 7.00-6.95 (m, 2 H), 5.52 (brs, 1 H), 4.84-4.81 (m, 1 H), 3.86 (d, 2 H, J = 6.0 Hz), 3.56-3.53 (m, 1 H), 3.47-3.42 (m, 1 H), 2.90 (d, 2 H, J = 11.2 Hz), 2.54 (s, 2 H), 2.50-2.46 (m, 1 H), 2.28-2.19 (m, 4 H), 2.14-2.11 (m, 4 H), 2.09-2.01 (m, 1 H), 1.99-1.91 (m, 2 H), 1.89-1.81 (m, 3 H), 1.68 (brs, 1 H), 1.46-1.43 (m, 2 H); MS (ESI) m/z 562 (M+ + H). |

TABLE 64-continued

| Compound No. | Compound Name, $^1$H-NMR, MS (ESI) |
|---|---|
| 844 | (R)-(3-fluoro-4'-((1-((1-(trifluoromethyl)cyclobutyl)methyl)piperidin-4-yl)methoxy)biphenyl-4-yl)(2-(hydroxymethyl)pyrrolidine-1-yl)methanone<br>1H NMR (400 MHz, CDCl$_3$) δ 7.53-7.46 (m, 3 H), 7.42-7.39 (m, 1 H), 7.31-7.27 (m, 1 H), 6.98 (d, 2 H, J = 8.7 Hz), 4.79 (d, 1 H, J = 6.1 Hz), 4.42-4.40 (m, 1 H), 3.86 (d, 2 H, J = 6.0 Hz), 3.84-3.81 (m, 1 H), 3.49-3.46 (m, 2 H), 2.90 (d, 2 H, J = 11.2 Hz), 2.54 (s, 2 H), 2.28-2.20 (m, 5 H), 2.18-1.99 (m, 3 H), 1.96-1.86 (m, 2 H), 1.83-1.80 (m, 4 H), 1.77-1.66 (m, 2 H), 1.50-1.43 (m, 2 H); MS (ESI) m/z 549 (M+ + H). |
| 845 | (S)-(3-fluoro-4'-((1-((1-(trifluoromethyl)cyclobutyl)methyl)piperidin-4-yl)methoxy)biphenyl-4-yl)(3-hydroxypyrrolidine-1-yl)methanone<br>1H NMR (400 MHz, CDCl$_3$) δ 7.52-7.45 (m, 3 H), 7.40-7.37 (m, 1 H), 7.30-7.25 (m, 1 H), 6.98 (d, 2 H, J = 8.1 Hz), 4.62-4.49 (m, 1 H), 3.85 (d, 2 H, J = 6.0 Hz), 3.79-3.61 (m, 1 H), 3.59-3.35 (m, 1 H), 2.91 (d, 2 H, J = 11.2 Hz), 2.55 (s, 2 H), 2.28-2.22 (m, 4 H), 2.19-2.01 (m, 5 H), 1.99-1.90 (m, 2 H), 1.89-1.81 (m, 4 H), 1.49-1.43 (m, 2 H); MS (ESI) m/z 535 (M+ + H). |
| 846 | (R)-(3-fluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, CDCl$_3$) δ 7.51 (d, 2 H, J = 8.6 Hz), 7.45-7.38 (m, 2 H), 7.27-7.26 (m, 1 H), 6.98 (d, 2 H, J = 8.6 Hz), 4.11-3.94 (m, 1 H), 3.85 (d, 2 H, J = 6.0 Hz), 3.62-3.50 (m, 1 H), 3.40-3.27 (m, 1 H), 2.90 (d, 2 H, J = 10.9 Hz), 2.54 (s, 2 H), 2.28-2.20 (m, 4 H), 2.11-2.01 (m, 10 H), 1.99-1.63 (m, 3 H), 1.49-1.34 (m, 3 H); MS (ESI) m/z 549 (M+ + H). |

Example 75. Compound 833: (S)-1-(2'-fluoro-4'-((1-((1-(trifluoromethyl)cyclobutyl)methyl)piperidin-4-yl)methoxy)biphenylcarbonyl)pyrrolidine-2-carboxamide

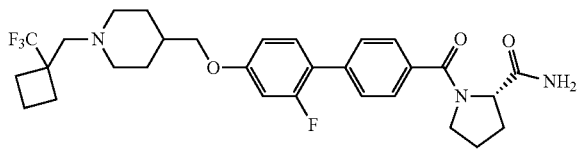 [SMILES: NC(=O)[C@@H]1CCCN1C(=O)c1ccc(-c2ccc(OCC3CCN(CC4(C(F)(F)F)CCC4)CC3)cc2F)cc1]

Step 1.

t-butyl 4-((2-fluoro-4'-hydroxybiphenyl-4-yloxy)methyl)piperidin-1-carboxylate: t-butyl 4-((4-bromo-3-fluorophenoxy)methyl)piperidin-1-carboxylate (the product of synthesis step 1 of compound 704; 3.7 g, 9.53 mmol), 4-hydroxyphenylboronic acid (1.31 g, 9.53 mmol), Pd(dppf)Cl$_2$ (778 mg, 0.95 mmol), Na$_2$CO$_3$ (2.02 g, 19.06 mmol) were dissolved in DME 15 mL and water 5 mL, and then refluxed with heating for a day. The reaction mixture was filtered through Celite. The filtrate was added with saturated NaHCO$_3$ aqueous solution, and extracted with EtOAc. The organic layer was dried over MgSO$_4$, filtered to remove the solid residue, and the filtrate was concentrated under reduced pressure. The concentrate was purified by column chromatography (ISCO silica gel cartridge, EtOAc/Hexane) to yield the title compound as white solid (2.8 g, 73%).

Step 2.

2'-fluoro-4'-(piperidin-4-ylmethoxy)biphenyl-4-ol hydrochloride: t-butyl 4-((2-fluoro-4'-hydroxybiphenyl-4-yloxy)methyl)piperidin-1-carboxylate (2.8 g, 6.97 mmol) was dissolved in CH$_2$Cl$_2$ 15 mL. 4 M HCl 2.09 mL was added thereto, following with stirring at room temperature for 2 hours. The reaction mixture was filtered, washed with EtOAc, and evaporated under reduced pressure to yield the title compound as white solid (2.3 g, 97%).

Step 3.

2'-fluoro-4'-((1-(1-(trifluoromethyl)cyclobutanecarbonyl)piperidin-4-yl)methoxy)biphenyl-4-yl 1-(trifluoromethyl)cyclobutanecarboxylate: 2'-fluoro-4'-(piperidin-4-ylmethoxy)biphenyl-4-ol hydrochloride (1.5 g, 4.44 mmol), 1-(trifluoromethyl)cyclobutanecarboxylic acid (1.12 g, 6.66 mmol) and BOP (3.93 g, 8.88 mmol) were dissolved in DMF 6 mL. After stirring for 10 minutes at room temperature, TEA (1.35 g, 13.32 mmol) was added thereto, following with stirring at 50° C. for 8 hours. The reaction mixture was added with water, and extracted with EtOAc. The organic layer was washed with saturated aqueous brine solution, dried over MgSO$_4$, filtered to remove the solid residue, and the filtrate was concentrated under reduced pressure. The concentrate was purified by column chromatography (40 g ISCO silica gel cartridge, EtOAc/hexane) to yield the title compound as white solid (580 mg, 29%).

Step 4.

2'-fluoro-4'-((1-((1-(trifluoromethyl)cyclobutyl)methyl)piperidin-4-yl)methoxy)biphenyl-4-ol: 2'-fluoro-4'-((1-(1-(trifluoromethyl)cyclobutanecarbonyl)piperidin-4-yl)methoxy)biphenyl-4-yl 1-(trifluoromethyl)cyclobutanecarboxylate (1.38 g, 2.23 mmol) was dissolved in dry THF 20 mL. At 0° C., LAH (6.88 mmol) was added thereto, following with stirring at 60° C. for a day. After the completion of the reaction, the reaction mixture was added with a little of water, and then extracted with excess amount of EtOAc. The organic layer was washed with saturated aqueous brine solution, dried over MgSO$_4$, filtered to remove the solid residue, and the filtrate was concentrated under reduced pressure. The concentrate was purified by column chromatography (12 g ISCO silica gel cartridge, 15-20% EtOAc/hexane) to yield the title compound as white solid (980 mg, 97%).

Step 5

2'-fluoro-4'-((1-((1-(trifluoromethyl)cyclobutyl)methyl)piperidin-4-yl)methoxy)biphenyl-4-yl trifluoromethanesulfonate: 2'-fluoro-4'-((1-((1-(trifluoromethyl)cyclobutyl)methyl)piperidin-4-yl)methoxy)biphenyl-4-ol (980 mg, 2.24 mmol) was dissolved in dry CH$_2$Cl$_2$ 6 mL. Pyridine (266 mg, 3.36 mmol) was added thereto. And then, trifluoromethanesulfonic anhydride (266 mg, 3.36 mmol) was added thereto at 0° C., following with stirring at room temperature for 3 hours. The reaction mixture was added with water, and extracted with CH$_2$Cl$_2$ twice. The obtained organic layer was washed with saturated aqueous brine solution, dried over MgSO$_4$, filtered to remove the solid residue, and the filtrate was concentrated under reduced pressure. The concentrate was purified by column chromatography (ISCO silica gel cartridge, EtOAc/Hexane) to yield the title compound as white solid (880 mg, 69%).

Step 6.

Methyl 2'-fluoro-4'-((1-((1-(trifluoromethyl)cyclobutyl)methyl)piperidin-4-yl)methoxy)biphenyl-4-carboxylate: 2'-fluoro-4'-((1-((1-(trifluoromethyl)cyclobutyl)methyl)piperidin-4-yl)methoxy)biphenyl-4-yl trifluoromethanesulfonate (880 mg, 1.55 mmol), Pd(OAc)$_2$ (17 mg, 0.08 mmol) and dppp (40 mg, 0.09 mmol) were dissolved in DMSO 6 mL. MeOH 6 mL was added thereto, following with sufficient infusion of carbon monoxide (CO). And then, TEA (782 mg, 7.73 mmol) was added thereto, following with stirring at 120° C. for 6 hours. After filtering through Celite, the reaction mixture was diluted with water, and extracted with EtOAc. The obtained organic layer was washed with saturated aqueous brine solution, dried over MgSO$_4$, filtered to remove the solid residue, and the filtrate was concentrated under reduced pressure. The concentrate was purified by column chromatography (ISCO silica gel cartridge, EtOAc/Hexane) to yield the title compound as white solid (470 mg, 63%).

Step 7.

2'-fluoro-4'-((1-((1-(trifluoromethyl)cyclobutyl)methyl)piperidin-4-yl)methoxy)biphenyl-4-carboxylic acid: Methyl 2'-fluoro-4'-((1-((1-(trifluoromethyl)cyclobutyl)methyl)piperidin-4-yl)methoxy)biphenyl-4-carboxylate (470 mg, 0.98 mmol) was dissolved in THF/MeOH/H$_2$O=632 mL. LiOH.H$_2$O (82 mg, 1.96 mmol) was added thereto, and refluxed with heating for 3 hours. After the completion of the reaction, the solvent was evaporated under reduced pressure, following with adjusting pH to below 6 using 1N HCl. The resulting precipitate was filtered to yield the title compound as white solid (410 mg, 89%).

Step 8.

Compound 833: 2'-fluoro-4'-((1-((1-(trifluoromethyl)cyclobutyl)methyl)piperidin-4-yl)methoxy)biphenyl-4-carboxylic acid (40 mg, 0.09 mmol), (S)-pyrrolidine-2-carboxamide (15 mg, 0.13 mmol) and BOP (76 mg, 0.17 mmol) were dissolved in DMF 1 mL. After stirring for 10 minutes at room temperature, TEA (26 mg, 0.26 mmol) was added thereto, following with stirring at 50° C. for 8 hours. The reaction mixture was added with water, and extracted with EtOAc. The organic layer was washed with saturated aqueous brine solution, dried over MgSO$_4$, filtered to remove the solid residue, and the filtrate was concentrated under reduced pressure. The concentrate was purified by column chromatography (ISCO silica gel cartridge, MeOH/CH$_2$Cl$_2$) to yield the title compound as white solid (22 mg, 45%).

1H NMR (400 MHz, CDCl$_3$) δ 7.54 (m, 4H), 7.35 (t, 1H, J=4.8 Hz), 6.99 (s, 1H), 6.73 (m, 2H), 5.50 (s, 1H), 4.82 (t, 2H, J=2.1 Hz), 3.83 (d, 2H, J=5.9 Hz), 3.58 (m, 2H), 2.90 (m, 2H), 2.49 (m, 3H), 2.30 (m, 4H), 2.09 (m, 5H), 1.89 (m, 5H), 0.98 (m, 2H)

According to the above-described synthesis process of compound 833, the compounds of Table 66 were synthesized using 2'-fluoro-4'-((1-((1-(trifluoromethyl)cyclobutyl)methyl)piperidin-4-yl)methoxy)biphenyl-4-carboxylic acid and the reactant of Table 65.

TABLE 65

| Compound No. | Reactant | Yield (%) |
|---|---|---|
| 834 | (R)-piperidin-3-ol | 50 |
| 835 | (S)-pyrrolidine-3-ol | 41 |
| 836 | (S)-piperidin-3-ol | 46 |
| 877 | (R)-piperidin-2-carboxamide hydrochloride | 61 |
| 878 | (S)-piperidin-2-carboxamide hydrochloride | 55 |
| 882 | (R)-piperidin-3-carboxamide hydrochloride | 69 |

TABLE 66

| Compound No. | Compound Name, $^1$H-NMR, MS (ESI) |
|---|---|
| 834 | (R)-(2'-fluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, CDCl$_3$) δ 7.55 (m, 2 H), 7.49 (m, 2 H), 7.34 (t, 1 H, J = 8.8 Hz), 6.73 (m, 2 H), 3.86 (m, 4 H), 3.46 (m, 3 H), 2.90 (m, 2 H), 2.55 (m, 2 H), 2.24 (m, 4 H), 1.96 (m, 12 H), 1.26 (m, 2 H). |
| 835 | (S)-(2'-fluoro-4'-((1-((1-(trifluoromethyl)cyclobutyl)methyl)piperidin-4-yl)methoxy)biphenyl-4-yl)(3-hydroxypyrrolidine-1-yl)methanone<br>1H NMR (400 MHz, CDCl$_3$) δ 7.54 (m, 4 H), 7.34 (t, 1 H, J = 8.8 Hz), 6.73 (m, 2 H), 4.58 (s, 0.5 H), 4.44 (s, 0.5 H), 3.83 (m, 4 H), 3.54 (m, 2 H), 2.91 (m, 2 H), 2.72 (m, 1 H), 2.55 (s, 2 H), 2.23 (m, 4 H), 2.07 (m, 9 H), 1.42 (m, 2 H). |
| 836 | (S)-(2'-fluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, CDCl$_3$) δ 7.51 (m, 4 H), 7.35 (t, 1 H, J = 8.9 Hz), 6.76 (m, 2 H), 3.84 (m, 4 H), 3.65 (m, 3 H), 3.05 (m, 2 H), 2.55 (m, 2 H), 2.35 (m, 4 H), 1.94 (m, 10 H), 1.26 (m, 4 H). |
| 877 | (R)-1-(2'-fluoro-4'-((1-((1-(trifluoromethyl)cyclobutyl)methyl)piperidin-4-yl)methoxy)biphenylcarbonyl)piperidin-2-carboxamide<br>1H NMR (400 MHz, CDCl$_3$) δ 7.64-7.44 (m, 4 H), 7.35 (t, 1 H, J = 8.7 Hz), 6.81-6.68 (m, 2 H), 3.84 (d, 3 H, J = 5.8 Hz), 3.12 (t, 1 H, J = 13.1 Hz), 2.91 (d, 2 H, J = 10.0 Hz), 2.55 (s, 2 H), 2.35 (d, 1 H, J = 12.8 Hz), 2.30-1.35 (m, 19 H); MS (ESI) m/z 576 (M+ + H). |
| 878 | (S)-1-(2'-fluoro-4'-((1-((1-(trifluoromethyl)cyclobutyl)methyl)piperidin-4-yl)methoxy)biphenylcarbonyl)piperidin-2-carboxamide<br>1H NMR (400 MHz, CDCl$_3$) δ 7.64-7.43 (m, 4 H), 7.35 (t, 1 H, J = 8.9 Hz), 6.83-6.67 (m, 2 H), 3.84 (d, 3 H, J = 6.0 Hz), 3.13 (t, 1 H, J = 12.7 Hz), 2.91 (d, 2 H, J = 9.5 Hz), 2.55 (s, 2 H), 2.35 (d, 1 H, J = 12.8 Hz), 2.30-1.37 (m, 19 H); MS (ESI) m/z 576 (M+ + H). |
| 882 | (R)-1-(2'-fluoro-4'-((1-((1-(trifluoromethyl)cyclobutyl)methyl)piperidin-4-yl)methoxy)biphenylcarbonyl)piperidin-3-carboxamide<br>1H NMR (400 MHz, CDCl$_3$) δ 7.56 (d, 2 H, J = 6.8 Hz), 7.46 (d, 2 H, J = 8.3 Hz), |

7.35 (t, 1 H, J = 8.8 Hz), 6.81-6.68 (m, 2 H), 3.84 (d, 3 H, J = 5.5 Hz), 3.62-3.52 (m, 1 H), 3.51-3.40 (m, 1 H), 2.89 (s, 2 H), 2.54 (s, 3 H), 2.32-1.36 (m, 20 H); MS (ESI) m/z 576 (M+ + H).

Example 76. Compound 908: (2,2'-difluoro-4'-((1-((1-(trifluoromethyl)cyclobutyl)methyl)piperidin-4-yl)methoxy)biphenyl-4-yl)((R)-2-(hydroxymethyl)pyrrolidine-1-yl)methanone

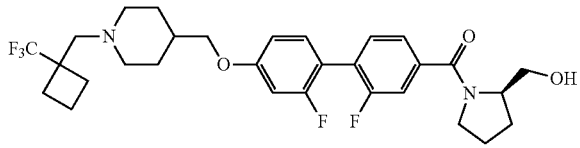 [SMILES: O=C(c1ccc(-c2ccc(OCC3CCN(CC4(C(F)(F)F)CCC4)CC3)cc2F)c(F)c1)N1CCC[C@@H]1CO]

Step 1.

(4-((4-bromo-3-fluorophenoxy)methyl)piperidin-1-yl)(1-(trifluoromethyl)cyclobutyl)methanone: 4-((4-bromo-3-fluorophenoxy)methyl)piperidine hydrochloride (the product of synthesis step 2 of compound 704; 2.60 g, 8.00 mmol), DIPEA (2.77 mL, 16.01 mmol), HOBt (2.16 g, 16.01 mmol), EDC (3.07 g, 16.01 mmol) and 1-(trifluoromethyl)cyclobutanecarboxylic acid (1.61 g, 9.61 mmol) were dissolved in DMF (30 mL) at 60° C., following with stirring at the same temperature for 18 hours. The reaction mixture was added with water, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, EtOAc/hexane=0% to 20%), and concentrated to yield the title compound as yellow oil (2.83 g, 80%).

Step 2.

4-((4-bromo-3-fluorophenoxy)methyl)-1-((1-(trifluoromethyl)cyclobutyl)methyl)piperidine: (4-((4-bromo-3-fluorophenoxy)methyl)piperidin-1-yl)(1-(trifluoromethyl)cyclobutyl)methanone (1.40 g, 3.33 mmol) was dissolved in THF (30 mL). At 0° C., 2.0 M BH₃.SMe₂ in THF (8.3 mL, 16.66 mmol) was added thereto, following with stirring at 60° C. for 2 hours The reaction mixture was added with water, and extracted with EtOAc. The organic layer was washed with saturated NH₄Cl aqueous solution, dried over anhydrous MgSO₄, and filtered. The filtrate was concentrated under reduced pressure. The concentrate was purified by column chromatography (SiO₂, EtOAc/hexane=5% to 20%), and concentrated to yield the title compound as white solid (1.84 g, 67%).

Step 3.

Methyl 2,2'-difluoro-4'-((4-((1-(trifluoromethyl)cyclobutyl)methyl)piperidin-4-yl)methoxy)biphenyl-4-carboxylate: To 4-((4-bromo-3-fluorophenoxy)methyl)-1-((1-(trifluoromethyl)cyclobutyl)methyl)piperidine (0.80 g, 1.89 mmol), 2-fluoro-4-(methoxycarbonyl)phenylboronic acid (0.44 g, 2.26 mmol), Pd(dppf)Cl₂ (0.07 g, 0.09 mmol) and Cs₂CO₃ (1.23 g, 3.78 mmol), DME (9 mL)/H₂O (3 mL) was added. With a microwave radiation, the mixture was heated at 110° C. for 20 minutes, and then cooled to room temperature. The reaction mixture was added with water, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, EtOAc/hexane=0% to 10%), and concentrated to yield the title compound as white solid (0.39 g, 42%).

Step 4.

2,2'-difluoro-4'-((1-((1-(trifluoromethyl)cyclobutyl)methyl)piperidin-4-yl)methoxy)biphenyl-4-carboxylic acid: Methyl 2,2'-difluoro-4'-((4-((1-(trifluoromethyl)cyclobutyl)methyl)piperidin-4-yl)methoxy)biphenyl-4-carboxylate (0.39 g, 0.78 mmol) and LiOH.H₂O (0.16 g, 3.92 mmol) were dissolved in THF/MeOH (20 mL)/H₂O (5 mL) at room temperature. The solution was stirred at the same temperature for 1 hour. The resulting precipitate was filtered, and dried to yield the title compound as white solid (0.21 g, 55%).

Step 5.

Compound 908: 2,2'-difluoro-4'-((1-((1-(trifluoromethyl)cyclobutyl)methyl)piperidin-4-yl)methoxy)biphenyl-4-carboxylic acid (0.04 g, 0.08 mmol), (R)-pyrrolidine-2-yl-methanol (0.01 g, 0.09 mmol), HOBt (0.02 g, 0.16 mmol), EDC (0.03 g, 0.16 mmol) and DIPEA (0.02 mL, 0.16 mmol) were dissolved in CH₂Cl₂ (1 mL) at room temperature. The solution was stirred at the same temperature for 18 hours, the reaction mixture was added with water, and extracted with EtOAc. The organic layer was washed with saturated NH₄Cl aqueous solution, dried over anhydrous MgSO₄, and filtered. The filtrate was concentrated under reduced pressure. The concentrate was purified by column chromatography (SiO₂, 4 g, methanol/dichloromethane=0% to 15%), and concentrated to yield the title compound as white solid (0.02 g, 57%).

1H NMR (400 MHz, CDCl₃) δ 7.43 (t, 1H, J=7.3 Hz), 7.27-7.37 (m, 3H), 6.78 (dd, 1H, J=8.5, 2.5 Hz), 6.73 (dd, 1H, J=11.9, 2.4 Hz), 4.40-4.44 (m, 1H), 3.74-3.84 (m, 4H), 3.53-3.64 (m, 2H), 2.89-2.92 (m, 2H), 2.54 (s, 2H), 2.20-2.28 (m, 4H), 1.65-2.11 (m, 10H), 1.40-1.48 (m, 2H), 1.25-1.26 (m, 2H); MS (ESI) m/z 567.2 (M++H).

According to the above-described synthesis process of compound 908, the compounds of Table 68 were synthesized using 2,2'-difluoro-4'-((1-((1-(trifluoromethyl)cyclobutyl)methyl)piperidin-4-yl)methoxy)biphenyl-4-carboxylic acid and the reactant of Table 67.

TABLE 67

| Compound No. | Reactant | Yield (%) |
| --- | --- | --- |
| 909 | L-prolinamide | 52 |
| 910 | (R)-piperidin-3-ol hydrochloride | 74 |
| 911 | (S)-piperidin-3-ol hydrochloride | 76 |

TABLE 68

| Compound No. | Compound Name, 1H-NMR, MS (ESI) |
|---|---|
| 909 | (2S)-1-(2,2'-difluoro-4'-((1-((1-(trifluoromethyl)cyclobutyl)methyl)piperidin-4-yl)methoxy)biphenylcarbonyl)pyrrolidine-2-carboxamide<br>1H NMR (400 MHz, CDCl3) δ 7.29-7.45 (m, 4 H), 6.92 (s, 1 H), 6.79 (dd, 1 H, J = 8.5, 2.4 Hz), 6.73 (dd, 1 H, J = 11.9, 2.4 Hz), 5.55 (s, 1 H), 4.80 (dd, 1 H, J = 7.6, 5.0 Hz), 3.84 (d, 2 H, J = 6.0 Hz), 3.58-3.67 (m, 2 H), 2.89-2.92 (m, 2 H), 2.54 (s, 2 H), 2.44-2.47 (m, 1 H), 2.19-2.28 (m, 4 H), 1.71-2.14 (m, 10 H), 1.39-1.48 (m, 2 H); MS (ESI) m/z 580.3 (M+ + H). |
| 910 | (2,2'-difluoro-4'-((1-((1-(trifluoromethyl)cyclobutyl)methyl)piperidin-4-yl)methoxy)biphenyl-4-yl)((R)-3-hydroxypiperidin-1-yl)methanone<br>1H NMR (400 MHz, CDCl3) δ 7.41 (t, 1 H, J = 7.5 Hz), 7.23-7.30 (m, 3 H), 6.78 (dd, 1 H, J = 8.5, 2.4 Hz), 6.73 (dd, 1 H, J = 11.9, 2.4 Hz), 3.83-3.97 (m, 4 H), 3.36-3.59 (m, 2 H), 2.89-2.92 (m, 2 H), 2.54 (s, 2 H), 2.20-2.28 (m, 4 H), 1.80-2.11 (m, 10 H), 1.35-1.46 (m, 2 H), 1.26-1.34 (m, 2 H); MS (ESI) m/z 567.3 (M+ + H). |
| 911 | (2,2'-difluoro-4'-((1-((1-(trifluoromethyl)cyclobutyl)methyl)piperidin-4-yl)methoxy)biphenyl-4-yl)((S)-3-hydroxypiperidin-1-yl)methanone<br>1H NMR (400 MHz, CDCl3) δ 7.41 (t, 1 H, J = 7.4 Hz), 7.23-7.30 (m, 3 H), 6.78 (dd, 1 H, J = 8.5, 2.5 Hz), 6.73 (dd, 1 H, J = 11.9, 2.4 Hz), 3.78-3.96 (m, 3 H), 3.32-3.62 (m, 3 H), 2.89-2.92 (m, 2 H), 2.54 (s, 2 H), 2.20-2.28 (m, 4 H), 1.68-2.11 (m, 10 H), 1.58-1.60 (m, 2 H), 1.40-1.48 (m, 2 H); MS (ESI) m/z 567.3 (M+ + H). |

Example 77. Compound 912: (R)-(2',3-difluoro-4'-((1-((1-(trifluoromethyl)cyclobutyl)methyl)piperidin-4-yl)methoxy)biphenyl-4-yl)(2-(hydroxymethyl)pyrrolidine-1-yl)methanone

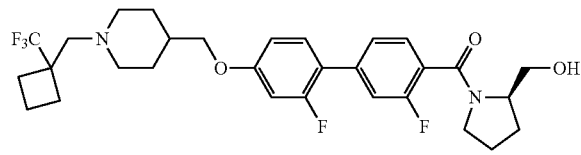

Step 1.

Ethyl 2',3-difluoro-4'-((1-((1-(trifluoromethyl)cyclobutyl)methyl)piperidin-4-yl)methoxy)biphenyl-4-carboxylate: To 4-((4-bromo-3-fluorophenoxy)methyl)-1-((1-(trifluoromethyl)cyclobutyl)methyl)piperidine (the product of synthesis step 2 of compound 908; 0.80 g, 1.89 mmol), 4-(ethoxycarbonyl)-3-fluorophenylboronic acid (0.48 g, 2.26 mmol), Pd(dppf)Cl2 (0.07 g, 0.09 mmol) and Cs2CO3 (1.23 g, 3.78 mmol), DME (9 mL)/H2O (3 mL) was added. With a microwave radiation, the mixture was heated at 110° C. for 20 minutes, and then cooled to room temperature. The reaction mixture was added with water, and extracted with EtOAc. The obtained organic layer was washed with saturated aqueous brine solution, dried over anhydrous MgSO4, and filtered. The filtrate was concentrated under reduced pressure. The concentrate was purified by column chromatography (SiO2, EtOAc/hexane=0% to 10%), and concentrated to yield the title compound as white solid (0.70 g, 75%).

Step 2.

2',3-difluoro-4'-((1-((1-(trifluoromethyl)cyclobutyl)methyl)piperidin-4-yl)methoxy)biphenyl-4-carboxylic acid: Ethyl 2',3-difluoro-4'-((1-((1-(trifluoromethyl)cyclobutyl)methyl)piperidin-4-yl)methoxy)biphenyl-4-carboxylate (0.70 g, 1.36 mmol) and LiOH.H2O (0.28 g, 6.84 mmol) were dissolved in THF/MeOH (20 mL)/H2O (5 mL) at room temperature. The solution was stirred at the same temperature for 1 hour. The resulting precipitate was filtered, and dried to yield the title compound as white solid (0.66 g, 99%).

Step 3.

Compound 912: 2',3-difluoro-4'-((1-((1-(trifluoromethyl)cyclobutyl)methyl)piperidin-4-yl)methoxy)biphenyl-4-carboxylic acid (0.07 g, 0.14 mmol), (R)-pyrrolidine-2-yl-methanol (0.01 g, 0.17 mmol), HOBt (0.03 g, 0.29 mmol), EDC (0.05 g, 0.29 mmol) and DIPEA (0.05 mL, 0.29 mmol) were dissolved in CH2Cl2 (1 mL) at room temperature. The solution was stirred at the same temperature for 18 hours, the reaction mixture was added with water, and extracted with EtOAc. The obtained organic layer was washed with saturated aqueous brine solution, dried over anhydrous MgSO4, and filtered. The filtrate was concentrated under reduced pressure. The concentrate was purified by column chromatography (SiO2, methanol/dichloromethane=0% to 15%), and concentrated to yield the title compound as white solid (0.07 g, 90%).

1H NMR (400 MHz, CDCl3) δ 7.48 (t, 1H, J=7.5 Hz), 7.27-7.38 (m, 2H), 6.78 (dd, 1H, J=8.6, 2.4 Hz), 6.72 (dd, 1H, J=12.7, 2.3 Hz), 4.78-4.79 (s, 1H), 4.40-4.44 (m, 1H), 3.75-3.84 (m, 4H), 3.46-3.50 (m, 2H), 2.89-2.92 (m, 2H), 2.54 (s, 2H), 2.19-2.28 (m, 5H), 2.01-2.11 (m, 3H), 1.90-1.99 (m, 2H), 1.82-1.89 (m, 4H), 1.64-1.79 (m, 2H), 1.42-1.48 (m, 2H); MS (ESI) m/z 567.3 (M++H).

According to the above-described synthesis process of compound 912, the compounds of Table 70 were synthesized using 2',3-difluoro-4'-((1-((1-(trifluoromethyl)cyclobutyl)methyl)piperidin-4-yl)methoxy)biphenyl-4-carboxylic acid and the reactant of Table 69.

TABLE 69

| Compound No. | Reactant | Yield (%) |
|---|---|---|
| 913 | L-prolinamide | 81 |
| 914 | (R)-piperidin-3-ol hydrochloride | 97 |
| 915 | (S)-piperidin-3-ol hydrochloride | 14 |
| 916 | (S)-pyrrolidine-3-ol | 98 |

TABLE 70

Compound No. Compound Name, $^1$H-NMR, MS (ESI)

913     (S)-1-(2',3-difluoro-4'-((1-((1-(trifluoromethyl)cyclobutyl)methyl)piperidin-4-yl)methoxy)biphenylcarbonyl)pyrrolidine-2-carboxamide
1H NMR (400 MHz, CDCl$_3$) δ 7.38-7.50 (m, 1 H), 7.28-7.37 (m, 2 H), 6.96 (s, 1 H), 6.77 (dd, 1 H, J = 8.6, 2.3 Hz), 6.71 (dd, 1 H, J = 12.7, 2.3 Hz), 5.86 (s, 1 H), 4.80 (dd, 1 H, J = 8.0, 4.1 Hz), 3.95-4.12 (m, 1 H), 3.84 (d, 2 H, J = 6.0 Hz), 3.41-3.58 (m, 1 H), 2.88-2.91 (m, 2 H), 2.54 (s, 2 H), 2.38-2.41 (m, 1 H), 2.21-2.27 (m, 5 H), 2.19-2.18 (m, 5 H), 1.78-1.93 (m, 3 H), 1.41-1.48 (m, 2 H), 1.24-1.26 (m, 2 H); MS (ESI) m/z 580.3 (M+ + H).

914     (R)-(2',3-difluoro-4'-((1-((1-(trifluoromemyl)cyclobutyl)methyl)piperidin-4-yl)methoxy)biphenyl-4-yl)(3-hydroxypiperidin-1-yl)methanone
1H NMR (400 MHz, CDCl$_3$) δ 7.44 (t, 1 H, J = 7.4 Hz), 7.26-7.37 (m, 3 H), 6.78 (dd, 1 H, J = 8.6, 2.4 Hz), 6.72 (dd, 1 H, J = 12.7, 2.4 Hz), 3.95-4.12 (m, 1 H), 3.84 (d, 2 H, J = 6.0 Hz), 3.52-3.61 (m, 1 H), 3.11-3.37 (m, 2 H), 2.89-2.92 (m, 2 H), 2.54 (s, 2 H), 2.19-2.28 (m, 4 H), 1.79-2.11 (m, 9 H), 1.42-1.48 (m, 2 H), 1.32-1.30 (m, 4 H); MS (ESI) m/z 567.3 (M+ + H).

915     (S)-(2',3-difluoro-4'-((1-((1-(trifluoromethyl)cyclobutyl)methyl)piperidin-4-yl)methoxy)biphenyl-4-yl)(3-hydroxypiperidin-1-yl)methanone
1H NMR (400 MHz, CDCl$_3$) δ 7.44 (t, 1 H, J = 7.4 Hz), 7.26-7.37 (m, 3 H), 6.78 (dd, 1 H, J = 8.6, 2.4 Hz), 6.72 (dd, 1 H, J = 12.6, 2.3 Hz), 3.94-4.14 (m, 1 H), 3.83 (d, 2 H, J = 6.0 Hz), 3.37-3.62 (m, 1 H), 3.14-3.29 (m, 2 H), 2.89-2.92 (m, 2 H), 2.54 (s, 2 H), 2.19-2.28 (m, 4 H), 1.79-2.11 (m, 10 H), 1.40-1.48 (m, 3 H), 1.26-1.28 (m, 2 H); MS (ESI) m/z 567.2 (M+ + H).

916     (S)-(2',3-difluoro-4'-((1-((1-(trifluoromethyl)cyclobutyl)methyl)piperidin-4-yl)methoxy)biphenyl-4-yl)(3-hydroxypyrrolidine-1-yl)methanone
1H NMR (400 MHz, CDCl$_3$) δ 7.45-7.50 (m, 1 H), 7.25-7.36 (m, 3 H), 6.70-6.79 (m, 2 H), 4.48-4.61 (m, 1 H), 3.78-3.84 (m, 3 H), 3.66-3.74 (m, 1 H), 3.57-3.61 (m, 1 H), 3.35-3.48 (m, 1 H), 2.89-2.92 (m, 2 H), 2.54 (s, 2 H), 2.22-2.30 (m, 5 H), 2.01-2.19 (m, 5 H), 1.86-1.99 (m, 1 H), 1.79-1.82 (m, 3 H), 1.39-1.48 (m, 2 H); MS (ESI) m/z 553.3 (M+ + H).

Example 78. Compound 883: (S)-(3'-fluoro-4'-((1-((1-(trifluoromethyl)cyclobutyl)methyl)piperidin-4-yl)methoxy)biphenyl-4-yl)(3-hydroxypiperidin-1-yl)methanone

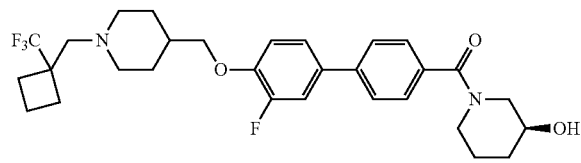 [SMILES: O=C(c1ccc(-c2ccc(OCC3CCN(CC4(C(F)(F)F)CCC4)CC3)c(F)c2)cc1)N1CCC[C@H](O)C1]

Step 1.

t-butyl 4-((3-fluoro-4'-hydroxybiphenyl-4-yloxy)methyl)piperidin-1-carboxylate: t-butyl 4-((4-bromo-2-fluorophenoxy)methyl)piperidin-1-carboxylate (the product of synthesis step 1 of compound 725; 3.75 g, 9.67 mmol), 4-hydroxyphenylboronic acid (1.33 g, 9.67 mmol), Pd(dppf)Cl$_2$ (789 mg, 0.97 mmol) and Na$_2$CO$_3$ (2.04 g, 19.32 mmol) were dissolved in DME 15 mL and water 5 mL, and then refluxed with heating for a day. The reaction mixture was filtered through Celite. The filtrate was added with saturated NaHCO$_3$ aqueous solution, and extracted with EtOAc. The organic layer was dried over MgSO$_4$, filtered to remove the solid residue, and the filtrate was concentrated under reduced pressure. The concentrate was purified by column chromatography (ISCO silica gel cartridge, EtOAc/Hexane) to yield the title compound as white solid (2.90 g, 75%).

Step 2.

3'-fluoro-4-(piperidin-4-ylmethoxy)biphenyl-4-ol hydrochloride: t-butyl 4-((3-fluoro-4'-hydroxybiphenyl-4-yloxy)methyl)piperidin-1-carboxylate (2.90 g, 7.22 mmol) was dissolved in CH$_2$Cl$_2$ 15 mL. 4 M HCl 2.17 mL was added thereto, following with stirring at room temperature for 2 hours. The reaction mixture was filtered, washed with EtOAc, and evaporated under reduced pressure to yield the title compound as white solid (2.40 g, 98%).

Step 3.

3-fluoro-4'-((1-(1-(trifluoromethyl)cyclobutanecarbonyl)piperidin-4-yl)methoxy)biphenyl-4-yl 1-(trifluoromethyl)cyclobutanecarboxylate: 3'-fluoro-4'-(piperidin-4-ylmethoxy)biphenyl-4-ol hydrochloride (0.83 g, 2.46 mmol), 1-(trifluoromethyl)cyclobutanecarboxylic acid (0.62 g, 3.69 mmol) and BOP (2.17 g, 4.93 mmol) were dissolved in DMF 6 mL. After stirring for 10 minutes at room temperature, TEA (0.75 g, 7.39 mmol) was added thereto, following with stirring at 50° C. for 8 hours. The reaction mixture was added with water, and extracted with EtOAc. The organic layer was washed with saturated aqueous brine solution, dried over MgSO$_4$, filtered to remove the solid residue, and the filtrate was concentrated under reduced pressure. The concentrate was purified by column chromatography (40 g ISCO silica gel cartridge, EtOAc/hexane) to yield the title compound as white solid (500 mg, 45%).

Step 4.

3'-fluoro-4'-((1-((1-(trifluoromethyl)cyclobutyl)methyl)piperidin-4-yl)methoxy)biphenyl-4-ol: 3-fluoro-4'-((1-(1-(trifluoromethyl)cyclobutanecarbonyl)piperidin-4-yl)methoxy)biphenyl-4-yl 1-(trifluoromethyl)cyclobutanecarboxylate (672 mg, 1.12 mmol) was dissolved in dry THF 15 mL. At 0° C., LAH (3.35 mmol) was added thereto, following with stirring at 60° C. for a day. After the completion of the reaction, the reaction mixture was added with a little of water, and then extracted with excess amount of EtOAc. The organic layer was washed with saturated aqueous brine solution, dried over MgSO$_4$, filtered to remove the solid residue, and the filtrate was concentrated under reduced pressure. The concentrate was purified by column chromatography (12 g ISCO silica gel cartridge, 15-20% EtOAc/hexane) to yield the title compound as white solid (485 mg, 99%).

Step 5.

3'-fluoro-4'-((1-((1-(trifluoromethyl)cyclobutyl)methyl)piperidin-4-yl)methoxy)biphenyl-4-yl trifluoromethanesulfonate: 3'-fluoro-4'-((1-((1-(trifluoromethyl)cyclobutyl)methyl)piperidin-4-yl)methoxy)biphenyl-4-ol (485 mg, 1.11 mmol) was dissolved in dry $CH_2Cl_2$ 6 mL. Pyridine (132 mg, 1.66 mmol) was added thereto. And then, trifluoromethanesulfonic anhydride (401 mg, 1.44 mmol) was added thereto at 0° C., following with stirring at room temperature for 3 hours. The reaction mixture was added with water, and extracted with $CH_2Cl_2$ twice. The obtained organic layer was washed with saturated aqueous brine solution, dried over $MgSO_4$, filtered to remove the solid residue, and the filtrate was concentrated under reduced pressure. The concentrate was purified by column chromatography (ISCO silica gel cartridge, EtOAc/Hexane) to yield the title compound as white solid (395 mg, 62%).

Step 6.

Methyl 3'-fluoro-4'-((1-((1-(trifluoromethyl)cyclobutyl)methyl)piperidin-4-yl)methoxy) biphenyl-4-carboxylate: 3'-fluoro-4'-((1-((1-(trifluoromethyl)cyclobutyl)methyl)piperidin-4-yl)methoxy)biphenyl-4-yl trifluoromethanesulfonate (785 mg, 1.38 mmol), $Pd(OAc)_2$ (16 mg, 0.07 mmol) and dppp (35 mg, 0.08 mmol) were dissolved in DMSO 3 mL. MeOH 2 mL was added thereto, following with sufficient infusion of carbon monoxide (CO). TEA (697 mg, 6.89 mmol) was added thereto, following with stirring at 120° C. for 4 hours. The reaction mixture was diluted with water, and extracted with EtOAc. The obtained organic layer was washed with saturated aqueous brine solution, dried over $MgSO_4$, filtered to remove the solid residue, and the filtrate was concentrated under reduced pressure. The concentrate was purified by column chromatography (ISCO silica gel cartridge, $EtOAcCH_2Cl_2$) to yield the title compound as white solid (380 mg, 57%).

Step 7.

2'-fluoro-4'-((1-((1-(trifluoromethyl)cyclobutyl)methyl)piperidin-4-yl)methoxy) biphenyl-4-carboxylic acid: Methyl 3'-fluoro-4'-((1-((1-(trifluoromethyl)cyclobutyl)methyl)piperidin-4-yl)methoxy)biphenyl-4-carboxylate (420 mg, 0.88 mmol) was dissolved in $THF/MeOH/H_2O=632$ mL. $LiOH.H_2O$ (73 mg, 1.75 mmol) was added thereto. And then, the mixture was refluxed with heating for 3 hours. After the completion of the reaction, the solvent was dried under reduced pressure, following with adjusting pH to below 6 using 1N HCl. The resulting precipitate was filtered to yield the title compound as white solid (380 mg, 93%).

Step 8.

Compound 883: 2'-fluoro-4'-((1-((1-(trifluoromethyl)cyclobutyl)methyl)piperidin-4-yl)methoxy)biphenyl-4-carboxylic acid (50 mg, 0.11 mmol), EDC (33 mg, 0.22 mmol), HOBt (29 mg, 0.22 mmol) and DIPEA (42 mg, 32 mmol) were dissolved in DMF 1 mL. After stirring for 10 minutes at room temperature, (S)-piperidin-3-ol (16 mg, 0.16 mmol) was added thereto, following with stirring at 50° C. for 8 hours. The reaction mixture was added with water, and extracted with EtOAc. The organic layer was washed with saturated aqueous brine solution, dried over $MgSO_4$, filtered to remove the solid residue, and the filtrate was concentrated under reduced pressure. The concentrate was purified by column chromatography (4 g ISCO silica gels: cartridge, $MeOH/CH_2Cl_2$) to yield the title compound as white solid (35 mg, 59%).

1H NMR (400 MHz, $CDCl_3$) δ 7.49 (m, 4H), 7.29 (m, 2H), 7.00 (t, 1H, J=8.5 Hz), 3.90 (m, u 4H), 3.59 (m, 3H), 2.88 (m, 2H), 2.53 (s, 2H), 2.21 (m, 4H), 1.98 (m, 10H), 1.24 (m, 3H); MS (ESI) m/z 549 (M+H).

According to the above-described synthesis process of compound 883, the compounds of Table 72 were synthesized using 2'-fluoro-4'-((1-((1-(trifluoromethyl)cyclobutyl)methyl)piperidin-4-yl)methoxy)biphenyl-4-carboxylic acid and the reactant of Table 71

TABLE 71

| Compound No. | Reactant | Yield (%) |
|---|---|---|
| 837 | (S)-pyrrolidine-2-carboxamide | 47 |
| 838 | (R)-pyrrolidine-2-ylmethanol | 44 |
| 839 | (S)-pyrrolidine-3-ol | 52 |
| 840 | (R)-piperidin-3-ol | 42 |
| 884 | (S)-piperidin-3-carboxamide hydrochloride | 48 |
| 885 | (R)-piperidin-3-carboxamide hydrochloride | 50 |
| 886 | (R)-piperidin-2-carboxamide hydrochloride | 61 |
| 887 | (S)-piperidin-2-carboxamide hydrochloride | 56 |

TABLE 72

| Compound No. | Compound Name, $^1$H-NMR, MS (ESI) |
|---|---|
| 837 | (S)-1-(3'-fluoro-4'-((1-((1-(trifluoromethyl)cyclobutyl)methyl)piperidin-4-yl)methoxy)biphenylcarbonyl)pyrrolidine-2-carboxamide<br>1H NMR (400 MHz, $CDCl_3$) δ 7.59 (m, 4 H), 7.33 (m, 2 H), 7.02 (m, 2 H), 5.57 (s, 1 H), 4.82 (t, 1 H, J = 6.2 Hz), 3.92 (d, 2 H, J = 6.2 Hz), 3.58 (m, 2 H), 2.91 (m, 2 H), 2.45 (m, 3 H), 2.25 (m, 4 H), 2.13 (m, 6 H), 1.98 (m, 4 H), 1.26 (m, 2 H). |
| 838 | (R)-(3'-fluoro-4'-((1-((1-(trifluoromethyl)cyclobutyl)methyl)piperidin-4-yl)methoxy)biphenyl-4-yl)(2-(hydroxymethyl)pyrrolidin-1-yl)methanone<br>1H NMR (400 MHz, $CDCl_3$) δ 7.47 (m, 4 H), 7.31 (m, 2 H), 7.03 (t, 1 H, J = 8.5 Hz), 4.94 (m, 1 H), 4.43 (m, 1 H), 3.91 (d, 2 H, J = 6.2 Hz), 3.78 (m, 2 H), 3.55 (m, 2 H), 3.13 (s, 1 H), 3.04 (s, 1 H), 2.89 (m, 2 H), 2.25 (s, 2 H), 2.23 (m, 5 H), 1.98 (m, 8 H), 1.42 (m, 2 H). |
| 839 | (S)-(3'-fluoro-4'-((1-((1-(trifluoromethyl)cyclobutyl)methyl)piperidin-4-yl)methoxy)biphenyl-4-yl)(3-hydroxypyrrolidin-1-yl)methanone<br>1H NMR (400 MHz, $CDCl_3$) δ 7.58 (m, 4 H), 7.30 (m, 2 H), 7.01 (t, 1 H, J = 8.5 Hz), 4.58 (s, 0.5 H), 4.45 (s, 0.5 H), 3.91 (d, 2 H, J = 6.2 Hz), 3.91 (d, 2 H, J = 6.2 Hz), 3.64 (m, 2 H), 3.54 (m, 1 H), 3.52 (m, 1 H), 2.91 (d, 2 H, J = 11.0 Hz), 2.81 (s, 0.5 H), 2.72 (s, 0.5 H), 2.55 (s, 2 H), 2.23 (m, 4 H), 2.04 (m, 10 H), 1.46 (m, 2 H). |
| 840 | (R)-(3'-fluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, $CDCl_3$) δ 7.53 (m, 4 H), 7.33 (m, 2 H), 7.02 (t, 1 H, J = 8.5 Hz), 3.92 (m, 4 H), 3.57 (m, 3 H), 3.16 (m, 2 H), 2.68 (m, 2 H), 2.24 (m, 4 H), 2.04 (m, 10 H), 1.85 (m, 2 H), 1.26 (m, 2 H). |

TABLE 72-continued

Compound No. Compound Name, $^1$H-NMR, MS (ESI)

884  (S)-1-(3'-fluoro-4'-((1-((1-(trifluoromethyl)cyclobutyl)methyl)piperidin-4-yl)methoxy)biphenylcarbonyl)piperidin-3-carboxamide
1H NMR (400 MHz, CDCl$_3$) δ 7.55 (d, 2 H, J = 8.1 Hz), 7.44 (d, 2 H, J = 8.3 Hz), 7.30 (m, 2 H), 7.01 (t, 1 H, J = 8.5 Hz), 6.75 (s, 1 H), 5.44 (s, 1 H), 4.12 (m, 1 H), 3.90 (d, 2 H, J = 6.2 Hz), 3.77 (m, 1 H), 3.55 (m, 1 H), 3.26 (m, 1 H), 2.90 (m, 2 H), 2.54 (m, 2 H), 2.54-1.46 (m, 16 H), 1.12 (m, 2 H).

885  (R)-1-(3'-fluoro-4'-((1-((1-(trifluoromethyl)cyclobutyl)methyl)piperidin-4-yl)methoxy)biphenylcarbonyl)piperidin-3-carboxamide
1H NMR (400 MHz, CDCl$_3$) δ 7.56 (d, 2 H, J = 8.0 Hz), 7.45 (d, 2 H, J = 8.1 Hz), 7.30 (m, 2 H), 7.02 (t, 1 H, J = 8.5 Hz), 6.80 (s, 1 H), 5.70 (s, 1 H), 4.16 (s, 1 H), 3.91 (d, 2 H, J = 6.2 Hz), 3.63 (m, 1 H), 3.37 (m, 1 H), 2.90 (m, 2 H), 2.55 (s, 2 H), 2.22-1.62 (m, 16 H), 1.43 (m, 3 H).

886  (R)-1-(3'-fluoro-4'-((1-((1-(trifluoromethyl)cyclobutyl)methyl)piperidin-4-yl)methoxy)biphenylcarbonyl)piperidin-2-carboxamide
1H NMR (400 MHz, CDCl$_3$) δ 7.55 (d, 2 H, J = 8.1 Hz), 7.44 (d, 2 H, J = 8.3 Hz), 7.31 (m, 2 H), 7.01 (t, 1 H, J = 8.5 Hz), 6.75 (s, 1 H), 5.54 (s, 1 H), 4.12 (m, 1 H), 3.90 (d, 2 H, J = 6.2 Hz), 3.77 (m, 1 H), 3.55 (m, 1 H), 3.26 (m, 1 H), 2.90 (m, 2 H), 2.54-1.61 (m, 15 H), 1.20 (m, 3 H); MS (ESI) m/z 576 (M + H).

887  (S)-1-(3'-fluoro-4'-((1-((1-(trifluoromethyl)cyclobutyl)methyl)piperidin-4-yl)methoxy)biphenylcarbonyl)piperidin-2-carboxamide
1H NMR (400 MHz, CDCl$_3$) δ 7.53 (m, 4 H), 7.31 (m, 2 H), 7.02 (t, 1 H, J = 8.5 Hz), 6.49 (s, 1 H), 5.51 (s, 1 H), 5.27 (s, 1 H), 3.91 (d, 2 H, J = 6.2 Hz), 3.78 (m, 2 H), 3.11 (m, 1 H), 2.89 (m, 2 H), 2.54 (s, 2 H), 1.97-1.24 (m, 14 H); MS (ESI) m/z 576 (M + H).

Example 79. Compound 847: (S)-1-(2,3'-difluoro-4'-((1-((1-(trifluoromethyl)cyclobutyl)methyl)piperidin-4-yl)methoxy)biphenylcarbonyl)pyrrolidine-2-carboxamide

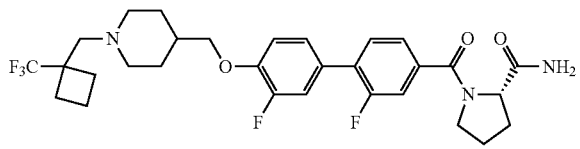 [SMILES: NC(=O)[C@@H]1CCCN1C(=O)c1ccc(-c2ccc(OCC3CCN(CC4(C(F)(F)F)CCC4)CC3)c(F)c2)c(F)c1]

Step 1.

(4-((4-bromo-2-fluorophenoxy)methyl)piperidin-1-yl)(1-(trifluoromethyl)cyclobutyl)methanone: 4-((4-bromophenoxy)methyl)piperidine hydrochloride (the product of synthesis step 2 of compound 725; 3.90 g, 12.01 mmol) was dissolved in CH$_2$Cl$_2$ (50 mL). EDC (4.61 g, 24.03 mmol), HOBt (3.25 g, 24.03 mmol), DIPEA (4.25 mL, 24.03 mmol), 1-(trifluoromethyl)cyclobutanecarboxylic acid (2.02 g, 12.01 mmol) was added thereto, following with stirring at room temperature for a day. After the completion of the reaction, the reaction mixture was added with water, and extracted with CH$_2$Cl$_2$. The obtained organic layer was extracted with saturated aqueous brine solution, dried over anhydrous MgSO$_4$, and concentrated under reduced pressure. The obtained concentrate was purified by silica gel column chromatography (EtOAc/hexane=30%~70%) to yield the title compound as white solid (3.10 g, 58%).

Step 2.

4-((4-bromo-2-fluorophenoxy)methyl)-1-((1-(trifluoromethyl)cyclobutyl)methyl)piperidine: (4-((4-bromo-2-fluorophenoxy)methyl)piperidin-1-yl)(1-(trifluoromethyl)cyclobutyl)methanone (2.28 g, 5.20 mmol) was dissolved in THF (50 mL). At 0° C., 2.0 M Borane dimethyl sulfide complex solution in THF (13.01 mL, 26.01 mmol) was added thereto, following with stirring at 50° C. for 5 hours. After the completion of the reaction, the reaction mixture was added with water, and extracted with EtOAc. The obtained organic layer was washed with saturated NaHCO$_3$ aqueous solution. The organic layer was dried over anhydrous MgSO$_4$, and concentrated under reduced pressure. The obtained concentrate was purified by silica gel column chromatography (EtOAc/hexane=20%~80%) to yield the title compound as white solid (1.50 g, 68%).

Step 3.

Methyl 2,3'-difluoro-4'-((1-((1-(trifluoromethyl)cyclobutyl)methyl)piperidin-4-yl)methoxy)biphenyl-4-carboxylate: To 4-((4-bromo-2-fluorophenoxy)methyl)-1-((1-(trifluoromethyl)cyclobutyl)methyl)piperidine (800 mg, 1.89 mmol), 2-fluoro-4-(methoxycarbonyl)phenylboronic acid (448 mg, 2.26 mmol), Pd(dppf)Cl$_2$ (154 mg, 0.19 mmol) and Cs$_2$CO$_3$ (1.23 g, 3.77 mmol), DME (6 mL)/H$_2$O (2 mL) was added, With a microwave radiation, the mixture was heated at 110° C. for 15 minutes, and then cooled to room temperature. The reaction mixture was added with water, and extracted with EtOAc. The obtained organic layer was washed with saturated aqueous brine solution, and then. The organic layer was dried over anhydrous MgSO$_4$, and filtered. The filtrate was concentrated under reduced pressure. The concentrate was purified by silica gel column chromatography (EtOAc/hexane=30%-70%) to yield the title compound as white solid (535 mg, 57%).

Step 4.

2,3'-difluoro-4'-((1-((1-(trifluoromethyl)cyclobutyl)methyl)piperidin-4-yl)methoxy)biphenyl-4-carboxylic acid: Methyl 2,3'-difluoro-4'-((1-((1-(trifluoromethyl)cyclobutyl)methyl)piperidin-4-yl)methoxy)biphenyl-4-carboxylate (535 mg, 1.08 mmol) was dissolved in THF (10 mL) and H$_2$O (5 mL). At room temperature, LiOH.H$_2$O (226 mg, 5.38 mmol) was added thereto, following with stirring for 1 hour. After the completion of the reaction, the reaction mixture was concentrated under reduced pressure. The resulting precipitate was filtered, and dried to yield the title compound as white solid (400 mg, 76%).

Step 5.

Compound 847: 2,3'-difluoro-4'-((1-((1-(trifluoromethyl)cyclobutyl)methyl)piperidin-4-yl)methoxy)biphenyl-4-carboxylic acid (50 mg, 0.10 mmol), EDC (40 mg, 0.21 mmol), HOBt (28 mg, 0.21 mmol) and DIPEA (37 µL, 0.21 mmol) were dissolved in CH$_2$Cl$_2$ (1 mL). (S)-pyrrolidine-2-carboxamide (24 mg, 0.21 mmol) was added thereto, following with stirring for a day. The reaction mixture was added with water, and extracted with EtOAc. The organic layer was washed with saturated NH₄Cl aqueous solution, dried over anhydrous MgSO₄, and concentrated under reduced pressure. The concentrate was purified by silica gel column chromatography (CH₂Cl₂/MeOH=95%~5%) to yield the title compound as white solid (43 mg, 71%).

1H NMR (400 MHz, CDCl₃) δ 7.48-7.45 (m, 1H), 7.40-7.27 (m, 4H), 7.03 (t, 1H, J=8.6 Hz), 6.91 (brs, 1H), 5.60 (brs, 1H), 4.81-4.78 (m, 1H), 3.92 (d, 2H, J=6.2 Hz), 3.68-3.54 (m, 2H), 2.90 (d, 2H, J=11.3 Hz), 2.54 (s, 2H), 2.49-2.42 (m, 1H), 2.27-2.20 (m, 4H), 2.16-1.98 (m, 5H), 1.96-1.91 (m, 4H), 1.90-1.73 (brs, 1H), 1.48-1.42 (m, 2H); MS (ESI) m/z 580 (M++H).

According to the above-described synthesis process of compound 847, the compounds of Table 74 were synthesized using 2,3'-difluoro-4'-((1-((1-(trifluoromethyl)cyclobutyl)methyl)piperidin-4-yl)methoxy)biphenyl-4-carboxylic acid and the reactant of Table 73.

TABLE 73

| Compound No. | Reactant | Yield (%) |
| --- | --- | --- |
| 848 | (R)-piperidin-3-ol hydrochloride | 66 |
| 849 | (R)-pyrrolidine-2-ylmethanol | 68 |
| 850 | (S)-piperidin-3-ol hydrochloride | 64 |
| 851 | (S)-pyrrolidine-3-ol | 61 |

TABLE 74

| Compound No. | Compound Name, ¹H-NMR, MS (ESI) |
| --- | --- |
| 848 | (R)-(2,3'-difluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, CDCl₃) δ 7.44 (t, 1 H, J = 7.8 Hz), 7.33-7.22 (m, 4 H), 7.03 (t, 1 H, J = 8.6 Hz), 3.93-3.79 (m, 3 H), 3.74 (brs, 1 H), 3.59-3.39 (m, 3 H), 2.90 (d, 2 H, J = 11.2 Hz), 2.48 (s, 2 H), 2.27-2.20 (m, 4 H), 2.19-2.04 (m, 2 H), 2.03-1.91 (m, 8 H), 1.90-1.61 (brs, 2 H), 1.48-1.40 (m, 2 H); MS (ESI) m/z 567 (M+ + H). |
| 849 | (R)-(2,3'-difluoro-4'-((1-((1-(trifluoromethyl)cyclobutyl)methyl)piperidin-4-yl)methoxy)biphenyl-4-yl)(2-(hydroxymethyl)pyrrolidin-1-yl)methanone<br>1H NMR (400 MHz, CDCl₃) δ 7.46 (t, 1 H, J = 7.8 Hz), 7.38-7.26 (m, 4 H), 7.03 (t, 1 H, J = 8.6 Hz), 4.71 (brs, 1 H), 4.44-4.42 (m, 1 H), 3.92 (d, 2 H, J = 6.3 Hz), 3.83-3.77 (m, 2 H), 3.61-3.54 (m, 2 H), 2.90 (d, 2 H, J = 11.4 Hz), 2.54 (s, 2 H), 2.27-2.20 (m, 5 H), 2.11-1.83 (m, 8 H), 1.70-1.65 (m, 2 H), 1.46-1.42 (m, 2 H); MS (ESI) m/z 567 (M+ + H). |
| 850 | (S)-(2,3'-difluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, CDCl₃) δ 7.44 (t, 1 H, J = 7.8 Hz), 7.33-7.22 (m, 4 H), 7.03 (t, 1 H, J = 8.6 Hz), 3.93-3.79 (m, 3 H), 3.74 (brs, 1 H), 3.59-3.39 (m, 3 H), 2.90 (d, 2 H, J = 11.2 Hz), 2.48 (s, 2 H), 2.27-2.20 (m, 4 H), 2.19-2.04 (m, 2 H), 2.03-1.91 (m, 8 H), 1.90-1.61 (brs, 2 H), 1.48-1.40 (m, 2 H); MS (ESI) m/z 567 (M+ + H). |
| 851 | (S)-(2,3'-difluoro-4'-((1-((1-(trifluoromethyl)cyclobutyl)methyl)piperidin-4-yl)methoxy)biphenyl-4-yl)(3-hydroxypyrrolidin-1-yl)methanone<br>1H NMR (400 MHz, CDCl₃) δ 7.46-7.26 (m, 5 H), 7.03 (t, 1 H, J = 8.6 Hz), 4.62-4.51 (m, 1 H), 3.92 (d, 2 H, J = 6.3 Hz), 3.87-3.81 (m, 2 H), 3.79-3.77 (m, 1 H), 3.71-3.49 (m, 1 H), 2.90 (d, 2 H, J = 11.3 Hz), 2.54 (s, 2 H), 2.27-2.20 (m, 4 H), 2.18-1.92 (m, 5 H), 1.91-1.83 (m, 4 H), 1.66 (s, 1 H), 1.48-1.42 (m, 2 H); MS (ESI) m/z 553 (M+ + H). |

Example 80. Compound 901: (S)-1-(3,3'-difluoro-4'-((1-((1-(trifluoromethyl)cyclobutyl)methyl)piperidin-4-yl)methoxy)biphenylcarbonyl)pyrrolidine-2-carboxamide

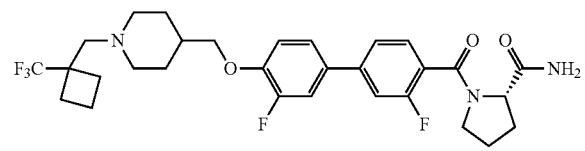 [SMILES: NC(=O)[C@@H]1CCCN1C(=O)c1ccc(-c2ccc(OCC3CCN(CC4(C(F)(F)F)CCC4)CC3)c(F)c2)cc1F]

Step 1.

Ethyl 3,3'-difluoro-4'-((1-((1-(trifluoromethyl)cyclobutyl)methyl)piperidin-4-yl)methoxy)biphenyl-4-carboxylate: To 4-((4-bromo-2-fluorophenoxy)methyl)-1-((1-(trifluoromethyl)cyclobutyl)methyl)piperidine (the product of synthesis step 2 of compound 847; 627 mg, 1.48 mmol), 4-(ethoxycarbonyl)-3-fluorophenylboronic acid (345 mg, 1.63 mmol), Pd(dppf)Cl₂ (121 mg, 0.15 mmol) and Cs₂CO₃ (963 mg, 2.96 mmol), DME (6 mL)/H₂O (2 mL) was added, With a microwave radiation, the mixture was heated at 110° C. for 15 minutes, and then cooled to room temperature. The reaction mixture was added with water, and extracted with EtOAc. The obtained organic layer was washed with saturated aqueous brine solution, and then. The organic layer was dried over anhydrous MgSO₄, and filtered. The filtrate was concentrated under reduced pressure. The concentrate was purified by silica gel column chromatography (EtOAc/hexane=30%~70%) to yield the title compound as white solid (580 mg, 76%).

Step 2.

3,3'-difluoro-4'-((1-((1-(trifluoromethyl)cyclobutyl)methyl)piperidin-4-yl)methoxy)biphenyl-4-carboxylic acid: Ethyl 3,3'-difluoro-4'-((1-((1-(trifluoromethyl)cyclobutyl)methyl)piperidin-4-yl)methoxy)biphenyl-4-carboxylate (580 mg, 1.13 mmol) was dissolved in THF (10 mL) and H₂O (5 mL). At room temperature, LiOH.H₂O (238 mg, 5.67 mmol) was added thereto, following with stirring for 1 hour. After the completion of the reaction, the reaction mixture was concentrated under reduced pressure. The resulting precipitate was filtered, and dried to yield the title compound as white solid (500 mg, 91%).

Step 3.

Compound 901: 3,3'-difluoro-4'-((1-((1-(trifluoromethyl)cyclobutyl)methyl)piperidin-4-yl)methoxy)biphenyl-4-carboxylic acid (60 mg, 0.12 mmol), EDC (48 mg, 0.25 mmol), HOBt (34 mg, 0.25 mmol) and DIPEA (44 μL, 0.25 mmol) were dissolved in CH₂Cl₂ (1 mL). (S)-pyrrolidine-2-carboxamide (28 mg, 0.25 mmol) was added thereto, following with stirring for a day. The reaction mixture was added with water, and extracted with EtOAc. The organic layer was washed with saturated NH₄Cl aqueous solution, dried over anhydrous MgSO₄, and concentrated under reduced pressure. The obtained concentrate was purified by silica gel column chromatography (CH₂Cl₂/MeOH=95%~5%) to yield the title compound as white solid (46 mg, 64%).

1H NMR (400 MHz, CDCl₃) δ 7.48 (t, 1H, J=7.5 Hz), 7.41-7.27 (m, 4H), 7.03 (t, 1H, J=8.5 Hz), 6.93 (brs, 1H), 5.65 (brs, 1H), 4.83-4.80 (m, 1H), 3.91 (d, 2H, J=6.3 Hz), 3.55-3.53 (m, 1H), 3.44-3.41 (m, 1H), 2.90 (d, 2H, J=11.4 Hz), 2.54 (s, 2H), 2.47-2.44 (m, 1H), 2.27-2.19 (m, 4H), 2.15-1.82 (m, 10H), 1.46-1.42 (m, 2H); MS (ESI) m/z 580 (M++H).

According to the above-described synthesis process of compound 901, the compounds of Table 76 were synthesized using 3,3'-difluoro-4'-((1-((1-(trifluoromethyl)cyclobutyl)methyl)piperidin-4-yl)methoxy)biphenyl-4-carboxylic acid and the reactant of Table 75.

TABLE 75

| Compound No. | Reactant | Yield (%) |
|---|---|---|
| 902 | (R)-piperidin-3-ol hydrochloride | 66 |
| 903 | (R)-pyrrolidine-2-ylmethanol | 62 |
| 904 | (S)-piperidin-3-ol hydrochloride | 55 |
| 905 | (S)-pyrrolidine-3-ol | 61 |
| 936 | 1-(piperazin-1-yl)ethanone | 79 |

Example 81. Compound 906: (S)-1-(5-(3-fluoro-4-((1-((1-(trifluoromethyl)cyclobutyl)methyl)piperidin-4-yl)methoxy)phenyl)picolinoyl)pyrrolidine-2-carboxamide

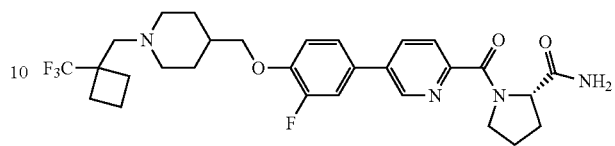

Step 1.

Methyl 5-(3-fluoro-4-((1-((1-(trifluoromethyl)cyclobutyl)methyl)piperidin-4-yl)methoxy)phenyl)picolinate: To 4-((4-bromo-2-fluorophenoxy)methyl)-1-((1-(trifluoromethyl)cyclobutyl)methyl)piperidine (the product of synthesis step 2 of compound 847; 856 mg, 2.02 mmol), 6-methoxycarbonyl)pyridine-3-yl boronic acid (402 mg, 2.22 mmol), Pd(dppf)Cl₂ (165 mg, 0.20 mmol) and Cs₂CO₃ (1.31 g, 4.04 mmol), DME (6 mL)/H₂O (2 mL) was added, With a microwave radiation, the mixture was heated at 110° C. for 15 minutes, and then cooled to room temperature. The reaction mixture was added with water, and extracted with EtOAc. The obtained organic layer was washed with saturated aqueous brine solution, and then. The organic layer was dried over anhydrous MgSO₄, and filtered. The filtrate was concentrated under reduced pressure. The obtained

TABLE 76

| Compound No. | Compound Name, ¹H-NMR, MS (ESI) |
|---|---|
| 902 | (R)-(3,3'-difluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, CDCl₃) δ 7.44 (t, 1 H, J = 7.4 Hz), 7.38-7.23 (m, 4 H), 7.02 (t, 1 H, J = 8.5 Hz), 4.07 (brs, 1 H), 3.91 (d, 2 H, J = 6.3 Hz), 3.60-3.56 (m, 1 H), 3.37-3.26 (m, 1 H), 2.90 (d, 2 H, J = 11.4 Hz), 2.54 (s, 2 H), 2.27-2.20 (m, 4 H), 2.10-1.83 (m, 10 H), 1.70-1.62 (m, 2 H), 1.48-1.40 (m, 3 H); MS (ESI) m/z 567 (M+ + H). |
| 903 | (R)-(3,3'-difluoro-4'-((1-((1-(trifluoromethyl)cyclobutyl)methyl)piperidin-4-yl)methoxy)biphenyl-4-yl)(2-(hydroxymethyl)pyrrolidin-1-yl)methanone<br>1H NMR (400 MHz, CDCl₃) δ 7.48 (t, 1 H, J = 7.5 Hz), 7.39-7.29 (m, 1 H), 7.29-7.26 (m, 3 H), 7.03 (t, 1 H, J = 8.4 Hz), 4.77 (brs, 1 H), 4.41-4.39 (m, 1 H), 3.91 (d, 2 H, J = 6.3 Hz), 3.82-3.75 (m, 2 H), 3.48-3.44 (m, 2 H), 2.90 (d, 2 H, J = 11.1 Hz), 2.54 (s, 2 H), 2.27-2.20 (m, 5 H), 2.19-1.69 (m, 10 H), 1.46-1.43 (m, 2 H); MS (ESI) m/z 567 (M+ + H). |
| 904 | (S)-(3,3'-difluoro-4'-((1-((1-(trifluoromethyl)cyclobutyl)methyl)piperidin-4-yl)methoxy)biphenyl-4-yl)(3-hydroxypiperidin-1-yl)methanone<br>1H NMR (400 MHz, CDCl₃) δ 7.44 (t, 1 H, J = 7.4 Hz), 7.38-7.23 (m, 4 H), 7.02 (t, 1 H, J = 8.5 Hz), 4.07 (brs, 1 H), 3.91 (d, 2 H, J = 6.3 Hz), 3.60-3.56 (m, 1 H), 3.37-3.26 (m, 1 H), 2.90 (d, 2 H, J = 11.4 Hz), 2.54 (s, 2 H), 2.27-2.20 (m, 4 H), 2.10-1.83 (m, 10 H), 1.70-1.62 (m, 2 H), 1.48-1.40 (m, 3 H); MS (ESI) m/z 567 (M+ + H). |
| 905 | (S)-(3,3'-difluoro-4'-((1-((1-(trifluoromethyl)cyclobutyl)methyl)piperidin-4-yl)methoxy)biphenyl-4-yl)(3-hydroxypyrrolidine-1-yl)methanone<br>1H NMR (400 MHz, CDCl₃) δ 7.51-7.46 (m, 1 H), 7.37-7.23 (m, 4 H), 7.02 (t, 1 H, J = 8.5 Hz), 4.62-4.51 (m, 1 H), 3.91 (d, 2 H, J = 6.2 Hz), 3.83-3.78 (m, 1 H), 3.73-3.58 (m, 1 H), 3.48-3.36 (m, 1 H), 2.90 (d, 2 H, J = 11.4 Hz), 2.54 (s, 2 H), 2.27-2.20 (m, 4 H), 2.19-1.83 (m, 9 H), 1.71 (brs, 1 H), 1.46-1.42 (m, 2 H); MS (ESI) m/z 553 (M+ + H). |
| 936 | 1-(4-(3,3'-difluoro-4'-((1-((-(trifluoromethyl)cyclobutyl)methyl)piperidin-4-yl)methoxy)biphenylcarbonyl)piperazin-1-yl)ethanone<br>1H NMR (400 MHz, CDCl₃) δ 7.50-7.46 (m, 1 H), 7.44-7.41 (m, 1 H), 7.39-7.26 (m, 3 H), 7.03 (t, 1 H, J = 8.5 Hz), 3.92 (d, 2 H, J-6.3 Hz), 3.85-3.75 (m, 3 H), 3.71-3.60 (m, 2 H), 3.59-3.39 (m, 2 H), 2.90 (d, 2 H, J = 11.5 Hz), 2.54 (s, 2 H), 2.28-1.83 (m, 13 H), 1.67 (brs, 1 H), 1.48-1.42 (m, 2 H), 1.39-1.38 (m, 1 H); MS (ESI) m/z 594 (M+ + H). | concentrate was purified by silica gel column chromatography (EtOAc/hexane=30%~70%) to yield the title compound as white solid (80 mg, 8%).

Step 2.

5-(3-fluoro-4-((1-((1-(trifluoromethyl)cyclobutyl)methyl)piperidin-4-yl)methoxy)phenyl)picolinic acid: Methyl 5-(3-fluoro-4-((1-((1-(trifluoromethyl)cyclobutyl)methyl)piperidin-4-yl)methoxy)phenyl)picolinate (80 mg, 0.17 mmol) was dissolved in THF (10 mL) and H$_2$O (5 mL). At room temperature, LiOH.H$_2$O (35 mg, 0.83 mmol) was added thereto, following with stirring for 1 hour. After the completion of the reaction, the reaction mixture was concentrated under reduced pressure. The resulting precipitate was filtered, and dried to yield the title compound as white solid (60 mg, 77%).

Step 3.

Compound 906: 5-(3-fluoro-4-((1-((1-(trifluoromethyl)cyclobutyl)methyl)piperidin-4-yl)methoxy)phenyl)picolinic acid (60 mg, 0.12 mmol), EDC (48 mg, 0.25 mmol), HOBt (34 mg, 0.25 mmol) and DIPEA (44 μL, 0.25 mmol) were dissolved in CH$_2$Cl$_2$ (1 mL). (S)-pyrrolidine-2-carboxamide (28 mg, 0.25 mmol) was added thereto, following with stirring for a day. The reaction mixture was added with water, and extracted with EtOAc. The organic layer was washed with saturated NH$_4$Cl aqueous solution, dried over anhydrous MgSO$_4$, and concentrated under reduced pressure. The concentrate was purified by silica gel column chromatography (CH$_2$Cl$_2$/MeOH=95%~5%) to yield the title compound as white solid (46 mg, 64%).

1H NMR (400 MHz, CDCl$_3$) δ 8.77-8.72 (m, 1H), 8.09-7.91 (m, 2H), 7.37-7.27 (m, 2H), 7.07 (t, 1H, J=8.7 Hz), 6.94 (brs, 0.5H), 6.53 (brs, 0.5H), 5.53 (brs, 1H), 5.06-5.05 (m, 0.5H), 4.86-4.83 (m, 0.5H), 4.07-3.82 (m, 3H), 2.90 (d, 2H, J=11.4 Hz), 2.54 (s, 2H), 2.41-2.37 (m, 1H), 2.36-1.78 (m, 15H), 1.48-1.40 (m, 2H); MS (ESI) m/z 563 (M++H).

According to the above-described synthesis process of compound 906, the compounds of Table 78 were synthesized using 5-(3-fluoro-4-((1-((1-(trifluoromethyl)cyclobutyl)methyl)piperidin-4-yl)methoxy)phenyl)picolinic acid and the reactant of Table 77.

TABLE 77

| Compound No. | Reactant | Yield (%) |
| --- | --- | --- |
| 907 | (R)-piperidin-3-ol hydrochloride | 48 |

TABLE 78

| Compound No. | Compound Name, $^1$H-NMR, MS (ESI) |
| --- | --- |
| 907 | (R)-(5-(3-fluoro-4-((1-((1-(trifluoromethyl)cyclobutyl)methyl)piperidin-4-yl)methoxy)phenyl)pyridine-2-yl)(3-hydroxypiperidin-1-yl)methanone<br>1H NMR (400 MHz, CDCl$_3$) δ 8.71-8.70 (m, 1 H), 7.98 (d, 1 H, J = 8.1 Hz), 7.85 (d, 1 H, J = 8.2 Hz), 7.36-7.27 (m, 2 H), 7.07 (t, 1 H; J = 8.4 Hz), 5.72 (s, 1 H), 4.61 (d, 1 H, J = 12.6 Hz), 4.09-4.04 (m, 2 H), 3.93 (d, 2 H, J = 6.3 Hz), 3.28 (d, 1 H, J = 13.0 Hz), 2.99-2.89 (m, 3 H), 2.54 (s, 2 H), 2.28-1.83 (m, 12 H), 1.70-1.60 (m, 3 H), 1.48-1.40 (m, 2 H); MS (ESI) m/z 550 (M+ + H). |

Example 82. Compound 576: N,N-dimethyl-4-(6-((1-((1-(trifluoromethyl)cyclobutyl)methyl)piperidin-4-yl)methoxy)pyridine-3-yl)benzamide

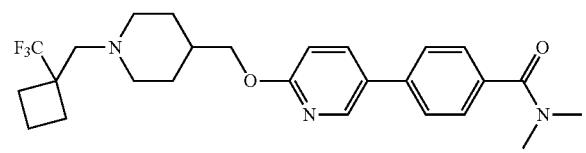 [SMILES: CN(C)C(=O)c1ccc(-c2ccc(OCC3CCN(CC4(C(F)(F)F)CCC4)CC3)nc2)cc1]

4-(6-((1-((1-(trifluoromethyl)cyclobutyl)methyl)piperidin-4-yl)methoxy)pyridine-3-yl)benzoic acid (the product of synthesis step 2 of compound 574; 20 mg, 0.05 mmol), dimethylamine (4 mg, 0.09 mmol), EDC (17 mg, 0.09 mmol) and HOBt (12 mg, 0.09 mmol) were dissolved in DMF 1 mL. DIPEA (11 mg, 0.09 mmol) was added thereto. The reaction was performed at room temperature for 16 hours. The reaction mixture was added with water, and extracted with EtOAc. The organic layer was dried over MgSO$_4$, and filtered. The filtrate was concentrated under reduced pressure. The concentrate was purified by silica gel column chromatography (20-70% EtOAc/hexane) to yield the title compound as white solid (9 mg, 42%).

1H NMR (400 MHz, CDCl$_3$) δ 8.38 (d, 1H, J=2.5 Hz), 7.80 (dd, 1H, J=8.6, 2.6 Hz), 7.52 (m, 4H), 6.83 (d, 1H, J=8.5 Hz), 4.20 (d, 2H, J=6.2 Hz), 3.14 (s, 3H), 3.05 (s, 3H), 2.88 (m, 2H), 2.26 (s, 2H), 2.06 (m, 4H), 1.90 (m, 7H), 1.43 (m, 2H); MS (ESI) m/z 476 (M++H).

Example 83. Compound 578: (S)-(3-hydroxypyrrolidine-1-yl)(4-(6-((1-((1-(trifluoromethyl)cyclobutyl)methyl)piperidin-4-yl)methoxy)pyridine-3-yl)phenyl)methanone

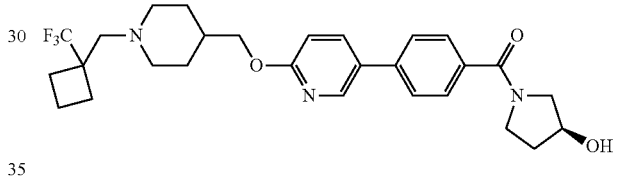

4-(6-((1-((1-(trifluoromethyl)cyclobutyl)methyl)piperidin-4-yl)methoxy)pyridine-3-yl)benzoic acid (the product of synthesis step 2 of compound 574; 30 mg, 0.07 mmol), (S)-pyrrolidine-3-ol (11 mg, 0.13 mmol) and BOP (59 mg, 0.13 mmol) were dissolved in DMF 1 mL. TEA (13 mg, 0.13 mmol) was added thereto. At 50° C., the reaction was performed for 16 hours. The reaction mixture was added with water, and extracted with CH$_2$Cl$_2$. The obtained organic layer was dried over MgSO$_4$, and filtered. The filtrate was concentrated under reduced pressure. The obtained concentrate was purified by silica gel column chromatography (5-10% MeOH/CH$_2$Cl$_2$) to yield the title compound as white solid (13 mg, 38%).

1H NMR (400 MHz, CDCl$_3$) δ 8.37 (s, 1H), 7.79 (m, 1H), 7.62 (m, 2H), 7.54 (m, 2H), 6.82 (d, 1H, J=8.5 Hz), 4.58 (m, 1H), 4.19 (d, 2H, J=6.2 Hz), 3.81 (m, 2H), 3.63 (m, 1H), 3.57 (m, 1H), 2.99 (m, 2H), 2.66 (s, 3H), 2.63 (s, 3H), 2.26 (s, 2H), 2.20 (m, 2H), 2.04 (m, 3H), 1.79 (m, 2H), 1.43 (m, 2H); MS (ESI) m/z 518 (M++H).

Example 84. Compound 581: (S)-1-(4-(6-((1-((1-(trifluoromethyl)cyclobutyl)methyl)piperidin-4-yl)methoxy)pyridine-3-yl)benzoyl)pyrrolidine-2-carboxamide

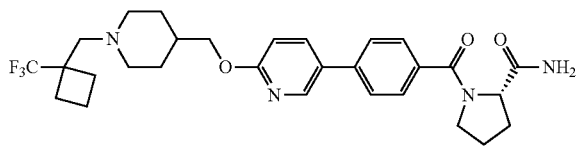 [SMILES: NC(=O)[C@@H]1CCCN1C(=O)c1ccc(-c2ccc(OCC3CCN(CC4(C(F)(F)F)CCC4)CC3)nc2)cc1]

4-(6-((1-((1-(trifluoromethyl)cyclobutyl)methyl)piperidin-4-yl)methoxy)pyridine-3-yl)benzoic acid (the product of synthesis step 2 of compound 574; 50 mg, 0.11 mmol), L-prolinamide (26 mg, 0.22 mmol), EDC (43 mg, 0.22 mmol) and HOBt (30 mg, 0.22 mmol) were dissolved in DMF 1 mL. DIPEA (29 mg, 0.22 mmol) was added thereto. At 60° C., the reaction was performed for 10 hours. The reaction mixture was cooled to room temperature, and added with water. The formed solid was filtered, washed with water, and dried to yield the title compound as white solid (40 mg, 66%).

1H NMR (400 MHz, CDCl$_3$) δ 8.38 (s, 1H), 7.80 (dd, 1H, J=8.4, 2.3 Hz), 7.60 (dd, 4H, J=19.3, 8.3 Hz), 7.00 (m, 1H), 6.83 (d, 1H, J=8.7 Hz), 5.54 (m, 1H), 4.84 (m, 1H), 4.21 (m, 2H), 3.65-3.54 (m, 2H), 2.88-2.65 (m, 2H), 2.52-2.47 (m, 2H), 2.22-1.79 (m, 15H), 1.46 (m, 2H); MS (ESI) m/z 545 (M++H).

According to the above-described synthesis process of compound 581, the compounds of Table 80 were synthesized using 4-(6-((1-((1-(trifluoromethyl)cyclobutyl)methyl)piperidin-4-yl)methoxy)pyridine-3-yl)benzoic acid and the reactant of Table 79.

TABLE 79

| Compound No. | Reactant | Yield (%) |
| --- | --- | --- |
| 579 | (R)-prolinol | 30 |
| 588 | piperidin-4-yl methanol | 71 |
| 595 | 3-(trifluoromethyl)-5,6,7,8-tetrahydro-[1,2,4]triazolo[4,3-a]pyrazine | 45 |
| 671 | D-prolinamide | 41 |
| 672 | (S)-3-hydroxypiperidine hydrochloride | 48 |
| 673 | (R)-3-hydroxypiperidine hydrochloride | 44 |

TABLE 80

| Compound No. | Compound Name, $^1$H-NMR, MS (ESI) |
| --- | --- |
| 579 | (R)-(2-(hydroxymethyl)pyrrolidine-1-yl)(4-(6-((1-((1-(trifluoromethyl)cyclobutyl)methyl)piperidin-4-yl)methoxy)pyridine-3-yl)phenyl)methanone<br>1H NMR (400 MHz, CDCl$_3$) δ 8.39 (d, 1 H, J = 2.4 Hz), 7.81 (dd, 1 H, J = 8.6, 2.5 Hz), 7.56 (m, 4 H), 6.83 (d, 1 H, J = 8.6 Hz), 4.94 (m, 1 H), 4.45 (m, 1 H), 4.20 (d, 2 H, J = 6.2 Hz), 3.79 (m, 2 H), 3.59 (m, 2 H), 2.88 (m, 2 H), 2.52 (s, 2 H), 2.11 (m, 5 H), 2.04 (m, 3 H), 1.89 (m, 2 H), 1.85 (m, 4 H), 1.68 (m, 1 H), 1.46 (m, 2 H);<br>MS (ESI) m/z 532 (M+ + H). |
| 588 | (4-(hydroxymethyl)piperidin-1-yl)(4-(6-((1-((1-(trifluoromethyl)cyclobutyl)methyl)piperidin-4-yl)methoxy)pyridine-3-yl)phenyl)methanone<br>1H NMR (400 MHz, CDCl3) δ 8.37 (d, 1 H, J = 2.2 Hz), 7.79 (dd, 1 H, J = 8.4, 2.3 Hz), 7.51 (dd, 4 H, J = 19.3, 8.3 Hz), 6.82 (d, 1 H, J = 8.7 Hz), 4.78 (m, 1 H), 4.20 (m, 2 H), 3.87 (m, 1 H), 3.55 (m, 2 H), 3.20-2.70 (m, 4 H), 2.54 (m, 2 H), 2.22 (m, 4 H), 2.15-1.65 (m, 11 H), 1.49-1.20 (m, 4 H); MS (ESI) m/z 546 (M+ + H). |
| 595 | (3-(trifluoromethyl)-5,6-dihydro-[1,2,4]triazolo[4,3-a]pyrazine-7(8H)-yl)(4-(6-((1-((1-(trifluoromethyl)cyclobutyl)methyl)piperidin-4-yl)methoxy)pyridine-3-yl)phenyl)methanone<br>1H NMR (400 MHz, CDCl$_3$) δ 8.40 (d, 1 H, J = 2.3 Hz), 7.81 (dd, 1 H, J = 8.6, 2.6 Hz), 7.60 (m, 4 H), 6.86 (d, 1 H, J = 8.6 Hz), 5.10 (s, 2 H), 4.28 (m, 2 H), 4.21 (m, 4 H), 2.90 (d, 2 H, J = 11.2 Hz), 2.53 (s, 2 H), 2.18 (m, 4 H), 2.02 (m, 2 H), 1.98 (m, 1 H), 1.92 (m, 1 H), 1.82 (m, 3 H), 1.47 (m, 2 H); MS (ESI) m/z 623 (M+ + H). |
| 671 | (R)-1-(4-(6-((1-((1-(trifluoromethyl)cyclobutyl)methyl)piperidin-4-yl)methoxy)pyridine-3-yl)benzoyl)pyrrolidine-2-carboxamide<br>1H NMR (400 MHz, CDCl$_3$) δ 8.38 (s, 1 H), 7.80 (dd, 1 H, J = 8.4, 2.3 Hz), 7.60 (dd, 4 H, J = 19.3, 8.3 Hz), 6.99 (m, 1 H), 6.83 (d, 1 H, J = 8.7 Hz), 5.44 (m, 1 H), 4.84 (m, 1 H), 4.21 (m, 2 H), 3.64-3.57 (m, 2 H), 2.90 (m, 2 H), 2.53-2.49 (m, 3 H), 2.24-2.18 (m, 4 H), 2.11-2.00 (m, 5 H), 2.00-1.80 (m, 5 H), 1.46 (m, 2 H); MS (ESI) m/z 545 (M+ + H). |
| 672 | (R)-(3-hydroxypiperidin-1-yl)(4-(6-((1-((1-(trifluoromethyl)cyclobutyl)methyl)piperidin-4-yl)methoxy)pyridine-3-yl)phenyl)methanone<br>1H NMR (400 MHz, CDCl$_3$) δ 8.38 (s, 1 H), 7.80 (dd, 1 H, J = 8.4, 2.3 Hz), 7.53 (dd, 4 H, J = 19.3, 8.3 Hz), 6.83 (d, 1 H, J = 8.7 Hz), 4.20 (m, 2 H), 4.05-3.20 (m, 15 H), 2.89 (m, 2 H), 2.53 (m, 2 H), 2.24-2.19 (m, 4 H), 2.15-1.75 (m, 9 H), 1.75-1.60 (m, 2 H), 1.46 (m, 2 H); MS (ESI) m/z 532 (M+ + H). |
| 673 | (S)-(3-hydroxypiperidin-1-yl)(4-(6-((1-((1-(trifluoromethyl)cyclobutyl)methyl)piperidin-4-yl)methoxy)pyridine-3-yl)phenyl)methanone<br>1H NMR (400 MHz, CDCl$_3$) δ 8.38 (s, 1 H), 7.80 (dd, 1 H, J = 8.4, 2,3 Hz), 7.53 (dd, 4 H, J = 19.3, 8.3 Hz), 6.83 (d, 1 H, J = 8.7 Hz), 4.20 (m, 2 H), 4.05-3.20 (m, 15 H), 2.89 (m, 2 H), 2.53 (m, 2 H), 2.24-2.19 (m, 4 H), 2.15-1.75 (m, 9 H), 1.75-1.60 (m, 2 H), 1.46 (m, 2 H); MS (ESI) m/z 532 (M+ + H). |

Example 85. Compound 931: (2S,4R)-methyl 4-hydroxy-1-(4-(6-((1-(1-(trifluoromethyl)cyclobutyl)methyl)piperidin-4-yl)methoxy)pyridine-3-yl)benzoyl)pyrrolidine-2-carboxylate

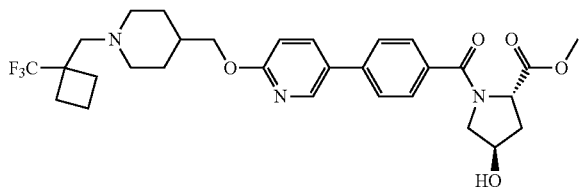 [SMILES: COC(=O)[C@@H]1C[C@@H](O)CN1C(=O)c1ccc(-c2ccc(OCC3CCN(CC4(C(F)(F)F)CCC4)CC3)nc2)cc1]

4-(6-((1-(((1-(trifluoromethyl)cyclobutyl)methyl)piperidin-4-yl)methoxy)pyridine-3-yl)benzoic acid (the product of synthesis step 2 of compound 574; 300 mg, 0.67 mmol), (2S,4R)-methyl 4-hydroxypyrrolidine-2-carboxylate hydrochloride (182 mg, 1.00 mmol), EDC (257 mg, 1.34 mmol), HOBt (181 mg, 1.34 mmol) and DIPEA (0.24 mL, 1.34 mmol) were dissolved in DMF (5 mL) at room temperature. The solution was stirred at 80° C. for 12 hours. The reaction mixture was added with saturated NH$_4$Cl aqueous solution, and extracted with dichloromethane. The obtained organic layer was washed with saturated aqueous brine solution, dried over anhydrous MgSO$_4$, and filtered. The filtrate was concentrated under reduced pressure. The concentrate was purified by column chromatography (SiO$_2$, 40 g cartridge; EtOAc/hexane=5% to 80%), and concentrated to yield the title compound as white solid (250 mg, 65%).

1H NMR (400 MHz, CDCl$_3$) δ 8.34 (m, 1H), 7.78 (m, 1H), 7.63 (m, 2H), 7.52 (m, 2H), 6.80 (m, 1H), 4.86 (m, 1H), 4.55 (m, 1H), 4.18 (m, 2H), 3.85-3.61 (m, 6H), 3.02 (m, 2H), 2.68 (m, 2H), 2.40-2.11 (m, 8H), 2.10-1.79 (m, 5H), 1.57 (m, 2H); MS (ESI) m/z 576 (M++H).

Example 86. Compound 933: (2S,4R)-4-hydroxy-1-(4-(6-((1-(((1-(trifluoromethyl)cyclobutyl)methyl)piperidin-4-yl)methoxy)pyridine-3-yl)benzoyl)pyrrolidine-2-carboxamide

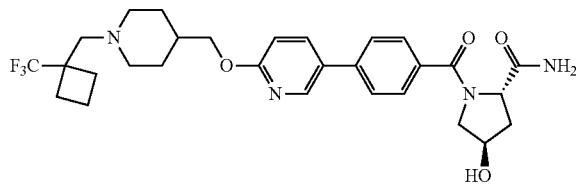 [SMILES: NC(=O)[C@@H]1C[C@@H](O)CN1C(=O)c1ccc(-c2ccc(OCC3CCN(CC4(C(F)(F)F)CCC4)CC3)nc2)cc1]

Step 1.

(2S,4R)-4-hydroxy-1-(4-(6-((1-(((1-(trifluoromethyl)cyclobutyl)methyl)piperidin-4-yl)methoxy)pyridine-3-yl)benzoyl)pyrrolidine-2-carboxylic acid: (2S,4R)-methyl 4-hydroxy-1-(4-(6-((1-(((1-(trifluoromethyl)cyclobutyl)methyl)piperidin-4-yl)methoxy)pyridine-3-yl)benzoyl)pyrrolidine-2-carboxylate (400 mg, 0.70 mmol) and LiOH.H$_2$O (58 mg, 1.39 mmol) were dissolved in THF (10 mL)/H$_2$O (5 mL) at room temperature. The solution was stirred at 60° C. for 10 hours. The reaction mixture was concentrated under reduced pressure to remove the solvent. The concentrate was added with 1 M-HCl aqueous solution, and concentrated under reduced pressure. The obtained material was used without further purifying process.

Step 2.

Compound 933: (2S,4R)-4-hydroxy-1-(4-(6-((1-(((1-(trifluoromethyl)cyclobutyl)methyl)piperidin-4-yl)methoxy)pyridine-3-yl)benzoyl)pyrrolidine-2-carboxylic acid (400 mg, 0.71 mmol), ammonium chloride (57 mg, 1.07 mmol), EDC (205 mg, 1.07 mmol), HOBt (144 mg, 1.07 mmol) and DIPEA (18 mg, 1.43 mmol) were dissolved in DMF (10 mL) at room temperature. The solution was stirred at 60° C. for 10 hours. The reaction mixture was added with water (10 mL), and stirred. The resulting precipitate was filtered, and dried to yield the title compound as brown solid (110 mg, 28%).

1H NMR (400 MHz, CDCl$_3$+MeOD) δ 8.33 (m, 1H), 7.79 (m, 1H), 7.62 (m, 2H), 7.54 (m, 2H), 7.22 (br, 1H), 6.80 (m, 1H), 5.97 (br, 1H), 4.86 (m, 1H), 4.41 (m, 1H), 4.18 (m, 2H), 3.78 (m, 1H), 3.55 (m, 1H), 2.78 (m, 2H), 2.60-1.65 (m, 16H), 1.42 (m, 2H); MS (ESI) mz 561 (M++H),

Example 87. Compound 715: (S)-(3-fluoro-4-(6-((1-(((1-(trifluoromethyl)cyclobutyl)methyl)piperidin-4-yl)methoxy)pyridine-3-yl)phenyl)(3-hydroxypyrrolidin-1-yl)methanone

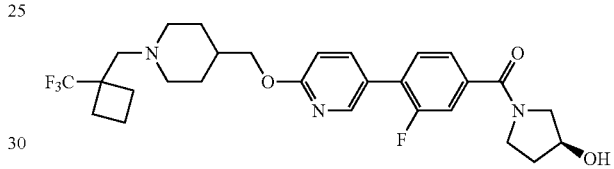

Step 1.

Ethyl 1-(1-(trifluoromethyl)cyclobutanecarbonyl)piperidin-4-carboxylate: 1-(trifluoromethyl)cyclobutanecarboxylic acid (500 mg, 2.97 mmol), ethyl piperidin-4-carboxylate (514 mg, 3.27 mmol), EDC (1.14 g, 5.94 mmol) and HOBt (803 mg, 5.95 mmol) were dissolved in CH$_2$Cl$_2$ 10 mL. DIPEA (1.05 mL, 5.95 mmol) was added thereto. The reaction was performed at room temperature for 8 hours. The reaction mixture was added with saturated NH$_4$Cl aqueous solution, and extracted with EtOAc. The extracted organic layer was dried over MgSO$_4$, and then filtered. The filtrate was purified by silica gel column chromatography (10-30% EtOAc/hexane) to yield the title compound as colorless oil (850 mg, 93%).

Step 2.

(1-((1-(trifluoromethyl)cyclobutyl)methyl)piperidin-4-yl)methanol: Ethyl 1-(1-(trifluoromethyl)cyclobutanecarbonyl)piperidin-4-carboxylate (1.73 g, 5.63 mmol) was dissolved in dry THF 40 mL. At 0° C., LAH (1 M in THF, 28.15 mL, 28.15 mmol) was added slowly thereto. At 50° C., the reaction was performed for 10 hours. The reaction was quenched by addition of MeOH slowly at 0° C. The reaction mixture was added with water, and then extracted with EtOAc. The obtained extracted organic layer was dried over MgSO$_4$, and then filtered to yield the title compound as colorless oil (1.4 g, 99%).

Step 3.

5-bromo-2-((1-(((1-(trifluoromethyl)cyclobutyl)methyl)piperidin-4-yl)methoxy)pyridine: (1-((1-(trifluoromethyl)cyclobutyl)methyl)piperidin-4-yl)methanol (760 mg, 3.02 mmol) was dissolved in THF 10 mL. At 0° C., NaH (109 mg, 4.54 mmol) was added slowly thereto. The reaction was performed at room temperature for 20 minutes. At 0° C., 2,5-dibromopyridine (788 mg, 3.32 mmol) in THF was added slowly thereto. At 50° C., the reaction was performed for 10 hours. After the completion of the reaction, the reaction mixture was added with ice water, and extracted with EtOAc. The obtained organic layer was dried over MgSO₄, and filtered. The filtrate was concentrated under reduced pressure. The obtained concentrate was purified by silica gel column chromatography (10-70% EtOAc/hexane) to yield the title compound as white solid (1.10 g, 89%).

Step 4.

Methyl 3-fluoro-4-(6-((1-((1-(trifluoromethyl)cyclobutyl)methyl)piperidin-4-yl)methoxy)pyridine-3-yl)benzoate: 5-bromo-2-((1-((1-(trifluoromethyl)cyclobutyl)methyl)piperidin-4-yl)methoxy)pyridine (550 mg, 1.35 mmol), 2-fluoro-4-(methoxycarbonyl)phenylboronic acid (294 mg, 1.48 mmol), Pd(dbpf)Cl₂ (26 mg, 0.04 mmol), Cs₂CO₃ (1.31 g, 4.05 mmol) were added into a microwave reactor, and then 1,4-dioxane 4 mL and water 2 mL were added thereto. With a microwave radiation, the reaction was performed for 30 minutes at 110° C. The reaction mixture was filtered through a Celite pad. The filtrate was added with water, and then extracted with EtOAc. The obtained organic layer was dried over MgSO₄, and filtered. The filtrate was concentrated under reduced pressure. The obtained concentrate was purified by silica gel column chromatography (20-70% EtOAc/hexane) to yield the title compound as white solid (300 mg, 46%).

Step 5.

3-fluoro-4-(6-((1-((1-(trifluoromethyl)cyclobutyl)methyl)piperidin-4-yl)methoxy)pyridine-3-yl)benzoic acid: Methyl 3-fluoro-4-(6-((1-((1-(trifluoromethyl)cyclobutyl)methyl)piperidin-4-yl)methoxy)pyridine-3-yl)benzoate (488 mg, 1.02 mmol) was dissolved in the mixed solvents of THF 10 mL/water 10 mL. LiOH.H₂O (85 mg, 2.03 mmol) was added thereto, and the reaction was performed at 60° C. for 4 hours. The solvent was concentrated under reduced pressure. After the addition of 1M HCl thereto, the resulting precipitate was filtered to yield the title compound as white solid (410 mg, 86%).

Step 6.

Compound 715: 3-fluoro-4-(6-((1-((1-(trifluoromethyl)cyclobutyl)methyl)piperidin-4-yl)methoxy)pyridine-3-yl)benzoic acid (50 mg, 0.11 mmol), (S)-pyrrolidine-3-ol (14 mg, 0.16 mmol), EDC (41 mg, 0.21 mmol) and HOBt (29 mg, 0.21 mmol) were dissolved in DMF 2 mL. DIPEA (0.04 mL, 0.21 mmol) was added thereto, the reaction was performed at 60° C. for 10 hours. The reaction mixture was cooled to room temperature, and added with water. The formed solid was filtered, washed with water thoroughly, and dried to yield the title compound as white solid (25 mg, 43%).

1H NMR (400 MHz, CDCl₃) δ 8.33 (s, 1H), 7.79 (d, 1H, J=8.8 Hz), 7.47-7.33 (m, 3H), 6.83 (dd, 1H, J=10.2, 3.6 Hz), 4.62-6.51 (m, 1H), 4.21 (d, 2H, J=5.5 Hz), 3.87-3.49 (m, 4H), 2.90 (m, 2H), 2.54 (s, 2H), 2.22-1.80 (m, 15H), 1.26 (m, 2H); MS (ESI) m/z 536 (M++H).

According to the above-described synthesis process of compound 715, the compounds of Table 82 were synthesized using 3-fluoro-4-(6-((1-((1-(trifluoromethyl)cyclobutyl)methyl)piperidin-4-yl)methoxy)pyridine-3-yl)benzoic acid and the reactant of Table 81.

TABLE 81

| Compound No. | Reactant | Yield (%) |
|---|---|---|
| 716 | (R)-pyrrolidine-2-ylmethanol | 42 |
| 717 | L-prolinamide | 37 |
| 718 | (R)-piperidin-3-ol hydrochloride | 48 |
| 719 | (S)-piperidin-3-ol hydrochloride | 37 |

TABLE 82

| Compound No. | Compound Name, ¹H-NMR, MS (ESI) |
|---|---|
| 716 | (R)-(3-fluoro-4-(6-((1-((1-(trifluoromethyl)cyclobutyl)methyl)piperidin-4-yl)methoxy)pyridine-3-yl)phenyl)(2-(hydroxymethyl)pyrrolidine-1-yl)methanone<br>1H NMR (400 MHz, CDCl₃) δ 8.33 (s, 1 H), 7.79 (dt, 1 H, J = 8.6, 2.1 Hz), 7.46 (m, 1 H), 7.38 (m, 2 H), 6.83 (dd, 1 H, J = 10.2, 3.6 Hz), 4.66 (dd, 1 H, J = 10.2, 3.6 Hz), 4.43 (m, 1 H), 4.21 (d, 2 H, J = 5.5 Hz), 3.84-3.76 (m, 2 H), 3.61-3.54 (m, 2 H), 2.89 (m, 2 H), 2.53 (s, 2 H), 2.22 (m, 4 H), 2.09-1.79 (m, 10 H), 1.43 (m, 2 H); MS (ESI) m/z 550 (M+ + H). |
| 717 | (S)-1-(3-fluoro-4-(6-((1-((1-(trifluoromethyl)cyclobutyl)methyl)piperidin-4-yl)methoxy)pyridine-3-yl)benzoyl)pyrrolidine-2-carboxamide<br>1H NMR (400 MHz, CDCl₃) δ 8.33 (s, 1 H), 7.79 (dt, 1 H, J = 8.6, 2.1 Hz), 7.46 (m, 1 H), 7.38 (m, 2 H), 6.89 (br, 1 H), 6.83 (dd, 1 H, J = 10.2, 3.6 Hz), 5.55 (br, 1 H), 4.79 (m, 1 H), 4.21 (d, 2 H, J = 5.5 Hz), 3.60 (m, 2 H), 2.89 (m, 2 H), 2.54-2.45 (m, 3 H), 2.23 (m, 4 H), 2.14-1.79 (m, 10 H), 1.43 (m, 2 H); MS (ESI) m/z 563 (M+ + H). |
| 718 | (R)-(3-fluoro-4-(6-((1-((1-(trifluoromethyl)cyclobutyl)methyl)piperidin-4-yl)methoxy)pyridine-3-yl)phenyl)(3-hydroxypiperidin-1-yl)methanone<br>1H NMR (400 MHz, CDCl₃) δ 8.33 (s, 1 H), 7.79 (dt, 1 H, J = 8.6, 2.1 Hz), 7.46 (m, 1 H), 7.29 (m, 2 H), 6.83 (dd, 1 H, J = 10.2, 3.6 Hz), 4.21 (m, 2 H), 4.00-3.22 (m, 6 H), 2.89 (m, 2 H), 2.53 (m, 2 H), 2.23 (m, 4 H), 2.15-1.79 (m, 10 H), 1.62 (m, 2 H), 1.44 (m, 2 H); MS (ESI) m/z 550 (M+ + H). |
| 719 | (S)-(3-fluoro-4-(6-((1-((1-(trifluoromethyl)cyclobutyl)methyl)piperidin-4-yl)methoxy)pyridine-3-yl)phenyl)(3-hydroxypiperidin-1-yl)memanone<br>1H NMR (400 MHz, CDCl₃) δ 8.33 (s, 1 H), 7.79 (dt, 1 H, J = 8.6, 2.1 Hz), 7.45 (t, 1 H, J = 7.8 Hz), 7.30-7.25 (m, 2 H), 6.83 (dd, 1 H, J = 10.2, 3.6 Hz), 4.21 (m, 2 H), 4.00-3.22 (m, 7 H), 2.89 (m, 2 H), 2.53 (m, 2 H), 2.22 (m, 4 H), 2.15-1.62 (m, 10 H), 1.62 (m, 2 H); MS (ESI) m/z 550 (M+ + H). |

Example 88. Compound 720: (S)-(2-fluoro-4-(6-((1-((1-(trifluoromethyl)cyclobutyl)methyl)piperidin-4-yl)methoxy)pyridine-3-yl)phenyl)(3-hydroxypyrrolidine-1-yl)methanone

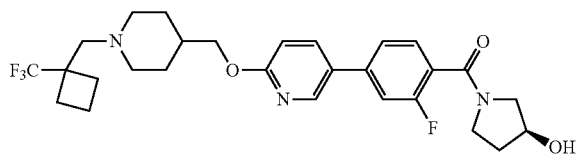

Step 1.

Ethyl 2-fluoro-4-(6-((1-((1-(trifluoromethyl)cyclobutyl)methyl)piperidin-4-yl)methoxy)pyridine-3-yl)benzoate:
5-bromo-2-((1-((1-(trifluoromethyl)cyclobutyl)methyl)piperidin-4-yl)methoxy)pyridine (the product of synthesis step 3 of compound 715; 250 mg, 0.61 mmol), 3-fluoro-4-(ethoxycarbonyl)phenylboronic acid (143 mg, 0.68 mmol), Pd(dbpf)Cl$_2$ (12 mg, 0.02 mmol), Cs$_2$CO$_3$ (596 mg, 1.84 mmol) were added into a microwave reactor, and then 1,4-dioxane 3 mL and water 2 mL were added thereto. With a microwave radiation, the reaction was performed at 110° C. for 30 minutes. The reaction mixture was filtered through a Celite pad. The filtrate was added with water, and then extracted with EtOAc. The obtained organic layer was dried over, MgSO$_4$, and filtered. The filtrate was concentrated under reduced pressure. The obtained concentrate was purified by silica gel column chromatography (20-70% EtOAc/hexane) to yield the title compound as white solid (200 mg, 66%).

Step 2.

2-fluoro-4-(6-((1-((1-(trifluoromethyl)cyclobutyl)methyl)piperidin-4-yl)methoxy)pyridine-3-yl)benzoic acid:
Ethyl 2-fluoro-4-(6-((1-((1-(trifluoromethyl)cyclobutyl)methyl)piperidin-4-yl)methoxy)pyridine-3-yl)benzoate (533 mg, 1.08 mmol) was dissolved in the mixed solvents of THF 10 mL/water 10 mL. LiOH.H$_2$O (90 mg, 2.16 mmol) was added thereto, and the reaction was performed at 60° C. for 4 hours. The solvent was concentrated under reduced pressure. After the addition of 1M HCl thereto, the resulting precipitate was filtered to yield the title compound as white solid (350 mg, 70%).

Step 3.

Compound 720: 2-fluoro-4-(6-((1-((1-(trifluoromethyl)cyclobutyl)methyl)piperidin-4-yl)methoxy)pyridine-3-yl)benzoic acid (50 mg, 0.11 mmol), (S)-pyrrolidine-3-ol (14 mg, 0.16 mmol), EDC (41 mg, 0.21 mmol) and HOBt (29 mg, 0.21 mmol) were dissolved in DMF 2 mL. DIPEA (0.04 mL, 0.21 mmol) was added thereto, and the reaction was performed at 60° C. for 10 hours. The reaction mixture was cooled to room temperature, and added with water. The formed solid was filtered, washed with water thoroughly, and dried to yield the title compound as white solid (21 mg, 37%).

$^1$H NMR (400 MHz, CDCl$_3$) δ 8.36 (t, 1H, J=1.8 Hz), 7.78 (dt, 1H, J=8.6, 1.3 Hz), 7.51 (m, 1H), 7.37 (dd, 1H, J=10.2, 3.6 Hz), 7.27 (m, 1H), 6.83 (d, 1H, J=8.5 Hz), 4.60 (m, 1H), 4.21 (d, 2H, J=5.8 Hz), 3.84-3.25 (m, 5H), 2.88 (m, 2H), 2.53 (m, 2H), 2.21-1.79 (m, 14H), 1.42 (m, 2H); MS (ESI) m/z 536.1 (M++H).

According to the above-described synthesis process of compound 720, the compounds of Table 84 were synthesized using 2-fluoro-4-(6-((1-((1-(trifluoromethyl)cyclobutyl)methyl)piperidin-4-yl)methoxy)pyridine-3-yl)benzoic acid and the reactant of Table 83.

TABLE 83

| Compound No. | Reactant | Yield (%) |
|---|---|---|
| 721 | (R)-pyrrolidine-2-ylmethanol | 41 |
| 722 | L-prolinamide | 32 |
| 723 | (R)-piperidin-3-ol hydrochloride | 36 |
| 724 | (S)-piperidin-3-ol hydrochloride | 37 |

TABLE 84

| Compound No. | Compound Name, $^1$H-NMR, MS (ESI) |
|---|---|
| 721 | (R)-(2-fluoro-4-(6-((1-((1-(trifluoromethyl)cyclobutyl)methyl)piperidin-4-yl)methoxy)pyridine-3-yl)phenyl)(2-(hydroxymethyl)pyrrolidine-1-yl)methanone<br>1H NMR (400 MHz, CDCl$_3$) δ 8.36 (t, 1 H, J = 1.8 Hz), 7.78 (dt, 1 H, J = 8.6, 1.3 Hz), 7.51 (m, 1 H), 7.37 (dd, 1 H, J = 10.2, 3.6 Hz), 7.27 (m, 1 H), 6.83 (d, 1 H, J = 8.5 Hz), 4.70 (m, 1 H), 4.41 (m, 1 H), 4.21 (m, 2 H), 3.84-3.77 (m, 2 H), 3.46 (m, 2 H), 2.89 (m, 2 H), 2.53 (m, 2 H), 2.24-1.78 (m, 16 H), 1.42 (m, 2 H); MS (ESI) m/z 550 (M+ + H). |
| 722 | (S)-1-(2-fluoro-4-(6-((1-((1-(trifluoromethyl)cyclobutyl)methyl)piperidin-4-yl)methoxy)pyridine-3-yl)benzoyl)pyrrolidine-2-carboxamide<br>1H NMR (400 MHz, CDCl$_3$) δ 8.36 (t, 1 H, J = 1.8 Hz), 7.78 (dt, 1 H, J = 8.6, 1.3 Hz), 7.50 (m, 1 H), 7.39 (dd, 1 H, J = 10.2, 3.6 Hz), 7.27 (m, 1 H), 6.90 (br, 1 H), 6.83 (d, 1 H, J = 8.5 Hz), 5.51 (br, 1 H), 4.83 (m, 1 H), 4.21 (m, 2 H), 3.52-3.44 (m, 2 H), 2.89 (m, 2 H), 2.49 (m, 3 H), 2.22 (m, 4 H), 2.21-1.61 (m, 12 H), 1.42 (m, 2 H); MS (ESI) m/z 563 (M+ + H). |
| 723 | (R)-(2-fluoro-4-(6-((1-((1-(trifluoromethyl)cyclobutyl)methyl)piperidin-4-yl)methoxy)pyridine-3-yl)phenyl)(3-hydroxypiperidin-1-yl)methanone<br>1H NMR (400 MHz, CDCl$_3$) δ 8.36 (t, 1 H, J = 1.8 Hz), 7.78 (dt, 1 H, J = 8.6, 1.3 Hz), 7.47 (m, 1 H), 7.36 (dd, 1 H, J = 10.2, 3.6 Hz), 7.27 (m, 1 H), 6.83 (d, 1 H, J = 8.5 Hz), 4.22 (m, 2 H), 4.12-3.95 (m, 2 H), 3.80-3.16 (m, 5 H), 2.89 (m, 2 H), 2.53 (m, 2 H), 2.41-1.71 (m, 16 H), 1.47 (m, 2 H); MS (ESI) m/z 550 (M+ + H). |
| 724 | (S)-(2-fluoro-4-(6-((1-((1-(trifluoromethyl)cyclobutyl)methyl)piperidin-4-yl)methoxy)pyridine-3-yl)phenyl)(3-hydroxypiperidin-1-yl)methanone<br>1H NMR (400 MHz, CDCl$_3$) δ 8.36 (m, 1 H), 7.78 (dt, 1 H, J = 8.6, 1.3 Hz), 7.47 (m, 1 H), 7.36 (dd, 1 H, J = 10.2, 3.6 Hz), 7.25 (m, 1 H), 6.83 (d, 1 H, J = 8.5 Hz), 4.22-3.61 (m, 4 H), 3.57-3.13 (m, 4 H), 2.89-2.70 (m, 2 H), 2.60-2.45 (m, 2 H), 2.24-1.63 (m, 14 H), 1.47 (m, 3 H); MS (ESI) m/z 550 (M+ + H). |

Example 89. Compound 970: (S)-(3-hydroxypyrrolidine-1-yl)(4-(2-((1-((1-(trifluoromethyl)cyclobutyl)methyl)piperidin-4-yl)methoxy)pyrimidin-5-yl)phenyl)methanone

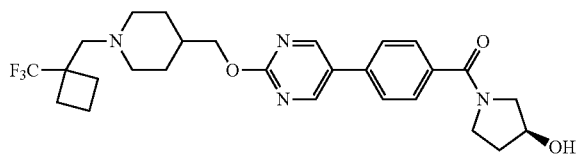 [SMILES: O=C(c1ccc(-c2cnc(OCC3CCN(CC4(C(F)(F)F)CCC4)CC3)nc2)cc1)N1CC[C@H](O)C1]

Step 1.

5-bromo-2-((1-((1-(trifluoromethyl)cyclobutyl)methyl)piperidin-4-yl)methoxy)pyrimidine: (1-((1-(trifluoromethyl)cyclobutyl)methyl)piperidin-4-yl)methanol (760 mg, 3.02 mmol) was dissolved in THF (40 mL). At 0° C., NaH (143 mg, 5.97 mmol) was added thereto, and stirred for 30 minutes. 5-bromo-2-iodopyrimidine (1.25 g, 4.38 mmol) was added thereto, following with stirring at 55° C. for 10 hours. The reaction mixture was added with water, and extracted with EtOAc. The organic layer was washed with saturated aqueous brine solution, dried over anhydrous MgSO$_4$, and filtered. The filtrate was concentrated under reduced pressure. The obtained material was used without further purifying process.

Step 2.

Methyl 4-(2-((1-((1-(trifluoromethyl)cyclobutyl)methyl)piperidin-4-yl)methoxy)pyrimidin-5-yl)benzoate: 5-bromo-2-((1-((1-(trifluoromethyl)cyclobutyl)methyl)piperidin-4-yl)methoxy)pyrimidine (450 mg, 1.10 mmol), 4-(methoxycarbonyl)phenylboronic acid (218 mg, 1.21 mmol), Pd(dbpf)Cl$_2$ (22 mg, 0.03 mmol) and Cs$_2$CO$_3$ (1.07 g, 3.31 mmol) were added to 1,4-dioxane (10 mL)/water (5 mL). With a microwave radiation, the mixture was heated at 110° C. for 45 minutes, and then cooled to room temperature. The reaction mixture was added with water, and extracted with dichloromethane. The organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=5% to 25%), and concentrated to yield the title compound as white solid (300 mg, 59%).

Step 3.

4-(2-((1-((1-(trifluoromethyl)cyclobutyl)methyl)piperidin-4-yl)methoxy)pyrimidin-5-yl)benzoic acid: Methyl 4-(2-((1-((1-(trifluoromethyl)cyclobutyl)methyl)piperidin-4-yl)methoxy)pyrimidin-5-yl)benzoate (300 mg, 0.65 mmol) and LiOH.H$_2$O (27 mg, 0.65 mmol) were dissolved in THF (10 mL)/water (5 mL) at room temperature. The solution was stirred at 60° C. for 6 hours, the reaction mixture was concentrated under reduced pressure. The concentrate was added with 1M HCl aqueous solution (10 mL) to be suspended, and filtered. The obtained solid was dried to yield the title compound as white solid (290 mg, 99%).

Step 4.

Compound 970: 4-(2-((1-((1-(trifluoromethyl)cyclobutyl)methyl)piperidin-4-yl)methoxy)pyrimidin-5-yl)benzoic acid (50 mg, 0.11 mmol), (S)-pyrrolidine-3-ol (15 mg, 0.17 mmol), EDC (32 mg, 0.17 mmol), HOBt (23 mg, 0.17 mmol) and DIPEA (0.04 mL, 0.22 mmol) were dissolved in DMF (4 mL) at room temperature. The solution was stirred at 60° C. for 16 hours, added with saturated NH$_4$Cl aqueous solution, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 4 g cartridge; methanol/dichloromethane=0% to 10%), and concentrated to yield the title compound as white solid (20 mg, 35%).

1H NMR (400 MHz, CDCl$_3$) δ 8.72 (s, 2H), 7.69-7.55 (m, 4H), 4.63-4.48 (m, 1H), 4.28 (m, 2H), 3.88-3.45 (m, 4H), 2.90 (m, 2H), 2.52 (s, 2H), 2.22-1.83 (m, 14H), 1.46 (m, 2H); MS (ESI) m/z 519 (M++H).

According to the above-described synthesis process of compound 970, the compounds of Table 86 were synthesized using 4-(2-((1-((1-(trifluoromethyl)cyclobutyl)methyl)piperidin-4-yl)methoxy)pyrimidin-5-yl)benzoic acid and the reactant of Table 85.

TABLE 85

| Compound No. | Reactant | Yield (%) |
|---|---|---|
| 971 | (R)-pyrrolidine-2-ylmethanol | 34 |
| 972 | (R)-piperidin-3-ol hydrochloride | 34 |
| 973 | L-prolinamide | 33 |

TABLE 86

| Compound No. | Compound Name, $^1$H-NMR, MS (ESI) |
|---|---|
| 971 | (R)-(2-(hydroxymethyl)pyrrolidin-1-yl)(4-(2-((1-((1-(trifluoromethyl)cyclobutyl)methyl)piperidin-4-yl)methoxy)pyrimidin-5-yl)phenyl)methanone<br>1H NMR (400 MHz, CDCl$_3$) δ 8.73 (s, 2 H), 7.66-7.57 (m, 4 H), 4.81 (m, 1 H), 4.45 (m, 1 H), 4.28 (m, 2 H), 3.85-3.77 (m, 2 H), 3.57 (m, 2 H), 2.89 (m, 2 H), 2.52 (s, 2 H), 2.21 (m, 4 H), 2.20-1.60 (m, 11 H), 1.48 (m, 2 H); MS (ESI) m/z 533 (M+ + H). |
| 972 | (R)-(3-hydroxypiperidin-1-yl)(4-(2-((1-((1-(trifluoromethyl)cyclobutyl)methyl)piperidin-4-yl)methoxy)pyrimidin-5-yl)phenyl)methanone<br>1H NMR (400 MHz, CDCl$_3$) δ 8.72 (s, 2 H), 7.56-7.53 (m, 4 H), 4.31 (m, 2 H), 3.97-3.38 (m, 3 H), 2.89 (m, 2 H), 2.52 (s, 2 H), 2.29-1.73 (m, 14 H), 1.64 (m, 2 H), 1.44 (m, 2 H), 1.29 (m, 2 H); MS (ESI) m/z 533 (M+ + H). |
| 973 | (S)-1-(4-(2-((1-((1-(trifluoromethyl)cyclobutyl)methyl)piperidin-4-yl)methoxy)pyrimidin-5-yl)benzoyl)pyrrolidine-2-carboxamide<br>1H NMR (400 MHz, CDCl$_3$) δ 8.73 (s, 2 H), 7.67-7.57 (m, 4 H), 6.94 (br, 1 H), 5.53 (br, 1 H), 4.82 (m, 1 H), 4.29 (m, 2 H), 3.65-3.51 (m, 2 H), 2.90 (m, 2 H), 2.50 (m, 3 H), 2.29-1.85 (m, 14 H), 1.48 (m, 2 H); MS (ESI) m/z 546 (M+ + H). |

Example 90. Compound 974: (S)-(3-fluoro-4-(2-((1-((1-(trifluoromethyl)cyclobutyl)methyl)piperidin-4-yl)methoxy)pyrimidin-5-yl)phenyl)(3-hydroxypyrrolidine-1-yl)methanone

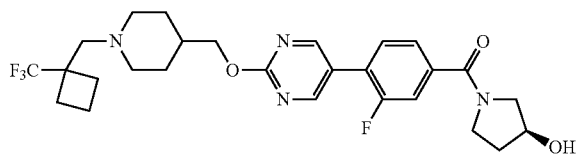 [SMILES: O=C(c1ccc(-c2cnc(OCC3CCN(CC4(C(F)(F)F)CCC4)CC3)nc2)c(F)c1)N1CC[C@H](O)C1]

Step 1.

Methyl 3-fluoro-4-(2-((1-((1-(trifluoromethyl)cyclobutyl)methyl)piperidin-4-yl)methoxy)pyrimidin-5-yl)benzoate: 5-bromo-2-((1-((1-(trifluoromethyl)cyclobutyl)methyl)piperidin-4-yl)methoxy)pyrimidine (the product of synthesis step 1 of compound 970; 450 mg, 1.10 mmol), 2-fluoro-4-(methoxycarbonyl)phenylboronic acid (240 mg, 1.21 mmol), Pd(dbpf)Cl₂ (22 mg, 0.03 mmol) and Cs₂CO₃ (1.07 mg, 3.31 mmol) were added to 1,4-dioxane (10 mL)/water (5 mL). With a microwave radiation, the mixture was heated at 110° C. for 45 minutes, and then cooled to room temperature. The reaction mixture was added with water, and extracted with dichloromethane. The obtained organic layer was washed with saturated aqueous brine solution, dried over anhydrous MgSO₄, and filtered. The filtrate was concentrated under reduced pressure. The concentrate was purified by column chromatography (SiO₂, 12 g cartridge; EtOAc/hexane=5% to 25%), and concentrated to yield the title compound as white solid (300 mg, 57%).

Step 2.

3-fluoro-4-(2-((1-((1-(trifluoromethyl)cyclobutyl)methyl)piperidin-4-yl)methoxy)pyrimidin-5-yl)benzoic acid: Methyl 3-fluoro-4-(2-((1-((1-(trifluoromethyl)cyclobutyl)methyl)piperidin-4-yl)methoxy)pyrimidin-5-yl)benzoate (300 mg, 0.62 mmol) and LiOH.H₂O (52 mg, 1.25 mmol) were dissolved in THF (10 mL)/water (5 mL) at room temperature. The solution was stirred at 60° C. for 6 hours, the reaction mixture was concentrated under reduced pressure. The concentrate was added with 1M HCl aqueous solution (10 mL) to be suspended, and filtered. The obtained solid was dried to yield the title compound as white solid (250 mg, 86%).

Step 3.

Compound 974: 3-fluoro-4-(2-((1-((1-(trifluoromethyl)cyclobutyl)methyl)piperidin-4-yl)methoxy)pyrimidin-5-yl)benzoic acid (50 mg, 0.11 mmol), (S)-pyrrolidine-3-ol (14 mg, 0.16 mmol), EDC (31 mg, 0.16 mmol), HOBt (22 mg, 0.16 mmol) and DIPEA (0.04 mL, 0.21 mmol) were dissolved in DMF (4 mL) at room temperature. The solution was stirred at 60° C. for 16 hours. The reaction mixture was added with saturated NH₄Cl aqueous solution, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, 4 g cartridge; methanol/dichloromethane=0% to 10%), and concentrated to yield the title compound as white solid (20 mg, 35%).

1H NMR (400 MHz, CDCl₃) δ 8.71 (s, 2H), 7.46-7.37 (m, 3H), 4.63-4.52 (m, 1H), 4.28 (m, 2H), 3.88-3.47 (m, 4H), 2.88 (m, 2H), 2.52 (s, 2H), 2.25-1.78 (m, 14H), 1.47 (m, 2H); MS (ESI) m/z 537 (M++H).

According to the above-described synthesis process of compound 974, the compounds of Table 88 were synthesized using 3-fluoro-4-(2-((1-((1-(trifluoromethyl)cyclobutyl)methyl)piperidin-4-yl)methoxy)pyrimidin-5-yl)benzoic acid and the reactant of Table 87.

TABLE 87

| Compound No. | Reactant | Yield (%) |
|---|---|---|
| 975 | (R)-pyrrolidine-2-ylmethanol | 34 |
| 976 | (R)-piperidin-3-ol hydrochloride | 34 |
| 977 | L-prolinamide | 33 |

TABLE 88

| Compound No. | Compound Name, ¹H-NMR, MS (ESI) |
|---|---|
| 975 | (R)-(3-fluoro-4-(2-((1-((1-(trifluoromethyl)cyclobutyl)methyl)piperidin-4-yl)methoxy)pyrimidin-5-yl)phenyl)(2-(hydroxymethyl)pyrrolidine-1-yl)methanone<br>1H NMR (400 MHz, CDCl₃) δ 8.71 (m, 2 H), 7.50-7.37 (m, 3 H), 4.58 (m, 1 H), 4.41 (m, 1 H), 4.28 (m, 2 H), 3.87-3.74 (m, 2 H), 3.56 (m, 2 H), 2.90 (m, 2 H), 2.53 (s, 2 H), 2.31-1.65 (m, 15 H), 1.48 (m, 2 H); MS (ESI) m/z 551 (M+ + H). |
| 976 | (R)-(3-fluoro-4-(2-((1-((1-(trifluoromethyl)cyclobutyl)methyl)piperidin-4-yl)methoxy)pyrimidin-5-yl)phenyl)(3-hydroxypiperidin-1-yl)methanone<br>1H NMR (400 MHz, CDCl₃) δ 8.70 (s, 2 H), 7.45 (m, 1 H), 7.29 (m, 2 H), 4.30 (m, 2 H), 3.97-3.35 (m, 5 H), 2.90 (m, 2 H), 2.53 (m, 2 H), 2.37-1.58 (m, 16 H), 1.49 (m, 2 H); MS (ESI) m/z 551 (M+ + H). |
| 977 | (S)-1-(3-fluoro-4-(2-((1-((1-(trifluoromethyl)cyclobutyl)methyl)piperidin-4-yl)methoxy)pyrimidin-5-yl)benzoyl)pyrrolidine-2-carboxamide<br>1H NMR (400 MHz, CDCl₃) δ 8.71 (s, 2 H), 7.50-7.40 (m, 3 H), 6.83 (br, 1 H), 5.55 (br, 1 H), 4.78 (m, 1 H), 4.29 (m, 2 H), 3.66-3.54 (m, 2 H), 2.89 (m, 2 H), 2.53-2.43 (m, 3 H), 2.25-1.68 (m, 14 H), 1.49 (m, 2 H); MS (ESI) m/z 564 (M+ + H). |

Example 91. Compound 978: (8)-(2-fluoro-4-(2-((1-((1-(trifluoromethyl)cyclobutyl)methyl)piperidin-4-yl)methoxy)pyrimidin-5-yl)phenyl)(3-hydroxypyrrolidine-1-yl)methanone

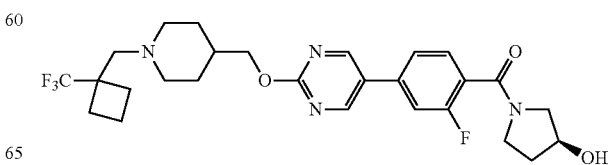

Step 1.

Ethyl 2-fluoro-4-(2-((1-((1-(trifluoromethyl)cyclobutyl)methyl)piperidin-4-yl)methoxy)pyrimidin-5-yl)benzoate: 5-bromo-2-((1-((1-(trifluoromethyl)cyclobutyl)methyl)piperidin-4-yl)methoxy)pyrimidine (the product of synthesis step 1 of compound 970; 450 mg, 1.10 mmol), 4-(ethoxycarbonyl)-3-fluorophenylboronic acid (257 mg, 1.21 mmol), Pd(dbpf)Cl$_2$ (22 mg, 0.03 mmol) and Cs$_2$CO$_3$ (1.07 mg, 3.31 mmol) were added to 1,4-dioxane (10 mL)/water (5 mL). With a microwave radiation, the mixture was heated at 110° C. for 45 minutes, and then cooled to room temperature. The reaction mixture was added with water, and extracted with dichloromethane. The obtained organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=5% to 25%), and concentrated to yield the title compound as white solid (300 mg, 55%).

Step 2.

2-fluoro-4-(2-((1-((1-(trifluoromethyl)cyclobutyl)methyl)piperidin-4-yl)methoxy)pyrimidin-5-yl)benzoic acid: Ethyl 2-fluoro-4-(2-((1-((1-(trifluoromethyl)cyclobutyl)methyl)piperidin-4-yl)methoxy)pyrimidin-5-yl)benzoate (300 mg, 0.61 mmol) and LiOH.H$_2$O (51 mg, 1.21 mmol) were dissolved in THF (10 mL)/water (5 mL) at room temperature. The solution was stirred at 60° C. for 6 hours, the reaction mixture was concentrated under reduced pressure. The concentrate was added with 1M HCl aqueous solution (10 mL) to be suspended, and filtered. The obtained solid was dried to yield the title compound as white solid (280 mg, 99%).

Step 3.

Compound 978: 2-fluoro-4-(2-((1-((1-(trifluoromethyl)cyclobutyl)methyl)piperidin-4-yl)methoxy)pyrimidin-5-yl)benzoic acid (50 mg, 0.11 mmol), (S)-pyrrolidine-3-ol (14 mg, 0.16 mmol), EDC (31 mg, 0.16 mmol), HOBt (22 mg, 0.16 mmol) and DIPEA (0.04 mL, 0.21 mmol) were dissolved in DMF (4 mL) at room temperature. After stirring at 60° C. for 16 hours, the reaction mixture was added with saturated NH$_4$Cl aqueous solution, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 4 g cartridge; methanol/dichloromethane=0% to 10%), and concentrated to yield the title compound as white solid (20 mg, 35%).

1H NMR (400 MHz, CDCl$_3$) δ 8.71 (m, 2H), 7.55 (m, 1H), 7.37 (m, 1H), 7.26 (m, 1H), 4.62-4.51 (m, 1H), 4.29 (m, 2H), 3.84-3.32 (m, 4H), 2.89 (m, 2H), 2.53 (m, 2H), 2.35-1.62 (m, 14H), 1.48 (m, 2H); MS (ESI) m/z 537 (M++H).

According to the above-described synthesis process of compound 978, the compounds of Table 90 were synthesized using 2-fluoro-4-(2-((1-((1-(trifluoromethyl)cyclobutyl)methyl)piperidin-4-yl)methoxy)pyrimidin-5-yl)benzoic acid and the reactant of Table 89.

TABLE 89

| Compound No. | Reactant | Yield (%) |
|---|---|---|
| 979 | (R)-pyrrolidine-2-ylmethanol | 36 |
| 980 | (R)-piperidin-3-ol hydrochloride | 34 |
| 981 | L-prolinamide | 33 |

TABLE 90

| Compound No. | Compound Name, $^1$H-NMR, MS (ESI) |
|---|---|
| 979 | (R)-(2-fluoro-4-(2-((1-((1-(trifluoromethyl)cyclobutyl)methyl)piperidin-4-yl)methoxy)pyrimidin-5-yl)phenyl)(2-(hydroxymethyl)pyirolidine-1-yl)methanone 1H NMR (400 MHz, CDCl$_3$) δ 8.71 (m, 2 H), 7.56 (m, 1 H), 7.38 (m, 1 H), 7.28 (m, 1 H), 4.61 (m, 1 H), 4.39 (m, 1 H), 4.28 (m, 2 H), 3.84-3.78 (m, 2 H), 3.45 (m, 2 H), 2.89 (m, 2 H), 2.53 (s, 2 H), 2.22 (m, 4 H), 2.18-1.62 (m, 11 H), 1.48 (m, 2 H); MS (ESI) m/z 551 (M+ + H). |
| 980 | (R)-(2-fluoro-4-(2-((1-((1-(trifluoromethyl)cyclobutyl)methyl)piperidin-4-yl)methoxy)pyrimidin-5-yl)phenyl)(3-hydroxypiperidin-1-yl)methanone 1H NMR (400 MHz, CDCl$_3$) δ 8.71 (m, 2 H), 7.52 (m, 1 H), 7.37 (m, 1 H), 7.25 (m, 1 H), 4.29 (m, 2 H), 4.10-3.08 (m, 7 H), 2.89 (m, 2 H), 2.53 (m, 2 H), 2.28-1.61 (m, 14 H), 1.48 (m, 2 H); MS (ESI) m/z 551 (M+ + H). |
| 981 | (S)-1-(2-fluoro-4-(2-((1-((1-(trifluoromethyl)cyclobutyl)methyl)piperidin-4-yl)methoxy)pyrimidin-5-yl)benzoyl)pyrrolidine-2-carboxamide 1H NMR (400 MHz, CDCl$_3$) δ 8.71 (m, 2 H), 7.56 (m, 1 H), 7.39 (m, 1 H), 7.28 (m, 1 H), 6.88 (br, 1 H), 5.55 (br, 1 H), 4.82 (m, 1 H), 4.29 (m, 2 H), 3.54-3.41 (m, 2 H), 2.89 (m, 2 H), 2.50 (m, 3 H), 2.38-1.81 (m, 14 H), 1.48 (m, 2 H); MS (ESI) m/z 564 (M+ + H). |

Example 92. Compound 1007: (R)-(2-(hydroxymethyl)pyrrolidine-1-yl)(4-(5-((1-((1-(trifluoromethyl)cyclobutyl)methyl)piperidin-4-yl)methoxy)pyrazine-2-yl)phenyl)methanone

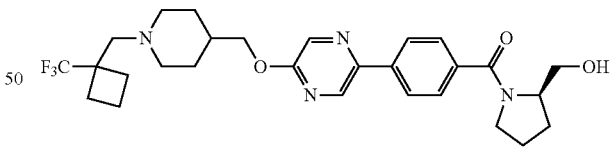

Step 1.

2-iodo-5-((1-((1-(trifluoromethyl)cyclobutyl)methyl)piperidin-4-yl)methoxy)pyrazine: (1-((1-(trifluoromethyl)cyclobutyl)methyl)piperidin-4-yl)methanol (880 mg, 3.50 mmol) was dissolved in THF (30 mL). At 0° C., NaH (126 mg, 5.25 mmol) was added thereto, and stirred for 30 minutes. 2-bromo-5-iodopyrazine (1.09 g, 3.85 mmol) was added thereto, following with stirring at 55° C. for 10 hours. The reaction mixture was added with water, and extracted with EtOAc. The obtained organic layer was washed with saturated aqueous brine solution, dried over anhydrous MgSO$_4$, and filtered. The filtrate was concentrated under reduced pressure. The obtained material was used without further purifying process.

Step 2.

Methyl 4-(5-((1-((1-(trifluoromethyl)cyclobutyl)methyl)piperidin-4-yl)methoxy)pyrazine-2-yl)benzoate: 2-iodo-5-((1-((1-(trifluoromethyl)cyclobutyl)methyl)piperidin-4-yl)methoxy)pyrazine (350 mg, 0.77 mmol), 4-(methoxycarbonyl)phenylboronic acid (152 mg, 0.85 mmol), Pd(dbpf)Cl₂ (15 mg, 0.02 mmol) and Cs₂CO₃ (747 mg, 2.31 mmol) were added to 1,4-dioxane (10 mL)/water (5 mL). With a microwave radiation, the mixture was heated at 110° C. for 45 minutes, and then cooled to room temperature. The reaction mixture was added with water, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, 12 g cartridge; EtOAc/hexane=5% to 25%), and concentrated to yield the title compound as white solid (210 mg, 59%).

Step 3.

4-(5-((1-((1-(trifluoromethyl)cyclobutyl)methyl)piperidin-4-yl)methoxy)pyrazine-2-yl)benzoic acid: Methyl 4-(5-((1-((1-(trifluoromethyl)cyclobutyl)methyl)piperidin-4-yl)methoxy)pyrazine-2-yl)benzoate (210 mg, 0.45 mmol) and LiOH.H₂O (38 mg, 0.91 mmol) were dissolved in THF (10 mL)/water (5 mL) at room temperature. The solution was stirred at 60° C. for 4 hours, the reaction mixture was concentrated under reduced pressure. The concentrate was added with 1M HCl aqueous solution (10 mL) to be suspended, and filtered. The obtained solid was dried to yield the title compound as white solid (200 mg, 98%).

Step 4.

Compound 1007: 4-(5-((1-((1-(trifluoromethyl)cyclobutyl)methyl)piperidin-4-yl)methoxy)pyrazine-2-yl)benzoic acid (50 mg, 0.11 mmol), (R)-pyrrolidine-2-ylmethanol (17 mg, 0.17 mmol), EDC (32 mg, 0.17 mmol), HOBt (23 mg, 0.17 mmol) and DIPEA (0.04 mL, 0.22 mmol) were dissolved in DMF (2 mL) at room temperature. The solution was stirred at 60° C. for 16 hours. The concentrate was added with water (4 mL) to be suspended, and filtered. The obtained solid was dried to yield the title compound as beige solid (25 mg, 42%).

1H NMR (400 MHz, CDCl₃) δ 8.52 (s, 1H), 8.29 (s, 1H), 7.98 (d, 2H, J=8.2 Hz), 7.63 (d, 2H, J=8.2 Hz), 4.91 (d, 1H, J=6.7 Hz), 4.44 (q, 1H, J=7.2 Hz), 4.24 (d, 2H, J=5.4 Hz), 3.81 (m, 2H), 3.55 (m, 2H), 2.89 (m, 2H), 2.53 (s, 2H), 2.25-1.62 (m, 15H), 1.45 (m, 2H); MS (ESI) m/z 533 (M++H).

According to the above-described synthesis process of compound 1007, the compounds of Table 92 were synthesized using 4-(5-((1-((1-(trifluoromethyl)cyclobutyl)methyl)piperidin-4-yl)methoxy)pyrazine-2-yl)benzoic acid and the reactant of Table 91.

TABLE 91

| Compound No. | Reactant | Yield (%) |
|---|---|---|
| 1008 | (R)-piperidin-3-ol hydrochloride | 37 |
| 1009 | L-prolinamide | 36 |

TABLE 92

| Compound No. | Compound Name, ¹H-NMR, MS (ESI) |
|---|---|
| 1008 | (R)-(3-hydroxypiperidin-1-yl)(4-(5-((1-((1-(trifluoromethyl)cyclobutyl)methyl)piperidin-4-yl)methoxy)pyrazine-2-yl)phenyl)methanone<br>1H NMR (400 MHz, CDCl₃) δ 8.51 (m, 1 H), 8.29 (m, 1 H), 7.96 (m, 2 H), 7.53 (m, 2 H), 4.23 (m, 2 H), 4.04-3.02 (m, 7 H), 2.90 (m, 2 H), 2.54 (s, 2 H), 2.38-1.44 (m, 16 H); MS (ESI) m/z 533 (M+ + H). |
| 1009 | (S)-1-(4-(5-((1-((1-(trifluoromethyl)cyclobutyl)metb.yl)piperidin-4-yl)methoxy)pyrazine-2-yl)benzoyl)pyrrolidine-2-carboxamide<br>1H NMR (400 MHz, CDCl₃) δ 8.52 (m, 1 H), 8.29 (m, 1 H), 7.98 (d, 2 H, J = 8.2 Hz), 7.65 (d, 2 H, J = 8.2 Hz), 6.99 (br, 1 H), 5.51 (br, 1 H), 4.83 (m, 1 H), 4.24 (m, 2 H), 3.62 (m, 2 H), 2.90 (m, 2 H), 2.54-2.45 (m, 3 H), 2.25-1.62 (m, 14 H), 1.45 (m, 2 H); MS (ESI) m/z 546 (M+ + H). |

Example 93. Compound 1010: (R)-(3-fluoro-4-(5-((1-((1-(trifluoromethyl)cyclobutyl)methyl)piperidin-4-yl)methoxy)pyrazine-2-yl)phenyl)(3-hydroxypiperidin-1-yl)methanone

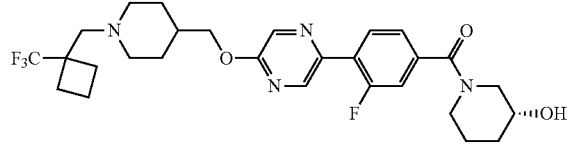 [SMILES: O=C(c1ccc(-c2cnc(OCC3CCN(CC4(C(F)(F)F)CCC4)CC3)cn2)c(F)c1)N1CCC[C@@H](O)C1]

Step 1.

Methyl 3-fluoro-4-(5-((1-((1-(trifluoromethyl)cyclobutyl)methyl)piperidin-4-yl)methoxy)pyrazine-2-yl)benzoate: 2-iodo-5-((1-((1-(trifluoromethyl)cyclobutyl)methyl)piperidin-4-yl)methoxy)pyrazine (the product of synthesis step 1 of compound 1007; 350 mg, 0.77 mmol), 2-fluoro-4-(methoxycarbonyl)phenylboronic acid (167 mg, 0.85 mmol), Pd(dbpf)Cl₂ (15 mg, 0.02 mmol) and Cs₂CO₃ (747 mg, 2.31 mmol) were added to 1,4-dioxane (10 mL)/water (5 mL). With a microwave radiation, the mixture was heated at 110° C. for 45 minutes, and then cooled to room temperature. The reaction mixture was added with water, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, 12 g cartridge; EtOAc/hexane=5% to 25%), and concentrated to yield the title compound as white solid (210 mg, 57%).

Step 2.

3-fluoro-4-(5-((1-((1-(trifluoromethyl)cyclobutyl)methyl)piperidin-4-yl)methoxy)pyrazine-2-yl)benzoic acid: Methyl 3-fluoro-4-(5-((1-((1-(trifluoromethyl)cyclobutyl)methyl)piperidin-4-yl)methoxy)pyrazine-2-yl)benzoate (210 mg, 0.44 mmol) and LiOH.H₂O (37 mg, 0.87 mmol) were dissolved in THF (10 mL)/water (5 mL) at room temperature. The solution was stirred at 60° C. for 4 hours, the reaction mixture was concentrated under reduced pressure. The concentrate was added with 1M HCl aqueous solution (10 mL) to be suspended, and filtered. The obtained solid was dried to yield the title compound as white solid (200 mg, 98%).

Step 3.

Compound 1010: 3-fluoro-4-(5-((1-((1-(trifluoromethyl)cyclobutyl)methyl)piperidin-4-yl)methoxy)pyrazine-2-yl)benzoic acid (50 mg, 0.11 mmol), (R)-piperidin-3-ol hydrochloride (22 mg, 0.16 mmol), EDC (31 mg, 0.16 mmol), HOBt (22 mg, 0.16 mmol) and DIPEA (0.04 mL, 0.21 mmol) were dissolved in DMF (2 mL) at room temperature. The solution was stirred at 60° C. for 16 hours. The concentrate was added with water (4 mL) to be suspended, and filtered. The obtained solid was dried to yield the title compound as beige solid (21 mg, 36%).

1H NMR (400 MHz, CDCl$_3$) δ 8.62 (s, 1H), 8.33 (m, 1H), 8.02 (t, 1H, J=7.8 Hz), 7.32 (m, 2H), 4.33 (m, 2H), 4.04-3.21 (m, 7H), 2.90 (m, 2H), 2.54 (s, 2H), 2.35-1.44 (m, 16H); MS (ESI) m/z 551 (M++H).

According to the above-described synthesis process of compound 1010, the compounds of Table 94 were synthesized using 3-fluoro-4-(5-((1-((1-(trifluoromethyl)cyclobutyl)methyl)piperidin-4-yl)methoxy)pyrazine-2-yl)benzoic acid and the reactant of Table 93.

TABLE 93

| Compound No. | Reactant | Yield (%) |
|---|---|---|
| 1011 | L-prolinamide | 40 |

TABLE 94

| Compound No. | Compound Name, $^1$H-NMR, MS (ESI) |
|---|---|
| 1011 | (S)-1-(3-fluoro-4-(5-((1-((1-(trifluoromethyl)cyclobutyl)methyl)piperidin-4-yl)methoxy)pyrazine-2-yl)benzoyl)pyrrolidine-2-carboxamide<br>1H NMR (400 MHz, CDCl$_3$) δ 8.63 (s, 1 H), 8.33 (s, 1 H), 8.05 (t, 1 H, J = 7.9 Hz), 7.43 (m, 2 H), 6.90 (s, 1 H), 5.53 (s, 1 H), 4.79 (dd, 1 H, J = 10.2, 3.6 Hz), 4.25 (d, 2 H, J = 6.0 Hz), 3.67-3.51 (m, 2 H), 2.90 (m, 2 H), 2.54-2.42 (m, 3 H), 2.16-1.66 (m, 14 H), 1.47 (m, 2 H); MS (ESI) m/z 564 (M+ + H). |

Example 94. Compound 1012: (R)-(2-fluoro-4-(5-((1-((1-(trifluoromethyl)cyclobutyl)methyl)piperidin-4-yl)methoxy)pyrazine-2-yl)phenyl)(2-(hydroxymethyl)pyrrolidine-1-yl)methanone

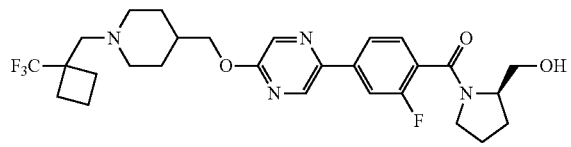 [SMILES: O=C(c1ccc(-c2cnc(OCC3CCN(CC4(C(F)(F)F)CCC4)CC3)cn2)cc1F)N1CCC[C@@H]1CO]

Step 1.

Ethyl 2-fluoro-4-(5-((1-((1-(trifluoromethyl)cyclobutyl)methyl)piperidin-4-yl)methoxy)pyrazine-2-yl)benzoate:
2-iodo-5-((1-((1-(trifluoromethyl)cyclobutyl)methyl)piperidin-4-yl)methoxy)pyrazine (the product of synthesis step 1 of compound 1007; 350 mg, 0.77 mmol), 4-(ethoxycarbonyl)-3-fluorophenylboronic acid (179 mg, 0.85 mmol), Pd(dbpf)Cl$_2$ (15 mg, 0.02 mmol) and Cs$_2$CO$_3$ (747 mg, 2.31 mmol) were added to 1,4-dioxane (10 mL)/water (5 mL).

With a microwave radiation, the mixture was heated at 110° C. for 45 minutes, and then cooled to room temperature. The reaction mixture was added with water, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=5% to 25%), and concentrated to yield the title compound as white solid (300 mg, 79%).

Step 2.

2-fluoro-4-(5-((1-((1-(trifluoromethyl)cyclobutyl)methyl)piperidin-4-yl)methoxy)pyrazine-2-yl)benzoic acid: Ethyl 2-fluoro-4-(5-((1-((1-(trifluoromethyl)cyclobutyl)methyl)piperidin-4-yl)methoxy)pyrazine-2-yl)benzoate (300 mg, 0.61 mmol) and LiOH.H$_2$O (51 mg, 1.21 mmol) were dissolved in THF (10 mL)/water (5 mL) at room temperature. The solution was stirred at 60° C. for 4 hours. The reaction mixture was concentrated under reduced pressure. The concentrate was added with 1M HCl aqueous solution (10 mL) to be suspended, and filtered. The obtained solid was dried to yield the title compound as white solid (280 mg, 99%).

Step 3.

Compound 1012: 2-fluoro-4-(5-((1-((1-(trifluoromethyl)cyclobutyl)methyl)piperidin-4-yl)methoxy)pyrazine-2-yl)benzoic acid (50 mg, 0.11 mmol), (R)-pyrrolidine-2-yl-methanol (16 mg, 0.16 mmol), EDC (31 mg, 0.16 mmol), HOBt (22 mg, 0.16 mmol) and DIPEA (0.04 mL, 0.21 mmol) were dissolved in DMF (2 mL) at room temperature. The solution was stirred at 60° C. for 16 hours. The concentrate was added with water (4 mL) to be suspended, and filtered. The obtained solid was dried to yield the title compound as beige solid (24 mg, 41%).

1H NMR (400 MHz, CDCl$_3$) δ 8.52 (m, 1H), 8.29 (m, 1H), 7.75 (m, 2H), 7.53 (m, 1H), 4.72 (m, 1H), 4.40 (m, 1H), 4.23 (d, 2H, J=5.4 Hz), 3.84-3.78 (m, 2H), 3.45 (m, 2H), 2.89 (m, 2H), 2.54 (s, 2H), 2.24-1.64 (m, 15H), 1.45 (m, 2H); MS (ESI) m/z 551 (M++H).

According to the above-described synthesis process of compound 1012, the compounds of Table 96 were synthesized using 2-fluoro-4-(5-((1-((1-(trifluoromethyl)cyclobutyl)methyl)piperidin-4-yl)methoxy)pyrazine-2-yl)benzoic acid and the reactant of Table 95.

TABLE 95

| Compound No. | Reactant | Yield (%) |
|---|---|---|
| 1013 | (R)-piperidin-3-ol hydrochloride | 43 |
| 1014 | L-prolinamide | 42 |

TABLE 96

| Compound No. | Compound Name, ¹H-NMR, MS (ESI) |
|---|---|
| 1013 | (R)-(2-fluoro-4-(5-((1-((1-(trifluoromethyl)cyclobutyl)methyl)piperidin-4-yl)methoxy)pyrazine-2-yl)phenyl)(3-hydroxypiperidin-1-yl)methanone<br>1H NMR (400 MHz, CDCl₃) δ 8.50 (s, 1 H), 8.28 (s, 1 H), 7.73 (m, 2 H), 7.49 (m, 1 H), 4.28 (m, 2 H), 4.17-3.11 (m, 7 H), 2.89 (m, 2 H), 2.54 (s, 2 H), 2.35-1.44 (m, 16 H); MS (ESI) m/z 551 (M+ + H). |
| 1014 | (S)-1-(2-fluoro-4-(5-((1-((1-(trifluoromethyl)cyclobutyl)methyl)piperidin-4-yl)methoxy)pyrazine-2-yl)benzoyl)pyrrolidine-2-carboxamide<br>1H NMR (400 MHz, CDCl₃) δ 8.51 (m, 1 H), 8.29 (m, 1 H), 7.77 (m, 2 H), 7.52 (m, 1 H), 6.91 (s, 1 H), 5.50 (s, 1 H), 4.82 (m, 1 H), 4.25 (m, 2 H), 3.53 (m, 1 H), 3.42 (m, 1 H), 2.91 (m, 2 H), 2.54-2.46 (m, 3 H), 2.26-1.75 (m, 14 H), 1.46 (m, 2 H); MS (ESI) m/z 564 (M+ + H). |

Example 95. Compound 772: (S)-(3-hydroxypyrrolidin-1-yl)(4-(6-((1-((1-(trifluoromethyl)cyclopentyl)methyl)piperidin-4-yl)methoxy)pyridine-3-yl)phenyl)methanone

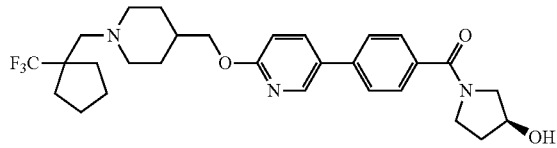 [SMILES: O=C(c1ccc(-c2ccc(OCC3CCN(CC4(C(F)(F)F)CCCC4)CC3)nc2)cc1)N1CC[C@H](O)C1]

Step 1.
Ethyl 1-(1-(trifluoromethyl)cyclopentanecarbonyl)piperidin-4-carboxylate: 1-(trifluoromethyl)cyclopentanecarboxylic acid (500 mg, 2.74 mmol), ethyl piperidin-4-carboxylate (518 mg, 3.29 mmol), EDC (1.05 g, 5.49 mmol) and HOBt (742 mg, 5.49 mmol) were dissolved in DMF 5 mL. DIPEA (0.97 mL, 5.49 mmol) was added thereto, and the reaction was performed at 60° C. for 8 hours. The reaction mixture was added with saturated NH₄Cl aqueous solution, and extracted with EtOAc. The extracted organic layer was dried over MgSO₄, and then filtered. The filtrate was purified by silica gel column chromatography (10-30% EtOAc/hexane) to yield the title compound as colorless oil (400 mg, 45%).

Step 2.
(1-((1-(trifluoromethyl)cyclopentyl)methyl)piperidin-4-yl)methanol: Ethyl 1-(1-(trifluoromethyl)cyclopentanecarbonyl)piperidin-4-carboxylate (1.06 g, 3.30 mmol) was dissolved in dry THF 20 mL. At 0° C., LAH (1 M in THF, 16.49 mL, 16.49 mmol) was added slowly thereto. The reaction was performed at 50° C. for 10 hours. The reaction was quenched by slow addition of MeOH at 0° C. The reaction mixture was added with water, and then extracted with EtOAc. The obtained extracted organic layer was dried over MgSO₄, and then filtered to yield the title compound as colorless oil (844 mg, 96%).

Step 3.
5-bromo-2-((1-((1-(trifluoromethyl)cyclopentyl)methyl)piperidin-4-yl)methoxy)pyridine: (1-((1-(trifluoromethyl)cyclopentyl)methyl)piperidin-4-yl)methanol (844 mg, 3.18 mmol) was dissolved in THF 10 mL. At 0° C., NaH (115 mg, 4.77 mmol) was added slowly thereto. The reaction was performed at room temperature for 20 minutes. At 0° C., 2,5-dibromopyridine (829 mg, 3.50 mmol) in THF was added slowly thereto. The reaction was performed at 50° C. for 10 hours. After the completion of the reaction, the reaction mixture was added with ice water, and extracted with EtOAc. The obtained organic layer was dried over MgSO₄, and filtered. The filtrate was concentrated under reduced pressure. The obtained concentrate was purified by silica gel column chromatography (10-70% EtOAc/hexane) to yield the title compound as white solid (900 mg, 67%).

Step 4.
Methyl 4-(6-((1-((1-(trifluoromethyl)cyclopentyl)methyl)piperidin-4-yl)methoxy)pyridine-3-yl)benzoate: 5-bromo-2-((1-((1-(trifluoromethyl)cyclopentyl)methyl)piperidin-4-yl)methoxy)pyridine (400 mg, 0.95 mmol), 4-(methoxycarbonyl)phenylboronic acid (188 mg, 1.04 mmol), Pd(dbpf)Cl₂ (19 mg, 0.03 mmol), Cs₂CO₃ (922 mg, 2.85 mmol) were added into a microwave reactor, and then 1,4-dioxane 4 mL and water 2 mL were added thereto. With a microwave radiation, the reaction was performed at 110° C. for 30 minutes. The reaction mixture was filtered through a Celite pad. The filtrate was added with water, and then extracted with EtOAc. The obtained organic layer was dried over MgSO₄, and filtered. The filtrate was concentrated under reduced pressure. The obtained concentrate was purified by silica gel column chromatography (20-70% EtOAc/hexane) to yield the title compound as white solid (330 mg, 73%).

Step 5.
4-(6-((1-((1-(trifluoromethyl)cyclopentyl)methyl)piperidin-4-yl)methoxy)pyridine-3-yl)benzoic acid: Methyl 4-(6-((1-((1-(trifluoromethyl)cyclopentyl)methyl)piperidin-4-yl)methoxy)pyridine-3-yl)benzoate (330 mg, 0.69 mmol) was dissolved in the mixed solvents of THF 4 mL/water 4 mL. LiOH.H₂O (58 mg, 1.38 mmol) was added thereto, and the reaction was performed at 60° C. for 4 hours. The solvent was concentrated under reduced pressure. After the addition of 1M HCl thereto, the resulting precipitate was filtered to yield the title compound as white solid (300 mg, 94%).

Step 6.
Compound 772: 4-(6-((1-((1-(trifluoromethyl)cyclopentyl)methyl)piperidin-4-yl)methoxy)pyridine-3-yl)benzoic acid (50 mg, 0.11 mmol), (S)-pyrrolidine-3-ol (14 mg, 0.16 mmol), EDC (41 mg, 0.22 mmol) and HOBt (29 mg, 0.22 mmol) were dissolved in DMF 2 mL. DIPEA (0.04 mL, 0.22 mmol) was added thereto, and the reaction was performed at 60° C. for 10 hours. The reaction mixture was cooled to room temperature, and added with water. The formed solid was filtered, washed with water thoroughly, and dried to yield the title compound as white solid (21 mg, 37%).

1H NMR (400 MHz, CDCl₃) δ 8.37 (s, 1H), 7.80 (dd, 1H, J=10.2, 3.6 Hz), 7.65-7.53 (m, 4H), 6.83 (d, 1H, J=8.6 Hz), 4.62-4.50 (m, 1H), 4.29-4.18 (m, 2H), 3.87-3.48 (m, 5H), 2.89 (m, 2H), 2.47 (s, 2H), 2.30 (t, 2H, J=11.2 Hz), 2.20-1.96 (m, 3H), 1.87-1.76 (m, 10H), 1.45 (m, 2H); MS (ESI) m/z 532 (M++H).

According to the above-described synthesis process of compound 772, the compounds of Table 98 were synthesized using 4-(6-((1-((1-(trifluoromethyl)cyclopentyl)methyl)piperidin-4-yl)methoxy)pyridine-3-yl)benzoic acid and the reactant of Table 97.

TABLE 97

| Compound No. | Reactant | Yield (%) |
|---|---|---|
| 773 | (R)-pyrrolidine-2-ylmethanol | 42 |
| 774 | L-prolinamide | 40 |
| 775 | (R)-piperidin-3-ol hydrochloride | 37 |

TABLE 98

| Compound No. | Compound Name, $^1$H-NMR, MS (ESI) |
|---|---|
| 773 | (R)-(2-(hydroxymethyl)pyrrolidine-1-yl)(4-(6-((1-((1-(trifluoromethyl)cyclopentyl)methyl)piperidin-4-yl)methoxy)pyridine-3-yl)phenyl)methanone 1H NMR (400 MHz, CDCl$_3$) δ 8.38 (d, 1 H, J = 2.3 Hz), 7.80 (dd, 1 H, J = 10.2, 3.6 Hz), 7.62-7.56 (m, 4 H), 6.83 (d, 1 H, J = 8.6 Hz), 4.91 (d, 1 H, J = 7.2 Hz), 4.47-4.42 (m, 1 H), 4.30-4.18 (m, 2 H), 3.86-3.51 (m, 4 H), 3.23 (m, 1 H), 2.90-2.81 (m, 2 H), 2.47 (s, 2 H), 2.32-2.19 (m, 3 H), 2.17-1.65 (m, 13 H), 1.42 (m, 2 H); MS (ESI) m/z 546 (M+ + H). |
| 774 | (S)-1-(4-(6-((1-((1-(trifluoromethyl)cyclopentyl)methyl)piperidin-4-yl)methoxy)pyridine-3-yl)benzoyl)pyrrolidine-2-carboxamide 1H NMR (400 MHz, CDCl$_3$) δ 8.38 (s, 1 H), 7.80 (dd, 1 H, J = 10.2, 3.6 Hz), 7.64-7.53 (m, 4 H), 6.98 (br, 1 H), 6.83 (d, 1 H, J = 8.6 Hz), 5.45 (br, 1 H), 4.84 (dd, 1 H, J = 10.2, 3.6 Hz), 4.31-4.19 (m, 2 H), 3.67-3.54 (m, 2 H), 3.23 (m, 1 H), 2.89-2.80 (m, 2 H), 2.52-2.47 (m, 3 H), 2.32 (m, 2 H), 2.16 (m, 4 H), 1.98-1.68 (m, 9 H), 1.42 (m, 2 H); MS (ESI) m/z 559 (M+ + H). |
| 775 | (R)-(3-hydroxypiperidin-1-yl)(4-(6-((1-((1-(trifluoromethyl)cyclopentyl)methyl)piperidin-4-yl)methoxy)pyridine-3-yl)phenyl)methanone 1H NMR (400 MHz, CDCl$_3$) δ 8.37 (d, 1 H, J = 2.3 Hz), 7.80 (dd, 1 H, J = 10.2, 3.6 Hz), 7.56 (d, 1 H, J = 8.4 Hz), 7.51 (d, 1 H, J = 8.3 Hz), 6.82 (d, 1 H, J = 8.6 Hz), 4.25-3.20 (m, 9 H), 2.89 (m, 2 H), 2.47 (s, 2 H), 2.30 (t, 2 H, J = 11.0 Hz), 2.09-1.68 (m, 14 H), 1.42 (m, 2 H); MS (ESI) m/z 546 (M+ + H). |

Example 96. Compound 776: (S)-(3-hydroxypyrrolidin-1-yl)(4-(6-((1-((1-(trifluoromethyl)cyclohexyl)methyl)piperidin-4-yl)methoxy)pyridine-3-yl)phenyl)methanone

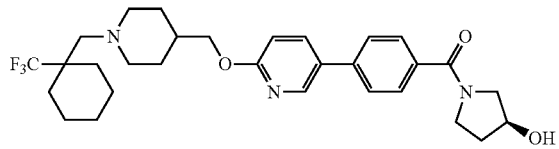 [SMILES: O=C(c1ccc(-c2ccc(OCC3CCN(CC4(C(F)(F)F)CCCCC4)CC3)nc2)cc1)N1CC[C@H](O)C1]

Step 1.
Ethyl 1-(1-(trifluoromethyl)cyclohexanecarbonyl)piperidin-4-carboxylate: 1-(trifluoromethyl)cyclohexanecarboxylic acid (500 mg, 2.55 mmol), ethyl piperidine-4-carboxylate (481 mg, 3.06 mmol), EDC (977 mg, 5.09 mmol) and HOBt (689 mg, 5.09 mmol) were dissolved in DMF 5 mL. DIPEA (0.90 mL, 5.09 mmol) was added thereto. The reaction was performed at 60° C. for 8 hours. The reaction mixture was added with saturated NH$_4$Cl aqueous solution and extracted with EtOAc: The extracted organic layer was dried over MgSO$_4$, and then filtered. The filtrate was purified by silica gel column chromatography (10-30% EtOAc/hexane) to yield the title compound as colorless oil (250 mg, 29%).
Step 2.
(1-((1-(trifluoromethyl)cyclohexyl)methyl)piperidin-4-yl)methanol: Ethyl 1-(1-(trifluoromethyl)cyclohexanecarbonyl)piperidin-4-carboxylate (576 mg, 1.72 mmol) was dissolved in dry THF 10 mL. At 0° C., LAH (1 M in THF, 8.59 mL, 8.59 mmol) was added slowly thereto. The reaction was performed at 50° C. for 10 hours. The reaction was quenched by slow addition of MeOH at 0° C. The reaction mixture was added with water, and then extracted with EtOAc. The obtained extracted organic layer was dried over MgSO$_4$, and then filtered to yield the title compound as colorless oil (430 mg, 90%).
Step 3.
5-bromo-2-((1-((1-(trifluoromethyl)cyclohexyl)methyl)piperidin-4-yl)methoxy)pyridine: (1-((1-(trifluoromethyl)cyclohexyl)methyl)piperidin-4-yl)methanol (430 mg, 1.54 mmol) was dissolved in THF 10 mL. At 0° C., NaH (55 mg, 2.31 mmol) was added slowly thereto. The reaction was performed at room temperature for 20 minutes. At 0° C., 2,5-dibromopyridine (401 mg, 1.69 mmol) in THF was added slowly thereto. The reaction was performed at 50° C. for 10 hours. After the completion of the reaction, the reaction mixture was added with ice water, and extracted with EtOAc. The obtained organic layer was dried over MgSO$_4$, and filtered. The filtrate was concentrated under reduced pressure. The obtained concentrate was purified by silica gel column chromatography (10-70% EtOAc/hexane) to yield the title compound as white solid (380 mg, 57%).
Step 4.
Methyl 4-(6-((1-((1-(trifluoromethyl)cyclohexyl)methyl)piperidin-4-yl)methoxy)pyridine-3-yl)benzoate: 5-bromo-2-((1-((1-(trifluoromethyl)cyclohexyl)methyl)piperidin-4-yl)methoxy)pyridine (380 mg, 0.87 mmol), 4-(methoxycarbonyl)phenylboronic acid (173 mg, 0.96 mmol), Pd(dbpf)Cl$_2$ (17 mg, 0.03 mmol), Cs$_2$CO$_3$ (848 mg, 2.62 mmol) were added into a microwave reactor, and then 1,4-dioxane 4 mL and water 2 mL were added thereto. With a microwave radiation, the reaction was performed at 110° C. for 30 minutes. The reaction mixture was filtered through a Celite pad. The filtrate was added with water, and extracted with EtOAc. The organic layer was dried over MgSO$_4$, and filtered. The filtrate was concentrated under reduced pressure. The concentrate was purified by silica gel column chromatography (20-70% EtOAc/hexane) to yield the title compound as white solid (250 mg, 58%).
Step 5.
4-(6-((1-((1-(trifluoromethyl)cyclohexyl)methyl)piperidin-4-yl)methoxy)pyridine-3-yl)benzoic acid: Methyl 4-(6-((1-((1-(trifluoromethyl)cyclohexyl)methyl)piperidin-4-yl)methoxy)pyridine-3-yl)benzoate (250 mg, 0.51 mmol) was dissolved in the mixed solvents of THF 4 mL/water 4 mL. LiOH.H$_2$O (43 mg, 1.02 mmol) was added thereto, and the reaction was performed at 60° C. for 4 hours. The solvent was concentrated under reduced pressure. After the addition of 1M HCl thereto, the resulting precipitate was filtered to yield the title compound as white solid (210 mg, 87%).
Step 6.

Compound 776: 4-(6-((1-((1-(trifluoromethyl)cyclohexyl)methyl)piperidin-4-yl)methoxy)pyridine-3-yl)benzoic acid (45 mg, 0.09 mmol), (S)-pyrrolidine-3-ol (12 mg, 0.14 mmol), EDC (36 mg, 0.19 mmol) and HOBt (26 mg, 0.19 mmol) were dissolved in DMF 2 mL. DIPEA (0.03 mL, 0.19 mmol) was added thereto, the reaction was performed at 60° C. for 10 hours. The reaction mixture was cooled to room temperature, and added with water. The formed solid was filtered, washed with water thoroughly, and dried to yield the title compound as white solid (24 mg, 47%).

1H NMR (400 MHz, CDCl$_3$) 8.37 (s, 1H), 7.80 (m, 1H), 7.67-7.54 (m, 4H), 6.81 (m, 1H), 4.61-4.45 (m, 1H), 4.28-4.17 (m, 2H), 3.84-3.48 (m, 4H), 2.87 (m, 2H), 2.48 (s, 2H), 2.32-2.00 (m, 5H), 1.88-1.35 (m, 15H); MS (ESI) m/z 546 (M++H).

According to the above-described synthesis process of compound 776, the compounds of Table 100 were synthesized using 4-(6-((1-((1-(trifluoromethyl)cyclohexyl)methyl)piperidin-4-yl)methoxy)pyridine-3-yl)benzoic acid and the reactant of Table 99.

TABLE 99

| Compound No. | Reactant | Yield (%) |
| --- | --- | --- |
| 777 | (R)-pyrrolidine-2-ylmethanol | 42 |
| 778 | L-prolinamide | 28 |
| 779 | (R)-piperidin-3-ol hydrochloride | 38 |

TABLE 100

| Compound No. | Compound Name, $^1$H-NMR, MS (ESI) |
| --- | --- |
| 777 | (R)-2-(hydroxymethyl)pyrrolidine-1-yl)(4-(6-((1-((1-(trifluoromethyl)cyclohexyl)methyl)piperidin-4-yl)methoxy)pyridine-3-yl)phenyl)methanone<br>1H NMR (400 MHz, CDCl$_3$) δ 8.38 (m, 1 H), 7.80 (m, 1 H), 7.62-7.56 (m, 4 H), 6.83 (m, 1 H), 4.89 (m, 1 H), 4.54 (m, 1 H), 4.30-4.18 (m, 2 H), 3.84-3.48 (m, 4 H), 2.87 (m, 2 H), 2.48 (s, 2 H), 2.32-2.18 (m, 3 H), 1.90-1.35 (m, 18 H); MS (ESI) m/z 560 (M+ + H). |
| 778 | (S)-1-(4-(6-((1-((1-(trifluoromethyl)cyclohexyl)methyl)piperidin-4-yl)methoxy)pyridine-3-yl)benzoyl)pyrrolidine-2-carboxamide<br>1H NMR (400 MHz, CDCl$_3$) δ 8.38 (m, 1 H), 7.80 (m, 1 H), 7.64-7.56 (m, 4 H), 7.00 (s, 1 H), 6.83 (m, 1 H), 5.58 (s, 1 H), 4.82 (m, 1 H), 4.30-4.18 (m, 2 H), 3.66-3.56 (m, 2 H), 2.85 (m, 2 H), 2.48 (m, 3 H), 2.32 (m, 2 H), 2.10 (m, 2 H), 1.93-1.35 (m, 16 H); MS (ESI) m/z 573 (M+ + H). |
| 779 | (R)-(3-hydroxypiperidin-1-yl)(4-(6-((1-((1-(trifluoromethyl)cyclohexyl)methyl)piperidin-4-yl)methoxy)pyridine-3-yl)phenyl)methanone<br>1H NMR (400 MHz, CDCl$_3$) δ 8.37 (m, 1 H), 7.78 (m, 1 H), 7.56-7.49 (m, 4 H), 6.83 (m, 1 H), 4.17 (m, 2 H), 4.04-3.18 (m, 6 H), 2.85 (m, 2 H), 2.48 (m, 2 H), 2.32 (m, 2 H), 2.03-1.35 (m, 19 H); MS (ESI) m/z 560 (M+ + H). |

Example 97. Compound 828: (S)-1-(4-(6-((1-(3,3,3-trifluoro-2,2-dimethylpropyl)piperidin-4-yl)methoxy)pyridine-3-yl)benzoyl)pyrrolidine-2-carboxamide

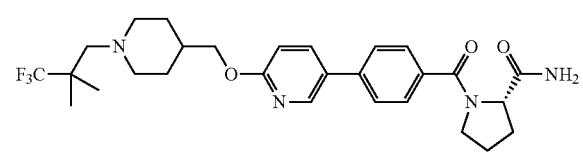 [SMILES: CC(C)(CN1CCC(COc2ccc(-c3ccc(C(=O)N4CCC[C@H]4C(N)=O)cc3)cn2)CC1)C(F)(F)F]

Step 1.

Ethyl 1-(3,3,3-trifluoro-2,2-dimethylpropanoyl)piperidin-4-carboxylate: 3,3,3-trifluoro-2,2-dimethylpropanoic acid (500 mg, 3.20 mmol), ethyl piperidin-4-carboxylate (604 mg, 3.84 mmol), EDC (1.23 g, 6.41 mmol) and HOBt (866 mg, 6.41 mmol) were dissolved in DMF 15 mL. DIPEA (1.13 mL, 6.41 mmol) was added thereto, and the reaction was performed at 60° C. for 8 hours. The reaction mixture was added with saturated NH$_4$Cl aqueous solution and extracted with EtOAc. The extracted organic layer was dried over MgSO$_4$, and then filtered. The filtrate was purified by silica gel column chromatography (10-30% EtOAc/hexane) to yield the title compound as colorless oil (300 mg, 36%).
Step 2.

(1-(3,3,3-trifluoro-2,2-dimethylpropyl)piperidin-4-yl)methanol: Ethyl 1-(3,3,3-trifluoro-2,2-dimethylpropanoyl)piperidin-4-carboxylate (260 mg, 0.88 mmol) was dissolved in dry THF 20 mL. At 0° C., LAH (1 M in THF, 4.40 mL, 4.40 mmol) was added slowly thereto and the reaction was performed at 50° C. for 10 hours. The reaction was quenched by slow addition of MeOH at 0° C. The reaction mixture was added with water, and then extracted with EtOAc. The obtained extracted organic layer was dried over MgSO$_4$, and then filtered to yield the title compound as colorless oil (170 mg, 81%).
Step 3.

5-bromo-2-((1-(3,3,3-trifluoro-2,2-dimethylpropyl)piperidin-4-yl)methoxy)pyridine: (1-(3,3,3-trifluoro-2,2-dimethylpropyl)piperidin-4-yl)methanol (170 mg, 0.71 mmol) was dissolved in THF 10 mL. At 0° C., NaH (26 mg, 1.07 mmol) was added slowly thereto. The reaction was performed at room temperature for 20 minutes. At 0° C., 2,5-dibromopyridine (185 mg, 0.78 mmol) in THF was added slowly thereto, and the reaction was performed at 50° C. for 10 hours. After the completion of the reaction, the reaction mixture was added with ice water, and extracted with EtOAc. The obtained organic layer was dried over MgSO$_4$, and filtered. The filtrate was concentrated under reduced pressure. The obtained concentrate was purified by silica gel column chromatography (10-70% EtOAc/hexane) to yield the title compound as colorless oil (260 mg, 93%).
Step 4.

Methyl 4-(6-((1-(3,3,3-trifluoro-2,2-dimethylpropyl)piperidin-4-yl)methoxy)pyridine-3-yl)benzoate: 5-bromo-2-((1-(3,3,3-trifluoro-2,2-dimethylpropyl)piperidin-4-yl)methoxy)pyridine (260 mg, 0.66 mmol), 4-(methoxycarbonyl)phenylboronic acid (130 mg, 0.72 mmol), Pd(dbpf)Cl₂ (13 mg, 0.02 mmol), Cs₂CO₃ (640 mg, 1.97 mmol) were added into a microwave reactor, and then 1,4-dioxane 6 mL and water 3 mL were added thereto. With a microwave radiation, the reaction was performed at 110° C. for 30 minutes. The reaction mixture was filtered through a Celite pad. The filtrate was added with water, and then extracted with EtOAc. The obtained organic layer was dried over MgSO₄, and filtered. The filtrate was concentrated under reduced pressure. The obtained concentrate was purified by silica gel column chromatography (20-70% EtOAc/hexane) to yield the title compound as white solid (200 mg, 68%).

Step 5.

4-(6-((1-(3,3,3-trifluoro-2,2-dimethylpropyl)piperidin-4-yl)methoxy)pyridine-3-yl)benzoic acid: Methyl 4-(6-((1-(3,3,3-trifluoro-2,2-dimethylpropyl)piperidin-4-yl)methoxy)pyridine-3-yl)benzoate (200 mg, 0.44 mmol) was dissolved in the mixed solvents of THF 10 mL/water 10 mL. LiOH.H₂O (37 mg, 0.89 mmol) was added thereto, and the reaction was performed at 60° C. for 4 hours. The solvent was concentrated under reduced pressure. After the addition of 1M HCl thereto, the resulting precipitate was filtered to yield the title compound as white solid (150 mg, 77%).

Step 6.

Compound 828: 4-(6-((1-(3,3,3-trifluoro-2,2-dimethylpropyl)piperidin-4-yl)methoxy)pyridine-3-yl)benzoic acid (40 mg, 0.09 mmol), L-prolinamide (16 mg, 0.14 mmol), EDC (35 mg, 0.18 mmol) and HOBt (25 mg, 0.18 mmol) were dissolved in DMF 2 mL. DIPEA (24 mg, 0.18 mmol) was added thereto, and the reaction was performed at 60° C. for 10 hours. The reaction mixture was cooled to room temperature, and added with water. The formed solid was filtered, washed with water thoroughly, and dried to yield the title compound as white solid (20 mg, 41%).

1H NMR (400 MHz, CDCl₃) δ 8.38 (d, 1H, J=2.1 Hz), 7.81 (dd, 1H, J=10.2, 3.6 Hz), 7.64-7.56 (m, 4H), 6.99 (s, 1H), 6.83 (d, 1H, J=8.6 Hz), 5.56 (s, 1H), 4.82 (dd, 1H, J=10.2, 3.6 Hz), 4.19 (d, 2H, J=4.8 Hz), 3.66-3.56 (m, 2H), 2.83 (d, 2H, J=9.0 Hz), 2.47-2.30 (m, 4H), 2.10 (m, 2H), 1.90-1.70 (m, 5H), 1.42 (m, 2H), 1.11 (m, 6H); MS (ESI) m/z 423 (M++H).

According to the above-described synthesis process of compound 828, the compounds of Table 102 were synthesized using 4-(6-((1-(3,3,3-trifluoro-2,2-dimethylpropyl)piperidin-4-yl)methoxy)pyridine-3-yl)benzoic acid and the reactant of Table 101.

TABLE 101

| Compound No. | Reactant | Yield (%) |
|---|---|---|
| 829 | (R)-piperidin-3-ol hydrochloride | 41 |

Example 98. Compound 809: (R)-(4'-((1-(2-ethyl-2-fluorobutyl)piperidin-4-yl)methoxy)biphenyl-4-yl)(3-hydroxypiperidin-1-yl)methanone

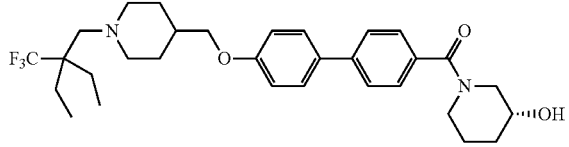 [SMILES: CCC(CC)(CN1CCC(COc2ccc(-c3ccc(C(=O)N4CCC[C@@H](O)C4)cc3)cc2)CC1)C(F)(F)F]

Step 1.

2,2-diethyloxirane: 3-methylenepentane (2 g, 23.76 mmol) and m-CPBA (6.56 g, 38.02 mmol) were dissolved in CH₂Cl₂ 30 mL. At 0° C., the reaction was performed for a day. The reaction mixture was added with saturated Na₂SO₃ aqueous solution, and extracted with CH₂Cl₂. The organic layer was washed with saturated aqueous brine solution, dried over MgSO₄, filtered to remove the solid residue, and the filtrate was concentrated under reduced pressure to yield the title compound as colorless oil (1.8 g, 75%).

Step 2.

3-((4-((4-bromophenoxy)methyl)piperidin-1-yl)methyl)pentane-3-ol: 4-((4-bromophenoxy)methyl)piperidine hydrochloride (the product of synthesis step 4 of compound 686; 500 mg, 1.85 mmol) was dissolved in EtOH 4 mL. 2,2-diethyloxirane (the product of synthesis step 1 of compound 809; 930 mg, 9.25 mmol), K₂CO₃ (512 mg, 3.70 mmol) and water 2 mL were added thereto, With a microwave radiation, the mixture was stirred at 110° C. for 20 minutes. After the completion of the reaction, EtOH was evaporated from the reaction mixture under reduced pressure, and then a little of water was added to thereto. The resulting precipitate was filtered, and dried under reduced pressure to yield the title compound as white solid (600 mg, 87%).

Step 3.

4-((4-bromophenoxy)methyl)-1-(2-ethyl-2-fluorobutyl)piperidine: 3-((4-((4-bromophenoxy)methyl)piperidin-1-yl)methyl)pentane-3-ol (596 mg, 1.61 mmol) was dissolved in CH₂Cl₂ 5 mL. DAST (285 mg, 1.77 mmol) was added thereto, following with stirring at room temperature for 3 hours. After the completion of the reaction, the reaction mixture was added with a saturated NaHCO₃ aqueous solution, and extracted with CH₂Cl₂. The organic layer washed with saturated aqueous brine solution, dried over MgSO₄, and filtered to remove the solid residue. The filtrate was concentrated under reduced pressure. The concentrate was purified by column chromatography (40 g ISCO silica gel cartridge, 15-20% EtOAc/Hexane) to yield the title compound as white solid (520 mg, 87%).

Step 4.

Methyl 4'-((1-(2-ethyl-2-fluorobutyl)piperidin-4-yl)methoxy)biphenyl-4-carboxylate: 4-((4-bromophenoxy)

TABLE 102

Compound No. Compound Name, ¹H-NMR, MS (ESI)

| 829 | (R)-(3-hydroxypiperidin-1-yl)(4-(6-((1-(3,3,3-trifluoro-2,2-dimethylpropyl)piperidin-4-yl)methoxy)pyridine-3-yl)phenyl)methanone<br>1H NMR (400 MHz, CDCl₃) δ 8.37 (d, 1 H, J = 2.1 Hz), 7.80 (dd, 1 H, J = 10.2, 3.6 Hz), 7.56-7.49 (m, 4 H), 6.83 (d, 1 H, J = 8.6 Hz), 4.19 (d, 2 H, J = 4.8 Hz), 4.00-3.10 (m, 7 H), 2.83 (d, 2 H, J = 9.0 Hz), 2.40-2.30 (m, 4 H), 2.00-1.39 (m, 8 H), 1.11 (m, 6 H); MS (ESI) m/z 520 (M+ + H). |
|---|---| methyl)-1-(2-ethyl-2-fluorobutyl)piperidine (130 mg, 0.35 mmol), 4-(methoxycarbonyl)phenylboronic acid (69 mg, 0.38 mmol), Pd(dbpf)Cl$_2$ (11 mg, 0.02 mmol) and Cs$_2$CO$_3$ (228 mg, 0.70 mmol) were dissolved in 1,4-dioxane 4 mL and water 1 mL. With a microwave radiation, the reaction was performed at 120° C. for 15 minutes. The reaction mixture was filtered through Celite. The filtrate was added with saturated NaHCO$_3$ aqueous solution, and extracted with EtOAc. The organic layer was dried over MgSO$_4$, filtered to remove the solid residue, and the filtrate was concentrated under reduced pressure. The concentrate was purified by column chromatography (ISCO silica gel cartridge, EtOAc/Hexane) to yield the title compound as white solid (105 mg, 70%).

Step 5.

4'-((1-(2-ethyl-2-fluorobutyl)piperidin-4-yl)methoxy)biphenyl-4-carboxylic acid: Methyl 4'-((1-(2-ethyl-2-fluorobutyl)piperidin-4-yl)methoxy)biphenyl-4-carboxylate (105 mg, 0.25 mmol) was dissolved in THF:MeOH:water=3:1.5:1 mL. LiOH.H$_2$O (21 mg, 0.49 mmol) was added thereto. And then, the mixture was refluxed with heating for 3 hours. After the completion of the reaction, the solvent was dried under reduced pressure, following with adjusting pH to below 6 using 1N HCl. The resulting precipitate was filtered to yield the title compound as white solid (72 mg, 71%).

Step 6.

Compound 809: 4'-((1-(2-ethyl-2-fluorobutyl)piperidin-4-yl)methoxy)biphenyl-4-carboxylic acid (35 mg, 0.09 mmol), (R)-piperidin-3-ol (13 mg, 0.13 mmol) and BOP (75 mg, 0.17 mmol) were dissolved in DMF 1 mL. After stirring for 10 minutes at room temperature, TEA (26 mg, 0.26 mmol) was added thereto, following with stirring at 50° C. for 8 hours. The reaction mixture was added with water, and extracted with EtOAc. The organic layer was washed with saturated aqueous brine solution, dried over MgSO$_4$, filtered to remove the solid residue, and the filtrate was concentrated under reduced pressure. The concentrate was purified by column chromatography (ISCO silica gel cartridge, MeOH/CH$_2$Cl$_2$) to yield the title compound as white solid (17 mg, 40%).

1H NMR (400 MHz, CDCl$_3$) δ 7.49 (m, 6H), 6.96 (d, 2H, J=6.8 Hz), 3.82 (m, 4H), 3.42 (m, 3H), 2.99 (m, 2H), 2.49 (s, 1H), 2.43 (s, 1H), 2.15 (m, 2H), 1.71 (m, 11H), 1.64 (m, 2H), 0.89 (t, 6H, J=7.5 Hz); MS (ESI) m/z 497 (M+H).

According to the above-described synthesis process of compound 809, the compounds of Table 104 were synthesized using 4'-((1-(2-ethyl-2-fluorobutyl)piperidin-4-yl)methoxy)biphenyl-4-carboxylic acid and the reactant of Table 103.

TABLE 103

| Compound No. | Reactant | Yield (%) |
| --- | --- | --- |
| 891 | (S)-pyrrolidine-2-carboxamide | 51 |
| 892 | (R)-pyrrolidine-2-ylmethanol | 63 |
| 893 | (S)-pyrrolidine-3-ol | 51 |
| 894 | (R)-pyrrolidine-3-ol | 61 |

TABLE 104

| Compound No. | Compound Name, $^1$H-NMR, MS (ESI) |
| --- | --- |
| 891 | (S)-1-(4'-((1-(2-ethyl-2-fluorobutyl)piperidin-4-yl)methoxy)biphenylcarbonyl)pyrrolidine-2-carboxamide<br>1H NMR (400 MHz, CDCl$_3$) δ 7.58 (s, 3 H), 7.52 (d, 2 H, J = 8.6 Hz), 7.01 (s, 1 H), 6.99 (d, 2 H, J = 6.5 Hz), 5.48 (s, 1 H), 4.82 (t, 1 H, J = 6.2 Hz), 3.84 (d, 2 H, J = 5.7 Hz), 3.63 (m, 2 H), 2.99 (m, 2 H), 2.46 (m, 2 H), 2.07 (m, 2 H), 2.02-1.42 (m, 12 H), 0.90 (t, 6 H, J = 7.5 Hz); MS (ESI) m/z 510 (M + H). |
| 892 | (R)-(4'-((1-(2-ethyl-2-fluorobutyl)piperidin-4-yl)methoxy)biphenyl-4-yl)(2-(hydroxymethyl)pyrrolidine-1-yl)methanone<br>MS (ESI) m/z 497 (M + H). |
| 893 | (S)-(4'-((1-(2-ethyl-2-fluorobutyl)piperidin-4-yl)methoxy)biphenyl-4-yl)(3-hydroxypyrrolidine-1-yl)methanone<br>1H NMR (400 MHz, CDCl$_3$) δ 7.52 (m, 6 H), 6.96 (d, 2 H, J = 8.7 Hz), 4.58-4.45 (m, 1 H), 3.84 (m, 2 H), 3.66 (m, 4 H), 3.02 (m, 2 H), 2.48 (m, 2 H), 2.46-1.98 (m, 7 H), 1.82-1.46 (m, 7 H), 0.90 (t, 6 H, J = 7.5 Hz); MS (ESI) m/z 483 (M + H). |
| 894 | (S)-(4'-((1-(2-ethyl-2-fluorobutyl)piperidin-4-yl)methoxy)biphenyl-4-yl)(3-hydroxypiperidin-1-yl)methanone<br>1H NMR (400 MHz, CDCl$_3$) δ 7.49 (m, 6 H), 6.97 (d, 2 H, J = 8.8 Hz), 3.84 (m, 4 H), 3.42 (m, 3 H), 2.98 (m, 2 H), 2.47 (m, 2 H), 1.92 (m, 2 H), 1.78-1.43 (m, 13 H), 0.89 (t, 6 H, J = 7.5 Hz); MS (ESI) m/z 497 (M + H). |

Example 99. Compound 888: (S)-(4'-((1-(2-ethyl-2-fluorobutyl)piperidin-4-yl)methoxy)-3-fluorobiphenyl-4-yl)(3-hydroxypyrrolidine-1-yl)methanone

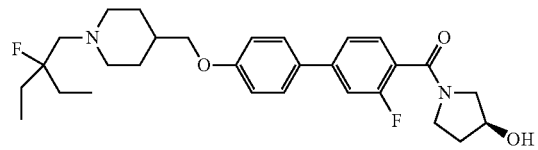 [SMILES: CCC(F)(CC)CN1CCC(COc2ccc(-c3ccc(C(=O)N4CC[C@H](O)C4)c(F)c3)cc2)CC1]

Step 1.

Ethyl 4'-((1-(2-ethyl-2-fluorobutyl)piperidin-4-yl)methoxy)-3-fluorobiphenyl-4-carboxylate: 4-((4-bromophenoxy)methyl)-1-(2-ethyl-2-fluorobutyl)piperidine (the product of synthesis step 3 of compound 809; 130 mg, 0.35 mmol), 4-(ethoxycarbonyl)-3-fluorophenylboronic acid (345 mg, 1.63 mmol), Pd(dppf)Cl$_2$ (60 mg, 0.07 mmol) and Na$_2$CO$_3$ (313 mg, 2.95 mmol) were dissolved in DME 12 mL and water 3 mL, and then refluxed with heating for a day. The reaction mixture was filtered through Celite. The filtrate was added with saturated NaHCO$_3$ aqueous solution, and extracted with EtOAc. The organic layer was dried over MgSO$_4$, filtered to remove the solid residue, and the filtrate was concentrated under reduced pressure. The concentrate was purified by column chromatography (ISCO silica gel cartridge, EtOAc/Hexane) to yield the title compound as white solid (390 mg, 54%).

Step 2.

4'-((1-(2-ethyl-2-fluorobutyl)piperidin-4-yl)methoxy)-3-fluorobiphenyl-4-carboxylic acid: Ethyl 4'-((1-(2-ethyl-2-fluorobutyl)piperidin-4-yl)methoxy)-3-fluorobiphenyl-4-carboxylate (390 mg, 0.85 mmol) was dissolved in THF/MeOH/water=632 mL. LiOH.H₂O (71 mg, 1.70 mmol) was added thereto. And then, the mixture was refluxed with heating for 3 hours. After the completion of the reaction, the solvent was dried under reduced pressure, following with adjusting pH to below 6 using 1 N HCl. The resulting precipitate was filtered to yield the title compound as white solid (340 mg, 92%).

Step 3.

Compound 888: 4'-((1-(2-ethyl-2-fluorobutyl)piperidin-4-yl)methoxy)-3-fluorobiphenyl-4-carboxylic acid (0.03 g, 0.07 mmol), EDC (0.03 g, 0.14 mmol), HOBt (0.02 g, 0.14 mmol) and DIPEA (0.036 mL, 0.209 mmol) were dissolved in DMF (1 mL). At room temperature, (S)-pyrrolidine-3-ol (0.01 g, 0.10 mmol) was added thereto, following with stirring at 50° C. for a day. The reaction mixture was added with water, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, methanol/dichloromethane=2% to 5%), and concentrated to yield the title compound as white solid (22 mg, 63%).

1H NMR (400 MHz, CDCl₃) δ 7.49 (m, 3H), 7.39 (m, 1H), 7.28 (m, 1H), 6.98 (d, 2H, J=8.7 Hz), 4.62 (s, 0.5H), 4.49 (s, 0.5H), 3.86 (m, 2H), 3.70 (m, 2H), 3.46 (m, 1H), 2.96 (m, 2H), 2.43 (m, 2H), 1.97-1.65 (m, 11H), 0.91 (t, 6H, J=7.4 Hz); MS (ESI) m/z 501 (M+H).

According to the above-described synthesis process of compound 888, the compounds of Table 106 were synthesized using 4'-((1-(2-ethyl-2-fluorobutyl)piperidin-4-yl)methoxy)-3-fluorobiphenyl-4-carboxylic acid and the reactant of Table 105.

TABLE 105

| Compound No. | Reactant | Yield (%) |
|---|---|---|
| 810 | (R)-pyrrolidine-2-ylmethanol | 44 |
| 814 | piperidin-4-carboxamide hydrochloride | 47 |
| 866 | (S)-pyrrolidine-2-carboxamide | |
| 889 | (S)-piperidin-3-ol | 63 |
| 890 | (R)-piperidin-3-ol | 67 |

TABLE 106

| Compound No. | Compound Name, ¹H-NMR, MS (ESI) |
|---|---|
| 810 | (R)-(4'-((1-(2-ethyl-2-fluorobutyl)piperidin-4-yl)methoxy)-3-fluorobiphenyl-4-yl)(2-(hydroxymethyl)pyrrolidine-1-yl)methanone<br>1H NMR (400 MHz, CDCl₃) δ 7.47 (m, 3 H), 7.33 (m, 2 H), 6.96 (m, 2 H), 5.74 (s, 1 H), 4.42 (m, 1 H), 3.84 (d, 2 H, J = 5.9 Hz), 3.74 (m, 2 H), 3.59 (m, 2 H), 2.98 (m, 2 H), 2.48 (s, 1 H), 2.42 (s, 1 H), 1.92 (m, 11 H), 1.72 (m, 11 H), 0.89 (t, 6 H, J = 7.5 Hz); MS (ESI) m/z 515 (M + H). |
| 814 | 1-(4'-((1-(2-ethyl-2-fluorobutyl)piperidin-4-yl)methoxy)-3-fluorobiphenylcarbonyl)piperidin-4-carboxamide<br>1H NMR (400 MHz, CDCl₃) δ 7.50 (m, 2 H), 7.32 (m, 2 H), 7.27 (m, 1 H), 6.98 (m, 2 H), 5.49 (m, 1 H), 4.73 (m, 1 H), 3.84 (m, 2 H), 3.72 (m, 1 H), 3.02 (m, 4 H),<br>2.46 (m, 3 H), 2.04 (m, 2 H), 1.83 (m, 1 H), 1.68 (m, 12 H), 0.91 (t, 6 H, J = 7.5 Hz) |
| 866 | (S)-1-(4'-((1-(2-ethyl-2-fluorobutyl)piperidin-4-yl)methoxy)-3-fluorobiphenylcarbonyl)pyrrolidine-2-carboxamide<br>MS (ESI) m/z 528 (M + H). |
| 889 | (S)-(4'-((1-(2-ethyl-2-fluorobutyl)piperidin-4-yl)methoxy)-3-fluorobiphenyl-4-yl)(3-hydroxypiperidin-1-yl)methanone<br>1H NMR (400 MHz, CDCl₃) δ 7.50 (m, 2 H), 7.41 (m, 2 H), 7.27 (m, 1 H), 6.98 (d, 2 H, J = 8.7 Hz), 4.00 (m, 2 H), 3.85 (d, 2 H, J = 5.9 Hz), 3.36 (m, 1 H), 3.26 (m, 2 H), 2.95 (m, 2 H), 2.37 (m, 2 H), 2.16 (m, 2 H), 1.82-1.26 (m, 14 H), 0.91 (t, 6 H, J = 7.5 Hz); MS (ESI) m/z 515 (M + H). |
| 890 | (R)-(4'-((1-(2-ethyl-2-fluorobutyl)piperidin-4-yl)methoxy)-3-fluorobiphenyl-4-yl)(3-hydroxypiperidin-1-yl)methanone<br>1H NMR (400 MHz, CDCl₃) δ 7.51 (m, 2 H), 7.42 (m, 2 H), 7.27 (m, 1 H), 6.98 (d, 2 H, J = 6.9 Hz), 4.01 (m, 2 H), 3.85 (d, 2 H, J = 5.9 Hz), 3.57 (m, 1 H), 3.33 (m, 2 H), 3.01 (m, 2 H), 2.48 (m, 2 H), 2.18 (m, 2 H), 1.94-1.48 (m, 14 H), 0.91 (t, 6 H, J = 7.5 Hz); MS (ESI) m/z 515 (M + H). |

Example 100. Compound 895: (S)-1-(4'-((1-(2-ethyl-2-fluorobutyl)piperidin-4-yl)methoxy)-2-fluorobiphenylcarbonyl)pyrrolidine-2-carboxamide

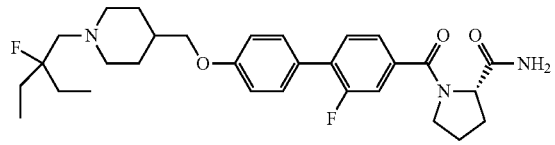 [SMILES: CCC(F)(CC)CN1CCC(COc2ccc(-c3ccc(C(=O)N4CCC[C@H]4C(N)=O)cc3)nc2)CC1]

Step 1.

Methyl 4'-((1-(2-ethyl-2-fluorobutyl)piperidin-4-yl)methoxy)-2-fluorobiphenyl-4-carboxylate: 4-((4-bromophenoxy)methyl)-1-(2-ethyl-2-fluorobutyl)piperidine (the product of synthesis step 3 of compound 809; 550 mg, 1.48 mmol), 2-fluoro-4-(methoxycarbonyl)phenylboronic acid (322 mg, 1.63 mmol), Pd(dppf)Cl₂ (60 mg, 0.07 mmol), Na₂CO₃ (313 mg, 2.95 mmol) were dissolved in DME 12 mL and water 3 mL, and then refluxed with heating for a day. The reaction mixture was filtered through Celite. The filtrate was added with saturated NaHCO₃ aqueous solution, and extracted with EtOAc. The organic layer was dried over MgSO₄, filtered to remove the solid residue, and the filtrate was concentrated under reduced pressure. The concentrate was purified by column chromatography (ISCO silica gel cartridge, EtOAc/Hexane) to yield the title compound as white solid (350 mg, 53%).
Step 2.

4'-((1-(2-ethyl-2-fluorobutyl)piperidin-4-yl)methoxy)-2-fluorobiphenyl-4-carboxylic acid: Methyl 4'-((1-(2-ethyl-2-fluorobutyl)piperidin-4-yl)methoxy)-2-fluorobiphenyl-4-carboxylate (350 mg, 0.79 mmol) was dissolved in THF/MeOH/water=632 mL. LiOH.H$_2$O (66 mg, 1.57 mmol) was added thereto. And then, the mixture was refluxed with heating for 3 hours. After the completion of the reaction, the solvent was dried under reduced pressure, following with adjusting pH to below 6 using 1 N HCl. The resulting precipitate was filtered to yield the title compound as white solid (310 mg, 91%).
Step 3.

Compound 895: 4'-((1-(2-ethyl-2-fluorobutyl)piperidin-4-yl)methoxy)-2-fluorobiphenyl-4-carboxylic acid (0.03 g, 0.07 mmol), EDC (0.03 g, 0.14 mmol), HOBt (0.02 g, 0.14 mmol) and DIPEA (0.04 mL, 0.21 mmol) were dissolved in DMF (1 mL). At room temperature, (S)-pyrrolidine-2-carboxamide (12 mg, 0.10 mmol) was added thereto, following with stirring at 50° C. for a day. The reaction mixture was added with water, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, methanol/dichloromethane=2% to 5%), and concentrated to yield the title compound as white solid (23 mg, 62%).

1H NMR (400 MHz, CDCl$_3$) δ 7.48 (m, 3H), 7.35 (m, 2H), 6.97 (d, 2H, J=8.7 Hz), 6.91 (s, 1H), 5.56 (s, 1H), 4.78 (m, 1H), 3.84 (d, 2H, J=5.9 Hz), 3.61 (m, 2H), 3.00 (m, 2H), 2.44 (m, 2H), 2.03 (m, 4H), 1.89-1.44 (m, 12H), 0.89 (t, 6H, J=7.5 Hz); MS (ESI) m/z 528 (M+H).

According to the above-described synthesis process of compound 895, the compounds of Table 108 were synthesized using 4'-((1-(2-ethyl-2-fluorobutyl)piperidin-4-yl)methoxy)-2-fluorobiphenyl-4-carboxylic acid and the reactant of Table 107.

TABLE 107

| Compound No. | Reactant | Yield (%) |
| --- | --- | --- |
| 811 | (R)-pyrrolidine-2-ylmethanol | 67 |
| 812 | (R)-piperidin-3-ol hydrochloride | 57 |

Example 101. Compound 896: (S)-1-(4-(5-((1-(2-ethyl-2-fluorobutyl)piperidin-4-yl)methoxy)pyridine-2-yl)benzoyl)pyrrolidine-2-carboxamide

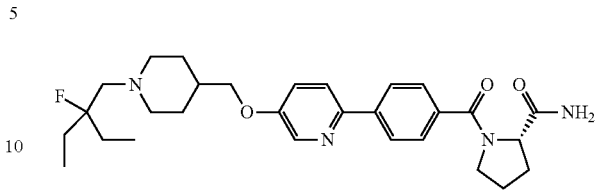

Step 1.

3-((4-(((6-chloropyridine-3-yloxy)methyl)piperidin-1-yl)methyl)pentane-3-ol: 2-chloro-5-(piperidin-4-ylmethoxy)pyridine hydrochloride (the product of synthesis step 2 of compound 691; 1.4 g, 5.32 mmol) was dissolved in EtOH 6 mL. 2,2-diethyloxirane (the product of synthesis step 1 of compound 809; 1.60 g, 15.96 mmol), K$_2$CO$_3$ (1.47 g, 10.64 mmol) and water 3 mL were added thereto, With a microwave radiation, the mixture was stirred at 110° C. for 20 minutes. Ethanol was evaporated from the reaction mixture under reduced pressure, and water was added thereto. The resulting precipitate was filtered, and dried under reduced pressure to yield the title compound as white solid (1.61 g, 92%).
Step 2.

2-chloro-5-((1-(2-ethyl-2-fluorobutyl)piperidin-4-yl)methoxy)pyridine: 3-((4-(((6-chloropyridine-3-yloxy)methyl)piperidin-1-yl)methyl)pentane-3-ol (1.61 g, 4.93 mmol) was dissolved in CH$_2$Cl$_2$ 10 mL. DAST (873 mg, 5.42 mmol) was added thereto, following with stirring at room temperature for 3 hours. After the completion of the reaction, the reaction mixture was added with a saturated NaHCO$_3$ aqueous solution, and extracted with CH$_2$Cl$_2$. The organic layer washed with saturated aqueous brine solution, dried over MgSO$_4$, and filtered to remove the solid residue. The filtrate was concentrated under reduced pressure. The concentrate was purified by column chromatography (40 g ISCO silica gel cartridge, 15-20% HexaneEtOAc) to yield the title compound as white solid (1.24 g, 76%).
Step 3.

Methyl 4-(5-((1-(2-ethyl-2-fluorobutyl)piperidin-4-yl)methoxy)pyridine-2-yl)benzoate: 2-chloro-5-((1-(2-ethyl-2-fluorobutyl)piperidin-4-yl)methoxy)pyridine (550 mg, 1.67 mmol), 4-(methoxycarbonyl)phenylboronic acid (331 mg, 1.84 mmol), Pd(dppf)Cl$_2$ (68 mg, 0.08 mmol) and Na$_2$CO$_3$ (354 mg, 3.35 mmol) were dissolved in DME 12 mL and water 3 mL, and then refluxed with heating and stirring for a day. The reaction mixture was filtered through Celite. The filtrate was added with saturated NaHCO$_3$ aqueous solution,

TABLE 108

| Compound No. | Compound Name, $^1$H-NMR, MS (ESI) |
| --- | --- |
| 811 | (R)-(4'-((1-(2-ethyl-2-fluorobutyl)piperidin-4-yl)methoxy)-2-fluorobiphenyl-4-yl)(2-(hydroxymethyl)pyrrolidine-1-yl)methanone<br>1H NMR (400 MHz, CDCl$_3$) δ 7.49 (m, 3 H), 7.37 (m, 2 H), 7.28 (m, 1 H), 6.95 (m, 2 H), 4.78 (s, 1 H), 4.37 (m, 1 H), 3.78 (m, 4 H), 3.45 (m, 2 H), 2.98 (m, 2 H), 2.47 (s, 1 H), 2.41 (s, 1 H), 2.17 (m, 3 H), 1.87 (m, 1 H), 1.75 (m, 10 H), 0.89 (t, 6 H, J = 7.5 Hz) |
| 812 | (R)-(4'-((1-(2-ethyl-2-fluorobutyl)piperidin-4-yl)methoxy)-2-fluorobiphenyl-4-yl)(3-hydroxypiperidin-1-yl)methanone<br>1H NMR (400 MHz, CDCl$_3$) δ 7.45 (m, 3 H), 7.21 (m, 2 H), 6.97 (m, 2 H), 3.91 (m, 4 H), 3.56 (m, 3 H), 2.99 (m, 2 H), 2.49 (s, 1 H), 2.43 (s, 1 H), 2.15 (m, 2 H), 1.71 (m, 13 H), 0.89 (t, 6 H, J = 7.5 Hz); MS (ESI) m/z 515 (M + H). | and extracted with EtOAc. The organic layer was dried over MgSO₄, filtered to remove the solid residue, and the filtrate was concentrated under reduced pressure. The concentrate was purified by column chromatography (ISCO silica gel cartridge, EtOAc/Hexane) to yield the title compound as white solid (310 mg, 43%).
Step 4.

4-(5-((1-(2-ethyl-2-fluorobutyl)piperidin-4-yl)methoxy)pyridine-2-yl)benzoic acid: methyl 4-(5-((1-(2-ethyl-2-fluorobutyl)piperidin-4-yl)methoxy)pyridine-2-yl)benzoate (310 mg, 0.98 mmol) was dissolved in THF/MeOH/water=632 mL. LiOH.H₂O (61 mg, 1.45 mmol) was added thereto. And then, the mixture was refluxed with heating for 3 hours. After the completion of the reaction, the solvent was dried under reduced pressure, following with adjusting pH to below 6 using 1 N HCl. The resulting precipitate was filtered to yield the title compound as white solid (210 mg, 70%).
Step 5.

Compound 896: 4-(5-((1-(2-ethyl-2-fluorobutyl)piperidin-4-yl)methoxy)pyridine-2-yl)benzoic acid (0.05 g, 0.12 mmol), EDC (0.05 g, 0.24 mmol), HOBt (0.03 g, 0.24 mmol) and DIPEA (0.06 mL, 0.36 mmol) were dissolved in CH₂Cl₂ (3 mL). At room temperature, (S)-pyrrolidine-2-carboxamide (0.02 g, 0.18 mmol) was added thereto, following with stirring with at the same temperature for a day. The reaction mixture was added with water, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, methanol/dichloromethane=2% to 5%), and concentrated to yield the title compound as white solid (0.04 g, 61%).

1H NMR (400 MHz, CDCl₃) δ 8.37 (d, 1H, J=2.6 Hz), 7.97 (d, 2H, J=8.2 Hz), 7.62 (m, 3H), 7.26 (m, 1H), 7.06 (s, 1H), 5.78 (s, 1H), 4.78 (m, 1H), 3.88 (d, 2H, J=5.9 Hz), 3.61 (m, 2H), 3.00 (d, 2H, J=10.7 Hz), 2.49-2.43 (m, 2H), 2.38 (m, 1H), 2.08 (m, 4H), 1.80 (m, 8H), 1.42 (m, 2H), 0.88 (t, 6H, J=7.5 Hz); MS (ESI) m/z 511 (M+H).

According to the above-described synthesis process of compound 896, the compounds of Table 110 were synthesized using 4-(5-((1-(2-ethyl-2-fluorobutyl)piperidin-4-yl)methoxy)pyridine-2-yl)benzoic acid and the reactant of Table 109.

TABLE 109

| Compound No. | Reactant | Yield (%) |
|---|---|---|
| 897 | (R)-piperidin-3-ol | 51 |

Example 102. Compound 898: (S)-1-(4-(5-((1-(2-ethyl-2-fluorobutyl)piperidin-4-yl)methoxy)pyridine-2-yl)-2-fluorobenzoyl)pyrrolidine-2-carboxamide

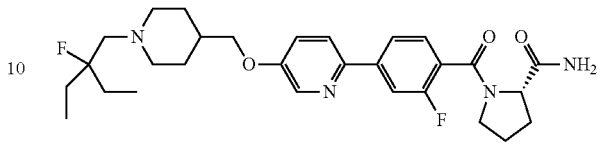

Step 1.

Ethyl 4-(5-((1-(2-ethyl-2-fluorobutyl)piperidin-4-yl)methoxy)pyridine-2-yl)-2-fluorobenzoate: 2-chloro-5-((1-(2-ethyl-2-fluorobutyl)piperidin-4-yl)methoxy)pyridine (the product of synthesis step 2 of compound 896; 550 mg, 1.67 mmol), 4-(ethoxycarbonyl)-3-fluorophenylboronic acid (390 mg, 1.84 mmol), Pd(dppf)Cl₂ (68 mg, 0.08 mmol) and Na₂CO₃ (354 mg, 3.35 mmol) were dissolved in DME 12 mL and water 3 mL, and then refluxed with heating for a day. The reaction mixture was filtered through Celite. The filtrate was added with saturated NaHCO₃ aqueous solution, and extracted with EtOAc. The organic layer was dried over MgSO₄, filtered to remove the solid residue, and the filtrate was concentrated under reduced pressure. The concentrate was purified by column chromatography (ISCO silica gel cartridge, EtOAc/Hexane) to yield the title compound as white solid (290 mg, 37%).
Step 2.

4-(5-((1-(2-ethyl-2-fluorobutyl)piperidin-4-yl)methoxy)pyridine-2-yl)-2-fluorobenzoic acid: Ethyl 4-(5-((1-(2-ethyl-2-fluorobutyl)piperidin-4-yl)methoxy)pyridine-2-yl)-2-fluorobenzoate (290 mg, 0.63 mmol) was dissolved in THF/MeOH/water=632 mL. LiOH.H₂O (53 mg, 1.26 mmol) was added thereto. And then, the mixture was refluxed with heating for 3 hours. After the completion of the reaction, the solvent was dried under reduced pressure, following with adjusting pH to below 6 using 1 N HCl. The resulting precipitate was filtered to yield the title compound as white solid (220 mg, 80%).
Step 3.

Compound 898: 4-(5-((1-(2-ethyl-2-fluorobutyl)piperidin-4-yl)methoxy)pyridine-2-yl)-2-fluorobenzoic acid (0.05 g, 0.12 mmol), EDC (0.05 g, 0.24 mmol), HOBt (0.03 g, 0.24 mmol) and DIPEA (0.06 mL, 0.36 mmol) were dissolved in CH₂Cl₂ (3 mL). At room temperature, (S)-pyrrolidine-2-carboxamide (0.02 g, 0.18 mmol) was added thereto, following with stirring with at the same temperature for a day. The reaction mixture was added with water, and extracted with EtOAc. The obtained organic layer was washed with saturated aqueous brine solution, dried over

TABLE 110

Compound No. Compound Name, ¹H-NMR, MS (ESI)

| 897 | (R)-(4-(5-((1-(2-ethyl-2-fluorobutyl)piperidin-4-yl)methoxy)pyridine-2-yl)phenyl)(3-hydroxypiperidin-1-yl)methanone<br>1H NMR (400 MHz, CDCl₃) δ 8.37 (d, 1 H, J = 2.8 Hz), 7.94 (d, 2 H, J = 8.1 Hz), 7.65 (d, 1 H, J = 8.7 Hz), 7.49 (d, 2 H, J = 8.0 Hz), 7.26 (dd, 1 H, J = 8.7, 2.8 Hz), 3.88 (m, 5 H), 3.26 (m, 3 H), 3.00 (d, 2 H, J = 10.4 Hz), 2.48-2.42 (m, 2 H), 2.14 (m, 2 H), 1.81 (m, 3 H), 1.74 (m, 7 H), 1.45 (m, 3 H), 0.89 (t, 6 H, J = 7.5 Hz); MS (ESI) m/z 498 (M + H). |
|---|---| anhydrous MgSO₄, and filtered. The filtrate was concentrated under reduced pressure. The concentrate was purified by column chromatography (SiO₂, methanol/dichloromethane=2% to 5%), and concentrated to yield the title compound as white solid (0.04 g, 61%).

1H NMR (400 MHz, CDCl₃) δ 8.37 (d, 1H, J=2.9 Hz), 7.75 (m, 2H), 7.67 (d, 1H, J=8.8 Hz), 7.49 (t, 1H, J=7.6 Hz), 7.27 (dd, 1H, J=8.5, 3.1 Hz), 6.93 (s, 1H), 5.64 (s, 1H), 4.81 (m, 1H), 3.89 (d, 2H, J=6.0 Hz), 3.50 (m, 1H), 3.40 (m, 1H), 3.00 (m, 2H), 2.43 (m, 3H), 2.08 (m, 4H), 1.92-1.46 (m, 10H), 0.89 (t, 6H, J=7.5 Hz); MS (ESI) m/z 529 (M+H).

According to the above-described synthesis process of compound 898, the compounds of Table 112 were synthesized using 4-(5-((1-(2-ethyl-2-fluorobutyl)piperidin-4-yl)methoxy)pyridine-2-yl)-2-fluorobenzoic acid and the reactant of Table 111.

TABLE 111

| Compound No. | Reactant | Yield (%) |
|---|---|---|
| 899 | (S)-pyrrolidine-3-ol | 51 |
| 900 | (R)-piperidin-3-ol | 58 |

TABLE 112

| Compound No. | Compound Name, ¹H-NMR, MS (ESI) |
|---|---|
| 899 | (S)-(4-(5-((1-(2-ethyl-2-fluorobutyl)piperidin-4-yl)methoxy)pyridine-2-yl)-2-fluorophenyl)(3-hydroxypyrrolidine-1-yl)methanone<br>1H NMR (400 MHz, CDCl₃) δ 8.38 (d, 1 H, J = 2.7 Hz), 7.75 (m, 2 H), 7.66 (d, 1 H, J = 8.7 Hz), 7.51 (m, 1 H), 7.27 (m, 1 H), 4.61 (s, 0.5 H), 4.49 (s, 0.5 H), 3.91 (d, 2 H, J = 5.8 Hz), 3.77 (m, 1 H), 3.59 (m, 2 H), 3.35 (m, 1 H), 3.02 (m, 2 H), 2.43 (m, 2 H), 2.07 (m, 5 H), 1.98 (m, 9 H), 0.91 (t, 6 H, J = 7.5 Hz); MS (ESI) m/z 502 (M + H). |
| 900 | (R)-(4-(5-((1-(2-ethyl-2-fluorobutyl)piperidin-4-yl)methoxy)pyridine-2-yl)-2-fluorophenyl)(3-hydroxypiperidin-1-yl)methanone<br>1H NMR (400 MHz, CDCl₃) δ 8.36 (m, 1 H), 7.65 (m, 3 H), 7.45 (t, 1 H, J = 7.5 Hz), 7.26 (dd, 1 H, J = 9.1, 2.5 Hz), 4.07 (m, 1 H), 3.89 (d, 2 H, J = 6.0 Hz), 3.52 (m, 2 H), 3.23 (m, 2 H), 3.00 (m, 2 H), 2.49-2.43 (m, 2 H), 2.15 (m, 2 H), 1.91-1.59 (m, 13 H), 0.91 (t, 6 H, J = 7.5 Hz); MS (ESI) m/z 516 (M + H). |

Example 103. Compound 954: (R)-(4-(6-((1-(2-ethyl-2-fluorobutyl)piperidin-4-yl)methoxy)pyridine-3-yl)phenyl)(3-hydroxypiperidin-1-yl)methanone

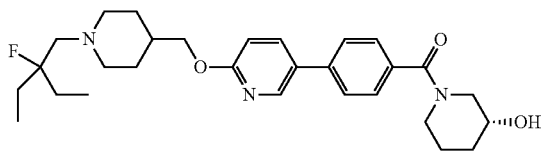 [SMILES: CCC(F)(CC)CN1CCC(COc2ccc(-c3ccc(C(=O)N4CCC[C@@H](O)C4)cc3)cn2)CC1]

Step 1.

3-((4-((5-bromopyridine-2-yloxy)methyl)piperidin-1-yl)methyl)pentane-3-ol: To 5-bromo-2-(piperidin-4-ylmethoxy)pyridine hydrochloride (the product of synthesis step 3 of compound 784; 2.70 g, 8.77 mmol), 2,2-diethyloxirane (the product of synthesis step 1 of compound 809; 4.39 g, 43.88 mmol) and K₂CO₃ (2.42 g, 17.55 mmol), EtOH (6 mL)/H₂O (3 mL) was added. With a microwave radiation, the mixture was heated at 115° C. for 20 minutes, and then cooled to room temperature. The reaction mixture was added with water, and extracted with EtOAc. The obtained organic layer was washed with saturated aqueous brine solution, dried over anhydrous MgSO₄, and filtered. The filtrate was concentrated under reduced pressure. The obtained material was used without further purifying process (1.50 g, 46%, yellow oil).

Step 2.

5-bromo-2-((1-(2-ethyl-2-fluorobutyl)piperidin-4-yl)methoxy)pyridine: 3-((4-((5-bromopyridine-2-yloxy)methyl)piperidin-1-yl)methyl)pentane-3-ol (1.50 g, 4.04 mmol) was dissolved in CH₂Cl₂ (8 mL). At 0° C., DAST (0.58 mL, 4.44 mmol) was added thereto, following with stirring at room temperature for 3 hours. After the completion of the reaction, the reaction mixture was added with saturated NaHCO₃ aqueous solution, and extracted with EtOAc. The obtained organic layer was washed with saturated aqueous brine solution, dried over anhydrous MgSO₄, and filtered. The filtrate was concentrated under reduced pressure. The obtained material was used without further purifying process (0.95 g, 63%, yellow oil).

Step 3.

Methyl 4-(6-((1-(2-ethyl-2-fluorobutyl)piperidin-4-yl)methoxy)pyridine-3-yl)benzoate: 5-bromo-2-((1-(2-ethyl-2-fluorobutyl)piperidin-4-yl)methoxy)pyridine (0.30 g, 0.80 mmol), 4-(methoxycarbonyl)phenylboronic acid (0.17 g, 0.96 mmol), Pd(dppf)Cl₂ (0.06 g, 0.08 mmol) and Na₂CO₃ (0.17 g, 1.60 mmol) were dissolved in DME (12 mL)/water (3 mL). With a microwave radiation, the mixture was heated at 120° C. for 20 minutes, and then cooled to room temperature. The reaction mixture was filtered through a Celite pad to remove a solid. The filtrate was added with saturated NaHCO₃ aqueous solution was added thereto, and extracted with EtOAc. The organic layer was washed with saturated aqueous brine solution, dried over anhydrous MgSO₄, and filtered. The filtrate was concentrated under reduced pressure. The concentrate was purified by column chromatography (SiO₂, 12 g cartridge; EtOAc/hexane=20% to 30%), and concentrated to yield the title compound as white solid (0.21 g, 61%).

Step 4.

4-(6-((1-(2-ethyl-2-fluorobutyl)piperidin-4-yl)methoxy)pyridine-3-yl)-2-fluorobenzoic acid: Methyl 4-(6-((1-(2-ethyl-2-fluorobutyl)piperidin-4-yl)methoxy)pyridine-3-yl)benzoate (0.18 g, 0.39 mmol) and LiOH.H₂O (0.03 g, 0.78 mmol) were dissolved in THF/MeOH (6 mL/3 mL)/water (2 mL). The mixture was refluxed with heating for 10 hours, and then cooled to room temperature, following with concentrating under reduced pressure. After the addition of water to the concentrate, the resulting precipitate was filtered, and dried to yield the title compound as yellow solid (0.15 g, 88%).

Step 5.

Compound 954: 4-(6-((1-(2-ethyl-2-fluorobutyl)piperidin-4-yl)methoxy)pyridine-3-yl)-2-fluorobenzoic acid (0.04 g, 0.09 mmol), EDC (0.03 g, 0.19 mmol), HOBt (0.02 g, 0.19 mmol) and DIPEA (0.03 g, 0.28 mmol) were dissolved in DMF (1 mL). At room temperature, (R)-piperidin-3-ol (0.02 g, 0.15 mmol) was added thereto, following with stirring at 50° C. for 8 hours. The reaction mixture was added with water, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, 4 g cartridge; dichloromethane/methanol=0% to 5%), and concentrated to yield the title compound as white solid (0.02 g, 31%).

1H NMR (400 MHz, CDCl₃) δ 8.36 (d, 1H, J=2.5 Hz), 7.78 (dd, 1H, J=8.6, 2.6 Hz), 7.52 (m, 4H), 6.81 (d, 1H, J=8.6 Hz), 4.17 (d, 2H, J=6.2 Hz), 3.98-3.05 (m, 6H). 2.96 (m, 2H), 2.46-2.39 (m, 2H), 2.11 (m, 2H), 1.95 (m, 3H), 1.69 (m, 8H), 1.43 (m, 3H), 0.88 (t, 6H, J=7.5 Hz); MS (ESI) m/z 498 (M+H).

According to the above-described synthesis process of compound 954, the compounds of Table 114 were synthesized using 4-(6-((1-(2-ethyl-2-fluorobutyl)piperidin-4-yl)methoxy)pyridine-3-yl)-2-fluorobenzoic acid and the reactant of Table 113.

TABLE 113

| Compound No. | Reactant | Yield (%) |
|---|---|---|
| 955 | (S)-piperidin-3-ol | 37 |

TABLE 114

| Compound No. | Compound Name, ¹H-NMR, MS (ESI) |
|---|---|
| 955 | (S)-(4-(6-((1-(2-ethyl-2-fluorobutyl)piperidin-4-yl)methoxy)pyridine-3-yl)phenyl)(3-hydroxypiperidin-1-yl)methanone<br>1H NMR (400 MHz, CDCl₃) δ 8.36 (d, 1 H, J = 2.5 Hz), 7.77 (dd, 1 H, J = 8.6, 2.5 Hz), 7.52 (m, 4 H), 6.81 (d, 1 H, J = 8.6 Hz), 4.17 (d, 2 H, J = 6.2 Hz), 4.01-3.08 (m, 5 H), 2.96 (m, 2 H), 2.46-2.40 (m, 2 H), 2.11 (m, 2 H), 1.93-1.63 (m, 12 H), 1.42 (m, 2 H), 0.88 (t, 6 H, J = 7.5 Hz)(S)-(4-(5-((1-(2-ethyl-2-fluorobutyl)piperidin-4-yl)methoxy)pyridine-2-yl)-2-fluorophenyl)(3-hydroxypyrrolidine-1-yl)methanone |

Example 104. Compound 956: (R)-(4-(6-((1-(2-ethyl-2-fluorobutyl)piperidin-4-yl)methoxy)pyridine-3-yl)-2-fluorophenyl)(3-hydroxypiperidin-1-yl)methanone

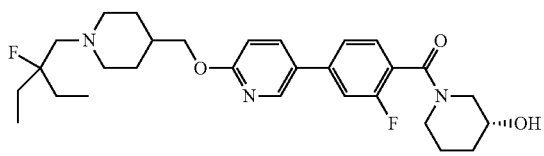 [SMILES: CCC(F)(CC)CN1CCC(COc2ccc(-c3ccc(C(=O)N4CCC[C@@H](O)C4)c(F)c3)cn2)CC1]

Step 1.

Ethyl 4-(6-((1-(2-ethyl-2-fluorobutyl)piperidin-4-yl)methoxy)pyridine-3-yl)-2-fluorobenzoate: To 5-bromo-2-((1-(2-ethyl-2-fluorobutyl)piperidin-4-yl)methoxy)pyridine (the product of synthesis step 2 of compound 954; 0.30 g, 0.80 mmol), 4-(ethoxycarbonyl)-3-fluorophenylboronic acid (0.18 g, 0.88 mmol), Pd(dppf)Cl₂ (0.06 g, 0.08 mmol) and Na₂CO₃ (0.17 g, 1.60 mmol), DME (12 mL)/water (3 mL) was added. With a microwave radiation, the mixture was heated at 120° C. for 20 minutes, and then cooled to room temperature. The reaction mixture was filtered through a Celite pad to remove a solid. The filtrate was added with saturated NaHCO₃ aqueous solution was added thereto, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, 12 g cartridge; EtOAc/hexane=20% to 30%), and concentrated to yield the title compound as white solid (0.18 g, 48%).

Step 2.

4-(6-((1-(2-ethyl-2-fluorobutyl)piperidin-4-yl)methoxy)pyridine-3-yl)-2-fluorobenzoic acid: Ethyl 4-(6-((1-(2-ethyl-2-fluorobutyl)piperidin-4-yl)methoxy)pyridine-3-yl)-2-fluorobenzoate (0.18 g, 0.39 mmol) and LiOH.H₂O (0.03 g, 0.78 mmol) were dissolved in THF/MeOH (6 mL/3 mL)/water (2 mL). The mixture was refluxed with heating for 10 hours, and then cooled to room temperature, following with concentrating under reduced pressure. After the addition of water to the concentrate, the resulting precipitate was filtered, and dried to yield the title compound as yellow solid (0.15 g, 88%).

Step 3.

Compound 956: 4-(6-((1-(2-ethyl-2-fluorobutyl)piperidin-4-yl)methoxy)pyridine-3-yl)-2-fluorobenzoic acid (0.04 g, 0.08 mmol), EDC (0.03 g, 0.16 mmol), HOBt (0.02 g, 0.16 mmol) and DIPEA (0.03 g, 0.24 mmol) were dissolved in DMF (1 mL). At room temperature, (R)-piperidin-3-ol (0.01 g, 0.12 mmol) was added thereto, following with stirring at 50° C. for 8 hours. The reaction mixture was added with water, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, 4 g cartridge; dichloromethane/methanol=0% to 5%), and concentrated to yield the title compound as white solid (17 mg, 40%).

1H NMR (400 MHz, CDCl₃) δ 8.34 (s, 1H), 7.75 (m, 1H), 7.44 (m, 1H), 7.35 (m, 1H), 7.24 (m, 1H), 6.81 (d, 1H, J=8.6 Hz), 4.17 (d, 2H, J=6.1 Hz), 3.92 (m, 2H), 3.33 (m, 3H), 2.96 (m, 2H), 2.46-2.40 (m, 2H), 1.96 (m, 6H), 1.69 (m, 8H), 1.39 (m, 2H), 0.88 (t, 6H, J=7.5 Hz); MS (ESI) m/z 516 (M+H).

According to the above-described synthesis process of compound 956, the compounds of Table 116 were synthesized using 4-(6-((1-(2-ethyl-2-fluorobutyl)piperidin-4-yl)methoxy)pyridine-3-yl)-2-fluorobenzoic acid and the reactant of Table 115.

TABLE 115

| Compound No. | Reactant | Yield (%) |
| --- | --- | --- |
| 957 | (S)-piperidin-3-ol | 35 |

TABLE 116

Compound No. Compound Name, $^1$H-NMR, MS (ESI)

| | |
| --- | --- |
| 957 | (S)-(4-(6-((1-(2-ethyl-2-fluorobutyl)piperidin-4-yl)methoxy)pyridine-3-yl)-2-fluorophenyl)(3-hydroxypiperidin-1-yl)methanone<br>1H NMR (400 MHz, CDCl$_3$) δ 8.33 (m, 1 H), 7.74 (m, 1 H), 7.43 (m, 1 H), 7.34 (m, 1 H), 7.24 (m, 1 H), 6.81 (d, 1 H, J = 8.6 Hz), 4.17 (d, 2 H, J = 6.2 Hz), 4.08-3.63 (m, 2 H), 3.58-3.02 (m, 3 H), 2.96 (m, 2 H), 2.45-2.39 (m, 2 H), 2.08 (m, 2 H), 1.95 (m, 3 H), 1.68 (m, 10 H), 1.42 (m, 2 H), 0.88 (t, 6 H, J = 7.5 Hz); MS (ESI) m/z 516 (M + H). |

Example 105. Compound 953: (S)-1-(4-(6-((1-(2-ethyl-2-fluorobutyl)piperidin-4-yl)methoxy)pyridazine-3-yl)benzoyl)pyrrolidine-2-carboxamide

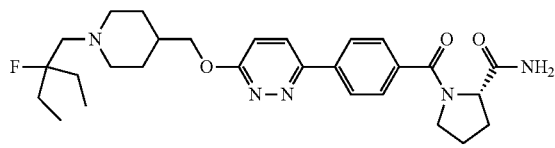 [SMILES: CCC(F)(CC)CN1CCC(COc2ccc(-c3ccc(C(=O)N4CCC[C@H]4C(N)=O)cc3)nn2)CC1]

Step 1.

t-butyl 4-((6-chloropyridazine-3-yloxy)methyl)piperidin-1-carboxylate: t-butyl 4-(hydroxymethyl)piperidin-1-carboxylate (the product of synthesis step 1 of compound 686; 3.00 g, 13.94 mmol) and NaH (0.50 g, 20.90 mmol) were dissolved in DMF (100 ml). At 0° C., 3,6-dichloropyridazine (2.49 g, 16.72 mmol) was added thereto, following with stirring at room temperature for 12 hours. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 40 g cartridge; EtOAc/hexane=0% to 50%), and concentrated to yield the title compound as white solid (2.60 g, 56%).

Step 2.

3-chloro-6-(piperidin-4-ylmethoxy)pyridazine: t-butyl 4-((6-chloropyridazine-3-yloxy)methyl)piperidin-1-carboxylate (2.60 g, 7.93 mmol) and HCl in 1,4-dioxane (4 M solution in 1,4-dioxane, 9.91 mL, 39.66 mmol) were dissolved in MeOH (30 mL) at room temperature. The solution was stirred at the same temperature for 3 hours, the reaction mixture was concentrated under reduced pressure. The resulting precipitate was filtered, and dried to yield the title compound as white solid (1.80 g, 85%).

Step 3.

3-((4-((6-chloropyridazine-3-yloxy)methyl)piperidin-1-yl)methyl)pentane-3-ol: 3-chloro-6-(piperidin-4-ylmethoxy)pyridazine (1.20 g, 5.27 mmol) and Et$_3$N (7.31 mL, 52.70 mmol) were dissolved in EtOH (10 mL). 2,2-diethyloxirane (the product of synthesis step 1 of compound 809; 1.06 g, 10.54 mmol) was added thereto. With a microwave radiation, the mixture was heated at 110° C. for 20 minutes, and then cooled to room temperature. The reaction mixture was added with water, and extracted with EtOAc. The obtained organic layer was washed with saturated aqueous brine solution, dried over anhydrous MgSO$_4$, and filtered. The filtrate was concentrated under reduced pressure. The obtained material was used without further purifying process (0.30 g, 17%, white solid).

Step 4.

3-chloro-6-((1-(2-ethyl-2-fluorobutyl)piperidin-4-yl)methoxy)pyridazine: 3-((4-((6-chloropyridazine-3-yloxy)methyl)piperidin-1-yl)methyl)pentane-3-ol (0.30 g, 0.91 mmol) was dissolved in dichloromethane (20 mL). At 0° C., DAST (0.16 g, 1.00 mmol) was added thereto, following with stirring at room temperature for 1 hour. The reaction mixture was added with water, and extracted with dichloromethane. The obtained organic layer was washed with saturated NaHCO$_3$ aqueous solution. The organic layer was dried over anhydrous MgSO$_4$, and filtered. The filtrate was concentrated under reduced pressure. The concentrate was purified by column chromatography (SiO$_2$, 12 g cartridge; EtOAc/hexane=0% to 50%), and concentrated to yield the title compound as yellow solid (0.14 g, 46%).

Step 5.

Methyl 4-(6-((1-(2-ethyl-2-fluorobutyl)piperidin-4-yl)methoxy)pyridazine-3-yl)benzoate: 3-chloro-6-((1-(2-ethyl-2-fluorobutyl)piperidin-4-yl)methoxy)pyridazine (0.14 g, 0.42 mmol), 4-(methoxycarbonyl)phenylboronic acid (0.08 g, 0.42 mmol), Pd(dbpf)Cl$_2$ (0.01 g, 0.02 mmol) and Cs$_2$CO$_3$ (0.27 g, 0.85 mmol) were added to 1,4-dioxane (12 mL)/H$_2$O (3 mL). With a microwave radiation, the mixture was heated at 115° C. for 20 minutes, and then cooled to room temperature. The reaction mixture was filtered through a Celite pad to remove a solid. The obtained filtrate was diluted with water, and extracted with dichloromethane. The obtained organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=0% to 80%), and concentrated to yield the title compound as white solid (0.05 g, 37%).

Step 6.

4-(6-((1-(2-ethyl-2-fluorobutyl)piperidin-4-yl)methoxy)pyridazine-3-yl)benzoic acid: methyl 4-(6-((1-(2-ethyl-2-fluorobutyl)piperidin-4-yl)methoxy)pyridazine-3-yl)benzoate (0.05 g, 0.12 mmol) and LiOH.H$_2$O (0.02 g, 0.58 mmol) were dissolved in THF (2 mL)/H$_2$O/MeOH (3 mL) at room temperature. The solution was stirred at the same temperature for 1 hour. The reaction mixture was concentrated under reduced pressure. The concentrate was added with water (10 mL) to be suspended, and filtered. The obtained solid was dried to yield the title compound as yellow solid (0.05 g, 93%).

Step 7.

Compound 953: 4-(6-((1-(2-ethyl-2-fluorobutyl)piperidin-4-yl)methoxy)pyridazine-3-yl)benzoic acid (0.02 g, 0.05 mmol), EDCI (0.02 g, 0.10 mmol), HOBt (0.01 g, 0.10 mmol) and DIPEA (0.03 g, 0.24 mmol) were dissolved in DMF (2 mL). At room temperature, (S)-pyrrolidine-2-carboxamide (0.01 g, 0.10 mmol) was added thereto, following with stirring at 60° C. for 12 hours. The concentrate was added with water (10 mL) to be suspended, and filtered. The obtained solid was dried, and purified by column chromatography (SiO$_2$, 4 g cartridge; methanol/dichloromethane=0% to 10%), and concentrated yield the title compound as light-yellow solid (0.01 g, 44%).

1H NMR (400 MHz, CDCl$_3$) δ 8.05 (d, 2H, J=8.1 Hz), 7.79 (d, 1H, J=9.3 Hz), 7.64 (d, 2H, J=10.0 Hz), 7.04 (d, 2H, J=9.3 Hz), 6.95 (brs, 1H), 4.81-4.80 (m, 1H), 4.42 (d, 2H, J=6.4 Hz), 3.59-3.53 (m, 2H), 2.96 (d, 2H, J=11.2 Hz), 2.44-2.38 (m, 3H), 2.13-1.62 (m, 11H), 1.46-1.23 (m, 3H), 0.87 (t, 6H, J=7.4 Hz); MS (ESI) m/z 512 (M++H).

Example 106. Compound 1004: (S)-1-(3'-cyano-4'-((1-(2-ethyl-2-fluorobutyl)piperidin-4-yl)methoxy)biphenylcarbonyl)pyrrolidine-2-carboxamide

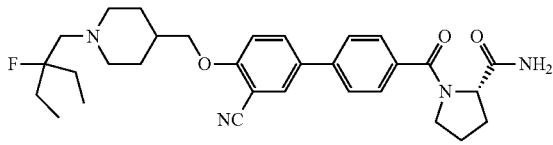 [SMILES: CCC(F)(CC)CN1CCC(COc2ccc(-c3ccc(C(=O)N4CCC[C@H]4C(N)=O)c(F)c3)cc2C#N)CC1]

Step 1.

Methyl 3'-cyano-4'-((1-(2-ethyl-2-fluorobutyl)piperidin-4-yl)methoxy)biphenyl-4-carboxylate: 5-bromo-2-((1-(2-ethyl-2-fluorobutyl)piperidin-4-yl)methoxy)benzonitrile (the product of synthesis step 4 of compound 1000; 400 mg, 1.01 mmol), 4-(methoxycarbonyl)phenylboronic acid (199 mg, 1.11 mmol), Pd(dppf)Cl$_2$ (82 mg, 0.10 mmol) and Cs$_2$CO$_3$ (656 mg, 2.01 mmol) were added to water (2 mL)/DME (6 mL). With a microwave radiation, the mixture was heated at 110° C. for 15 minutes, and then cooled to room temperature. The reaction mixture was added with water, and extracted with EtOAc. The obtained organic layer was washed with saturated aqueous brine solution, dried over anhydrous MgSO$_4$, and concentrated under reduced pressure. The obtained concentrate was purified by silica gel column chromatography (EtOAc/hexane=30%~70%) to yield the title compound as white solid (184 mg, 40%).

Step 2.

3'-cyano-4'-((1-(2-ethyl-2-fluorobutyl)piperidin-4-yl)methoxy)biphenyl-4-carboxylic acid: Methyl 3'-cyano-4'-((1-(2-ethyl-2-fluorobutyl)piperidin-4-yl)methoxy)biphenyl-4-carboxylate (184 mg, 0.41 mmol) was dissolved in THF (10 mL) and water (5 mL). LiOH.H$_2$O (85 mg, 2.03 mmol) was added thereto little by little at room temperature, following with stirring for 1 hour. After the completion of the reaction, the reaction mixture was concentrated under reduced pressure. The resulting precipitate was filtered, and dried to yield the title compound as white solid (158 mg, 88%).

Step 3.

Compound 1004: 3'-cyano-4'-((1-(2-ethyl-2-fluorobutyl)piperidin-4-yl)methoxy)biphenyl-4-carboxylic acid (35 mg, 0.08 mmol), (S)-pyrrolidine-2-carboxamide (18 mg, 0.16 mmol), EDC (31 mg, 0.16 mmol) and HOBt (22 mg, 0.16 mmol) was added thereto, DIPEA (28 μL, 0.16 mmol) was dissolved in CH$_2$Cl$_2$ (1 mL). After stirring at room temperature for a day, the reaction mixture was added with water, and extracted with EtOAc. The obtained organic layer was washed with saturated aqueous brine solution, and then. The organic layer was dried over anhydrous MgSO$_4$, and concentrated under reduced pressure. The obtained concentrate was purified by silica gel column chromatography (CH$_2$Cl$_2$/MeOH=95%~5%) to yield the title compound as white solid (22 mg, 51%).

1H NMR (400 MHz, CDCl$_3$) δ 7.79-7.70 (m, 2H), 7.63-7.60 (m, 2H), 7.54-7.52 (m, 2H), 7.34-7.27 (m, 1H), 7.02-6.99 (m, 1H), 5.72 (brs, 1H), 4.80-4.78 (m, 1H), 3.94 (d, 2H, J=6.3 Hz), 3.66-3.63 (m, 1H), 3.52-3.48 (m, 3H), 3.00 (s, 1H), 2.95 (s, 1H), 2.71-2.60 (m, 2H), 2.48-2.37 (m, 1H), 2.10-1.99 (m, 5H), 1.82-1.69 (m, 7H), 0.87-0.83 (m, 6H); MS (ESI) m/z 535 (M++H).

According to the above-described synthesis process of compound 1004, the compounds of Table 118 were synthesized using 3'-cyano-4'-((1-(2-ethyl-2-fluorobutyl)piperidin-4-yl)methoxy)biphenyl-4-carboxylic acid and the reactant of Table 117.

TABLE 117

| Compound No. | Reactant | Yield (%) |
|---|---|---|
| 1005 | (R)-pyrrolidine-2-ylmethanol | 48 |
| 1006 | (S)-pyrrolidine-3-ol | 71 |

TABLE 118

| Compound No. | Compound Name, $^1$H-NMR, MS (ESI) |
|---|---|
| 1005 | (R)-4-((1-(2-ethyl-2-fluorobutyl)piperidin-4-yl)methoxy)-4'-(2-(hydroxymethyl)pyrrolidine-1-carbonyl)biphenyl-3-carbonitrile<br>1H NMR (400 MHz, CDCl$_3$) δ 7.79-7.74 (m, 2 H), 7.63-7.56 (m, 4 H), 7.05 (d, 1 H, J = 8.8 Hz), 4.43-4.39 (m, 1 H), 3.96 (d, 2 H, J = 6.2 Hz), 3.84-3.77 (m, 2 H), 3.62-3.49 (m, 4 H), 3.10 (s, 1 H), 3.05 (s, 1 H), 2.80-2.74 (m, 2 H), 2.23-2.18 (m, 1 H), 2.17-2.02 (m, 4 H), 1.92-1.86 (m, 3 H), 1.81-1.67 (m, 6 H), 0.86-0.82 (m, 6 H); MS (ESI) m/z 522 (M+ + H). |
| 1006 | (S)-4-((1-(2-ethyl-2-fluorobutyl)piperidin-4-yl)methoxy)-4'-(3-hydroxypyrrolidine-1-carbonyl)biphenyl-3-carbonitrile<br>1H NMR (400 MHz, CDCl$_3$) δ 7.76-7.72 (m, 2 H), 7.63-7.58 (m, 2 H), 7.54-7.51 (m, 2 H), 7.03 (d, 1 H, J = 8.8 Hz), 4.60 (brs, 0.5 H), 4.48 (brs, 0.5 H), 3.94 (d, 2 H, J = 6.4 Hz), 3.82-3.78 (m, 2 H), 3.71-3.62 (m, 1 H), 3.54-3.50 (m, 1 H), 3.02 (brs, 2 H), 2.63-2.46 (m, 3 H), 2.18-2.11 (m, 2 H), 2.04-2.00 (m, 2 H), 1.99-1.86 (m, 3 H), 1.76-1.66 (m, 4 H), 1.47 (brs, 2 H), 0.92-0.88 (m, 6 H); MS (ESI) m/z 508 (M+ + H). |

Example 107. Compound 1000: (S)-1-(3'-cyano-4'-((1-(2-ethyl-2-fluorobutyl)piperidin-4-yl)methoxy)-3-fluorobiphenylcarbonyl)pyrrolidine-2-carboxamide

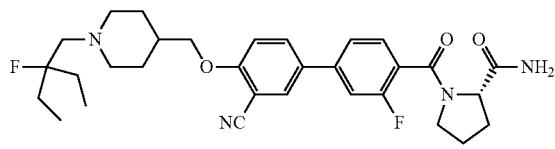

Step 1.

5-bromo-2-((1-(2-ethyl-2-hydroxybutyl)piperidin-4-yl)methoxy)benzonitrile: To 5-bromo-2-(piperidin-4-ylmethoxy)benzonitrile hydroxychloride (the product of synthesis step 2 of compound 938; 1.00 g, 3.39 mmol), 2,2-diethyloxirane (1.70 g, 16.94 mmol) and $K_2CO_3$ (937 mg, 6.78 mmol), EtOH (5 mL)/$H_2O$ (5 mL) was added. With a microwave radiation, the mixture was heated at 110° C. for 20 minutes, and then cooled to room temperature. The reaction mixture was added with water, and extracted with EtOAc. The obtained organic layer was washed with saturated aqueous brine solution, dried over anhydrous $MgSO_4$, and filtered. The filtrate was concentrated under reduced pressure. The obtained material, which is the title compound as white solid (1.33 g, 99%), was used without further purification.

Step 2.

5-bromo-2-((1-(2-ethyl-2-fluorobutyl)piperidin-4-yl)methoxy)benzonitrile: 5-bromo-2-((1-(2-ethyl-2-hydroxybutyl)piperidin-4-yl)methoxy)benzonitrile (1.33 g, 3.36 mmol) was dissolved in $CH_2Cl_2$ (10 mL). At 0° C., DAST (444 μL, 3.36 mmol) was added thereto, following with stirring at room temperature for 1 hour. The reaction mixture was added with water, and extracted with EtOAc. The obtained organic layer was washed with saturated aqueous brine solution, dried over anhydrous $MgSO_4$, and filtered. The filtrate was concentrated under reduced pressure. The obtained material, which is the title compound as yellow oil (800 mg, 59%), was used without further purification.

Step 3.

Ethyl 3'-cyano-4'-((1-(2-ethyl-2-fluorobutyl)piperidin-4-yl)methoxy)-3-fluorobiphenyl-4-carboxylate: 5-bromo-2-((1-(2-ethyl-2-fluorobutyl)piperidin-4-yl)methoxy)benzonitrile (400 mg, 1.01 mmol), 4-(ethoxycarbonyl)-3-fluorophenylboronic acid (235 mg, 1.11 mmol), Pd(dppf)$Cl_2$ (82 mg, 0.10 mmol) and $Cs_2CO_3$ (656 mg, 2.01 mmol) were added to water (2 mL)/DME (6 mL). With a microwave radiation, the mixture was heated at 110° C. for 15 minutes, and then cooled to room temperature. The reaction mixture was added with water, and extracted with EtOAc. The obtained organic layer was washed with saturated aqueous brine solution, dried over anhydrous $MgSO_4$, and concentrated under reduced pressure. The obtained concentrate was purified by silica gel column chromatography (EtOAc/hexane=30%~70%) to yield the title compound as white solid (189 mg, 38%).

Step 4.

3'-cyano-4'-((1-(2-ethyl-2-fluorobutyl)piperidin-4-yl)methoxy)-3-fluorobiphenyl-4-carboxylic acid: Ethyl 3'-cyano-4'-((1-(2-ethyl-2-fluorobutyl)piperidin-4-yl)methoxy)-3-fluorobiphenyl-4-carboxylate (189 mg, 0.39 mmol) was dissolved in THF (10 mL) and water (5 mL). LiOH.$H_2O$ (82 mg, 1.95 mmol) was added thereto little by little at room temperature, following with stirring for 1 hour. After the completion of the reaction, the reaction mixture was concentrated under reduced pressure. The resulting precipitate was filtered, and dried to yield the title compound as white solid (161 mg, 90%).

Step 5.

Compound 1000: 3'-cyano-4'-((1-(2-ethyl-2-fluorobutyl)piperidin-4-yl)methoxy)-3-fluorobiphenyl-4-carboxylic acid (35 mg, 0.08 mmol), (S)-pyrrolidine-2-carboxamide (18 mg, 0.15 mmol), EDC (29 mg, 0.15 mmol) and HOBt (21 mg, 0.15 mmol) was added thereto, DIPEA (27 μL, 0.15 mmol) was dissolved in $CH_2Cl_2$ (1 mL). After stirring at room temperature for a day, the reaction mixture was added with water, and extracted with EtOAc. The obtained organic layer was washed with saturated aqueous brine solution, and then. The organic layer was dried over anhydrous $MgSO_4$, and concentrated under reduced pressure. The obtained concentrate was purified by silica gel column chromatography ($CH_2Cl_2$/MeOH=95%~5%) to yield the title compound as white solid (25 mg, 59%).

1H NMR (400 MHz, $CDCl_3$) δ 7.77-7.71 (m, 2H), 7.51 (t, 1H, J=7.5 Hz), 7.38 (d, 1H, J=8.0 Hz), 7.30-7.26 (m, 1H), 7.05 (d, 1H, J=8.8 Hz), 6.90 (brs, 1H), 5.57 (brs, 1H), 4.83-4.80 (m, 1H), 3.96 (d, 2H, J=6.2 Hz), 3.56-3.39 (m, 2H), 3.02 (brs, 2H), 2.50-2.43 (m, 2H), 2.18-2.03 (m, 4H), 1.95-1.87 (m, 4H), 1.74-1.68 (m, 5H), 1.45 (brs, 2H), 0.92-0.88 (m, 6H); MS (ESI) m/z 553 (M++H).

According to the above-described synthesis process of compound 1000, the compounds of Table 120 were synthesized using 3'-cyano-4'-((1-(2-ethyl-2-fluorobutyl)piperidin-4-yl)methoxy)-3-fluorobiphenyl-4-carboxylic acid and the reactant of Table 119.

TABLE 119

| Compound No. | Reactant | Yield (%) |
|---|---|---|
| 1001 | (R)-piperidin-3-ol hydrochloride | 65 |
| 1002 | (R)-pyrrolidine-2-ylmethanol | 62 |
| 1003 | (S)-pyrrolidine-3-ol | 47 |

TABLE 120

| Compound No. | Compound Name, 1H-NMR, MS (ESI) |
|---|---|
| 1001 | (R)-4-((1-(2-ethyl-2-fluorobutyl)piperidin-4-yl)methoxy)-3'-fluoro-4'-(3-hydroxypiperidin-1-carbonyl)biphenyl-3-carbonitrile<br>1H NMR (400 MHz, $CDCl_3$) δ 7.75-7.69 (m, 2 H), 7.47 (t, 1 H, J = 7.4 Hz), 7.37-7.33 (m, 1 H), 7.27-7.22 (m, 1 H), 7.05 (d, 1 H, J = 8.8 Hz), 4.14-4.07 (m, 1 H), 3.95 (d, 2 H, J = 6.3 Hz), 3.58-3.55 (m, 1 H), 3.34-3.25 (m, 1 H), 3.15-3.02 (m, 2 H), 2.51-2.46 (m, 2 H), 2.31-2.01 (m, 6 H), 1.99-1.87 (m, 6 H), 1.48 (brs, 2 H), 1.28-1.24 (m, 2 H), 0.92-0.88 (m, 6 H); MS (ESI) m/z 540 (M+ + H). |
| 1002 | (R)-4-((1-(2-ethyl-2-fluorobutyl)piperidin-4-yl)methoxy)-3'-fluoro-4'-(2-(hydroxymethyl)pyrrolidine-1-carbonyl)biphenyl-3-carbonitrile |

TABLE 120-continued

Compound No. Compound Name, 1H-NMR, MS (ESI)

1H NMR (400 MHz, CDCl$_3$) δ 7.77-7.71 (m, 2 H), 7.52 (t, 1 H, J = 7.5 Hz), 7.37 (d, 1 H, J = 8.0 Hz), 7.28-7.25 (m, 1 H), 7.05 (d, 1 H, J = 8.8 Hz), 4.69-4.67 (m, 1 H), 4.42-4.39 (m, 1 H), 3.96 (d, 2 H, J = 6.2 Hz), 3.84-3.78 (m, 2 H), 3.47-3.44 (m, 2 H), 3.01 (brs, 2 H), 2.47 (brs, 2 H), 2.24-2.18 (m, 2 H), 1.93-1.82 (m, 5 H), 1.81-1.71 (m, 6 H), 1.43 (brs, 2 H), 0.93-0.89 (m, 6 H); MS (ESI) m/z 540 (M+ + H).

1003  (S)-4-((1-(2-ethyl-2-fluorobutyl)piperidine-4-yl)methoxy)-3'-fluoro-4'-(3-hydroxypyrrolidine-1-carbonyl)biphenyl-3-carbonitrile
1H NMR (400 MHz, CDCl$_3$) δ 7.76-7.70 (m, 2 H), 7.55-7.50 (m, 1 H), 7.36-7.34 (m, 1 H), 7.27-7.22 (m, 1 H), 7.05 (d, 1 H, J = 8.8 Hz), 4.63 (brs, 0.5 H), 4.50 (brs, 0.5 H), 3.96 (d, 2 H, J = 6.0 Hz), 3.84-3.74 (m, 2 H), 3.67-3.57 (m, 1 H), 3.45-3.33 (m, 1 H), 3.01 (brs, 2 H), 2.43 (brs, 3 H), 2.09-2.02 (m, 2 H), 1.89-1.87 (m, 3 H), 1.73-1.68 (m, 5 H), 1.44 (brs, 2 H), 0.92-0.87 (m, 6 H); MS (ESI) m/z 526 (M+ + H).

Example 108. Compound 1124: (S)-1-(2'-cyano-4'-((1-(2-ethyl-2-fluorobutyl)piperidin-4-yl)methoxy)biphenylcarbonyl)pyrrolidine-2-carboxamide

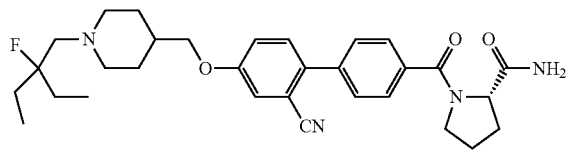 [SMILES: CCC(F)(CC)CN1CCC(COc2ccc(-c3ccc(C(=O)N4CCC[C@H]4C(N)=O)cc3)c(C#N)c2)CC1]

Step 1.
2-bromo-5-((1-(2-ethyl-2-hydroxybutyl)piperidin-4-yl)methoxy)benzonitrile: 5-bromo-2-(piperidin-4-ylmethoxy)benzonitrile hydroxychloride (the product of synthesis step 2 of compound 1028; 3.00 g, 9.05 mmol) was dissolved in EtOH 6 mL. 2,2-diethyloxirane (the product of synthesis step 1 of compound 809; 2.72 g, 27.14 mmol), K$_2$CO$_3$ (2.50 g, 18.09 mmol) and water 3 mL were added thereto, With a microwave radiation, the mixture was stirred at 110° C. for 15 minutes. Ethanol was evaporated from the reaction mixture under reduced pressure. After the addition of water thereto, the resulting precipitated was filtered, and dried under reduced pressure to yield the title compound as white solid (2.9 g, 81%).
Step 2.
2-bromo-5-((1-(2-ethyl-2-fluorobutyl)piperidin-4-yl)methoxy)benzonitrile: 2-bromo-5-((1-(2-ethyl-2-hydroxybutyl)piperidin-4-yl)methoxy)benzonitrile (2.90 g, 7.34 mmol) was dissolved in CH$_2$Cl$_2$ (10 mL). At room temperature, DAST (1.30 g, 8.07 mmol) was added thereto, following with stirring at the same temperature for 3 hours. The reaction mixture was added with saturated NaHCO$_3$ aqueous solution, and extracted with ethyl acetate. The organic layer was washed with saturated aqueous brine solution, dried over anhydrous MgSO$_4$, and filtered. The filtrate was concentrated under reduced pressure. The obtained material (yellow oil) was used without further purifying process (2.20 g, 75%).
Step 3.
Methyl 2'-cyano-4'-((1-(2-ethyl-2-fluorobutyl)piperidin-4-yl)methoxy)biphenyl-4-carboxylate: 2-bromo-5-((1-(2-ethyl-2-fluorobutyl)piperidin-4-yl)methoxy)benzonitrile (700 mg, 1.76 mmol), 4-(methoxycarbonyl)phenylboronic acid (381 mg, 2.11 mmol), Pd(dbpf)Cl$_2$ (57 mg, 0.09 mmol) and Cs$_2$CO$_3$ (1.15 g, 3.52 mmol) were dissolved in 1,4-dioxane (3 mL)/H$_2$O (1 mL). At 120° C., the mixture was stirred for 15 minutes. The reaction mixture was filtered through a Celite pad to remove a solid. The obtained filtrate was added with saturated NaHCO$_3$ aqueous solution, and extracted with ethyl acetate. The organic layer was washed with saturated aqueous brine solution, dried over anhydrous MgSO$_4$, and filtered. The filtrate was concentrated under reduced pressure. The concentrate was purified by column chromatography (SiO$_2$, 40 g cartridge; ethyl acetate-hexane=20% to 30%), and concentrated to yield the title compound as white solid (0.52 g, 65%).
Step 4.
2'-cyano-4'-((1-(2-ethyl-2-fluorobutyl)piperidin-4-yl)methoxy)biphenyl-4-carboxylic acid: Methyl 2'-cyano-4'-((1-(2-ethyl-2-fluorobutyl)piperidin-4-yl)methoxy)biphenyl-4-carboxylate (0.52 g, 1.15 mmol) and LiOH.H$_2$O (0.10 g, 2.30 mmol) were dissolved in THF/MeOH (6 mL/3 mL)/Water (2 mL) at room temperature. The solution was stirred at the same temperature for 12 hours, the reaction mixture was concentrated under reduced pressure. The concentrate was added with a little of conc.HCl to be suspended, and filtered. The obtained solid was dried to yield the title compound as white solid (0.45 g, 89%).
Step 5.
Compound 1124: 2'-cyano-4'-((1-(2-ethyl-2-fluorobutyl)piperidin-4-yl)methoxy)biphenyl-4-carboxylic acid (0.60 g, 0.14 mmol), EDC (0.05 g, 0.27 mmol), HOBt (0.04 g, 0.27 mmol) and DIPEA (0.05 g, 0.41 mmol) were dissolved in CH$_2$Cl$_2$ (1 mL). At room temperature, (S)-pyrrolidine-2-carboxamide (0.02 g, 0.16 mmol) was added thereto, following with stirring at the same temperature for 8 hours. The reaction mixture was added with water, and extracted with dichloromethane. The organic layer was washed with saturated aqueous brine solution, dried over anhydrous MgSO$_4$, and filtered. The filtrate was concentrated under reduced pressure. The concentrate was purified by column chromatography (SiO$_2$, 4 g cartridge; methanol/dichloromethane=2% to 5%), and concentrated to yield the title compound as white solid (0.05 g, 61%).
1H NMR (400 MHz, CDCl$_3$) δ 7.66 (d, 2H, J=8.2 Hz), 7.58 (d, 2H, J=8.2 Hz), 7.41 (d, 1H, J=8.6 Hz), 7.20 (m, 2 Hz), 7.07 (s, 1H), 5.82 (s, 1H), 4.80 (m, 1H), 3.85 (d, 2H, J=6.0 Hz), 3.66 (m, 2H), 3.01-2.98 (m, 2H), 2.48 (s, 1H), 2.42 (s, 1H), 2.40 (m, 1H), 2.09 (m, 4H), 1.88-1.65 (m, 8H), 1.41 (m, 2H), 0.90 (t, 6H, J=7.5 Hz)
According to the above-described synthesis process of compound 1124, the compounds of Table 122 were synthesized using 2'-cyano-4'-((1-(2-ethyl-2-fluorobutyl)piperidin-4-yl)methoxy)biphenyl-4-carboxylic acid and the reactant of Table 121.

TABLE 121

| Compound No. | Reactant | Yield (%) |
|---|---|---|
| 1125 | (R)-piperidin-2-carboxamide hydrochloride | 55 |
| 1126 | (R)-piperidin-3-ol hydrochloride | 67 |

TABLE 122

| Compound No. | Compound Name, ¹H-NMR, MS (ESI) |
|---|---|
| 1125 | (R)-1-(2'-cyano-4'-((1-(2-ethyl-2-fluorobutyl)piperidin-4-yl)methoxy)biphenylcarbonyl)piperidin-2-carboxamide<br>1H NMR (400 MHz, CDCl$_3$) δ 7.55 (m, 4 H), 7.39 (d, 1 H, J = 8.6 Hz), 7.15 (m, 2 H), 6.53 (s, 1 H), 5.90 (s, 1 H), 5.28 (m, 1 H), 3.81 (m, 3 H), 3.15 (m, 1 H), 2.97-2.95 (m, 2 H), 2.45 (s, 1 H), 2.39 (s, 1 H), 2.29 (m, 1 H), 2.11 (t, 2 H, J = 11.0 Hz), 1.77-1.62 (m, 10 H), 1.43 (m, 4 H), 0.90 (t, 6H, J = 8.8 Hz) |
| 1126 | (R)-4-((1-(2-ethyl-2-fluorobutyl)piperidin-4-yl)methoxy)-4'-(3-hydroxypiperidin-1-carbonyl)biphenyl-2-carbonitrile<br>1H NMR (400 MHz, CDCl$_3$) δ 7.52 (m, 4 H), 7.38 (d, 1 H, J = 8.6 Hz), 7.22 (m, 1 H), 7.16 (dd, 1 H, J = 8.7, 2.6 Hz), 4.07-3.62 (m, 4 H), 3.60-3.01 (m, 4 H), 2.98-2.95 (m, 2 H), 2.45 (s, 1 H), 2.39 (s, 1 H), 2.11 (t, 2 H, J = 10.9 Hz), 1.92-1.62 (m, 11 H), 1.41 (m, 2 H), 0.90 (t, 6 H, J = 7.5 Hz) |

Example 109. Compound 1119: (S)-1-(3'-cyano-4'-((1-(2-ethyl-2-fluorobutyl)piperidin-4-yl)methoxy)-2-fluorobiphenylcarbonyl)pyrrolidine-2-carboxamide

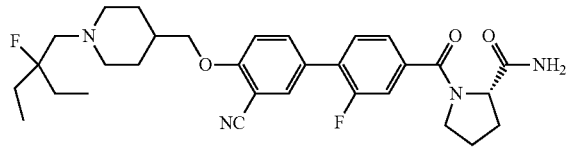 [SMILES: CCC(F)(CC)CN1CCC(COc2ccc(-c3ccc(C(=O)N4CCC[C@H]4C(N)=O)cc3F)cc2C#N)CC1]

Step 1.

Methyl 3'-cyano-4'-((1-(2-ethyl-2-fluorobutyl)piperidin-4-yl)methoxy)-2-fluorobiphenyl-4-carboxylate: 5-bromo-2-((1-(2-ethyl-2-fluorobutyl)piperidin-4-yl)methoxy)benzonitrile (the product of synthesis step 4 of compound 1000; 850 mg, 2.14 mmol), 2-fluoro-4-(methoxycarbonyl)phenylboronic acid (508 mg, 2.57 mmol), Pd(dbpf)Cl$_2$ (70 mg, 0.11 mmol) and Cs$_2$CO$_3$ (1.39 g, 4.28 mmol) were added to 1,4-dioxane (3 mL)/H$_2$O (1 mL). With a microwave radiation, the mixture was heated at 120° C. for 15 minutes, and then cooled to room temperature. The reaction mixture was filtered through a Celite pad to remove a solid. The obtained filtrate was added with saturated NaHCO$_3$ aqueous solution, and extracted with ethyl acetate. The organic layer was washed with saturated aqueous brine solution, dried over anhydrous MgSO$_4$, and filtered. The filtrate was concentrated under reduced pressure. The concentrate was purified by column chromatography (SiO$_2$, 40 g cartridge; ethyl acetatehexane=20% to 30%), and concentrated to yield the title compound as white solid (0.71 g, 70%).

Step 2.

3'-cyano-4'-((1-(2-ethyl-2-fluorobutyl)piperidin-4-yl)methoxy)-2-fluorobiphenyl-4-carboxylic acid: Methyl 3'-cyano-4'-((1-(2-ethyl-2-fluorobutyl)piperidin-4-yl)methoxy)-2-fluorobiphenyl-4-carboxylate (710 mg, 1.51 mmol) and LiOH.H$_2$O (0.13 g, 3.02 mmol) were dissolved in THF/MeOH (6 mL/3 mL)/water (2 mL) at room temperature. The solution was stirred at the same temperature for 12 hours, the reaction mixture was concentrated under reduced pressure. The concentrate was added with a little of conc.HCl to be suspended, and filtered. The obtained solid was dried to yield the title compound as white solid (0.62 g, 90%).

Step 3.

Compound 1119: 3'-cyano-4'-((1-(2-ethyl-2-fluorobutyl)piperidin-4-yl)methoxy)-2-fluorobiphenyl-4-carboxylic acid (0.06 g, 0.13 mmol), EDC (0.05 g, 0.26 mmol), HOBt (0.04 g, 0.26 mmol) and DIPEA (0.05 g, 0.39 mmol) were dissolved in CH$_2$Cl$_2$ (1 mL). At room temperature, (S)-pyrrolidine-2-carboxamide (0.02 g, 0.16 mmol) was added thereto, following with stirring at the same temperature for 8 hours. The reaction mixture was added with water, and extracted with dichloromethane. The organic layer was washed with saturated aqueous brine solution, dried over anhydrous MgSO$_4$, and filtered. The filtrate was concentrated under reduced pressure. The concentrate was purified by column chromatography (SiO$_2$, 4 g cartridge; methanol/dichloromethane=2% to 5%), and concentrated to yield the title compound as white solid (0.04 g, 53%).

1H NMR (400 MHz, CDCl$_3$) δ 7.72 (s, 1H), 7.70 (d, 2H, J=8.9 Hz), 7.38 (m, 3H), 7.03 (d, 1H, J=8.8 Hz), 6.90 (s, 1H), 5.75 (s, 1H), 4.75 (m, 1H), 3.93 (d, 2H, J=6.4 Hz), 3.62 (m, 2H), 3.54 (m, 2H), 2.98-2.95 (m, 2H), 2.38 (m, 2H), 2.06 (m, 5H), 1.88 (m, 4H), 1.70 (m, 4H), 1.41 (m, 2H), 0.90 (t, 6H, J=7.5 Hz); MS (ESI) m/z 553 (M++H).

According to the above-described synthesis process of compound 1119, the compounds of Table 124 were synthesized using 3'-cyano-4'-((1-(2-ethyl-2-fluorobutyl)piperidin-4-yl)methoxy)-2-fluorobiphenyl-4-carboxylic acid and the reactant of Table 123.

TABLE 123

| Compound No. | Reactant | Yield (%) |
|---|---|---|
| 1120 | (S)-pyrrolidine-3-ol | 53 |
| 1121 | (R)-piperidin-2-carboxamide hydrochloride | 50 |
| 1123 | (R)-piperidin-3-ol hydrochloride | 59 |

TABLE 124

| Compound No. | Compound Name, 1H-NMR, MS (ESI) |
|---|---|
| 1120 | (R)-1-(3'-cyano-4'-((1-(2-ethyl-2-fluorobutyl)piperidin-4-yl)methoxy)-2-fluorobiphenylcarbonyl)piperidin-2-carboxamide<br>1H NMR (400 MHz, CDCl$_3$) δ 7.70 (m, 2 H), 7.37 (m, 3 H), 7.03 (d, 1 H, J = 8.8 Hz), 4.82 (m, 1 H), 4.39 (m, 2 H), 3.92 (d, 2 H, J = 6.4 Hz), 3.73 (m, 2 H), 3.52 (m, 2 H), 2.98-2.95 (m, 2 H), 2.45 (s, 1 H), 2.39 (s, 1 H), 2.12 (m, 3 H), 1.90-1.61 (m, 10 H), 1.38 (m, 2 H), 0.91 (t, 6 H, J = 7.5 Hz) |
| 1121 | (S)-4-((1-(2-ethyl-2-fluorobutyl)piperidin-4-yl)methoxy)-2'-fluoro-4'-(3-hydroxypyrrolidine-1-carbonyl)biphenyl-3-carbonitrile<br>1H NMR (400 MHz, CDCl$_3$) δ 7.70 (m, 2 H), 7.37 (m, 3 H), 7.03 (d, 1 H, J = 8.8 Hz), 4.60-4.48 (s, 1 H), 3.93 (d, 2 H, J = 6.4 Hz), 3.82-3.46 (m, 4 H), 2.98-2.96 (m, 2 H), 2.48 (m, 3 H), 2.03 (m, 4 H), 1.99 (m, 3 H), 1.71 (m, 4 H), 1.42 (m, 2 H), 0.90 (t, 6 H, J = 7.5 Hz) |
| 1123 | (R)-4-((1-(2-ethyl-2-fluorobutyl)piperidin-4-yl)methoxy)-2'-fluoro-4'-(3-hydroxypiperidin-1-carbonyl)biphenyl-3-carbonitrile<br>1H NMR (400 MHz, CDCl$_3$) δ 7.72 (m, 2 H), 7.42 (t, 1 H, J = 7.8 Hz), 7.30 (m, 2 H), 7.05 (d, 1 H, J = 8.8 Hz), 3.95 (m, 3 H), 3.82-3.25 (m, 5 H), 3.01-2.98 (m, 2 H), 2.49 (s, 1 H), 2.43 (s, 1 H), 2.15 (m, 2 H), 1.88 (m, 5 H), 1.71 (m, 5 H), 1.43 (m, 2 H), 0.91 (t, 6 H, J = 7.5 Hz) |

Example 110. Compound 1018: (S)-1-(4-(5-((1-(2-ethyl-2-fluorobutyl)piperidin-4-yl)methoxy)pyrazine-2-yl)benzoyl)pyrrolidine-2-carboxamide

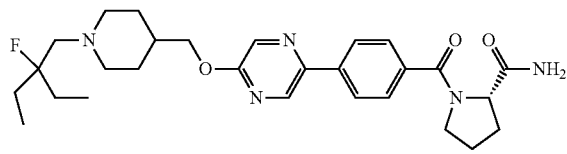

Step 1.

3-((4-((5-iodopyrazine-2-yloxy)methyl)piperidin-1-yl)methyl)pentane-3-ol: To 2-iodo-5-(piperidin-4-ylmethoxy)pyrazine hydrochloride (the product of synthesis step 2 of compound 944; 1.00 g, 2.81 mmol), 2,2-diethyloxirane (1.01 g, 14.06 mmol) and K$_2$CO$_3$ (1.94 g, 14.06 mmol), EtOH (8 mL)/H$_2$O (2 mL) was added. With a microwave radiation, the mixture was heated at 110° C. for 20 minutes, and then cooled to room temperature. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The resulting precipitate was filtered, and dried to yield the title compound as white solid (1.15 g, 97%).

Step 2.

2-((1-(2-ethyl-2-fluorobutyl)piperidin-4-yl)methoxy)-5-iodopyrazine: 3-((4-((5-iodopyrazine-2-yloxy)methyl)piperidin-1-yl)methyl)pentane-3-ol (2.00 g, 5.44 mmol) was dissolved in CH$_2$Cl$_2$ (20 mL). At 0° C., DAST (0.87 mL, 6.53 mmol) was added thereto, following with stirring at room temperature for 2 hours. After the completion of the reaction, the reaction mixture was added with saturated NaHCO$_3$ aqueous solution, and extracted with EtOAc. The obtained organic layer was washed with saturated NaHCO$_3$ aqueous solution. The organic layer was dried over anhydrous MgSO$_4$, and filtered. The filtrate was concentrated under reduced pressure. The concentrate was purified by column chromatography (SiO$_2$, 12 g cartridge; EtOAc/hexane=0% to 10%), and concentrated to yield the title compound as white solid (0.41 g, 17%).

Step 3.

Methyl 4-(5-((1-(2-ethyl-2-fluorobutyl)piperidin-4-yl)methoxy)pyrazine-2-yl)benzoate: To 2-((1-(2-ethyl-2-fluorobutyl)piperidin-4-yl)methoxy)-5-iodopyrazine (0.40 g, 0.94 mmol), 4-(methoxycarbonyl)phenylboronic acid (0.20 g, 1.13 mmol), Pd(dppf)Cl$_2$ (0.03 g, 0.04 mmol) and Cs$_2$CO$_3$ (0.61 g, 1.89 mmol), DME (3 mL)/H$_2$O (1 mL) was added. With a microwave radiation, the mixture was heated at 110° C. for 20 minutes, and then cooled to room temperature. The reaction mixture was filtered through a Celite pad to remove a solid. The obtained filtrate was diluted with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; EtOAc/hexane=0% to 30%), and concentrated to yield the title compound as white solid (0.08 g, 19%).

Step 4.

4-(5-((1-(2-ethyl-2-fluorobutyl)piperidin-4-yl)methoxy)pyrazine-2-yl)benzoic acid: Methyl 4-(5-((1-(2-ethyl-2-fluorobutyl)piperidin-4-yl)methoxy)pyrazine-2-yl)benzoate (0.08 g, 0.18 mmol) and LiOH.H$_2$O (0.03 g, 0.93 mmol) were dissolved in THF/MeOH (8 mL)/H$_2$O (1 mL) at 60° C., following with stirring at the same temperature for 18 hours. The reaction mixture was concentrated under reduced pressure. The resulting precipitate was filtered, and dried to yield the title compound as white solid (0.04 g, 54%).

Step 5.

Compound 1018: 4-(5-((1-(2-ethyl-2-fluorobutyl)piperidin-4-yl)methoxy)pyrazine-2-yl)benzoic acid (0.04 g, 0.10 mmol), L-prolinamide (0.01 g, 0.12 mmol), HOBt (0.02 g, 0.20 mmol), EDC (0.03 g, 0.20 mmol) and DIPEA (0.03 mL, 0.20 mmol) were dissolved in CH$_2$Cl$_2$ (1 mL) at room temperature. The solution was stirred at the same temperature for 18 hours, the reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 4 g cartridge; dichloromethane/methanol=0% to 15%), and concentrated to yield the title compound as white solid (0.01 g, 34%).

1H NMR (400 MHz, CDCl$_3$) δ 8.53 (s, 1H), 8.30 (s, 1H), 7.98 (d, 2H, J=8.3 Hz), 7.65 (d, 2H, J=8.2 Hz), 6.69 (s, 1H), 5.46 (s, 1H), 4.83 (dd, 1H, J=7.4, 4.7 Hz), 4.22 (d, 2H, J=6.2 Hz), 3.54-4.03 (m, 2H), 2.98-3.00 (m, 2H), 2.48-2.51 (m, 2H), 2.43 (s, 1H), 2.03-2.16 (m, 3H), 1.65-1.89 (m, 7H), 1.39-1.48 (m, 2H), 1.26-1.31 (m, 2H), 0.90 (t, 6H, J=7.5 Hz); MS (ESI) m/z 512.3 (M++H).

Example 111. Compound 1051: (S)-1-(4-(5-((1-(2-ethyl-2-fluorobutyl)piperidin-4-yl)methoxy)pyrimidin-2-yl)benzoyl)pyrrolidine-2-carboxamide

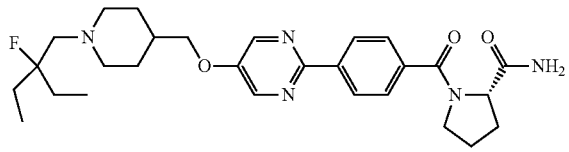 [SMILES: CCC(F)(CC)CN1CCC(COc2cnc(-c3ccc(C(=O)N4CCC[C@H]4C(N)=O)cc3)cn2)CC1]

Step 1.
3-((4-((2-chloropyrimidin-5-yloxy)methyl)piperidin-1-yl)methyl)pentane-3-ol: EtOH (4 mL)/H$_2$O (1 mL) was added to 2-chloro-5-(piperidin-4-ylmethoxy)pyrimidine hydrochloride (the product of synthesis step 2 of compound 1032; 1.20 g, 4.54 mmol), 2,2-diethyloxirane (3.18 g, 31.80 mmol) and K$_2$CO$_3$ (1.25 g, 9.08 mmol). With a microwave radiation, the mixture was heated at 110° C. for 20 minutes, and then cooled to room temperature. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The obtained material was used without further purifying process (1.47 g, 98%, white solid).
Step 2.
2-chloro-5-((1-(2-ethyl-2-fluorobutyl)piperidin-4-yl)methoxy)pyrimidine: 3-((4-((2-chloropyrimidin-5-yloxy)methyl)piperidin-1-yl)methyl)pentane-3-ol (1.47 g, 4.48 mmol) was dissolved in CH$_2$Cl$_2$ (20 mL). At 0° C., DAST (0.70 mL, 5.38 mmol) was added thereto, following with stirring at room temperature for 3 hours. The reaction mixture was added with saturated NaHCO$_3$ aqueous solution, and extracted with EtOAc. The obtained organic layer was washed with saturated NaHCO$_3$ aqueous solution, dried over anhydrous MgSO$_4$, and filtered. The filtrate was concentrated under reduced pressure. The concentrate was purified by column chromatography (SiO$_2$, 12 g cartridge; EtOAc/hexane=0% to 30%), and concentrated to yield the title compound as white solid (0.71 g, 48%).
Step 3.
Methyl 4-(5-((1-(2-ethyl-2-fluorobutyl)piperidin-4-yl)methoxy)pyrimidin-2-yl)benzoate: DME (4 mL)/H$_2$O (1 mL) was added to 2-chloro-5-((1-(2-ethyl-2-fluorobutyl)piperidin-4-yl)methoxy)pyrimidine (0.20 g, 0.60 mmol), 4-(methoxycarbonyl)phenylboronic acid (0.13 g, 0.72 mmol), Pd(dppf)Cl$_2$ (0.02 g, 0.03 mmol) and Cs$_2$CO$_3$ (0.39 g, 1.21 mmol). With a microwave radiation, the mixture was heated at 120° C. for 20 minutes, and then cooled to room temperature. The reaction mixture was filtered through a Celite pad to remove a solid. The filtrate was added with saturated NH$_4$Cl aqueous solution, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 4 g cartridge; EtOAc/hexane=0% to 30%), and concentrated to yield the title compound as white solid (0.20 g, 76%).
Step 4.
4-(5-((1-(2-ethyl-2-fluorobutyl)piperidin-4-yl)methyloxy)pyrimidin-2-yl)benzoic acid: Methyl 4-(5-((1-(2-ethyl-2-fluorobutyl)piperidin-4-yl)methoxy)pyrimidin-2-yl)benzoate (0.20 g, 0.46 mmol) and LiOH.H$_2$O (0.09 g, 2.32 mmol) were dissolved in THF (4 mL)/MeOH (4 mL)/H$_2$O (1 mL) at room temperature. The solution was stirred at the same temperature for 5 hours, the reaction mixture was concentrated under reduced pressure. The concentrate was added with water (20 mL), and stirred. The resulting precipitate was filtered, and dried to yield the title compound as white solid (0.15 g, 77%).
Step 5.
Compound 1051: 4-(5-((1-(2-ethyl-2-fluorobutyl)piperidin-4-yl)methyloxy)pyrimidin-2-yl)benzoic acid (0.04 g, 0.10 mmol), L-prolinamide (0.01 g, 0.13 mmol), HOBt (0.02 g, 0.21 mmol), EDC (0.04 g, 0.21 mmol) and DIPEA (0.03 mL, 0.21 mmol) were dissolved in CH$_2$Cl$_2$ (1 mL) at room temperature. The solution was stirred at the same temperature for 18 hours. The reaction mixture was added with saturated NH$_4$Cl aqueous solution, and extracted with EtOAc. The organic layer was washed with water, dried over anhydrous MgSO$_4$, and filtered. The filtrate was concentrated under reduced pressure. The concentrate was purified by column chromatography (SiO$_2$, 4 g cartridge; methanol/dichloromethane=0% to 15%), and concentrated to yield the title compound as white solid (0.05 g, 93%).
1H NMR (400 MHz, CDCl$_3$) δ 8.48 (s, 2H), 8.41 (d, 2H, J=8.4 Hz), 7.64 (d, 2H, J=8.3 Hz), 7.08 (s, 1H), 5.71 (s, 1H), 4.82 (dd, 1H, J=7.3, 5.1 Hz), 3.95 (d, 2H, J=6.0 Hz), 3.50-3.66 (m, 2H), 2.99-3.02 (m, 2H), 2.40-2.49 (m, 3H), 2.05-2.17 (m, 4H), 1.65-1.91 (m, 4H), 1.41-1.49 (m, 4H), 1.20-1.26 (m, 2H), 0.91 (t, 6H, J=7.5 Hz); MS (ESI) m/z 512.3 (M++H).

According to the above-described synthesis process of compound 1051, the compounds of Table 126 were synthesized using 4-(5-((1-(2-ethyl-2-fluorobutyl)piperidin-4-yl)methyloxy)pyrimidin-2-yl)benzoic acid and the reactant of Table 125.

TABLE 125

| Compound No. | Reactant | Yield (%) |
| --- | --- | --- |
| 1052 | (R)-piperidin-3-ol hydrochloride | 50 |
| 1053 | (R)-piperidin-2-carboxamide hydrochloride | 77 |

TABLE 126

| Compound No. | Compound Name, $^1$H-NMR, MS (ESI) |
| --- | --- |
| 1052 | (R)-(4-(5-((1-(2-ethyl-2-fluorobutyl)piperidin-4-yl)methoxy)pyrimidin-2-yl)phenyl)(3-hydroxypiperidin-1-yl)methanone<br>1H NMR (400 MHz, CDCl$_3$) δ 8.48 (s, 2 H), 8.39 (d, 2 H, J = 8.3 Hz), 7.52 (d, 2 H, J = 8.2 Hz), 3.95-4.01 (m, 3 H), 3.33-3.88 (m, 4 H), 2.99-3.02 (m, 2 H), 2.49 (s, 1 H), 2.43 (s, 1 H), 2.15 (t, 2 H, J = 11.0 Hz), 1.27-2.06 (m, 14 H), 0.91 (t, 6 H, J = 7.5 Hz); MS (ESI) m/z 499.3 (M+ + H). |

TABLE 126-continued

| Compound No. | Compound Name, $^1$H-NMR, MS (ESI) |
|---|---|
| 1053 | (R)-1-(4-(5-((1-(2-ethyl-2-fluorobutyl)piperidin-4-yl)methoxy)pyriniidin-2-yl)benzoyl)piperidin-2-carboxamide<br>1H NMR (400 MHz, CDCl$_3$) δ 8.48 (s, 2 H), 8.42 (d, 2 H, J = 7.8 Hz), 7.56 (d, 2 H, J = 8.0 Hz), 6.53 (s, 1 H), 5.63 (s, 1 H), 5.31 (s, 1 H), 3.96 (d, 2 H, J = 5.8 Hz), 3.75-3.78 (m, 1 H), 3.09-3.15 (m, 1 H), 2.99-3.02 (m, 2 H), 2.49 (s, 1 H), 2.43 (s, 1 H), 2.33-2.36 (m, 1 H), 2.15 (t, 2 H, J = 11.4 Hz), 1.19-2.06 (m, 14 H), 0.91 (t, 6 H, J = 7.5 Hz); MS (ESI) m/z 526.3 (M+ + H). |

Example 112. Compound 1056: (R)-(4-(5-((1-(2-ethyl-2-fluorobutyl)piperidin-4-yl)methoxy)pyrimidin-2-yl)-3-fluorophenyl)(3-hydroxypiperidin-1-yl)methanone

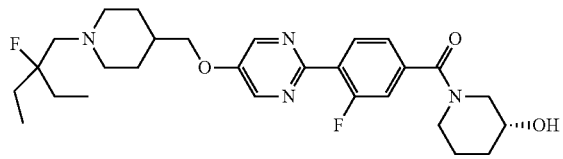 [SMILES: CCC(F)(CC)CN1CCC(COc2cnc(-c3ccc(C(=O)N4CCC[C@@H](O)C4)cc3F)nc2)CC1]

Step 1.

Methyl 4-(5-((1-(2-ethyl-2-fluorobutyl)piperidin-4-yl)methoxy)pyrimidin-2-yl)-3-fluorobenzoate: To 2-chloro-5-((1-(2-ethyl-2-fluorobutyl)piperidin-4-yl)methoxy)pyrimidine (the product of synthesis step 2 of compound 1051; 0.25 g, 0.75 mmol), 2-fluoro-4-(methoxycarbonyl)phenylboronic acid (0.16 g, 0.83 mmol), Pd(dppf)Cl$_2$ (0.03 g, 0.03 mmol) and Cs$_2$CO$_3$ (0.49 g, 1.51 mmol), DME (4 mL)/H$_2$O (1 mL) was added. With a microwave radiation, the mixture was heated at 120° C. for 20 minutes, and then cooled to room temperature. The reaction mixture was filtered through a Celite pad to remove a solid. The filtrate was added with saturated NH$_4$Cl aqueous solution, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 4 g cartridge; EtOAc/hexane=0% to 30%), and concentrated to yield the title compound as white solid (0.21 g, 61%).

Step 2.

4-(5-((1-(2-ethyl-2-fluorobutyl)piperidin-4-yl)methoxy)pyrimidin-2-yl)-3-fluorobenzoic acid: Methyl 4-(5-((1-(2-ethyl-fluorobutyl)piperidin-4-yl)methoxy)pyrimidin-2-yl)-3-fluorobenzoate (0.21 g, 0.46 mmol) and LiOH.H$_2$O (0.09 g, 2.34 mmol) were dissolved in THF (4 mL)/MeOH (4 mL)/H$_2$O (1 mL) at room temperature. The solution was stirred at the same temperature for 5 hours, the reaction mixture was concentrated under reduced pressure. The concentrate was added with water (30 mL), and stirred. The resulting precipitate was filtered; and dried to yield the title compound as white solid (0.14 g, 71%).

Step 3.

Compound 1056: 4-(5-((1-(2-ethyl-2-fluorobutyl)piperidin-4-yl)methoxy)pyrimidin-2-yl)-3-fluorobenzoic acid (0.04 g, 0.10 mmol), (R)-piperidin-3-ol hydrochloride (0.01 g, 0.12 mmol), HOBt (0.02 g, 0.20 mmol), EDC (0.04 g, 0.20 mmol) and DIPEA (0.02 g, 0.20 mmol) were dissolved in CH$_2$Cl$_2$ (1 mL) at room temperature. The solution was stirred at the same temperature for 18 hours. The reaction mixture was added with saturated NH$_4$Cl aqueous solution, and extracted with EtOAc. The organic layer was washed with water, dried over anhydrous MgSO$_4$, and filtered. The filtrate was concentrated under reduced pressure. The concentrate was purified by column chromatography (SiO$_2$, 4 g cartridge; methanol/dichloromethane=0% to 15%), and concentrated to yield the title compound as white solid (0.02 g, 42%).

1H NMR (400 MHz, CDCl$_3$) δ 8.53 (s, 2H), 8.06 (t, 1H, J=7.8 Hz), 7.24-7.33 (m, 2H), 3.97 (d, 2H, J=6.0 Hz), 3.29-3.79 (m, 4H), 3.00-3.02 (m, 2H), 2.49 (s, 1H), 2.43 (s, 1H), 2.15 (t, 2H, J=11.0 Hz), 1.27-2.06 (m, 15H), 0.91 (t, 6H, J=7.5 Hz); MS (ESI) m/z 517.3 (M++H).

According to the above-described synthesis process of compound 1056, the compounds of Table 128 were synthesized using 4-(5-((1-(2-ethyl-2-fluorobutyl)piperidin-4-yl)methoxy)pyrimidin-2-yl)-3-fluorobenzoic acid and the reactant of Table 127.

TABLE 127

| Compound No. | Reactant | Yield (%) |
|---|---|---|
| 1057 | (R)-piperidin-2-carboxamide hydrochloride | 14 |

TABLE 128

| Compound No. | Compound Name, $^1$H-NMR, MS (ESI) |
|---|---|
| 1057 | (R)-1-(4-(5-((1-(2-ethyl-2-fluorobutyl)piperidin-4-yl)methoxy)pyrimidin-2-yl)-3-fluorobenzoyl)piperidin-2-carboxamide<br>1H NMR (400 MHz, CDCl$_3$) δ 8.55 (s, 2 H), 8.10 (t, 1 H, J = 7.4 Hz), 7.23~7.36 (m, 2 H), 6.39 (s, 1 H), 5.41 (s, 1 H), 5.28~5.29 (m, 1 H), 3.98 (d, 2 H, J = 6.1 Hz), 3.78~3.97 (m, 1 H), 3.11~3.18 (m, 1 H), 2.94~3.04 (m, 2 H), 2.50 (s, 1 H), 2.43 (s, 1 H), 2.28~2.37 (m, 1 H), 2.13~2.18 (m, 2 H), 1.42~1.87 (m, 14 H), 0.91 (t, 6 H, J = 7.5 Hz); MS (ESI) m/z 544.3 (M+ + H). |

Example 113. Compound 1054: (S)-1-(4-(5-((1-(2-ethyl-2-fluorobutyl)piperidin-4-yl)methoxy)pyrimidin-2-yl)-2-fluorobenzoyl)pyrrolidine-2-carboxamide

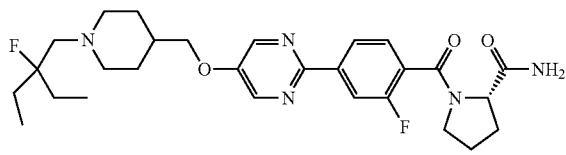 [SMILES: CCC(F)(CC)CN1CCC(COc2cnc(-c3ccc(C(=O)N4CCC[C@H]4C(N)=O)c(F)c3)nc2)CC1]

Step 1.

Ethyl 4-(5-((1-(2-ethyl-2-fluorobutyl)piperidin-4-yl)methoxy)pyrimidin-2-yl)-2-fluorobenzoate: DME (4 mL)/H₂O (1 mL) was added to 2-chloro-5-((1-(2-ethyl-2-fluorobutyl)piperidin-4-yl)methoxy)pyrimidine (the product of synthesis step 2 of compound 1051; 0.25 g, 0.75 mmol), 4-(ethoxycarbonyl)-3-fluorophenylboronic acid (0.17 g, 0.83 mmol), Pd(dppf)Cl₂ (0.03 g, 0.03 mmol) and Cs₂CO₃ (0.49 g, 1.51 mmol). With a microwave radiation, the mixture was heated at 120° C. for 20 minutes, and then cooled to room temperature. The reaction mixture was filtered through a Celite pad to remove a solid. The filtrate was added with saturated NH₄Cl aqueous solution, and extracted with EtOAc. The obtained organic layer was washed with saturated aqueous brine solution, dried over anhydrous MgSO₄, and filtered. The filtrate was concentrated under reduced pressure. The concentrate was purified by column chromatography (SiO₂, 4 g cartridge; EtOAc/hexane=0% to 30%), and concentrated to yield the title compound as white solid (0.26 g, 74%).

Step 2.

4-(5-((1-(2-ethyl-2-fluorobutyl)piperidin-4-yl)methoxy)pyrimidin-2-yl)-2-fluorobenzoic acid: Ethyl 4-(5-((1-(2-ethyl-2-fluorobutyl)piperidin-4-yl)methoxy)pyrimidin-2-yl)-2-fluorobenzoate (0.26 g, 0.60 mmol) and LiOH·H₂O (0.12 g, 3.02 mmol) were dissolved in THF (4 mL)/MeOH (4 mL)/H₂O (1 mL) at room temperature. The solution was stirred at the same temperature for 5 hours, the reaction mixture was concentrated under reduced pressure. The concentrate was added with water (20 mL), and stirred. The resulting precipitate was filtered, and dried to yield the title compound as white solid (0.19 g, 72%).

Step 3.

Compound 1054: 4-(5-((1-(2-ethyl-2-fluorobutyl)piperidin-4-yl)methoxy)pyrimidin-2-yl)-2-fluorobenzoic acid (0.04 g, 0.10 mmol), L-prolinamide (0.01 g, 0.12 mmol), HOBt (0.02 g, 0.20 mmol), EDC (0.04 g, 0.20 mmol) and DIPEA (0.03 mL, 0.20 mmol) were dissolved in CH₂Cl₂ (1 mL) at room temperature. The solution was stirred at the same temperature for 18 hours. The reaction mixture was added with saturated NH₄Cl aqueous solution, and extracted with EtOAc. The organic layer was washed with water, dried over anhydrous MgSO₄, and filtered. The filtrate was concentrated under reduced pressure. The concentrate was purified by column chromatography (SiO₂, 4 g cartridge; methanol/dichloromethane=0% to 15%), and concentrated to yield the title compound as white solid (0.05 g, 90%).

1H NMR (400 MHz, CDCl₃) δ 8.47 (s, 2H), 823 (d, 1H, J=8.0 Hz), 8.14 (d, 1H, J=11.1 Hz), 7.52 (t, 1H, J=7.5 Hz), 6.96 (s, 1H), 5.71 (s, 1H), 4.81-4.84 (m, 1H), 3.96 (d, 2H, J=6.0 Hz), 3.38-3.56 (m, 2H), 3.03-3.00 (m, 2H), 2.44-2.50 (m, 3H), 1.26-2.18 (m, 14H), 0.90 (t, 6H, J=7.5 Hz); MS (ESI) m/z 530.3 (M++H).

According to the above-described synthesis process of compound 1054, the compounds of Table 130 were synthesized using 4-(5-((1-(2-ethyl-2-fluorobutyl)piperidin-4-yl)methoxy)pyrimidin-2-yl)-2-fluorobenzoic acid and the reactant of Table 129

TABLE 129

| Compound No. | Reactant | Yield (%) |
|---|---|---|
| 1055 | (R)-piperidin-2-carboxamide hydrochloride | 33 |

TABLE 130

| Compound No. | Compound Name, ¹H-NMR, MS (ESI) |
|---|---|
| 1055 | (R)-1-(4-(5-((1-(2-ethyl-2-fluorobutyl)piperidin-4-yl)methoxy)pyrimidin-2-yl)-2-fluorobenzoyl)piperidin-2-carboxamide<br>1H NMR (400 MHz, CDCl₃) δ 8.48 (s, 2 H), 8.27 (d, 1 H, J = 8.0 Hz), 8.15 (d, 1 H, J = 11.2 Hz), 7.54 (t, 1 H, J = 7.5 Hz), 6.33 (s, 1 H), 5.47-5.56 (m, 2 H), 3.97 (d, 2 H, J = 6.1 Hz), 3.57-3.61 (m, 1 H), 3.20-3.22 (m, 1 H), 3.02-3.05 (m, 2 H), 2.45-2.51 (m, 2 H), 2.08 (t, 2 H, J = 19.7 Hz), 1.20-1.83 (m, 15H), 0.91 (t, 6 H, J = 7.5 Hz); MS (ESI) m/z 544.3 (M+ + H). |

Example 114. Compound 937: (S)-1-(4'-((1-(2-ethyl-2-fluorobutyl)piperidin-4-yl)methoxy)-2,3'-difluorobiphenylcarbonyl)pyrrolidine-2-carboxamide

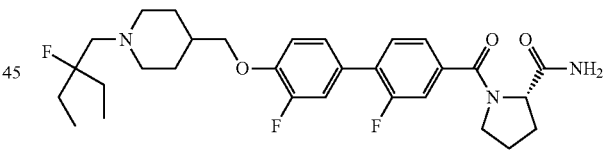

Step 1.

3-((4-((4-bromo-2-fluorophenoxy)methyl)piperidin-1-yl)methyl)pentan-3-ol: EtOH (5 mL)/H₂O (5 mL) was added to 4-((4-bromo-2-fluorophenoxy)methyl)piperidine hydrochloride (the product of synthesis step 2 of compound 725; 500 mg, 1.54 mmol), 2,2-diethyloxirane (771 mg, 7.70 mmol) and K₂CO₃ (426 mg, 3.08 mmol). With a microwave radiation, the mixture was heated at 110° C. for 20 minutes, and then cooled to room temperature. The reaction mixture was added (with water, and extracted with EtOAc. The obtained organic layer was washed with saturated aqueous brine solution, dried over anhydrous MgSO₄, and filtered. The filtrate was concentrated under reduced pressure. The obtained material, which is the title compound as white solid (542 mg, 90%), was used without further purification.

Step 2.

4-((bromo-2-fluorophenoxy)methyl)-1-(2-ethyl-2-fluorobutyl)piperidine: 3-((4-((4-bromo-2-fluorophenoxy)

methyl)piperidin-1-yl)methyl)pentane-3-ol (524 mg, 1.40 mmol) was dissolved in CH$_2$Cl$_2$ (10 mL). At 0° C., DAST (184 μL, 1.40 mmol) was added thereto, following with stirring at room temperature for 1 hour. The reaction mixture was added with water, and extracted with EtOAc. The obtained organic layer was washed with saturated aqueous brine solution, dried over anhydrous MgSO$_4$, and filtered. The filtrate was concentrated under reduced pressure. The concentrate was purified by silica gel column chromatography (EtOAc/hexane=30%~70%) to yield the title compound as white solid (371 mg, 68%).

Step 3.

Ethyl 4'-((1-(2-ethyl-2-fluorobutyl)piperidin-4-yl)methoxy)-2,3'-difluorobiphenyl-4-carboxylate: 4-((bromo-2-fluorophenoxy)methyl)-1-(2-ethyl-2-fluorobutyl)piperidine (371 mg, 0.95 mmol), 2-fluoro-4-(methoxycarbonyl)phenylboronic acid (188 mg, 0.95 mmol), Pd(dppf)Cl$_2$ (78 mg, 0.10 mmol) and Cs$_2$CO$_3$ (619 mg, 1.90 mmol) were added to water (2 mL)/DME (6 mL). With a microwave radiation, the mixture was heated at 110° C. for 15 minutes, and then cooled to room temperature. The reaction mixture was added with water, and extracted with EtOAc. The obtained organic layer was washed with saturated aqueous brine solution, dried over anhydrous MgSO$_4$, and concentrated under reduced pressure. The obtained concentrate was purified by silica gel column chromatography (EtOAc/hexane=30%-70%) to yield the title compound as white solid (242 mg, 53%).

Step 4.

4'-((1-(2-ethyl-2-fluorobutyl)piperidin-4-yl)methoxy)-2,3'-difluorobiphenyl-4-carboxylic acid: Ethyl 4'-((1-(2-ethyl-2-fluorobutyl)piperidin-4-yl)methoxy)-2,3'-difluorobiphenyl-4-carboxylate (242 mg, 0.51 mmol) was dissolved in THF (10 mL) and water (5 mL). LiOH.H$_2$O (106 mg, 2.53 mmol) was added thereto little by little at room temperature, following with stirring for 1 hour. After the completion of the reaction, the reaction mixture was concentrated under reduced pressure. The resulting precipitate was filtered, and dried to yield the title compound as white solid (200 mg, 87%).

Step 5.

Compound 937: 4'-((1-(2-ethyl-2-fluorobutyl)piperidin-4-yl)methoxy)-2,3'-difluorobiphenyl-4-carboxylic acid (40 mg, 0.09 mmol), EDC (34 mg, 0.18 mmol) and HOBt (24 mg, 0.18 mmol) was added thereto, DIPEA (32 μL, 0.18 mmol) was dissolved in CH$_2$Cl$_2$ (1 mL). At room temperature, (S)-pyrrolidine-2-carboxamide (20 mg, 0.18 mmol) was added thereto, following with stirring for a day. The reaction mixture was added with water, and extracted with EtOAc. The obtained organic layer was washed with saturated aqueous brine solution, and then. The organic layer was dried over anhydrous MgSO$_4$, and concentrated under reduced pressure. The concentrate was purified by silica gel column chromatography (CH$_2$Cl$_2$/MeOH=95%~5%) to yield the title compound as white solid (35 mg, 87%).

1H NMR (400 MHz, CDCl$_3$) δ 7.47 (t, 1H, J=7.8 Hz), 7.40-7.27 (m, 4H), 7.03 (t, 1H, J=8.6 Hz), 6.89 (brs, 0.5H), 5.47 (brs, 0.5H), 4.82-4.79 (m, 1H), 3.92 (d, 2H, J=6.2 Hz), 3.66-3.57 (m, 2H), 3.00 (d, 2H, J=10.4 Hz), 2.49-2.43 (m, 2H), 2.18-2.06 (m, 4H), 1.92-1.66 (m, 10H), 1.47-1.41 (m, 2H), 0.92 (s, 3H), 0.88 (s, 3H); MS (ESI) m/z 546 (M++H).

According to the above-described synthesis process of compound 937, the compounds of Table 132 were synthesized using 4'-((1-(2-ethyl-2-fluorobutyl)piperidin-4-yl)methoxy)-2,3'-difluorobiphenyl-4-carboxylic acid and the reactant of Table 131.

TABLE 131

| Compound No. | Reactant | Yield (%) |
| --- | --- | --- |
| 940 | (R)-piperidin-3-ol hydrochloride | 71 |
| 941 | (R)-pyrrolidine-2-ylmethanol | 65 |
| 942 | (S)-piperidin-3-ol hydrochloride | 69 |
| 943 | (S)-pyrrolidine-3-ol | 67 |

TABLE 132

| Compound No. | Compound Name, $^1$H-NMR, MS (ESI) |
| --- | --- |
| 940 | (R)-(4'-((1-(2-ethyl-2-fluorobutyl)piperidin-4-yl)methoxy)-2,3'-difluorobiphenyl-4-yl)(3-hydroxypiperidin-1-yl)methanone<br>1H NMR (400 MHz, CDCl$_3$) δ 7.40 (t, 1 H, J = 7.6 Hz), 7.34-7.22 (m, 4 H), 6.98 (t, 1 H, J = 8.6 Hz), 4.02-3.91 (m, 1 H), 3.89 (d, 2 H, J = 6.3 Hz), 3.84-3.75 (m, 1 H), 3.49 (brs, 1 H), 3.48 (d, 2 H, J= 11.8 Hz), 3.40-3.21 (m, 1 H), 2.97-2.91 (m, 2 H), 2.58 (t, 2 H, J = 11.8 Hz), 2.05-1.71 (m, 12 H), 1.28-1.25 (m, 2 H), 0.89-0.81 (m, 6 H); MS (ESI) m/z 533 (M+ + H). |
| 941 | (R)-(4'-((1-(2-ethyl-2-fluorobutyl)piperidin-4-yl)methoxy)-2,3'-difluorobiphenyl-4-yl)(2-(hydroxymethyl)pyrrolidin-1-yl)methanone<br>1H NMR (400 MHz, CDCl$_3$) δ 7.46 (t, 1 H, J = 7.8 Hz), 7.38-7.27 (m, 4 H), 7.03 (t, 1 H, J = 8.6 Hz), 4.44-4.42 (m, 1 H), 3.92 (d, 2 H, J = 6.2 Hz), 3.86-3.74 (m, 2 H), 3.61-3.53 (m, 2 H), 2.99 (d, 2 H, J = 11.2 Hz), 2.48 (s, 1 H), 2.12 (s, 1 H), 2.23-2.12 (m, 3 H), 1.93-1.88 (m, 1 H), 1.83 (d, 3 H, J =11.9 Hz), 1.75-1.63 (m, 6 H), 1.47-1.41 (m, 2 H), 1.38-1.26 (m, 1 H), 0.93-0.79 (m, 6 H); MS (ESI) m/z 533 (M+ + H). |
| 942 | (S)-(4'-((1-(2-ethyl-2-fluorobutyl)piperidin-4-yl)methoxy)-2,3'-difluorobiphenyl-4-yl)(3-hydroxypiperidin-1-yl)methanone<br>1H NMR (400 MHz, CDCl$_3$) δ 7.40 (t, 1 H, J = 7.6 Hz), 7.34-7.22 (m, 4 H), 6.98 (t, 1 H, J = 8.6 Hz), 4.02-3.91 (m, 1 H), 3.89 (d, 2 H, J = 6.3 Hz), 3.84-3.75 (m, 1 H), 3.49 (brs, 1 H), 3.48 (d, 2 H, J = 11.8 Hz), 3.40-3.21 (m, 1 H), 2.97-2.91 (m, 2 H), 2.58 (t, 2 H, J = 11.8 Hz), 2.05-1.71 (m, 12 H), 1.28-1.25 (m, 2 H), 0.89-0.81 (m, 6 H); MS (ESI) m/z 533 (M+ + H). |
| 943 | (S)-(4'-((1-(2-ethyl-2-fluorobutyl)piperidin-4-yl)methoxy)-2,3'-difluorobiphenyl-4-yl)(3-hydroxypyrrolidin-1-yl)methanone<br>1H NMR (400 MHz, CDCl$_3$) δ 7.44-7.26 (m, 5 H), 7.03 (t, 1 H, J = 8.6 Hz), 4.62-4.61 (m, 1 H), 3.91 (d, 2 H, J = 6.2 Hz), 3.83-3.82 (m, 2 H), 3.80-3.79 (m, 1 H), 3.71-3.67 (m, 1 H), 2.99 (d, 2 H, J = 11.5 Hz), 2.48 (s, 1 H), 2.42 (s, 1 H), 2.17-2.12 (m, 2 H), 2.02-1.85 (m, 3 H), 1.82-1.81 (m, 3 H), 1.75-1.65 (m, 4 H), 1.44-1.40 (m, 2 H), 0.92-0.88 (m, 6 H); MS (ESI) m/z 519 (M+ + H). |

Example 115. Compound 922: (S)-1-(4'-((1-((1-fluorocyclobutyl)methyl)piperidin-4-yl)methoxy)biphenylcarbonyl)pyrrolidine-2-carboxamide

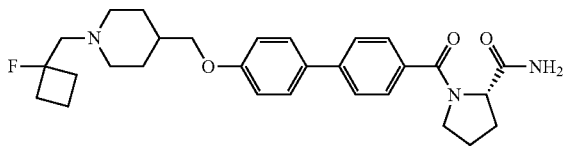 [SMILES: NC(=O)[C@@H]1CCCN1C(=O)c1ccc(-c2ccc(OCC3CCN(CC4(F)CCC4)CC3)cc2)cc1]

Step 1.
1-((4-((4-bromophenoxy)methyl)piperidin-1-yl)methyl)cyclobutanol: 4-((4-bromophenoxy)methyl)piperidine (the product of synthesis step 4 of compound 686; 0.10 g, 0.33 mmol), 1-oxaspiro[2,3]hexane (55 mg, 0.65 mmol) and Et$_3$N (0.23 μL, 1.63 mmol) were dissolved in EtOH 2 mL. With a microwave radiation, the reaction was performed at 110° C. for 20 minutes. The reaction mixture was diluted with water, and extracted with CH$_2$Cl$_2$. The organic layer was dried over MgSO$_4$, and filtered to remove a solid. The filtrate was concentrated under reduced pressure to yield the title compound as white solid (90 mg, 78%).

Step 2.
4-((4-bromophenoxy)methyl)-1-((1-fluorocyclobutyl)methyl)piperidine: 1-((4-((4-bromophenoxy)methyl)piperidin-1-yl)methyl)cyclobutanol (0.61 g, 1.72 mmol) was dissolved in CH$_2$Cl$_2$ 10 mL. DAST (0.23 μL, 1.72 mmol) was added thereto. After stirring for 1 hour at room temperature, a saturated NaHCO$_3$ aqueous solution was added thereto, and extracted with CH$_2$Cl$_2$. The organic layer was dried over MgSO$_4$, and filtered to remove a solid. The filtrate was concentrated under reduced pressure. The concentrate was purified by column chromatography (12 g, ISU silica gel cartridge, 0-5% MeOH/CH$_2$Cl$_2$) to yield the title compound as white solid (234 mg, 38%).

Step 3.
Methyl 4'-((1-((1-fluorocyclobutyl)methyl)piperidin-4-yl)methoxy)biphenyl-4-carboxylate: 4-((4-bromophenoxy)methyl)-1-((1-fluorocyclobutyl)methyl)piperidine (234 mg, 0.66 mmol), 4-(methoxycarbonyl)phenylboronic acid (0.14 g, 0.79 mmol), Pd(dbpf)Cl$_2$ (13 mg, 0.02 mmol) and Cs$_2$CO$_3$ (0.64 g, 1.97 mmol) were added to the mixed solvents of 1,4-dioxane/H$_2$O 3 mL/1 mL. With a microwave radiation, the mixture was heated at 140° C. for 15 minutes, and then cooled to room temperature. The reaction mixture was added with water, and extracted with CH$_2$Cl$_2$. The obtained organic layer was washed with saturated aqueous brine solution, dried over anhydrous MgSO$_4$, filtered through Celite to remove a solid, and then concentrated under reduced pressure. The concentrate was purified by column chromatography (SiO$_2$, methanol/dichloromethane=0% to 5%), and concentrated to yield the title compound as light-yellow solid (194 mg, 72%).

Step 4.
4'-((1-((1-fluorocyclobutyl)methyl)piperidin-4-yl)methoxy)biphenyl-4-carboxylic acid: Methyl 4'-((1-((1-fluorocyclobutyl)methyl)piperidin-4-yl)methoxy)biphenyl-4-carboxylate (0.19 g, 0.47 mmol) and LiOH.H$_2$O (0.1 g, 2.35 mmol) were dissolved in THF/MeOH/H$_2$O 6 mL/2 mL/2 mL, and then refluxed with heating and stirring for 4 hours. The reaction mixture was cooled to room temperature, and added with water. The resulting precipitate was filtered, and dried to yield the title compound as light-brown solid (0.18 g, 94%).

Step 5.
Compound 922: 4'-((1-((1-fluorocyclobutyl)methyl)piperidin-4-yl)methoxy)biphenyl-4-carboxylic acid (0.04 g, 0.10 mmol), EDCI (0.04 g, 0.20 mmol), HOBt (0.03 g, 0.20 mmol) and DIPEA (0.09 mL, 0.50 mmol) were dissolved in DMF (2 mL). At room temperature, (0.02 g, 0.20 mmol) was added thereto, following with stirring at 60° C. for 12 hours. The concentrate was added with water (10 mL) to be suspended, and filtered. The obtained solid was dried, and purified by column chromatography (SiO$_2$; methanol/dichloromethane=0% to 10%), and concentrated yield the title compound as light-yellow solid (0.03 g, 58%).

1H NMR (400 MHz, CDCl$_3$) δ 7.59 (s, 4H), 7.53 (d, 2H, J=8.8 Hz), 7.04 (brs, 1H), 6.98 (d, 2H, J=9.0 Hz), 5.65 (brs, 1H), 4.81 (brs, 1H), 3.85 (d, 2H, J=6.0 Hz), 3.63-3.59 (m, 2H), 3.01 (d, 2H, J=11.4 Hz), 2.66 (s, 1H), 2.60 (s, 1H), 2.28-2.00 (m, 10H), 1.87-1.81 (m, 3H), 1.50-1.44 (m, 4H); MS (ESI) m/z 494 (M++H).

According to the above-described synthesis process of compound 922, the compounds of Table 134 were synthesized using 4'-((1-((1-fluorocyclobutyl)methyl)piperidin-4-yl)methoxy)biphenyl-4-carboxylic acid and the reactant of Table 133.

TABLE 133

| Compound No. | Reactant | Yield (%) |
|---|---|---|
| 923 | (R)-pyrrolidine-2-ylmethanol | 38 |
| 924 | (S)-pyrrolidine-3-ol | 70 |
| 925 | (R)-piperidin-3-ol | 46 |

TABLE 134

| Compound No. | Compound Name, $^1$H-NMR, MS (ESI) |
|---|---|
| 923 | (R)-(4'-((1-((1-fluorocyclobutyl)methyl)piperidin-4-yl)methoxy)biphenyl-4-yl)(2-(hydroxymethyl)pyrrolidin-1-yl)methanone<br>1H NMR (400 MHz, CDCl$_3$) δ 7.58-7.53 (m, 4 H), 7.51 (d, 2 H, J = 12.0 Hz), 6.96 (d, 2 H, J = 8.8 Hz), 4.52-4.48 (m, 1 H), 3.83-3.59 (m, 6 H), 2.98 (d, 2 H, J = 11.6 Hz), 2.64 (s, 1 H), 2.57 (s, 1 H), 2.26-2.12 (m, 8 H), 1.86-1.78 (m, 6 H), 1.48-1.41 (m, 5 H); MS (ESI) m/z 481 (M+ + H). |
| 924 | (S)-(4'-((1-((1-fluorocyclobutyl)methyl)piperidin-4-yl)methoxy)biphenyl-4-yl)(3-hydroxypyrrolidin-1-yl)methanone<br>1H NMR (400 MHz, CDCl$_3$) δ 7.55-7.49 (m, 6 H), 6.96 (d, 2 H, J = 11.6 Hz), 4.49 (d, 1 H, J = 49.6 Hz), 3.84-3.47 (m, 6 H), 3.01 (d, 2 H, J = 11.2 Hz), 2.66 (s, 1 H), 2.60 (s, 1 H), 2.34-2.03 (m, 8 H), 1.96-1.80 (m, 3 H), 1.55-1.26 (m, 4 H); MS (ESI) m/z 467 (M+ + H). |
| 925 | (R)-(4'-((1-((1-fluorocyclobutyl)methyl)piperidin-4-yl)methoxy)biphenyl-4-yl)(3-hydroxypiperidin-1-yl)methanone<br>1H NMR (400 MHz, CDCl$_3$) δ 7.58-7.45 (m, 6 H), 6.98-6.96 (m, 2 H), 4.02- |

TABLE 134-continued

Compound No. Compound Name, ¹H-NMR, MS (ESI)

3.41 (m, 7 H), 4.02-3.41 (m, 7 H), 3.01 (d, 2 H, J = 11.2 Hz), 2.66 (s, 1 H), 2.60 (s, 1 H), 2.34-2.03 (m, 7 H), 1.95-1.64 (m, 8 H), 1.55-1.41 (m, 4 H); MS (ESI) m/z 481 (M+ + H).

Example 116. Compound 760: (S)-1-(4'-((1-((1-fluorocyclohexyl)methyl)piperidin-4-yl)methoxy)biphenylcarbonyl)pyrrolidine-2-carboxamide

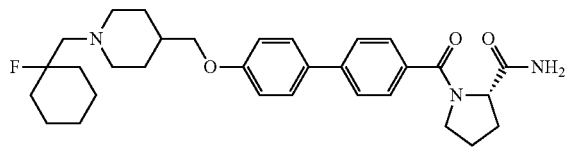 [SMILES: NC(=O)[C@@H]1CCCN1C(=O)c1ccc(-c2ccc(OCC3CCN(CC4(F)CCCCC4)CC3)cc2)cc1]

Step 1.

1-((4-((4-bromophenoxy)methyl)piperidin-1-yl)methyl)cyclohexanol: 4-((4-bromophenoxy)methyl)piperidine hydrochloride (500 mg, 1.63 mmol), 1-oxaspiro[2.5]octane (274 mg, 2.45 mmol) and K₂CO₃ (113 mg, 0.82 mmol) were added into a microwave reactor, and then ethanol 4 mL and water 2 mL were added thereto. With a microwave radiation, the reaction was performed at 110° C. for 30 minutes. After removing ethanol, a little of water was added to the reaction mixture. The resulting precipitate was washed thoroughly with water, and dried to yield the title compound as white solid (520 mg, 83%).

Step 2.

4-((4-bromophenoxy)methyl)-1-((1-fluorocyclohexyl)methyl)piperidine: 1-((4-((4-bromophenoxy)methyl)piperidin-1-yl)methyl)cyclohexanol (400 mg, 1.05 mmol) was dissolved in CH₂Cl₂ 10 ml. Deoxo-Fluor® (0.23 mL, 1.26 mmol) was added thereto, following with stirring at room temperature for 5 hours. A saturated NaHCO₃ aqueous solution was added thereto, and the mixture was extracted with CH₂Cl₂. The obtained organic layer was dried over MgSO₄, and filtered. The filtrate was concentrated under reduced pressure. The obtained concentrate was purified by silica gel column chromatography (10-50% EtOAc/hexane) to yield the title compound as white solid (100 mg, 25%).

Step 3.

Methyl 4'-((1-((1-fluorocyclohexyl)methyl)piperidin-4-yl)methoxy)biphenyl-4-carboxylate: 4-((4-bromophenoxy)methyl)-1-((1-fluorocyclohexyl)methyl)piperidine (115 mg, 0.30 mmol), 4-(methoxycarbonyl)phenylboronic acid (60 mg, 0.33 mmol), Pd(dbpf)Cl₂ (6 mg, 0.01 mmol), Cs₂CO₃ (291 mg, 0.90 mmol) were added into a microwave reactor, and then 1,4-dioxane 4 mL and water 2 mL were added thereto. With a microwave radiation, the reaction was performed at 110° C. for 30 minutes. The reaction mixture was filtered through a Celite pad. The filtrate was added with water, and then extracted with EtOAc. The obtained organic layer was dried over MgSO₄, and filtered. The filtrate was concentrated under reduced pressure. The obtained concentrate was purified by silica gel column chromatography (20-70% EtOAc/hexane) to yield the title compound as white solid (100 mg, 76%).

Step 4.

4'-((1-((1-fluorocyclohexyl)methyl)piperidin-4-yl)methoxy)biphenyl-4-carboxylic acid: Methyl 4'-((1-((1-fluorocyclohexyl)methyl)piperidin-4-yl)methoxy)biphenyl-4-carboxylate (100 mg, 0.23 mmol) was dissolved in the mixed solvents of THF 2 mL/water 2 mL. LiOH.H₂O (20 mg, 0.46 mmol) was added thereto, and the reaction was performed at 60° C. for 4 hours. The solvent was concentrated under reduced pressure. After the addition of 1M HCl thereto, the resulting precipitate was filtered to yield the title compound as white solid (95 mg, 98%).

Step 5.

Compound 760: 4'-((1-((1-fluorocyclohexyl)methyl)piperidin-4-yl)methoxy)biphenyl-4-carboxylic acid (50 mg, 0.12 mmol), L-prolinamide (20 mg, 0.18 mmol), EDC (45 mg, 0.24 mmol) and HOBt (32 mg, 0.24 mmol) were dissolved in DMF 2 mL. DIPEA (30 mg, 0.24 mmol) was added thereto, and the reaction was performed at 60° C. for 10 hours. The reaction mixture was cooled to room temperature, and added with water. The formed solid was filtered, washed with water thoroughly, and dried to yield the title compound as yellow solid (15 mg, 25%).

1H NMR (400 MHz, CDCl₃) δ 7.62-7.52 (m, 5H), 7.02-6.97 (m, 3H), 5.42 (s, 1H), 4.85 (t, 1H, J=6.2 Hz), 3.86 (s, 2H), 3.61 (m, 2H), 3.01 (m, 2H), 2.53 (m, 3H), 2.21-2.04 (m, 4H), 1.85 (m, 6H), 1.65-1.24 (m, 11H); MS (ESI) m/z 522 (M++H).

According to the above-described synthesis process of compound 760, the compounds of Table 136 were synthesized using 4'-((1-((1-fluorocyclohexyl)methyl)piperidin-4-yl)methoxy)biphenyl-4-carboxylic acid and the reactant of Table 135.

TABLE 135

| Compound No. | Reactant | Yield (%) |
| --- | --- | --- |
| 761 | (R)-piperidin-3-ol hydrochloride | 28 |

TABLE 136

Compound No. Compound Name, ¹H-NMR, MS (ESI)

761  (R)-(4'-((1-((1-fluorocyclohexyl)methyl)piperidin-4-yl)methoxy)biphenyl-4-yl)(3-hydroxypiperidin-1-yl)methanone
1H NMR (400 MHz, CDCl₃) δ 7.58 (d, 2 H, J = 8.2 Hz), 7.53 (d, 2 H, J = 8.8 Hz), 7.48 (d, 2 H, J = 8.3 Hz), 6.98 (d, 2 H, J = 8.0 Hz), 4.02-3.42 (m, 7 H), 3.07 (m, 2 H), 2.59-2.06 (m, 5 H), 2.00-1.80 (m, 8 H), 1.80-1.24 (m, 11 H); MS (ESI) m/z 509 (M+ + H).

Example 117. Compound 857: (R)-1-(4'-((1-(2-fluoro-2-methylpropyl)piperidin-4-yl)methylamino)biphenylcarbonyl)piperidin-2-carboxamide

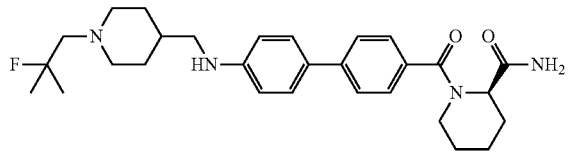 [SMILES: CC(C)(F)CN1CCC(CNc2ccc(-c3ccc(C(=O)N4CCCC[C@@H]4C(N)=O)cc3)cc2)CC1]

Step 1.

t-butyl 4-((4-bromophenylamino)methyl)piperidin-1-carboxylate: 4-bromobenzeneamine (4.00 g, 18.76 mmol) was dissolved in MeOH 100 mL. Acetic acid (1.03 mL, 18.76 mmol) and t-butyl 4-formylpiperidin-1-carboxylate (3.38 g, 19.69 mmol) were added thereto, following with stirring at room temperature for 5 hours. NaCNBH$_3$ (1.17 g, 18.75 mmol) was added thereto slowly at 0° C., following with stirring at room temperature for 3 hours and extracting with CH$_2$Cl$_2$. The obtained organic layer was washed with saturated aqueous brine solution three times. The obtained organic layer was dried over Na$_2$SO$_4$, and filtered. The filtrate was concentrated under reduced pressure. The concentrate was purified by column chromatography (4 g ISCO silica gel cartridge, 0-30% EtOAc/hexane) to yield the title compound as light-yellow solid (3.00 g, 43%).

Step 2.

t-butyl 4-((benzyl(4-bromophenyl)amino)methyl)piperidin-1-carboxylate: t-butyl 4-((4-bromophenylamino)methyl)piperidin-1-carboxylate (3.00 g, 8.12 mmol) and NaH (0.39 g, 16.24 mmol) were dissolved in DMF (100 mL). At 0° C., benzyl bromide (2.08 g, 12.18 mmol) was added thereto, following with stirring at room temperature for 12 hours. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, EtOAc/hexane=0% to 20%), and concentrated to yield the title compound as white solid (2.70 g, 72%).

Step 3.

N-benzyl-4-bromo-N-(piperidin-4-ylmethyl)benzeneamine hydrochloride: t-butyl 4-((benzyl(4-bromophenyl)amino)methyl)piperidin-1-carboxylate (5.20 g, 14.08 mmol) was dissolved in EtOAc (100 mL). At room temperature, HCl in 1,4-dioxane (17.60 mL, 70.40 mmol) was added thereto, following with stirring at the same temperature for 2 hours. The resulting precipitate was filtered, and dried to yield the title compound as white solid (4.80 g, 86%).

Step 4.

1-(4-((benzyl(4-bromophenyl)amino)methyl)piperidin-1-yl)-2 methylpropan-2-ol: N-benzyl-4-bromo-N-(piperidin-4-ylmethyl)benzeneamine hydrochloride (2.40 g, 6.70 mmol) and K$_2$CO$_3$ (4.63 g, 33.51 mmol) were dissolved in EtOH (10 mL)/H$_2$O (10 mL). 1,2-epoxy-2-methylpropane (5.95 mL, 67.02 mmol) was added thereto. With a microwave radiation, the mixture was heated at 110° C. for 20 minutes, and then cooled to room temperature. The reaction mixture was added with water, and extracted with dichloromethane. The obtained organic layer was washed with saturated aqueous brine solution, dried over anhydrous MgSO$_4$, and filtered. The filtrate was concentrated under reduced pressure. The concentrate was used without further purification for the next step (2.00 g, 69%, colorless oil).

Step 5.

N-benzyl-4-bromo-N-((1-(2-fluoro-2-methylpropyl)piperidin-2-yl)methyl)benzeneamine: 1-(4-((benzyl(4-bromophenyl)amino)methyl)piperidin-1-yl)-2 methylpropan-2-ol (4.00 g, 9.27 mmol) was dissolved in CH$_2$Cl$_2$ (100 mL). At 0° C., DAST (1.64 g, 10.19 mmol) was added thereto. Following with stirring at the same temperature for 1 hour. The reaction mixture was added with water, and extracted with dichloromethane. The obtained organic layer was washed with saturated aqueous brine solution, dried over anhydrous MgSO$_4$, and filtered. The filtrate was concentrated under reduced pressure. The concentrate was purified by column chromatography (SiO$_2$, EtOAc/hexane=0% to 20%), and concentrated to yield the title compound as colorless oil (2.87 g, 71%).

Step 6.

Methyl 4'-(benzyl((1-(2-fluoro-2-methylpropyl)piperidin-4-yl)methyl)amino)biphenyl-4-carboxylate: N-benzyl-4-bromo-N-((1-(2-fluoro-2-methylpropyl)piperidin-2-yl)methyl)benzeneamine (1.00 g, 2.30 mmol), 4-(methoxycarbonyl)phenylboronic acid (0.41 g, 2.30 mmol), Pd(dbpf)Cl$_2$ (0.07 g, 0.11 mmol) and Cs$_2$CO$_3$ (1.50 g, 4.61 mmol) were added to 1,4-dioxane (12 mL)/H$_2$O (3 mL). With a microwave radiation, the mixture was heated at 120° C. for 20 minutes, and then cooled to room temperature. The reaction mixture was filtered through a Celite pad to remove a solid. The obtained filtrate was diluted with water, and extracted with EtOAc. The organic layer was washed with saturated aqueous brine solution, dried over anhydrous MgSO$_4$, and filtered. The filtrate was concentrated under reduced pressure. The concentrate was purified by column chromatography (SiO$_2$, EtOAc/hexane=0% to 20%), and concentrated to yield the title compound as yellow oil (0.89 g, 78%).

Step 7.

Methyl 4'-((1-(2-fluoro-2-methylpropyl)piperidin-4-yl)methylamino)biphenyl-4-carboxylate: Methyl 4'-(benzyl((1-(2-fluoro-2-methylpropyl)piperidin-4-yl)methyl)amino)biphenyl-4-carboxylate (0.89 g, 1.82 mmol) was dissolved in MeOH (3 mL)/EtOAc (5 mL). At room temperature, NH$_4$COOH (1.14 g, 18.21 mmol) was added thereto, following with stirring at 80° C. for 2 hours. The reaction mixture was filtered through a Celite pad to remove a solid. The obtained filtrate was diluted with water, and extracted with dichloromethane. The obtained organic layer was washed with saturated aqueous brine solution, dried over anhydrous MgSO$_4$, and filtered. The filtrate was concentrated under reduced pressure. The concentrate was purified by column chromatography (SiO$_2$, EtOAc/hexane=0% to 30%), and concentrated yield the title compound as light-yellow solid (0.40 g, 55%).

Step 8.

4'-((1-(2-fluoro-2-methylpropyl)piperidin-4-yl)methylamino)biphenyl-4-carboxylic acid: Methyl 4'-((1-(2-fluoro-2-methylpropyl)piperidin-4-yl)methylamino)biphenyl-4-carboxylate (0.40 g, 1.0 mmol) was dissolved in THF (3 mL)/H$_2$O/MeOH (2 mL). At room temperature, LiOH.H$_2$O (0.21 g, 5.01 mmol) was added thereto, following with stirring at the same temperature for 1 hour. The reaction mixture was concentrated under reduced pressure. The concentrate was added with water (10 mL), and stirred. The resulting precipitate was filtered, and dried to yield the title compound as white solid (0.32 g, 84%).

Step 9.

Compound 857: 4'-((1-(2-fluoro-2-methylpropyl)piperidin-4-yl)methylamino)biphenyl-4-carboxylic acid (0.10 g, 0.23 mmol), EDCI (0.09 g, 0.47 mmol), HOBt (0.06 g, 0.47 mmol) and DIPEA (0.15 g, 1.18 mmol) were dissolved in DMF (2 mL). At room temperature, (R)-piperidin-2-carboxamide (0.06 g, 0.47 mmol) was added thereto, following with stirring at 60° C. for 5 hours. The concentrate was added with water (6 mL), and stirred. The resulting precipitate was filtered, dried, and purified by column chromatography (SiO$_2$, dichloromethane/methanol=0% to 5%), and concentrated to yield the title compound as light-yellow solid (0.06 g, 51%).

1H NMR (400 MHz, CDCl$_3$) δ 7.56-7.27 (m, 6H), 6.67-6.61 (m, 3H), 5.92 (brs, 1H), 5.28 (brs, 1H), 3.83 (d, 1H, J=12.0 Hz), 3.13-2.94 (m, 5H), 2.45 (s, 1H), 2.39 (s, 1H), 2.33 (d, 1H, J=12.0 Hz), 2.12 (t, 2H, J=11.4 Hz), 1.75-1.55 (m, 8H), 1.38-1.23 (m, 8H); MS (ESI) m/z 495 (M++H)

According to the above-described synthesis process of compound 857, the compounds of Table 138 were synthesized using 4'-((1-(2-fluoro-2-methylpropyl)piperidin-4-yl)methylamino)biphenyl-4-carboxylic acid and the reactant of Table 137.

TABLE 137

| Compound No. | Reactant | Yield (%) |
|---|---|---|
| 858 | (S)-pyrrolidine-2-ylmethanol | 78 |
| 859 | (R)-pyrrolidine-2-ylmethanol | 69 |
| 867 | (R)-piperidin-3-ol | 54 |
| 868 | (S)-pyrrolidine-2-carboxamide | 68 |
| 869 | (S)-pyrrolidine-3-ol | 66 |

Example 118. Compound 870: (S)-1-(3-fluoro-4'-((1-(2-fluoro-2-methylpropyl)piperidin-4-yl)methylamino)biphenylcarbonyl)pyrrolidine-2-carboxamide

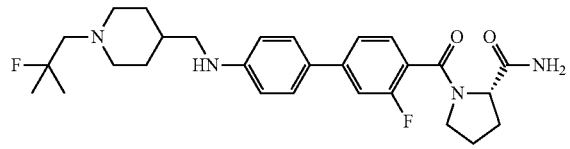 [SMILES: CC(C)(F)CN1CCC(CNc2ccc(-c3ccc(C(=O)N4CCC[C@H]4C(N)=O)c(F)c3)cc2)CC1]

Step 1.

Ethyl 4'-(benzyl((1-(2-fluoro-2-methylpropyl)piperidin-4-yl)methyl)amino)-3-fluorobiphenyl-4-carboxylate:

N-benzyl-4-bromo-N-((1-(2-fluoro-2-methylpropyl)piperidin-4-yl)methyl)benzeneamine (0.80 g, 1.84 mmol), 4-(ethoxycarbonyl)-3-fluorophenylboronic acid (0.36 g, 1.84 mmol), Pd(dbpf)Cl$_2$ (0.06 g, 0.09 mmol) and Cs$_2$CO$_3$ (1.20 g, 3.69 mmol) were added to 1,4-dioxane (12 mL)/H$_2$O (3 mL). With a microwave radiation, the mixture was heated at 120° C. for 20 minutes, and then cooled to room temperature. The reaction mixture was filtered through a Celite pad to remove a solid. The obtained filtrate was added with saturated aqueous brine solution was added thereto, and then extracted with dichloromethane. The obtained organic layer was washed with saturated aqueous brine solution, dried over anhydrous MgSO$_4$, and filtered. The filtrate was concentrated under reduced pressure. The concentrate was purified by column chromatography (SiO$_2$, EtOAc/hexane=0% to 20%), and concentrated to yield the title compound as yellow oil (0.74 g, 79%).

TABLE 138

| Compound No. | Compound Name, $^1$H-NMR, MS (ESI) |
|---|---|
| 858 | (S)-(4'-((1-(2-fluoro-2-methylpropyl)piperidin-4-yl)methylamino)biphenyl-4-yl)(2-(hydroxymethyl)pyrrolidin-1-yl)methanone<br>1H NMR (400 MHz, CDCl$_3$) δ 7.56-7.50 (m, 4 H), 7.43 (d, 2 H, J = 8.0 Hz), 6.65 (d, 2 H, J = 8.5 Hz), 4.37 (m, 1 H), 3.75-3.57 (m, 4 H), 3.03 (d, 2 H, J = 6.4 Hz), 2.95 (d, 2 H, J = 11.6 Hz), 2.13-2.07 (m, 3 H), 1.73-1.70 (m, 6 H), 1.37-1.31 (m, 8 H); MS (ESI) m/z 468 (M+ + H). |
| 859 | (R)-(4'-((1-(2-fluoro-2-methylpropyl)piperidin-4-yl)methylamino)biphenyl-4-yl)(2-(hydroxymethyl)pyrrolidin-1-yl)methanone<br>1H NMR (400 MHz, CDCl$_3$) δ 7.56-7.50 (m, 4 H), 7.42 (d, 2 H, J = 8.0 Hz), 6.65 (d, 2 H, J = 8.3 Hz), 4.38-4.36 (m, 1 H), 3.75-3.73 (m, 2 H), 3.58-3.53 (m, 2 H), 3.03 (d, 2 H, J = 6.4 Hz), 2.95 (d, 2 H, J = 11.6 Hz), 2.44-2.38 (m, 3 H), 2.13-2.07 (m, 3 H), 1.92-1.56 (m, 5 H), 1.36-1.31 (m, 8 H); MS (ESI) m/z 468 (M+ + H). |
| 867 | (R)-(4'-((1-(2-fluoro-2-methylpropyl)piperidin-4-yl)methylamino)biphenyl-4-yl)(3-hydroxypiperidin-1-yl)methanone;<br>MS (ESI) m/z 468 (M+ + H). |
| 868 | (S)-1-(4'-((1-(2-fluoro-2-methylpropyl)piperidin-4-yl)methylamino)biphenylcarbonyl)pyrrolidine-2-carboxamide<br>1H NMR (400 MHz, CDCl$_3$) δ 7.57-7.52 (m, 4 H), 7.42 (d, 2 H, J = 8.2 Hz), 6.64 (d, 2 H, J = 8.2 Hz), 4.68 (t, 1 H, J = 6.9 Hz), 3.67-3.55 (m, 2 H), 3.02 (d, 2 H, J = 6.5 Hz), 2.95 (d, 2 H, J = 11.4 Hz), 2.43 (s, 1 H), 2.38 (s, 1 H), 2.21-2.00 (m, 5 H), 1.72-1.69 (m, 4 H), 1.56-1.23 (m, 8 H); MS (ESI) m/z 482 (M+ + H). |
| 869 | (S)-(4'-((1-(2-fluoro-2-methylpropyl)piperidin-4-yl)methylamino)biphenyl-4-yl)(3-hydroxypyrrolidin-1-yl)methanone<br>1H NMR (400 MHz, CDCl$_3$) δ 7.50-7.37 (m, 4 H), 7.36 (d, 2 H, J = 6.8 Hz), 6.60 (d, 2 H, J = 8.8 Hz), 4.43-4.26 (m, 1 H), 3.72-3.53 (m, 5 H), 2.97 (d, 2 H, J = 6.4 Hz), 2.90 (d, 2 H, J = 11.6 Hz), 2.39 (s, 1 H), 2.33 (s, 1 H), 2.06-1.87 (m, 4 H), 1.67 (d, 2 H, J = 12.4 Hz), 1.59-1.56 (m, 1 H), 1.33-1.25 (m, 8 H); MS (ESI) m/z 454 (M+ + H). |

Step 2.

Ethyl 3-fluoro-4'-((1-(2-fluoro-2-methylpropyl)piperidin-4-yl)methylamino)biphenyl-4-carboxylate: Ethyl 4'-(benzyl((1-(2-fluoro-2-methylpropyl)piperidin-4-yl)methyl)amino)-3-fluorobiphenyl-4-carboxylate (0.74 g, 1.41 mmol) was dissolved in MeOH (3 mL)/EtOAc (5 mL). At room temperature, NH$_4$COOH (0.89 g, 14.15 mmol) was added thereto, following with stirring at 80° C. for 2 hours. The reaction mixture was filtered through a Celite pad to remove a solid. The obtained filtrate was diluted with water, and extracted with dichloromethane. The obtained organic layer was washed with saturated aqueous brine solution, dried over anhydrous MgSO$_4$, and filtered. The filtrate was concentrated under reduced pressure. The concentrate was purified by column chromatography (SiO$_2$, EtOAc/hexane=0% to 20%), and concentrated to yield the title compound as light-yellow solid (0.40 g, 67%).

Step 3.

3-fluoro-4'-((1-(2-fluoro-2-methylpropyl)piperidin-4-yl)methylamino)biphenyl-4-carboxylic acid: Ethyl 3-fluoro-4'-((1-(2-fluoro-2-methylpropyl)piperidin-4-yl)methylamino)biphenyl-4-carboxylate (0.37 g, 0.88 mmol) was dissolved in THF (3 mL)/H$_2$OMeOH (2 mL). At room temperature, LiOH.H$_2$O (0.18 g, 4.44 mmol) was added thereto, following with stirring at the same temperature for 1 hour. The reaction mixture was concentrated under reduced pressure. The concentrate was added with water (10 mL), and stirred. The resulting precipitate was filtered, and dried to yield the title compound as white solid (0.35 g, 97%).

Step 4.

Compound 870: 3-fluoro-4'-((1-(2-fluoro-2-methylpropyl)piperidin-4-yl)methylamino)biphenyl-4-carboxylic acid (0.06 g, 0.14 mmol), EDCI (0.05 g, 0.29 mmol), HOBt (0.04 g, 0.29 mmol) and DIPEA (0.13 mL, 0.74 mmol) were dissolved in DMF (2 mL). At room temperature, (S)-pyrrolidine-2-carboxamide (0.03 g, 0.29 mmol) was added thereto, following with stirring at 60° C. for 5 hours. The concentrate was added with water (5 mL) to be suspended, and filtered. The obtained solid was dried, and purified by column chromatography (SiO$_2$, dichloromethane/methanol=0% to 10%), and concentrated yield the title compound as light-yellow solid (0.04 g, 61%).

1H NMR (400 MHz, CDCl$_3$) δ 7.57-7.37 (m, 4H), 7.27 (t, 1H, J=5.6 Hz), 6.95 (brs, 1H), 6.67 (d, 2H, J=8.8 Hz), 5.59 (brs, 1H), 4.83-4.80 (m, 1H), 3.55-3.42 (m, 2H), 3.06 (d, 2H, J=6.8 Hz), 2.98 (d, 2H, J=11.2 Hz), 2.46-2.40 (m, 3H), 2.15-1.86 (m, 5H), 1.74 (d, 2H, J=12.4 Hz), 1.60-1.56 (m, 1H), 1.39-1.26 (m, 8H); MS (ESI) m/z 499 (M++H).

According to the above-described synthesis process of compound 870, the compounds of Table 140 were synthesized using 3-fluoro-4'-((1-(2-fluoro-2-methylpropyl)piperidin-4-yl)methylamino)biphenyl-4-carboxylic acid and the reactant of Table 139.

TABLE 139

| Compound No. | Reactant | Yield (%) |
|---|---|---|
| 871 | (R)-piperidin-3-carboxamide | 40 |

TABLE 140

| Compound No. | Compound Name, $^1$H-NMR, MS (ESI) |
|---|---|
| 871 | (R)-1-(3-fluoro-4'-((1-(2-fluoro-2-methylpropyl)piperidin-4-yl)methylamino)biphenylcarbonyl)piperidin-3-carboxamide<br>1H NMR (400 MHz, CDCl3) δ 7.42 (d, 2 H, J = 8.4 Hz), 7.37 (s, 1 H), 7.27-7.21 (m, 3 H), 6.66 (d, 2 H, J = 8.0 Hz), 5.54 (brs, 1 H), 4.17-4.14 (m, 1 H), 3.79-3.74 (m, 1 H), 3.48-3.32 (m, 2 H), 3.06 (d, 2 H, J = 6.4 Hz), 2.98 (d, 2 H, J = 11.2 Hz), 2.58 (brs, 1 H), 2.46 (s, 1 H), 2.41 (s, 1 H), 2.15-1.46 (m, 9 H), 1.39-1.18 (m, 8 H); MS (ESI) m/z 513 (M+ + H). |

Example 119. Compound 1020: (S)-(3-hydroxypyrrolidine-1-yl)(4'-((1-((1-(trifluoromethyl)cyclobutyl)methyl)piperidin-4-yl)methylamino)biphenyl-4-yl)methanone

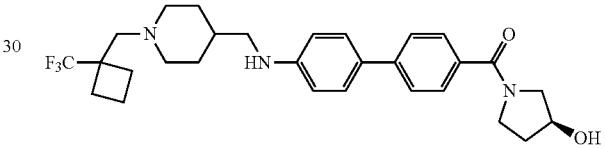

Step 1.

(4-((benzyl(4-bromophenyl)amino)methyl)piperidin-1-yl)(1-(trifluoromethyl)cyclobutyl)methanone: N-benzyl-4-bromo-N-(piperidin-4-ylmethyl)benzeneamine hydrochloride (the product of synthesis step 3 of compound 857; 0.80 g, 4.75 mmol), EDCI (1.82 g, 9.51 mmol), HOBt (1.28 g, 9.51 mmol) and DIPEA (4.15 mL, 23.79 mmol) were dissolved in DMF (20 mL). At room temperature, 1-(trifluoromethyl)cyclobutanecarboxylic acid (1.97 g, 4.99 mmol) was added thereto, following with stirring at the same temperature for 12 hours. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; EtOAc/hexane=0% to 20%), and concentrated to yield the title compound as yellow oil (1.30 g, 53%).

Step 2.

N-benzyl-4-bromo-N-((1-((1-(trifluoromethyl)cyclobutyl)methyl)piperidin-4-yl)methyl)benzeneamine: (4-((benzyl(4-bromophenyl)amino)methyl)piperidin-1-yl)(1-(trifluoromethyl)cyclobutyl)methanone (1.30 g, 2.55 mmol) was dissolved in THF (15 mL) and then cooled to room temperature, following with concentrating under reduced pressure. The concentrate with heating and stirring for 1 hour, and then cooled to room temperature. The reaction mixture was added with water, and extracted with EtOAc. The obtained organic layer was washed with saturated NaHCO$_3$ aqueous solution. The organic layer was dried over anhydrous MgSO$_4$, and filtered. The filtrate was concentrated under reduced pressure. The concentrate was purified by column chromatography (SiO$_2$, 40 g cartridge; EtOAc/hexane=0% to 10%), and concentrated to yield the title compound as white solid (0.96 g, 75%).

Step 3.

Methyl 4'-(benzyl((1-((1-(trifluoromethyl)cyclobutyl)methyl)piperidin-4-yl)methyl)amino)biphenyl-4-carboxylate: N-benzyl-4-bromo-N-((1-((1-(trifluoromethyl)cyclobutyl)methyl)piperidin-4-yl)methyl)benzeneamine (0.96 g, 1.93 mmol), 4-(methoxycarbonyl)phenylboronic acid (0.34 g, 1.93 mmol), Pd(dbpf)Cl$_2$ (0.06 g, 0.09 mmol) and Cs$_2$CO$_3$ (1.26 g, 3.87 mmol) were added to 1,4-dioxane (12 mL)/H$_2$O (3 mL). With a microwave radiation, the mixture was heated at 115° C. for 20 minutes, and then cooled to room temperature. The reaction mixture was added with water, and extracted with dichloromethane. The obtained organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=0% to 20%), and concentrated to yield the title compound as white solid (0.80 g, 75%).

Step 4.

Methyl 4'-((1-((1-(trifluoromethyl)cyclobutyl)methyl)piperidin-4-yl)methylamino) biphenyl-4-carboxylate: Methyl 4'-(benzyl((1-((1-(trifluoromethyl)cyclobutyl)methyl)piperidin-4-yl)methyl)amino)biphenyl-4-carboxylate (0.80 g, 1.45 mmol) and 10% wt Pd/C (0.3 g), NH$_4$COOH (0.91 g, 14.52 mmol) were dissolved in MeOH (6 mL)/EtOAc (12 mL). The reaction mixture was refluxed with heating for 3 hours, and then cooled to room temperature. The reaction mixture was filtered through a Celite pad to remove a solid. The obtained filtrate was concentrated under reduced pressure to remove the solvent. The concentrate was diluted with water, and extracted with EtOAc. The organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=0% to 20%), and concentrated to yield the title compound as white solid (0.44 g, 65%).

Step 5.

4'-((1-((1-(trifluoromethyl)cyclobutyl)methyl)piperidin-4-yl)methylamino)biphenyl-4-carboxylic acid: Methyl 4'-((1-((1-(trifluoromethyl)cyclobutyl)methyl)piperidin-4-yl)methylamino)biphenyl-4-carboxylate (0.44 g, 0.95 mmol) and LiOH.H$_2$O (0.20 g, 4.77 mmol) were dissolved in THF (2 mL)/H$_2$O/MeOH (3 mL) at room temperature. The solution was stirred at the same temperature for 12 hours, the reaction mixture was concentrated under reduced pressure. The concentrate was added with water (20 mL) to be suspended, and filtered. The obtained solid was dried to yield the title compound as white solid (0.42 g, 98%).

Step 6.

Compound 1020: 4'-((1-((1-(trifluoromethyl)cyclobutyl)methyl)piperidin-4-yl)methylamino)biphenyl-4-carboxylic acid (0.05 g, 0.11 mmol), EDCI (0.04 g, 0.22 mmol), HOBt (0.03 g, 0.22 mmol) and DIPEA (0.09 mL, 0.56 mmol) were dissolved in DMF (2 mL). At room temperature, (S)-pyrrolidine-3-ol (0.02 g, 0.22 mmol) was added thereto, following with stirring at 60° C. for 12 hours. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; methanol/dichloromethane=0% to 10%), and concentrated to yield the title compound as yellow solid (0.03 g, 64%).

1H NMR (400 MHz, CDCl$_3$) δ 7.56 (d, 2H, J=7.2 Hz), 7.45 (d, 2H, J=8.4 Hz), 6.67 (d, 2H, J=8.5 Hz), 4.62 (brs, 0.5H), 4.41 (brs, 0.5H), 3.81-3.43 (m, 5H), 3.07 (d, 2H, J=6.6 Hz), 2.88 (d, 2H, J=11.6 Hz), 2.23-1.73 (m, 12H), 1.39-1.35 (m, 3H)); MS (ESI) m/z 516 (M++H).

According to the above-described synthesis process of compound 1020, the compounds of Table 142 were synthesized using 4'-((1-((1-(trifluoromethyl)cyclobutyl)methyl)piperidin-4-yl)methylamino)biphenyl-4-carboxylic acid and the reactant of Table 141.

TABLE 141

| Compound No. | Reactant | Yield (%) |
|---|---|---|
| 926 | (R)-piperidin-3-ol | 70 |
| 1021 | (S)-pyrrolidine-2-carboxamide | 64 |
| 1022 | (S)-piperidin-3-ol | 60 |
| 1023 | (R)-piperidin-2-carboxamide | 61 |

TABLE 142

| Compound No. | Compound Name, $^1$H-NMR, MS (ESI) |
|---|---|
| 926 | (R)-(3-hydroxypiperidin-1-yl)(4'-((1-((1-(trifluoromethyl)cyclobutyl)methyl)piperidin-4-yl)methylamino)biphenyl-4-yl)methanone<br>1H NMR (400 MHz, CDCl$_3$) δ 7.54 (d, 2 H, J = 8.0 Hz), 7.42 (d, 4 H, J = 7.4 Hz), 6.65 (d, 2 H, J = 8.4 Hz), 3.87-3.22 (m, 5 H), 3.05 (d, 2 H, J = 6.4 Hz), 2.86 (d, 2 H, J = 10.8 Hz), 2.50 (s, 2 H), 2.25-1.58 (m, 15 H), 1.39-1.31 (m, 2 H); MS (ESI) m/z 530 (M+ + H). |
| 1021 | (S)-1-(4'-((1-((1-(trifluoromethyl)cyclobutyl)methyl)piperidin-4-yl)methylamino)biphenylcarbonyl)pyrrolidine-2-carboxamide<br>1H NMR (400 MHz, CDCl$_3$) δ 7.57 (s, 4 H), 7.46 (d, 2 H, J = 8.4 Hz), 7.27 (brs, 1 H), 6.67 (d, 2 H, J = 8.5 Hz), 5.59 (brs, 1 H), 4.82 (m, 1 H), 3.70-3.58 (m, 2 H), 3.07 (d, 2 H, J = 6.6 Hz), 2.88 (d, 2 H, J = 11.2 Hz), 2.52 (s, 2 H), 2.24-1.73 (m, 15 H), 1.39-1.35 (m, 2 H); MS (ESI) m/z 543 (M+ + H). |
| 1022 | (S)-(3-hydroxypiperidin-1-yl)(4'-((1-((1-(trifluoromethyl)cyclobutyl)methyl)piperidin-4-yl)methylamino)biphenyl-4-yl)methanone<br>1H NMR (400 MHz, CDCl$_3$) δ7.56 (d, 2 H, J = 8.2 Hz), 7.45 (d, 4 H, J = 8.8 Hz), 6.67 (d, 2 H, J = 8.6 Hz), 3.91-3.31 (m, 5 H), 3.07 (d, 2 H, J = 6.6 Hz), 2.88 (d, 2 H, J = 11.4 Hz), 2.52 (s, 2 H), 2.24-1.76 (m, 15 H), 1.73-1.36 (m, 2 H); MS (ESI) m/z 530 (M+ + H). |
| 1023 | (R)-1-(4'-((1-((1-(trifluoromethyl)cyclobutyl)methyl)piperidin-4-yl)methylamino)biphenylcarbonyl)piperidin-2-carboxamide<br>1H NMR (400 MHz, CDCl$_3$) δ 7.59-7.58 (m, 2 H), 7.49-7.44 (m, 4 H), 6.68 (d, 2 H, J = 8.4 Hz), 6.58 (brs, 1 H), 5.52 (brs, 1 H), 5.29 (brs, 1 H), 3.92-3.80 (m, 2 |

TABLE 142-continued

Compound No. Compound Name, ¹H-NMR, MS (ESI)

H), 3.08-3.06 (m, 3 H), 2.88 (d, 2 H, J = 11.2 Hz), 2.52 (s, 2 H), 2.23-1.57 (m, 16 H), 1.39-1.35 (m, 2 H); MS (ESI) m/z 557 (M+ + H).

Example 120. Compound 1024: (S)-(3-hydroxypyr-rolidine-1-yl)(4'-((1-(3,3,3-trifluoro-2,2-dimethyl-propyl)piperidin-4-yl)methylamino)biphenyl-4-yl)methanone

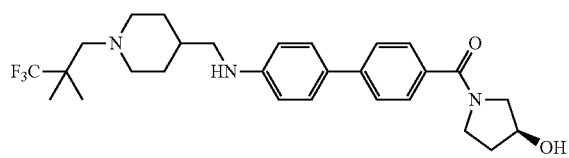 [SMILES: CC(C)(CN1CCC(CNc2ccc(-c3ccc(C(=O)N4CC[C@H](O)C4)cc3)cc2)CC1)C(F)(F)F]

Step 1.

1-(4-((benzyl(4-bromophenyl)amino)methyl)piperidin-1-yl)-3,3,3-trifluoro-2,2-dimethylpropan-1-one: N-benzyl-4-bromo-N-(piperidin-4-ylmethyl)benzeneamine hydrochloride (the product of synthesis step 3 of compound 857; 0.80 g, 5.12 mmol), EDCI (1.96 g, 10.25 mmol), HOBt (1.38 g, 10.25 mmol) and DIPEA (4.47 mL, 25.62 mmol) were dissolved in DMF (20 mL). At room temperature, 3,3,3-trifluoro-2,2-dimethylpropanoic acid (2.13 g, 5.38 mmol) was added thereto, following with stirring at the same temperature for 12 hours. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; EtOAc/hexane=0% to 20%), and concentrated to yield the title compound as light-yellow solid (1.54 g, 60%).

Step 2.

N-benzyl-4-bromo-N-((1-(3,3,3-trifluoro-2,2-dimethylpropyl)piperidin-4-yl)methyl)benzeneamine: 1-(4-((benzyl(4-bromophenyl)amino)methyl)piperidin-1-yl)-3,3,3-trifluoro-2,2-dimethylpropan-1-one (1.54 g, 3.09 mmol) was dissolved in THF (15 mL) and then cooled to room temperature, following with concentrating under reduced pressure. The concentrate with heating for 1 hour, and then cooled to room temperature. The reaction mixture was added with water, and extracted with EtOAc. The obtained organic layer was washed with saturated NaHCO$_3$ aqueous solution. The organic layer was dried over anhydrous MgSO$_4$, and filtered. The filtrate was concentrated under reduced pressure. The concentrate was purified by column chromatography (SiO$_2$, 40 g cartridge; EtOAc/hexane=0% to 10%), and concentrated to yield the title compound as transparent oil (0.42 g, 28%).

Step 3.

Methyl 4'-(benzyl((1-(3,3,3-trifluoro-2,2-dimethylpropyl)piperidin-4-yl)methyl)amino)biphenyl-4-carboxylate: N-benzyl-4-bromo-N-((1-(3,3,3-trifluoro-2,2-dimethylpropyl)piperidin-4-yl)methyl)benzeneamine (0.42 g, 0.86 mmol), 4-(methoxycarbonyl)phenylboronic acid (0.15 g, 0.86 mmol), Pd(dppf)Cl$_2$ (0.02 g, 0.04 mmol) and Cs$_2$CO$_3$ (0.56 g, 1.73 mmol) were added to 1,4-dioxane (12 mL)/H$_2$O (3 mL). With a microwave radiation, the mixture was heated at 115° C. for 20 minutes, and then cooled to room temperature. The reaction mixture was added with water, and extracted with dichloromethane. The obtained organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=0% to 20%), and concentrated to yield the title compound as white solid (0.37 g, 79%).

Step 4.

Methyl 4'-((1-(3,3,3-trifluoro-2,2-dimethylpropyl)piperidin-4-yl)methylamino) biphenyl-4-carboxylate: Methyl 4'-(benzyl((1-(3,3,3-trifluoro-2,2-dimethylpropyl)piperidin-4-yl)methyl)amino)biphenyl-4-carboxylate (0.37 g, 0.68 mmol), 10% Pd/C (0.15 g) and NH$_4$COOH (0.43 g, 6.86 mmol) were added to MeOH (3 mL)/EtOAc (6 mL). The mixture was refluxed with heating for 5 hours, and then cooled to room temperature. The reaction mixture was filtered through a Celite pad to remove a solid. The obtained filtrate was concentrated under reduced pressure. The obtained concentrate was diluted with water, and extracted with EtOAc. The obtained organic layer was washed with saturated aqueous brine solution, dried over anhydrous MgSO$_4$, and filtered. The filtrate was concentrated under reduced pressure. The concentrate was purified by column chromatography (SiO$_2$, 12 g cartridge; EtOAc/hexane=0% to 20%), and concentrated to yield the title compound as white solid (0.24 g, 77%).

Step 5.

4'-((1-(3,3,3-trifluoro-2,2-dimethylpropyl)piperidin-4-yl)methylamino)biphenyl-4-carboxylic acid: Methyl 4'-((1-(3,3,3-trifluoro-2,2-dimethylpropyl)piperidin-4-yl)methylamino)biphenyl-4-carboxylate (0.24 g, 0.53 mmol) and LiOH.H$_2$O (0.11 g, 2.67 mmol) were dissolved in THF (2 mL)/H$_2$O/MeOH (3 mL) at room temperature. The solution was stirred at the same temperature for 12 hours, the reaction mixture was concentrated under reduced pressure. The concentrate was added with water (20 mL) to be suspended, and filtered. The obtained solid was dried to yield the title compound as white solid (0.22 g, 94%).

Step 6.

Compound 1024: 4'-((1-(3,3,3-trifluoro-2,2-dimethylpropyl)piperidin-4-yl)methylamino)biphenyl-4-carboxylic acid (0.06 g, 0.13 mmol), EDCI (0.05 g, 0.27 mmol), HOBt (0.03 g, 0.27 mmol) and DIPEA (0.12 mL, 0.69 mmol) were dissolved in DMF (2 mL). At room temperature, (S)-pyrrolidine-3-ol (0.02 g, 0.27 mmol) was added thereto, following with stirring at 60° C. for 12 hours. The reaction mixture was added with water, and extracted with EtOAc. The organic layer was washed with saturated NH$_4$Cl aqueous solution, dried over anhydrous MgSO$_4$, and filtered. The filtrate was concentrated under reduced pressure. The concentrate was purified by column chromatography (SiO$_2$, 12 g cartridge; methanol/dichloromethane=0% to 10%), and concentrated to yield the title compound as yellow solid (0.04 g, 67%).

1H NMR (400 MHz, CDCl$_3$) δ 7.55-7.53 (m, 4H), 7.44 (d, 2H, J=8.4 Hz), 6.66 (d, 2H, J=8.5 Hz), 4.58 (brs, 0.5H), 4.41 (brs, 0.5H), 3.82-3.43 (m, 5H), 3.05 (d, 2H, J=6.4 Hz), 2.82 (d, 2H, J=11.6 Hz), 2.39 (s, 2H), 2.29 (t, 2H, J=11.0 Hz), 1.95-1.70 (m, 5H), 1.37-1.31 (m, 2H), 1.10 (s, 6H); MS (ESI) m/z 504 (M++H).

According to the above-described synthesis process of compound 1024, the compounds of Table 144 were synthesized using 4'-((1-(3,3,3-trifluoro-2,2-dimethylpropyl)piperidin-4-yl)methylamino)biphenyl-4-carboxylic acid and the reactant of Table 143.

TABLE 143

| Compound No. | Reactant | Yield (%) |
|---|---|---|
| 927 | (R)-piperidin-3-ol | 34 |
| 1025 | (S)-pyrrolidine-2-carboxamide | 67 |
| 1026 | (S)-piperidin-3-ol | 72 |

TABLE 144

| Compound No. | Compound Name, ¹H-NMR, MS (ESI) |
|---|---|
| 927 | (R)-(3-hydroxypiperidin-1-yl)(4'-((1-(3,3,3-trifluoro-2,2-dimethylpropyl)piperidin-4-yl)methylamino)biphenyl-4-yl)methanone<br>1H NMR (400 MHz, CDCl₃) δ 7.54 (d, 2 H, J = 8.0 Hz), 7.43-7.41 (m, 4 H), 7.07 (d, 2 H, J = 8.4 Hz), 3.87-3.40 (m, 5 H), 3.04 (d, 2 H, J = 6.6 Hz), 2.81-2.78 (m, 2 H), 2.37 (s, 2 H), 2.28 (t, 2 H, J = 11.4 Hz), 1.93-1.52 (m, 7 H), 1.36-1.24 (m, 2 H), 1.08 (d, 6 H); MS (ESI) m/z 518 (M+ + H). |
| 1025 | (S)-1-(4'-((1-(3,3,3-trifluoro-2,2-dimethylpropyl)piperidin-4-yl)methylamino)biphenylcarbonyl)pyrrolidine-2-carboxamide<br>1H NMR (400 MHz, CDCl₃) δ 7.52 (s, 4 H), 7.46 (d, 2 H, J = 8.0 Hz), 7.07 (brs, 1 H), 6.67 (d, 2 H, J = 8.4 Hz), 5.66 (brs, 1 H), 5.66 (brs, 1 H), 4.82-7.80 (m, 1 H), 3.92 (brs, 1 H), 3.65-3.60 (m, 2 H), 3.06 (d, 2 H, J = 6.8 Hz), 2.82 (d, 2 H, J = 11.2 Hz), 2.43-2.38 (m, 3 H), 2.29 (t, 2 H, J = 11.4 Hz), 2.13-1.57 (m, 7 H), 1.37-1.26 (m, 2 H), 1.10 (s, 6 H); MS (ESI) m/z 531 (M+ + H). |
| 1026 | (S)-(3-hydroxypiperidin-1-yl)(4'-((1-(3,3,3-trifluoro-2,2-dimethylpropyl)piperidin-4-yl)methylamino)biphenyl-4-yl)methanone<br>1H NMR (400 MHz, CDCl₃) δ 7.56 (d, 2 H, J = 8.4 Hz), 7.45 (d, 4 H, J = 8.4 Hz), 6.67 (d, 2 H, J = 8.4 Hz), 3.90-3.32 (m, 5 H), 3.06 (d, 2 H, J = 6.6 Hz), 2.82 (d, 2 H, J = 11.6 Hz), 2.39 (s, 2 H), 2.28 (t, 2 H, J = 12.2 Hz), 2.05-1.57 (m, 6 H), 1.35-1.26 (m, 3 H), 1.10 (s, 6 H); MS (ESI) m/z 518 (M+ + H). |

Example 121. Compound 852: (R)-(4'-(((1-(2-fluoro-2-methylpropyl)piperidin-4-yl)methyl)(methyl)amino)biphenyl-4-yl)(3-hydroxypiperidin-1-yl)methanone

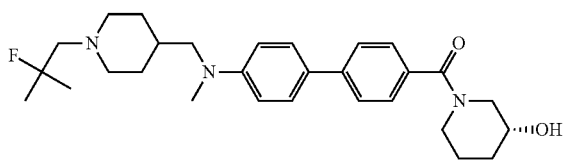 [SMILES: CN(CC1CCN(CC(C)(C)F)CC1)c1ccc(-c2ccc(C(=O)N3CCC[C@@H](O)C3)cc2)cc1]

(R)-(4'-((1-(2-fluoro-2-methylpropyl)piperidin-4-yl)methylamino)biphenyl-4-yl)(3-hydroxypiperidin-1-yl)methanone (compound 867, 0.02 g, 0.05 mmol) was dissolved in acetonitrile 5 mL. Formaldehyde (0.01 mL, 0.27 mmol) and acetic acid (0.30 mL, 0.05 mmol) were added thereto, following with stirring for a day and then cooling the temperature. At 0° C., NaCNBH₃ (0.30 mg, 0.05 mmol) was added slowly thereto, following with increasing the temperature and stirring at room temperature for 2 hours. After the reaction was quenched by addition of a little of water, the reaction mixture was added with water, and then extracted with CH₂Cl₂. The obtained organic layer was washed several times with H₂O, dried over anhydrous MgSO₄, and filtered. The filtrate was concentrated under reduced pressure to yield the title compound as yellow solid (0.01 g, 62%).

1H NMR (400 MHz, CDCl₃) δ 7.57 (d, 2H, J=8.0 Hz), 7.47 (dd, 4H, J=20.7, 8.7 Hz), 6.74 (d, 2H, J=8.8 Hz), 3.98 (brs, 2H), 3.24 (d, 2H, J=6.8 Hz), 3.02-2.96 (m, 5H), 2.50-2.41 (m, 5H), 2.13-1.65 (m, 9H), 1.39-1.26 (m, 8H); MS (ESI) m/z 482 (M++H).

According to the above-described synthesis process of compound 852, the compounds of Table 146 were synthesized using (R)-(4'-((1-(2-fluoro-2-methylpropyl)piperidin-4-yl)methylamino) biphenyl-4-yl)(3-hydroxypiperidin-1-yl)methanone and the reactant of Table 145.

TABLE 145

| Compound No. | Reactant | Yield (%) |
|---|---|---|
| 853 | Acetaldehyde | 45 |

TABLE 146

| Compound No. | Compound Name, ¹H-NMR, MS (ESI) |
|---|---|
| 853 | (R)-(4'-(ethyl((1-(2-fluoro-2-methylpropyl)piperidin-4-yl)methyl)amino)biphenyl-4-yl)(3-hydroxypiperidin-1-yl)methanone<br>1H NMR (400 MHz, CDCl₃) δ 7.57 (d, 2 H, J = 8.4 Hz), 7.49-7.27 (m, 4 H), 6.73 (d, 2 H, J = 8.8 Hz), 4.21-3.87 (m, 3 H), 3.46-3.41 (m, 4 H), 3.18 (d, 2 H, |

J = 8.0 Hz), 2.97 (d, 2 H, J = 12.0 Hz), 2.46 (s, 1 H), 2.40 (s, 1 H), 2.12-1.96 (m, 6 H), 1.72-1.69 (m, 3 H), 1.39-1.26 (m, 8 H), 1.17 (t, 3 H, J = 7.0 Hz); MS (ESI) m/z 496 (M+ + H).

Example 122. Compound 928: (R)-(3-hydroxypiperidin-1-yl)(4'-(methyl((1-((1-(trifluoromethyl)cyclobutyl)methyl)piperidin-4-yl)methyl)amino)biphenyl-4-yl)methanone Example 123. Compound 930: (R)-(3-hydroxypiperidin-1-yl)(4'-(methyl((1-(3,3,3-trifluoro-2,2-dimethylpropyl)piperidin-4-yl)methyl)amino)biphenyl-4-yl)methanone

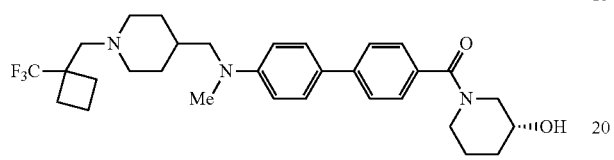

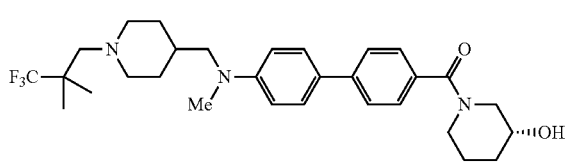 [SMILES: CN(CC1CCN(CC(C)(C)C(F)(F)F)CC1)c1ccc(-c2ccc(C(=O)N3CCC[C@@H](O)C3)cc2)cc1]

(R)-(3-hydroxypiperidin-1-yl)(4'-((1-((1-trifluoromethyl)cyclobutyl)methyl)piperidin-4-yl)methylamino)biphenyl-4-yl)methanone (compound 926, 0.03 g, 0.05 mmol), formaldehyde (8 μL, 0.28 mmol) and AcOH (3 μL, 0.05 mmol) were dissolved in Acetonitrile (3 mL), following with stirring with at 12 hours at room temperature and cooling the temperature slowly to 0° C. NaCNBH₃ (4 mg, 0.05 mmol) was added thereto at 0° C., following with stirring at room temperature for 1 hour. The concentrate was added with water (10 mL) to be suspended, and filtered. The obtained solid was dried, and purified by column chromatography (SiO₂, 12 g cartridge; methanol/dichloromethane=0% to 10%), and concentrated to yield the title compound as white solid (0.02 g, 81%).

1H NMR (400 MHz, CDCl₃) δ 7.58 (d, 2H, J=8.0 Hz), 7.51 (d, 2H, J=8.8 Hz), 7.45 (d, 2H, J=8.0 Hz), 6.75 (d, 2H, J=8.8 Hz), 4.03-3.42 (m, 5H), 3.25 (d, 2H, J=7.1 Hz), 3.02 (s, 3H), 2.86 (d, 2H, J=11.2 Hz), 2.51 (s, 2H), 2.24-1.65 (m, 15H), 1.38-1.34 (m, 2H); MS (ESI) m/z 544 (M++H).

According to the above-described synthesis process of compound 928, the compounds of Table 148 were synthesized using (R)-(3-hydroxypiperidin-1-yl)(4'-((1-((1-(trifluoromethyl)cyclobutyl)methyl)piperidin-4-yl)methylamino)biphenyl-4-yl)methanone and the reactant of Table 147.

(R)-(3-hydroxypiperidin-1-yl)(4'-((1-(3,3,3-trifluoro-2,2-dimethylpropyl)piperidin-4-yl)methylamino)biphenyl-4-yl)methanone (the product of synthesis of compound 927; 0.03 g, 0.05 mmol), formaldehyde (8 μL, 0.29 mmol) and AcOH (3 μL, 0.05 mmol) were dissolved in Acetonitrile (3 mL). At 0° C., NaCNBH₃ (4.00 mg, 0.05 mmol) was added thereto, following with stirring at room temperature for 2 hours. The concentrate was added with water (8 mL) to be suspended, and filtered. The obtained solid was dried, and purified by column chromatography (SiO₂, 12 g cartridge; methanol/dichloromethane=0% to 10%), and concentrated to yield the title compound as white solid (0.01 g, 48%).

1H NMR (400 MHz, CDCl₃) δ 7.58 (d, 2H, J=8.4 Hz), 7.48 (dd, 4H, J=20.3, 8.5 Hz), 6.74 (d, 2H, J=8.9 Hz), 4.17-3.42 (m, 5H), 3.24 (d, 2H, J=7.2 Hz), 3.02 (s, 3H), 2.80 (d, 2H, J=11.4 Hz), 2.37 (s, 2H), 2.27 (t, 2H, J=5.9 Hz), 2.23-1.50 (m, 7H), 1.37-1.24 (m, 2H), 1.51 (s, 6H); MS (ESI) m/z 532 (M++H).

Example 124. Compound 552: N,N-dimethyl-4'-((1-((1-(trifluoromethyl)cyclopropyl)methyl)piperidin-4-yl)methoxy)biphenyl-4-carboxamide

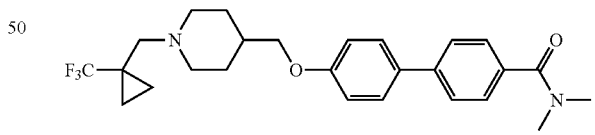

TABLE 147

| Compound No. | Reactant | Yield (%) |
|---|---|---|
| 929 | Acetaldehyde | 72 |

TABLE 148

Compound No. Compound Name, ¹H-NMR, MS (ESI)

929 (R)-(4'-(ethyl((1-((1-(trifluoromethyl)cyclobutyl)methyl)piperidin-4-yl)methyl)amino)biphenyl-4-yl)(3-hydroxypiperidin-1-yl)methanone
1H NMR (400 MHz, CDCl₃) δ 7.56 (d, 2 H, J = 8.0 Hz), 7.48-7.42 (m, 4 H), 6.72 (d, 2 H, J = 7.2 Hz), 3.98-3.67 (m, 2 H), 3.45-3.39 (m, 5 H), 3.17 (d, 2 H, J = 6.6 Hz), 2.86 (d, 2 H, J = 11.2 Hz), 2.500 (s, 2 H), 2.25-1.67 (m, 15 H), 1.43-1.17 (m, 5 H); MS (ESI) m/z 558 (M+ + H).

Step 1.
(4-((4-bromophenoxy)methyl)piperidin-1-yl)(1-(trifluoromethyl)cyclopropyl)methanone: 4-((4-bromophenoxy)methyl)piperidine hydrochloride (the product of synthesis step 1 of compound 498; 200 mg, 0.65 mmol) and 1-(trifluoromethyl)cyclopropanecarboxylic acid (101 mg, 0.65 mmol) were dissolved in CH$_2$Cl$_2$ 4 mL. EDC (250 mg, 1.31 mmol) and HOBt (176 mg, 1.31 mmol) were added thereto. Lastly, DIPEA (0.57 mL, 3.26 mmol) was added thereto, following with stirring at room temperature for 15 hours. The reaction mixture was diluted with water, and extracted with CH$_2$Cl$_2$ three times. The organic layer was dried over MgSO$_4$, filtered to remove the solid residue, and the filtrate was concentrated under reduced pressure. The obtained concentrate was purified by silica gel column chromatography (0-50% EtOAc/Hexane) to yield the title compound as white solid (239 mg, 90%).

Step 2.
4-((4-bromophenoxy)methyl)-1-((1-(trifluoromethyl)cyclopropyl)methyl)piperidine: (4-((4-bromophenoxy)methyl)piperidin-1-yl)(1-(trifluoromethyl)cyclopropyl)methanone (239 mg, 0.59 mmol) was dissolved in dry THF 10 mL, and then cooled with ice bath. 1 M LAH in THF (1.77 mL, 1.77 mmol) was added dropwise slowly thereto, following with increasing the temperature to room temperature slowly and stirring for 1 hour. The reaction was quenched by addition of water. After the addition of EtOAc thereto, the resulting precipitate was filtered, and extracted with EtOAc. The organic layer was dried over MgSO$_4$, filtered to remove the solid residue, and the filtrate was concentrated under reduced pressure. The obtained concentrate was purified by silica gel column chromatography (0-40% EtOAc/hexane) to yield the title compound as colorless liquid (64 mg, 28%).

Step 3.
Methyl 4'-((1-((1-(trifluoromethyl)cyclopropyl)methyl)piperidin-4-yl)methoxy) biphenyl-4-carboxylate: 4-((4-bromophenoxy)methyl)-1-((1-(trifluoromethyl)cyclopropyl)methyl)piperidine (50 mg, 0.127 mmol) and 4-(methoxycarbonyl)phenylboronic acid (28 mg, 0.15 mmol) were dissolved in dioxane 1 mL. Water 0.3 mL was added thereto. Pd(dbpf)Cl$_2$ (30 µg, 0.01 mmol) and Cs$_2$CO$_3$ (125 mg, 0.38 mmol) were added thereto. With a microwave radiation, the reaction was performed at 140° C. for 15 minutes. The reaction mixture was diluted with water, and extracted with CH$_2$Cl$_2$ three times. The organic layer was dried over MgSO$_4$, filtered through Celite to remove solid, and then concentrated under reduced pressure. The obtained concentrate was purified by silica gel column chromatography (0-40% EtOAc/Hexane) to yield the title compound as light-yellow solid (30 mg, 53%).

Step 4.
4'-((1-((1-(trifluoromethyl)cyclopropyl)methyl)piperidin-4-yl)methoxy)biphenyl-4-carboxylic acid: Methyl 4'-((1-((1-(trifluoromethyl)cyclopropyl)methyl)piperidin-4-yl)methoxy)biphenyl-4-carboxylate (30 mg, 0.07 mmol) was dissolved in THF 2 mL. MeOH 1 mL and H$_2$O 1 mL were added thereto. LiOH (14 mg, 0.34 mmol) was added thereto, following with stirring at room temperature for 15 hours. After acidification with 1 N HCl, the resulting precipitate was filtered to yield the title compound as white solid (28 mg, 97%).

Step 5.
Compound 552: 4'-((1-((1-(trifluoromethyl)cyclopropyl)methyl)piperidin-4-yl)methoxy)biphenyl-4-carboxylic acid (28 mg, 0.07 mmol) and dimethylamine hydrochloride (11 mg, 0.13 mmol) were dissolved in DMF 1 mL. EDC (25 mg, 0.13 mmol) and HOBt (18 mg, 0.13 mmol) were added thereto. Lastly, DIPEA (57 µL, 0.26 mmol) was added thereto, following with stirring at room temperature for 15 hours. Water 5 mL was added thereto, and filtered to give a solid. The residue was purified by silica gel column chromatography (0-5% MeOH/CH$_2$Cl$_2$) to yield the title compound as white solid (23 mg, 76%).

1H NMR (400 MHz, CDCl$_3$) δ 7.60-7.55 (m, 2H), 7.55-7.50 (m, 2H), 7.50-7.45 (m, 2H), 7.00-6.93 (m, 2H), 3.83 (d, 2H, J=6.0 Hz), 3.13 (s, 3H), 3.04 (s, 3H), 2.98 (d, 2H, J=11.3 Hz), 2.54 (s, 2H), 2.03-1.94 (m, 2H), 1.86-1.74 (m, 3H), 1.40 (dd, 2H, J=12.2, 2.6 Hz), 1.02-0.95 (m, 2H), 0.65 (s, 2H); MS (ESI) m/z 461 (M++H).

Example 125. Compound 580: N,N-dimethyl-4-(6-((1-((1-(trifluoromethyl)cyclopropyl)methyl)piperidin-4-yl)methoxy)pyridine-3-yl)benzamide

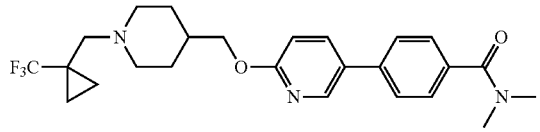 [SMILES: CN(C)C(=O)c1ccc(-c2ccc(OCC3CCN(CC4(C(F)(F)F)CC4)CC3)nc2)cc1]

Step 1.
Methyl 4-(6-((1-((1-(trifluoromethyl)cyclopropyl)methyl)piperidin-4-yl)methoxy)pyridine-3-yl)benzoate: 5-bromo-2-((1-((1-(trifluoromethyl)cyclopropyl)methyl)piperidin-4-yl)methoxy)pyridine (the product of synthesis step 3 of compound 589; 0.50 g, 1.27 mmol), 4-(methoxycarbonyl)phenylboronic acid (0.25 g, 1.40 mmol), Pd(dbpf)Cl$_2$ (24 mg, 0.04 mmol), Cs$_2$CO$_3$ (1.24 g, 3.81 mmol) were added into a microwave reactor, and then dioxane 6 mL and water 3 mL were added thereto. With a microwave radiation, the reaction was performed at 100° C. for 30 minutes. The reaction mixture was added with water, and extracted with EtOAc. The obtained organic layer was dried over MgSO$_4$, and filtered. The filtrate was concentrated under reduced pressure. The obtained concentrate was purified by silica gel column chromatography (20-70% EtOAc/hexane) to yield the title compound as white solid (0.40 g, 70%).

Step 2.
4-(6-((1-((1-(trifluoromethyl)cyclopropyl)methyl)piperidin-4-yl)methoxy)pyridine-3-yl)benzoic acid: Methyl 4-(6-((1-((1-(trifluoromethyl)cyclopropyl)methyl)piperidin-4-yl)methoxy)pyridine-3-yl)benzoate (0.40 g, 0.89 mmol) was dissolved in THF 10 mL. LiOH.H$_2$O (0.07 g, 1.78 mmol) in water 10 mL was added thereto, and the reaction was performed at 60° C. for 4 hours. The solvent was concentrated under reduced pressure. After the addition of 1M HCl 5 mL thereto, the resulting precipitate was filtered to yield the title compound as white solid (0.37 g, 96%).

Step 3.
Compound 580: 4-(6-((1-((1-(trifluoromethyl)cyclopropyl)methyl)piperidin-4-yl)methoxy)pyridine-3-yl)benzoic acid (0.05 g, 0.12 mmol), dimethylamine hydrochloride (0.02 g, 0.23 mmol), EDC (0.04 g, 0.23 mmol) and HOBt (0.03 g, 0.23 mmol) were dissolved in DMF 2 mL. DIPEA (0.04 mL, 0.23 mmol) was added thereto, following with stirring at room temperature for 10 hours. The reaction mixture was added with saturated NH$_4$Cl aqueous solution, and extracted with CH$_2$Cl$_2$. The obtained organic layer was dried over MgSO$_4$, and filtered. The filtrate was concentrated under reduced pressure. The obtained concentrate was purified by silica gel column chromatography (10-70% EtOAc/hexane) to yield the title compound as white solid (0.01 g, 19%).

1H NMR (400 MHz, CDCl$_3$) δ 8.37 (s, 1H), 7.80 (dd, 1H, J=8.4, 2.3 Hz), 7.54 (dd, 4H, J=19.3, 8.3 Hz), 6.83 (d, 1H,

J=8.7 Hz), 4.26-4.19 (m, 2H), 3.14-2.98 (m, 8H), 2.54 (m, 2H), 2.19-1.80 (m, 5H), 1.52-1.26 (m, 2H), 1.03 (m, 2H), 0.66 (m, 2H); MS (ESI) mz 462.2 (M++H); MS (ESI) m/z 462 (M++H).

According to the above-described synthesis process of compound 580 (Step 3), the compounds of Table 150 were synthesized using 4-(6-((1-((1-(trifluoromethyl)cyclopropyl)methyl)piperidin-4-yl)methoxy)pyridine-3-yl)benzoic acid and the reactant of Table 149.

TABLE 149

| Compound No. | Reactant | Yield (%) |
|---|---|---|
| 582 | morpholine | 22 |
| 583 | piperidine | 26 |
| 584 | pyrrolidine | 32 |
| 585 | (S)-3-pyrrolidinol | 29 |
| 586 | L-prolinamide | 41 |
| 587 | 4-piperidinemethanol | 65 |

TABLE 150

| Compound No. | Compound Name, $^1$H-NMR, MS (ESI) |
|---|---|
| 582 | morpholino(4-(6-((1-((1-(trifluoromethyl)cyclopropyl)methyl)piperidin-4-yl)methoxy)pyridine-3-yl)phenyl)methanone<br>1H NMR (400 MHz, CDCl$_3$) δ8.37 (s, 1 H), 7.80 (dd, 1 H, J = 8.4, 2.3 Hz), 7.54 (dd, 4 H, J = 19.3, 8.3 Hz), 6.83 (d, 1 H, J = 8.7 Hz), 4.21-4.18 (m, 2 H), 3.82-3.25 (m, 9 H), 3.09-2.40 (m, 4 H), 2.25-1.25 (m, 6 H), 0.98 (m, 2 H), 0.66 (m, 2 H); MS (ESI) m/z 504 (M+ + H). |
| 583 | piperidin-1-yl(4-(6-((1-((1-(trifluoromethyl)cyclopropyl)methyl)piperidin-4-yl)methoxy)pyridine-3-yl)phenyl)methanone<br>1H NMR (400 MHz, CDCl$_3$) δ8.37 (s, 1 H), 7.80 (dd, 1 H, J = 8.4, 2.3 Hz), 7.52 (dd, 4 H, J = 19.3, 8.3 Hz), 6.82 (d, 1 H, J = 8.7 Hz), 4.21-4.18 (m, 2 H), 3.80-3.60 (m, 2 H), 3.50-3.30 (m, 2 H), 2.97 (m, 2 H), 2.54 (m, 2 H), 2.10-1.25 (m, 13 H), 0.98 (m, 2 H), 0.66 (m, 2 H); MS (ESI) m/z 502 (M+ + H). |
| 584 | pyrrolidine-1-yl(4-(6-((1-((1-(trifluoromethyl)cyclopropyl)methyl)piperidin-4-yl)methoxy)pyridine-3-yl)phenyl)methanone<br>1H NMR (400 MHz, CDCl$_3$) δ8.37 (s, 1 H), 7.80 (dd, 1 H, J = 8.4, 2.3 Hz), 7.58 (dd, 4 H, J = 19.3, 8.3 Hz), 6.82 (d, 1 H, J = 8.7 Hz), 4.29-4.20 (m, 2 H), 3.68 (t, 2 H, J = 6.9 Hz), 3.50 (t, 2 H, J = 6.5 Hz), 2.99 (m, 2 H), 2.11 (m, 2 H), 2.08-1.26 (m, 11 H), 0.98 (m, 2 H), 0.66 (m, 2 H); MS (ESI) m/z 488 (M+ + H). |
| 585 | (S)-(3-hydroxypyrrolidine-1-yl)(4-(6-((1-((1-(trifluoromethyl)cyclopropyl)methyl)piperidin-4-yl)methoxy)pyridine-3-yl)phenyl)methanone<br>1H NMR (400 MHz, CDCl$_3$) δ8.37 (s, 1 H), 7.79 (m, 1 H), 7.58 (m, 4 H), 6.82 (m, 1 H), 4.61-4.48 (m, 1 H), 4.20 (m, 2 H), 3.86-3.48 (m, 4 H), 2.99 (m, 2 H), 2.54 (m, 2 H), 2.22-1.63 (m, 8 H), 1.57-1.38 (m, 2 H), 0.98 (m, 2 H), 0.66 (m, 2 H); MS (ESI) m/z 504 (M+ + H). |
| 586 | (S)-1-(4-(6-((1-((1-(trifluoromethyl)cyclopropyl)methyl)piperidin-4-yl)methoxy)pyridine-3-yl)benzoyl)pyrrolidine-2-carboxamide<br>1H NMR (400 MHz, CDCl$_3$) δ8.38 (s, 1 H), 7.80 (dd, 1 H, J = 8.4, 2.3 Hz), 7.60 (dd, 4 H, J = 19.3, 8.3 Hz), 7.00 (m, 1 H), 6.83 (d, 1 H, J = 8.7 Hz), 5.43 (m, 1 H), 4.83 (m, 1 H), 4.21 (m, 2 H), 3.65-3.54 (m, 2 H), 3.01-2.90 (m, 2 H), 2.79-2.42 (m, 2 H), 2.22-1.65 (m, 9 H), 1.42 (m, 2 H), 0.98 (m, 2 H), 0.66 (m, 2 H); MS (ESI) m/z 531 (M+ + H). |
| 587 | (4-(hydroxymethyl)piperidin-1-yl)(4-(6-((1-((1-(trifluoromethyl)cyclopropyl)methyl)piperidin-4-yl)methoxy)pyridine-3-yl)phenyl)methanone<br>1H NMR (400 MHz, CDCl$_3$) δ8.38 (d, 1 H, J = 2.2 Hz), 7.79 (dd, 1 H, J = 8.4, 2.3 Hz), 7.51 (dd, 4 H, J = 19.3, 8.3 Hz), 6.82 (d, 1 H, J = 8.7 Hz), 4.77 (m, 1 H), 4.20 (m, 2 H), 3.87 (m, 1 H), 3.55 (m, 2 H), 3.20-2.70 (m, 4 H), 2.54 (m, 2 H), 2.05-1.65 (m, 9 H), 1.42-1.11 (m, 4 H), 0.98 (m, 2 H), 0.66 (m, 2 H); MS (ESI) m/z 532 (M+ + H). |

Example 126. Compound 688: 4'-((1-(2-fluoropropyl)piperidin-4-yl)methoxy)-N,N-dimethylbiphenyl-4-carboxamide

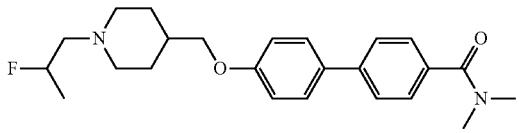 [SMILES: CC(F)CN1CCC(COc2ccc(-c3ccc(C(=O)N(C)C)cc3)cc2)CC1]

Step 1.

1-(4-((4-bromophenoxy)methyl)piperidin-1-yl)propan-2-ol: 4-((4-bromophenoxy)methyl)piperidine hydrochloride (the product of synthesis step 2 of compound 686; 200 mg, 0.65 mmol) was dissolved in EtOH 1 mL. 2-methyloxirane (379 mg, 6.52 mmol), K$_2$CO$_3$ (180 mg, 1.31 mmol) and water 1 mL were added thereto. With a microwave radiation, the mixture was stirred at 110° C. for 20 minutes. After the completion of the reaction, EtOH was evaporated from the reaction mixture under reduced pressure, and then a little of water was added to thereto. The resulting precipitate was filtered, and dried under reduced pressure to yield the title compound as red oil (190 mg, 88%).

Step 2.

4-((4-bromophenoxy)methyl)-1-(2-fluoropropyl)piperidine: 1-(4-((4-bromophenoxy)methyl)piperidin-1-yl)propan-2-ol (190 mg, 0.58 mmol) was dissolved in CH$_2$Cl$_2$ 2 mL. Deoxo-fluor (141 mg, 0.64 mmol) was added thereto, following with stirring at room temperature for 3 hours. After the completion of the reaction, the reaction mixture was added with a saturated NaHCO$_3$ aqueous solution, and extracted with CH$_2$Cl$_2$. The organic layer washed with saturated aqueous brine solution, dried over MgSO$_4$, and filtered to remove the solid residue. The filtrate was concentrated under reduced pressure. The concentrate was purified by column chromatography (ISCO silica gel cartridge, EtOAc/Hexane) to yield the title compound as yellow oil (180 mg, 94%).

Step 3.

Methyl 4'-((1-(2-fluoropropyl)piperidin-4-yl)methoxy)biphenyl-4-carboxylate: 4-((4-bromophenoxy)methyl)-1-(2- fluoropropyl)piperidine (190 mg, 0.58 mmol), 4-(methoxycarbonyl)phenylboronic acid (124 mg, 0.69 mmol), Pd(dbpf)Cl$_2$ (19 mg, 0.03 mmol) and Cs$_2$CO$_3$ (375 mg, 1.15 mmol) were dissolved in 1,4-dioxane 2 mL and water 0.5 mL. With a microwave radiation, the mixture was stirred at 120° C. for 20 minutes. The reaction mixture was added with saturated NaHCO$_3$ aqueous solution, and extracted with CH$_2$Cl$_2$. The obtained organic layer was dried over MgSO$_4$, and filtered to remove the solid residue. The filtrate was concentrated under reduced pressure. The concentrate was purified by column chromatography (ISCO silica gel cartridge, MeOH/CH$_2$Cl$_2$) to yield the title compound as yellow solid (87 mg, 39%).

Step 4.

4'-((1-(2-fluoropropyl)piperidin-4-yl)methoxy)biphenyl-4-carboxylic acid: methyl 4'-((1-(2-fluoropropyl)piperidin-4-yl)methoxy)biphenyl-4-carboxylate (87 mg, 0.23 mmol) was dissolved in THF:MeOH:water=4:2:1. LiOH.H$_2$O (19 mg, 0.45 mmol) was added thereto, and refluxed with heating for 7 hours. After the reaction was complete, the solvent was evaporated under reduced pressure. After adjusting pH to below 6 using 1 N HCl, the resulting precipitate was washed with EtOAc thoroughly, and filtered to yield the title compound as gray solid (80 mg, 95%).

Step 5.

Compound 688: 4'-((1-(2-fluoropropyl)piperidin-4-yl)methoxy)biphenyl-4-carboxylic acid (40 mg, 0.11 mmol), dimethylamine hydrochloride (18 mg, 0.22 mmol) and PyBOP (84 mg, 0.16 mmol) were dissolved in CH$_2$Cl$_2$ 1 mL. After stirring at room temperature for 10 minutes, DIPEA (28 mg, 0.22 mmol) was added thereto, following with stirring at room temperature for 8 hours. The reaction mixture was added with water, and extracted with EtOAc. The organic layer was washed with saturated aqueous brine solution, dried over MgSO$_4$, filtered to remove the solid residue, and the filtrate was concentrated under reduced pressure. The concentrate was purified by column chromatography (ISCO silica gel cartridge, EA) to yield the title compound as white solid (17 mg, 45%).

1H NMR (400 MHz, CDCl$_3$) δ 7.52 (m, 6H), 6.98 (d, 2H, J=8.8 Hz), 4.71 (m, 0.5H), 4.58 (m, 0.5H), 3.86 (d, 2H, J=6.0 Hz), 3.01 (m, 6H), 2.66 (m, 1H), 2.47 (m, 1H), 2.14 (m, 2H), 1.81 (m, 3H), 1.66 (m, 2H), 1.57 (m, 2H), 1.01 (t, 3H, J=7.5 Hz); MS (ESI) m/z 413 (M++H).

According to the above-described synthesis process of compound 688, the compounds of Table 152 were synthesized using 4'-((1-(2-fluoropropyl)piperidin-4-yl)methoxy)biphenyl-4-carboxylic acid and the reactant of Table 151.

TABLE 151

| Compound No. | Reactant | Yield (%) |
| --- | --- | --- |
| 689 | (R)-pyrrolidine-2-ylmethanol | 30 |

Example 127. Compound 690: (4'-((1-(2-fluorobutyl)piperidin-4-yl)methoxy)biphenyl-4-yl)(3-hydroxypiperidin-1-yl)methanone

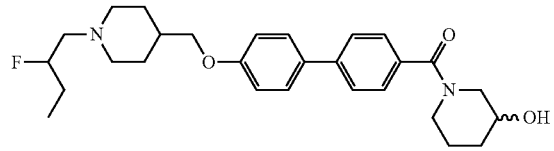 [SMILES: CCC(F)CN1CCC(COc2ccc(-c3ccc(C(=O)N4CCCC(O)C4)cc3)cc2)CC1]

Step 1.

1-(4-((4-bromophenoxy)methyl)piperidin-1-yl)butan-2-ol: 4-((4-bromophenoxy)methyl)piperidine hydrochloride (the product of synthesis step 2 of compound 686; 200 mg, 0.65 mmol) was dissolved in EtOH 1 mL. 2-ethyloxirane (470 mg, 6.52 mmol), K$_2$CO$_3$ (180 mg, 1.31 mmol) and water 1 mL were added thereto. With a microwave radiation, the mixture was stirred at 110° C. for 20 minutes. After the completion of the reaction, EtOH was evaporated from the reaction mixture under reduced pressure, and then a little of water was added to thereto. The resulting precipitate was filtered, and dried under reduced pressure to yield the title compound as red oil (134 mg, 88%).

Step 2.

4-((4-bromophenoxy)methyl)-1-(2-fluorobutyl)piperidine: 1-(4-((4-bromophenoxy)methyl)piperidin-1-yl)butan-2-ol (134 mg, 0.39 mmol) was dissolved in CH$_2$Cl$_2$ 2 mL. Deoxo-fluor (95 mg, 0.43 mmol) was added thereto, following with stirring at room temperature for 3 hours. After the completion of the reaction, the reaction mixture was added with a saturated NaHCO$_3$ aqueous solution, and extracted with CH$_2$Cl$_2$. The organic layer washed with saturated aqueous brine solution, dried over MgSO$_4$ and filtered to remove the solid residue. The filtrate was concentrated under reduced pressure. The concentrate was purified by column chromatography (ISCO silica gel cartridge, EtOAc/Hexane) to yield the title compound as yellow oil (120 mg, 89%).

Step 3.

Methyl 4'-((1-(2-fluorobutyl)piperidin-4-yl)methoxy)biphenyl-4-carboxylate: 4-((4-bromophenoxy)methyl)-1-(2-fluorobutyl)piperidine (150 mg, 0.44 mmol), 4-(methoxycarbonyl)phenylboronic acid (94 mg, 0.52 mmol), Pd(dbpf)Cl$_2$ (14 mg, 0.02 mmol), Cs$_2$CO$_3$ (284 mg, 0.87 mmol) was dissolved in 1,4-dioxane 2 mL and water 0.5 mL. With a microwave radiation, the mixture was stirred at 120° C. for 20 minutes. The reaction mixture was added with saturated NaHCO$_3$ aqueous solution, and extracted with CH$_2$Cl$_2$. The obtained organic layer was dried over MgSO$_4$, and filtered to remove the solid residue. The filtrate was concentrated under reduced pressure. The concentrate was purified by

TABLE 152

| Compound No. | Compound Name, 1H-NMR, MS (ESI) |
| --- | --- |
| 689 | (4'-((1-(2-fluoropropyl)piperidin-4-yl)methoxy)biphenyl-4-yl)(3-hydroxypiperidin-1-yl)methanone<br>1H NMR (400 MHz, CDCl$_3$) δ 7.51 (m, 6 H), 6.98 (d, 2 H, J = 8.8 Hz), 4.99 (m, 0.5 H), 4.72 (m, 0.5 H), 3.86 (m, 4 H), 3.46 (m, 2 H), 3.04 (m, 2 H), 2.68 (m, 1 H), 2.52 (m, 1 H), 2.13 (m, 2 H), 1.85 (m, 7 H), 1.61 (m, 2 H), 1.51 (m, 2 H) 1.30 (m, 3 H); MS (ESI) m/z 455 (M+ + H). | column chromatography (ISCO silica gel cartridge, MeOH/$CH_2Cl_2$) to yield the title compound as yellow solid (30 mg, 17%).

Step 4.

4'-((1-(2-fluorobutyl)piperidin-4-yl)methoxy)biphenyl-4-carboxylic acid: Methyl 4'-((1-(2-fluorobutyl)piperidin-4-yl)methoxy)biphenyl-4-carboxylate (30 mg, 0.08 mmol) was dissolved in THF:MeOH:water=4:2:1. $LiOH.H_2O$ (6 mg, 0.15 mmol) was added thereto, and refluxed with heating for 7 hours. After the reaction was complete, the solvent was evaporated under reduced pressure. After adjusting pH to below 6 using 1 N HCl, the resulting precipitate was washed with EtOAc thoroughly, and filtered to yield the title compound as gray solid (21 mg, 72%).

Step 5.

Compound 690: 4'-((1-(2-fluorobutyl)piperidin-4-yl)methoxy)biphenyl-4-carboxylic acid (21 mg, 0.05 mmol), piperidin-3-ol (11 mg, 0.11 mmol) and PyBOP (43 mg, 0.08 mmol) were dissolved in $CH_2Cl_2$ 1 mL. After stirring at room temperature for 10 minutes, DIPEA (14 mg, 0.11 mmol) was added thereto, following with stirring at room temperature for 8 hours. The reaction mixture was added with water, and extracted with EtOAc. The organic layer was washed with saturated aqueous brine solution, dried over $MgSO_4$, filtered to remove the solid residue, and the filtrate was concentrated under reduced pressure. The concentrate was purified by column chromatography (ISCO silica gel cartridge, MeOH/$CH_2Cl_2$) to yield the title compound as white solid (14 mg, 54%).

1H NMR (400 MHz, $CDCl_3$) δ 7.53 (m, 6H), 6.97 (d, 2H, J=6.8 Hz), 4.60 (m, 0.5H), 3.86 (m, 0.5H), 3.08 (m, 4H), 3.45 (m, 2H), 2.66 (m, 2H), 2.53 (m, 1H), 2.45 (m, 1H), 2.13 (m, 2H), 1.82 (m, 6H), 1.64 (m, 3H), 1.59 (m, 3H), 1.01 (t, 3H, J=7.4 Hz); MS (ESI) m/z 469 (M++H).

Example 128. Compound 655: (R)-(4'-((1-(2-fluoropentyl)piperidin-4-yl)methoxy)biphenyl-4-yl)(2-(hydroxymethyl)pyrrolidin-1-yl)methanone

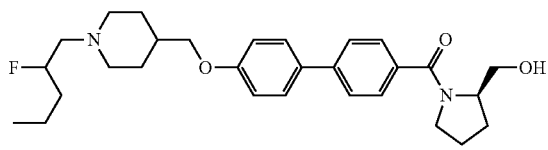 [SMILES: CCCC(F)CN1CCC(COc2ccc(-c3ccc(C(=O)N4CCC[C@@H]4CO)cc3)cc2)CC1]

Step 1.

1-(4-((4-bromophenoxy)methyl)piperidin-1-yl)pentane-2-ol: 4-((4-bromophenoxy)methyl)piperidine hydrochloride (the product of synthesis step 1 of compound 498; 500 mg, 1.63 mmol) and $K_2CO_3$ (450 mg, 3.26 mmol) were suspended in EtOH 2 mL. Water 2 mL was added thereto, and the mixture was suspended with a little heating. 2-propyloxirane (1.40 g, 16.31 mmol) was added thereto. With a microwave radiation, the reaction was performed at 110° C. for 20 minutes. The reaction mixture was diluted with water, and extracted with EtOAc. The obtained organic layer was dried over $MgSO_4$, and filtered. The filtrate was concentrated under reduced pressure to yield the title compound as white solid (510 mg, 88%).

Step 2.

4-((4-bromophenoxy)methyl)-1-(2-fluoropentyl)piperidine: 1-(4-((4-bromophenoxy)methyl)piperidin-1-yl)pentane-2-ol (510 mg, 1.43 mmol) was dissolved in $CH_2Cl_2$ 4 mL. Deoxo-Fluor (348 mg, 1.58 mmol) was added thereto.

After stirring for 3 hours at room temperature, A saturated $NaHCO_3$ aqueous solution was added thereto, and the mixture was extracted with $CH_2Cl_2$. The organic layer was dried over $MgSO_4$, and filtered to remove a solid. The filtrate was concentrated under reduced pressure to yield the title compound as yellow oil (395 mg, 77%).

Step 3.

Methyl 4'-((1-(2-fluoropentyl)piperidin-4-yl)methoxy)biphenyl-4-carboxylate: 4-((4-bromophenoxy)methyl)-1-(2-fluoropentyl)piperidine (250 mg, 0.70 mmol) and 4-(methoxycarbonyl)phenylboronic acid (151 mg, 0.84 mmol) were dissolved in dioxane 2 mL. Water 0.5 mL was added thereto. $Pd(dbpf)Cl_2$ (23 mg, 0.04 mmol) and $Cs_2CO_3$ (455 mg, 1.40 mmol) were added thereto. With a microwave radiation, the reaction was performed at 120° C. for 20 minutes. The reaction mixture was filtered through Celite. The filtrate was added with a saturated $NaHCO_3$ aqueous solution, and extracted with $CH_2Cl_2$. The organic layer was dried over $MgSO_4$, and then concentrated under reduced pressure. The obtained concentrate was purified by silica gel column chromatography (MeOH/$CH_2Cl_2$) to yield the title compound as white solid (115 mg, 40%).

Step 4.

4'-((1-(2-fluoropentyl)piperidin-4-yl)methoxy)biphenyl-4-carboxylic acid: Methyl 4'-((1-(2-fluoropentyl)piperidin-4-yl)methoxy)biphenyl-4-carboxylate (115 mg, 0.28 mmol) was dissolved in THF 2 mL. MeOH 1 mL and $H_2O$ 0.5 mL were added thereto. The mixture was added with $LiOH.H_2O$ (23 mg, 0.56 mmol), and then refluxed with heating and stirring for a day. After acidification with 1 N HCl, the resulting precipitate was filtered to yield the title compound as white solid (100 mg, 90%).

Step 5.

Compound 655: 4'-((1-(2-fluoropentyl)piperidin-4-yl)methoxy)biphenyl-4-carboxylic acid (40 mg, 0.10 mmol), (R)-pyrrolidine-2-ylmethanol (15 mg, 0.15 mmol) and PyBOP (78 mg, 0.15 mmol) were dissolved in DMF 1 mL. DIPEA (26 mg, 0.20 mmol) was added thereto. The reaction was performed at room temperature for 8 hours. The reaction mixture was added with water, and extracted with EtOAc. The obtained organic layer was dried over $MgSO_4$, and filtered. The obtained concentrate was purified by silica gel column chromatography (MeOH/$CH_2Cl_2$) to yield the title compound as light-yellow solid (21 mg, 43%).

1H NMR (400 MHz, $CDCl_3$) δ 7.57 (m, 4H), 7.52 (d, 2H, J=8.7 Hz), 6.97 (d, 2H, J=8.7 Hz), 4.78 (m, 0.5H), 4.64 (m, 0.5H), 4.42 (m, 1H), 3.75 (m, 4H), 3.55 (m, 2H), 3.16 (m, 2H), 2.62 (m, 1H), 2.53 (m, 1H), 2.17 (m, 3H), 1.80 (m, 5H), 1.63 (m, 2H), 1.47 (m, 3H), 0.95 (t, 3H, J=7.1 Hz); MS (ESI) m/z 483 (M++H).

According to the above-described synthesis process of compound 655 (Step 5), the compounds of Table 154 were synthesized using 4'-((1-(2-fluoropentyl)piperidin-4-yl)methoxy)biphenyl-4-carboxylic acid and the reactant of Table 153.

TABLE 153

| Compound No. | Reactant | Yield (%) |
|---|---|---|
| 656 | L-prolinamide | 48 |

TABLE 154

| Compound No. | Compound Name, $^1$H-NMR, MS (ESI) |
|---|---|
| 656 | (S)-1-(4'-((1-(2-fluoropentyl)piperidin-4-yl)methoxy)biphenylcarbonyl)pyrrolidine-2-carboxamide<br>$^1$H NMR (400 MHz, CDCl$_3$) δ 7.58 (s, 3 H), 7.52 (d, 2 H, J = 8.6 Hz), 7.02 (s, 1 H), 6.96 (d, 2 H, J = 8.6 Hz), 5.57 (s, 1 H), 4.79 (m, 1.5 H), 4.65 (m, 0.5 H), 3.84 (d, 2 H, J = 5.8 Hz), 3.63 (m, 2 H), 3.15 (m, 1 H), 3.07 (m, 2 H), 2.64 (m, 1 H), 2.44 (m, 2 H), 2.08 (m, 4 H), 1.81 (m, 5 H), 1.48 (m, 4 H), 0.94 (t, 3 H, J = 7.1 Hz); MS (ESI) m/z 496 (M$^+$ + H). |

The structural formulae are as following Tables 155-180.

TABLE 155

| Compound | Structure |
|---|---|
| 431 | 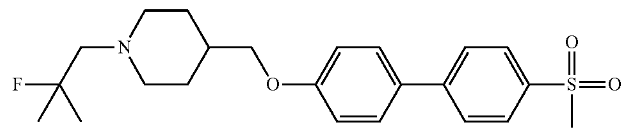 |
| 470 | 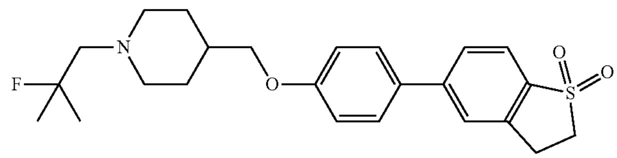 [SMILES: CC(C)(F)CN1CCC(COc2ccc(-c3ccc4c(c3)CCS4(=O)=O)cc2)CC1] |
| 498 | 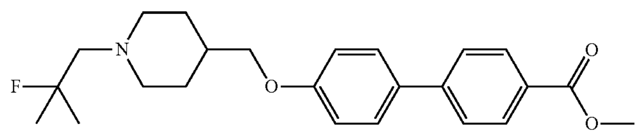 [SMILES: COC(=O)c1ccc(-c2ccc(OCC3CCN(CC(C)(C)F)CC3)cc2)cc1] |
| 499 | 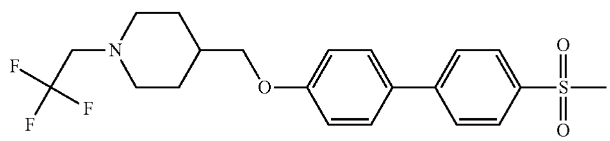 [SMILES: CS(=O)(=O)c1ccc(-c2ccc(OCC3CCN(CC(F)(F)F)CC3)cc2)cc1] |
| 500 | 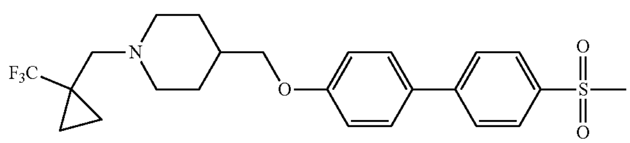 [SMILES: CS(=O)(=O)c1ccc(-c2ccc(OCC3CCN(CC4(C(F)(F)F)CC4)CC3)cc2)cc1] |
| 515 | 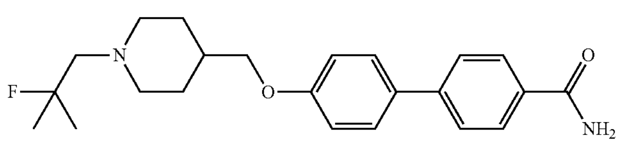 [SMILES: CC(C)(F)CN1CCC(COc2ccc(-c3ccc(C(N)=O)cc3)cc2)CC1] |
| 516 | 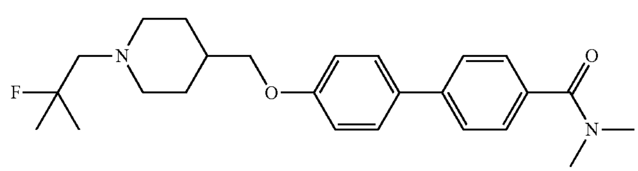 [SMILES: CN(C)C(=O)c1ccc(-c2ccc(OCC3CCN(CC(C)(C)F)CC3)cc2)cc1] |
| 517 | 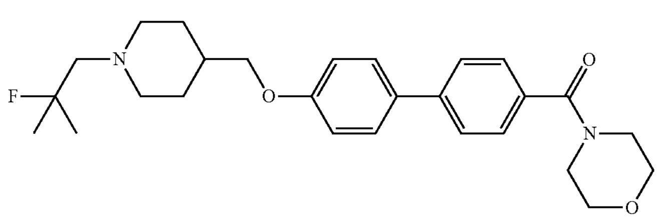 [SMILES: CC(C)(F)CN1CCC(COc2ccc(-c3ccc(C(=O)N4CCOCC4)cc3)cc2)CC1] |

TABLE 155-continued

| Compound | Structure |
|---|---|
| 524 | 1-(3,3,3-trifluoropropyl)piperidin-4-yl)methoxy-biphenyl-methylsulfonyl |
| 526 | 1-(3-fluoro-2,2-dimethylpropyl)piperidin-4-yl)methoxy-biphenyl-S(=O)-NH-cyclopropyl |
| 527 | 1-(3-fluoro-2,2-dimethylpropyl)piperidin-4-yl)methoxy-biphenyl-C(=O)NH-cyclobutyl |
| 528 | 1-(3-fluoro-2,2-dimethylpropyl)piperidin-4-yl)methoxy-biphenyl-C(=O)NH-cyclopentyl |
| 529 | 1-(3-fluoro-2,2-dimethylpropyl)piperidin-4-yl)methoxy-biphenyl-C(=O)NH-cyclohexyl |
| 530 | 1-(3-fluoro-2,2-dimethylpropyl)piperidin-4-yl)methoxy-biphenyl-C(=O)-pyrrolidinyl |
| 531 | 1-(3-fluoro-2,2-dimethylpropyl)piperidin-4-yl)methoxy-biphenyl-C(=O)-piperidinyl |
| 533 | 1-(3-fluoro-2,2-dimethylpropyl)piperidin-4-yl)methoxy-biphenyl-C(=O)NH-(CH2)4-OH |
| 534 | 1-(3-fluoro-2,2-dimethylpropyl)piperidin-4-yl)methoxy-biphenyl-C(=O)NH-methyl |

TABLE 155-continued

| Compound | Structure |
|---|---|
| 540 | 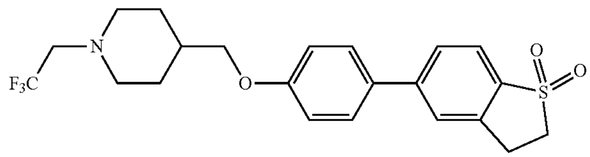 [SMILES: O=S1(=O)CCc2cc(-c3ccc(OCC4CCN(CC(F)(F)F)CC4)cc3)ccc21] |
| 542 | 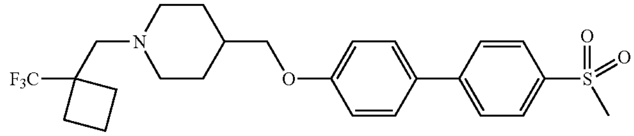 [SMILES: CS(=O)(=O)c1ccc(-c2ccc(OCC3CCN(CC4(C(F)(F)F)CCC4)CC3)cc2)cc1] |
| 546 | 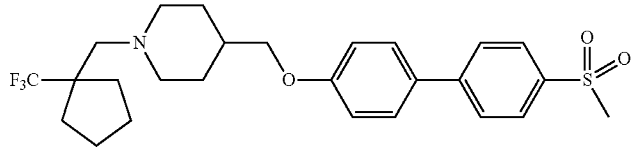 [SMILES: CS(=O)(=O)c1ccc(-c2ccc(OCC3CCN(CC4(C(F)(F)F)CCCC4)CC3)cc2)cc1] |

TABLE 156

| Compound | Structure |
|---|---|
| 547 | 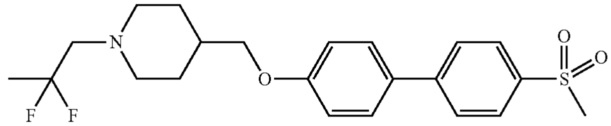 [SMILES: CC(F)(F)CN1CCC(COc2ccc(-c3ccc(S(C)(=O)=O)cc3)cc2)CC1] |
| 548 | 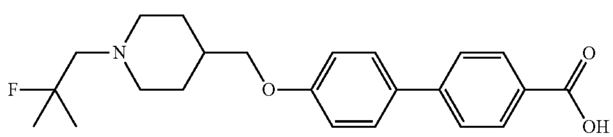 [SMILES: CC(C)(F)CN1CCC(COc2ccc(-c3ccc(C(=O)O)cc3)cc2)CC1] |
| 549 | 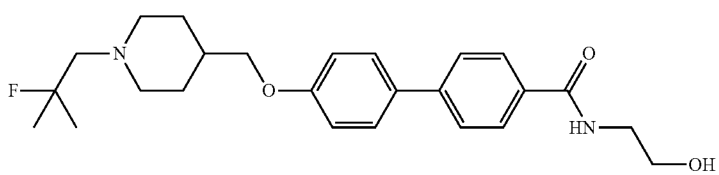 [SMILES: CC(C)(F)CN1CCC(COc2ccc(-c3ccc(C(=O)NCCO)cc3)cc2)CC1] |
| 550 | 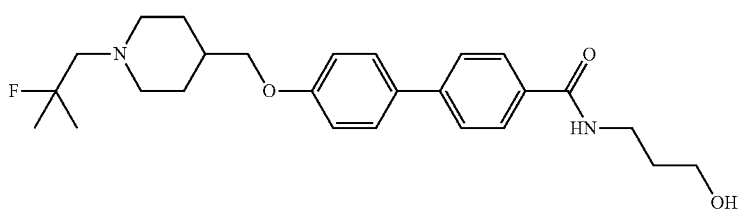 [SMILES: CC(C)(F)CN1CCC(COc2ccc(-c3ccc(C(=O)NCCCO)cc3)cc2)CC1] |
| 551 | 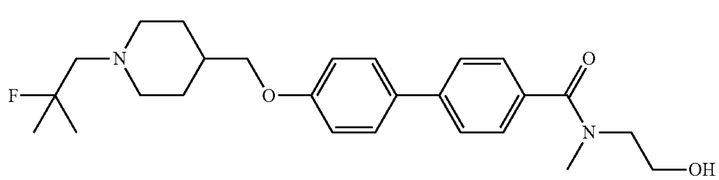 |

TABLE 156-continued

| Compound | Structure |
|---|---|
| 552 | 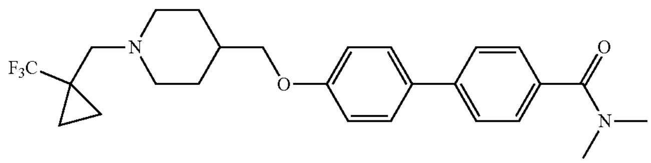 [SMILES: CN(C)C(=O)c1ccc(-c2ccc(OCC3CCN(CC4(C(F)(F)F)CC4)CC3)cc2)cc1] |
| 553 | 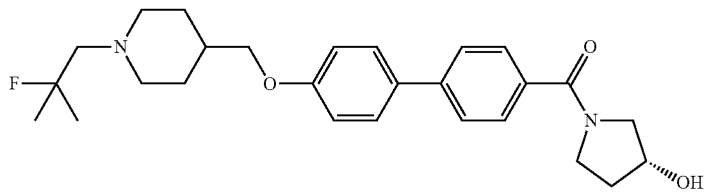 [SMILES: CC(C)(F)CN1CCC(COc2ccc(-c3ccc(C(=O)N4CC[C@@H](O)C4)cc3)cc2)CC1] |
| 554 | 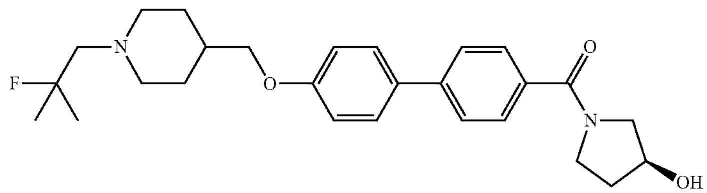 [SMILES: CC(C)(F)CN1CCC(COc2ccc(-c3ccc(C(=O)N4CC[C@H](O)C4)cc3)cc2)CC1] |
| 555 | 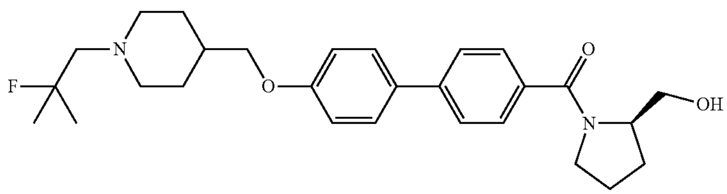 [SMILES: CC(C)(F)CN1CCC(COc2ccc(-c3ccc(C(=O)N4CCC[C@@H]4CO)cc3)cc2)CC1] |
| 556 | 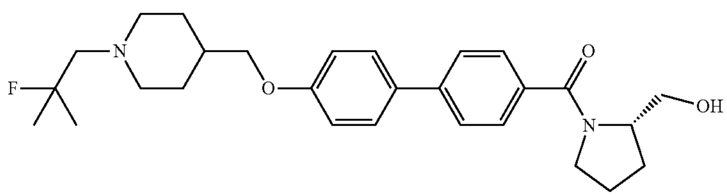 [SMILES: CC(C)(F)CN1CCC(COc2ccc(-c3ccc(C(=O)N4CCC[C@H]4CO)cc3)cc2)CC1] |
| 557 | 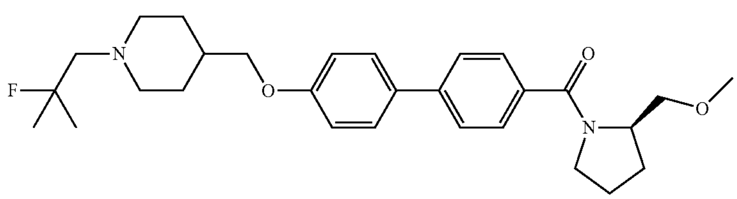 [SMILES: COC[C@H]1CCCN1C(=O)c1ccc(-c2ccc(OCC3CCN(CC(C)(C)F)CC3)cc2)cc1] |
| 558 | 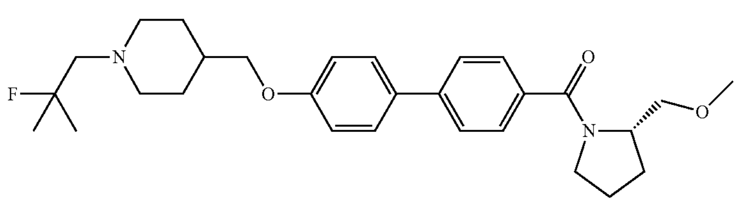 [SMILES: COC[C@@H]1CCCN1C(=O)c1ccc(-c2ccc(OCC3CCN(CC(C)(C)F)CC3)cc2)cc1] |
| 559 | 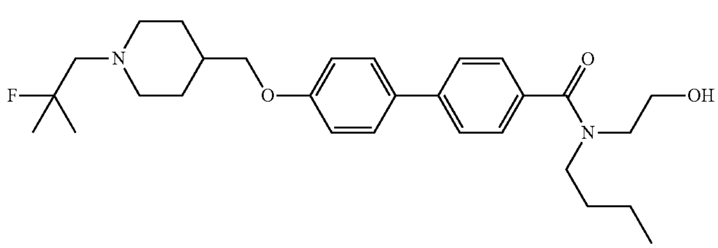 [SMILES: CCCCN(CCO)C(=O)c1ccc(-c2ccc(OCC3CCN(CC(C)(C)F)CC3)cc2)cc1] |

TABLE 156-continued

| Compound | Structure |
|---|---|
| 560 | 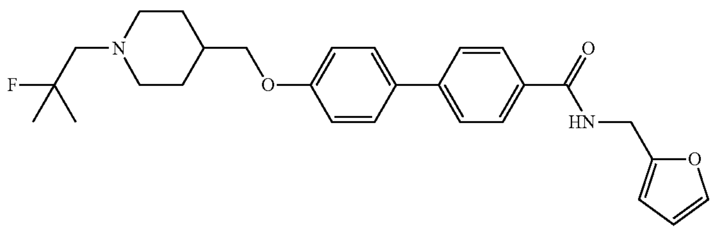 [SMILES: CC(C)(F)CN1CCC(COc2ccc(-c3ccc(C(=O)NCc4ccco4)cc3)cc2)CC1] |
| 561 | 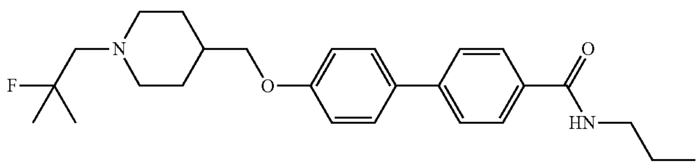 [SMILES: CCCNC(=O)c1ccc(-c2ccc(OCC3CCN(CC(C)(C)F)CC3)cc2)cc1] |
| 562 | 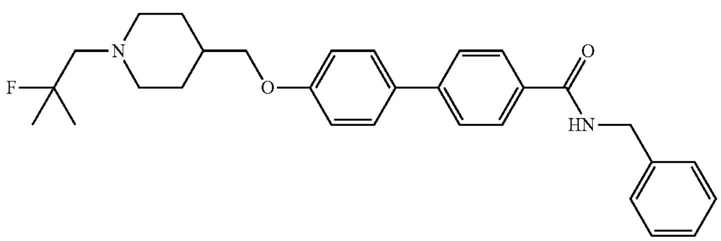 |
| 563 | 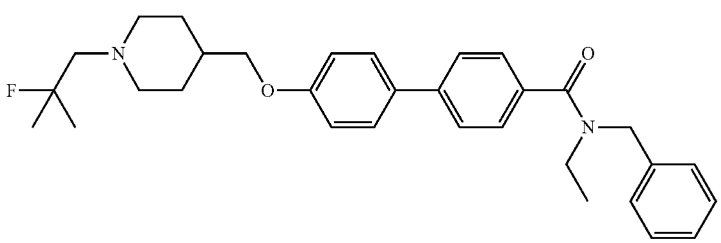 [SMILES: CCN(Cc1ccccc1)C(=O)c1ccc(-c2ccc(OCC3CCN(CC(C)(C)F)CC3)cc2)cc1] |
| 564 | 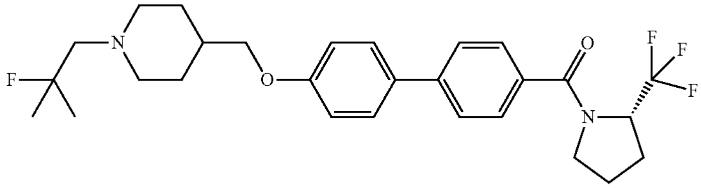 [SMILES: CC(C)(F)CN1CCC(COc2ccc(-c3ccc(C(=O)N4CCC[C@H]4C(F)(F)F)cc3)cc2)CC1] |
| 565 | 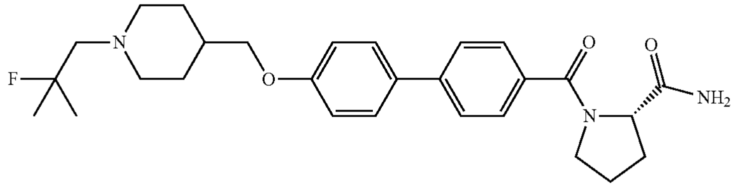 [SMILES: CC(C)(F)CN1CCC(COc2ccc(-c3ccc(C(=O)N4CCC[C@H]4C(N)=O)cc3)cc2)CC1] |
| 566 | 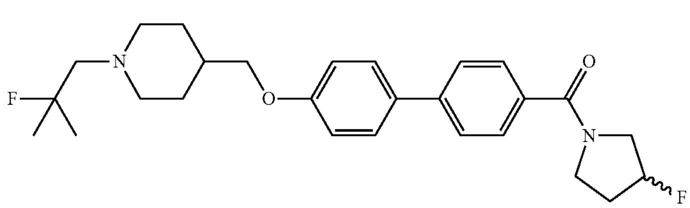 |

TABLE 157

| Compound | Structure |
|---|---|
| 567 | 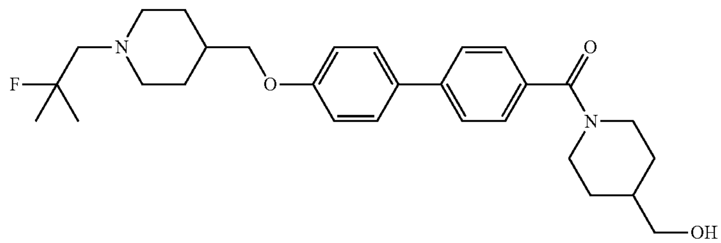 [SMILES: CC(C)(F)CN1CCC(COc2ccc(-c3ccc(C(=O)N4CCC(CO)CC4)cc3)cc2)CC1] |
| 568 | 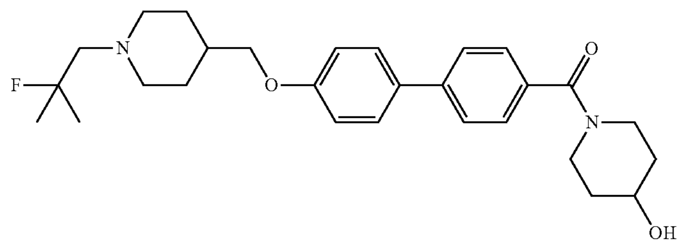 [SMILES: CC(C)(F)CN1CCC(COc2ccc(-c3ccc(C(=O)N4CCC(O)CC4)cc3)cc2)CC1] |
| 569 | 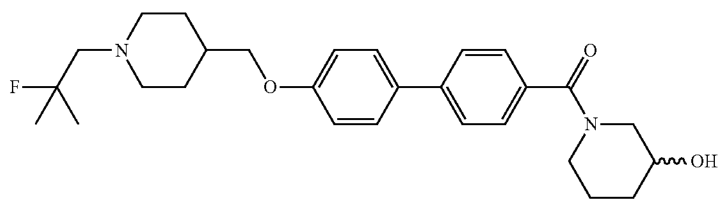 [SMILES: CC(C)(F)CN1CCC(COc2ccc(-c3ccc(C(=O)N4CCCC(O)C4)cc3)cc2)CC1] |
| 570 | 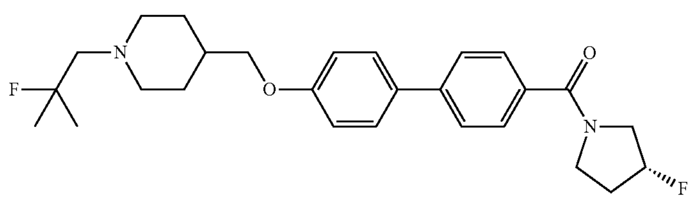 [SMILES: CC(C)(F)CN1CCC(COc2ccc(-c3ccc(C(=O)N4CC[C@@H](F)C4)cc3)cc2)CC1] |
| 571 | 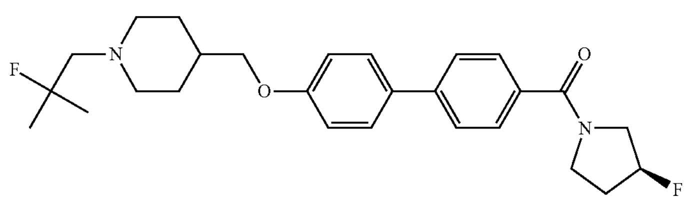 [SMILES: CC(C)(F)CN1CCC(COc2ccc(-c3ccc(C(=O)N4CC[C@H](F)C4)cc3)cc2)CC1] |
| 574 | 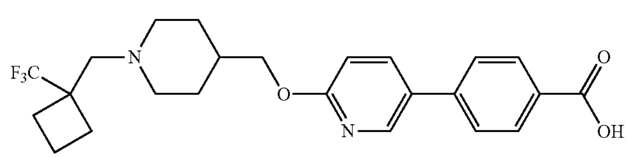 [SMILES: O=C(O)c1ccc(-c2ccc(OCC3CCN(CC4(C(F)(F)F)CCC4)CC3)nc2)cc1] |
| 575 | 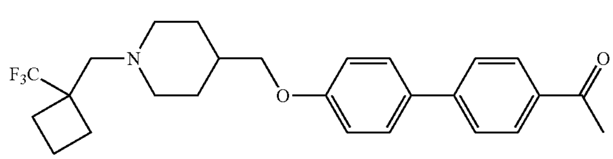 |
| 576 | 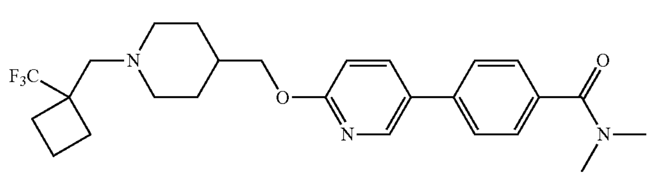 [SMILES: CN(C)C(=O)c1ccc(-c2ccc(OCC3CCN(CC4(C(F)(F)F)CCC4)CC3)nc2)cc1] |

TABLE 157-continued

| Compound | Structure |
|---|---|
| 578 | 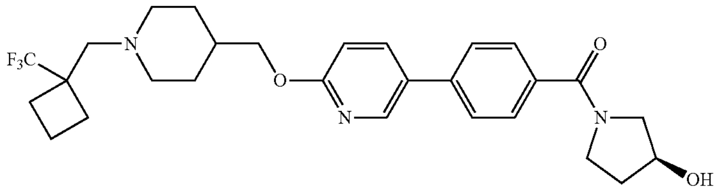 [SMILES: O=C(c1ccc(-c2ccc(OCC3CCN(CC4(C(F)(F)F)CCC4)CC3)nc2)cc1)N1CC[C@H](O)C1] |
| 579 | 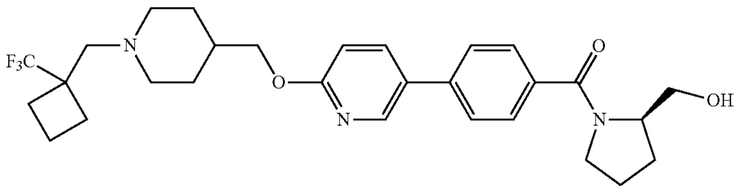 |
| 580 | 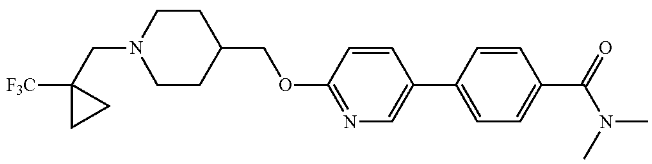 [SMILES: CN(C)C(=O)c1ccc(-c2ccc(OCC3CCN(CC4(C(F)(F)F)CC4)CC3)nc2)cc1] |
| 581 | 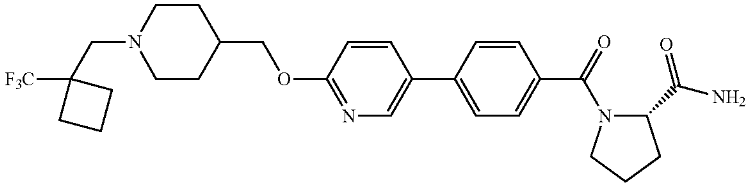 [SMILES: NC(=O)[C@@H]1CCCN1C(=O)c1ccc(-c2ccc(OCC3CCN(CC4(C(F)(F)F)CCC4)CC3)nc2)cc1] |
| 582 | 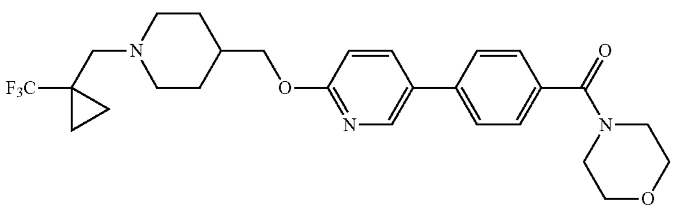 [SMILES: O=C(c1ccc(-c2ccc(OCC3CCN(CC4(C(F)(F)F)CC4)CC3)nc2)cc1)N1CCOCC1] |
| 583 | 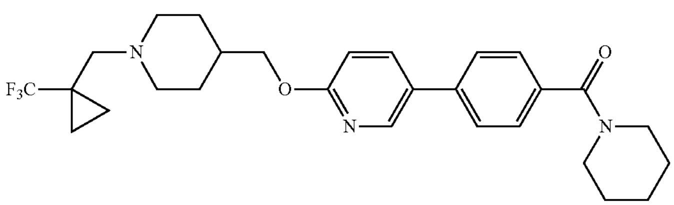 [SMILES: O=C(c1ccc(-c2ccc(OCC3CCN(CC4(C(F)(F)F)CC4)CC3)nc2)cc1)N1CCCCC1] |
| 584 | 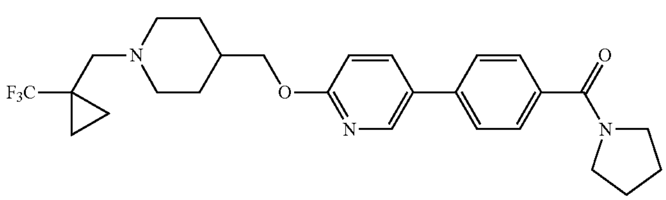 [SMILES: O=C(c1ccc(-c2ccc(OCC3CCN(CC4(C(F)(F)F)CC4)CC3)nc2)cc1)N1CCCC1] |
| 585 | 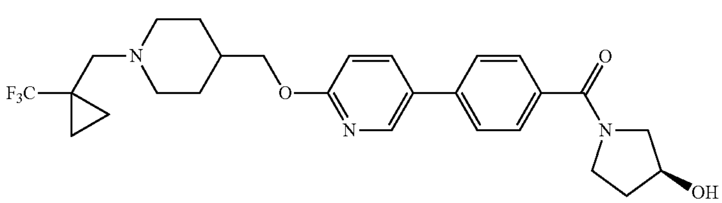 [SMILES: O=C(c1ccc(-c2ccc(OCC3CCN(CC4(C(F)(F)F)CC4)CC3)nc2)cc1)N1CC[C@H](O)C1] |

TABLE 157-continued

| Compound | Structure |
| --- | --- |
| 586 | (structure) |
| 587 | (structure) |
| 588 | (structure) |
| 589 | (structure) |

TABLE 158

| Compound | Structure |
| --- | --- |
| 593 | (structure) |
| 594 | (structure) |

TABLE 158-continued

| Compound | Structure |
|---|---|
| 595 | (structure) |
| 596 | (structure) |
| 597 | (structure) |
| 598 | (structure) |
| 599 | (structure) |
| 600 | (structure) |
| 601 | (structure) |
| 602 | (structure) |

TABLE 158-continued

| Compound | Structure |
|---|---|
| 603 | *structure* |
| 604 | *structure* |
| 605 | *structure* |
| 606 | *structure* |
| 607 | *structure* |
| 608 | *structure* |
| 609 | *structure* |
| 610 | *structure* |
| 611 | *structure* |

TABLE 158-continued

| Compound | Structure |
|---|---|
| 612 | (structure) |

TABLE 159

| Compound | Structure |
|---|---|
| 613 | (structure) |
| 614 | (structure) |
| 615 | (structure) |
| 616 | (structure) |
| 617 | (structure) |
| 618 | (structure) |

TABLE 159-continued

| Compound | Structure |
|---|---|
| 619 | 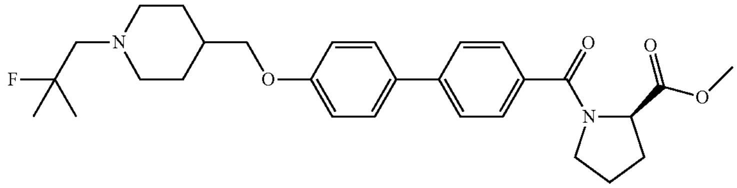 [SMILES: COC(=O)[C@H]1CCCN1C(=O)c1ccc(-c2ccc(OCC3CCN(CC(C)(C)F)CC3)cc2)cc1] |
| 620 | 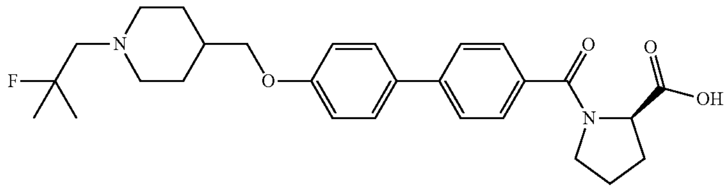 [SMILES: CC(C)(F)CN1CCC(COc2ccc(-c3ccc(C(=O)N4CCC[C@@H]4C(=O)O)cc3)cc2)CC1] |
| 621 | 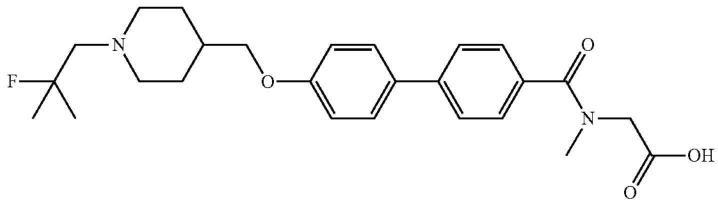 [SMILES: CN(CC(=O)O)C(=O)c1ccc(-c2ccc(OCC3CCN(CC(C)(C)F)CC3)cc2)cc1] |
| 622 | 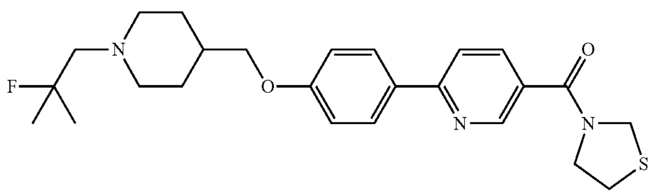 [SMILES: CC(C)(F)CN1CCC(COc2ccc(-c3ccc(C(=O)N4CCSC4)cn3)cc2)CC1] |
| 623 | 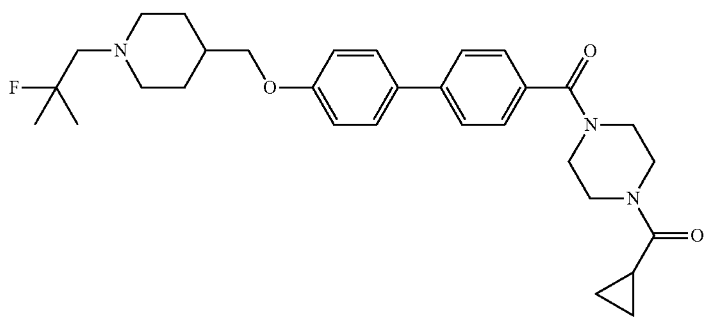 [SMILES: CC(C)(F)CN1CCC(COc2ccc(-c3ccc(C(=O)N4CCN(C(=O)C5CC5)CC4)cc3)cc2)CC1] |
| 624 | 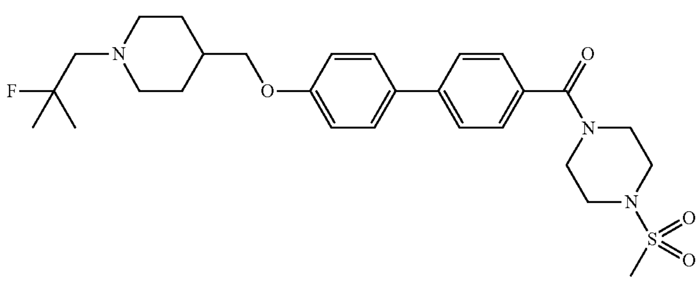 [SMILES: CC(C)(F)CN1CCC(COc2ccc(-c3ccc(C(=O)N4CCN(S(C)(=O)=O)CC4)cc3)cc2)CC1] |
| 625 | 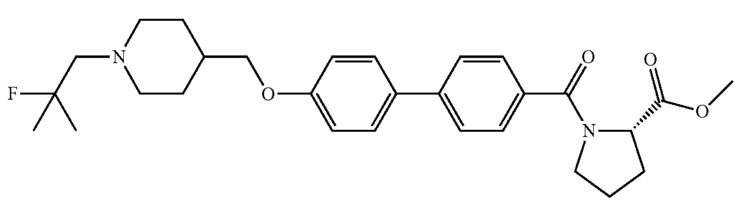 [SMILES: COC(=O)[C@@H]1CCCN1C(=O)c1ccc(-c2ccc(OCC3CCN(CC(C)(C)F)CC3)cc2)cc1] |

TABLE 159-continued

| Compound | Structure |
|---|---|
| 626 | 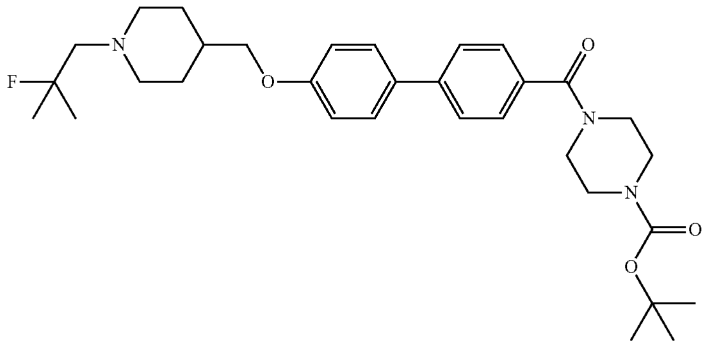 [SMILES: CC(C)(F)CN1CCC(COc2ccc(-c3ccc(C(=O)N4CCN(C(=O)OC(C)(C)C)CC4)cc3)cc2)CC1] |
| 627 | 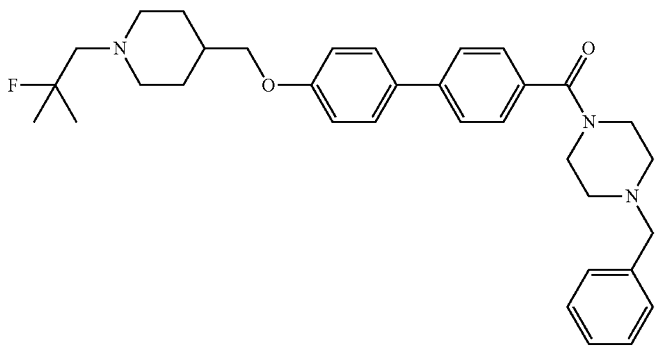 [SMILES: CC(C)(F)CN1CCC(COc2ccc(-c3ccc(C(=O)N4CCN(Cc5ccccc5)CC4)cc3)cc2)CC1] |
| 628 | 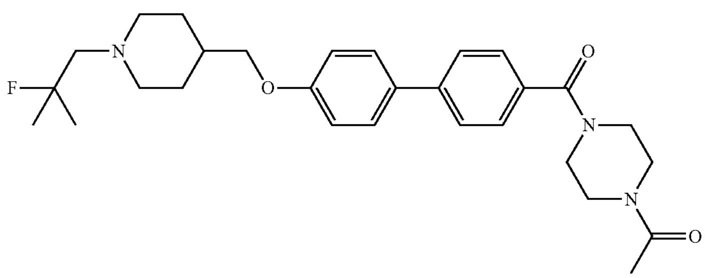 [SMILES: CC(=O)N1CCN(C(=O)c2ccc(-c3ccc(OCC4CCN(CC(C)(C)F)CC4)cc3)cc2)CC1] |
| 629 | 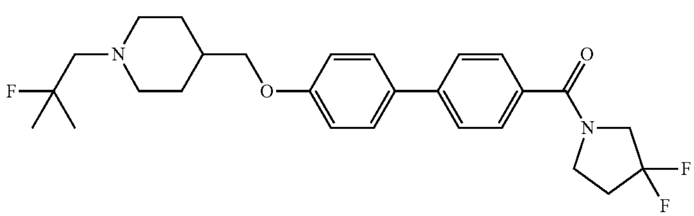 [SMILES: CC(C)(F)CN1CCC(COc2ccc(-c3ccc(C(=O)N4CCC(F)(F)C4)cc3)cc2)CC1] |
| 630 | 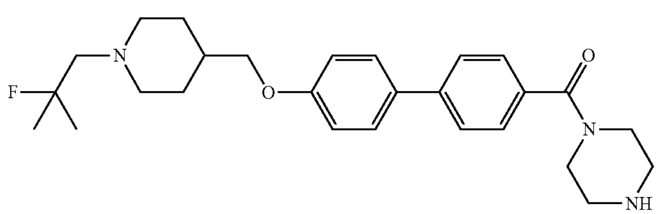 [SMILES: CC(C)(F)CN1CCC(COc2ccc(-c3ccc(C(=O)N4CCNCC4)cc3)cc2)CC1] |
| 631 | 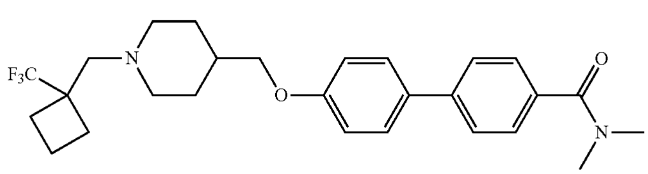 |

TABLE 159-continued
| Compound | Structure |
|---|---|
| 632 | 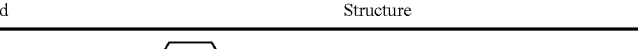 |
TABLE 160
| Compound | Structure |
|---|---|
| 633 | 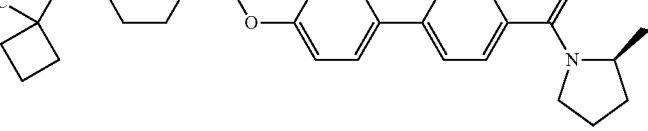 |
| 634 | 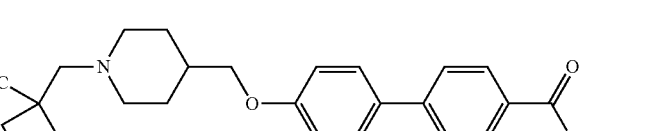 |
| 635 | 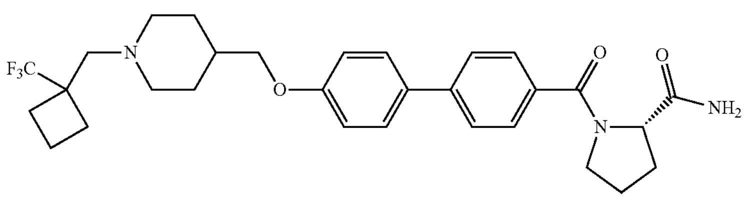 [SMILES: NC(=O)[C@@H]1CCCN1C(=O)c1ccc(-c2ccc(OCC3CCN(CC4(C(F)(F)F)CCC4)CC3)cc2)cc1] |
| 636 | 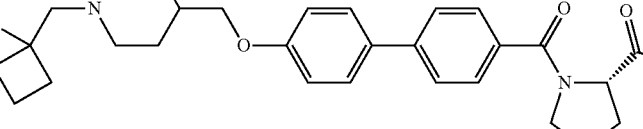 |
| 637 | 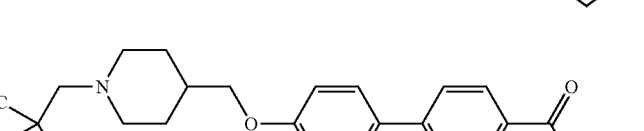 |
| 638 | 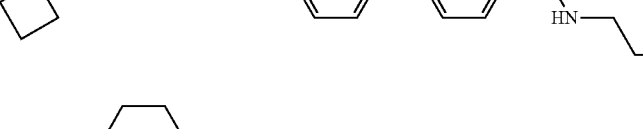 |

TABLE 160-continued
| Compound | Structure |
|---|---|
| 639 | 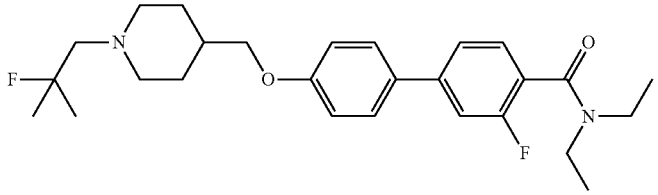 [SMILES: CCN(CC)C(=O)c1ccc(-c2ccc(OCC3CCN(CC(C)(C)F)CC3)cc2)cc1F] |
| 640 | 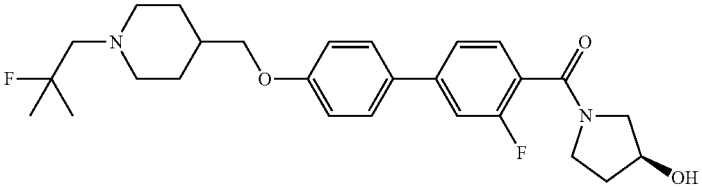 [SMILES: CC(C)(F)CN1CCC(COc2ccc(-c3ccc(C(=O)N4CC[C@H](O)C4)c(F)c3)cc2)CC1] |
| 641 | 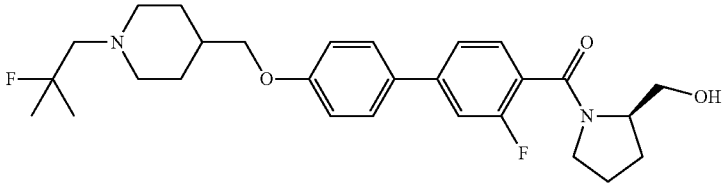 [SMILES: CC(C)(F)CN1CCC(COc2ccc(-c3ccc(C(=O)N4CCC[C@@H]4CO)c(F)c3)cc2)CC1] |
| 642 | 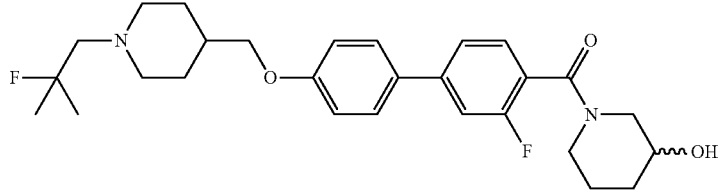 |
| 643 | 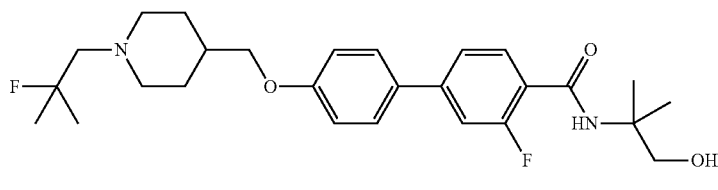 |
| 644 | 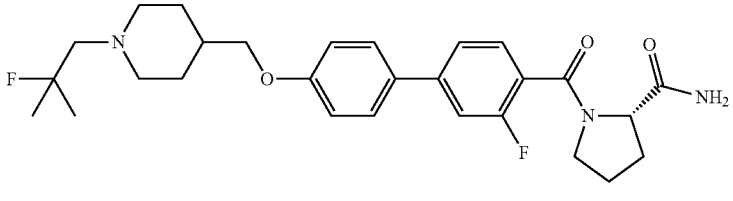 |
| 645 | 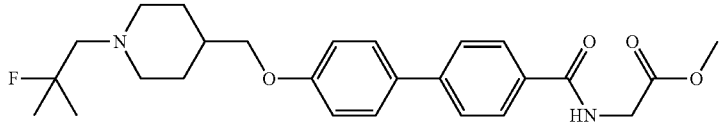 |
| 646 | 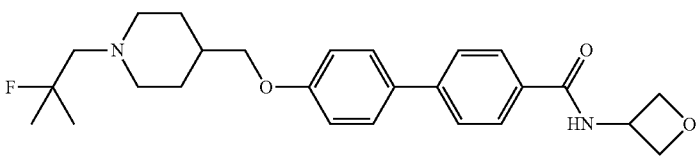 [SMILES: CC(C)(F)CN1CCC(COc2ccc(-c3ccc(C(=O)NC4COC4)cc3)cc2)CC1] |

TABLE 160-continued
| Compound | Structure |
|---|---|
| 647 | 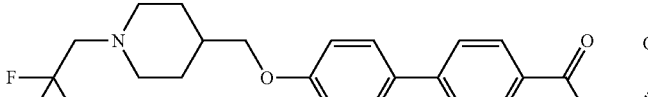 |
| 648 | 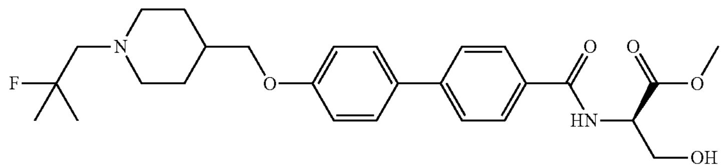 [SMILES: COC(=O)[C@@H](CO)NC(=O)c1ccc(-c2ccc(OCC3CCN(CC(C)(C)F)CC3)cc2)cc1] |
| 649 | 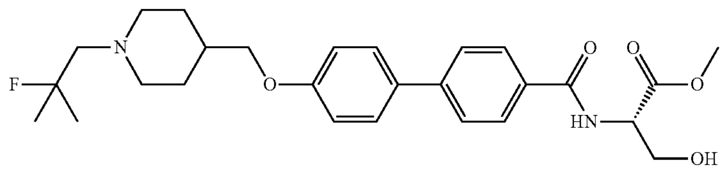 [SMILES: COC(=O)[C@H](CO)NC(=O)c1ccc(-c2ccc(OCC3CCN(CC(C)(C)F)CC3)cc2)cc1] |
| 650 | 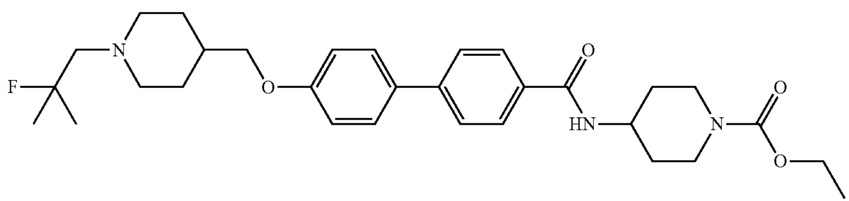 [SMILES: CCOC(=O)N1CCC(NC(=O)c2ccc(-c3ccc(OCC4CCN(CC(C)(C)F)CC4)cc3)cc2)CC1] |
| 651 | 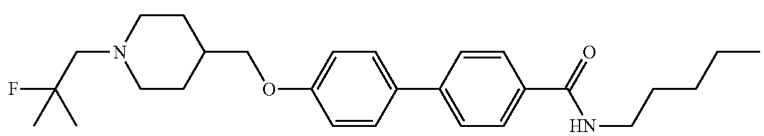 [SMILES: CCCCCNC(=O)c1ccc(-c2ccc(OCC3CCN(CC(C)(C)F)CC3)cc2)cc1] |
| 652 | 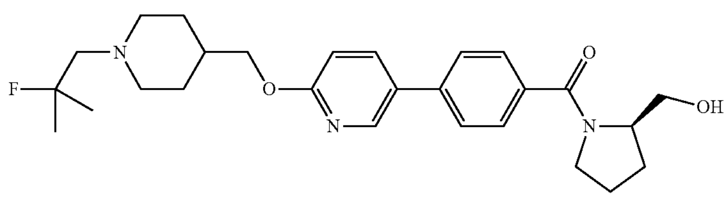 [SMILES: CC(C)(F)CN1CCC(COc2ccc(-c3ccc(C(=O)N4CCC[C@@H]4CO)cc3)cn2)CC1] |
TABLE 161
| Compound | Structure |
|---|---|
| 653 | 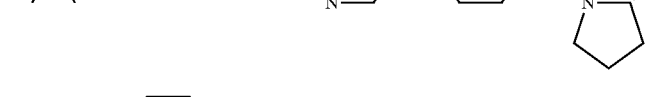 |
| 654 | 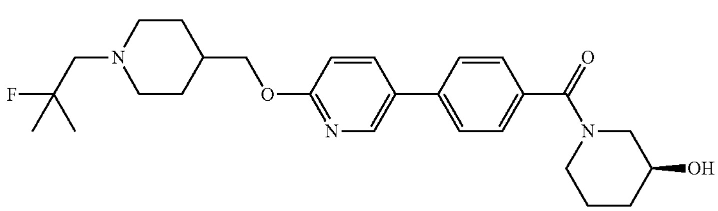 [SMILES: CC(C)(F)CN1CCC(COc2ccc(-c3ccc(C(=O)N4CCC[C@H](O)C4)cc3)cn2)CC1] |

TABLE 161-continued

| Compound | Structure |
|---|---|
| 655 | 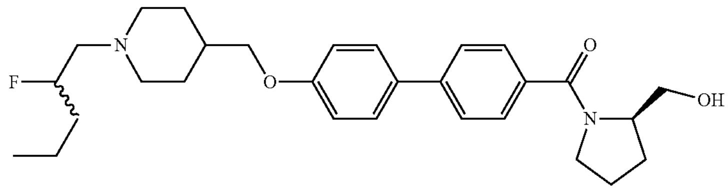 [SMILES: CCCC(F)CN1CCC(COc2ccc(-c3ccc(C(=O)N4CCC[C@@H]4CO)cc3)cc2)CC1] |
| 656 | 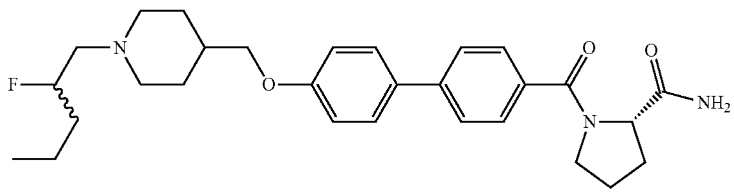 [SMILES: CCCC(F)CN1CCC(COc2ccc(-c3ccc(C(=O)N4CCC[C@H]4C(N)=O)cc3)cc2)CC1] |
| 657 | 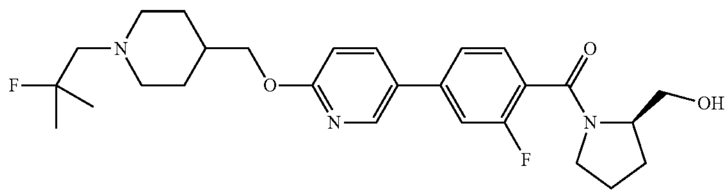 [SMILES: CC(C)(F)CN1CCC(COc2ccc(-c3ccc(C(=O)N4CCC[C@@H]4CO)c(F)c3)cn2)CC1] |
| 658 | 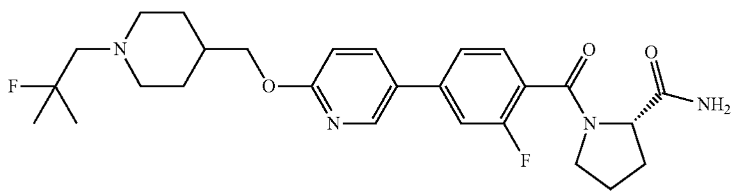 |
| 659 | 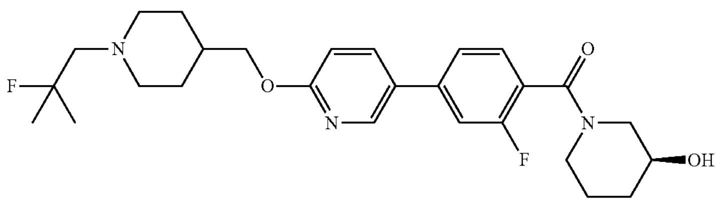 [SMILES: CC(C)(F)CN1CCC(COc2ccc(-c3ccc(C(=O)N4CCC[C@H](O)C4)c(F)c3)cn2)CC1] |
| 666 | 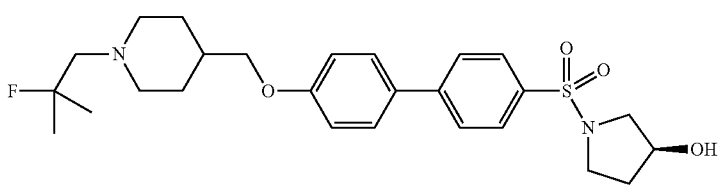 [SMILES: CC(C)(F)CN1CCC(COc2ccc(-c3ccc(S(=O)(=O)N4CC[C@H](O)C4)cc3)cc2)CC1] |
| 667 | 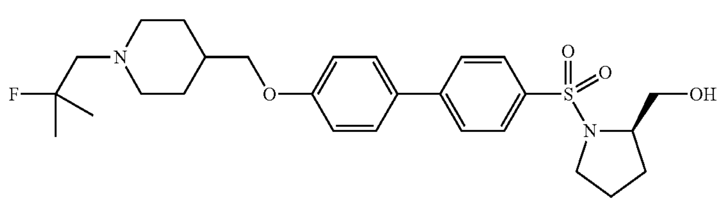 [SMILES: CC(C)(F)CN1CCC(COc2ccc(-c3ccc(S(=O)(=O)N4CCC[C@@H]4CO)cc3)cc2)CC1] |
| 668 | 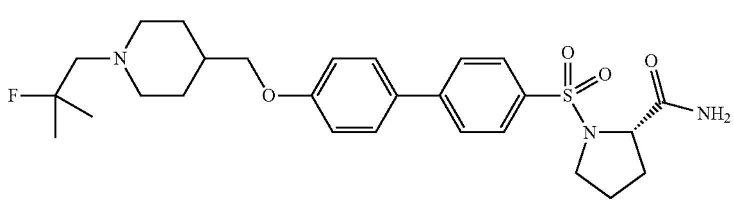 [SMILES: CC(C)(F)CN1CCC(COc2ccc(-c3ccc(S(=O)(=O)N4CCC[C@H]4C(N)=O)cc3)cc2)CC1] |

TABLE 161-continued

| Compound | Structure |
|---|---|
| 669 | 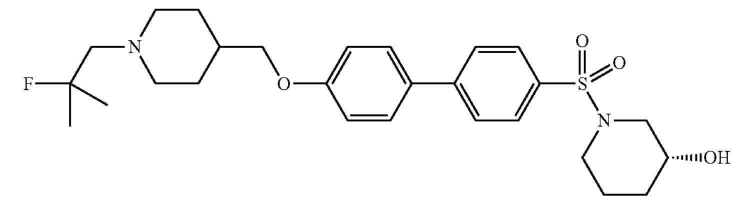 [SMILES: CC(C)(F)CN1CCC(COc2ccc(-c3ccc(S(=O)(=O)N4CCC[C@@H](O)C4)cc3)cc2)CC1] |
| 670 | 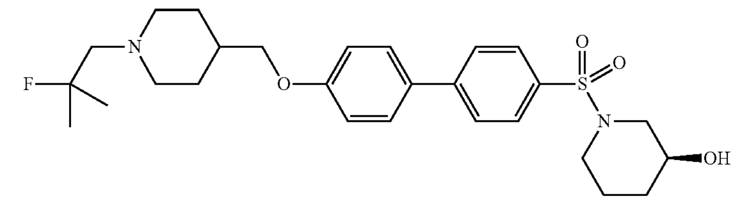 [SMILES: CC(C)(F)CN1CCC(COc2ccc(-c3ccc(S(=O)(=O)N4CCC[C@H](O)C4)cc3)cc2)CC1] |
| 671 | 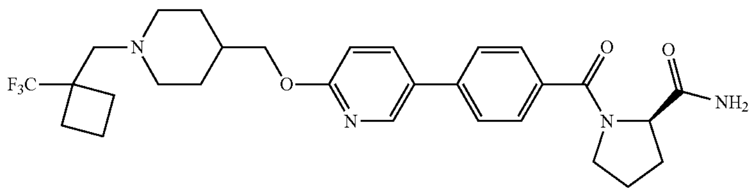 [SMILES: NC(=O)[C@H]1CCCN1C(=O)c1ccc(-c2ccc(OCC3CCN(CC4(C(F)(F)F)CCC4)CC3)nc2)cc1] |
| 672 | 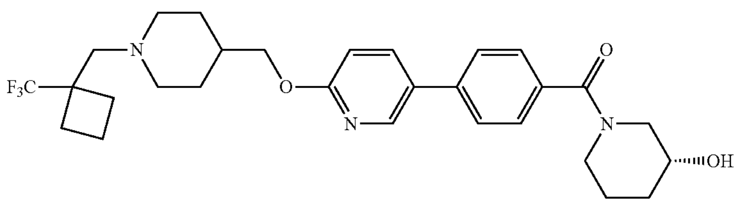 |
| 673 | 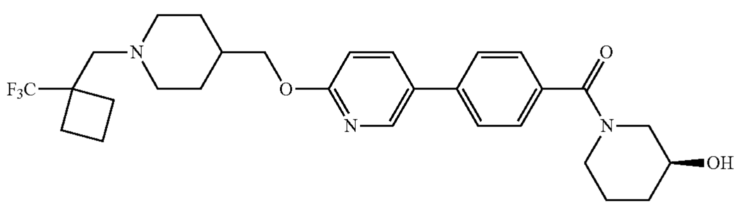 [SMILES: O=C(c1ccc(-c2ccc(OCC3CCN(CC4(C(F)(F)F)CCC4)CC3)nc2)cc1)N1CCC[C@H](O)C1] |
| 674 | 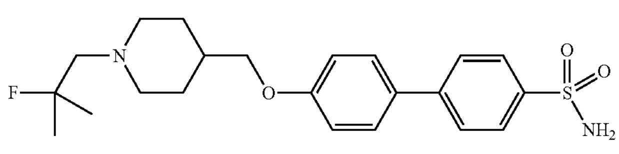 [SMILES: CC(C)(F)CN1CCC(COc2ccc(-c3ccc(S(N)(=O)=O)cc3)cc2)CC1] |
| 675 | 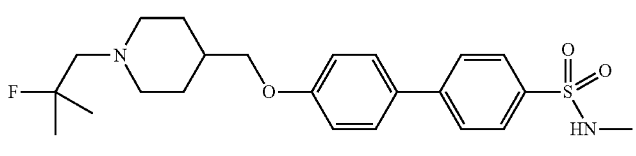 [SMILES: CNS(=O)(=O)c1ccc(-c2ccc(OCC3CCN(CC(C)(C)F)CC3)cc2)cc1] |
| 676 | 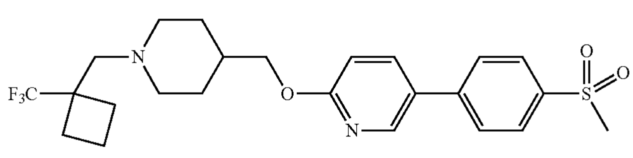 [SMILES: CS(=O)(=O)c1ccc(-c2ccc(OCC3CCN(CC4(C(F)(F)F)CCC4)CC3)nc2)cc1] |

TABLE 161-continued

| Compound | Structure |
|---|---|
| 677 | 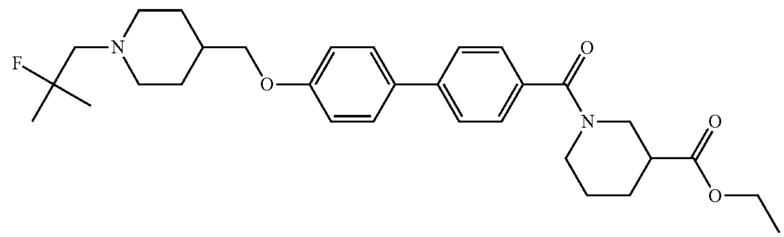 [SMILES: CCOC(=O)C1CCCN(C(=O)c2ccc(-c3ccc(OCC4CCN(CC(C)(C)F)CC4)cc3)cc2)C1] |
| 678 | 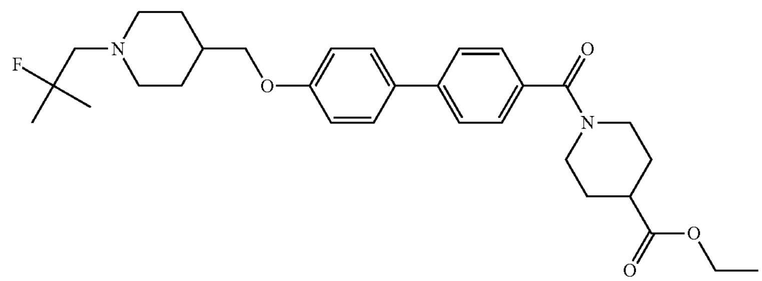 [SMILES: CCOC(=O)C1CCN(C(=O)c2ccc(-c3ccc(OCC4CCN(CC(C)(C)F)CC4)cc3)cc2)CC1] |

TABLE 162

| Compound | Structure |
|---|---|
| 679 | 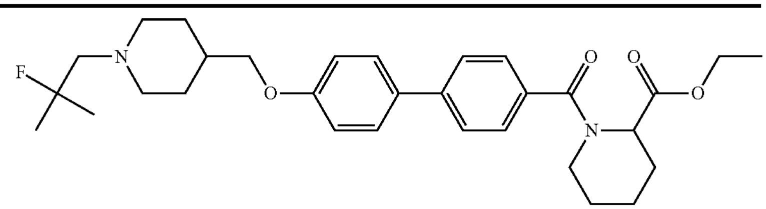 |
| 680 | 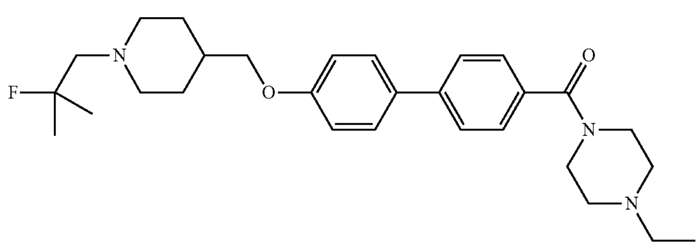 [SMILES: CCN1CCN(C(=O)c2ccc(-c3ccc(OCC4CCN(CC(C)(C)F)CC4)cc3)cc2)CC1] |
| 681 | 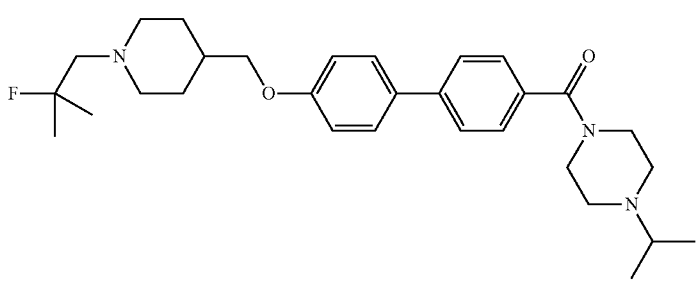 [SMILES: CC(C)N1CCN(C(=O)c2ccc(-c3ccc(OCC4CCN(CC(C)(C)F)CC4)cc3)cc2)CC1] |
| 682 | 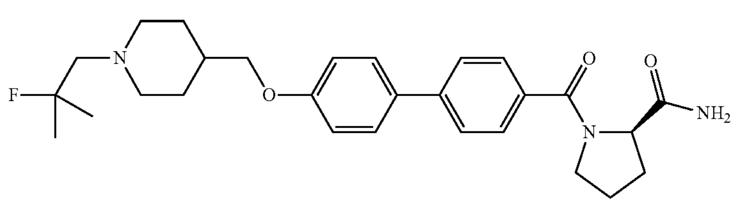 [SMILES: CC(C)(F)CN1CCC(COc2ccc(-c3ccc(C(=O)N4CCC[C@@H]4C(N)=O)cc3)cc2)CC1] |

TABLE 162-continued

| Compound | Structure |
|---|---|
| 683 | 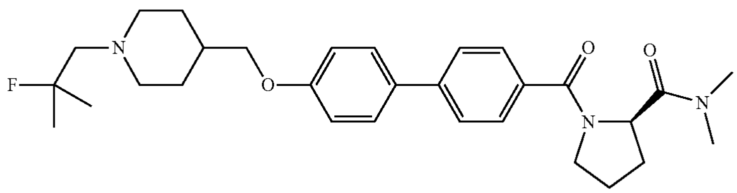 [SMILES: CNC(=O)[C@H]1CCCN1C(=O)c1ccc(-c2ccc(OCC3CCN(CC(C)(C)F)CC3)cc2)cc1] |
| 684 | 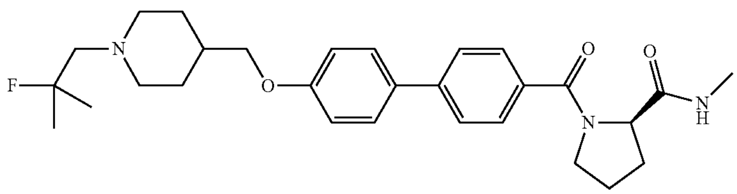 |
| 685 | 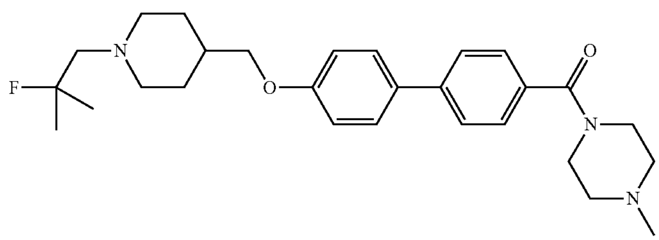 [SMILES: CN1CCN(C(=O)c2ccc(-c3ccc(OCC4CCN(CC(C)(C)F)CC4)cc3)cc2)CC1] |
| 686 | 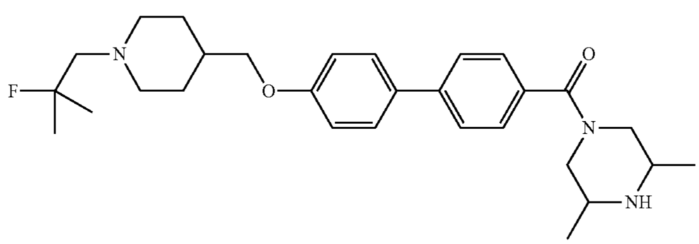 [SMILES: CC1CN(C(=O)c2ccc(-c3ccc(OCC4CCN(CC(C)(C)F)CC4)cc3)cc2)CC(C)N1] |
| 687 | 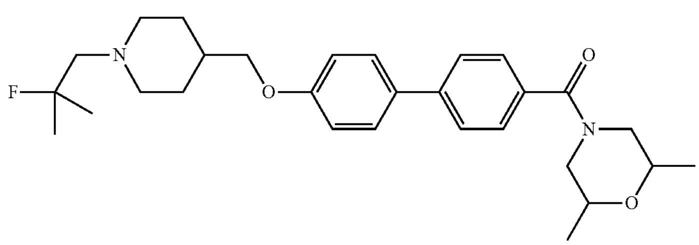 [SMILES: CC1CN(C(=O)c2ccc(-c3ccc(OCC4CCN(CC(C)(C)F)CC4)cc3)cc2)CC(C)O1] |
| 688 | 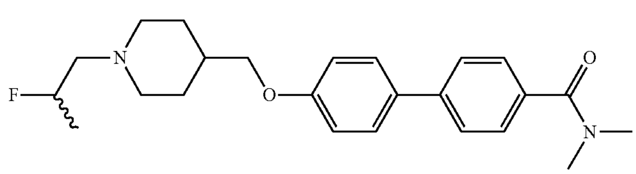 |
| 689 | 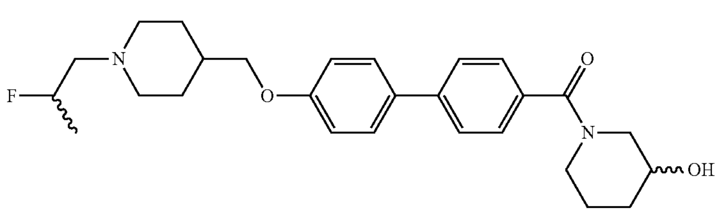 |

TABLE 162-continued

| Compound | Structure |
|---|---|
| 690 | 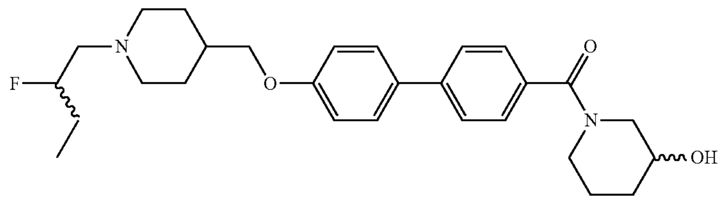 [SMILES: CCC(F)CN1CCC(COc2ccc(-c3ccc(C(=O)N4CCCC(O)C4)cc3)cc2)CC1] |
| 691 | 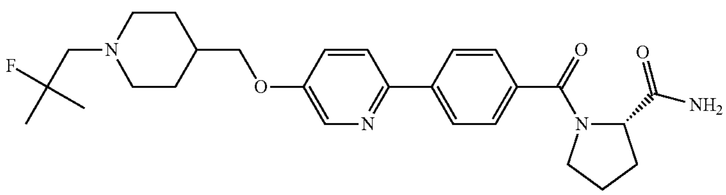 |
| 692 | 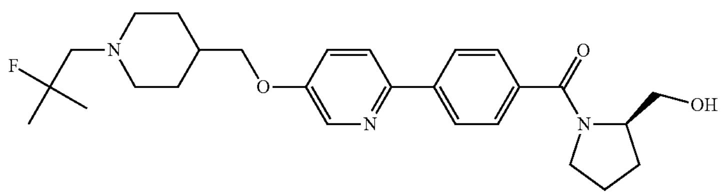 [SMILES: CC(C)(F)CN1CCC(COc2ccc(-c3ccc(C(=O)N4CCC[C@@H]4CO)cc3)nc2)CC1] |
| 693 | 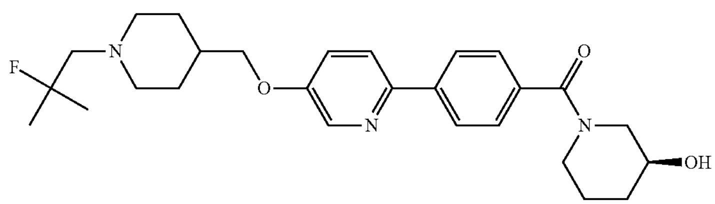 [SMILES: CC(C)(F)CN1CCC(COc2ccc(-c3ccc(C(=O)N4CCC[C@H](O)C4)cc3)nc2)CC1] |
| 694 | 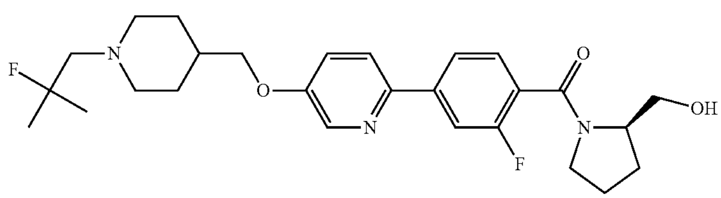 [SMILES: CC(C)(F)CN1CCC(COc2ccc(-c3ccc(C(=O)N4CCC[C@@H]4CO)c(F)c3)nc2)CC1] |
| 695 | 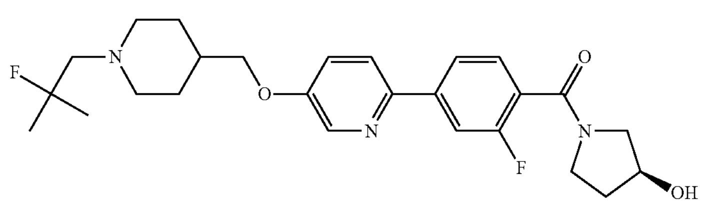 |
| 696 | 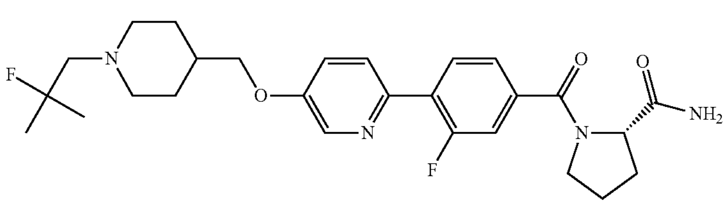 |
| 697 | 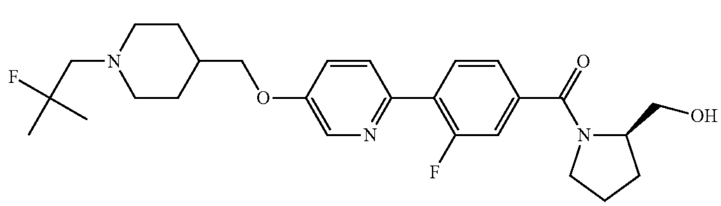 [SMILES: CC(C)(F)CN1CCC(COc2ccc(-c3ccc(C(=O)N4CCC[C@@H]4CO)cc3F)nc2)CC1] |

TABLE 162-continued

| Compound | Structure |
|---|---|
| 698 | 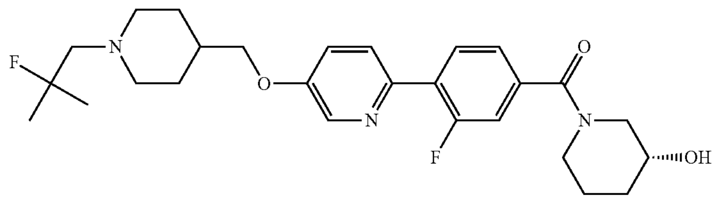 [SMILES: CC(C)(F)CN1CCC(COc2ccc(-c3ccc(C(=O)N4CCC[C@@H](O)C4)cc3F)nc2)CC1] |

TABLE 163

| Compound | Structure |
|---|---|
| 699 | 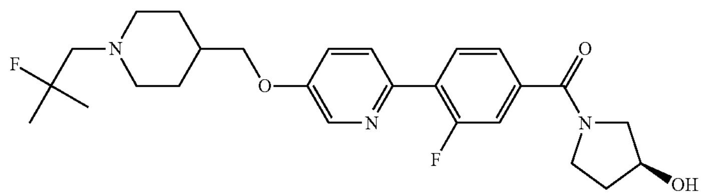 |
| 700 | 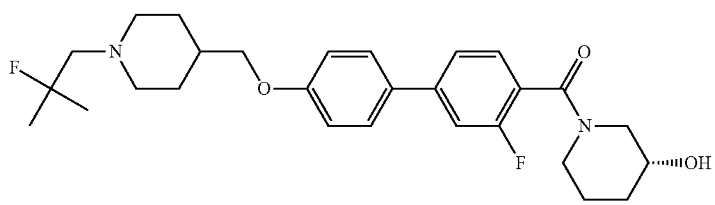 [SMILES: CC(C)(F)CN1CCC(COc2ccc(-c3ccc(C(=O)N4CCC[C@@H](O)C4)c(F)c3)cc2)CC1] |
| 701 | 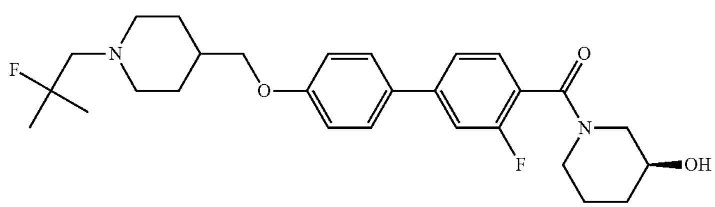 |
| 702 | 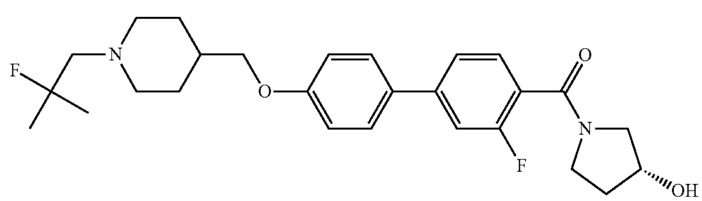 [SMILES: CC(C)(F)CN1CCC(COc2ccc(-c3ccc(C(=O)N4CC[C@@H](O)C4)c(F)c3)cc2)CC1] |
| 703 | 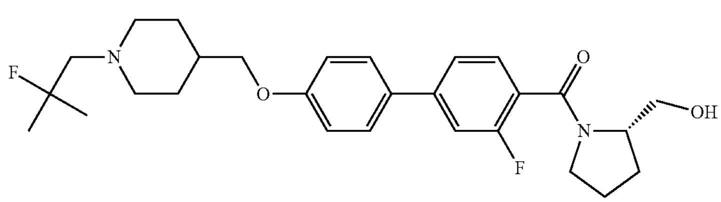 [SMILES: CC(C)(F)CN1CCC(COc2ccc(-c3ccc(C(=O)N4CCC[C@H]4CO)c(F)c3)cc2)CC1] |
| 704 | 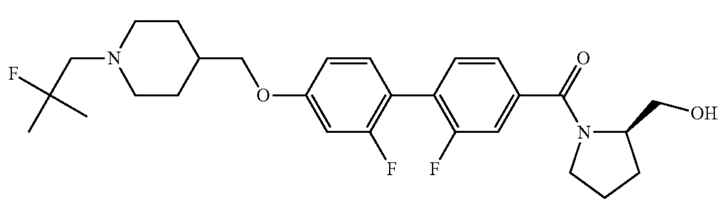 [SMILES: CC(C)(F)CN1CCC(COc2ccc(-c3ccc(C(=O)N4CCC[C@@H]4CO)cc3F)c(F)c2)CC1] |

TABLE 163-continued
| Compound | Structure |
|---|---|
| 705 | 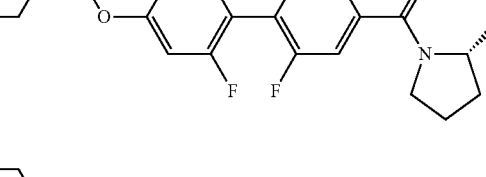 |
| 706 | 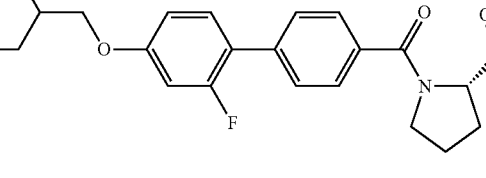 |
| 707 | 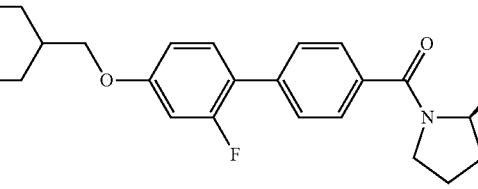 |
| 708 | 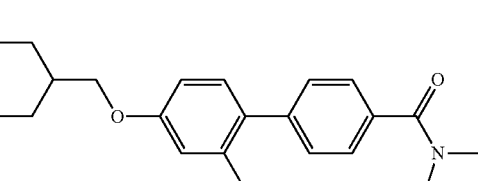 |
| 709 | 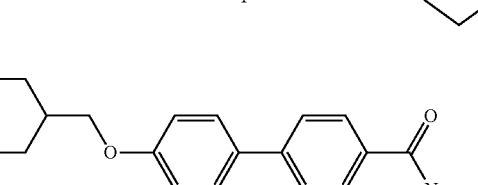 |
| 710 | 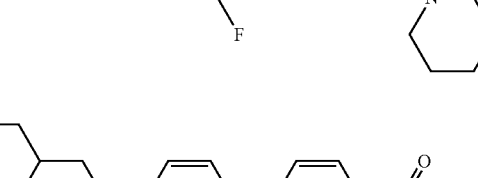 |
| 711 | 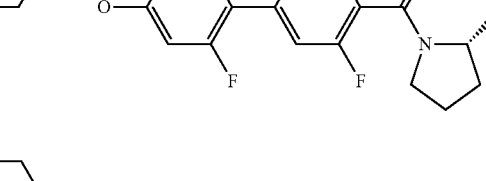 |

TABLE 163-continued

| Compound | Structure |
|---|---|
| 712 | 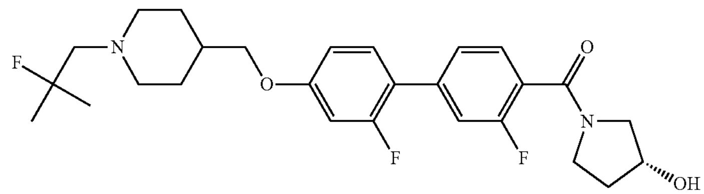 [SMILES: CC(C)(F)CN1CCC(COc2ccc(-c3ccc(C(=O)N4CC[C@@H](O)C4)c(F)c3)c(F)c2)CC1] |
| 713 | 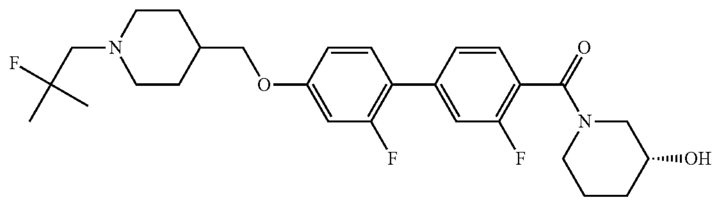 |
| 714 | 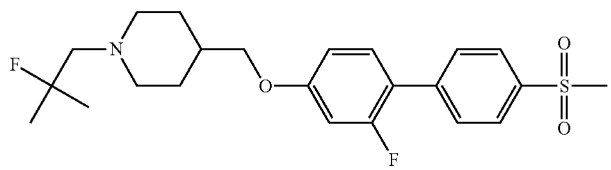 [SMILES: CC(C)(F)CN1CCC(COc2ccc(-c3ccc(S(C)(=O)=O)cc3)c(F)c2)CC1] |
| 715 | 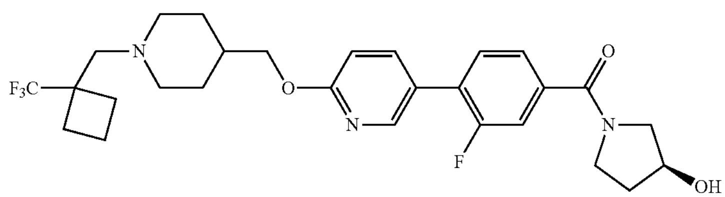 [SMILES: O=C(c1ccc(-c2ccc(OCC3CCN(CC4(C(F)(F)F)CCC4)CC3)nc2)c(F)c1)N1CC[C@H](O)C1] |
| 716 | 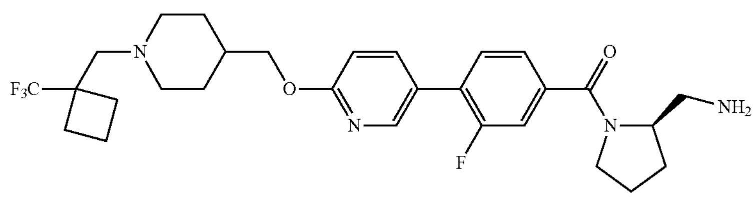 [SMILES: NC[C@H]1CCCN1C(=O)c1ccc(-c2ccc(OCC3CCN(CC4(C(F)(F)F)CCC4)CC3)nc2)c(F)c1] |
| 717 | 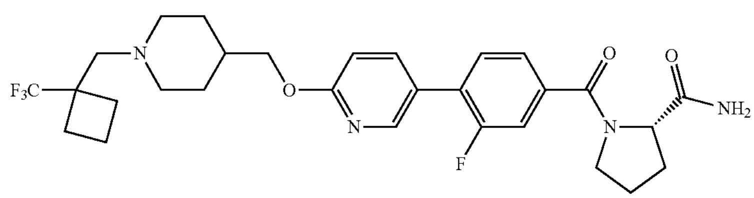 [SMILES: NC(=O)[C@@H]1CCCN1C(=O)c1ccc(-c2ccc(OCC3CCN(CC4(C(F)(F)F)CCC4)CC3)nc2)c(F)c1] |
| 718 | 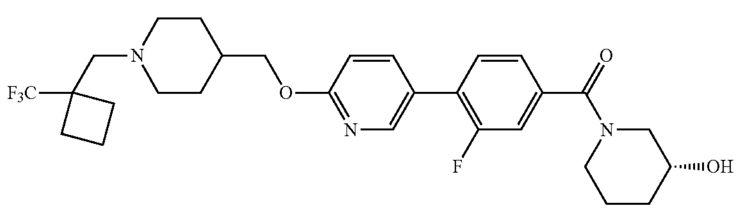 [SMILES: O=C(c1ccc(-c2ccc(OCC3CCN(CC4(C(F)(F)F)CCC4)CC3)nc2)c(F)c1)N1CCC[C@@H](O)C1] |

TABLE 164

| Compound | Structure |
|---|---|
| 719 | 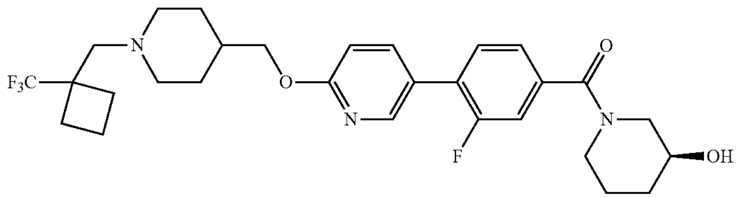 [SMILES: O=C(c1ccc(-c2ccc(OCC3CCN(CC4(C(F)(F)F)CCC4)CC3)nc2)c(F)c1)N1CCC[C@H](O)C1] |
| 720 | 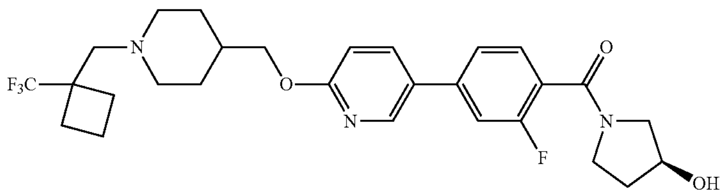 [SMILES: O=C(c1ccc(-c2ccc(OCC3CCN(CC4(C(F)(F)F)CCC4)CC3)nc2)cc1F)N1CC[C@H](O)C1] |
| 721 | 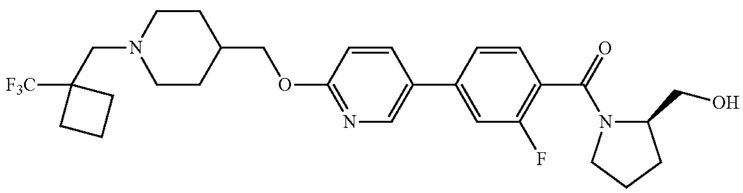 [SMILES: O=C(c1ccc(-c2ccc(OCC3CCN(CC4(C(F)(F)F)CCC4)CC3)nc2)cc1F)N1CCC[C@@H]1CO] |
| 722 | 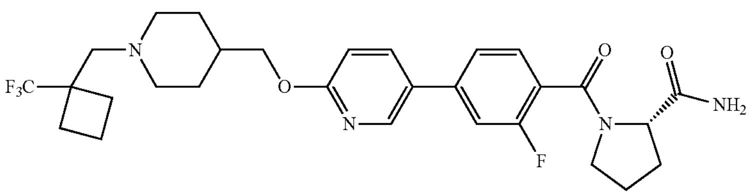 [SMILES: NC(=O)[C@@H]1CCCN1C(=O)c1ccc(-c2ccc(OCC3CCN(CC4(C(F)(F)F)CCC4)CC3)nc2)cc1F] |
| 723 | 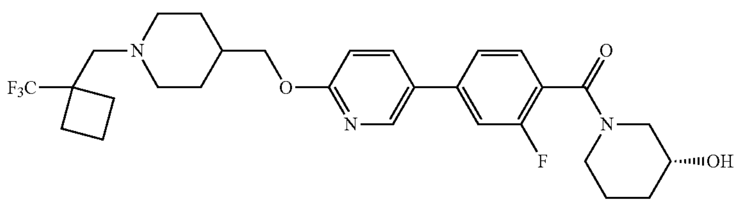 |
| 724 | 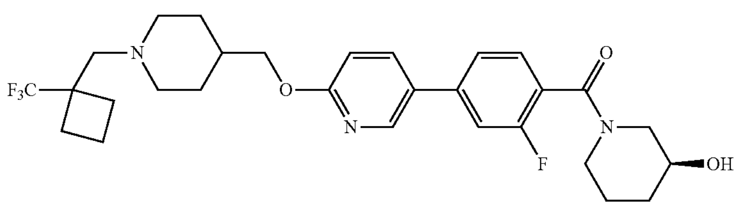 [SMILES: O=C(c1ccc(-c2ccc(OCC3CCN(CC4(C(F)(F)F)CCC4)CC3)nc2)cc1F)N1CCC[C@H](O)C1] |
| 725 | 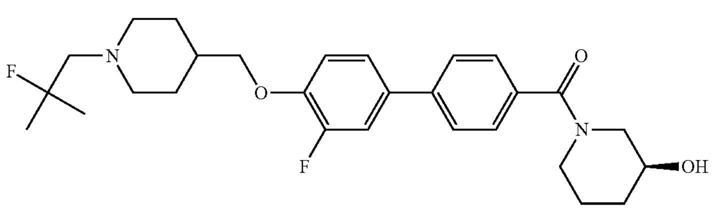 [SMILES: CC(C)(F)CN1CCC(COc2ccc(-c3ccc(C(=O)N4CCC[C@H](O)C4)cc3)cc2F)CC1] |
| 726 | 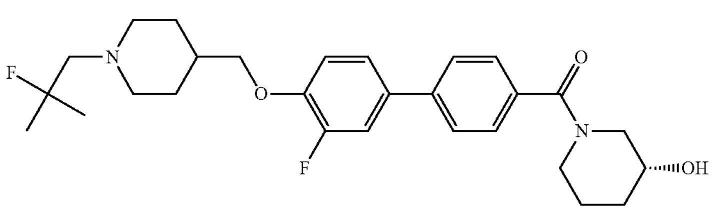 [SMILES: CC(C)(F)CN1CCC(COc2ccc(-c3ccc(C(=O)N4CCC[C@@H](O)C4)cc3)cc2F)CC1] |

TABLE 164-continued

| Compound | Structure |
|---|---|
| 727 | 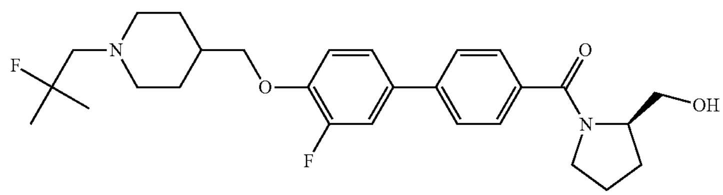 |
| 728 | 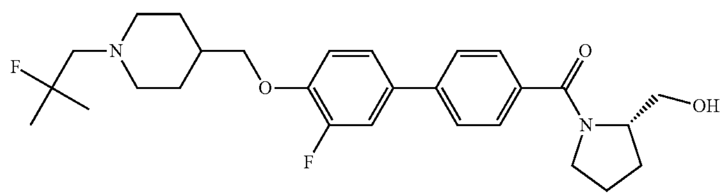 [SMILES: CC(C)(F)CN1CCC(COc2ccc(-c3ccc(C(=O)N4CCC[C@H]4CO)cc3)cc2F)CC1] |
| 729 | 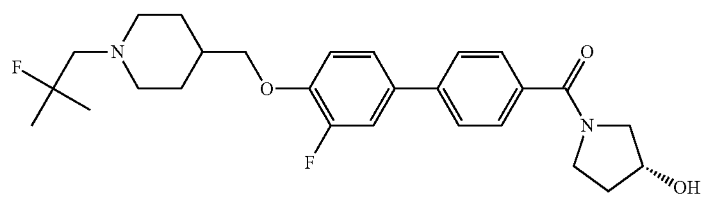 [SMILES: CC(C)(F)CN1CCC(COc2ccc(-c3ccc(C(=O)N4CC[C@@H](O)C4)cc3)cc2F)CC1] |
| 730 | 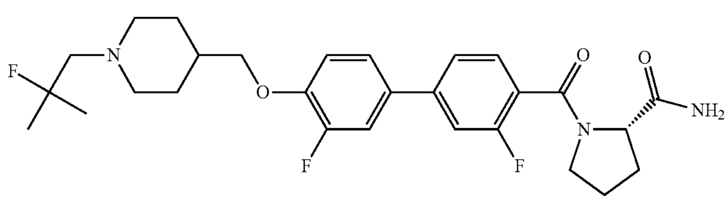 [SMILES: CC(C)(F)CN1CCC(COc2ccc(-c3ccc(C(=O)N4CCC[C@H]4C(N)=O)c(F)c3)cc2F)CC1] |
| 731 | 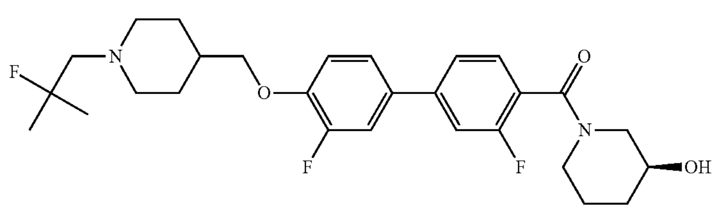 [SMILES: CC(C)(F)CN1CCC(COc2ccc(-c3ccc(C(=O)N4CCC[C@H](O)C4)c(F)c3)cc2F)CC1] |
| 732 | 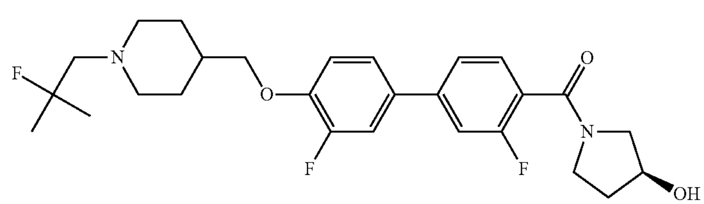 [SMILES: CC(C)(F)CN1CCC(COc2ccc(-c3ccc(C(=O)N4CC[C@H](O)C4)c(F)c3)cc2F)CC1] |
| 733 | 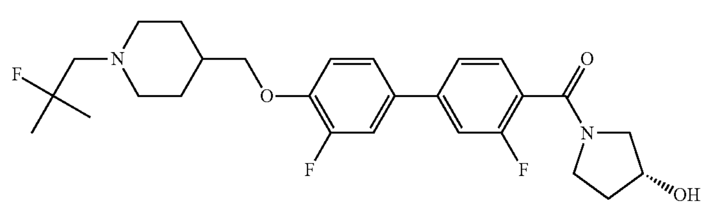 [SMILES: CC(C)(F)CN1CCC(COc2ccc(-c3ccc(C(=O)N4CC[C@@H](O)C4)c(F)c3)cc2F)CC1] |

TABLE 164-continued

| Compound | Structure |
|---|---|
| 734 | (structure) |
| 735 | (structure) |
| 736 | (structure) |
| 737 | (structure) |
| 738 | (structure) |

TABLE 165

| Compound | Structure |
|---|---|
| 739 | (structure) |
| 740 | (structure) |

TABLE 165-continued
| Compound | Structure |
|---|---|
| 741 | 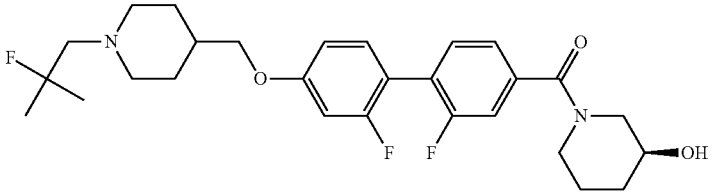 [SMILES: CC(C)(F)CN1CCC(COc2ccc(-c3ccc(C(=O)N4CCC[C@H](O)C4)cc3F)c(F)c2)CC1] |
| 742 | 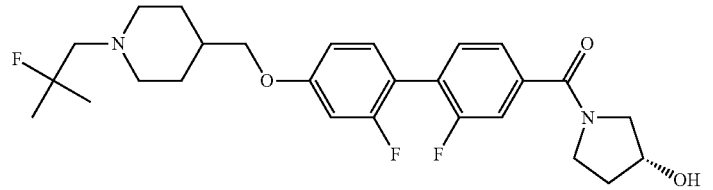 [SMILES: CC(C)(F)CN1CCC(COc2ccc(-c3ccc(C(=O)N4CC[C@@H](O)C4)cc3F)c(F)c2)CC1] |
| 743 | 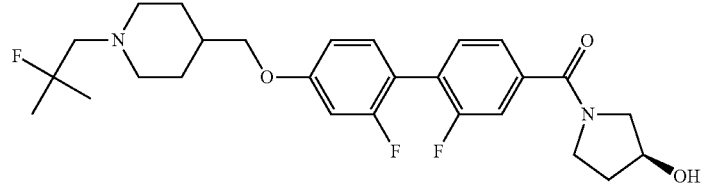 |
| 744 | 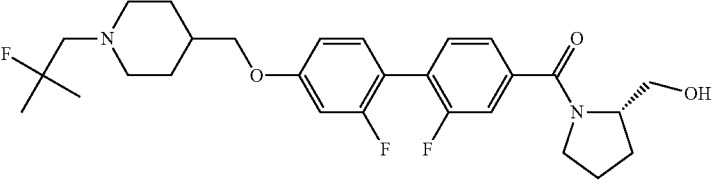 [SMILES: CC(C)(F)CN1CCC(COc2ccc(-c3ccc(C(=O)N4CCC[C@H]4CO)cc3F)c(F)c2)CC1] |
| 745 | 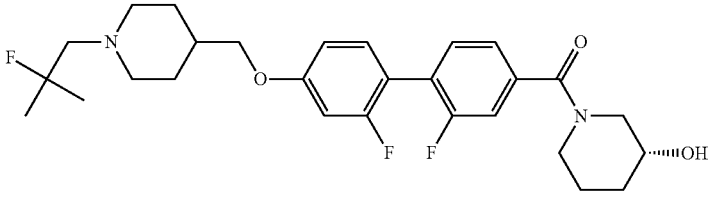 [SMILES: CC(C)(F)CN1CCC(COc2ccc(-c3ccc(C(=O)N4CCC[C@@H](O)C4)cc3F)c(F)c2)CC1] |
| 746 | 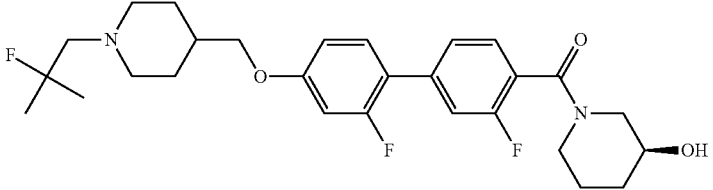 |
| 747 | 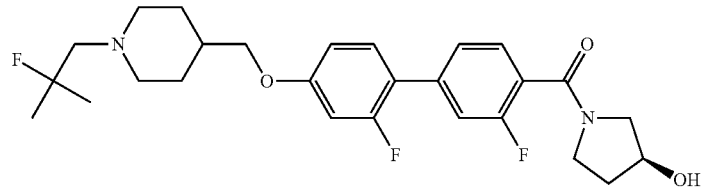 [SMILES: CC(C)(F)CN1CCC(COc2ccc(-c3ccc(C(=O)N4CC[C@H](O)C4)c(F)c3)c(F)c2)CC1] |
| 748 | 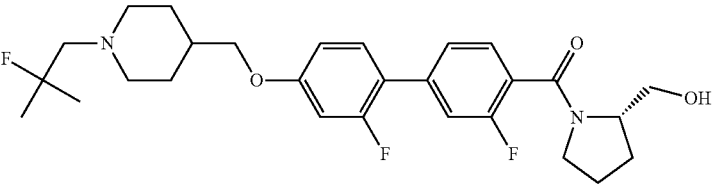 [SMILES: CC(C)(F)CN1CCC(COc2ccc(-c3ccc(C(=O)N4CCC[C@H]4CO)c(F)c3)c(F)c2)CC1] |

TABLE 165-continued
| Compound | Structure |
|---|---|
| 749 | 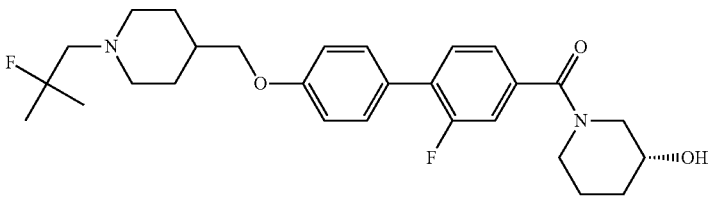 |
| 750 | 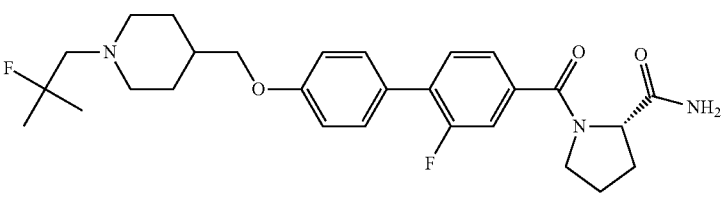 |
| 751 | 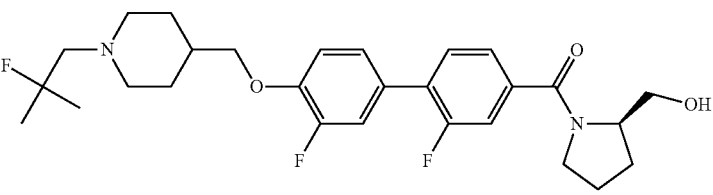 [SMILES: CC(C)(F)CN1CCC(COc2ccc(-c3ccc(C(=O)N4CCC[C@@H]4CO)cc3F)cc2F)CC1] |
| 752 | 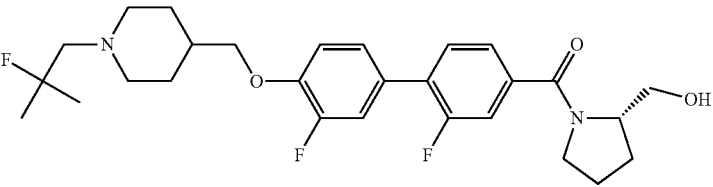 [SMILES: CC(C)(F)CN1CCC(COc2ccc(-c3ccc(C(=O)N4CCC[C@H]4CO)cc3F)cc2F)CC1] |
| 753 | 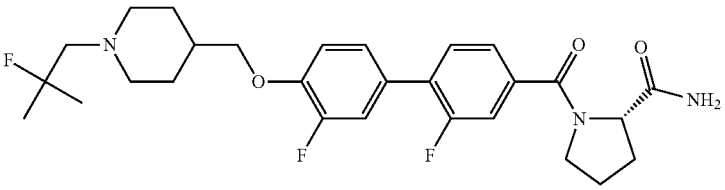 |
| 754 | 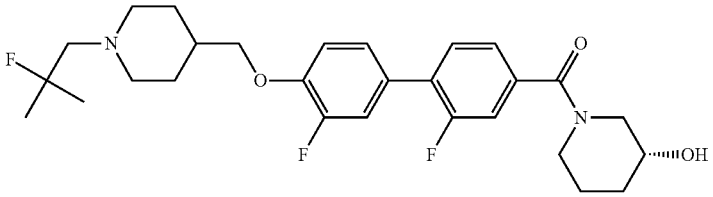 |
| 755 | 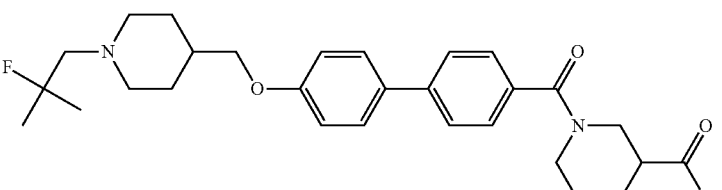 |

TABLE 165-continued

| Compound | Structure |
|---|---|
| 756 | 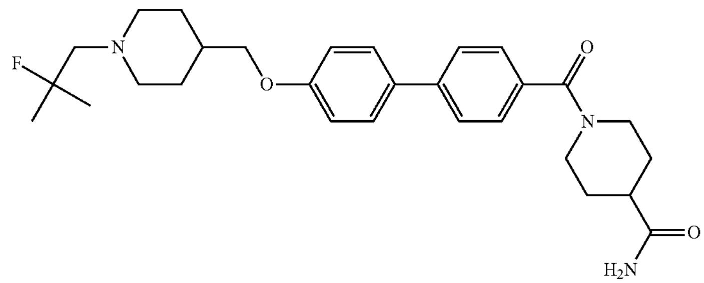 [SMILES: CC(C)(F)CN1CCC(COc2ccc(-c3ccc(C(=O)N4CCC(C(N)=O)CC4)cc3)cc2)CC1] |
| 757 | 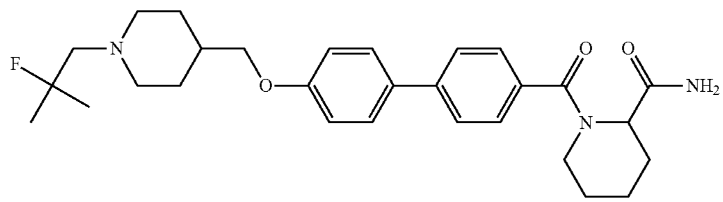 [SMILES: CC(C)(F)CN1CCC(COc2ccc(-c3ccc(C(=O)N4CCCCC4C(N)=O)cc3)cc2)CC1] |
| 758 | 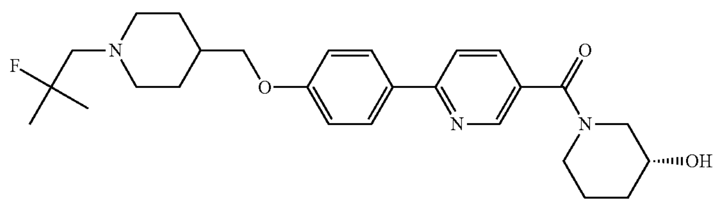 [SMILES: CC(C)(F)CN1CCC(COc2ccc(-c3ccc(C(=O)N4CCC[C@@H](O)C4)cn3)cc2)CC1] |

TABLE 166

| Compound | Structure |
|---|---|
| 759 | 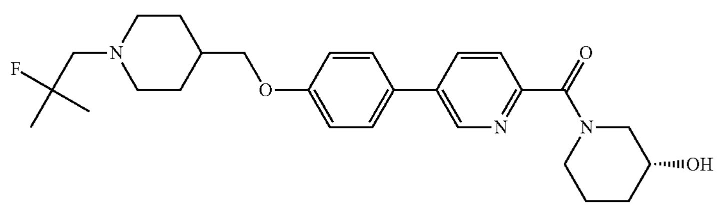 [SMILES: CC(C)(F)CN1CCC(COc2ccc(-c3ccc(C(=O)N4CCC[C@@H](O)C4)nc3)cc2)CC1] |
| 760 | 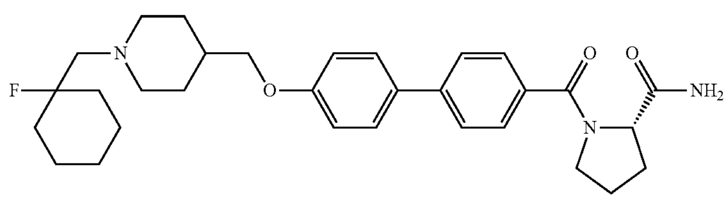 [SMILES: NC(=O)[C@@H]1CCCN1C(=O)c1ccc(-c2ccc(OCC3CCN(CC4(F)CCCCC4)CC3)cc2)cc1] |
| 761 | 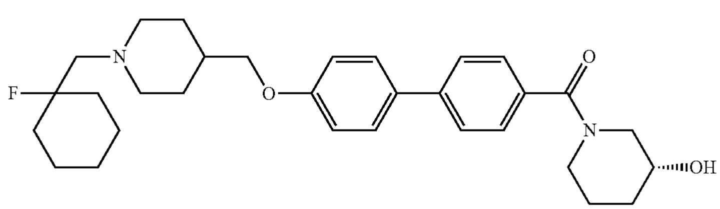 [SMILES: O=C(c1ccc(-c2ccc(OCC3CCN(CC4(F)CCCCC4)CC3)cc2)cc1)N1CCC[C@@H](O)C1] |

| Compound | Structure |
|---|---|
| 763 | 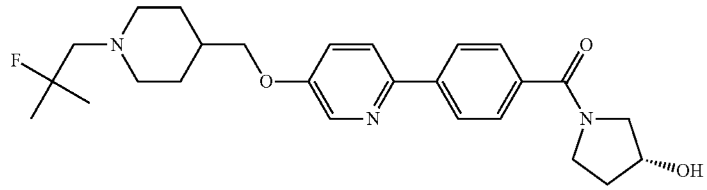 |
| 764 | 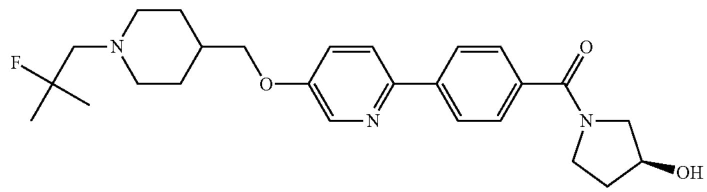 [SMILES: CC(C)(F)CN1CCC(COc2ccc(-c3ccc(C(=O)N4CC[C@H](O)C4)cc3)nc2)CC1] |
| 765 | 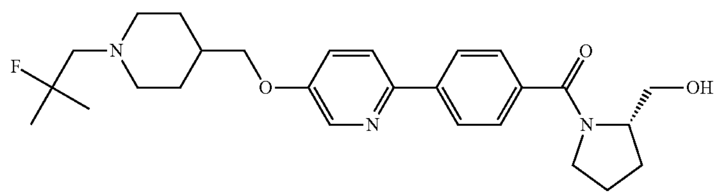 |
| 766 | 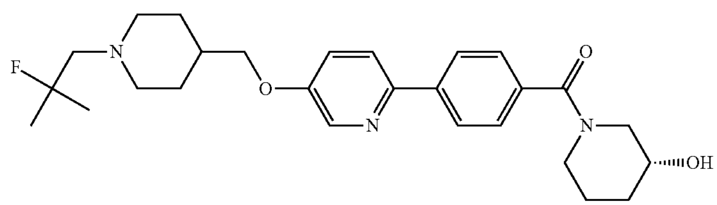 |
| 767 | 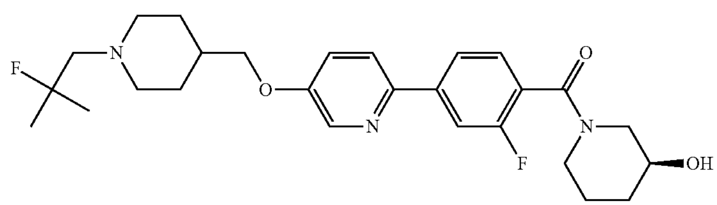 |
| 768 | 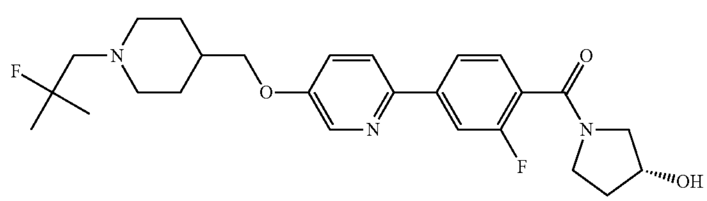 [SMILES: CC(C)(F)CN1CCC(COc2ccc(-c3ccc(C(=O)N4CC[C@@H](O)C4)c(F)c3)nc2)CC1] |
| 769 | 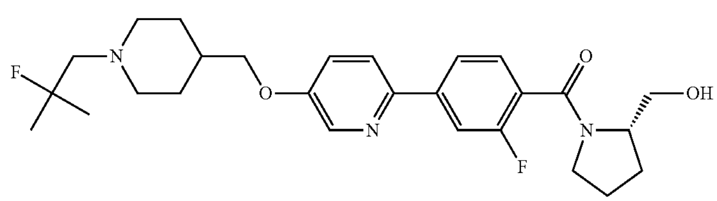 [SMILES: CC(C)(F)CN1CCC(COc2ccc(-c3ccc(C(=O)N4CCC[C@H]4CO)c(F)c3)nc2)CC1] |

TABLE 166-continued
| Compound | Structure |
|---|---|
| 770 | 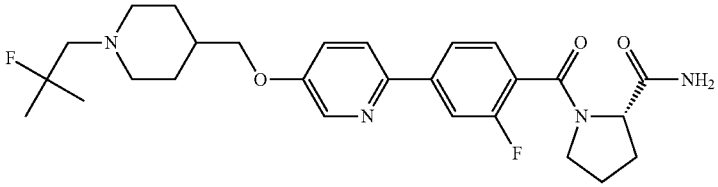 [SMILES: CC(C)(F)CN1CCC(COc2ccc(-c3ccc(C(=O)N4CCC[C@H]4C(N)=O)c(F)c3)nc2)CC1] |
| 771 | 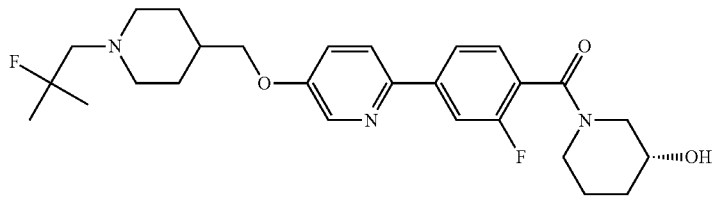 [SMILES: CC(C)(F)CN1CCC(COc2ccc(-c3ccc(C(=O)N4CCC[C@@H](O)C4)c(F)c3)nc2)CC1] |
| 772 | 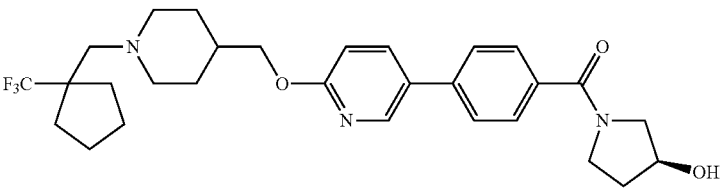 [SMILES: O=C(c1ccc(-c2ccc(OCC3CCN(CC4(C(F)(F)F)CCCC4)CC3)nc2)cc1)N1CC[C@H](O)C1] |
| 773 | 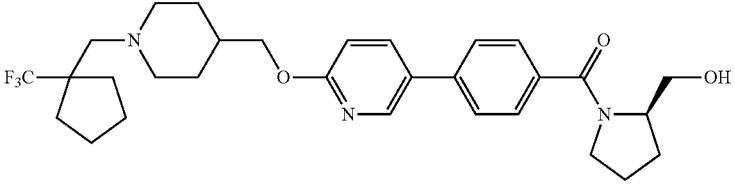 [SMILES: O=C(c1ccc(-c2ccc(OCC3CCN(CC4(C(F)(F)F)CCCC4)CC3)nc2)cc1)N1CCC[C@@H]1CO] |
| 774 | 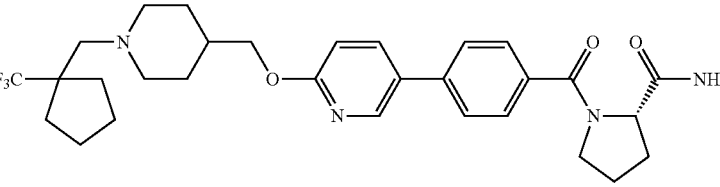 |
| 775 | 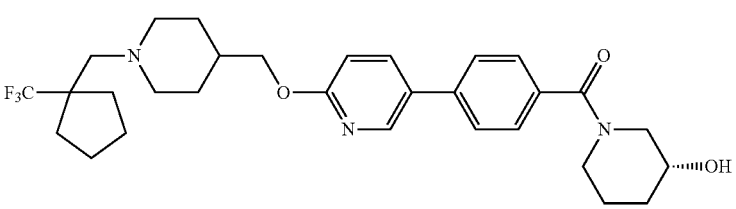 [SMILES: O=C(c1ccc(-c2ccc(OCC3CCN(CC4(C(F)(F)F)CCCC4)CC3)nc2)cc1)N1CCC[C@@H](O)C1] |
| 776 | 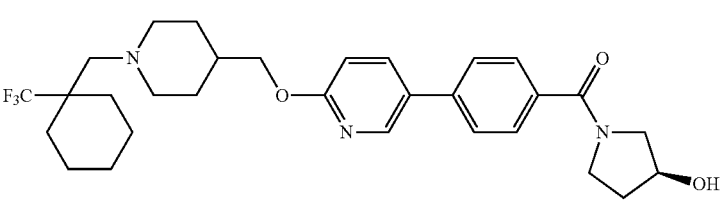 [SMILES: O=C(c1ccc(-c2ccc(OCC3CCN(CC4(C(F)(F)F)CCCCC4)CC3)nc2)cc1)N1CC[C@H](O)C1] |

TABLE 166-continued
| Compound | Structure |
|---|---|
| 777 | 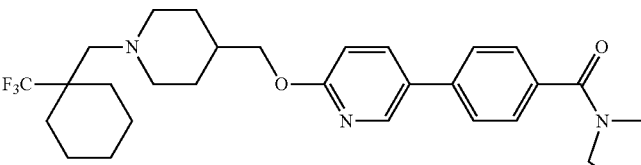 |
| 778 | 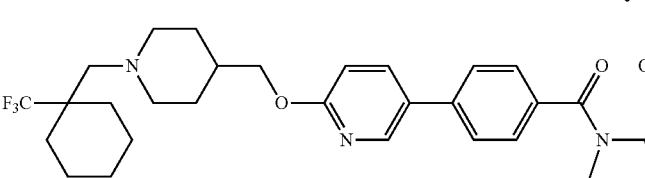 |
| 779 | 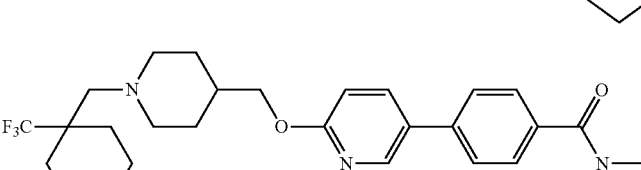 |
TABLE 167
| Compound | Structure |
|---|---|
| 782 | 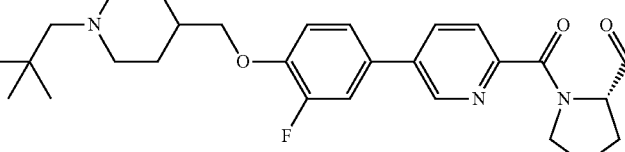 |
| 783 | 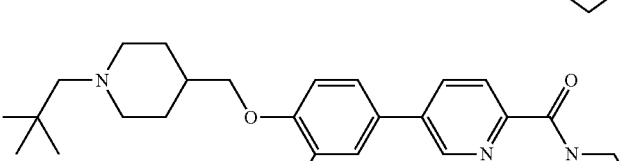 |
| 784 | 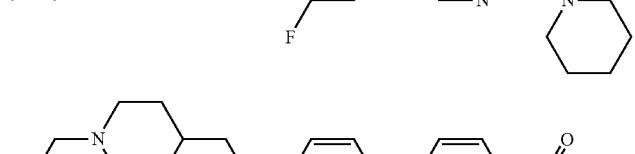 |
| 785 | 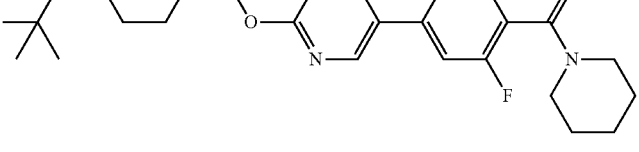 |

TABLE 167-continued

| Compound | Structure |
|---|---|
| 786 | 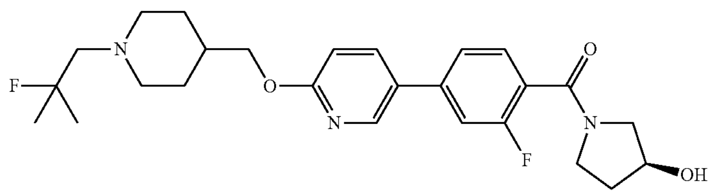 |
| 787 | 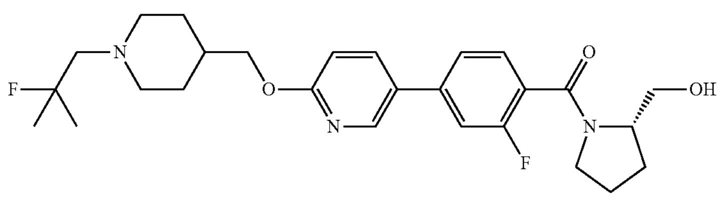 |
| 789 | 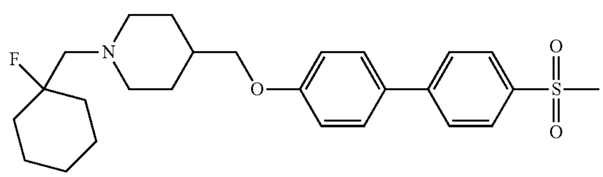 [SMILES: CS(=O)(=O)c1ccc(-c2ccc(OCC3CCN(CC4(F)CCCCC4)CC3)cc2)cc1] |
| 790 | 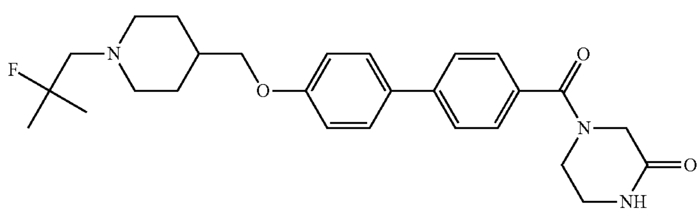 [SMILES: CC(C)(F)CN1CCC(COc2ccc(-c3ccc(C(=O)N4CCNC(=O)C4)cc3)cc2)CC1] |
| 791 | 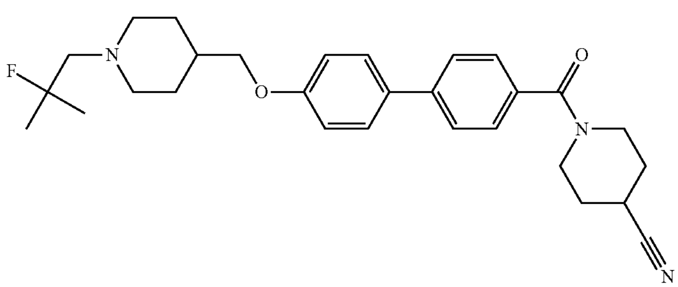 [SMILES: CC(C)(F)CN1CCC(COc2ccc(-c3ccc(C(=O)N4CCC(C#N)CC4)cc3)cc2)CC1] |
| 792 | 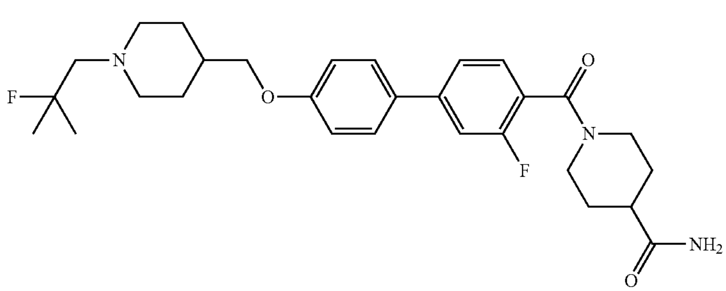 [SMILES: CC(C)(F)CN1CCC(COc2ccc(-c3ccc(C(=O)N4CCC(C(N)=O)CC4)c(F)c3)cc2)CC1] |

TABLE 167-continued
| Compound | Structure |
|---|---|
| 793 | 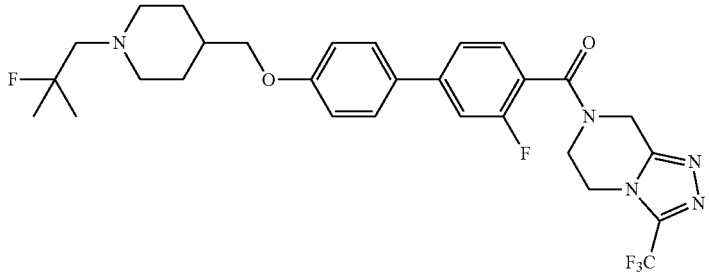 [SMILES: CC(C)(F)CN1CCC(COc2ccc(-c3ccc(C(=O)N4CCn5c(nnc5C(F)(F)F)C4)c(F)c3)cc2)CC1] |
| 794 | 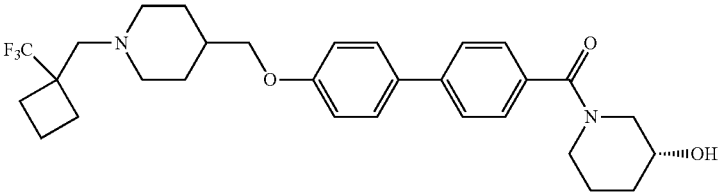 |
| 795 | 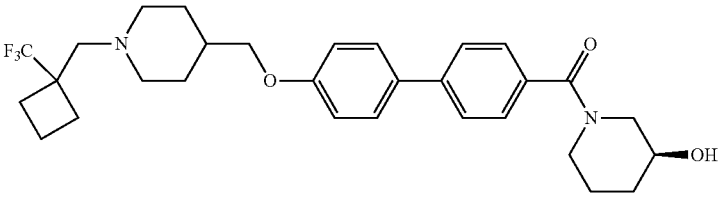 [SMILES: O=C(c1ccc(-c2ccc(OCC3CCN(CC4(C(F)(F)F)CCC4)CC3)cc2)cc1)N1CCC[C@H](O)C1] |
| 796 | 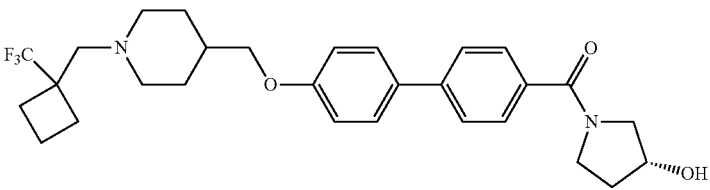 |
| 797 | 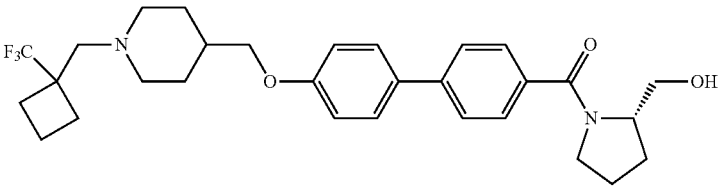 [SMILES: O=C(c1ccc(-c2ccc(OCC3CCN(CC4(C(F)(F)F)CCC4)CC3)cc2)cc1)N1CCC[C@H]1CO] |
| 798 | 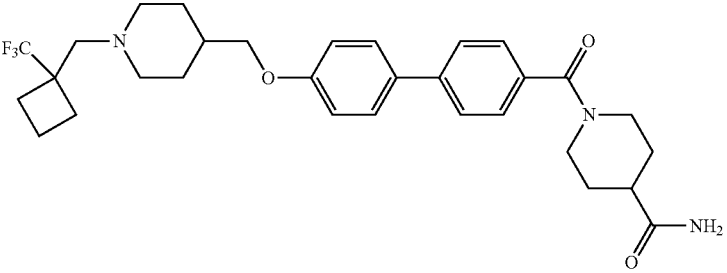 [SMILES: NC(=O)C1CCN(C(=O)c2ccc(-c3ccc(OCC4CCN(CC5(C(F)(F)F)CCC5)CC4)cc3)cc2)CC1] |

TABLE 167-continued
| Compound | Structure |
|---|---|
| 799 | 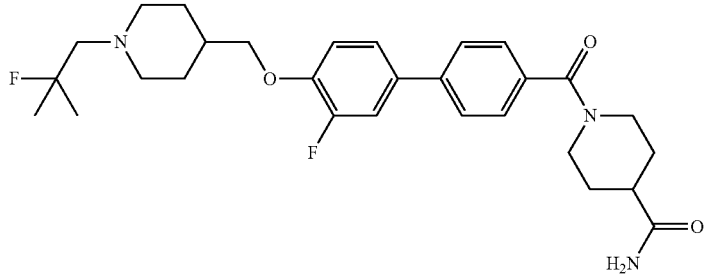 |
| 800 | 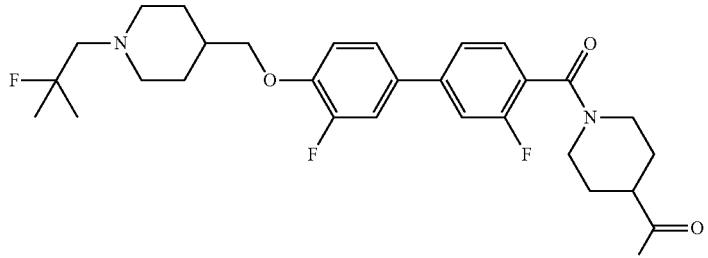 |
| 801 | 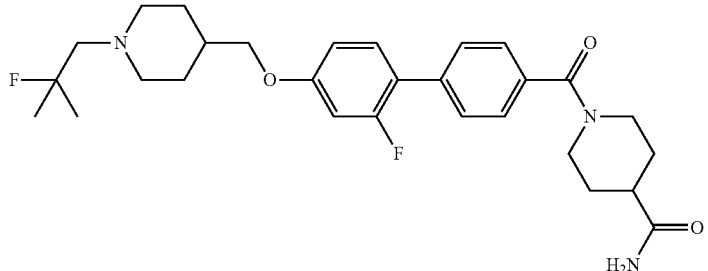 |
TABLE 168
| Compound | Structure |
|---|---|
| 802 | 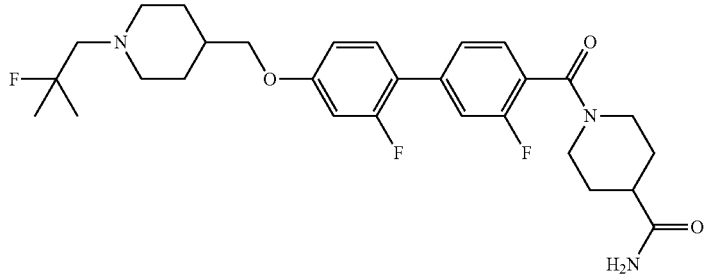 [SMILES: CC(C)(F)CN1CCC(COc2ccc(-c3ccc(C(=O)N4CCC(C(N)=O)CC4)c(F)c3)c(F)c2)CC1] |

TABLE 168-continued
| Compound | Structure |
|---|---|
| 803 | 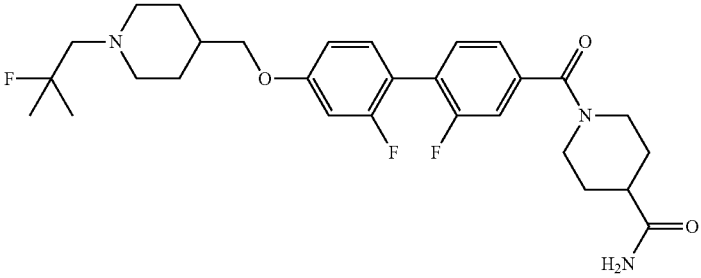 |
| 804 | 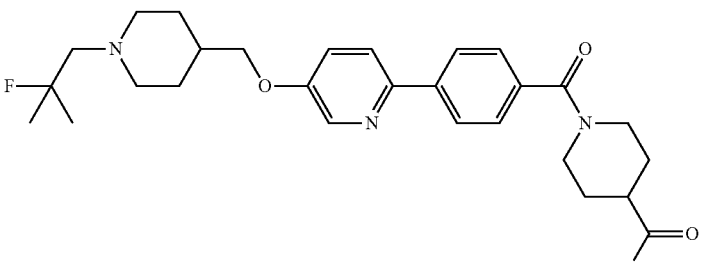 |
| 805 | 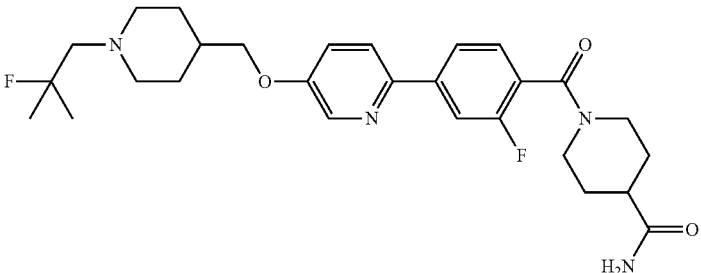 |
| 806 | 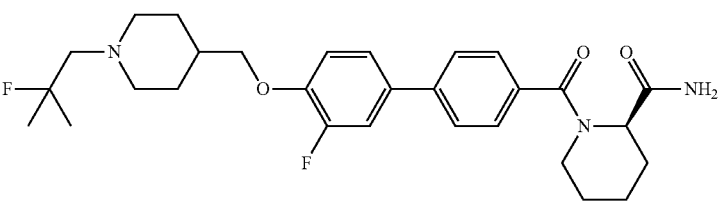 [SMILES: CC(C)(F)CN1CCC(COc2ccc(-c3ccc(C(=O)N4CCCC[C@@H]4C(N)=O)cc3)cc2F)CC1] |
| 807 | 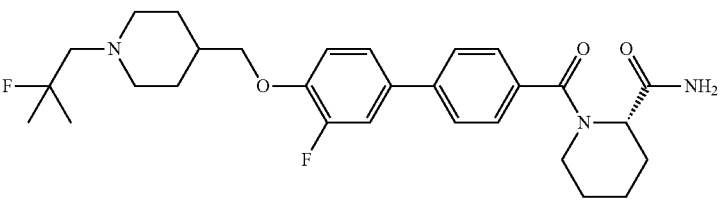 [SMILES: CC(C)(F)CN1CCC(COc2ccc(-c3ccc(C(=O)N4CCCC[C@H]4C(N)=O)cc3)cc2F)CC1] |
| 809 | 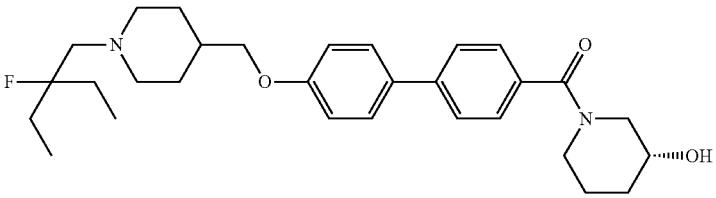 [SMILES: CCC(F)(CC)CN1CCC(COc2ccc(-c3ccc(C(=O)N4CCC[C@@H](O)C4)cc3)cc2)CC1] |

TABLE 168-continued
| Compound | Structure |
|---|---|
| 810 | 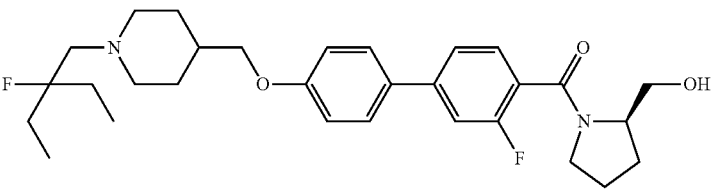 |
| 811 | 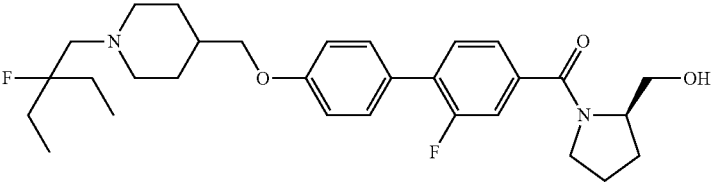 [SMILES: CCC(F)(CC)CN1CCC(COc2ccc(-c3ccc(C(=O)N4CCC[C@@H]4CO)cc3F)cc2)CC1] |
| 812 | 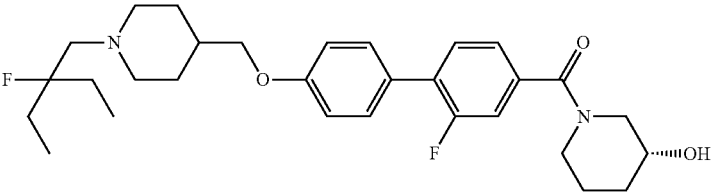 [SMILES: CCC(F)(CC)CN1CCC(COc2ccc(-c3ccc(C(=O)N4CCC[C@@H](O)C4)cc3F)cc2)CC1] |
| 813 | 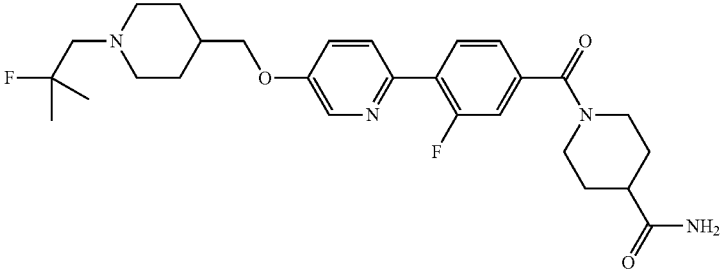 [SMILES: CC(C)(F)CN1CCC(COc2ccc(-c3ccc(C(=O)N4CCC(C(N)=O)CC4)cc3F)nc2)CC1] |
| 814 | 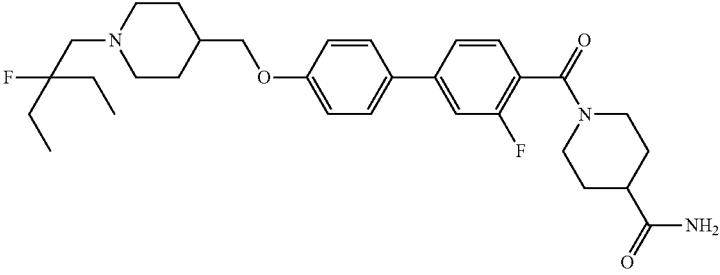 [SMILES: CCC(F)(CC)CN1CCC(COc2ccc(-c3ccc(C(=O)N4CCC(C(N)=O)CC4)c(F)c3)cc2)CC1] |
| 815 | 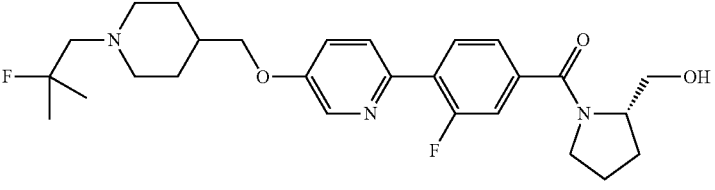 [SMILES: CC(C)(F)CN1CCC(COc2ccc(-c3ccc(C(=O)N4CCC[C@H]4CO)cc3F)nc2)CC1] |
| 816 | 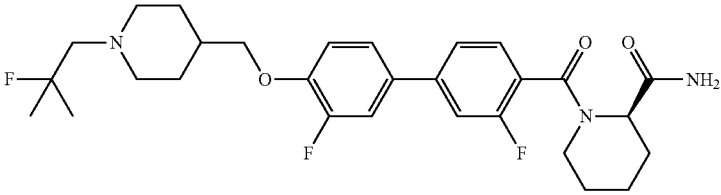 [SMILES: CC(C)(F)CN1CCC(COc2ccc(-c3ccc(C(=O)N4CCCC[C@@H]4C(N)=O)c(F)c3)cc2F)CC1] |

TABLE 168-continued

| Compound | Structure |
|---|---|
| 817 | 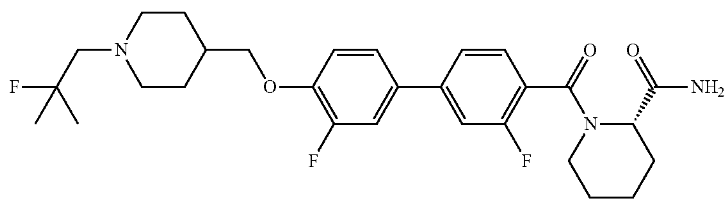 [SMILES: CC(C)(F)CN1CCC(COc2ccc(-c3ccc(C(=O)N4CCCC[C@H]4C(N)=O)c(F)c3)cc2F)CC1] |
| 818 | 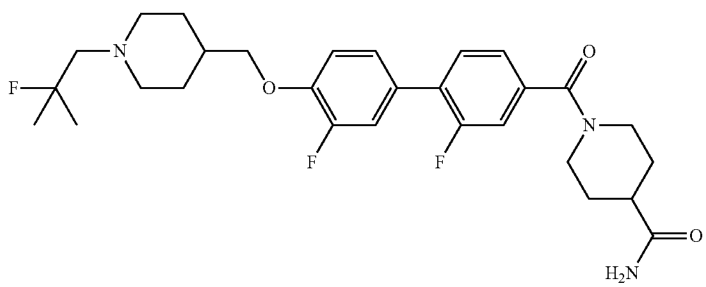 |
| 819 | 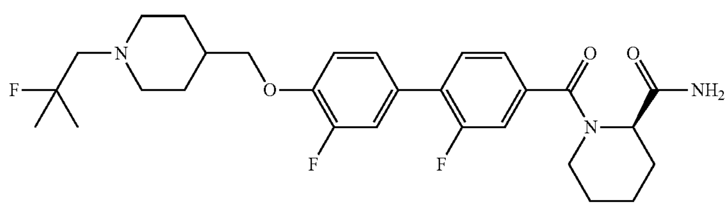 [SMILES: CC(C)(F)CN1CCC(COc2ccc(-c3ccc(C(=O)N4CCCC[C@@H]4C(N)=O)cc3F)cc2F)CC1] |
| 820 | 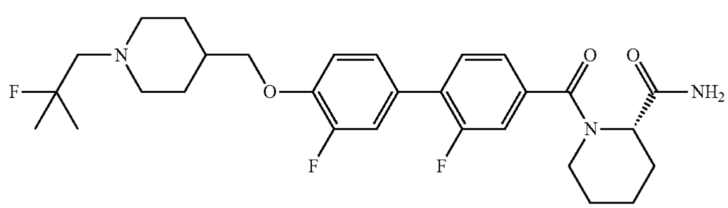 [SMILES: CC(C)(F)CN1CCC(COc2ccc(-c3ccc(C(=O)N4CCCC[C@H]4C(N)=O)cc3F)cc2F)CC1] |
| 821 | 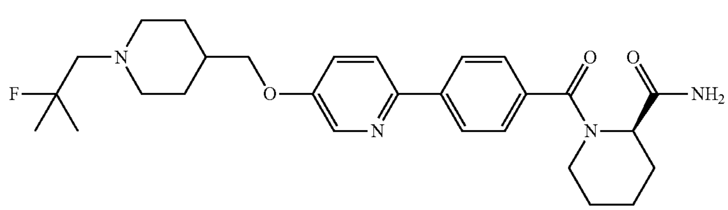 [SMILES: CC(C)(F)CN1CCC(COc2ccc(-c3ccc(C(=O)N4CCCC[C@@H]4C(N)=O)cc3)nc2)CC1] |
| 822 | 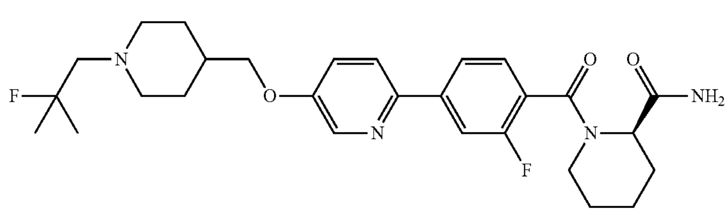 [SMILES: CC(C)(F)CN1CCC(COc2ccc(-c3ccc(C(=O)N4CCCC[C@@H]4C(N)=O)c(F)c3)nc2)CC1] |

TABLE 169
| Compound | Structure |
|---|---|
| 823 | 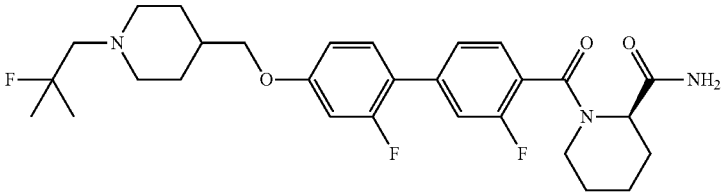 [SMILES: CC(C)(F)CN1CCC(COc2ccc(-c3ccc(C(=O)N4CCCC[C@@H]4C(N)=O)c(F)c3)c(F)c2)CC1] |
| 824 | 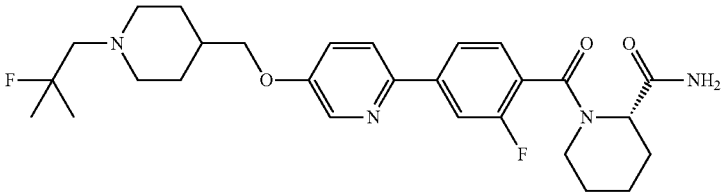 |
| 825 | 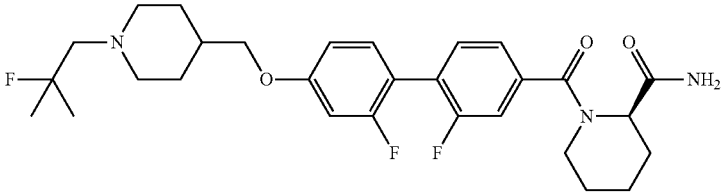 [SMILES: CC(C)(F)CN1CCC(COc2ccc(-c3ccc(C(=O)N4CCCC[C@@H]4C(N)=O)cc3F)c(F)c2)CC1] |
| 828 | 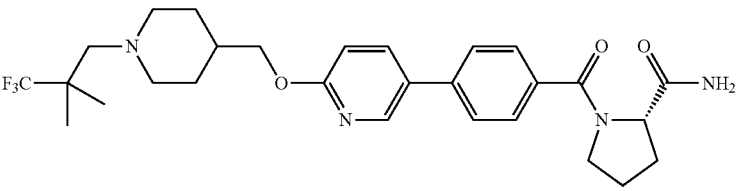 |
| 829 | 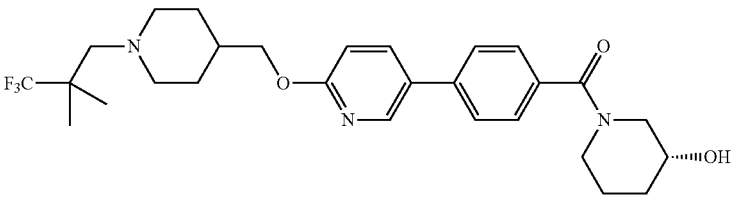 [SMILES: CC(C)(CN1CCC(COc2ccc(-c3ccc(C(=O)N4CCC[C@@H](O)C4)cc3)cn2)CC1)C(F)(F)F] |
| 830 | 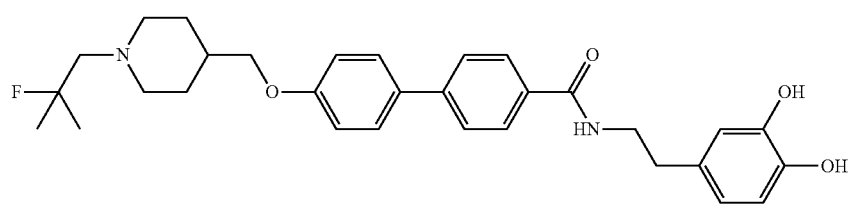 [SMILES: CC(C)(F)CN1CCC(COc2ccc(-c3ccc(C(=O)NCCc4ccc(O)c(O)c4)cc3)cc2)CC1] |
| 831 | 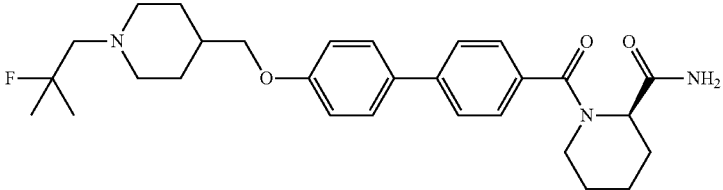 [SMILES: CC(C)(F)CN1CCC(COc2ccc(-c3ccc(C(=O)N4CCCC[C@@H]4C(N)=O)cc3)cc2)CC1] |

TABLE 169-continued

| Compound | Structure |
|---|---|
| 832 | 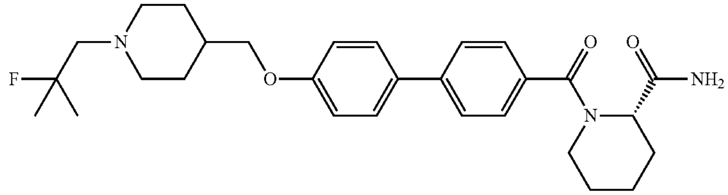 [SMILES: CC(C)(F)CN1CCC(COc2ccc(-c3ccc(C(=O)N4CCCC[C@H]4C(N)=O)cc3)cc2)CC1] |
| 833 | 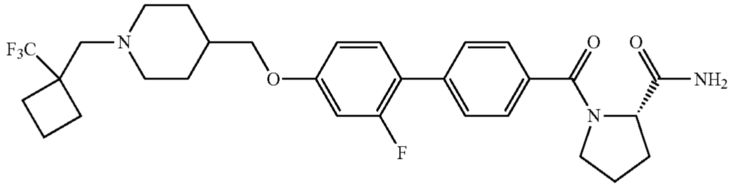 [SMILES: NC(=O)[C@@H]1CCCN1C(=O)c1ccc(-c2ccc(OCC3CCN(CC4(C(F)(F)F)CCC4)CC3)cc2F)cc1] |
| 834 | 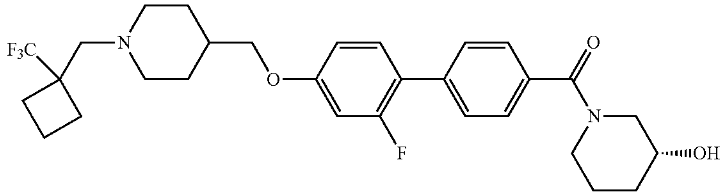 [SMILES: O=C(c1ccc(-c2ccc(OCC3CCN(CC4(C(F)(F)F)CCC4)CC3)cc2F)cc1)N1CCC[C@@H](O)C1] |
| 835 | 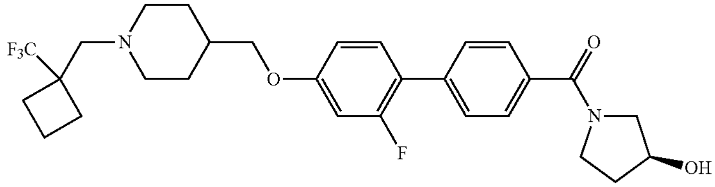 [SMILES: O=C(c1ccc(-c2ccc(OCC3CCN(CC4(C(F)(F)F)CCC4)CC3)cc2F)cc1)N1CC[C@H](O)C1] |
| 836 | 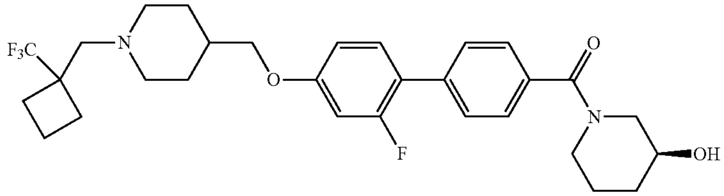 [SMILES: O=C(c1ccc(-c2ccc(OCC3CCN(CC4(C(F)(F)F)CCC4)CC3)cc2F)cc1)N1CCC[C@H](O)C1] |
| 837 | 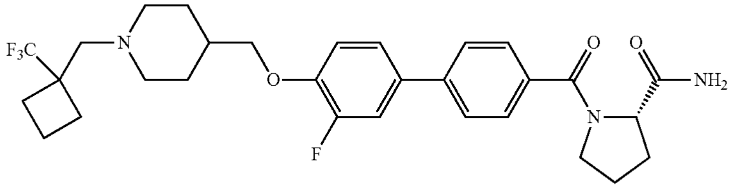 |
| 838 | 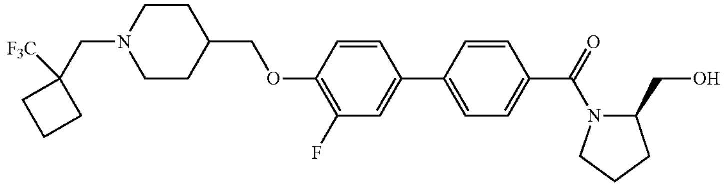 |

TABLE 169-continued

| Compound | Structure |
|---|---|
| 839 | (structure) |
| 840 | (structure) |
| 842 | (structure) |
| 843 | (structure) |
| 844 | (structure) |

TABLE 170

| Compound | Structure |
|---|---|
| 845 | (structure) |
| 846 | (structure) |

TABLE 170-continued
| Compound | Structure |
|---|---|
| 847 | 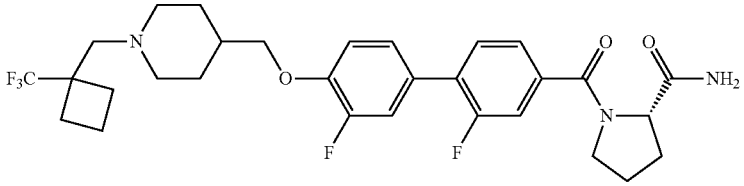 |
| 848 | 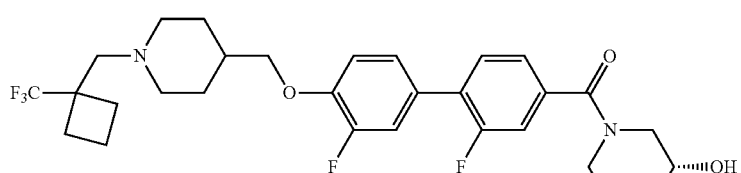 |
| 849 | 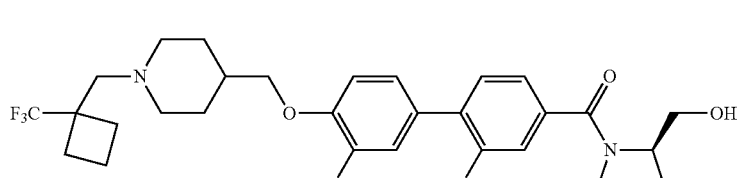 |
| 850 | 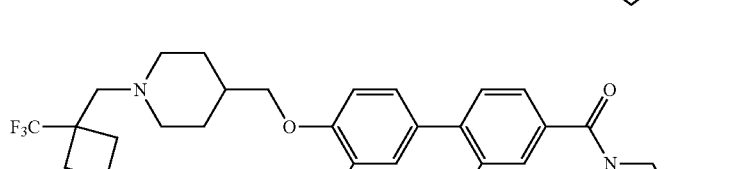 |
| 851 | 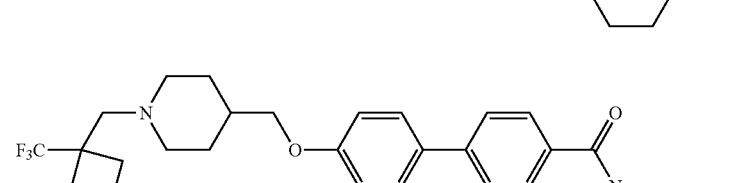 |
| 852 | 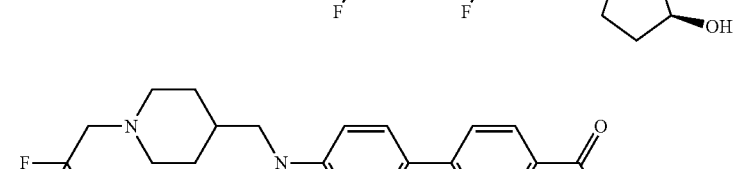 |
| 853 | 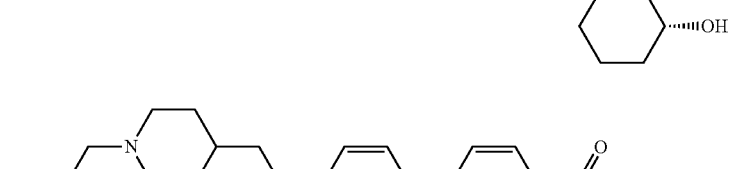 |

TABLE 170-continued

| Compound | Structure |
|---|---|
| 854 | 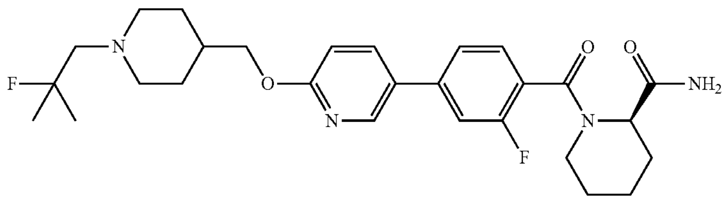 [SMILES: CC(C)(F)CN1CCC(COc2ccc(-c3ccc(C(=O)N4CCCC[C@@H]4C(N)=O)c(F)c3)cn2)CC1] |
| 855 | 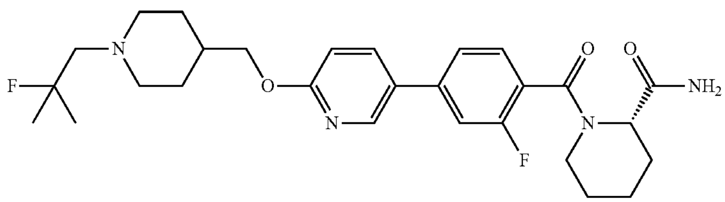 [SMILES: CC(C)(F)CN1CCC(COc2ccc(-c3ccc(C(=O)N4CCCC[C@H]4C(N)=O)c(F)c3)cn2)CC1] |
| 856 | 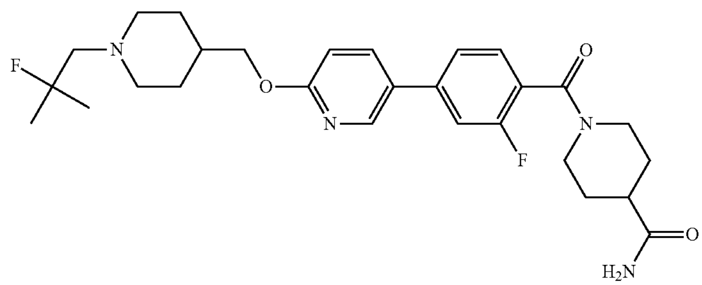 [SMILES: CC(C)(F)CN1CCC(COc2ccc(-c3ccc(C(=O)N4CCC(C(N)=O)CC4)c(F)c3)cn2)CC1] |
| 857 | 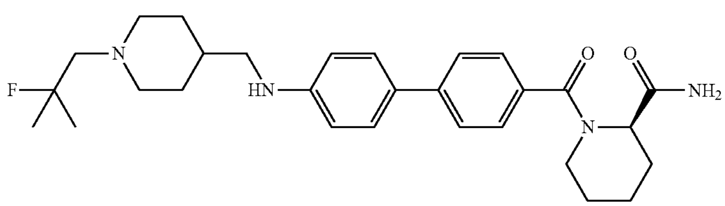 [SMILES: CC(C)(F)CN1CCC(CNc2ccc(-c3ccc(C(=O)N4CCCC[C@@H]4C(N)=O)cc3)cc2)CC1] |
| 858 | 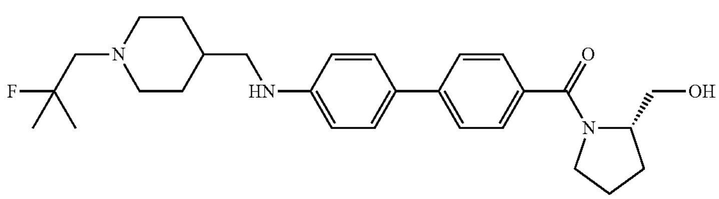 [SMILES: CC(C)(F)CN1CCC(CNc2ccc(-c3ccc(C(=O)N4CCC[C@H]4CO)cc3)cc2)CC1] |
| 859 | 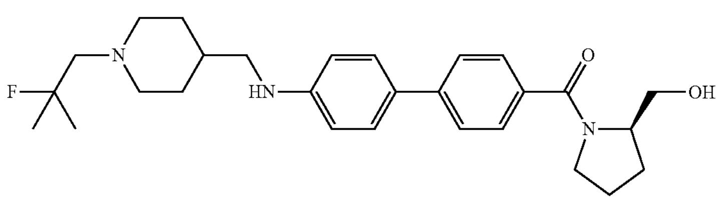 [SMILES: CC(C)(F)CN1CCC(CNc2ccc(-c3ccc(C(=O)N4CCC[C@@H]4CO)cc3)cc2)CC1] |
| 860 | 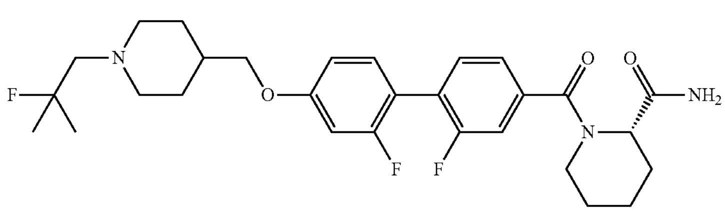 [SMILES: CC(C)(F)CN1CCC(COc2ccc(-c3ccc(C(=O)N4CCCC[C@H]4C(N)=O)cc3F)c(F)c2)CC1] |

TABLE 170-continued

| Compound | Structure |
|---|---|
| 861 | 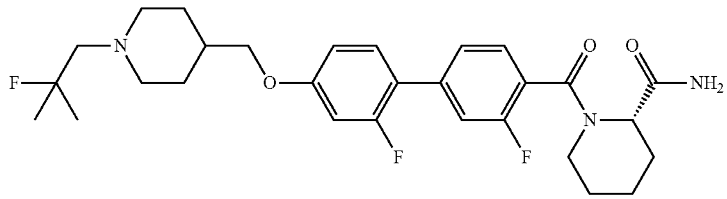 [SMILES: CC(C)(F)CN1CCC(COc2ccc(-c3ccc(C(=O)N4CCCC[C@H]4C(N)=O)c(F)c3)c(F)c2)CC1] |
| 862 | 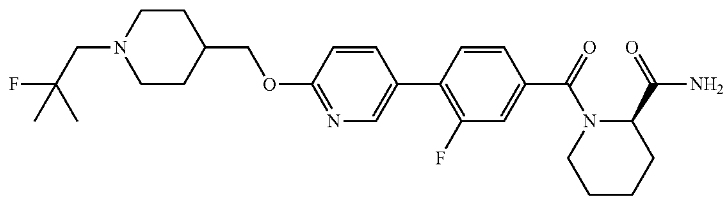 [SMILES: CC(C)(F)CN1CCC(COc2ccc(-c3ccc(C(=O)N4CCCC[C@@H]4C(N)=O)cc3F)cn2)CC1] |
| 863 | 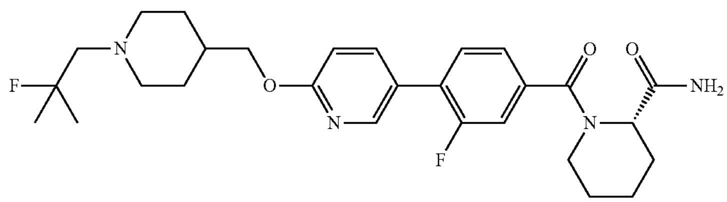 [SMILES: CC(C)(F)CN1CCC(COc2ccc(-c3ccc(C(=O)N4CCCC[C@H]4C(N)=O)cc3F)cn2)CC1] |
| 864 | 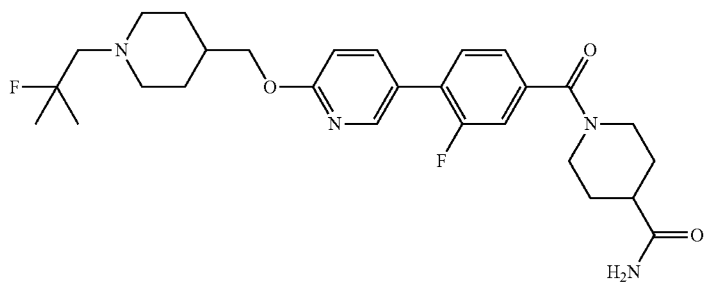 [SMILES: CC(C)(F)CN1CCC(COc2ccc(-c3ccc(C(=O)N4CCC(C(N)=O)CC4)cc3F)cn2)CC1] |

TABLE 171

| Compound | Structure |
|---|---|
| 866 | 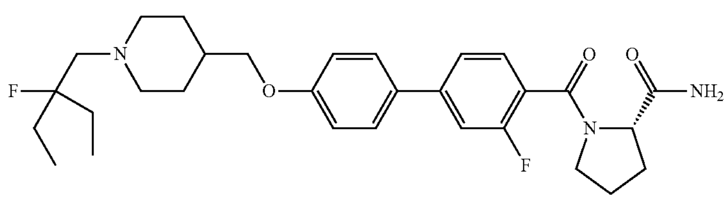 [SMILES: CCC(F)(CC)CN1CCC(COc2ccc(-c3ccc(C(=O)N4CCC[C@H]4C(N)=O)c(F)c3)cc2)CC1] |
| 867 | 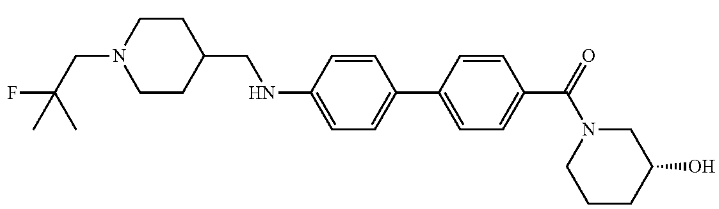 |

TABLE 171-continued

| Compound | Structure |
|---|---|
| 868 | 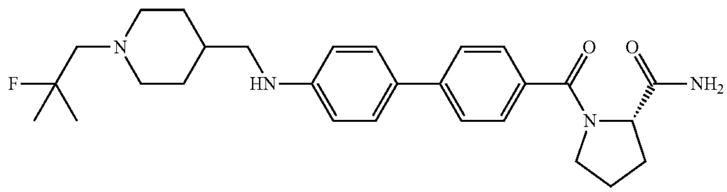 |
| 869 | 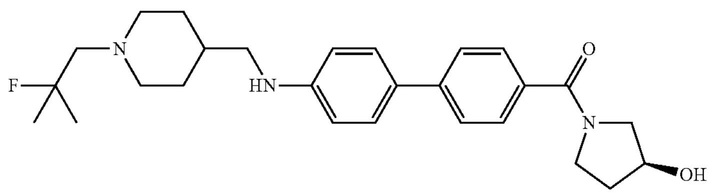 [SMILES: CC(C)(F)CN1CCC(CNc2ccc(-c3ccc(C(=O)N4CC[C@H](O)C4)cc3)cc2)CC1] |
| 870 | 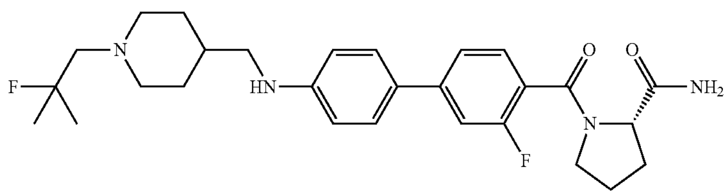 [SMILES: CC(C)(F)CN1CCC(CNc2ccc(-c3ccc(C(=O)N4CCC[C@H]4C(N)=O)c(F)c3)cc2)CC1] |
| 871 | 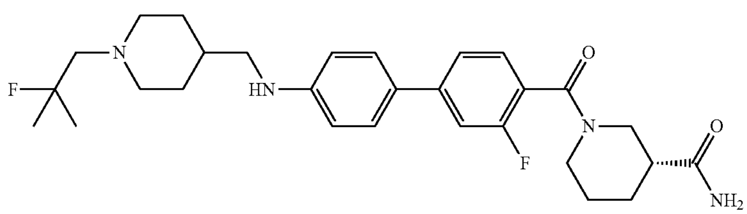 [SMILES: CC(C)(F)CN1CCC(CNc2ccc(-c3ccc(C(=O)N4CCC[C@@H](C(N)=O)C4)c(F)c3)cc2)CC1] |
| 872 | 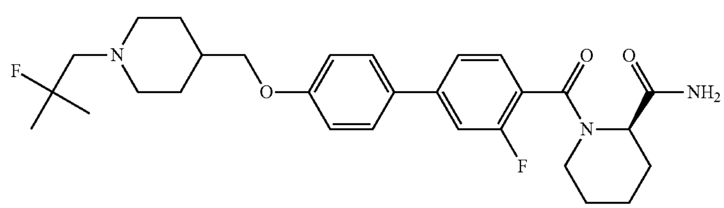 [SMILES: CC(C)(F)CN1CCC(COc2ccc(-c3ccc(C(=O)N4CCCC[C@@H]4C(N)=O)c(F)c3)cc2)CC1] |
| 873 | 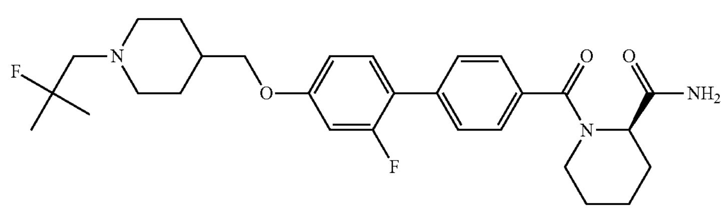 [SMILES: CC(C)(F)CN1CCC(COc2ccc(-c3ccc(C(=O)N4CCCC[C@@H]4C(N)=O)cc3)c(F)c2)CC1] |
| 874 | 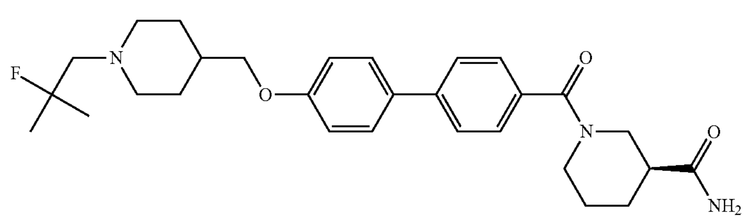 [SMILES: CC(C)(F)CN1CCC(COc2ccc(-c3ccc(C(=O)N4CCC[C@H](C(N)=O)C4)cc3)cc2)CC1] |

TABLE 171-continued

| Compound | Structure |
|---|---|
| 875 | 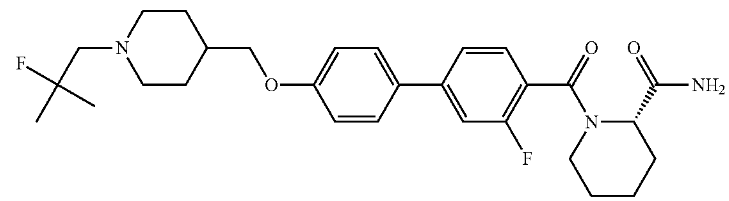 [SMILES: CC(C)(F)CN1CCC(COc2ccc(-c3ccc(C(=O)N4CCCC[C@H]4C(N)=O)c(F)c3)cc2)CC1] |
| 876 | 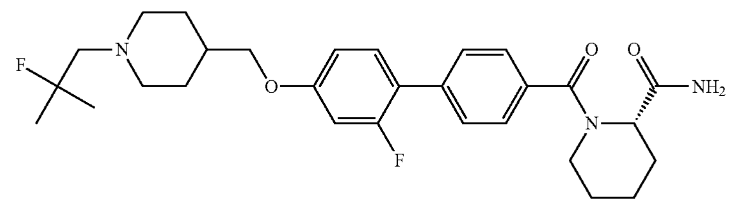 [SMILES: CC(C)(F)CN1CCC(COc2ccc(-c3ccc(C(=O)N4CCCC[C@H]4C(N)=O)cc3)c(F)c2)CC1] |
| 877 | 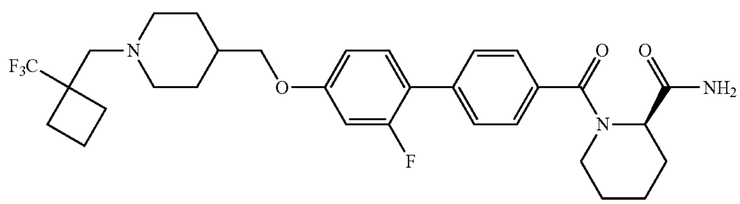 [SMILES: NC(=O)[C@H]1CCCCN1C(=O)c1ccc(-c2ccc(OCC3CCN(CC4(C(F)(F)F)CCC4)CC3)cc2F)cc1] |
| 878 | 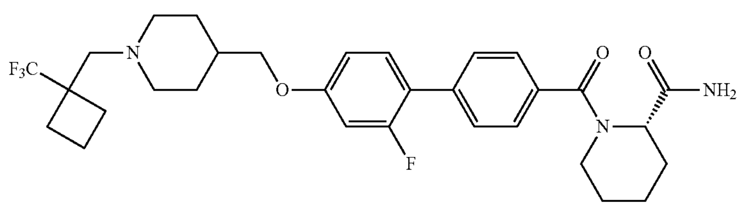 [SMILES: NC(=O)[C@@H]1CCCCN1C(=O)c1ccc(-c2ccc(OCC3CCN(CC4(C(F)(F)F)CCC4)CC3)cc2F)cc1] |
| 879 | 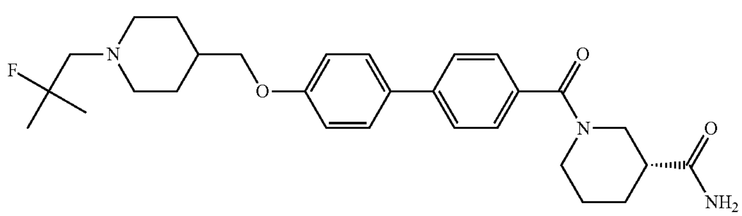 |
| 880 | 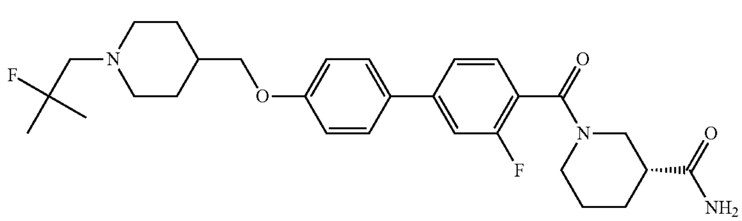 [SMILES: CC(C)(F)CN1CCC(COc2ccc(-c3ccc(C(=O)N4CCC[C@@H](C(N)=O)C4)c(F)c3)cc2)CC1] |
| 881 | 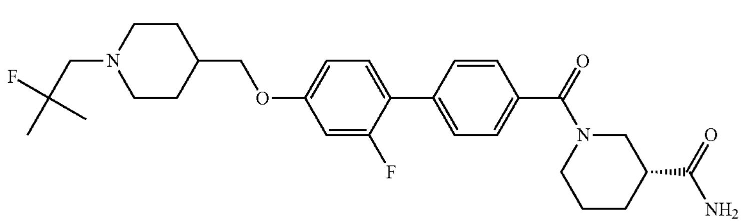 [SMILES: CC(C)(F)CN1CCC(COc2ccc(-c3ccc(C(=O)N4CCC[C@@H](C(N)=O)C4)cc3)c(F)c2)CC1] |

TABLE 171-continued
| Compound | Structure |
|---|---|
| 882 | 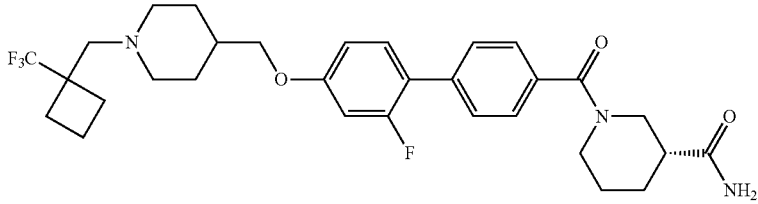 [SMILES: NC(=O)[C@@H]1CCCN(C(=O)c2ccc(-c3ccc(OCC4CCN(CC5(C(F)(F)F)CCC5)CC4)cc3F)cc2)C1] |
| 883 | 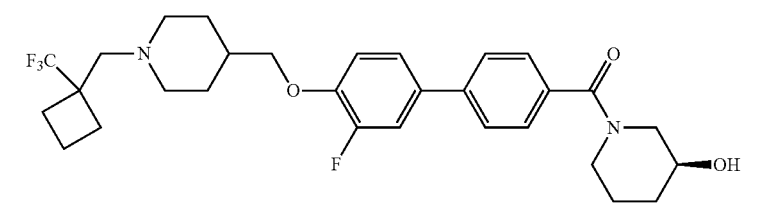 |
| 884 | 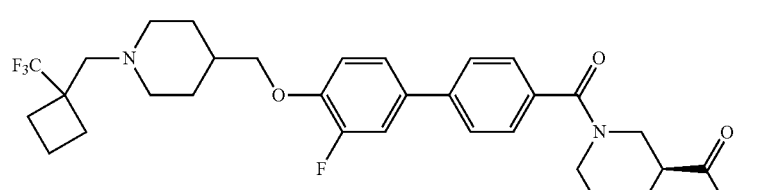 |
| 885 | 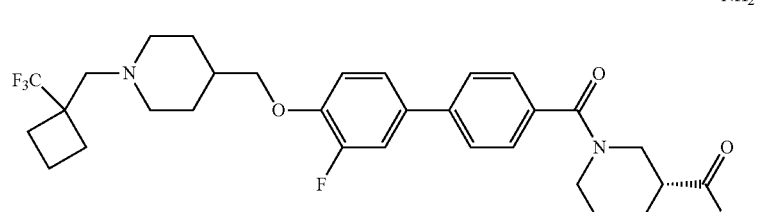 |
TABLE 172
| Compound | Structure |
|---|---|
| 886 | 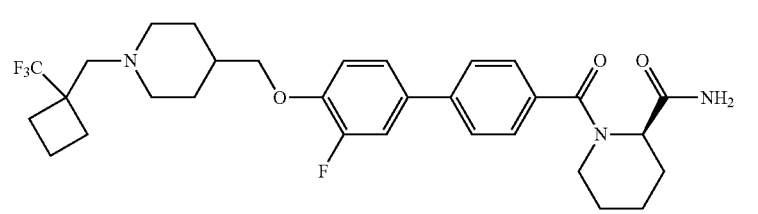 [SMILES: NC(=O)[C@H]1CCCCN1C(=O)c1ccc(-c2ccc(OCC3CCN(CC4(C(F)(F)F)CCC4)CC3)c(F)c2)cc1] |
| 887 | 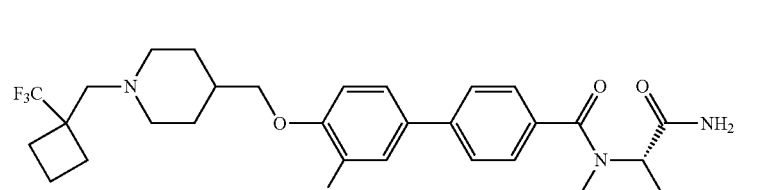 |

TABLE 172-continued
| Compound | Structure |
|---|---|
| 888 | 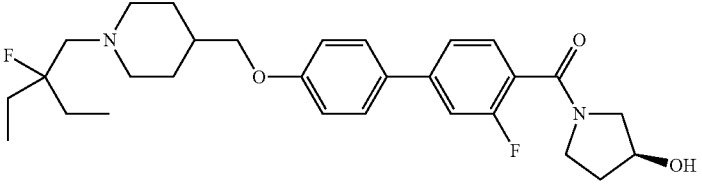 [SMILES: CCC(F)(CC)CN1CCC(COc2ccc(-c3ccc(C(=O)N4CC[C@H](O)C4)c(F)c3)cc2)CC1] |
| 889 | 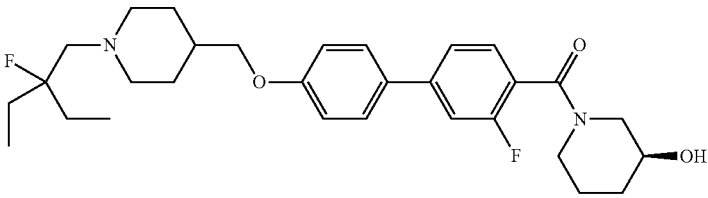 [SMILES: CCC(F)(CC)CN1CCC(COc2ccc(-c3ccc(C(=O)N4CCC[C@H](O)C4)c(F)c3)cc2)CC1] |
| 890 | 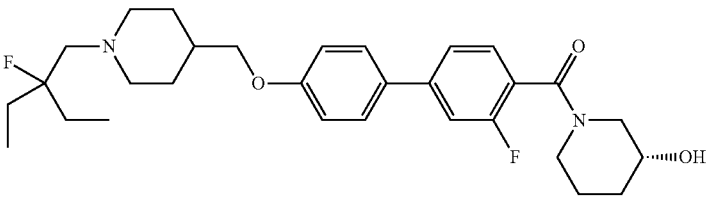 [SMILES: CCC(F)(CC)CN1CCC(COc2ccc(-c3ccc(C(=O)N4CCC[C@@H](O)C4)c(F)c3)cc2)CC1] |
| 891 | 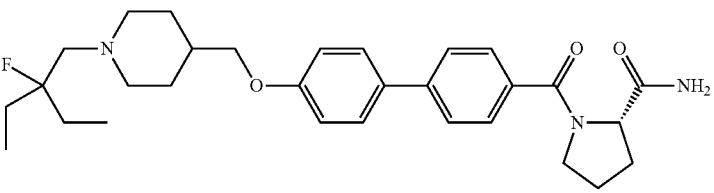 [SMILES: CCC(F)(CC)CN1CCC(COc2ccc(-c3ccc(C(=O)N4CCC[C@H]4C(N)=O)cc3)cc2)CC1] |
| 892 | 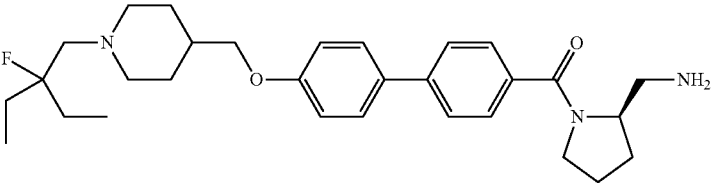 |
| 893 | 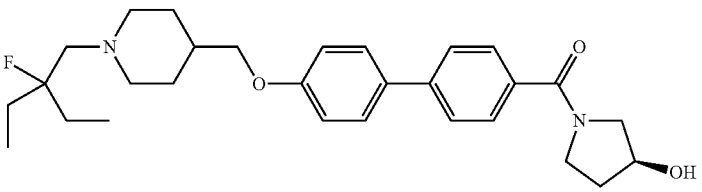 [SMILES: CCC(F)(CC)CN1CCC(COc2ccc(-c3ccc(C(=O)N4CC[C@H](O)C4)cc3)cc2)CC1] |
| 894 | 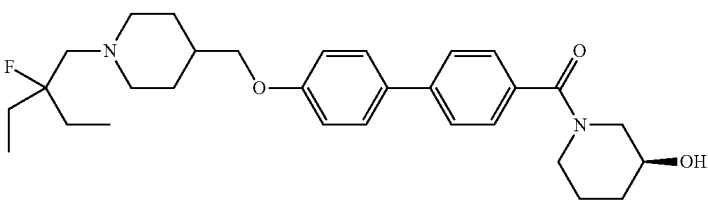 [SMILES: CCC(F)(CC)CN1CCC(COc2ccc(-c3ccc(C(=O)N4CCC[C@H](O)C4)cc3)cc2)CC1] |

TABLE 172-continued
| Compound | Structure |
|---|---|
| 895 | 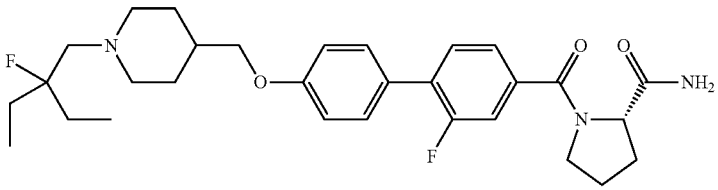 |
| 896 | 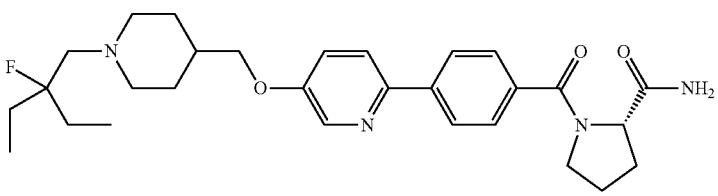 [SMILES: CCC(F)(CC)CN1CCC(COc2ccc(-c3ccc(C(=O)N4CCC[C@H]4C(N)=O)cc3)nc2)CC1] |
| 897 | 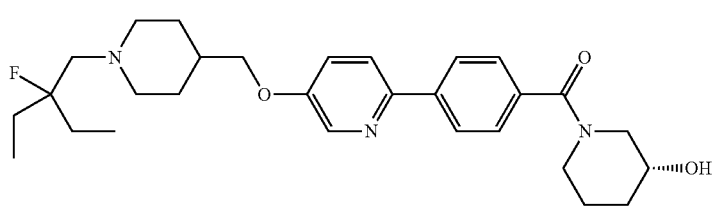 [SMILES: CCC(F)(CC)CN1CCC(COc2ccc(-c3ccc(C(=O)N4CCC[C@@H](O)C4)cc3)nc2)CC1] |
| 898 | 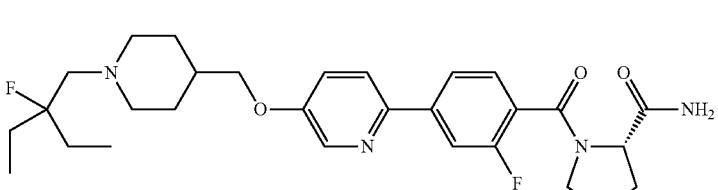 |
| 899 | 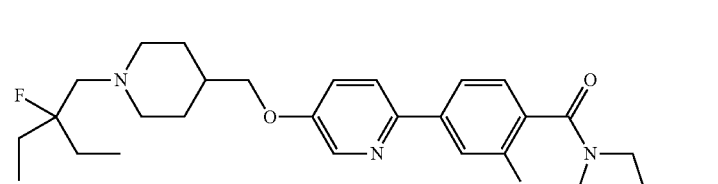 |
| 900 | 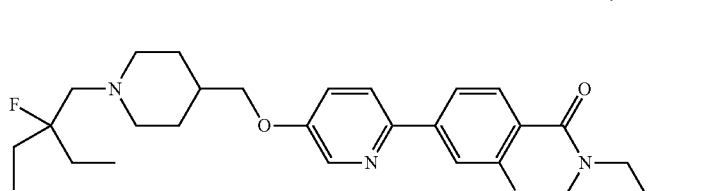 |
| 901 | 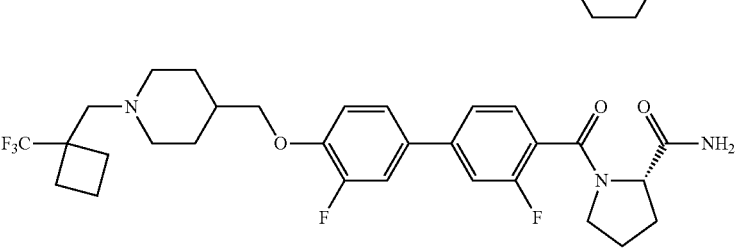 |

TABLE 172-continued
| Compound | Structure |
|---|---|
| 902 | 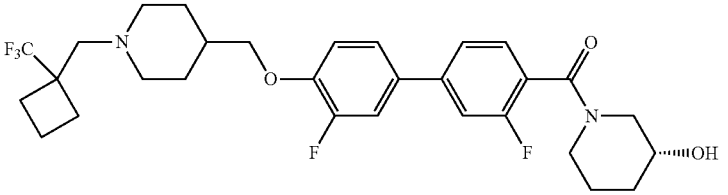 [SMILES: O=C(c1ccc(-c2ccc(OCC3CCN(CC4(C(F)(F)F)CCC4)CC3)c(F)c2)cc1F)N1CCC[C@@H](O)C1] |
| 903 | 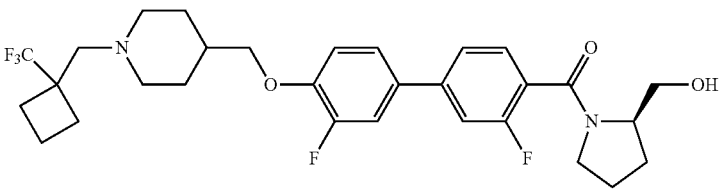 |
| 904 | 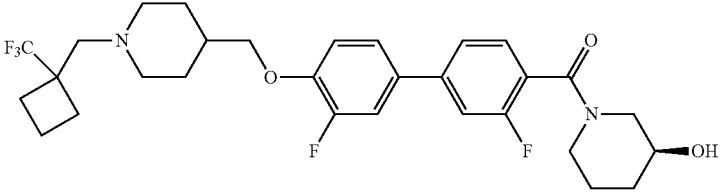 [SMILES: O=C(c1ccc(-c2ccc(OCC3CCN(CC4(C(F)(F)F)CCC4)CC3)c(F)c2)cc1F)N1CCC[C@H](O)C1] |
| 905 | 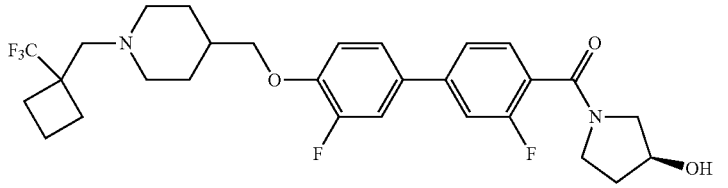 |
TABLE 173
| Compound | Structure |
|---|---|
| 906 | 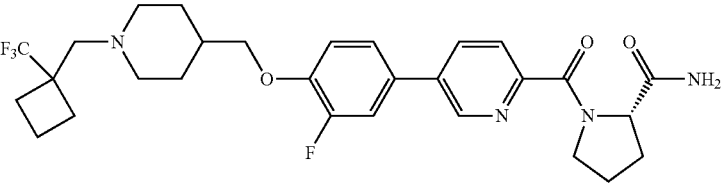 [SMILES: NC(=O)[C@@H]1CCCN1C(=O)c1ccc(-c2ccc(OCC3CCN(CC4(C(F)(F)F)CCC4)CC3)c(F)c2)cn1] |
| 907 | 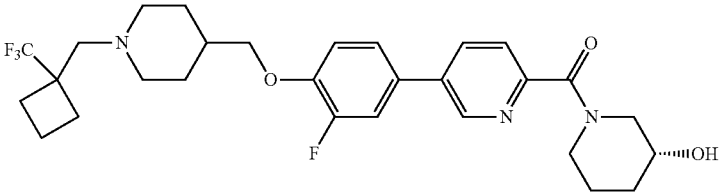 [SMILES: O=C(c1ccc(-c2ccc(OCC3CCN(CC4(C(F)(F)F)CCC4)CC3)c(F)c2)cn1)N1CCC[C@@H](O)C1] |
| 908 | 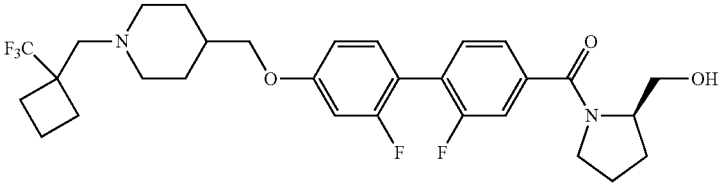 |

TABLE 173-continued
| Compound | Structure |
|---|---|
| 909 | 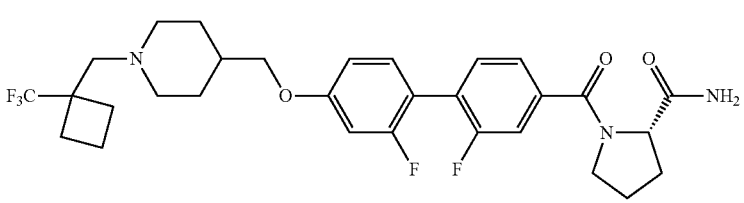 |
| 910 | 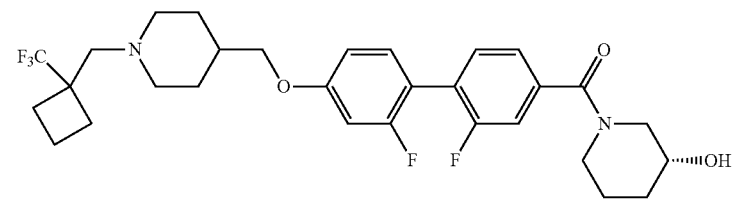 |
| 911 | 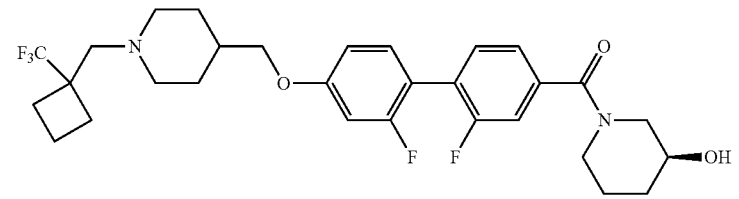 |
| 912 | 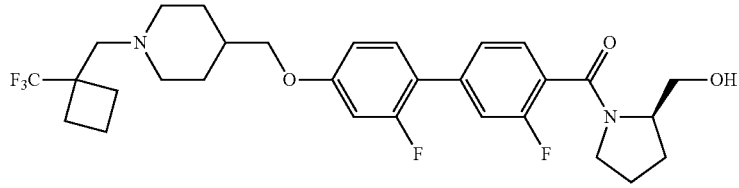 |
| 913 | 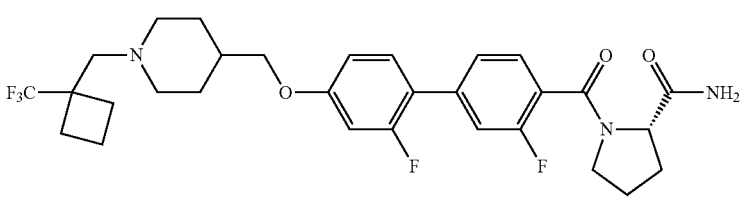 |
| 914 | 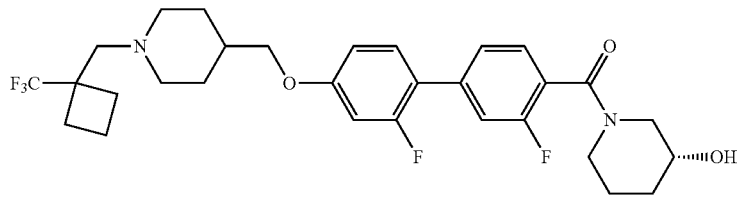 [SMILES: O=C(c1ccc(-c2ccc(OCC3CCN(CC4(C(F)(F)F)CCC4)CC3)cc2F)cc1F)N1CCC[C@@H](O)C1] |
| 915 | 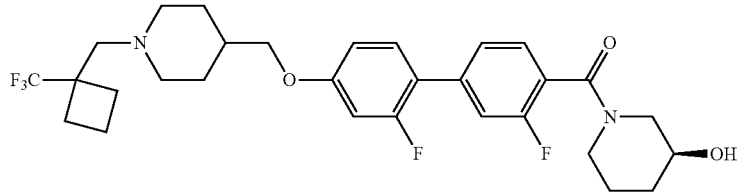 [SMILES: O=C(c1ccc(-c2ccc(OCC3CCN(CC4(C(F)(F)F)CCC4)CC3)cc2F)cc1F)N1CCC[C@H](O)C1] |

TABLE 173-continued
| Compound | Structure |
|---|---|
| 916 | 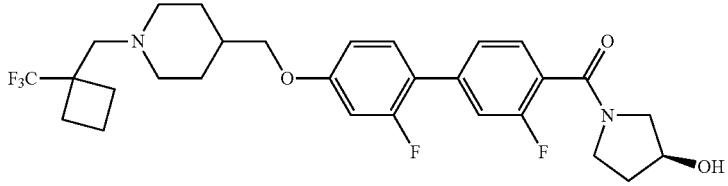 |
| 917 | 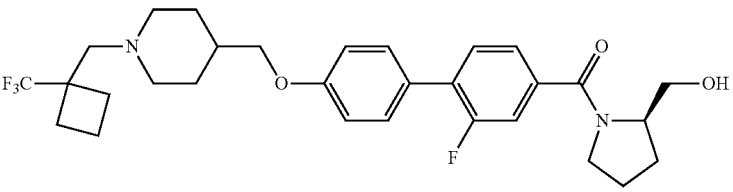 |
| 918 | 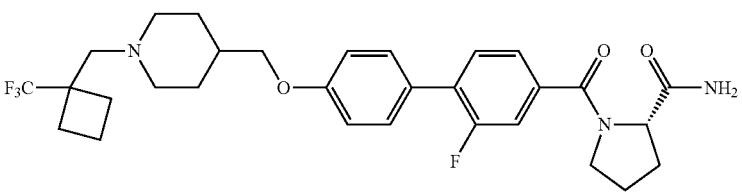 |
| 919 | 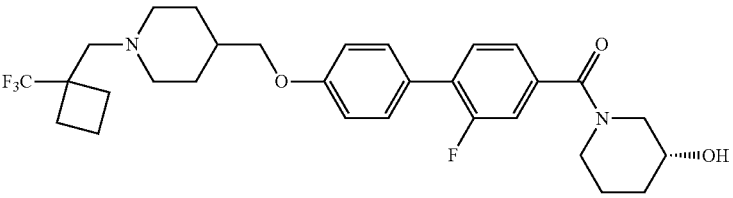 |
| 920 | 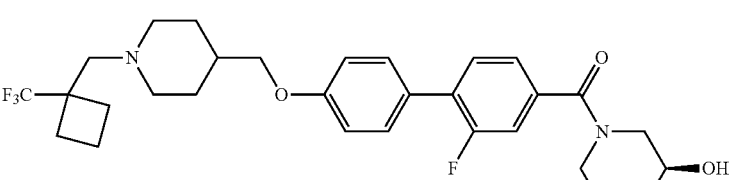 |
| 921 | 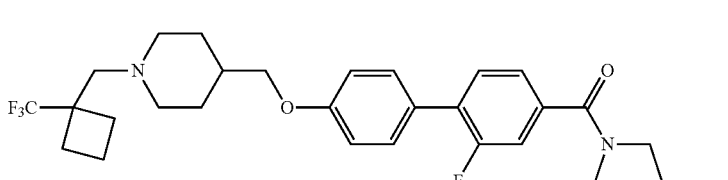 |
| 922 | 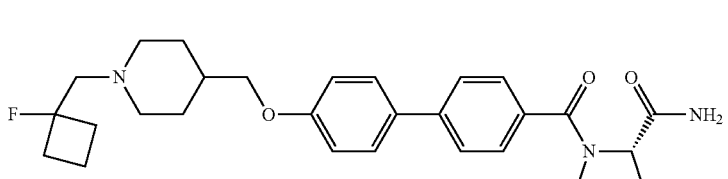 |

TABLE 173-continued
| Compound | Structure |
|---|---|
| 923 | 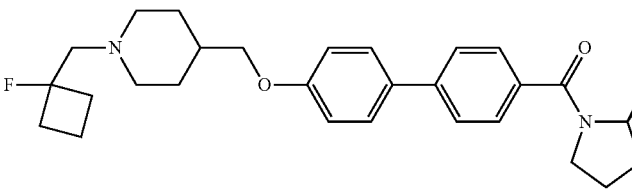 |
| 924 | 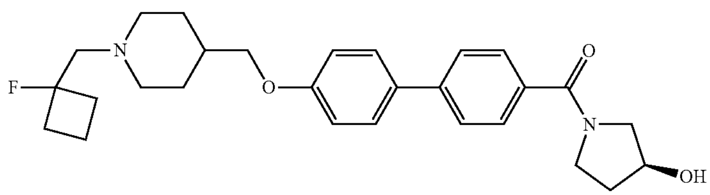 [SMILES: O=C(c1ccc(-c2ccc(OCC3CCN(CC4(F)CCC4)CC3)cc2)cc1)N1CC[C@H](O)C1] |
| 925 | 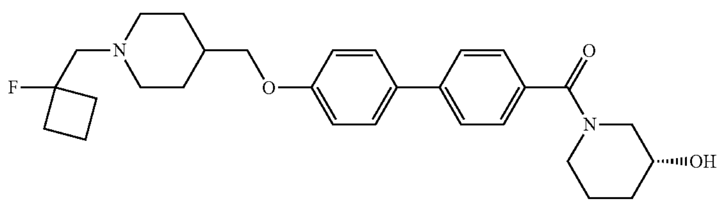 [SMILES: O=C(c1ccc(-c2ccc(OCC3CCN(CC4(F)CCC4)CC3)cc2)cc1)N1CCC[C@@H](O)C1] |
TABLE 174
| Compound | Structure |
|---|---|
| 926 | 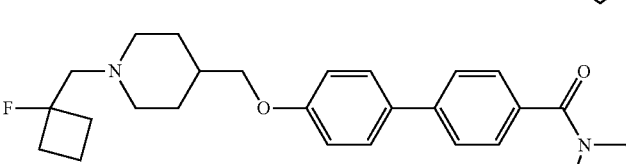 |
| 927 | 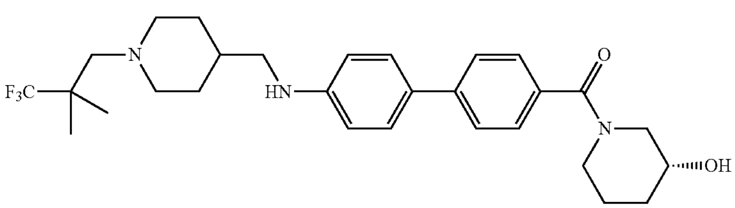 [SMILES: CC(C)(CN1CCC(CNc2ccc(-c3ccc(C(=O)N4CCC[C@@H](O)C4)cc3)cc2)CC1)C(F)(F)F] |
| 928 | 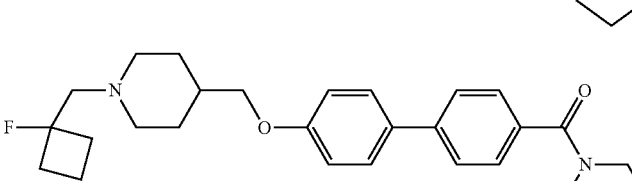 |

TABLE 174-continued
| Compound | Structure |
|---|---|
| 929 | 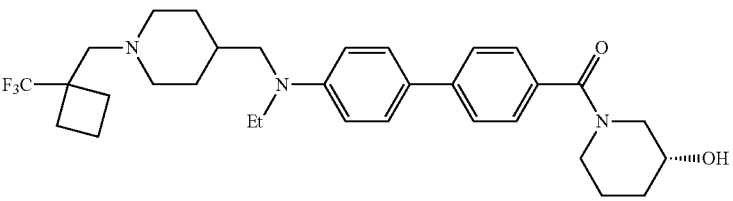 [SMILES: CCN(CC1CCN(CC2(C(F)(F)F)CCC2)CC1)c1ccc(-c2ccc(C(=O)N3CCC[C@@H](O)C3)cc2)cc1] |
| 930 | 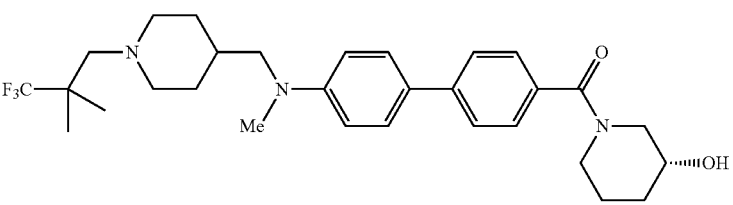 [SMILES: CN(CC1CCN(CC(C)(C)C(F)(F)F)CC1)c1ccc(-c2ccc(C(=O)N3CCC[C@@H](O)C3)cc2)cc1] |
| 931 | 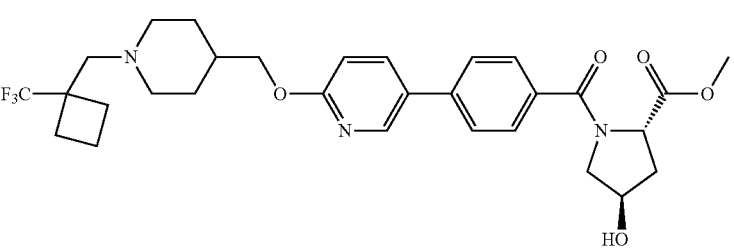 [SMILES: COC(=O)[C@@H]1C[C@@H](O)CN1C(=O)c1ccc(-c2ccc(OCC3CCN(CC4(C(F)(F)F)CCC4)CC3)nc2)cc1] |
| 932 | 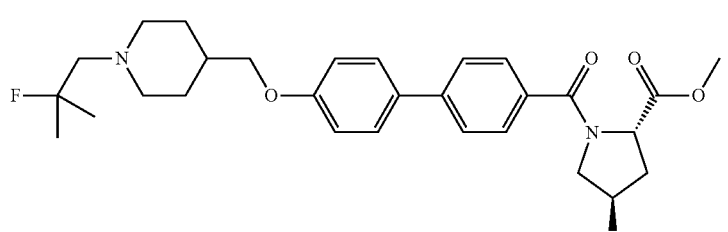 |
| 933 | 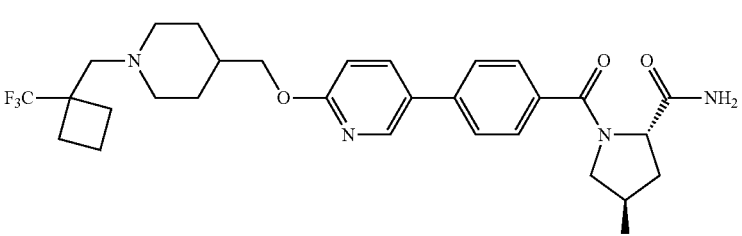 |
| 934 | 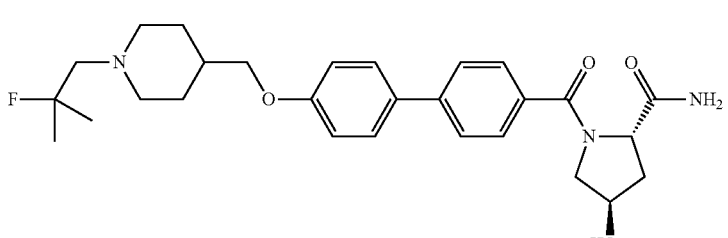 |
| 935 | 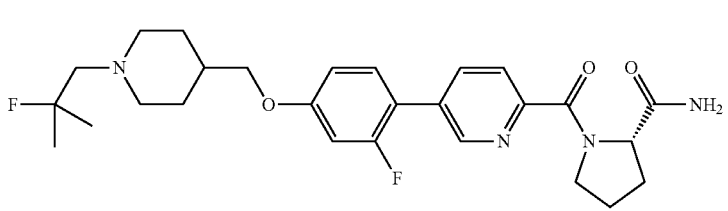 [SMILES: CC(C)(F)CN1CCC(COc2ccc(-c3ccc(C(=O)N4CCC[C@H]4C(N)=O)nc3)c(F)c2)CC1] |

TABLE 174-continued
| Compound | Structure |
|---|---|
| 936 | 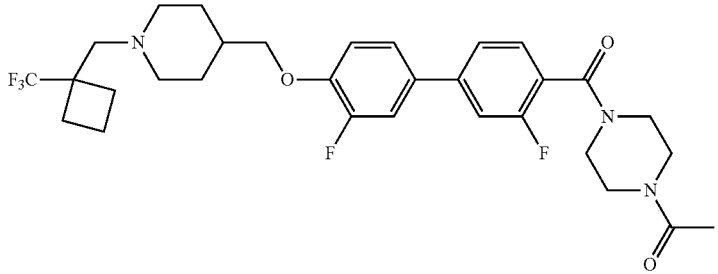 [SMILES: CC(=O)N1CCN(C(=O)c2ccc(-c3ccc(OCC4CCN(CC5(C(F)(F)F)CCC5)CC4)c(F)c3)cc2F)CC1] |
| 937 | 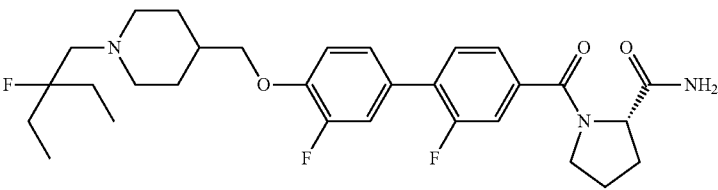 |
| 938 | 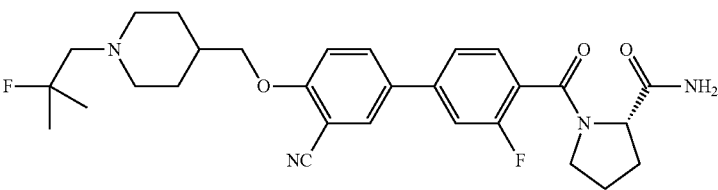 [SMILES: CC(C)(F)CN1CCC(COc2ccc(-c3ccc(C(=O)N4CCC[C@H]4C(N)=O)c(F)c3)cc2C#N)CC1] |
| 939 | 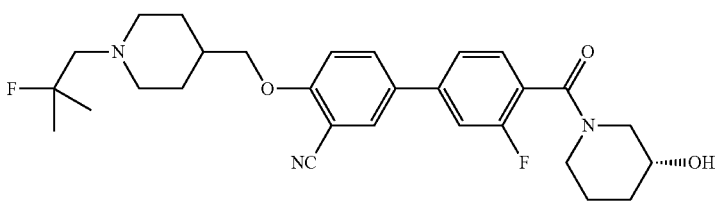 [SMILES: CC(C)(F)CN1CCC(COc2ccc(-c3ccc(C(=O)N4CCC[C@@H](O)C4)c(F)c3)cc2C#N)CC1] |
| 940 | 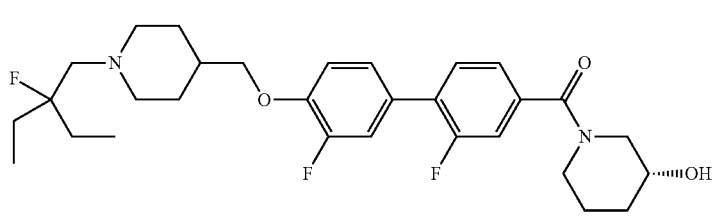 [SMILES: CCC(F)(CC)CN1CCC(COc2ccc(-c3ccc(C(=O)N4CCC[C@@H](O)C4)cc3F)cc2F)CC1] |
| 941 | 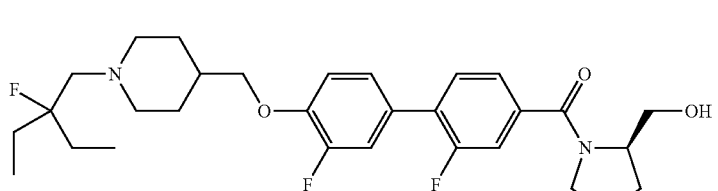 |
| 942 | 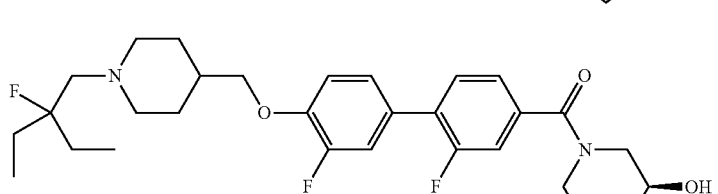 |

TABLE 174-continued
| Compound | Structure |
|---|---|
| 943 | 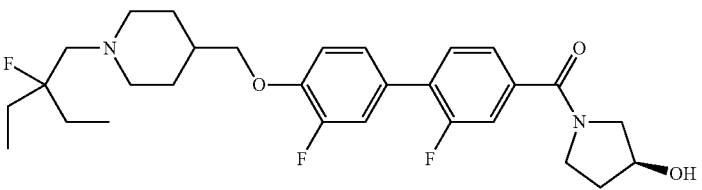 [SMILES: CCC(F)(CC)CN1CCC(COc2ccc(-c3ccc(C(=O)N4CC[C@H](O)C4)cc3F)cc2F)CC1] |
| 944 | 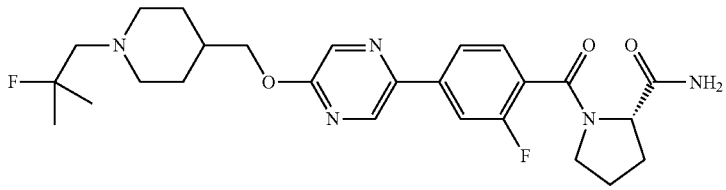 |
| 945 | 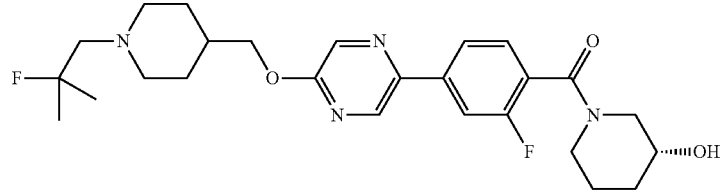 [SMILES: CC(C)(F)CN1CCC(COc2cnc(-c3ccc(C(=O)N4CCC[C@@H](O)C4)c(F)c3)cn2)CC1] |
TABLE 175
| Compound | Structure |
|---|---|
| 946 | 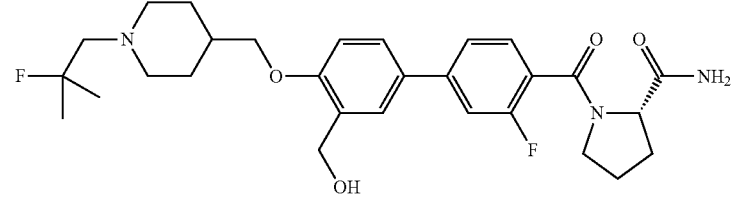 [SMILES: CC(C)(F)CN1CCC(COc2ccc(-c3ccc(C(=O)N4CCC[C@H]4C(N)=O)c(F)c3)cc2CO)CC1] |
| 947 | 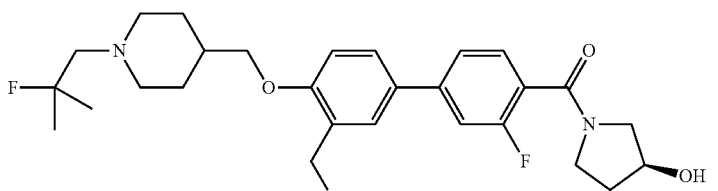 |
| 948 | 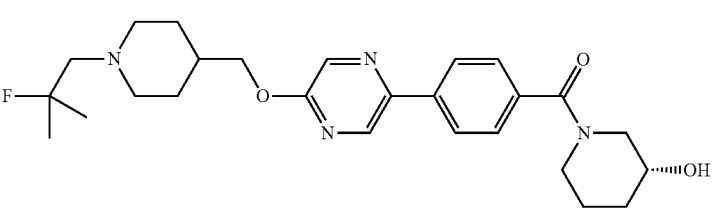 [SMILES: CC(C)(F)CN1CCC(COc2cnc(-c3ccc(C(=O)N4CCC[C@@H](O)C4)cc3)cn2)CC1] |

TABLE 175-continued

| Compound | Structure |
|---|---|
| 949 | 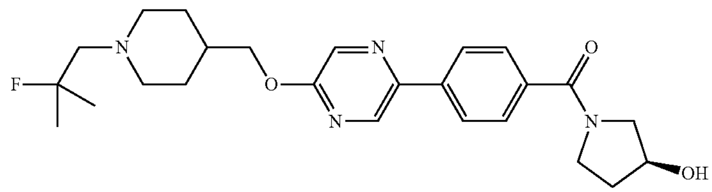 [SMILES: CC(C)(F)CN1CCC(COc2cnc(-c3ccc(C(=O)N4CC[C@H](O)C4)cc3)cn2)CC1] |
| 950 | 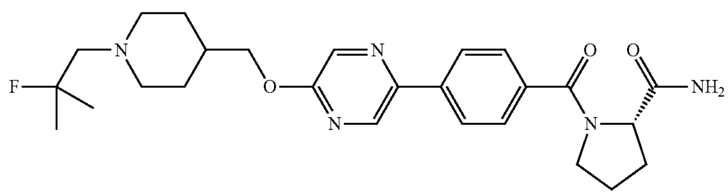 |
| 951 | 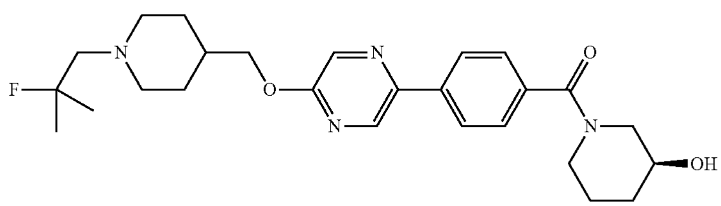 |
| 953 | 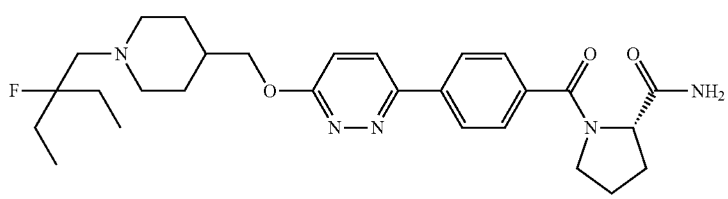 |
| 954 | 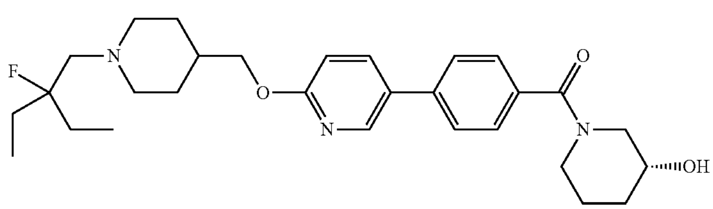 |
| 955 | 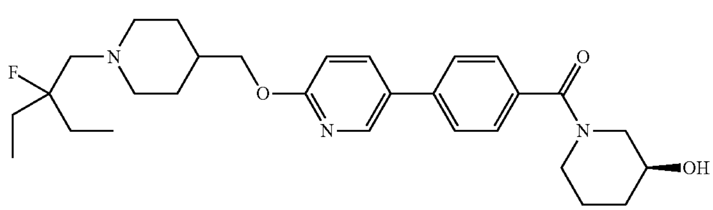 [SMILES: CCC(F)(CC)CN1CCC(COc2ccc(-c3ccc(C(=O)N4CCC[C@H](O)C4)cc3)cn2)CC1] |
| 956 | 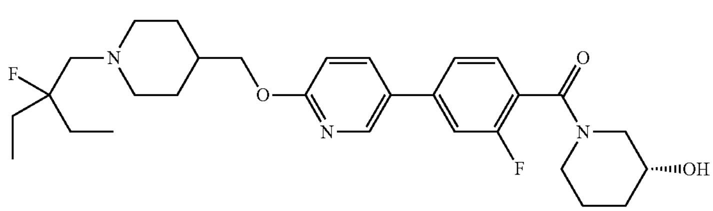 [SMILES: CCC(F)(CC)CN1CCC(COc2ccc(-c3ccc(C(=O)N4CCC[C@@H](O)C4)c(F)c3)cn2)CC1] |

TABLE 175-continued

| Compound | Structure |
|---|---|
| 957 | 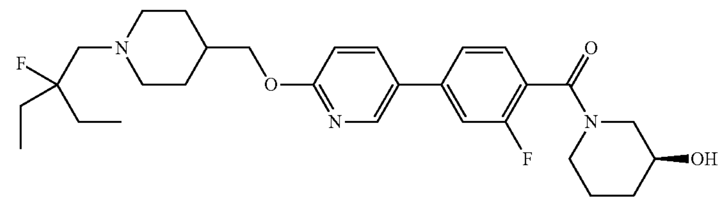 [SMILES: CCC(F)(CC)CN1CCC(COc2ccc(-c3ccc(C(=O)N4CCC[C@H](O)C4)c(F)c3)cn2)CC1] |
| 963 | 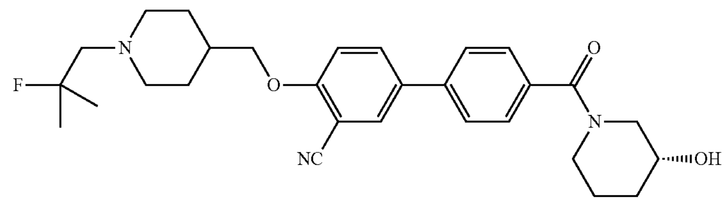 |
| 964 | 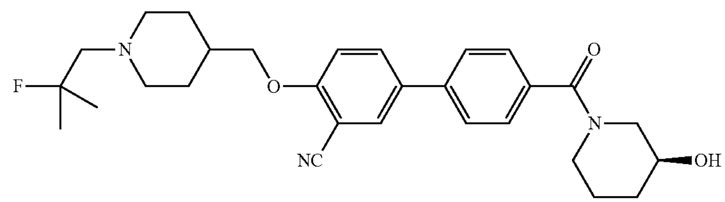 [SMILES: CC(C)(F)CN1CCC(COc2ccc(-c3ccc(C(=O)N4CCC[C@H](O)C4)cc3)cc2C#N)CC1] |
| 965 | 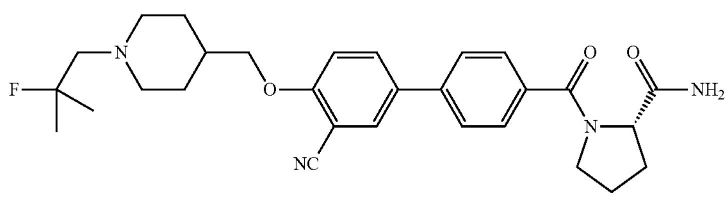 |
| 966 | 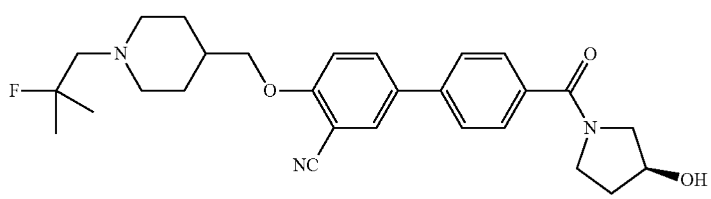 [SMILES: CC(C)(F)CN1CCC(COc2ccc(-c3ccc(C(=O)N4CC[C@H](O)C4)cc3)cc2C#N)CC1] |
| 967 | 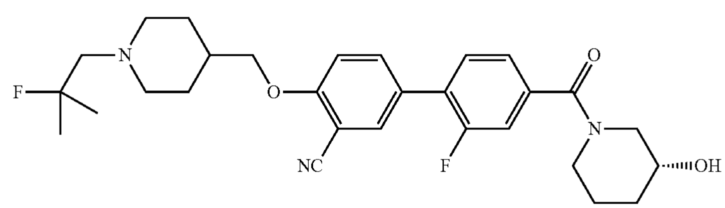 [SMILES: CC(C)(F)CN1CCC(COc2ccc(-c3ccc(C(=O)N4CCC[C@@H](O)C4)cc3F)cc2C#N)CC1] |
| 968 | 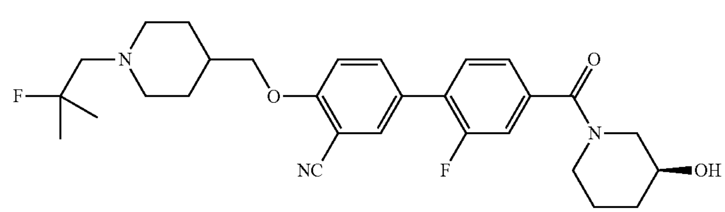 [SMILES: CC(C)(F)CN1CCC(COc2ccc(-c3ccc(C(=O)N4CCC[C@H](O)C4)cc3F)cc2C#N)CC1] |

TABLE 175-continued
| Compound | Structure |
|---|---|
| 969 | 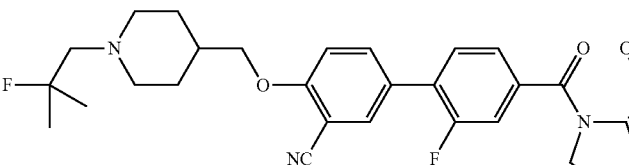 |
| 970 | 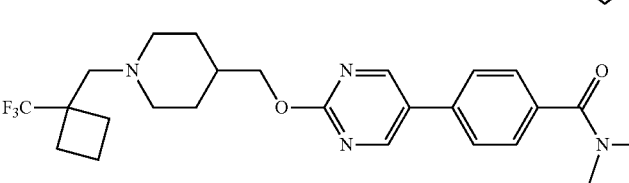 |
| 971 | 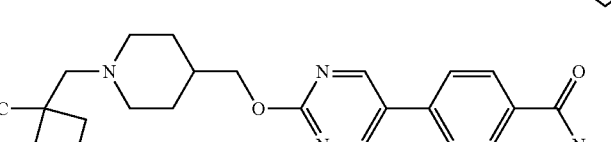 |
TABLE 176
| Compound | Structure |
|---|---|
| 972 | 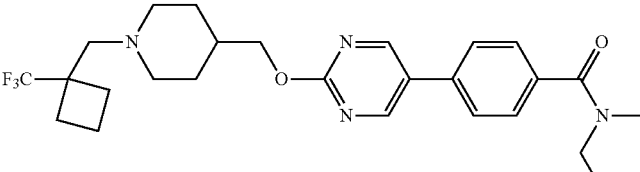 |
| 973 | 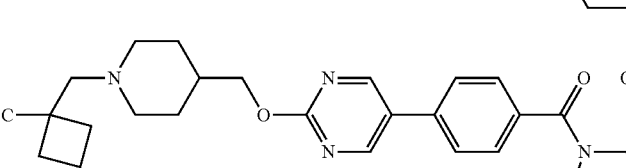 |
| 974 | 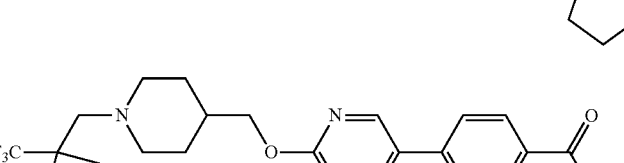 |
| 975 | 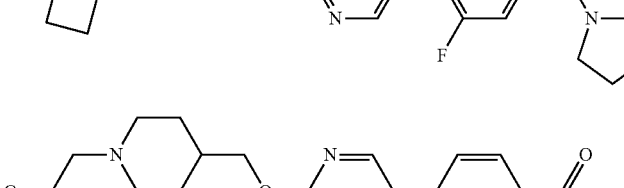 |

TABLE 176-continued
| Compound | Structure |
|---|---|
| 976 | 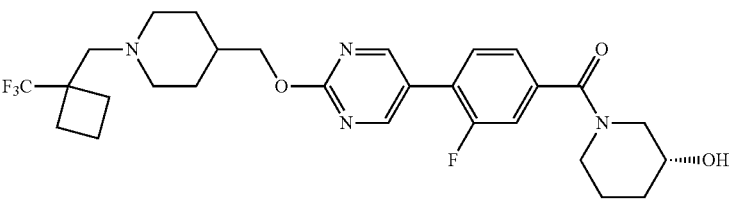 [SMILES: O=C(c1ccc(-c2cnc(OCC3CCN(CC4(C(F)(F)F)CCC4)CC3)nc2)c(F)c1)N1CCC[C@@H](O)C1] |
| 977 | 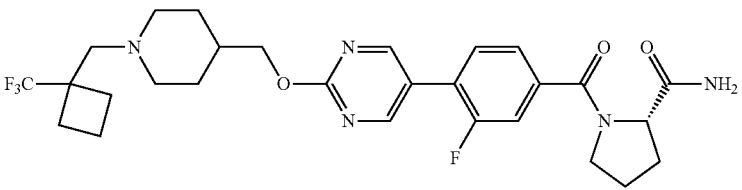 |
| 978 | 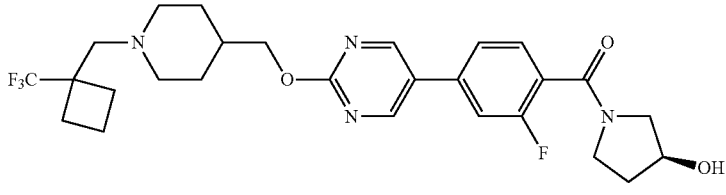 [SMILES: O=C(c1ccc(-c2cnc(OCC3CCN(CC4(C(F)(F)F)CCC4)CC3)nc2)cc1F)N1CC[C@H](O)C1] |
| 979 | 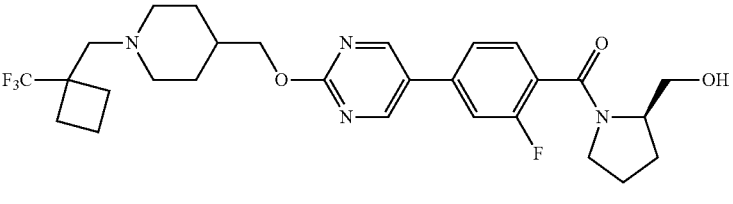 |
| 980 | 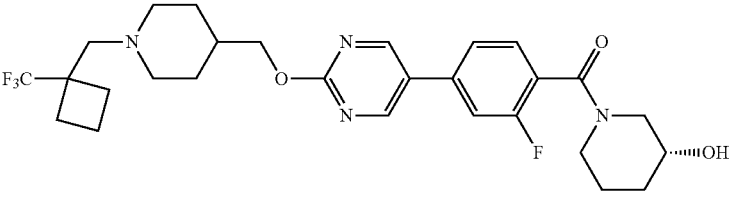 [SMILES: O=C(c1ccc(-c2cnc(OCC3CCN(CC4(C(F)(F)F)CCC4)CC3)nc2)cc1F)N1CCC[C@@H](O)C1] |
| 981 | 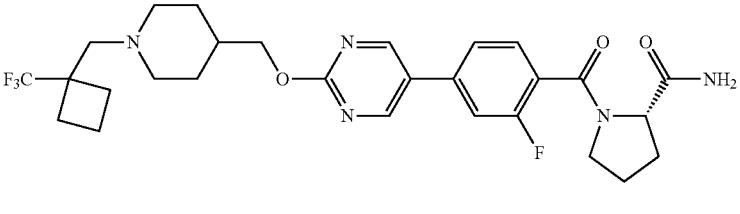 |
| 982 | 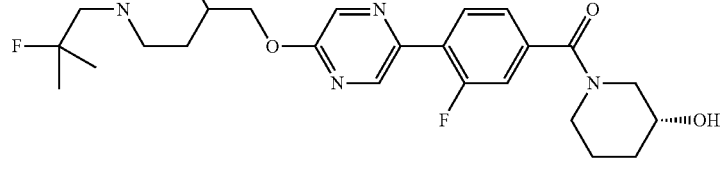 |

TABLE 176-continued
| Compound | Structure |
|---|---|
| 983 | 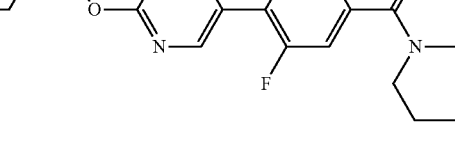 |
| 984 | 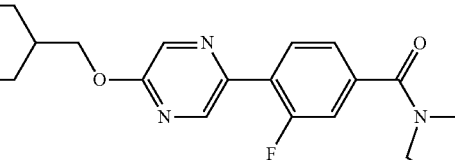 |
| 985 | 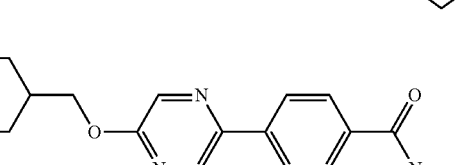 |
| 986 | 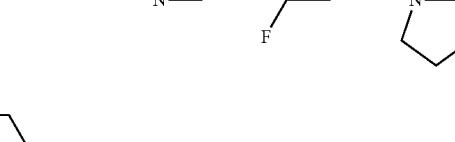 |
| 987 | 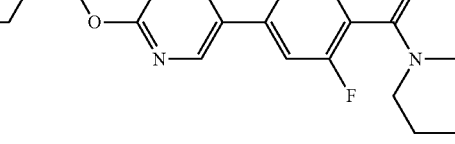 |
| 988 | 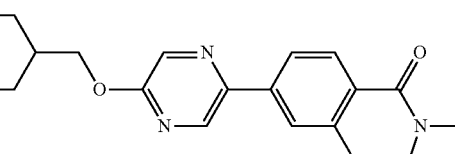 |
| 989 | 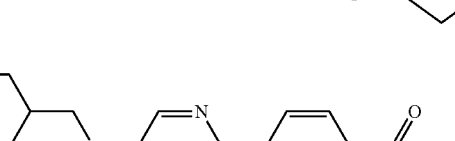 |

TABLE 176-continued
| Compound | Structure |
|---|---|
| 990 | 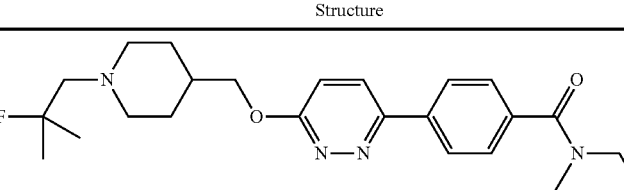 |
| 991 | 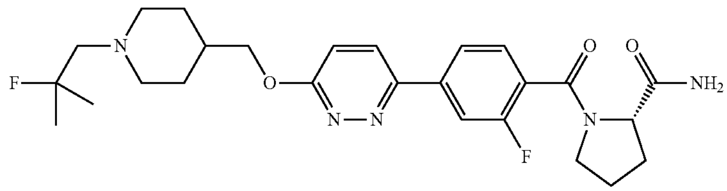 |
TABLE 177
| Compound | Structure |
|---|---|
| 992 | 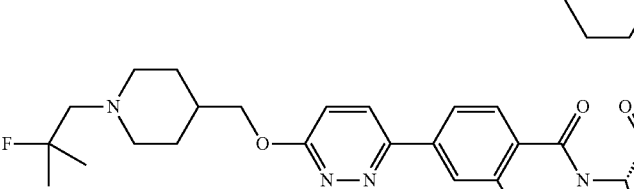 |
| 1000 | 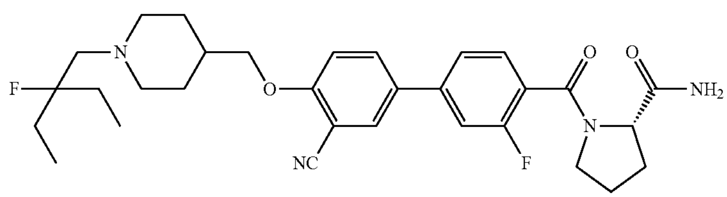 [SMILES: CCC(F)(CC)CN1CCC(COc2ccc(-c3ccc(C(=O)N4CCC[C@H]4C(N)=O)c(F)c3)cc2C#N)CC1] |
| 1001 | 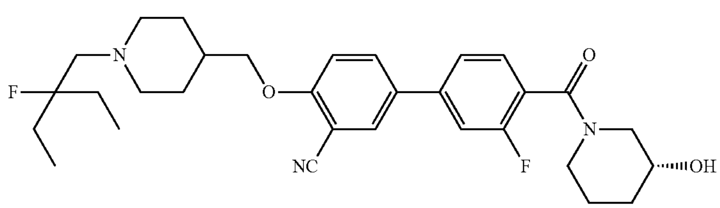 [SMILES: CCC(F)(CC)CN1CCC(COc2ccc(-c3ccc(C(=O)N4CCC[C@@H](O)C4)c(F)c3)cc2C#N)CC1] |
| 1002 | 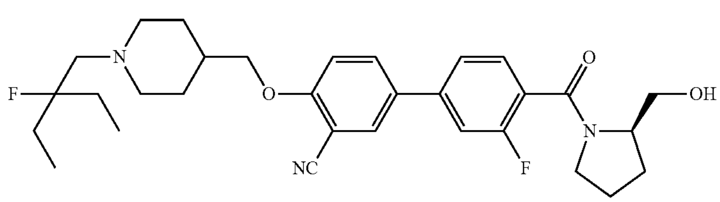 [SMILES: CCC(F)(CC)CN1CCC(COc2ccc(-c3ccc(C(=O)N4CCC[C@@H]4CO)c(F)c3)cc2C#N)CC1] |

TABLE 177-continued

| Compound | Structure |
|---|---|
| 1003 | 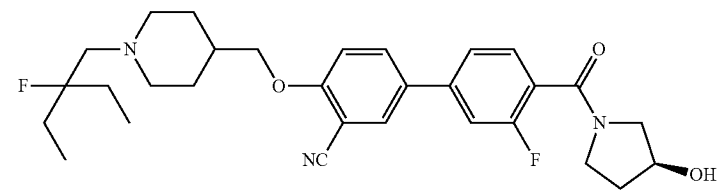 [SMILES: CCC(F)(CC)CN1CCC(COc2ccc(-c3ccc(C(=O)N4CC[C@H](O)C4)c(F)c3)cc2C#N)CC1] |
| 1004 | 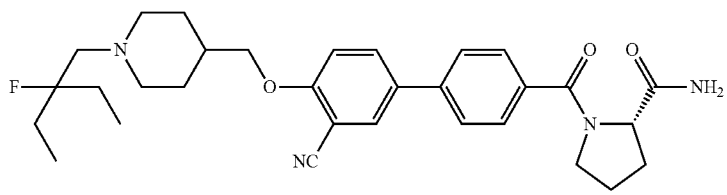 |
| 1005 | 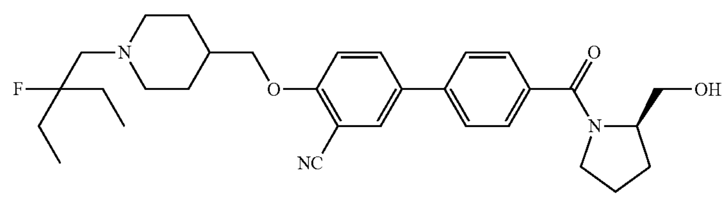 [SMILES: CCC(F)(CC)CN1CCC(COc2ccc(-c3ccc(C(=O)N4CCC[C@@H]4CO)cc3)cc2C#N)CC1] |
| 1006 | 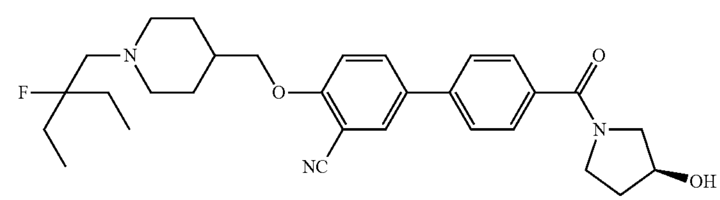 [SMILES: CCC(F)(CC)CN1CCC(COc2ccc(-c3ccc(C(=O)N4CC[C@H](O)C4)cc3)cc2C#N)CC1] |
| 1007 | 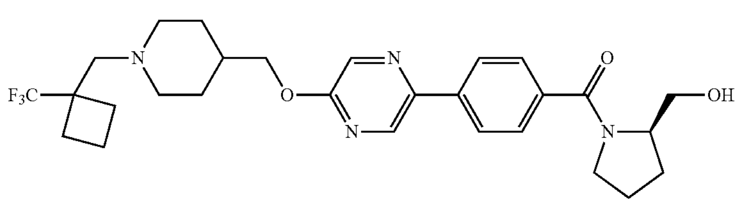 [SMILES: O=C(c1ccc(-c2cnc(OCC3CCN(CC4(C(F)(F)F)CCC4)CC3)cn2)cc1)N1CCC[C@@H]1CO] |
| 1008 | 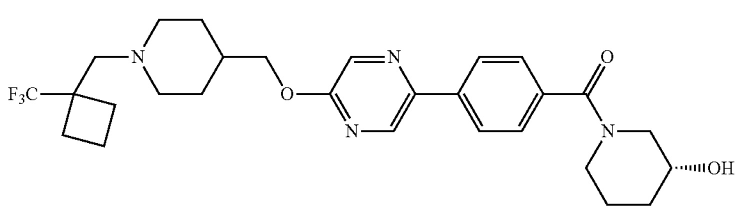 [SMILES: O=C(c1ccc(-c2cnc(OCC3CCN(CC4(C(F)(F)F)CCC4)CC3)cn2)cc1)N1CCC[C@@H](O)C1] |
| 1009 | 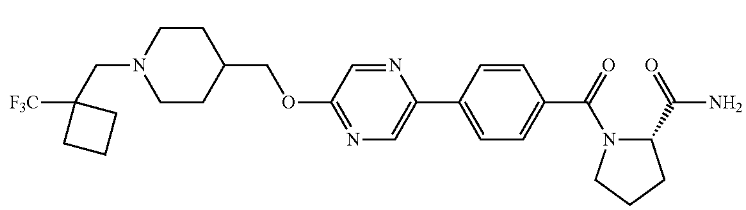 [SMILES: NC(=O)[C@@H]1CCCN1C(=O)c1ccc(-c2cnc(OCC3CCN(CC4(C(F)(F)F)CCC4)CC3)cn2)cc1] |

TABLE 177-continued

| Compound | Structure |
|---|---|
| 1010 | 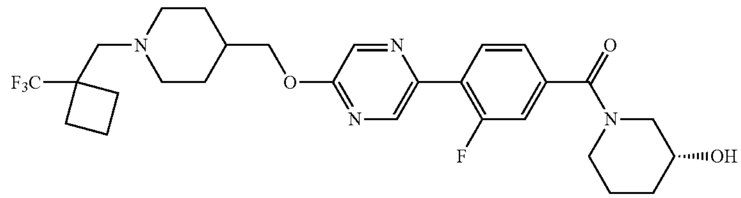 [SMILES: O=C(c1ccc(-c2cnc(OCC3CCN(CC4(C(F)(F)F)CCC4)CC3)cn2)c(F)c1)N1CCC[C@@H](O)C1] |
| 1011 | 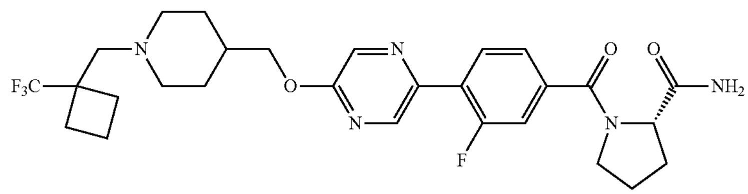 [SMILES: NC(=O)[C@@H]1CCCN1C(=O)c1ccc(-c2cnc(OCC3CCN(CC4(C(F)(F)F)CCC4)CC3)cn2)c(F)c1] |
| 1012 | 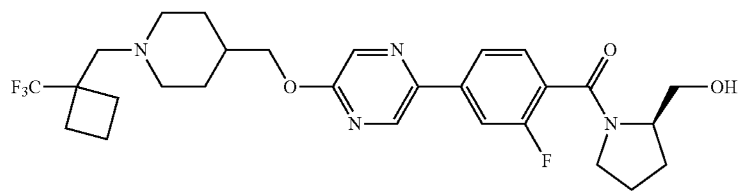 [SMILES: O=C(c1ccc(-c2cnc(OCC3CCN(CC4(C(F)(F)F)CCC4)CC3)cn2)cc1F)N1CCC[C@@H]1CO] |
| 1013 | 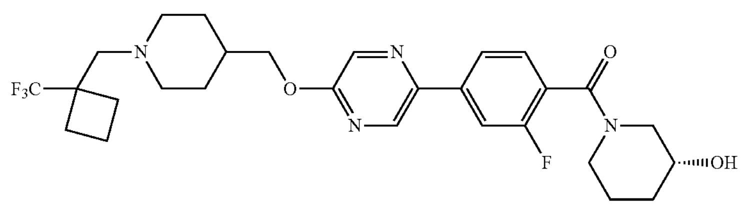 [SMILES: O=C(c1ccc(-c2cnc(OCC3CCN(CC4(C(F)(F)F)CCC4)CC3)cn2)cc1F)N1CCC[C@@H](O)C1] |
| 1014 | 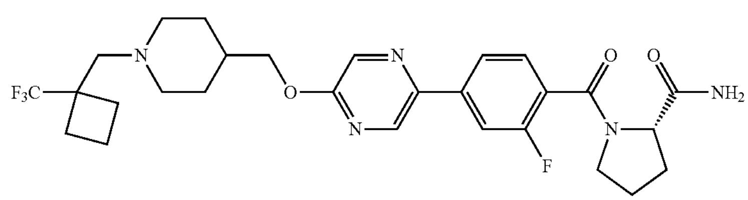 |
| 1015 | 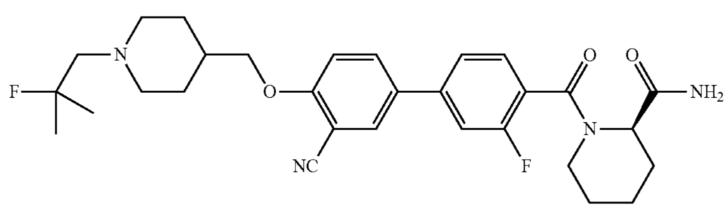 [SMILES: CC(C)(F)CN1CCC(COc2ccc(-c3ccc(C(=O)N4CCCC[C@@H]4C(N)=O)c(F)c3)cc2C#N)CC1] |
| 1016 | 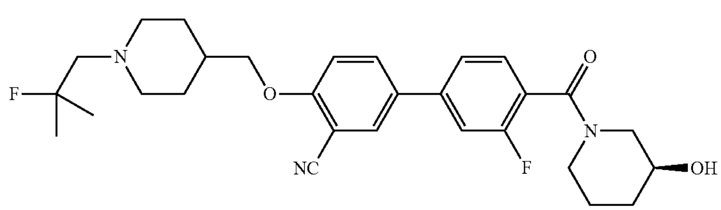 [SMILES: CC(C)(F)CN1CCC(COc2ccc(-c3ccc(C(=O)N4CCC[C@H](O)C4)c(F)c3)cc2C#N)CC1] |

TABLE 177-continued

| Compound | Structure |
|---|---|
| 1017 | 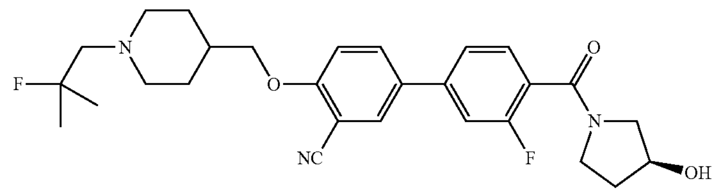 |
| 1018 | 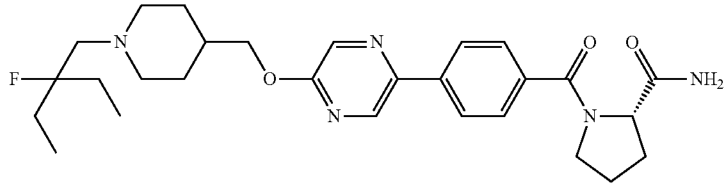 [SMILES: CCC(F)(CC)CN1CCC(COc2cnc(-c3ccc(C(=O)N4CCC[C@H]4C(N)=O)cc3)cn2)CC1] |

TABLE 178

| Compound | Structure |
|---|---|
| 1020 | 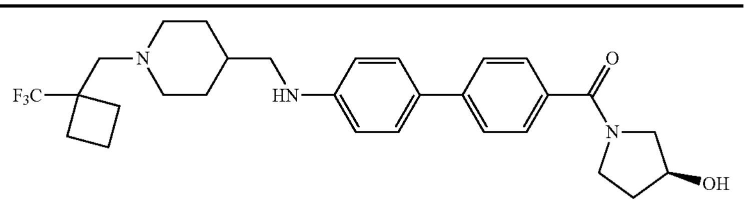 |
| 1021 | 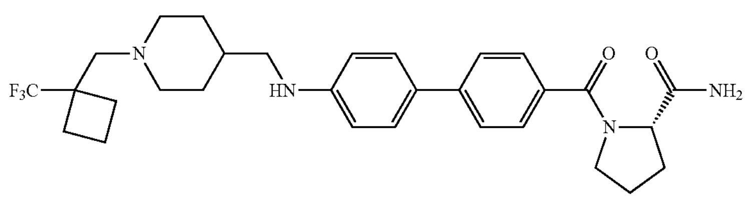 |
| 1022 | 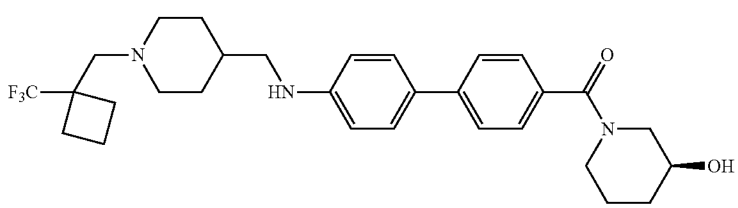 [SMILES: O=C(c1ccc(-c2ccc(NCC3CCN(CC4(C(F)(F)F)CCC4)CC3)cc2)cc1)N1CCC[C@H](O)C1] |
| 1023 | 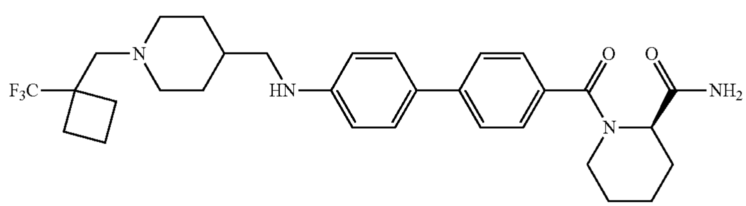 [SMILES: NC(=O)[C@H]1CCCCN1C(=O)c1ccc(-c2ccc(NCC3CCN(CC4(C(F)(F)F)CCC4)CC3)cc2)cc1] |
| 1024 | 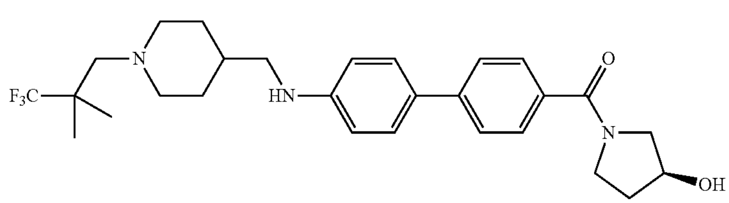 [SMILES: CC(C)(CN1CCC(CNc2ccc(-c3ccc(C(=O)N4CC[C@H](O)C4)cc3)cc2)CC1)C(F)(F)F] |

TABLE 178-continued

| Compound | Structure |
|---|---|
| 1025 | 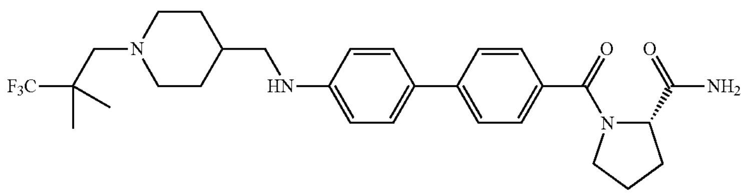 [SMILES: CC(C)(CN1CCC(CNc2ccc(-c3ccc(C(=O)N4CCC[C@H]4C(N)=O)cc3)cc2)CC1)C(F)(F)F] |
| 1026 | 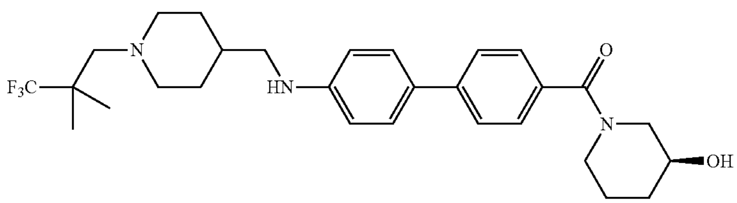 [SMILES: CC(C)(CN1CCC(CNc2ccc(-c3ccc(C(=O)N4CCC[C@H](O)C4)cc3)cc2)CC1)C(F)(F)F] |
| 1028 | 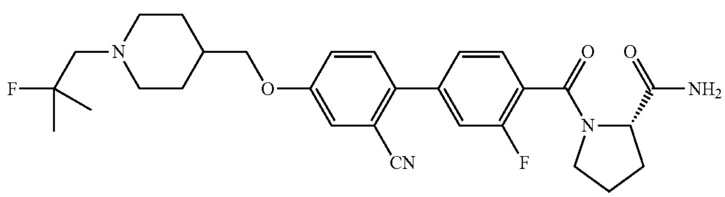 |
| 1029 | 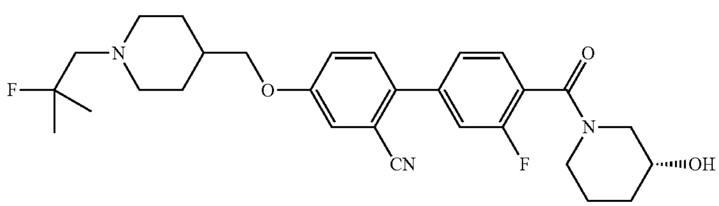 |
| 1030 | 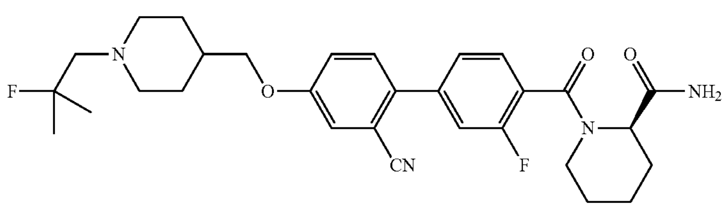 [SMILES: CC(C)(F)CN1CCC(COc2ccc(-c3ccc(C(=O)N4CCCC[C@@H]4C(N)=O)c(F)c3)c(C#N)c2)CC1] |
| 1031 | 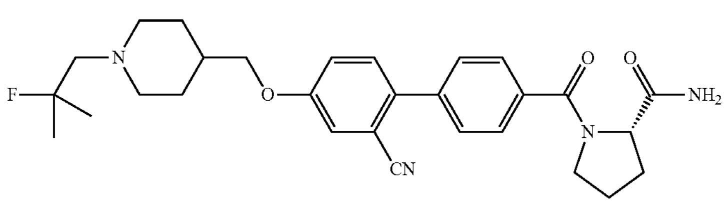 [SMILES: CC(C)(F)CN1CCC(COc2ccc(-c3ccc(C(=O)N4CCC[C@H]4C(N)=O)cc3)c(C#N)c2)CC1] |
| 1032 | 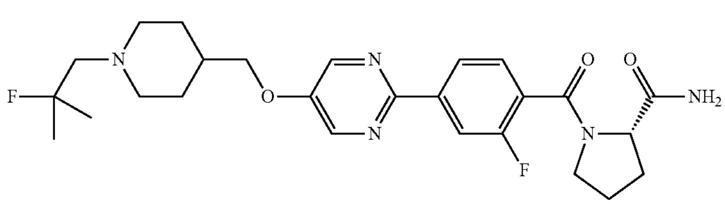 [SMILES: CC(C)(F)CN1CCC(COc2cnc(-c3ccc(C(=O)N4CCC[C@H]4C(N)=O)c(F)c3)nc2)CC1] |

TABLE 178-continued

| Compound | Structure |
|---|---|
| 1033 | 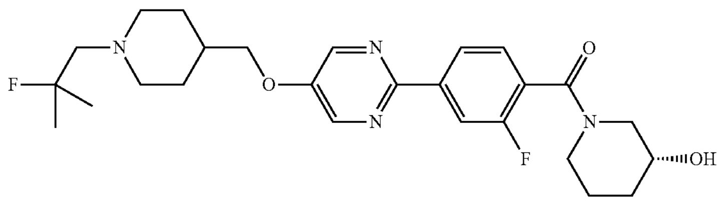 [SMILES: CC(C)(F)CN1CCC(COc2cnc(-c3ccc(C(=O)N4CCC[C@@H](O)C4)c(F)c3)nc2)CC1] |
| 1034 | 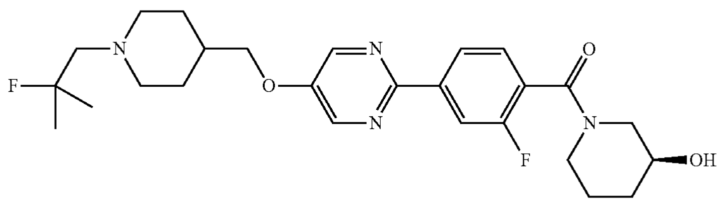 [SMILES: CC(C)(F)CN1CCC(COc2cnc(-c3ccc(C(=O)N4CCC[C@H](O)C4)c(F)c3)nc2)CC1] |
| 1035 | 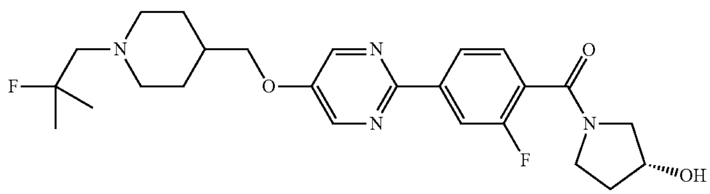 [SMILES: CC(C)(F)CN1CCC(COc2cnc(-c3ccc(C(=O)N4CC[C@@H](O)C4)c(F)c3)nc2)CC1] |
| 1036 | 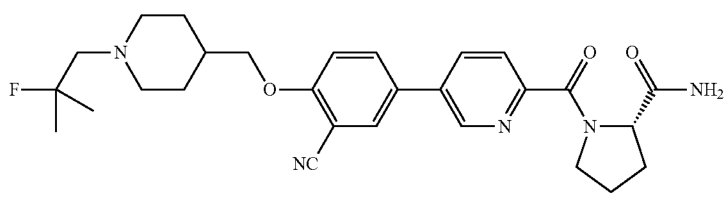 [SMILES: CC(C)(F)CN1CCC(COc2ccc(-c3ccc(C(=O)N4CCC[C@H]4C(N)=O)nc3)cc2C#N)CC1] |
| 1037 | 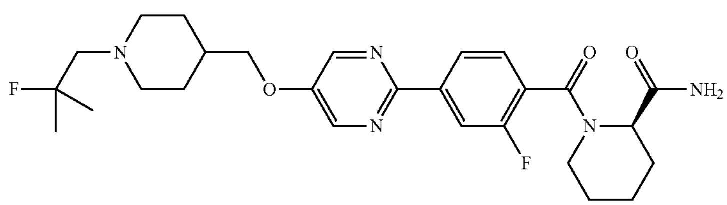 [SMILES: CC(C)(F)CN1CCC(COc2cnc(-c3ccc(C(=O)N4CCCC[C@@H]4C(N)=O)c(F)c3)nc2)CC1] |
| 1038 | 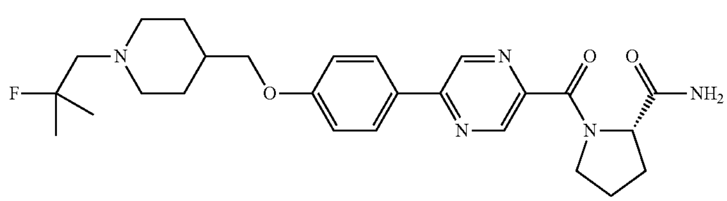 |
| 1051 | 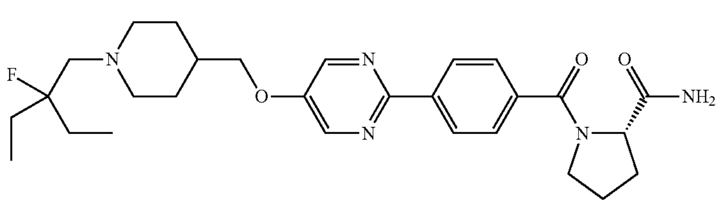 [SMILES: CCC(F)(CC)CN1CCC(COc2cnc(-c3ccc(C(=O)N4CCC[C@H]4C(N)=O)cc3)nc2)CC1] |

TABLE 178-continued

| Compound | Structure |
|---|---|
| 1052 | (structure) |

TABLE 179

| Compound | Structure |
|---|---|
| 1053 | (structure) |
| 1054 | (structure) |
| 1055 | (structure) |
| 1056 | (structure) |
| 1057 | (structure) |

TABLE 179-continued
| Compound | Structure |
|---|---|
| 1067 | 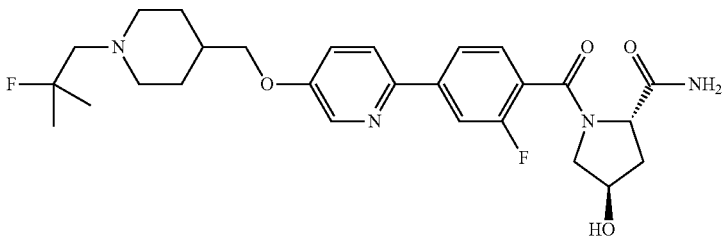 |
| 1072 | 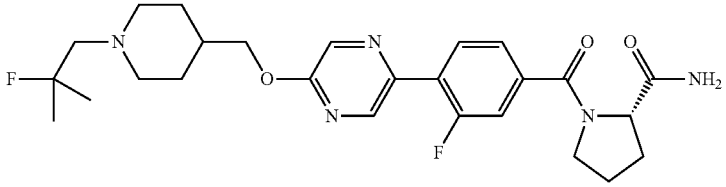 |
| 1073 | 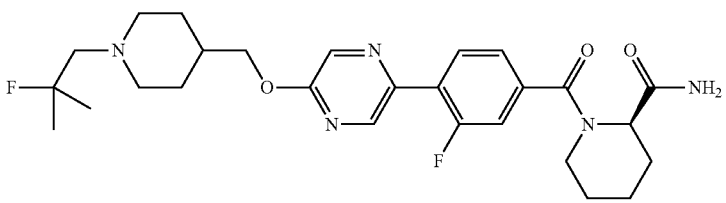 [SMILES: CC(C)(F)CN1CCC(COc2cnc(-c3ccc(C(=O)N4CCCC[C@@H]4C(N)=O)cc3F)cn2)CC1] |
| 1076 | 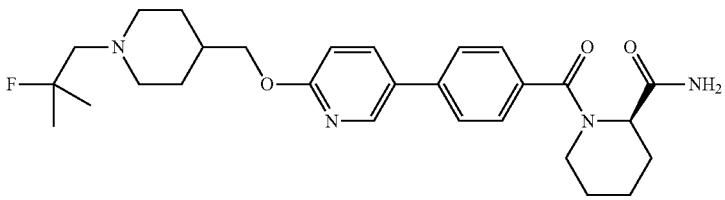 [SMILES: CC(C)(F)CN1CCC(COc2ccc(-c3ccc(C(=O)N4CCCC[C@@H]4C(N)=O)cc3)cn2)CC1] |
| 1077 | 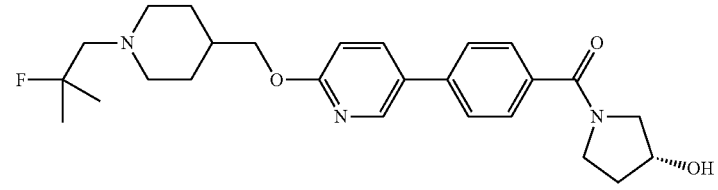 |
| 1078 | 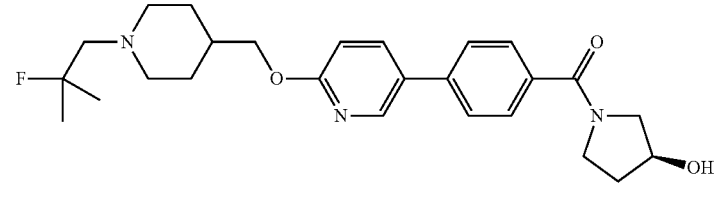 [SMILES: CC(C)(F)CN1CCC(COc2ccc(-c3ccc(C(=O)N4CC[C@@H](O)C4)cc3)cn2)CC1] |
| 1079 | 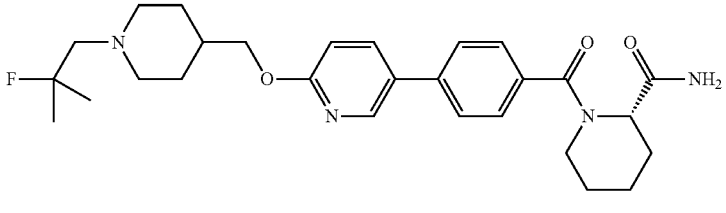 [SMILES: CC(C)(F)CN1CCC(COc2ccc(-c3ccc(C(=O)N4CCCC[C@H]4C(N)=O)cc3)cn2)CC1] |

TABLE 179-continued

| Compound | Structure |
|---|---|
| 1080 | 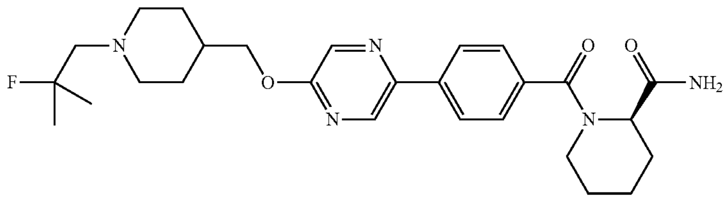 |
| 1081 | 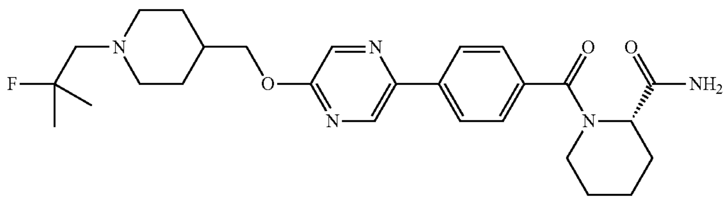 |
| 1082 | 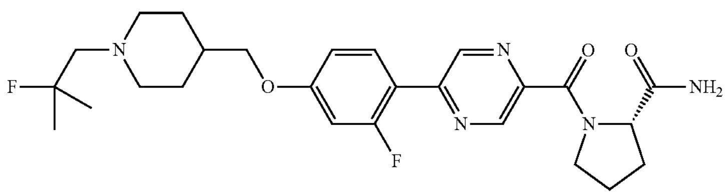 [SMILES: CC(C)(F)CN1CCC(COc2ccc(-c3cnc(C(=O)N4CCC[C@H]4C(N)=O)cn3)c(F)c2)CC1] |
| 1097 | 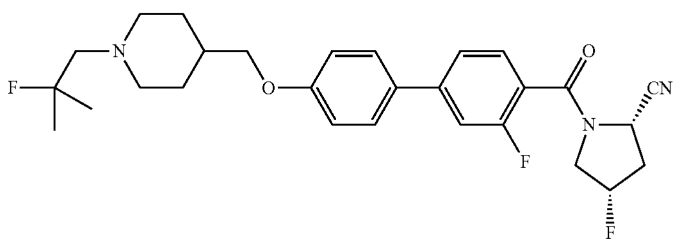 [SMILES: CC(C)(F)CN1CCC(COc2ccc(-c3ccc(C(=O)N4C[C@@H](F)C[C@H]4C#N)c(F)c3)cc2)CC1] |
| 1098 | 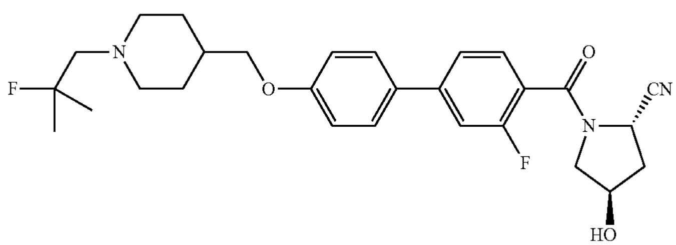 [SMILES: CC(C)(F)CN1CCC(COc2ccc(-c3ccc(C(=O)N4C[C@H](O)C[C@H]4C#N)c(F)c3)cc2)CC1] |
| 1099 | 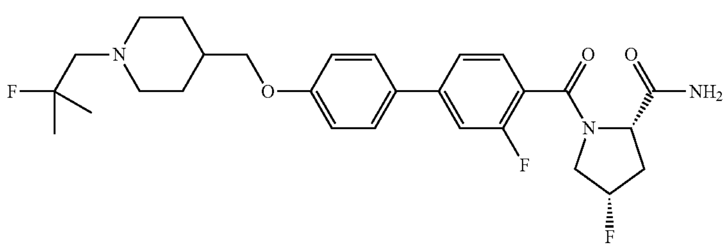 [SMILES: CC(C)(F)CN1CCC(COc2ccc(-c3ccc(C(=O)N4C[C@@H](F)C[C@H]4C(N)=O)c(F)c3)cc2)CC1] |
| 1100 | 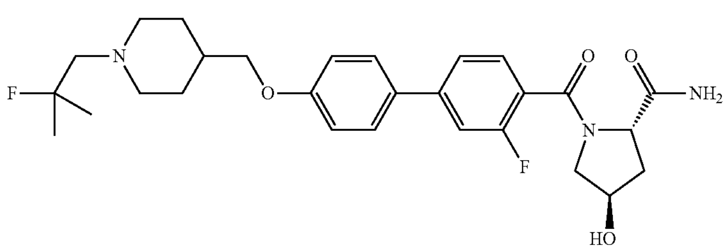 [SMILES: CC(C)(F)CN1CCC(COc2ccc(-c3ccc(C(=O)N4C[C@H](O)C[C@H]4C(N)=O)c(F)c3)cc2)CC1] |

TABLE 179-continued
| Compound | Structure |
|---|---|
| 1115 | 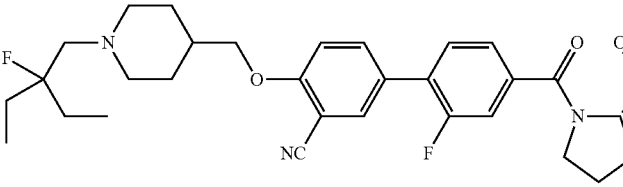 |
TABLE 180
| Compound | Structure |
|---|---|
| 1119 | 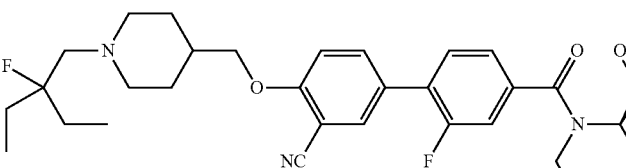 |
| 1120 | 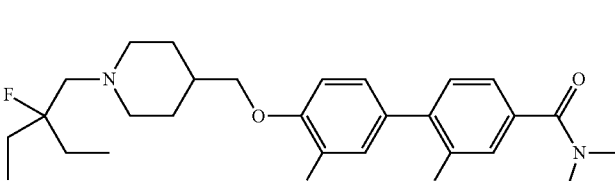 |
| 1121 | 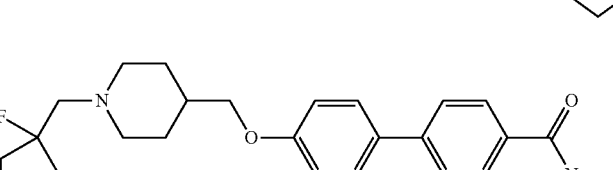 |
| 1123 | 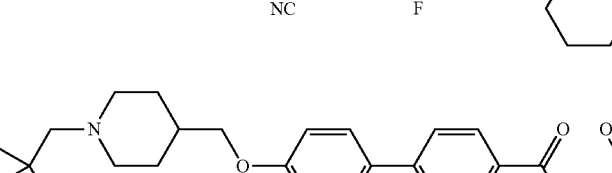 |
| 1124 | 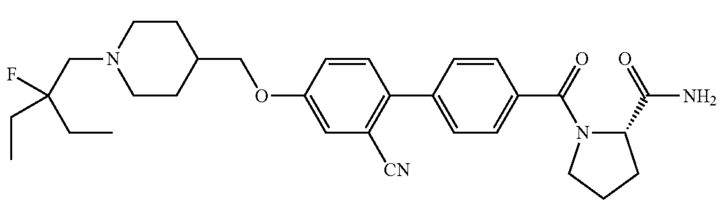 |

TABLE 180-continued

| Compound | Structure |
|---|---|
| 1125 | (structure: F-substituted alkyl-piperidine-CH2-O-phenyl(CN)-phenyl-C(=O)-piperidine-C(=O)NH2) |
| 1126 | (structure: F-substituted alkyl-piperidine-CH2-O-phenyl(CN)-phenyl-C(=O)-piperidine-OH) |

Protocol of Experiment: Activity Test of the Compound of the Present Invention

Using the commercial product as a control group, the treatment activities of the compounds of formula 1 according to the present invention for type II diabetes were tested, and the safety of the compound of formula 1 was also tested.

Experimental Example 1. Activity Test for the GPR 119 Receptor (In Vitro)

1. Human GPR119 Receptor Cell

As a human GPR119 receptor expression cell for this test, the cell line "GeneBLAzer™ T-Rex GPR 119 CHO-K1 DA cells" that is commercially available from Invitrogen, was used. The cell was incubated in the DMEM media containing 1% dialyzed fetal bovine serum etc. The cell incubator was kept at constant temperature and constant humidity of 37° C., 5% $CO_2$.

2. Activity Test for Human GPR119 Receptor

The human GPR119 receptor expressing cell was used to this test. Each of test compounds was added to be final concentrations of 0.1, 1, 10 µM in 96 well and tested in duplicate. A fixed amount of cell was added to each well of 96 well separately, and then treated with the test compound for 5 hours. After treatment of color development agent for 2 hours, the fluorescence value was determined with plate reader. To the luminous wavelength of control well, which was not treated with the agonist sample, but in which only a vehicle (i.e., cell) was contained, the ratio of the luminous wavelength of test well, which was treated with the agonist sample, was calculated, and then converted to obtain % value.

3. Statistical Processing

All the results were expressed as mean±SD, and each test groups and the control group were compared using student's t-test to adjudge the effects of each test groups.

4. Result of Activity Test for Human GPR119

TABLE 181

Result of activity test for human GPR119

| Compound | Conc.(µM) | % Activation |
|---|---|---|
| MBX-2982 | 0.1 | 180 |
|  | 1 | 206 |
|  | 10 | 200 |
| 500 | 0.1 | 214 |
|  | 1 | 298 |
|  | 10 | 310 |
| 516 | 0.1 | 185 |
|  | 1 | 243 |
|  | 10 | 289 |
| 517 | 0.1 | 192 |
|  | 1 | 244 |
|  | 10 | 291 |
| 542 | 0.1 | 256 |
|  | 1 | 347 |
|  | 10 | 376 |
| 551 | 0.1 | 135 |
|  | 1 | 232 |
|  | 10 | 288 |
| 553 | 0.1 | 149 |
|  | 1 | 204 |
|  | 10 | 253 |
| 554 | 0.1 | 141 |
|  | 1 | 219 |
|  | 10 | 279 |
| 555 | 0.1 | 190 |
|  | 1 | 269 |
|  | 10 | 272 |
| 581 | 0.1 | 254 |
|  | 1 | 344 |
|  | 10 | 273 |
| 586 | 0.1 | 213 |
|  | 1 | 310 |
|  | 10 | 379 |
| 587 | 0.1 | 227 |
|  | 1 | 288 |
|  | 10 | 297 |
| 628 | 0.1 | 138 |
|  | 1 | 210 |
|  | 10 | 257 |

TABLE 181-continued

Result of activity test for human GPR119

| Compound | Conc.(μM) | % Activation |
|---|---|---|
| 629 | 0.1 | 199 |
|  | 1 | 229 |
|  | 10 | 269 |
| 635 | 0.1 | 265 |
|  | 1 | 305 |
|  | 10 | 239 |
| 641 | 0.1 | 167 |
|  | 1 | 220 |
|  | 10 | 246 |
| 644 | 0.1 | 213 |
|  | 1 | 295 |
|  | 10 | 294 |
| 658 | 0.1 | 289 |
|  | 1 | 248 |
|  | 10 | 311 |
| 720 | 0.1 | 160 |
|  | 1 | 228 |
|  | 10 | 262 |
| 722 | 0.1 | 198 |
|  | 1 | 269 |
|  | 10 | 261 |
| 768 | 0.1 | 162 |
|  | 1 | 260 |
|  | 10 | 313 |
| 770 | 0.1 | 228 |
|  | 1 | 280 |
|  | 10 | 310 |
| 794 | 0.1 | 256 |
|  | 1 | 296 |
|  | 10 | 252 |
| 829 | 0.1 | 257 |
|  | 1 | 313 |
|  | 10 | 303 |
| 837 | 0.1 | 251 |
|  | 1 | 296 |
|  | 10 | 306 |
| 886 | 0.1 | 164 |
|  | 1 | 241 |
|  | 10 | 246 |
| 944 | 0.1 | 180 |
|  | 1 | 291 |
|  | 10 | 310 |
| 950 | 0.1 | 191 |
|  | 1 | 232 |
|  | 10 | 307 |
| 999 | 0.1 | 145 |
|  | 1 | 264 |
|  | 10 | 365 |
| 1000 | 0.1 | 311 |
|  | 1 | 367 |
|  | 10 | 374 |
| 1009 | 0.1 | 235 |
|  | 1 | 314 |
|  | 10 | 340 |
| 1013 | 0.1 | 410 |
|  | 1 | 490 |
|  | 10 | 426 |
| 1028 | 0.1 | 187 |
|  | 1 | 348 |
|  | 10 | 402 |
| 1032 | 0.1 | 321 |
|  | 1 | 459 |
|  | 10 | 430 |
| 1037 | 0.1 | 223 |
|  | 1 | 478 |
|  | 10 | 439 |
| 1055 | 0.1 | 407 |
|  | 1 | 474 |
|  | 10 | 408 |
| 1119 | 0.1 | 406 |
|  | 1 | 428 |
|  | 10 | 482 |

In Table 181, "% activation" shows the extent that human GPR119 receptor is activated by test compounds of each concentration. The higher value of % activation means the more excellent activity. The maximum % activation of control compound (MBX-2982) is 200, and the most of the compounds of the present invention show more than 200 of % activation. The compounds 1013 and 1028 show the excellent activity with 490 and 402 of % activation respectively.

Experimental Example 2. Animal Test of Activity for the GPR 119 Receptor in Normal Mouse (In Vivo)

1. Method of Glucose Tolerance Test

Male C57/6J Jms mice of 6-7 weeks of age were fasted for 16 hours before the start of glucose tolerance test. The experimental animal groups consist of:
A. a vehicle group (10% EtOH, 20% HPBCD in saline),
B. a positive control group administered with MBX-2982 (10 mg/kg), and
C. test groups administered with compound 516, 581, 586, 612, 640, 644 or etc. (10 mg/kg).

Before compound administration, that is, at 0 hour, whole blood glucose level was determined using a Glucometer (ACCU-CHEK, Roche). At 30 minutes after compound administration, whole blood glucose level was determined once again, and 20% glucose (2 g/kg/10 mL) was administered orally. Whole blood glucose level was determined at 20, 40, 60, 80, and 120 minutes after 20% glucose administration. Area under the curve (AUC) of whole blood glucose level was obtained using GraphPad Prism 5.0. The effect of glucose tolerance was adjudged with the corrected area under the curve (cAUC), on which the base value of glucose area under the curve was excluded.

2. Result of Glucose Tolerance Test

In Table 182, "Decrease % of AUC" shows the extent that whole blood glucose level is decreased by the test compounds administrated after oral administration of glucose into normal mouse. The higher value of decrease % of AUC means the more excellent drop effect in blood glucose level. The control compound (MBX-2982) shows only 24% of the excellent drop effect in blood glucose level, and some of the compounds of the present invention show more than 40% of the excellent drop effect in blood glucose level. The compounds 612 and 1028 show the very excellent drop effect in blood glucose level with 50 and 46% respectively.

TABLE 182

Result of glucose tolerance test

|  | Decrease % of AUC at 10 mg/kg |
|---|---|
| MBX-2982 | 24 |
| Compound 516 | 43 |
| Compound 581 | 50 |
| Compound 586 | 34 |
| Compound 612 | 50 |
| Compound 640 | 52 |
| Compound 644 | 39 |
| Compound 658 | 38 |
| Compound 768 | 40 |
| Compound 770 | 47 |
| Compound 944 | 32 |
| Compound 950 | 39 |
| Compound 999 | 39 |
| Compound 1000 | 38 |
| Compound 1028 | 46 |
| Compound 1032 | 31 |
| Compound 1037 | 42 |

Experimental Example 3. Disease Model Animal Test of Activity for the GPR 119 Receptor (DIO Mouse)

1. Method of Glucose Tolerance Test

Male C57BL/6J mice of 6.5 weeks of age were taken with high fat diet (60% kcal, Research Diets) for 12 weeks. The obtained male diet induced obesity (DIO) C57BL/6J mice of 18.5 weeks of age were fasted for 16 hours before the start of glucose tolerance test. The experimental animal groups consist of:
- A. a vehicle group (10% EtOH, 20% HPBCD in D.W.),
- B. a positive control group administered with Sitagliptin (30 mg/kg), and
- C. test groups administered with compound 770 and Compound 1028 (10, 30 mgkg and combination administration with sitagliptin 30 mg/kg).

Each test compounds was administered at the same time of every day for 2 weeks. Before the compound administration, whole blood glucose level was determined using a Glucometer (ACCU-CHEK, Roche). At 30 minutes after compound administration, whole blood glucose level was determined once again, and 20% glucose (2 g/kg/10 mL) was administered orally. Whole blood glucose level was determined at 20, 40, 60, 80, and 120 minutes after 20% glucose administration. Area under the curve (AUC) of whole blood glucose level was obtained using GraphPad Prism 5.0. The effect of glucose tolerance was adjudged with the corrected area under the curve (cAUC), on which the base value of glucose area under the curve was excluded.

2. Measurement of Whole Blood Glucose Level Change

Whole blood glucose level was measured at about 1 hour after test compound administration from caudal vein of mice using Glucometer. Whole blood glucose level was determined three times totally, that is, (1) at prior to the start of drug administration, (2) after 1 week from the start of 2-weeks drug administration, and (3) after the termination of 2-weeks drug administration. Each determination was started with 20% glucose administration, and then perfomed at 20, 40, 60, 80, and 120 minutes after 20% glucose administration.

3. Result of Glucose Tolerance Test (DIO)

Table 183 shows the extent that whole blood glucose level is decreased by the test compounds administrated after oral administration of glucose into disease model mouse (DIO mouse). The higher value means the more excellent drop effect in blood glucose level. The effect was tested, separately, after administration of test compound alone and after co-administration of test compound with Sitagliptin, which is a DPP IV inhibitor. As a result, the compounds alone of the present invention show more than 20% of the excellent drop effect in blood glucose level, and the co-administration of the compound of the present invention with Sitagliptin show also the excellent effect. The compound 1028 shows 28.5% for alone-administration and 32.3% for co-administration.

TABLE 183

| Group | Whole Blood Glucose Level Change (%) by drug administration | | |
|---|---|---|---|
| | 0 week | 1 week | 2 weeks |
| Sitagliptin (30 mpk) | 0 | 25.5 | 31.7 |
| Compound 770 (10 mpk) | 0 | 22.9 | 24.0 |
| Compound 770 (30 mpk) | 0 | 25.5 | 26.6 |

TABLE 183-continued

| Group | Whole Blood Glucose Level Change (%) by drug administration | | |
|---|---|---|---|
| | 0 week | 1 week | 2 weeks |
| Compound 770 (30 mpk) + Sitagliptin (30 mpk) | 0 | 26.7 | 31.6 |
| Compound 1028 (10 mpk) | 0 | 22.5 | 26.5 |
| Compound 1028 (30 mpk) | 0 | 28.5 | 29.0 |
| Compound 1028 (30 mpk) + Sitagliptin (30 mpk) | 0 | 32.3 | 30.0 |

The invention claimed is:

1. A piperidine derivative of the following formula 1, stereoisomers thereof or pharmaceutically acceptable salts thereof:

[Formula 1]

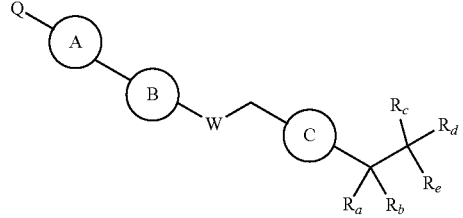

wherein

W is O or N—$R_h$;

$R_a$, $R_b$ and $R_h$ are each independently H or $C_{1-3}$ alkyl;

$R_c$ is —F or —$C_{1-3}$ hyperfluoride alkyl;

$R_d$ and $R_e$ are each independently selected from the group consisting of H, halogen, and —$C_{1-5}$ alkyl or $R_d$ and $R_e$ are combined to form a —$C_{3-7}$ cycloalkyl;

is selected from the group consisting of:

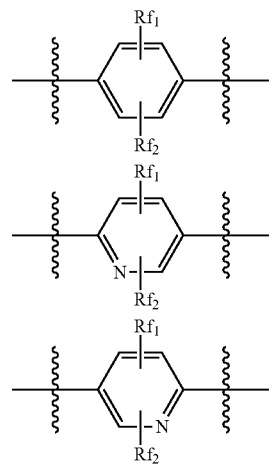

-continued

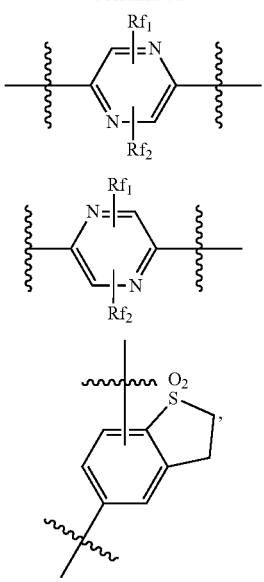

wherein Rf₁ and Rf₂ are each independently H, halogen, or —CN;

B is selected from the group consisting of:

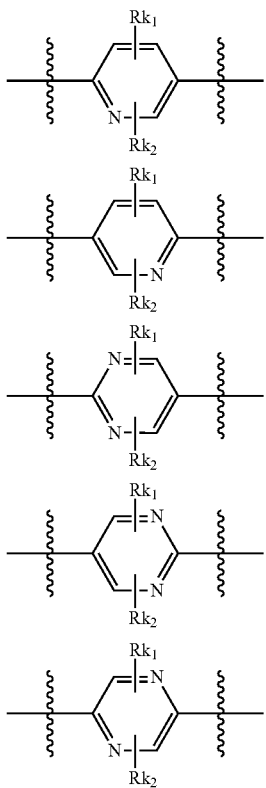

-continued

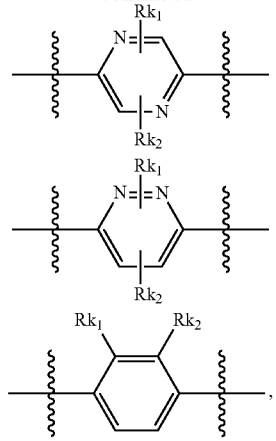

wherein Rk₁ and Rk₂ are each independently H, CN, halogen or $C_{1-5}$ alkyl(OH);

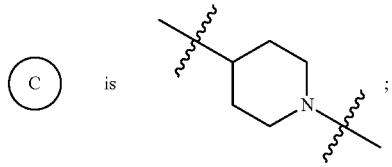

Q is $C(O)NR_2R_3$,
wherein
R₂ and R₃ together with the N atoms to which they are bonded may form a 5- or 6-membered heterocyclic non-aromatic ring-compound further optionally having 0 to 2 members selected independently from the group consisting of N, O, S and C(O), wherein the heterocyclic non-aromatic ring compound may be substituted with Rx₁ and Rx₂,
wherein Rx₁ is $C(O)NH_2$; and
Rx₂ is H, —OH, halogen, —CN, —CF₃, —$C_{1-5}$ alkyl, —$C_{1-5}$ alkyl(OH), —$C_{1-5}$ alkyl-O—$C_{1-5}$ alkyl, —C(O)NR₄R₅, —C(O)R₄, —C(O)OR₄, —S(O)₂R₄,

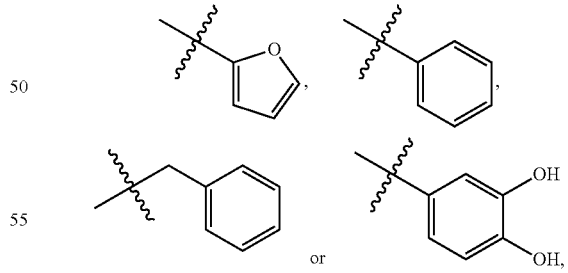

[wherein R₄ and R₅ are each independently H, —$C_{1-5}$ alkyl or —$C_{3-7}$ cycloalkyl].

2. The piperidine derivative, stereoisomers thereof or pharmaceutically acceptable salts thereof according to claim 1, wherein
W is O;
R_a and R_b are each independently H;
R_c is —F or —CF₃;
R_d and R_e are each independently —$C_{1-5}$ alkyl, Ⓐ is selected from the group consisting of:

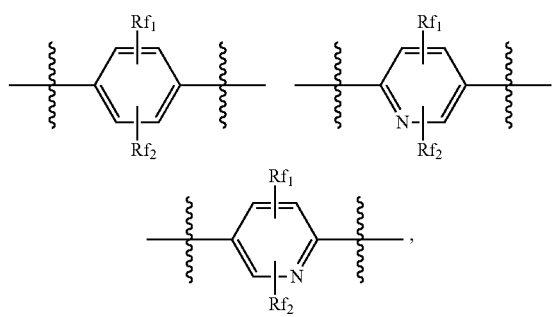

wherein $Rf_1$ and $Rf_2$ are each independently H, halogen or —CN;

Ⓑ is selected from the group consisting of:

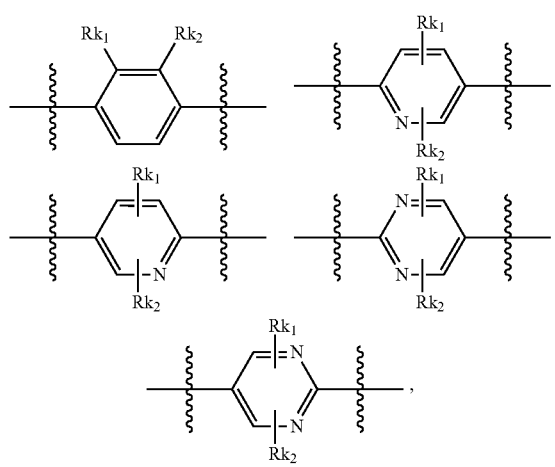

wherein $Rk_1$ and $Rk_2$ are each independently H, CN, halogen, or —$C_{1-5}$ alkyl(OH);

Ⓒ is

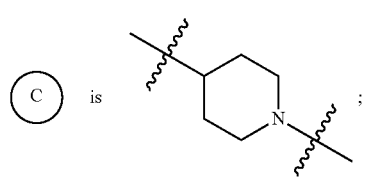

Q is $C(O)NR_2R_3$ $R_2$ and $R_3$ together with the N atoms to which they are bonded may form a 5- or 6-membered heterocyclic or non-aromatic ring compound further optionally having 0 to 2 members selected independently from the group consisting of N, O, S and C(O), wherein the heterocyclic non-aromatic ring compound may be substituted with $Rx_1$ and $Rx_2$, wherein $Rx_1$ is —$C(O)NH_2$; and $Rx_2$ is H, —OH, halogen, —CN, —$CF_3$, —$C_{1-5}$ alkyl, —$C_{1-5}$ alkyl(OH), —$C_{1-5}$ alkyl-O—$C_{1-5}$ alkyl, —$C(O)NR_4R_5$, —$C(O)R_4$, —$C(O)OR_4$, or —$S(O)_2R_4$,

[wherein $R_4$ and $R_5$ are each independently H, —$C_{1-5}$ alkyl or —$C_{3-7}$ cycloalkyl.

3. The piperidine derivative, stereoisomers thereof or pharmaceutically acceptable salts thereof according to claim 1, wherein W is O;

$R_a$ and $R_b$ are each independently H;

$R_c$ is —F or —$CF_3$;

$R_d$ and $R_e$ are each independently —$C_{1-5}$ alkyl, or $R_d$ and $R_e$ are combined to form —$C_{3-7}$ cycloalkyl;

Ⓐ is selected from the group consisting of:

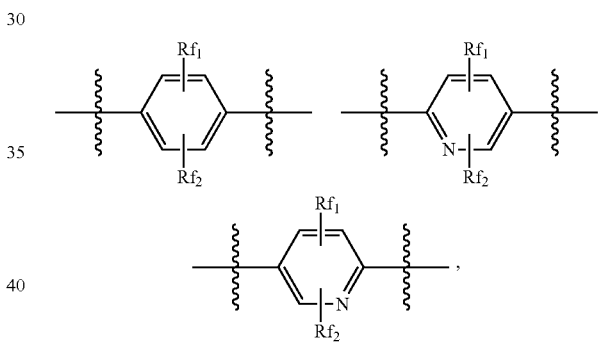

wherein $Rf_1$ and $Rf_2$ are each independently H, halogen- or —CN;

Ⓑ is selected from the group consisting of:

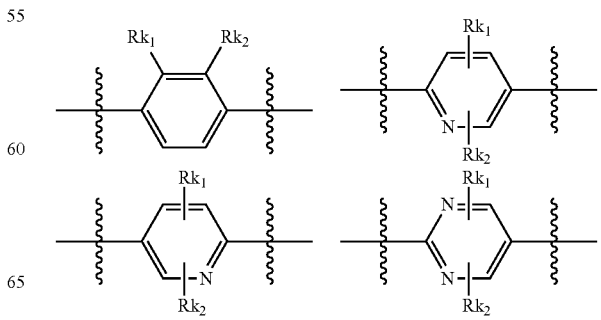

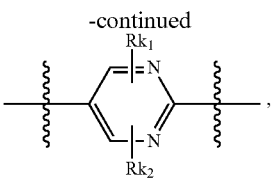

wherein Rk₁ and Rk₂ are each independently H, CN, halogen or —C₁₋₅ alkyl(OH);

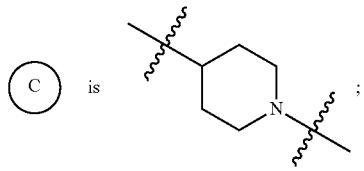

Q is —C(O)NR₂R₃,
wherein R₂ and R₃ together with the N atoms to which they are bonded may form a 5- or 6-membered heterocyclic non-aromatic ring compound further optionally having 0 to 2 members selected independently from the group consisting of N, O, S and C(O),
wherein the heterocyclic non-aromatic ring compound may be substituted with Rx₁ and Rx₂,
wherein Rx₁ is C(O)NH₂; and
Rx₂ is H, —OH, halogen, —CN, —CF₃, —C₁₋₅ alkyl, —C₁₋₅ alkyl(OH), —C₁₋₅ alkyl-O—C₁₋₅ alkyl, —C(O)NR₄R₅, —C(O)R₄, —C(O)OR₄, —S(O)₂R₄ or —OR₄
wherein R₄ and R₅ are each independently H, —C₁₋₅ alkyl or —C₃₋₇ cycloalkyl.

4. The piperidine derivative, stereoisomers thereof or pharmaceutically acceptable salts thereof according to claim 1, wherein
W is O;
Rₐ and Rᵦ are each independently H;
Rᵤ is —F or —CF₃;
R_d and R_e are each independently selected from the group consisting of —CH₃ and —CH₂CH₃

Ⓐ is selected from the group consisting of:

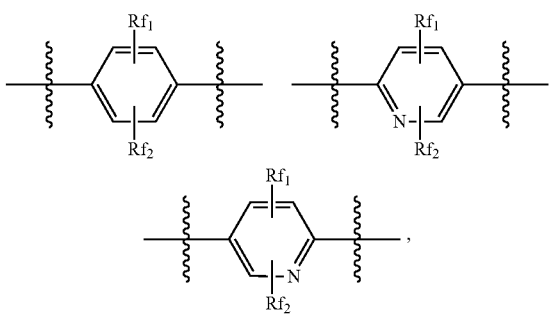

wherein Rf₁ and Rf₂ are each independently H, —F or —CN;

Ⓑ is selected from the group consisting of:

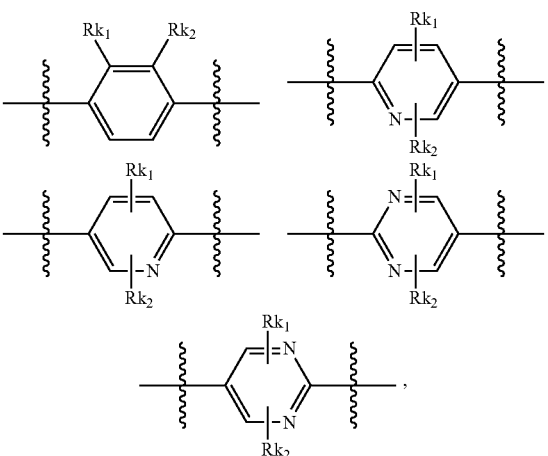

wherein Rk₁ and Rk₂ are each independently H, —F or —CN;

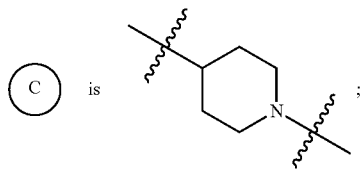

Q is selected from the group consisting of:

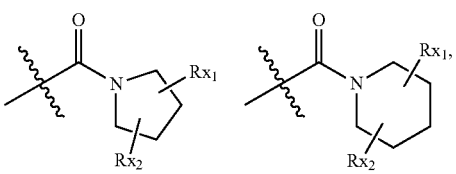

wherein Rx₁ is C(O)NH₂, and
Rx₂ is H, OH, —F, —CN, —CF₃, —CH₂OH or —C(O)NH₂.

5. The piperidine derivative, stereoisomers thereof, pharmaceutically acceptable salts thereof according to claim 1, wherein the piperidine derivative is selected from the group consisting of:
(S)-1-(4'-((1-(2-fluoro-2-methylpropyl)piperidin-4-yl)methoxy)biphenylcarbonyl)pyrrolidine-2-carboxamide;
(S)-1-(4-(6-((1-((1-(trifluoromethyl)cyclobutyl)methyl)piperidin-4-yl)methoxy)pyridin-3-yl)benzoyl)pyrrolidine-2-carboxamide;
(S)-1-(4-(6-((1-((1-(trifluoromethyl)cyclopropyl)methyl)piperidin-4-yl)methoxy)pyridin-3-yl)benzoyl)pyrrolidine-2-carboxamide;
(S)-1-(4'-((1-((1-(trifluoromethyl)cyclobutyl)methyl)piperidin-4-yl)methoxy)biphenylcarbonyl)pyrrolidine-2-carboxamide;

(S)-1-(3-fluoro-4'-((1-(2-fluoro-2-methylpropyl)piperidin-4-yl)methoxy)biphenylcarbonyl)pyrrolidine-2-carboxamide;
(S)-1-(4-(6-((1-(2-fluoro-2-methylpropyl)piperidin-4-yl)methoxy)pyridin-3-yl)benzoyl)pyrrolidine-2-carboxamide;
(S)-1-(4'-((1-(2-fluoropentyl)piperidin-4-yl)methoxy)biphenylcarbonyl)pyrrolidine-2-carboxamide;
(S)-1-(2-fluoro-4-(6-((1-(2-fluoro-2-methylpropyl)piperidin-4-yl)methoxy)pyridin-3-yl)benzoyl)pyrrolidine-2-carboxamide;
(R)-1-(4-(6-((1-((1-(trifluoromethyl)cyclobutyl)methyl)piperidin-4-yl)methoxy)pyridin-3-yl)benzoyl)pyrrolidine-2-carboxamide;
(R)-1-(4'-((1-(2-fluoro-2-methylpropyl)piperidin-4-yl)methoxy)biphenylcarbonyl)pyrrolidine-2-carboxamide;
(S)-1-(4-(5-((1-(2-fluoro-2-methylpropyl)piperidin-4-yl)methoxy)pyridin-2-yl)benzoyl)pyrrolidine-2-carboxamide;
(S)-1-(3-fluoro-4-(5-((1-(2-fluoro-2-methylpropyl)piperidin-4-yl)methoxy)pyridin-2-yl)benzoyl)pyrrolidine-2-carboxamide;
(2S)-1-(2,2'-difluoro-4'-(1-(2-fluoro-2-methylpropyl)piperidin-4-yl)methoxy)biphenylcarbonyl)pyrrolidine-2-carboxamide;
(S)-1-(2'-fluoro-4'-((1-(2-fluoro-2-methylpropyl)piperidin-4-yl)methoxy)biphenylcarbonyl)pyrrolidine-2-carboxamide;
(S)-1-(2',3-difluoro-4'-((1-(2-fluoro-2-methylpropyl)piperidin-4-yl)methoxy)biphenylcarbonyl)pyrrolidine-2-carboxamide;
(S)-1-(3-fluoro-4-(6-((1-((1-(trifluoromethyl)cyclobutyl)methyl)piperidin-4-yl)methoxy)pyridin-3-yl)benzoyl)pyrrolidine-2-carboxamide;
(S)-1-(2-fluoro-4-(6-((1-((1-(trifluoromethyl)cyclobutyl)methyl)piperidin-4-yl)methoxy)pyridin-3-yl)benzoyl)pyrrolidine-2-carboxamide;
(S)-1-(3,3'-difluoro-4'-((1-(2-fluoro-2-methylpropyl)piperidin-4-yl)methoxy)biphenylcarbonyl)pyrrolidine-2-carboxamide;
(S)-1-(2-fluoro-4'-((1-(2-fluoro-2-methylpropyl)piperidin-4-yl)methoxy)biphenylcarbonyl)pyrrolidine-2-carboxamide;
(S)-1-(2,3'-difluoro-4'-((1-(2-fluoro-2-methylpropyl)piperidin-4-yl)methoxy)biphenylcarbonyl)pyrrolidine-2-carboxamide;
1-(4'-((1-(2-fluoro-2-methylpropyl)piperidin-4-yl)methoxy)biphenylcarbonyl)piperidine-4-carboxamide;
1-(4'-((1-(2-fluoro-2-methylpropyl)piperidin-4-yl)methoxy)biphenylcarbonyl)piperidine-2-carboxamide;
1-(4'-((1-(2-fluoro-2-methylpropyl)piperidin-4-yl)methoxy)biphenylcarbonyl)piperidine-2-carboxamide;
(S)-1-(4'-((1-((1-fluorocyclohexyl)methyl)piperidin-4-yl)methoxy)biphenylcarbonyl)pyrrolidine-2-carboxamide;
(S)-1-(2-fluoro-4-(5-((1-(2-fluoro-2-methylpropyl)piperidin-4-yl)methoxy)pyridin-2-yl)benzoyl)pyrrolidine-2-carboxamide;
(S)-1-(4-(6-((1-((1-(trifluoromethyl)cyclopentyl)methyl)piperidin-4-yl)methoxy)pyridin-3-yl)benzoyl)pyrrolidin-2-carboxamide;
(S)-1-(4-(6-((1-((1-(trifluoromethyl)cyclohexyl)methyl)piperidin-4-yl)methoxy)pyridin-3-yl)benzoyl)pyrrolidin-2-carboxamide;

(S)-1-(5-(3-fluoro-4-((1-(2-fluoro-2-methylpropyl)piperidin-4-yl)methoxy)phenyl)picolinoyl)pyrrolidine-2-carboxamide;
1-(3-fluoro-4'-((1-(2-fluoro-2-methylpropyl)piperidin-4-yl)methoxy)biphenylcarbonyl)piperidine-4-carboxamide;
1-(4'((1-((1-(trifluoromethyl)cyclobutyl)methyl)piperidin-4-yl)methoxy)biphenylcarbonyl)piperidine-4-carboxamide;
1-(3'-difluoro-4'-((1-(2-fluoro-2-methylpropyl)piperidin-4-yl)methoxy)biphenylcarbonyl)piperidine-4-carboxamide;
1-(3,3'-difluoro-4'-((1-(2-fluoro-2-methylpropyl)piperidin-4-yl)methoxy)biphenylcarbonyl)piperidine-4-carboxamide;
1-(2'-fluoro-4'-((1-(2-fluoro-2-methylpropyl)piperidin-4-yl)methoxy)biphenylcarbonyl)piperidine-4-carboxamide;
1-(2',3-difluoro-4'-((1-(2-fluoro-2-methylpropyl)piperidin-4-yl)methoxy)biphenylcarbonyl)piperidine-4-carboxamide;
1-(2,2'-difluoro-4'-((1-(2-fluoro-2-methylpropyl)piperidin-4-yl)methoxy)biphenylcarbonyl)piperidine-4-carboxamide;
1-(4-(5-((1-(2-fluoro-2-methylpropyl)piperidin-4-yl)methoxy)pyridin-2-yl)benzoyl)piperidine-4-carboxamide;
1-(2-fluoro-4-(5-((1-(2-fluoro-2-methylpropyl)piperidin-4-yl)methoxy)pyridin-2-yl)benzoyl)piperidine-4-carboxamide;
(R)-1-(3'-fluoro-4'-((1-(2-fluoro-2-methylpropyl)piperidin-4-yl)methoxy)biphenylcarbonyl)piperidine-2-carboxamide;
(S)-1-(3'-fluoro-4'-((1-(2-fluoro-2-methylpropyl)piperidin-4-yl)methoxy)biphenylcarbonyl)piperidine-2-carboxamide;
1-(3-fluoro-4-(5-((1-(2-fluoro-2-methylpropyl)piperidin-4-yl)methoxy)pyridin-2-yl)benzoyl)piperidine-4-carboxamide;
1-(4'-((1-(2-ethyl-2-fluorobutyl)piperidin-4-yl)methoxy)-3-fluorobiphenylcarbonyl)piperidine-4-carboxamide;
(R)-1-(3,3'-difluoro-4'-((1-(2-fluoro-2-methylpropyl)piperidin-4-yl)methoxy)biphenylcarbonyl)piperidine-2-carboxamide;
(S)-1-(3,3'-difluoro-4'-((1-(2-fluoro-2-methylpropyl)piperidin-4-yl)methoxy)biphenylcarbonyl)piperidine-2-carboxamide;
1-(2,3'-difluoro-4'-((1-(2-fluoro-2-methylpropyl)piperidin-4-yl)methoxy)biphenylcarbonyl)piperidine-4-carboxamide;
(R)-1-(2,3'-difluoro-4'-((1-(2-fluoro-2-methylpropyl)piperidin-4-yl)methoxy)biphenylcarbonyl)piperidine-2-carboxamide;
(S)-1-(2,3'-difluoro-4'-((1-(2-fluoro-2-methylpropyl)piperidin-4-yl)methoxy)biphenylcarbonyl)piperidine-2-carboxamide;
(R)-1-(4-(5-((1-(2-fluoro-2-methylpropyl)piperidin-4-yl)methoxy)pyridin-2-yl)benzoyl)piperidine-2-carboxamide;
(R)-1-(2-fluoro-4-(5-((1-(2-fluoro-2-methylpropyl)piperidin-4-yl)methoxy)pyridin-2-yl)benzoyl)piperidine-2-carboxamide;
(R)-1-(2',3-difluoro-4'-((1-(2-fluoro-2-methylpropyl)piperidin-4-yl)methoxy)biphenylcarbonyl)piperidine-2-carboxamide;

(S)-1-(2-fluoro-4-(5-((1-(2-fluoro-2-methylpropyl)piperi-
din-4-yl)methoxy)pyridin-2-yl)benzoyl)piperidine-2-
carboxamide;
(2R)-1-(2,2'-difluoro-4'-((1-(2-fluoro-2-methylpropyl)pi-
peridin-4-yl)methoxy)biphenylcarbonyl)piperidine-2-
carboxamide;
(S)-1-(4-(6-((1-(3,3,3-trifluoro-2,2-dimethylpropyl)pip-
eridin-4-yl)methoxy)pyridin-3-yl)benzoyl)pyrrolidine-
2-carboxamide;
(R)-1-(4'-((1-(2-fluoro-2-methylpropyl)piperidin-4-yl)
methoxy)biphenylcarbonyl)piperidine-2-carboxamide;
(S)-1-(4'-((1-(2-fluoro-2-methylpropyl)piperidin-4-yl)
methoxy)biphenylcarbonyl)piperidine-2-carboxamide;
(S)-1-(2'-fluoro-4'-((1-((1-(trifluoromethyl)cyclobutyl)
methyl)piperidin-4-yl)methoxy)biphenylcarbonyl)pyr-
rolidine-2-carboxamide;
(S)-1-(3'-fluoro-4'-((1-((1-(trifluoromethyl)cyclobutyl)
methyl)piperidin-4-yl)methoxy)biphenylcarbonyl)pyr-
rolidine-2-carboxamide;
(S)-1-(3-fluoro-4'-((1-((1-(trifluoromethyl)cyclobutyl)
methyl)piperidin-4-yl)methoxy)biphenylcarbonyl)pyr-
rolidine-2-carboxamide;
(S)-1-(2,3'-difluoro-4'-((1-((1-(trifluoromethyl)cyclobu-
tyl)methyl)piperidin-4-yl)methoxy)biphenylcarbonyl)
pyrrolidine-2-carboxamide;
(R)-1-(2-fluoro-4-(6-(1 ((1-(2-fluoro-2-methylpropyl)pi-
peridin-4-yl)methoxy)pyridin-3-yl)benzoyl)piperidine-
2-carboxamide;
(S)-1-(2-fluoro-4-(6-((1-(2-fluoro-2-methylpropyl)piperi-
din-4-yl)methoxy)pyridin-3-yl)benzoyl)piperidine-2-
carboxamide;
1-(2-fluoro-4-(6-((1-(2-fluoro-2-methylpropyl)piperidin-
4-yl)methoxy)pyridin-3-yl)benzoyl)piperidine-2-car-
boxamide;
(R)-1-(4'-((1-(2-fluoro-2-methylpropyl)piperidin-4-yl)
methylamino)biphenylcarbonyl)piperidine-2-carbox-
amide;
(2S)-1-(2,6'-difluoro-4'-((1-(2-fluoro-2-methylpropyl)pi-
peridin-4-yl)methoxy)biphenylcarbonyl)piperidine-2-
carboxamide;
(S)-1-(3,6'-difluoro-4'-((1-(2-fluoro-2-methylpropyl)pip-
eridin-4-yl)methoxy)biphenylcarbonyl)piperidine-2-
carboxamide;
(R)-1-(3-fluoro-4-(6-((1-(2-fluoro-2-methylpropyl)pip-
eridin-4-yl)methoxy)pyridin-3-yl)benzoyl)piperidine-
2-carboxamide;
(S)-1-(3-fluoro-4-(6-((1-(2-fluoro-2-methylpropyl)piperi-
din-4-yl)methoxy)pyridin-3-yl)benzoyl)piperidine-2-
carboxamide;
1-(3-fluoro-4-(6-((1-(2-fluoro-2-methylpropyl)piperidin-
4-yl)methoxy)pyridin-3-yl)benzoyl)piperidine-4-car-
boxamide;
(S)-1-(4'-((1-(2-ethyl-2-fluorobutyl)piperidin-4-yl)
methoxy)-3-fluorobiphenylcarbonyl)pyrrolidine-2-car-
boxamide;
(S)-1-(4-((1-(2-fluoro-2-methylpropyl)piperidin-4-yl)
methyl amino)biphenylcarbonyl)pyrrolidine-2-carbox-
amide;
(S)-1-(3-fluoro-4'-((1-(2-fluoro-2-methylpropyl)piperi-
din-4-yl)methylamino)biphenylcarbonyl)pyrrolidine-
2-carboxamide;
(R)-1-(3-fluoro-4'-((1-(2-fluoro-2-methylpropyl)piperi-
din-4-yl)methylamino)biphenylcarbonyl)piperidine-3-
carboxamide;
(R)-1-(3-fluoro-4'-((1-(2-fluoro-2-methylpropyl)piperi-
din-4-yl)methoxy)biphenylcarbonyl)piperidine-2-car-
boxamide;
(R)-1-(2'-fluoro-4'-((1-(2-fluoro-2-methylpropyl)piperi-
din-4-yl)methoxy)biphenylcarbonyl)piperidine-2-car-
boxamide;
(S)-1-(4'-((1-(2-fluoro-2-methylpropyl)piperidin-4-yl)
methoxy)biphenylcarbonyl)piperidine-3-carboxamide;
(S)-1-(3-fluoro-4'-((1-(2-fluoro-2-methylpropyl)piperi-
din-4-yl)methoxy)biphenylcarbonyl)piperidine-2-car-
boxamide;
(S)-1-(2'-fluoro-4'-((1-(2-fluoro-2-methylpropyl)piperi-
din-4-yl)methoxy)biphenylcarbonyl)piperidine-2-car-
boxamide;
(R)-1-(2'-fluoro-4'-((1-((1-(trifluoromethyl)cyclobutyl)
methyl)piperidin-4-yl)methoxy)biphenylcarbonyl)pip-
eridine-2-carboxamide;
(S)-1-(2'-fluoro-4'-((1-((1-(trifluoromethyl)cyclobutyl)
methyl)piperidin-4-yl)methoxy)biphenylcarbonyl)pip-
eridine-2-carboxamide;
(R)-1-(4'-((1-(2-fluoro-2-methylpropyl)piperidin-4-yl)
methoxy)biphenylcarbonyl)piperidine-3-carboxamide;
(R)-1-(3-fluoro-4'-((1-(2-fluoro-2-methylpropyl)piperi-
din-4-yl)methoxy)biphenylcarbonyl)piperidine-3-car-
boxamide;
(R)-1-(2'-fluoro-4'-((1-(2-fluoro-2-methylpropyl)piperi-
din-4-yl)methoxy)biphenylcarbonyl)piperidine-3-car-
boxamide;
(R)-1-(2'-fluoro-4'-((1-((1-(trifluoromethyl)cyclobutyl)
methyl)piperidin-4-yl)methoxy)biphenylcarbonyl)pip-
eridine-3-carboxamide;
(S)-1-(3'-fluoro-4'-((1-((1-(trifluoromethyl)cyclobutyl)
methyl)piperidin-4-yl)methoxy)biphenylcarbonyl)pip-
eridine-3-carboxamide;
(R)-1-(3'-fluoro-4'-((1-((1-(trifluoromethyl)cyclobutyl)
methyl)piperidin-4-yl)methoxy)biphenylcarbonyl)pip-
eridine-3-carboxamide;
(R)-1-(3'-fluoro-4'-((1-((1-(trifluoromethyl)cyclobutyl)
methyl)piperidin-4-yl)methoxy)biphenylcarbonyl)pip-
eridine-2-carboxamide;
(S)-1-(3'-fluoro-4'-((1-((1-(trifluoromethyl)cyclobutyl)
methyl)piperidin-4-yl)methoxy)biphenyl carbonyl)pip-
eridine-2-carboxamide;
(S)-1-(4'-((1-(2-ethyl-2-fluorobutyl)piperidin-4-yl)
methoxy)biphenylcarbonyl)pyrrolidine-2-carboxam-
ide;
(S)-1 (4'-((1-(2-ethyl-2-fluorobutyl)piperidin-4-yl)
methoxy)-2-fluorobiphenylcarbonyl)pyrrolidine-2-car-
boxamide;
(S)-1-(4-(5-((1-(2-ethyl-2-fluorobutyl)piperidin-4-yl)
methoxy)pyridin-2-yl)benzoyl)pyrrolidine-2-carbox-
amide;
(S)-1-(4-(5-((1-(2-ethyl-2-fluorobutyl)piperidin-4-yl)
methoxy)pyridin-2-yl)-2-fluorobenzoyl)pyrrolidine-2-
carboxamide;
(S)-1-(3,3'-difluoro-4'-((1-((1-(trifluoromethyl)cyclobu-
tyl)methyl)piperidin-4-yl)methoxy)biphenylcarbonyl)
pyrrolidine-2-carboxamide;
(S)-1-(5-(3-fluoro-4-((1-((1-(trifluoromethyl)cyclobutyl)
methyl)piperidin-4-yl)methoxy)phenyl)picolinoyl)pyr-
rolidine-2-carboxamide;
(2S)-1-(2,2'-difluoro-4'-((1-((1-(trifluoromethyl)cyclobu-
tyl)methyl)piperidin-4-yl)methoxy)biphenylcarbonyl)
pyrrolidine-2-carboxamide;
(S)-1-(2',3-difluoro-4'-((1-((1-(trifluoromethyl)cyclobu-
tyl)methyl)piperidin-4-yl)methoxy)biphenylcarbonyl)
pyrrolidine-2-carboxamide;
(S)-1-(2-fluoro-4'-((1-((1-(trifluoromethyl)cyclobutyl)
methyl)piperidin-4-yl)methoxy)biphenylcarbonyl)pyr-
rolidine-2-carboxamide;

(S)-1-(4'-((1-((1-fluorocyclobutyl)methyl)piperidin-4-yl)methoxy)biphenylcarbonyl)pyrrolidine-2-carboxamide;

(2S,4R)-4-hydroxy-1-(4-(6-((1-((1-(trifluoromethyl)cyclobutyl)methyl)piperidin-4-yl)methoxy)pyridin-3-yl)benzoyl)pyrrolidine-2-carboxamide;

(2S,4R)-1-(4'-((1-(2-fluoro-2-methylpropyl)piperidin-4-yl)methoxy)biphenylcarbonyl)-4-hydroxypyrrolidine-2-carboxamide;

(S)-1-(5-(2-fluoro-4-((1-(2-fluoro-2-methylpropyl)piperidin-4-yl)methoxy)phenyl)picolinoyl)pyrrolidine-2-carboxamide;

(S)-1-(4'-((1-(2-ethyl-2-fluorobutyl)piperidin-4-yl)methoxy)-2,3'-difluorobiphenylcarbonyl)pyrrolidine-2-carboxamide;

(S)-1-(3'-cyano-3-fluoro-4'-((1-(2-fluoro-2-methylpropyl)piperidin-4-yl)methoxy)biphenylcarbonyl)pyrrolidine-2-carboxamide;

(S)-1-(2-fluoro-4-(5-((1-(2-fluoro-2-methylpropyl)piperidin-4-yl)methoxy)pyrazin-2-yl)benzoyl)pyrrolidine-2-carboxamide;

(S)-1-(3-fluoro-4'-((1-(2-fluoro-2-methylpropyl)piperidin-4-yl)methoxy)-3-(hydroxymethyl)biphenylcarbonyl)pyrrolidine-2-carboxamide;

(S)-1-(4-(5-((1-(2-fluoro-2-methylpropyl)piperidin-4-yl)methoxy)pyrazin-2-yl)benzoyl)pyrrolidine-2-carboxamide;

(S)-1-(4-(6-((1-(2-ethyl-2-fluorobutyl)piperidin-4-yl)methoxy)pyridazin-3-yl)benzoyl)pyrrolidine-2-carboxamide;

(S)-1-(3'-cyano-4'-((1-(2-fluoro-2-methylpropyl)piperidin-4-yl)methoxy)biphenylcarbonyl)pyrrolidine-2-carboxamide;

(S)-1-(3'-cyano-2-fluoro-4'-((1-(2-fluoro-2-methylpropyl)piperidin-4-yl)methoxy)biphenylcarbonyl)pyrrolidine-2-carboxamide, (S)-1-(4-(2-((1-((1-(trifluoromethyl)cyclobutyl)methyl)piperidin-4-yl)benzoyl)pyrrolidine-2-carboxamide;

(S)-1-(3-fluoro-4-(2-((1-((1-(trifluoromethyl)cyclobutyl)methyl)piperdin-4-yl)methoxy)pyrimidin-5-yl)benzoyl)pyrrolidine-2-carboxamide;

(S)-1-(2-fluoro-4-(2-((1-((1-(trifluoromethyl)cyclobutyl)methyl)piperidin-4-yl)methoxy)pyrimidin-5-yl)benzoyl)pyrrolidine-2-carboxamide;

(S)-1-(4-(6-((1-(2-fluoro-2-methylpropyl)piperidin-4-yl)methoxy)pyridazin-3-yl)benzoyl)pyrrolidine-2-carboxamide;

(S)-1-(2-fluoro-4-(6-((1-(2-fluoro-2-methylpropyl)piperidin-4-yl)methoxy)pyridazin-3-yl)benzoyl)pyrrolidine-2-carboxamide;

(S)-1-(3'-cyano-4'-((1-(2-ethyl-2-fluorobutyl)piperidin-4-yl)methoxy)-3-fluorobiphenylcarbonyl)pyrrolidine-2-carboxamide;

(S)-1-(3'-cyano-4'-((1-(2-ethyl-2-fluorobutyl)piperidin-4-yl)methoxy)biphenylcarbonyl)pyrrolidine-2-carboxamide;

(S)-1-(4-(5-((1-((1-(trifluoromethyl)cyclobutyl)methyl)piperidin-4-yl)methoxy)pyrazin-2-yl)benzoyl)pyrrolidine-2-carboxamide;

(S)-1-(3-fluoro-4-(5-((1-((1-(trifluoromethyl)cyclobutyl)methyl)piperidin-4-yl)methoxy)pyrazin-2-yl)benzoyl)pyrrolidine-2-carboxamide;

(S)-1-(2-fluoro-4-(5-((1-((1-(trifluoromethyl)cyclobutyl)methyl)piperidin-4-yl)methoxy)pyrazin-2-yl)benzoyl)pyrrolidine-2-carboxamide;

(R)-1-(3'-cyano-3-fluoro-4'-((1-(2-fluoro-2-methylpropyl)piperidin-4-yl)methoxy)biphenylcarbonyl)piperidine-2-carboxamide;

(S)-1-(4-(5-((1-(2-ethyl-2-fluorobutyl)piperidin-4-yl)methoxy)pyrazin-2-yl)benzoyl)pyrrolidine-2-carboxamide;

(S)-1-(4'-((1-((1-(trifluoromethyl)cyclobutyl)methyl)piperidin-4-yl)methylamino)biphenylcarbonyl)pyrrolidine-2-carboxamide;

(R)-1-(4'-((1-((1-(trifluoromethyl)cyclobutyl)methyl)piperidin-4-yl)methylamino)biphenylcarbonyl)piperidine-2-carboxamide;

(S)-1-(4-((1-(3,3,3-trifluoro-2,2-dimethylpropyl)piperidin-4-yl)methylamino)biphenylcarbonyl)pyrrolidine-2-carboxamide;

(S)-1-(2'-cyano-3-fluoro-4'-((1-(2-fluoro-2-methylpropyl)piperidin-4-yl)methoxy)biphenylcarbonyl)pyrrolidine-2-carboxamide;

(R)-1-(2'-cyano-3-fluoro-4'-((1-(2-fluoro-2-methylpropyl)piperidin-4-yl)methoxy)biphenylcarbonyl)piperidine-2-carboxamide;

(S)-1 (2'-cyano-4'-((1-(2-fluoro-2-methylpropyl)piperidin-4-yl)methoxy)biphenylcarbonyl)pyrrolidine-2-carboxamide;

(S)-1-(2-fluoro-4-(5-((1-(2-fluoro-2-methylpropyl)piperidin-4-yl)methoxy)pyrimidin-2-yl)benzoyl)pyrrolidine-2-carboxamide;

(S)-1-(5-(3-cyano-4-((1-(2-fluoro-2-methylpropyl)piperidin-4-yl)methoxy)phenyl)picolinoyl)pyrrolidine-2-carboxamide;

(R)-1-(2-fluoro-4-(5-((1-(2-fluoro-2-methylpropyl)piperidin-4-yl)methoxy)pyrimidin-2-yl)benzoyl)piperidine-2-carboxamide;

(S)-1-(5-(4-((1-(2-fluoro-2-methylpropyl)piperidin-4-yl)methoxy)phenyl)pyrazine-2-carbonyl)pyrrolidine-2-carboxamide;

(S)-1-(4-(5-((1-(2-ethyl-2-fluorobutyl)piperidin-4-yl)methoxy)pyrimidin-2-yl)benzoyl)pyrrolidine-2-carboxamide;

(R)-1-(4-(5-((1-(2-ethyl-2-fluorobutyl)piperidin-4-yl)methoxy)pyrimidin-2-yl)benzoyl)piperidine-2-carboxamide;

(S)-1-(4-(5-((1-(2-ethyl-2-fluorobutyl)piperidin-4-yl)methoxy)pyrimidin-2-yl)-2-fluorobenzoyl)pyrrolidine-2-carboxamide;

(R)-1-(4-(5-((1-(2-ethyl-2-fluorobutyl)piperidin-4-yl)methoxy)pyrimidin-2-yl)-2-fluorobenzoyl)piperidine-2-carboxamide;

(R)-1-(4-(5-((1-(2-ethyl-2-fluorobutyl)piperidin-4-yl)methoxy)pyrimidin-2-yl)-3-fluorobenzoyl)piperidine-2-carboxamide;

(2S,4R)-1-(2-fluoro-4-(5-((1-(2-fluoro-2-methylpropyl)piperidin-4-yl)methoxy)pyridin-2-yl)benzoyl)-4-hydroxypyrrolidine-2-carboxamide;

(S)-1-(3-fluoro-4-(5-((1-(2-fluoro-2-methylpropyl)piperidin-4-yl)methoxy)pyrazin-2-yl)benzoyl)pyrrolidine-2-carboxamide;

(R)-1-(3-fluoro-4-(5-((1-(2-fluoro-2-methylpropyl)piperidin-4-yl)methoxy)pyrazin-2-yl)benzoyl)piperidine-2-carboxamide;

(R)-1-(4-(6-((1-(2-fluoro-2-methylpropyl)piperidin-4-yl)methoxy)pyridin-3-yl)benzoyl)piperidine-2-carboxamide;

(S)-1-(4-(6-((1-(2-fluoro-2-methylpropyl)piperidin-4-yl)methoxy)pyridin-3-yl)benzoyl)piperidine-2-carboxamide;

(R)-1-(4-(5-((1-(2-fluoro-2-methylpropyl)piperidin-4-yl)methoxy)pyrazin-2-yl)benzoyl)piperidine-2-carboxamide;

(S)-1-(4-(5-((1-(2-fluoro-2-methylpropyl)piperidin-4-yl)methoxy)pyrazin-2-yl)benzoyl)piperidine-2-carboxamide;

(S)-1-(5-(2-fluoro-4-((1-(2-fluoro-2-methylpropyl)piperidin-4-yl)methoxy)phenyl)pyrazine-2-carbonyl)pyrrolidine-2-carboxamide;

(2S,4S)-4-fluoro-1-(3-fluoro-4-((1-(2-fluoro-2-methylpropyl)piperidin-4-yl)methoxy)biphenylcarbonyl)pyrrolidine-2-carboxamide;

(2S,4R)-1-(3-fluoro-4'-((1-(2-fluoro-2-methylpropyl)piperidin-4-yl)methoxy)biphenylcarbonyl)-4-hydroxypyrrolidine-2-carboxamide;

(S)-1-(3'-cyano-4'-((1-(2-ethyl-2-fluorobutyl)piperidin-4-yl)methoxy)-2-fluorobiphenylcarbonyl)pyrrolidine-2-carboxamide;

(R)-1-(3'-cyano-4'-((1-(2-ethyl-2-fluorobutyl)piperidin-4-yl)methoxy)-2-fluorobiphenylcarbonyl)piperidine-2-carboxamide;

(S)-1-(2'-cyano-4'-((1-(2-ethyl-2-fluorobutyl)piperidin-4-yl)methoxy)biphenylcarbonyl)pyrrolidine-2-carboxamide; and (R)-1-(2'-cyano-4'-((1-(2-ethyl-2-fluorobutyl)piperidin-4-yl)methoxy)biphenylcarbonyl)piperidine-2-carboxamide.

6. The piperidine derivative, stereoisomers thereof or pharmaceutically acceptable salts thereof according to claim 5, wherein the piperidine derivative is selected from the group consisting of:

(S)-1-(2-fluoro-4-(5-((1-(2-fluoro-2-methylpropyl)piperidin-4-yl)methoxy)pyridin-2-yl)benzoyl)pyrrolidine-2-carboxamide;

(S)-1-(4-(5-((1-(2-ethyl-2-fluorobutyl)piperidin-4-yl)methoxy)pyridin-2-yl)benzoyl)pyrrolidine-2-carboxamide;

(S)-1-(3'-cyano-3-fluoro-4'-((1-(2-fluoro-2-methylpropyl)piperidin-4-yl)methoxy)biphenylcarbonyl)pyrrolidine-2-carboxamide;

(S)-1-(2'-cyano-3-fluoro-4'-((1-(2-fluoro-2-methylpropyl)piperidin-4-yl)methoxy)biphenylcarbonyl)pyrrolidine-2-carboxamide; and (S)-1-(2-fluoro-4-(5-((1-(2-fluoro-2-methylpropyl)piperidin-4-yl)methoxy)pyrimidin-2-yl)benzoyl)pyrrolidine-2-carboxamide.

7. A pharmaceutical composition comprising the piperidine derivative, stereoisomers thereof or pharmaceutically acceptable salts thereof according to claim 1 and pharmaceutically acceptable carriers.

8. A pharmaceutical composition comprising the piperidine derivative, stereoisomers thereof or pharmaceutically acceptable salts thereof according to claim 5 and pharmaceutically acceptable carriers.

* * * * *

UNITED STATES PATENT AND TRADEMARK OFFICE
CERTIFICATE OF CORRECTION

PATENT NO. : 9,944,600 B2
APPLICATION NO. : 14/407214
DATED : April 17, 2018
INVENTOR(S) : Lee et al.

Page 1 of 2

It is certified that error appears in the above-identified patent and that said Letters Patent is hereby corrected as shown below:

In the Claims

Column 453, Line 24: Claim 5, Delete "(2S)-1-(2,2'-difluoro-4'-(1-" and insert -- (2S)-1-(2,2'-difluoro-4'-((1- --

Column 453, Line 49: Claim 5, Delete ")piperidine-4-carboxamide" and insert -- )piperidine-3-carboxamide --

Column 453, Line 51: Claim 5, Delete ")piperidine-2-carboxamide" and insert -- )piperidine-4-carboxamide --

Column 454, Line 10: Claim 5, Delete "1-(3'-difluoro-4'-((" and insert -- 1-(3'-fluoro-4'-(( --

Column 455, Line 26: Claim 5, Delete "(R)-1-(2-fluoro-4-(6-1 ((1-2-" and insert -- (R)-1-(2-fluoro-4-(6-((1-2- --

Column 455, Line 33: Claim 5, Delete ")piperidine-2-carboxamide" and insert -- )piperidine-4-carboxamide --

Column 455, Line 56: Claim 5, Delete "(S)-1-(4-((1-(2-fluoro-" and insert -- (S)-1-(4'-((1-(2-fluoro- --

Column 455, Line 57: Claim 5, Delete "methyl amino)" and insert -- methylamino) --

Column 456, Line 39: Claim 5, Delete "methoxy)biphenyl carbonyl)piperidine-" and insert -- methoxy)biphenylcarbonyl)piperidine- --

Column 456, Line 44: Claim 5, Delete "(S)-1 (4'-((1-(2-ethyl" and insert -- (S)-1-(4'-((1-(2-ethyl- --

Signed and Sealed this
Twenty-fourth Day of July, 2018

Andrei Iancu
*Director of the United States Patent and Trademark Office*

CERTIFICATE OF CORRECTION (continued)
U.S. Pat. No. 9,944,600 B2

Column 457, Line 23: Claim 5, Delete ")methoxy)-3-(hydroxymethyl)" and insert -- )methoxy)-3'-(hydroxymethyl) --

Column 457, Line 38: Claim 5, Delete ")piperidin-4-yl)benzoyl)" and insert -- )piperidin-4-yl)methoxy)pyrimidin-5-yl)benzoyl) --

Column 458, Line 13: Claim 5, Delete "(S)-1-(4-((1-(3,3,3-trifluoro-" and insert -- (S)-1-(4'-((1-(3,3,3-trifluoro- --

Column 458, Line 22: Claim 5, Delete "(S)-1 (2'cyano-4'-((" and insert -- (S)-1-(2'cyano-4'-(( --

Column 458, Line 62: Claim 5, Delete "methoxy)pyri din-3-yl)" and insert -- methoxy)pyridin-3-yl) --

Column 459, Line 10: Claim 5, Delete "(3-fluoro-4-((1-(2-fluoro-" and insert -- (3-fluoro-4'-((1-(2-fluoro- --